United States Patent
Luo et al.

(10) Patent No.: US 10,760,132 B2
(45) Date of Patent: Sep. 1, 2020

(54) METHODS FOR DIAGNOSING PROSTATE CANCER AND PREDICTING PROSTATE CANCER RELAPSE

(71) Applicant: University of Pittsburgh—of the Commonwealth System of Higher Education, Pittsburgh, PA (US)

(72) Inventors: Jianhua Luo, Wexford, PA (US); George Konstantine Michalopoulos, Pittsburgh, PA (US); Joel B. Nelson, Pittsburgh, PA (US); Chi Song, New Haven, CT (US); Chien-Cheng Tseng, Pittsburgh, PA (US); Yanping Yu, Wexford, PA (US)

(73) Assignee: UNIVERSITY OF PITTSBURGH—OF THE COMMONWEALTH SYSTEM OF HIGHER EDUCATION, Pittsburgh, PA (US)

( * ) Notice: Subject to any disclaimer, the term of this patent is extended or adjusted under 35 U.S.C. 154(b) by 0 days.

(21) Appl. No.: 14/336,965

(22) Filed: Jul. 21, 2014

(65) Prior Publication Data

US 2015/0050647 A1    Feb. 19, 2015

Related U.S. Application Data

(63) Continuation of application No. 13/619,556, filed on Sep. 14, 2012, now abandoned.

(60) Provisional application No. 61/535,240, filed on Sep. 15, 2011.

(51) Int. Cl.
*C12Q 1/68* (2018.01)
*C12Q 1/6886* (2018.01)
*C12Q 1/6874* (2018.01)

(52) U.S. Cl.
CPC ......... *C12Q 1/6886* (2013.01); *C12Q 1/6874* (2013.01); *C12Q 2600/112* (2013.01); *C12Q 2600/118* (2013.01); *C12Q 2600/156* (2013.01)

(58) Field of Classification Search
None
See application file for complete search history.

(56) References Cited

U.S. PATENT DOCUMENTS

| | | | |
|---|---|---|---|
| 2008/0274909 A1* | 11/2008 | Brothnnan | C12Q 1/6883 506/9 |
| 2009/0029362 A1 | 1/2009 | Timms et al. | |
| 2010/0261617 A1* | 10/2010 | Poustka | C12Q 1/6886 506/9 |
| 2011/0287034 A1* | 11/2011 | Frank | G01N 33/57415 424/178.1 |
| 2012/0220672 A1 | 8/2012 | Pestano et al. | |
| 2013/0079241 A1 | 3/2013 | Luo et al. | |
| 2013/0225420 A1* | 8/2013 | Albertson | C12Q 1/6886 506/2 |

FOREIGN PATENT DOCUMENTS

| | | |
|---|---|---|
| WO | WO 03/101530 A2 | 12/2003 |
| WO | WO 2006/012646 A2 | 2/2006 |
| WO | WO 2008/016374 A2 | 2/2008 |
| WO | WO 2008/023087 A2 | 2/2008 |
| WO | WO 2010/056337 A2 | 5/2010 |
| WO | WO 2010/138460 A1 | 12/2010 |
| WO | WO 2012/139134 A2 | 10/2012 |
| WO | WO 2013/037118 A1 | 3/2013 |
| WO | WO 2014/018673 A2 | 1/2014 |
| WO | WO 2014/039556 A1 | 3/2014 |
| WO | WO 2015/103057 A1 | 7/2015 |
| WO | WO 2015/106341 A1 | 7/2015 |

OTHER PUBLICATIONS

Enard et al. (Science 2002 vol. 296 p. 340).*
El Gammal et al. (Clin Cancer Research Jan. 2010 VOl. 16 p. 56).*
Sheu et al. (Cancer Epidemiol Biomarkers Prey vol. 18 Oct. 2009 p. 2709) (Year: 2009).*
U.S. Appl. No. 13/619,556 (US 2013/0079241), filed Sep. 30, 2014 (Mar. 28, 2013) (Abandoned).
Bae, et al., "Low Frequency Mutation of the Ephrin Receptor A3 Gene in Hepatocellular Carcinoma", *Neoplasma*, 56(4):331-334 (2009).
Bettendorf, et al., "Cytogenetic Changes and Loss of Heterozygosity in Atypical Adenomatous Hyperplasia, in Carcinoma of the Prostate and in Non-Neoplastic Prostate Tissue Using Comparative Genomic Hybridization and Multiplex-PCR", *International Journal of Oncology*, 26(1):267-274 (2005).
Blackford, et al., "Genetic Mutations Associated with Cigarette Smoking in Pancreatic Cancer", *Cancer Research*, 69(8):3681-3688 (2009).
Budd, et al., "Circulating Tumor Cells Versus Imaging-Predicting overall survival in Metastatic Breast Cancer", *Clinical Cancer Research*, 12(21):6403-6409 (2006).
Clifford, et al., "The EphA3 Receptor is Expressed in a Subset of Rhabdomyosarcoma Cell Lines and Suppresses Cell Adhesion and Migration", *Journal of Cellular Biochemistry*, 105:1250-1259 (2008).
Golub, et al., "Molecular Classification of Cancer: Class Discovery and Class Prediction by Gene Expression Monitoring", *Science*, 286:531-537 (1999).

(Continued)

*Primary Examiner* — Katherine D Salmon
(74) *Attorney, Agent, or Firm* — Baker Botts L.L.P.

(57) ABSTRACT

The present invention relates to methods and compositions for diagnosing prostate cancer and/or determining whether a prostate cancer patient is at increased risk of suffering a relapse, or a rapid relapse, of his cancer. It is based, at least in part, on the results of a comprehensive genome analysis on 241 prostate cancer samples (104 prostate cancer, 85 matched bloods, 49 matched benign prostate tissues adjacent to cancer, and 3 cell lines) which indicate that (i) genome copy number variation (CNV) occurred in both cancer and non-cancer tissues, and (ii) CNV predicts prostate cancer progression.

2 Claims, 15 Drawing Sheets

Figure 1A:
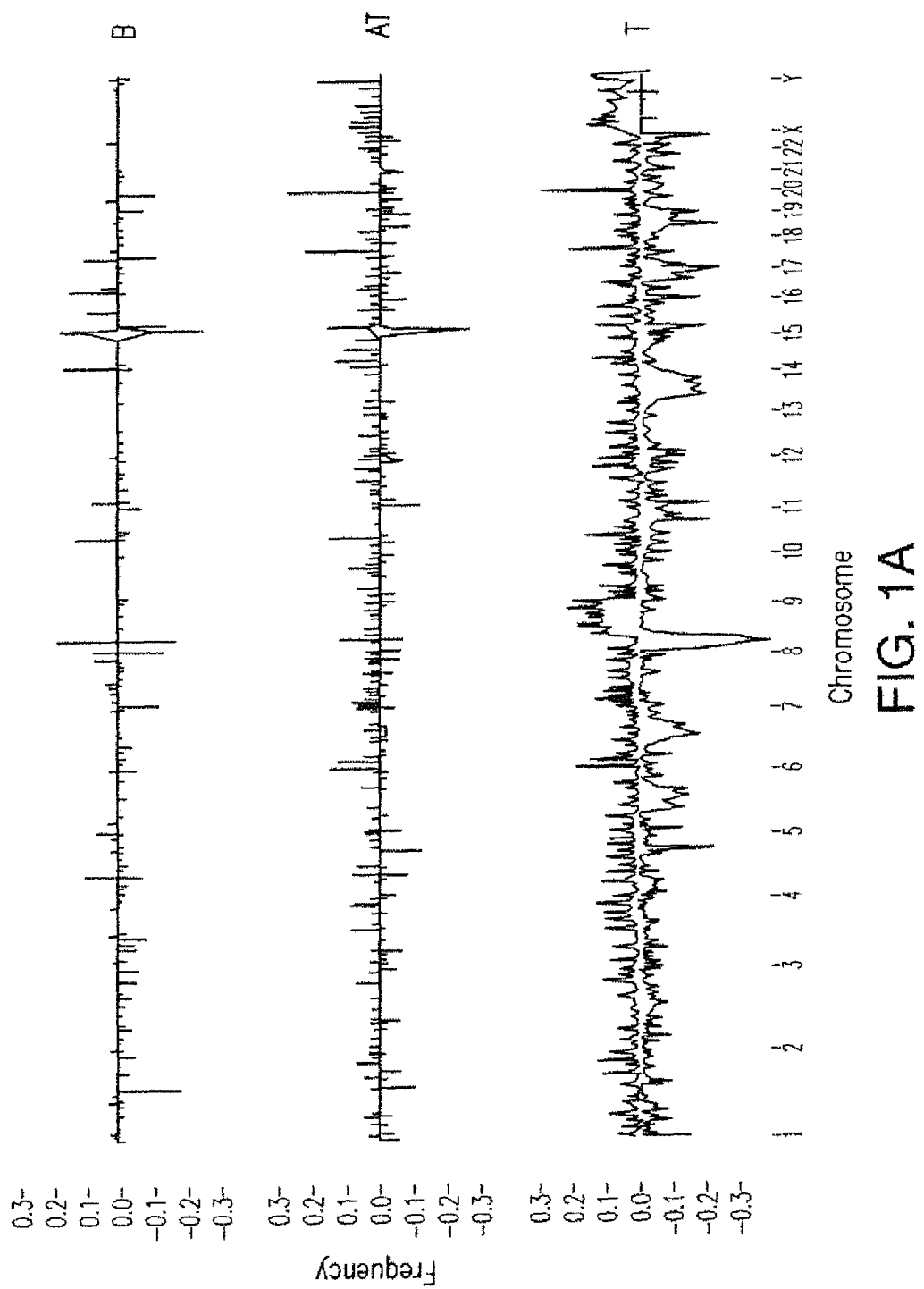
Figure 1B:
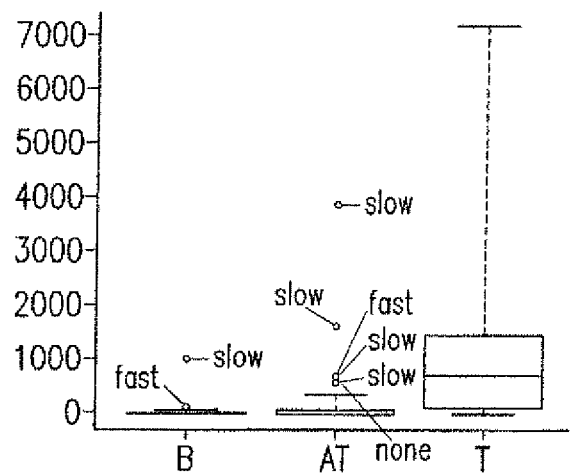

Specification includes a Sequence Listing.

(56) References Cited

OTHER PUBLICATIONS

Green, et al., "Integrative analysis Reveals Selective 9p24.1 Amplification, Increased PD-1 Ligand Expression, and Further Induction Via JAK2 in Nodular Sclerosing Hodgkin Lymphoma and Primary Mediastinal Large B-Cell Lymphoma", *Blood*, 116(17):3268-3277 (2010).
Hanczar, et al., "Small-Sample Precision of ROC-Related Estimates", *Bioinformatics*, 26(6):822-830 (2010).
Hanks, et al., "Pretreatment Prostate-Specific Antigen Doubling times: Clinical Utility of this Predictor of Prostate Cancer Behavior", *Int. J. Radiation Oncology_Biol. Phys.*, 34(3):549-553 (1996).
Isaacs, "Molecular Markers for Prostate Cancer Metastasis", *American Journal of Pathology*, 150(5):1511-1521 (1997).
Jemal, et al., "Global Cancer Statistic", *CA Cancer J. Clin.*, 61:69-90 (2011).
Jemal, et al., "Global Cancer Statistic", *CA Cancer J. Clin.*, 59:225-249 (2009).
Jemal, et al., "Global Cancer Statistic", *CA Cancer J. Clin.*, 60:277-300 (2010).
Kim, et al., "Integrative analysis of Genomic Aberrations Associated with Prostate Cancer Progression", *Cancer Research*, 67(17):8229-8239 (2007).
Koutras, et al., "The Upgrade Role of HER3 and HER4 Receptors in Breast cancer", *Critical Reviews in Oncology/Hematology*, 74:73-78 (2010).
Kraus, et al., "High-Resolution genomic Profiling of Occult Micrometastatic Tumor Cells", *Genes, Chromosomes & cancer*, 36:159-166 (2003).
Lee, et al., "Somatic Mutation in Epidermal Growth Factor Receptor Signaling Pathway Genes in Non-Small Cell Lung Cancers", *Journal of Thoracic Oncology*, 5(11):1734-1740 (2010).
Liu, et al., "Copy Number Analysis Indicates Monoclonal Origin of Lethal Metastatic Prostate Cancer", *Nature Medicine*, 15(5):559-565.
Macoska, et al., "Evolution of 8p Loss in Transformed Human Prostate Epithelial cells", *Cancer Genetics and Cytogenetics*, 154:36-43 (2004).
Matsui, et al., "Molecular Characterization of a Consistent 4.5-Megabase Deletion at 4q28 in Prostate Cancer Cells", *Cancer Genetics and Cytogenetics*, 159:18-26 (2005).
Moreno, et al., "Detection of Hematogenous Micrometastasis in Patients with Prostate Cancer", *Cancer Research*, 52:6110-6112 (1992).
Ren, et al., MCMl amplification and Overexpression are Associated with Prostate Cancer Progression, *Oncogene*, 25:1090-198 (2006).
Stephenson, et al., "Salvage Radiotherapy for Recurrent Prostate Cancer After Radical Prostatectomy", *JAMA*, 291(11):1325-1332 (2004).
Strassburger, et al., "Compatible Simultaneous Lower Confidence Bounds for the Holm Procedure and other Bonferroni-Based Closed Tests", *Statistics in Medicine*, 27:4914-4927 (2008).
Strausberg, et al., "Generation and Initial Analysis of More Than 15,000 Full-Length Human and Mouse cDNA Sequences", *PNAS*, 99(26):16899-16903 (2002).
Taylor et al., "Integrative Genomic Profiling of Human Prostate Cancer", *Cancer Cell*, 18:11-22, including supplementary material (2010).
Teixeira, et al., "Genomic analysis of Prostate Carcinoma Specimens Obtained via Ultrasound-guided Needle Biopsy May Be of Use in Preoperative Decision-Making", *American Cancer Society*, 101:1786-1793 (2004).
Tsang, et al., "SCAPER, a Novel Cyclin A-Interacting Protein that Regulates Cell Cycle Progression", *Journal of Cell Biology*, 178(4):621-633 (2007).
Yang, et al., "Deletion of the WWOX gene and Frequent Loss of its Protein Expression in Human Osteosarcoma", *Cancer Letter*, 291:31-38 (2010).
Yu, et al., "Genome Abnormalities Precede Prostate Cancer and Predict Clinical Relapse", *The American Journal of Pathology*, 180(6):2240-2248 (2012).
Yu, et al., "Gene Expression Alterations in Prostate Cancer Predicting Tumor Aggression and Preceding Development of Malignancy", *Journal of Clinical Oncology*, 22(14):2790-2799 (2004).
Zhao, et al., "Genome-Wide Characterization of Gene Expression Variations and DNA Copy Number Changes on Prostate cancer Cell Lines", *The Prostate*, 63:187-197 (2005).
Heitzer et al., "Tumor-associated copy number changes in the circulation of patients with prostate cancer identified through whole-genome sequencing," Genome Medicine 5:30 (2013).
Hieronymus et al., "Copy number alteration burden predicts prostate cancer relapse," PNAS 111(30):11139-11144 (2014).
International Search Report dated Oct. 17, 2016 in International Application No. PCT/US2016/046051.
Liu et al., "Comprehensive Assessment of DNA Copy Number Alterations in Human Prostate Cancers Using Affymetrix 100K SNP Mapping Array," Genes, Chromosomes & Cancer 45:1018-1032 (2006).
Yu et al., "Genomic Copy Number Variations in the Genomes of Leukocytes Predict Prostate Cancer Clinical Outcomes," PloS ONE 10(8):E0135982 (2015).
Yu et al., "Novel Fusion Transcripts Associate With Progressive Prostate Cancer," The American Journal of Pathology 184(10):2840-2849 (2014).
Agarwal et al., (2003) Zinc metalloproteinase, ZMPSTE24, is mutated in mandibuloacral dysplasia, Human Molecular Genetics 12(16):1995-2001 (2003).
Ahn et al., "Fer Protein-Tyrosine Kinase Promotes Lung Adenocarcinoma Cell Invasion and Tumor Metastasis," Mol Cancer Res 11(8):952-963 (2013).
Anderson et al., "A simple method for the rapid generation of recombinant adenovirus vectors," Gene Therapy 7:1034-1038 (2000).
Antonarakis et al., "Changes in PSA Kinetics Predict Metastasis-Free Survival in Men with PSA-Recurrent Prostate Cancer Treated With Nonhormonal Agents: Combined Analysis of 4 Phase II Trials," Cancer 118:1533-1542 (2012).
Baca et al., "Punctuated Evolution of Prostate Cancer Genomes," Cell 153:666-677 (2013).
Bar-Peled et al., "A Tumor Suppressor Complex with GAP Activity for the Rag GTPases That Signal Amino Acid Sufficiency to mTORC1," Science 340:1100-1106 (2013).
Berger et al., "The genomic complexity of primary human prostate cancer," Nature 470:214-220 (2011).
Carver et al., "ETS rearrangements and prostate cancer initiation," Nature 457:E1; discussion E2-3 (2009).
Chi et al., "ETV1 is a lineage survival factor that cooperates with KIT in gastrointestinal stromal tumours," Nature 467:849-853 (2010).
Clark et al., "ETS gene fusions in prostate cancer," Nat Rev Urol. 6:429-439 (2009).
Corban-Wilhelm et al., "Cytosine deaminase versus thymidine kinase: a comparison of the antitumor activity," Clinical and Experimental Medicine, 3(3):150-156 (2003).
Demichelis et al., "TMPRSS2:ERG gene fusion associated with lethal prostate cancer in a watchful waiting cohort," Oncogene, 26:4596-4599 (2007).
Derwent Abstract Accession No. 2013-E07845 (accessed on Sep. 21, 2016).
Edgren et al., "Identification of fusion genes in breast cancer by paired-end RNA-sequencing," Genome Biol. 12:R6 (2011).
Enninga et al., "Sec13 Shuttles between the Nucleus and the Cytoplasm and Stably Interacts with Nup96 at the Nuclear Pore Complex," Molecular and Cellular Biology 23(20):7271-7284 (2003).
Esvelt et al., "Concerning RNA-guided gene drives for the alteration of wild populations," eLife 3:e03401 (2014).
Fisher et al., "A Novel Cyclin Associates with M015/CDK7 to Form the CDK-Activating Kinase," Cell 78:713-724 (1994).
Fitzgerald et al., "Association of TMPRSS2-ERG gene fusion with clinical characteristics and outcomes: results from a population-based study of prostate cancer," BMC Cancer 8:230 (2008).
Freedland et al., "Death in Patients With Recurrent Prostate Cancer After Radical Prostatectomy: Prostate-Specific Antigen Doubling Time Subgroups and Their Associated Contributions to All-Cause Mortality," J Clin Oncol. 25(13):1765-1771 (2007).

(56) References Cited

OTHER PUBLICATIONS

Guo et al., "FER tyrosine kinase (FER) overexpression mediates resistance to quinacrine through EGF-dependent activation of NF-κB," PNAS USA 108(19):7968-7973 (2011).
Hakkarainen et al., "A conditionally replicative adenovirus that codes for a TKGFP fusion protein (Ad5Delta24TK-GFP) for evaluation of the potency of oncolytic virotherapy combined with molecular chemotherapy," International Journal of Molecular Medicine, 18(4):751-759 (2006).
Han et al., "Interaction of integrin-linked kinase (ILK) and MCM7 mediating integrin α7 induced cell growth suppression," Cancer Research 70(11):4375-4384 (2010).
Han et al., "Metallothionein 1 h tumour suppressor activity in prostate cancer is mediated by euchromatin methyltransferase 1," The Journal of Pathology 230(2):184-193 (2013).
Hao et al., "Isolation and Sequence Analysis of a Novel Human Tyrosine Kinase Gene," Mol Cell Biol 9(4):1587-1593 (1989).
International Search Report and Written Opinion dated Apr. 1, 2015 in International Application No. PCT/US2014/072268.
International Search Report dated Oct. 7, 2015 in International Application No. PCT/US2015/041029.
Ivanova et al., "FER kinase promotes breast cancer metastasis by regulating α6- and β1-integrin-dependent cell adhesion and anoikis resistance," Oncogene 32:5582-5592 (2013).
Jane-Valbuena et al., "An Oncogenic Role for ETV1 in Melanoma," Cancer Research 70(5):2075-2084 (2010).
Jeon et al., "A variant Ewing's sarcoma translocation (7;22) fuses the EWS gene to the ETS gene ETV1," Oncogene 10:1229-1234 (1995).
Jinek et al., "A Programmable Dual-RNA-Guided DNA Endonuclease in Adaptive Bacterial Immunity," Science 337:816-821 (2012).
Jing et al., "Expression of Myopodin Induces Suppression of Tumor Growth and Metastasis," The American Journal of Pathology 164(5):1799-1806 (2004).
Kawakami et al., "FER overexpression is associated with poor postoperative prognosis and cancer-cell survival in non-small cell lung cancer," Int J Clin Exp Pathol 6(4):598-612 (2013).
Krastev et al., "A systematic RNAi synthetic interaction screen reveals a link between p53 and snoRNP assembly," Nature Cell Biology 13(7):809-818 (2011).
Krolewski et al., "Identification and chromosomal mapping of new human tyrosine kinase genes," Oncogene 5:277-282 (1990).
Kwok et al., "FES Kinase Promotes Mast Cell Recruitment to Mammary Tumors via the Stem Cell Factor/KIT Receptor Signaling Axis," Mol. Cancer Res 10(7):881-891 (2012).
Li et al., "Fast and accurate long-read alignment with Burrows-Wheeler transform," Bioinformatics 26(5):589-595 (2010).
Li et al., "Identification of tyrosine-phosphorylated proteins associated with metastasis and functional analysis of FER in human hepatocellular carcinoma cells," BMC Cancer 9:366 (2009).
Loimas et al., "Human prostate carcinoma cells as targets for herpes simplex virus thymidine kinase-mediated suicide gene therapy," Cancer Gene Therapy, 8(2):137-144 (2001).
Luo et al., "(-)-Epigallocatechin-3-gallate induces Du 145 prostate cancer cell death via downregulation of inhibitor of DNA binding 2, a dominant negative helix-loop-helix protein," Cancer Science 101(3):707-712 (2010).
Luo et al., "Discovery and Classification of Fusion Transcripts in Prostate Cancer and Normal Prostate Tissue," Am J Pathol 185:1834-1845 (2015).
Luo et al., "Gene Expression Analysis of Prostate Cancers," Molecular Carcinog. 33:25-35 (2002).
Misago et al., "Molecular cloning and expression of cDNAs encoding human α-mannosidase II and a previously unrecognized α-mannosidase IIx isozyme," Proc Natl Acad Sci USA 92:11766-11770 (1995).
Miyata et al., "Feline sarcoma-related protein expression correlates with malignant aggressiveness and poor prognosis in renal cell carcinoma," Cancer Sci 104(6):681-686 (2013).
Mojica et al., "Intervening Sequences of Regularly Spaced Prokaryotic Repeats Derive from Foreign Genetic Elements," J Mol Evol 60:174-182 (2005).
Monaco, "Fatty Acid Metabolism in Breast Cancer Subtypes," Oncotarget 8(17):29487-29500 (2017).
Moremen et al., "Isolation, Characterization, and Expression of cDNAs Encoding Murine α-Mannosidase II, a Golgi Enzyme That Controls Conversion of High Mannose to Complex N-Glycans," J Cell Biol 115(6):1521-1534 (1991).
Nam et al., "Expression of TMPRSS2 ERG Gene Fusion in Prostate Cancer Cells is an Important Prognostic Factor for Cancer Progression," Cancer Biology & Therapy 6(1):40-45 (2007).
Nellist et al., "Phosphorylation and binding partner analysis of the TSC1-TSC2 complex," Biochemical and Biophysical Research Communications 333:818-826 (2005).
Nunez, et al., "WWOX Protein Expression Varies Among Ovarian Carcinoma Histotypes and Correlates with Less Favorable Outcome", BMC Cancer, 5:64 (2005).
Pang, et al., "Cytogenetic and Expression Profiles Associated with Transformation to Androgen-Resistant Prostate Cancer", The Prostate, 66:157-172 (2006).
Parkin, et al., "Acquired Genomic Copy Number Aberrations and Survival in Adult Acute Myelogenous Leukemia", Blood, 116(23):4958-4967 (2010).
Parr-Sturgess et al., "Copper Modulates Zinc Metalloproteinase-Dependent Ectodomain Shedding of Key Signaling and Adhesion Proteins and Promotes the Invasion of Prostate Cancer Epithelial Cells," Mol Cancer Res 10(10):1282-1293 (2012).
Partial Supplemental European Search Report dated Jul. 12, 2017 in EP Application No. 14875963.2.
Perner et al., "784-TMPRSS2-ERG Gene Fusion Defines A Metastatic Phenotype of Prostate Cancer," Eur Urol Suppl 8(4):316 (2009).
Prakash et al., "Expression of Conjoined Genes: Another Mechanism for Gene Regulation in Eukaryotes," PLoS One 5(10):e13284 (2010).
Ran et al., "Double Nicking by RNA-Guided CRISPR Cas9 for Enhanced Genome Editing Specificity," Cell, 154:1380-1389 (2013).
Ren et al., "Analysis of Integrin α7 Mutations in Prostate Cancer, Liver Cancer, Glioblastoma Multiforme, and Leiomyosarcoma," J Natl Cancer Inst 99:868-880 (2007).
Rickman et al., "SLC45A3-ELK4 is a novel and frequent erythroblast transformation-specific fusion transcript in prostate cancer," Cancer Research, 69(7):2734-2738 (2009).
Robin et al., "pROC: an open-source package for R and S+ to analyze and compare ROC curves," BMC Bioinformatics 12:77 (2011).
Rocha et al., "The Fer tyrosine kinase acts as a downstream interleukin-6 effector of androgen receptor activation in prostate cancer," Mol Cell Endocrinol 381:140-149 (2013).
Sander et al., "CRIRISPR-Cas systems for editing, regulating and targeting genomes," Nature Biotechnology, 32(4):347-355 (2014).
Savolainen et al., "A mouse model for α-methylacyl-CoA racemase deficiency: adjustment of bile acid synthesis and intolerance to dietary methyl-branched lipids," Hum Mol Genet 13(9):955-965 (2004).
Shchors et al., "Cell Death Inhibiting RNA (CDIR) Derived from a 3'-Untranslated Region Binds AUF1 and Heat Shock Protein 27*," The Journal of Biological Chemistry 277(49):47061-47072 (2002).
Shi et al., "Inhibition of prostate cancer growth and metastasis using small interference RNA specific for minichromosome complex maintenance component 7," Cancer Gene Therapy 17(10):694-699 (2010).
Siegel et al., "Cancer Statistics, 2012," CA Cancer J Clin. 62:10-29 (2012).
Siegel et al., "Cancer Statistics, 2015," CA Cancer J Clin 65:5-29 (2015).
Sinclair et al., "A Fluorescence in situ Hybridization Map of 6q Deletions in Acute Lymphocytic Leukemia: Identification and Analysis of a Candidate Tumor Suppressor Gene," Cancer Res. 64:4089-4098 (2004).
Smith et al., "A New Nucleoside Analog, 9-[[2-Hydroxy-1-(Hydroxymethyl)Ethoxy]Methyl] Guanine, Highly Active in Vitro

(56) References Cited

OTHER PUBLICATIONS

Against Herpes Simplex Virus Types 1 and 2," Antimicrobial Agents and Chemotherapy 22:55-61 (1982).
Swanson et al., "TMPRSS2/ERG Fusion Gene Expression Alters Chemo- and Radio-Responsiveness in Cell Culture Models of Androgen Independent Prostate Cancer," The Prostate 71:1548-1558 (2011).
Tomlins et al., "Recurrent Fusion of TMPRSS2 and ETS Transcription Factor Genes in Prostate Cancer," Science 310:644-648 (2005).
Towns et al., "Transfer RNA Methytransferases and their Corresponding Modifications in Budding Yeast and Humans: Activities, Predications, and Potential Roles in Human Health," DNA and Cell Biology 31(4):434-454 (2012).
Trapnell et al., "Differential gene and transcript expression analysis of RNA-seq experiments with TopHat and Cufflinks," Nat Protoc. 7(3):562-578 (2012).
Trapnell et al., "TopHat: discovering splice junctions with RNA-Seq.," Bioinformatics 25(9):1105-1111 (2009).
Trapnell et al., "Transcript assembly and quantification by RNA-Seq reveals unannotated transcripts and isoform switching during cell differentiation," Nat. Biotechnol. 28(5):511-515 (2010).
Vitari et al., "COP1 is a tumour suppressor that causes degradation of ETS transcription factors," Nature 474:402-408 (2011).
Voisset et al., "The tyrosine kinase FES is an essential effector of KITD816V proliferation signal," Blood 110(7):2593-2599 (2007).
Wang et al., "Expression of variant TMPRSS2/ERG fusion messenger RNAs is associated with aggressive prostate cancer," Cancer Research, 66(17):8347-8351 (2006).
Wang et al., "p53-induced Gene 3 Mediates Cell Death Induced by Glutathione Peroxidase 3," J Biol Chem 287(20):16890-16902 (2012).
Watabe-Uchida et al., "The Rac Activator DOCK7 Regulates Neuronal Polarity through Local Phosphorylation of Stathmin/Op18," Neuron 51:727-739 (2006).
Wei et al., "High expression of FER tyrosine kinase predicts poor prognosis in clear cell renal cell carcinoma," Oncol Lett 5:473-478 (2013).
Willardsen et al., "The ETS transcription factor Etv 1 mediates FGF signaling to initiate proneural gene expression during Xenopus laevis retinal development," Mechanisms of Development 131:57-67 (2014).
Yakicier, et al., "Identification of Homozygous Deletions at Chromosome 16q23 in Aflatoxin B1 Exposed Hepatocellular Carcinoma", Oncogene, 20:5232-5238 (2001).
Yang et al., "mTOR kinase structure, mechanism and regulation," Nature 497:217-223 (2013).
Yang et al., "The Histone Demethylase JMJD2B is Regulated by Estrogen Receptor $\alpha$ and Hypoxia, and is a Key Mediator of Estrogen Induced Growth," Cancer Res 70(16):6456-6466 (2010).
Youden, "Index for Rating Diagnostic Tests," Cancer 3:32-35 (1950).
Yu et al., "CSR1 Suppresses Tumor Growth and Metastasis of Prostate Cancer," American Journal of Pathology 168(2):597-607 (2006).
Yu et al., "Glutathione Peroxidase 3, Deleted or Methylated in Prostate Cancer, Suppresses Prostate Cancer Growth and Metastasis," Cancer Res. 67(17):8043-8050 (2007).
Zeng et al., "Visualizing Interchange Patterns in Massive Movement Data," Computer Graphics Forum 32(3):271-280 (2013).
Zha et al., "$\alpha$-Methylacyl-CoA Racemase as an Androgen-Independent Growth Modifier in Prostate Cancer," Cancer research 63:7365-7376 (2003).
Zhen et al., "Nuclear Import of Exogenous FGF1 Requires the ER-Protein LRRC59 and the Importins Kpn$\alpha$1 and Kpn$\beta$1," Traffic 13:650-664 (2012).
Zhu et al., "CSR1 induces cell death through inactivation of CPSF3," Oncogene 28:41-51 (2009).
Zhu et al., "Integrin Alpha 7 Interacts with High Temperature Requirement A2 (HtrA2) to Induce Prostate Cancer Cell Death," The American Journal of Pathology 177(3):1176-1186 (2010).
U.S. Appl. No. 13/619,556 (US 2013/0079241), filed Sep. 14, 2012 (Mar. 28, 2013) (Abandoned).
U.S. Appl. No. 13/619,556, dated Sep. 30, 2014 Notice of Abandonment.
U.S. Appl. No. 13/619,556, dated Jul. 3, 2014 Advisory Action.
U.S. Appl. No. 13/619,556, dated Jun. 19, 2014 Response to Final Office Action.
U.S. Appl. No. 13/619,556, dated Feb. 21, 2014 Final Office Action.
U.S. Appl. No. 13/619,556, dated Nov. 14, 2013 Response to Non-Final Office Action.
U.S. Appl. No. 13/619,556, dated Jul. 16, 2013 Non-Final Office Action.
U.S. Appl. No. 13/619,556, dated May 13, 2013 Response to Restriction Requirement.
U.S. Appl. No. 13/619,556, dated Mar. 12, 2013 Restriction Requirement.
U.S. Appl. No. 15/199,056 (US 2016/0376666), filed Jun. 30, 2016 (Dec. 29, 2016).
U.S. Appl. No. 15/406,472, filed Jan. 13, 2017.
U.S. Appl. No. 15/199,056, dated Aug. 1, 2017 Response to Non-Final Office Action.
U.S. Appl. No. 15/199,056, dated May 3, 2017 Non-Final Office Action.
U.S. Appl. No. 15/199,056, dated Mar. 8, 2017 Response to Restriction Requirement.
U.S. Appl. No. 15/199,056, dated Mar. 3, 2017 Applicant Initiated Interview Summary.
U.S. Appl. No. 15/199,056, dated Nov. 9, 2016 Restriction Requirement.

\* cited by examiner

US 10,760,132 B2

SEQUENCE LISTING

<160> NUMBER OF SEQ ID NOS: 28

<210> SEQ ID NO 1
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1
aacctgagtc tgccaaggac tagc                                          24

<210> SEQ ID NO 2
<211> LENGTH: 24
<212> TYPE: DNA
<213> ORGANISM: Artificial Sequence
<220> FEATURE:
<223> OTHER INFORMATION: Description of Artificial Sequence: Synthetic primer

<400> SEQUENCE: 2
ttccacacac cactggccat cttc                                          24

<210> SEQ ID NO 3
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 3
acagaagtct gggatgtgga                                               20

<210> SEQ ID NO 4
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 4
gcccaaaaag acagacagaa                                               20

<210> SEQ ID NO 5
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 5
gatcccaagc tcttcctctt                                               20

<210> SEQ ID NO 6
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 6
acgtttgtgt gtgcatctgt                                               20

<210> SEQ ID NO 7
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 7
gggtgatttt cctctttggt                                               20

<210> SEQ ID NO 8
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 8
tgattccaat catagccaca                                          20

<210> SEQ ID NO 9
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 9
tgtcatagtt tagaacgaac taacg                                    25

<210> SEQ ID NO 10
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 10
ctgaggtatc aaaaactcag agg                                      23

<210> SEQ ID NO 11
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 11
gtgggctgaa aagctcccga ttat                                     24

<210> SEQ ID NO 12
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 12
attcaaaggg tatctgggct ctgg                                     24

<210> SEQ ID NO 13
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 13
ctggcacaga acaggcactt agg                                      23

<210> SEQ ID NO 14
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

```
<400> SEQUENCE: 14
ggaggaactg ggaaccacac aggt                                              24

<210> SEQ ID NO 15
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 15
ccctagtgga tgataagaat aatcagtatg                                        30

<210> SEQ ID NO 16
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 16
ggacagatga taaatacata ggatggatgg                                        30

<210> SEQ ID NO 17
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 17
actgtcatag cagtgctgag g                                                 21

<210> SEQ ID NO 18
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 18
acttacctac tgtagggacg g                                                 21

<210> SEQ ID NO 19
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 19
aggaaggcct attcgttctc g                                                 21

<210> SEQ ID NO 20
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 20
```
gaacagtatg ggaggagttc g                                      21

<210> SEQ ID NO 21
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 21
gccagttgat gtgacaactg c                                      21

<210> SEQ ID NO 22
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 22
cagctgagag tggtttcttt gc                                     22

<210> SEQ ID NO 23
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 23
atcaggactt accaggtgtg c                                      21

<210> SEQ ID NO 24
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 24
accgtgtctg gaaacatagc c                                      21

<210> SEQ ID NO 25
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 25
agtggcctgt ccttgcttat c                                      21

<210> SEQ ID NO 26
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 26

```
cagagcaaca attctgaccg g                                              21

<210> SEQ ID NO 27
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 27
tctttgcact ttctgcatgt cccc                                           24

<210> SEQ ID NO 28
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 28
gtccatcacg atgccagtgg tac                                            23
```

METHODS FOR DIAGNOSING PROSTATE CANCER AND PREDICTING PROSTATE CANCER RELAPSE

PRIORITY CLAIM

This application claims priority to U.S. Provisional Application No. 61/535,240, filed Sep. 15, 2011, the contents of which is hereby incorporated by reference in its entirety herein.

GRANT SUPPORT

This invention was made with government support under Grant No. CA098249 awarded by the National Institutes of Health. The government has certain rights in the invention.

SEQUENCE LISTING

The instant application contains a Sequence Listing which has been submitted electronically in ASCII format and is hereby incorporated by reference in its entirety. Said ASCII copy, created on Oct. 14, 2014, is named 072396.0574_SL.txt and is 6,786 bytes in size.

1. INTRODUCTION

The present invention relates to methods and compositions for diagnosing prostate cancer and/or determining whether a subject having prostate cancer is at increased risk for relapse or rapid relapse.

2. BACKGROUND OF THE INVENTION

Prostate cancer is one of the most common and lethal malignancies in men: The annual mortality rate reached 32,000 in the US in 2009 (1-3). Previous cytogenetic and other genome studies suggest a clear link between genome abnormalities and the prostate cancer (4-9). Currently, several treatment options are available for prostate cancer patients including watchful waiting, radiation, hormonal/chemo-therapy and radical prostatectomy. Gleason's grading alone or in combination with other clinical indicators such as serum prostate specific antigen levels and pathological or clinical staging has been the guiding tool in selecting these treatment options. Significant numbers of prostate cancer patients, however, experienced relapse after surgical resection of the prostate gland. There is clearly a need for better prediction of the behavior of prostate cancer.

3. SUMMARY OF THE INVENTION

The present invention relates to methods and compositions for diagnosing prostate cancer and/or determining whether a prostate cancer patient is at increased risk of suffering a relapse, or a rapid relapse, of his cancer. It is based, at least in part, on the results of a comprehensive genome analysis on 241 prostate cancer samples (104 prostate cancer, 85 matched bloods, 49 matched benign prostate tissues adjacent to cancer, and 3 cell lines) which indicate that (i) genome copy number variation (CNV) occurred in both cancer and non-cancer tissues, and (ii) CNV predicts prostate cancer progression.

Armed with the present invention, the health care practitioner is better able to advise a prostate cancer patient whether or not to undergo more aggressive forms of therapy or whether watchful waiting would be an appropriate recommendation, where in subjects at higher risk more aggressive forms of therapy may be recommended, including but not limited to prostate resection, antiandrogen therapy, radiotherapy and/or chemotherapy.

4. BRIEF DESCRIPTION OF THE FIGURES

FIG. 1A-D. Deletion and amplification of segments of genomes in blood, benign prostate tissues adjacent to cancer, and prostate cancer samples. (A) Histograms of genome deletion (blue) or amplification (red) of blood (B), benign prostate tissues adjacent to tumor (AT), and tumor (T) in 23 pairs of human chromosomes. (B) Box plot of number of genes overlapping with CNV per sample. Outliers in B and AT samples are indicated. (C) Venn diagram of deleted or amplified genes occurring in at least one sample overlapping between B, AT and T. (D) The spectrum of genes that are amplified or deleted in B, AT, tumors that did not relapse (Tnone), tumors that relapsed and had PSADT at or after 15th months of radical prostatectomy (Tslow), and tumors that relapsed and had PSADT within 4 months of radical prostatectomy (Tfast).

Figure 2A:
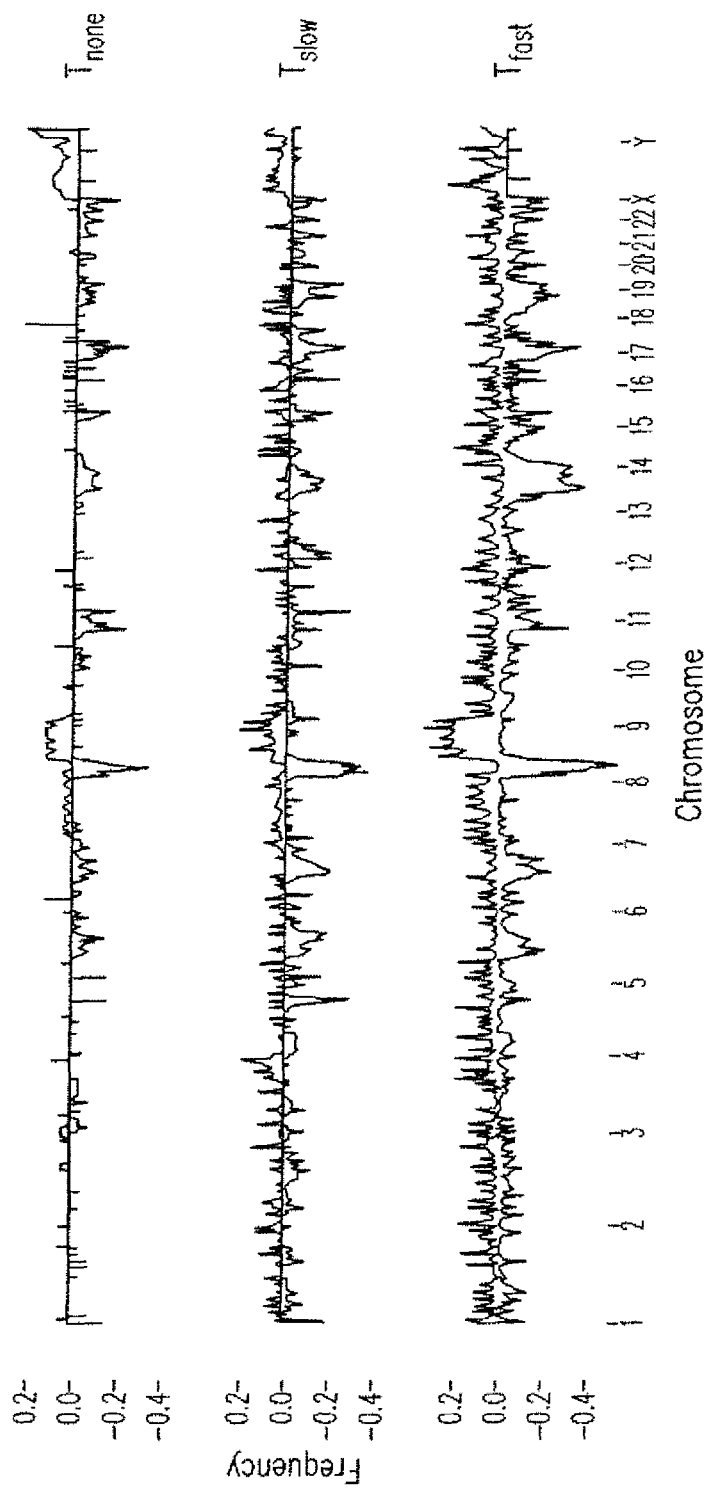
Figure 2B:
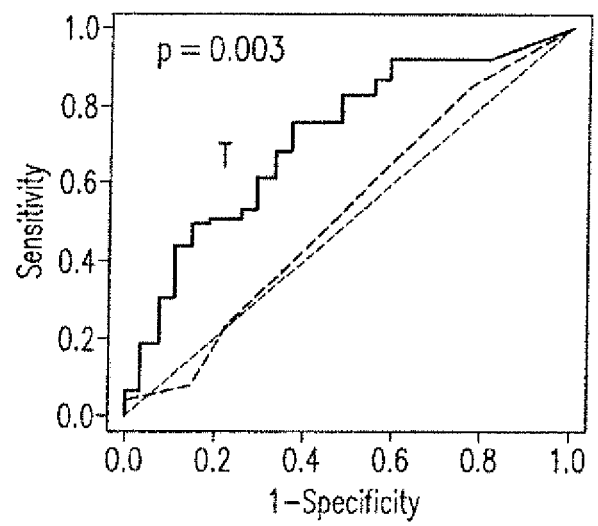
Figure 2C:
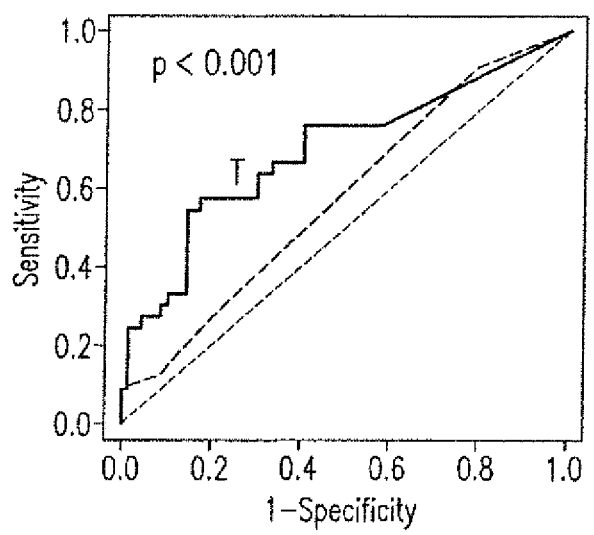

FIG. 2A-C. Genome copy variation in prostate cancer predicts relapse. (A) Histograms of genome deletion (blue) or amplification (red) of Tnone, Tslow and Tfast in 23 pairs of human chromosomes. (B) Receiver operating characteristic (ROC) curves of predicting prostate cancer relapse. The prostate cancer were separated into a group that relapsed within 5 years of prostatectomy (n=75) and a group that did not relapse (n=27). Prediction using gene deletions or amplifications unique to relapsing group generated through "leave-one-out" analysis was carried out to produce the ROC chart. The dotted line represents random prediction baseline. The broken line represents prediction generated from Gleason's grading. (C) ROC curves of predicting prostate cancer fast relapse. The prostate cancer were separated into a group that had PSADT within 4 months of prostatectomy (n=33) and a group that did not (n=69). Prediction using gene deletions or amplifications unique to fast relapsing group generated through "leave-one-out" analysis was carried out to produce the ROC chart. The dotted line represents random prediction baseline. The broken line represents prediction generated from Gleason's grading.

FIG. 3A-D. Genome copy variation in benign prostate tissues adjacent to cancer predicts prostate cancer relapse. (A) Histograms of genome deletion (blue) or amplification (red) of AT no relapse, AT relapse, AT not fast relapse, AT fast relapse in 23 pairs of human chromosomes. (B) ROC curves of AT predicting prostate cancer relapse. The AT samples were separated into a group that relapsed within 5 years of prostatectomy (n=21) and a group that did not relapse (n=28). Prediction using gene deletions or amplifications unique to relapsing group generated through "leave-one-out" analysis was carried out to produce the ROC chart. The dotted line represents random prediction baseline. (C) ROC curves of AT predicting prostate cancer fast relapse. The AT samples were separated into a group that had PSADT within 4 months of prostatectomy (n=8) and a group that did not (n=41). Prediction using gene deletions or amplifications unique to fast relapsing group generated through "leave-one-out" analysis was carried out to produce the ROC chart. The dotted line represents random prediction baseline.

FIG. 4A-D. Median size variation of CNV of blood and tumor samples predicts prostate cancer relapse and fast relapse. (A) ROC curves of CNV median size of B predicting prostate cancer relapse. The B samples were separated as described in (A). Prediction using various CNV median sizes was carried out to produce the ROC chart. The dotted line represents random prediction baseline. The optimal prediction rates for CNV median size of B model are 86% ($57/66$) sensitivity and 61% ($11/18$) specificity. (B) ROC curves of CNV median size of B predicting prostate cancer fast relapse. The B samples were separated into a group that had PSADT within 4 months of prostatectomy (n=31) and a group that did not (n=53). Prediction using various CNV median sizes was carried out to produce the ROC chart. The dotted line represents random prediction baseline. The optimal prediction rates for CNV median size of B model are 68% ($21/31$) sensitivity and 70% ($37/53$) specificity. (C) ROC curves of predicting prostate cancer relapse using median sizes of CNV from T samples. The prostate cancer were separated into a group that relapsed within 5 years of prostatectomy (n=75) and a group that did not relapse (n=27). Prediction using various CNV median sizes was carried out to produce the ROC chart. The dotted line represents random prediction baseline. The broken line represents prediction generated from Gleason's grading. The optimal prediction rates for CNV median size of T model are 71% ($53/75$) sensitivity and 89% ($24/27$) specificity. (D) ROC curves of predicting prostate cancer fast relapse using CNV median sizes from T samples. The prostate cancer were separated into a group that had PSADT within 4 months of prostatectomy (n=33) and a group that did not (n=69). Prediction using various CNV median sizes was carried out to produce the ROC chart. The dotted line represents random prediction baseline. The broken line represents prediction generated from Gleason's grading. The optimal prediction rates for CNV median size of T model are 61% ($20/33$) sensitivity and 90% ($62/69$) specificity.

FIG. 5A-D. (A.) Percent overlap of genome segment abnormalities of B, AT, and T, comparing results of study for FIG. 1 and further experiments including additional samples. (B.) Percent deletions with loss of heterozygosity. (C.) Results of quantitative PCR analysis for genes ARL17B, SCAPER, EPHA3 and ERBB4. (D) Sensitivity versus specificity.

FIG. 6A-D. (A,B) Sensitivity versus specificity in B samples. (C,D) Sensitivity versus specificity in T samples.

Figure 7A:
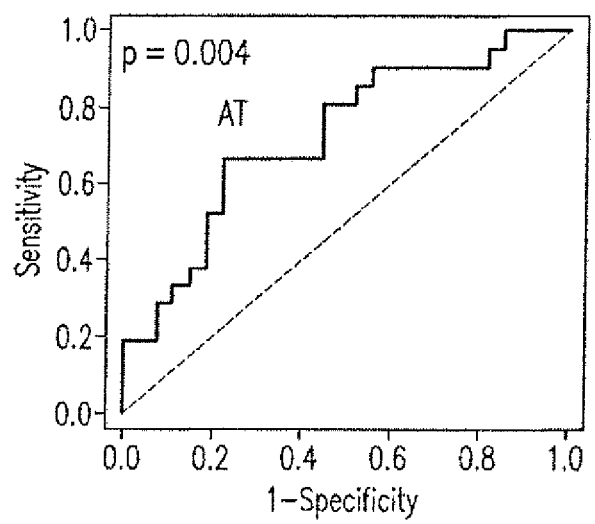
Figure 7B:
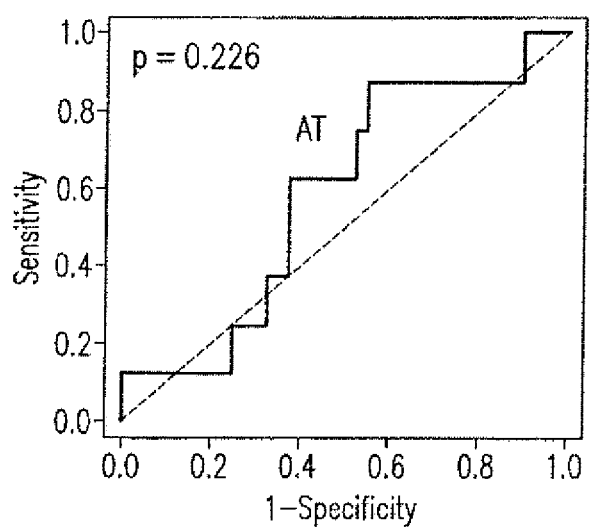
Figure 8A:
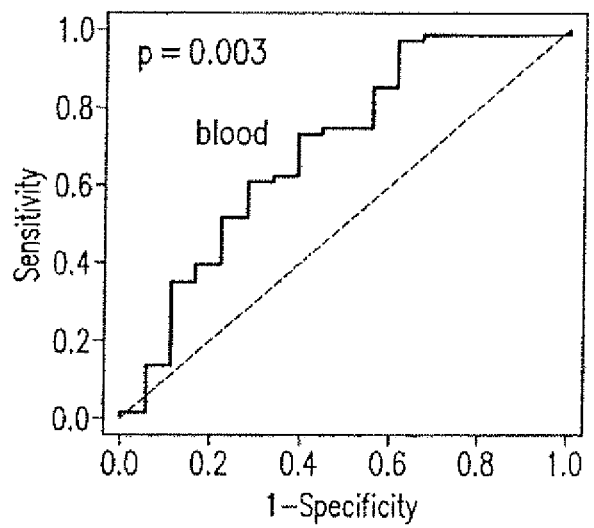
Figure 8B:
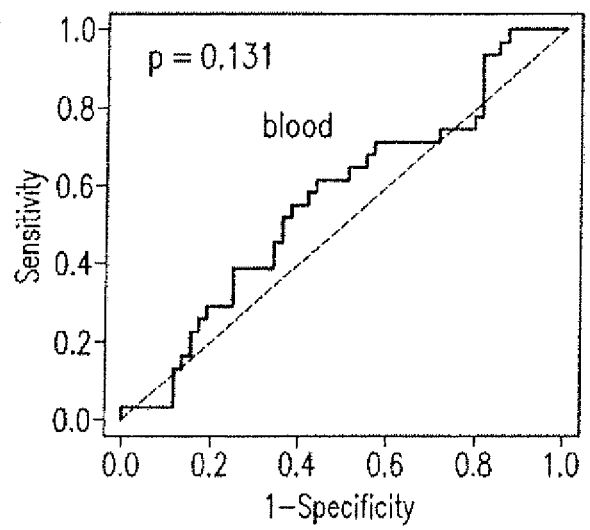
Figure 8C:
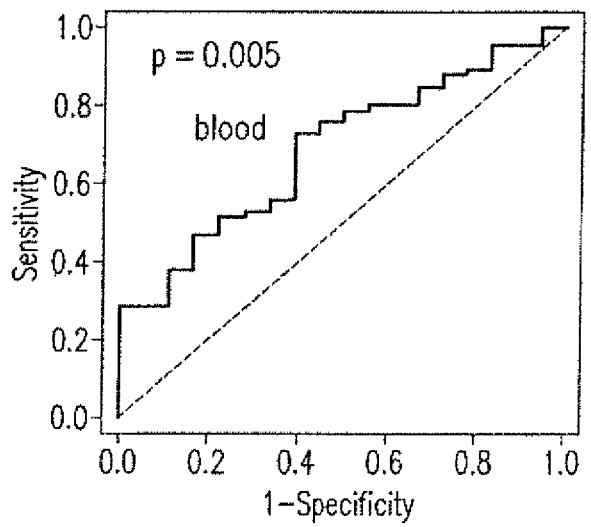
Figure 8D:
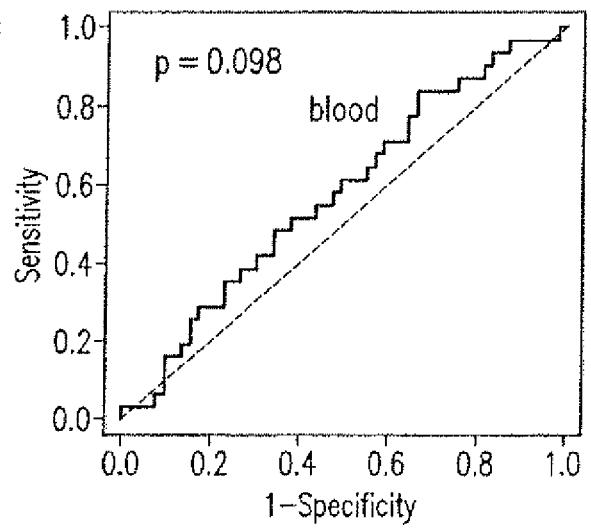
Figure 9A:
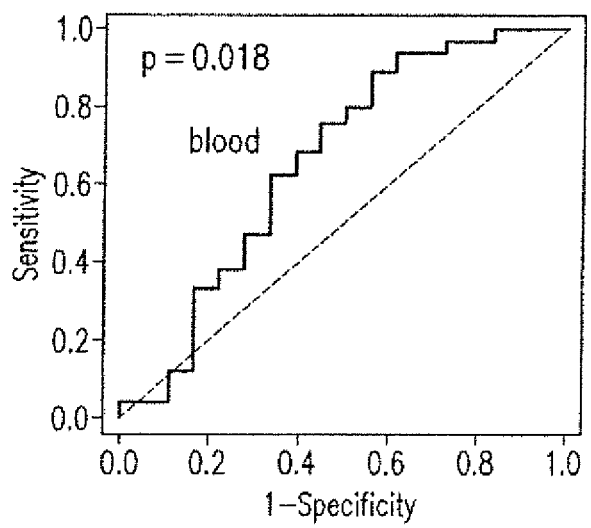
Figure 9B:
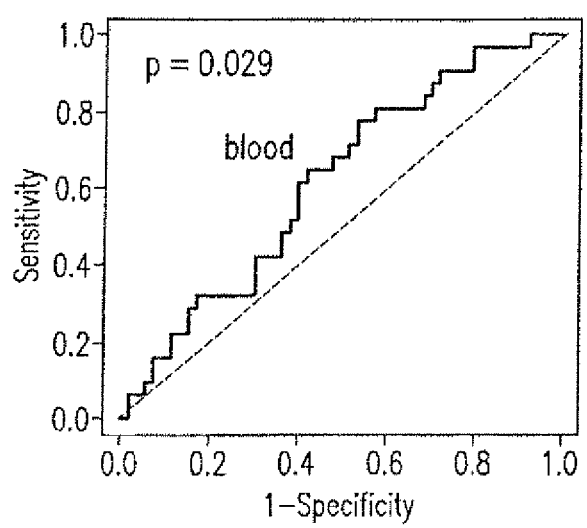
Figure 9C:
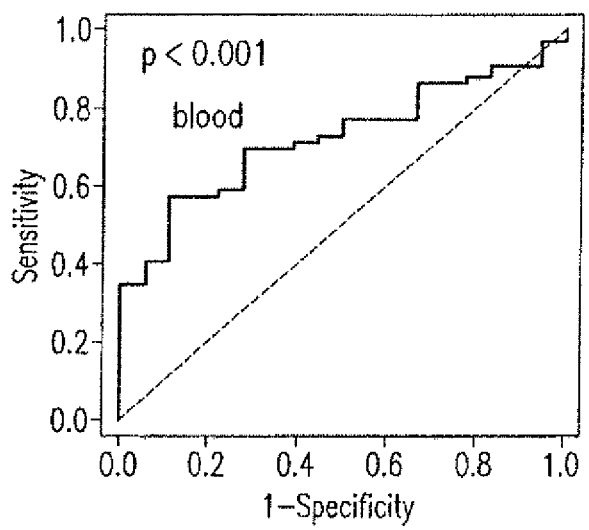
Figure 9D:
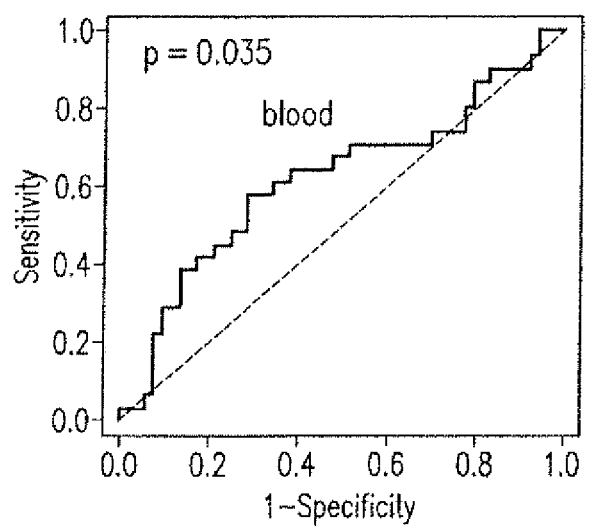
Figure 10A:
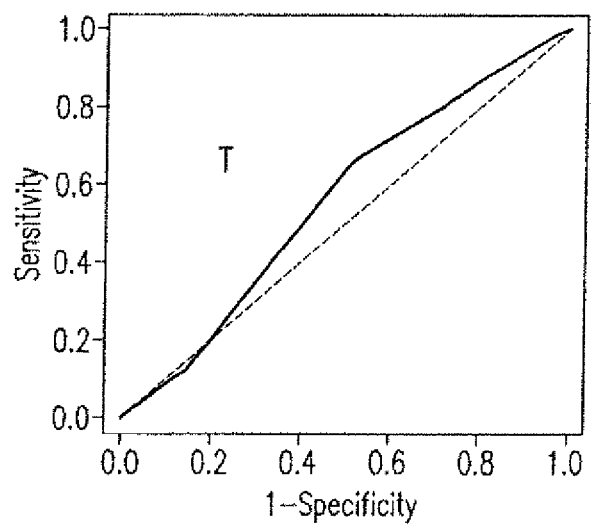
Figure 10B:
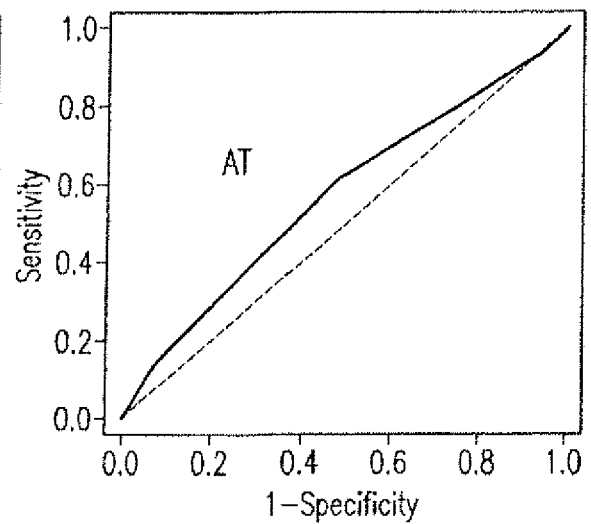
Figure 10C:
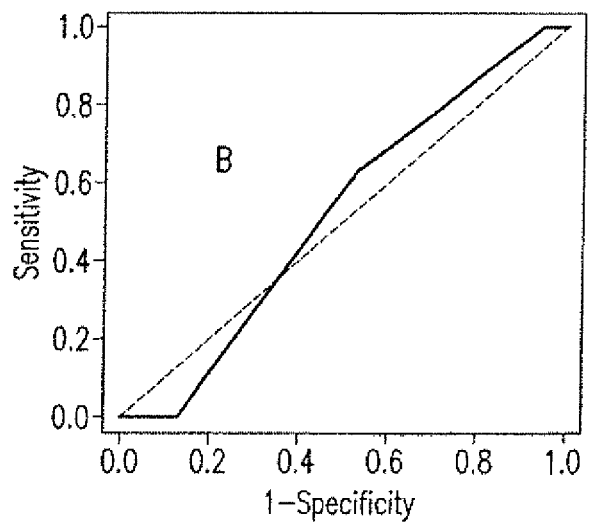
Figure 10D:
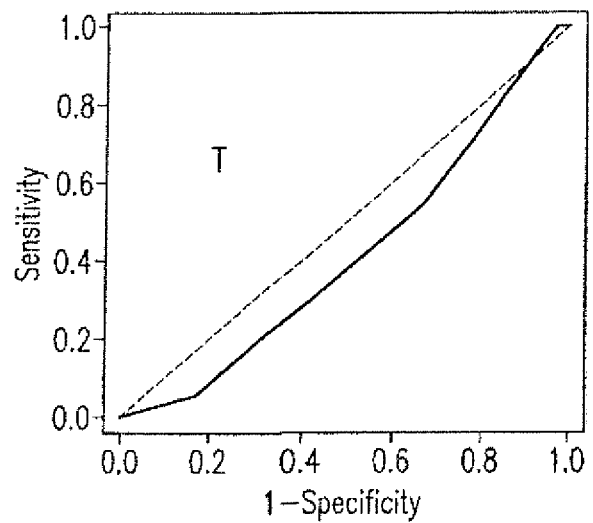
Figure 10E:
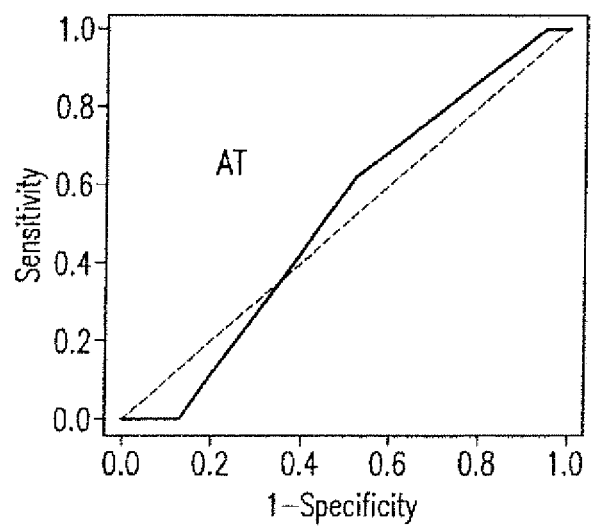
Figure 10F:
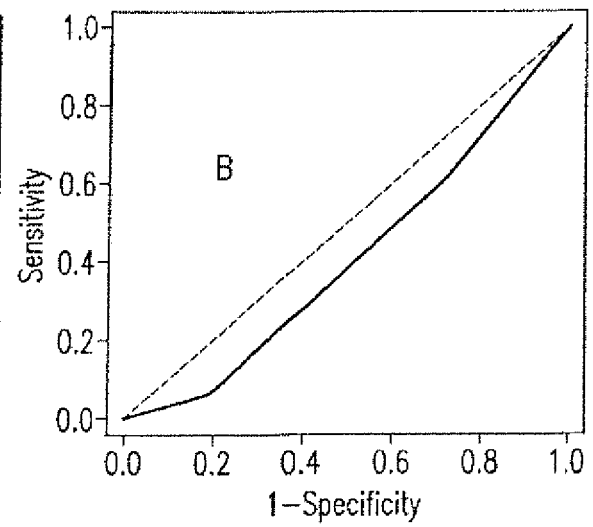

FIG. 7A-B. Sensitivity versus specificity in AT samples (A) and (B).

FIG. 8A-D. (A,B) Sensitivity versus specificity in B samples. (C,D) Sensitivity versus specificity in T samples.

FIGS. 9A-D. (A), (B), (C) and (D) Sensitivity versus specificity in B samples.

FIG. 10A-F. Sensitivity versus specificity in T samples (A,D), B samples (C,F), and AT samples (B,E).

5. DETAILED DESCRIPTION OF THE INVENTION

In certain non-limiting embodiments, the present invention provides for methods and compositions for diagnosing prostate cancer in a subject. In other non-limiting embodiments, the present invention provides for methods and compositions for determining whether a prostate cancer patient is at increased risk of suffering a relapse, or a rapid relapse, of his cancer. In other non-limiting embodiments, the present invention provides for methods and compositions for determining whether a prostate cancer patient is at decreased risk of suffering a relapse, or a rapid relapse, of his cancer (in other words, is at increased risk or has an increased likelihood of not suffering a relapse).

A "prostate cancer patient" is a subject having or who has had a carcinoma of the prostate. The use of the term "patient" does not suggest that the subject has received any treatment for the cancer, but rather that the subject has at some point come to the attention of the healthcare system. Said patient/subject, prior to or contemporaneous with the practicing of the invention, may be untreated for prostate cancer or may have received treatment, including but not limited to surgical, chemotherapeutic, antiandrogen, or radiologic treatment.

"Increased risk" means an increased likelihood that relapse will occur relative to other prostate cancer patients. In particular non-limiting embodiments, there is a statistically validated increase in the likelihood of relapse or rapid relapse relative to subjects without relapse or rapid relapse with a p value of 0.003 for relapse and <0.001 for fast relapse when using "gene specific" CNV of prostate cancer samples, 0.04 for relapse and 0.015 for fast relapse when using "gene specific" CNV of AT samples, <0.001 for relapse and 0.001 for fast relapse when using median sizes of CNV of blood samples from prostate cancer patients, <0.001 for both relapse and fast relapse when using "median sizes" CNV of prostate cancer samples, and 0.004 for relapse when using "mean sizes" of CNV of AT samples.

"Relapse," as that term is used herein, refers to a clinical course including one or more of the following: (i) where the cancer had been removed or put into remission, a recurrence of prostate cancer at the original site or occurrence at a new site, including metastatic spread; (ii) where the cancer had not been removed or put into remission, extension of the cancer and/or metastatic spread; (iii) whether or not the cancer had been treated, an advancement in the clinical grade, for example the Gleasons grade, of the cancer; and/or a prostate specific antigen ("PSA") doubling time of 15 months or longer.

By "rapid", or "relapse quickly", it is meant that relapse occurs within a period of 5 years. In certain embodiments, patients suffering a rapid relapse also manifest a PSA doubling time of 3 months or less or 4 months or less.

In particular, non-limiting embodiments, the method of the invention may be performed as follows. One or more sample may be obtained from a subject. For example, the sample may be a sample of malignant tumor (or presumptively malignant tumor, where a diagnosis has not yet been made) tissue (e.g., microdissection may be performed to achieve a tumor purity of at least about 70 percent or at least about 80 percent or greater than 80%). As another example, a sample may be tissue adjacent a malignant tumor tissue (e.g., prostate tissue that is not identified as tumor located in a prostate gland that contains tumor; in certain non-limiting embodiments the adjacent tissue is non-malignant prostate tissue located at least 3 mm from tumor tissue). As another example, a sample may be a tissue sample which is considered by a skilled artisan to appear abnormal (microscopically and/or macroscopically) and is to be tested to determine whether it is cancerous. As another example, a sample may be a blood sample that contains at least some nucleated cells (to serve as a source of DNA, e.g., whole blood or buffy coat). Multiple samples may be prepared for a single subject; for example, samples of tumor (meaning malignant) tissue, tissue adjacent tumor tissue, and blood may be prepared and the results of analysis of each may be compared.

For example, DNA may be extracted from a sample, for example using a Qiagen tissue kit or other method known in the art. Then genotyping may be performed to identify CNVs across the genome or a portion of the genome, for example, by fragmenting the DNA using restriction enzymes, ligated with adaptors, amplifying the fragments using primers that correspond to the adaptor sequences (for example, Genome wide human snp NSP/STY assay kit, Affymetrix, Calif.), optionally performing an additional fragmentation step, labeling the amplified (optionally further fragmented) DNA product, and then hybridizing the resulting labeled DNA with a plurality of test DNA molecules representative of the genome or a genome portion of interest, for example, but not limited to, as provided in an array such as Affymetrix Genome-Wide Human SNP Array 6.0, under appropriate conditions (for example as described by the array manufacturer). The results may then be interpreted to determine the number or approximate number of CNVs in the genome or portion thereof. For example, Partek Genome Suite 6.6™ or a Affymetrix Genotyping Console may be used.

In one set of non-limiting embodiments of the invention, the number of CNVs across the genome are determined. The present invention provides for a method of diagnosing a prostate cancer in a subject comprising determining the number and/or size of CNVs in a tumor sample, a sample of tissue adjacent a tumor, and/or in a blood sample, where if the number and/or size of CNVs exceeds a particular threshold, a diagnosis of prostate cancer is indicated. The present invention also provides for a method of determining that a prostate cancer patient is at increased risk for relapse or rapid relapse comprising determining the number and/or size of CNVs in a prostate tumor sample, tissue adjacent a prostate tumor, and/or blood, where if the number and/or size of CNVs exceeds a particular threshold, the subject is deemed at risk for relapse or rapid relapse.

In another set of non-limiting embodiments of the invention, CNV of one or more particular gene or chromosome or chromosome region is determined. In specific, non-limiting embodiments of the invention, genes for which CNVs may be determined may include one or more of the genes listed in Tables 2-5, where a CNV in one of the genes listed is indicative of increased risk of relapse (in Table 2 based on a prostate cancer tissue sample or in Table 4 based on tissue adjacent to prostate cancer tissue) or rapid relapse (in Table 3 based on a prostate cancer tissue sample or in Table 5 based on tissue adjacent to prostate cancer tissue). The present invention provides for a method of determining that a prostate cancer patient is at increased risk for relapse or rapid relapse comprising determining the number and/or size of CNVs of a specific gene as listed in Table 2, 3, 4 or 5 in a prostate tumor sample, tissue adjacent a prostate tumor, and/or blood, where if the number of CNVs for the gene exceeds a particular threshold, a diagnosis of prostate cancer is indicated and/or the subject is deemed at risk for relapse or rapid relapse.

For clarity of description and not by way of limitation, the detailed description of the invention is divided into the following subsections:
(i) Diagnosis based on CNV number and size;
(ii) Assessment of risk based on CNV number and size;
(iii) Assessment of risk based on CNV of particular genes; and
(iv) Kits.

5.1 Diagnosis Based on CNV Number and Size

In non-limiting embodiments of the invention, the number of CNVs across the genome are determined. CNV may be detected using methodology known in the art, including the hybridization to gene arrays and the analysis of the results of hybridization using software that determines copy number variation, including, but not limited to, the method using Affymetrix products described above. In non-limiting embodiments of the invention, the entire genome or a portion thereof may be analyzed; for example, in a subset of non-limiting embodiments, the chromosome region for which CNVs is determined is one or more of 8p, 13p, 16p, 17p, and/or 8q.

In certain non-limiting embodiments, the present invention provides for a method of diagnosing a prostate cancer in a subject comprising determining the number and/or size of CNVs in DNA from a tumor sample, a sample of tissue adjacent a tumor, and/or in a blood sample, where if the number and/or size of CNVs exceeds a particular threshold, a diagnosis of prostate cancer is indicated.

In a tissue, CNV in at least about 90 loci, each locus being at least 10 kb in length, is consistent with a diagnosis of prostate cancer rather than benign tissue. Accordingly, the present invention provides for a method of diagnosing a prostate cancer in a subject comprising determining the number and size of CNVs in DNA from a tumor or prostate tissue sample, where if the number of CNVs exceeds 90 loci, each locus being at least 10 kb in length, a diagnosis of prostate cancer is indicated.

In a blood sample, CNV in at least 4 loci, each locus being at least 10 kb in length, is consistent with a diagnosis of prostate cancer rather than no malignancy. Accordingly, the present invention provides for a method of diagnosing a prostate cancer in a subject, where said subject is a male having one or more of the following clinical findings: increased serum prostate specific antigen, enlarged prostate on physical exam, difficulty urinating and/or urinary retention, comprising determining the number and/or size of CNVs in DNA from a blood sample from the subject, where if the number of CNVs exceeds 4 loci, each locus being at least 10 kb in length, a diagnosis of prostate cancer is indicated.

In a tissue or a blood sample, a deletion of at least 3 megabases in one or more of the following chromosome regions is consistent with a diagnosis of prostate cancer rather than benign tissue: 8p, 13p, 16q, and/or 17p. Deletions in these regions can be deduced from CNV information. Accordingly, the present invention provides for a method of diagnosing a prostate cancer in a subject comprising determining the presence of deletions in one or more of chromosome regions 8p, 13p, 16q, and/or 17p in DNA from a prostate tissue or a blood sample from the subject, where if there is a deletion of at least 3 megabases in one or more of these regions, a diagnosis of prostate cancer is indicated.

In a tissue or a blood sample, an amplification of a locus in chromosome region 8q and/or X is consistent with a diagnosis of prostate cancer rather than benign tissue. Amplification in these regions can be deduced using CNV information. Accordingly, the present invention provides for a method of diagnosing a prostate cancer in a subject comprising determining the presence of amplification in one or more of chromosome regions 8q and X in DNA from a prostate tissue or a blood sample from the subject, where if there is amplification of a locus in one or more of these regions, a diagnosis of prostate cancer is indicated.

If a diagnosis of prostate cancer is indicated, a healthcare provider may optionally take the further step of recommending and/or performing a further diagnostic test, such as a biopsy or prostate ultrasound, and/or recommending and/or performing a therapeutic procedure, for example but not limited to surgical excision, radiotherapy, and/or chemotherapy.

5.2 Assessment of Risk Based on CNV Size

In non-limiting embodiments of the invention, CNVs across the genome are determined. CNV may be detected using methodology known in the art, including the hybridization to gene arrays and the analysis of the results of hybridization using software that determines copy number variation, including, but not limited to, the method using Affymetrix products described above. In non-limiting embodiments of the invention, the entire genome or a portion thereof may be analyzed; for example, in a subset of non-limiting embodiments, the chromosome region for which CNVs is determined is one or more of 8p, 13p, 16p, 17p, and/or 8q.

In non-limiting embodiments, the present invention provides for a method of determining that a prostate cancer patient is at decreased risk for relapse or rapid relapse comprising determining the size of CNVs in a prostate tumor sample, tissue adjacent a prostate tumor, and/or blood, where if the size of CNVs is less than a particular threshold, the patient is deemed to be at decreased risk for relapse or rapid relapse.

In non-limiting embodiments, the present invention provides for a method of determining that a prostate cancer patient is at decreased risk for relapse or rapid relapse comprising determining the mean and/or median size of CNVs in a prostate tumor sample, tissue adjacent a prostate tumor, and/or blood, where if the mean or median size of CNVs is less than a particular threshold, the patient is deemed to be at decreased risk for relapse or rapid relapse.

In non-limiting embodiments, the present invention may utilize the average (mean) size of CNV to assess the likelihood that a prostate cancer will relapse. CNV size may be determined using the same genotyping analysis techniques as described above and as are known in the art. In particular non-limiting embodiments of the invention, using the Partek software described above, segments with copy number change may be obtained (including amplification and deletions), and those with the criteria p<0.001, length >2000 bp and >10 markers, may be selected and then the mean length of the CNVs thus identified may be determined.

In certain non-limiting embodiments, the present invention provides for a method of determining that a prostate cancer patient is at decreased risk for relapse comprising determining the size of CNVs in DNA from a blood sample from the patient, where if the average (i.e., mean) size of CNVs is 40 kb or less or 33 kb or less, the patient is deemed to be at decreased risk for relapse.

In certain non-limiting embodiments, the present invention provides for a method of determining that a prostate cancer patient is at decreased risk for relapse comprising determining the size of CNVs in DNA from a sample of tissue adjacent a prostate cancer from the patient, where if the mean size of CNVs is 95 kb or less or 81.1 kb or less, the patient is deemed to be at decreased risk for relapse.

In certain non-limiting embodiments, the present invention provides for a method of determining that a prostate cancer patient is at decreased risk for relapse comprising determining the size of CNVs in DNA from a sample of prostate cancer tissue from the patient, where if the mean size of CNVs is 385 kb or less or 105 kb or less, the patient is deemed to be at decreased risk for relapse.

In further non-limiting embodiments, the present invention provides for a method of determining that a prostate cancer patient is at increased risk for relapse or rapid relapse comprising determining the mean or median size of CNVs in a prostate tumor sample, tissue adjacent a prostate tumor, and/or blood, where if the mean or median size of CNVs exceeds a particular threshold, the patient is deemed to be at increased risk for relapse or rapid relapse.

In one non-limiting embodiment, in a blood sample from a prostate cancer patient, an average (mean) CNV size of 70 kb or more, is consistent with a likelihood that the prostate cancer will relapse. Accordingly, the present invention provides for a method of determining that a prostate cancer patient is at increased risk for relapse comprising determining the mean size of CNVs in DNA from a blood sample from the patient, where if the average (i.e., mean) size of CNVs is 70 kb or more, the patient is deemed to be at increased risk for relapse.

In other non-limiting embodiments, the present invention provides for a method of determining that a prostate cancer patient is at increased risk for relapse comprising determining the mean size of CNVs in DNA from a sample of tissue adjacent to prostate cancer from the patient, where if the mean size of CNVs is 246 kb or more, the patient is deemed to be at increased risk for relapse.

In other non-limiting embodiments, the present invention provides for a method of determining that a prostate cancer patient is at increased risk for relapse comprising determining the mean size of CNVs in DNA from a sample of prostate cancer tissue from the patient, where if the mean size of CNVs is 817 kb or more, the patient is deemed to be at increased risk for relapse.

In other non-limiting embodiments, the present invention provides for a method of determining that a prostate cancer patient is at increased risk for rapid relapse comprising determining the mean size of CNVs in DNA from a sample of prostate cancer tissue from the patient, where if the mean size of CNVs is 1060 kb or more, the patient is deemed to be at increased risk for rapid relapse.

In further non-limiting embodiments, the present invention may utilize the median size of CNV to assess the likelihood that a prostate cancer will relapse. CNV size may be determined using the same genotyping analysis techniques as described above and as are known in the art. In particular non-limiting embodiments of the invention, using the Partek software described above, segments with copy number change may be obtained (including amplification and deletions), and those with the criteria p<0.001, length >2000 bp and >10 markers, may be selected and then the median length of the CNVs thus identified may be determined.

In one non-limiting embodiment, in a blood sample from a prostate cancer patient, a median CNV size of about 17 kb or less is consistent with a likelihood that the prostate cancer will not relapse. Accordingly, the present invention provides for a method of determining that a prostate cancer patient is at decreased risk for relapse comprising determining the median size of CNVs in a blood sample, where if the median size of CNVs is 17 kb or less, the subject is deemed to be at decreased risk for relapse.

In certain non-limiting embodiments, the present invention provides for a method of determining that a prostate cancer patient is at decreased risk for relapse comprising determining the median size of CNVs in DNA from a sample of tissue adjacent to a prostate cancer from the patient, where if the median size of CNVs is 16 kb or less, the patient is deemed to be at decreased risk for relapse.

In certain non-limiting embodiments, the present invention provides for a method of determining that a prostate cancer patient is at decreased risk for relapse comprising determining the median size of CNVs in DNA from a sample of prostate cancer tissue from the patient, where if the median size of CNVs is 185 kb or less, the patient is deemed to be at decreased risk for relapse.

In certain other non-limiting embodiments, the present invention provides for a method of determining that a prostate cancer patient is at increased risk for relapse comprising determining the median size of CNVs in DNA from a blood sample from the patient, where if the median size of CNVs is 23 kb or more, the patient is deemed to be at increased risk for relapse.

In other non-limiting embodiments, the present invention provides for a method of determining that a prostate cancer patient is at increased risk for relapse comprising determining the median size of CNVs in DNA from a sample of tissue adjacent to prostate cancer from the patient, where if the median size of CNVs is 17384 or more or 18 kb or more, the patient is deemed to be at increased risk for relapse.

In other non-limiting embodiments, the present invention provides for a method of determining that a prostate cancer patient is at increased risk for rapid relapse comprising determining the median size of CNVs in DNA from a sample of tissue adjacent to prostate cancer from the patient, where if the median size of CNVs is 32651 bp or more, or 33 kb or more, the patient is deemed to be at increased risk for rapid relapse.

In other non-limiting embodiments, the present invention provides for a method of determining that a prostate cancer patient is at increased risk for relapse comprising determining the median size of CNVs in DNA from a sample of prostate cancer tissue from the patient, where if the median size of CNVs is 647 kb or more, the patient is deemed to be at increased risk for relapse.

If is determined that the patient is at increased risk for relapse or rapid relapse, a healthcare provider may optionally take the further step of recommending and/or performing frequent monitoring of the patient for recurrence (e.g., a PSA test or imaging (e.g. ultrasound, CT scan, MRI or PET scan)) and/or recommending and/or performing a therapeutic procedure, for example but not limited to surgical excision, radiotherapy, and/or chemotherapy.

5.3 Assessment of Risk by Cnv of Particular Genes

In non-limiting embodiments of the invention, the number of CNVs across the genome are determined. CNV may be detected using methodology known in the art, including the hybridization to gene arrays and the analysis of the results of hybridization using software that determines copy number variation, including, but not limited to, the method using Affymetrix products described above. In non-limiting embodiments of the invention, the entire genome or a portion thereof may be analyzed; for example, in a subset of non-limiting embodiments, the chromosome region for which CNVs is determined is one or more of 8p, 13p, 16p, 17p, and/or 8q. Further, the CNV of particular genes may be determined and utilized as set forth in this section.

In further non-limiting embodiments, a CNV in a gene in a prostate cancer tissue from a subject, where the gene is listed in Table 2, indicates that the subject is likely to relapse. In further non-limiting embodiments, a CNV in a gene in a prostate cancer tissue from a subject, where the gene is listed in Table 3, indicates that the subject is likely to experience rapid relapse.

In further non-limiting embodiments, a CNV in a gene in a tissue adjacent to prostate cancer tissue from a subject, where the gene is listed in Table 4, indicates that the subject is likely to relapse. In further non-limiting embodiments, a CNV in a gene in a tissue adjacent a prostate cancer tissue from a subject, where the gene is listed in Table 5, indicates that the subject is likely to experience rapid relapse.

In on set of non-limiting embodiments, the present invention provides for a gene-based prediction in any one or more of four scenarios: relapse or fast relapse prediction in tumor (T) or tissues adjacent to tumor (AT). According to this set of embodiments, the methods for these four scenarios are the same except for the gene lists used are different. In particular, for each scenario, two gene lists are utilized: one list for genes amplified (list "a") and one list for genes deleted (list "b"). Using Partek, the copy number change status of each gene for each sample could be determined; the status could be amplified, deleted or unchanged.

For a given T sample, the number of genes in list "a" that are amplified and the number of genes in list "b" that are deleted are counted, and the number of amplified genes in list "a" may be designated "a" and the number of deleted genes in list "b" may be designated "b". Genes in list "a" for relapse include HECTD1, MIR1827, UBXN8, SMAP1, C6orf147, DDX43, SLC17A5, LRRIQ4, LRRC31, SAMD7, LOC100128164, SEC62, GPR160, and PHC3. Genes in list "b" for relapse include SLC7A5, CASA, BANP, ZFPM1, ZC3H18, IL17C, CYBA, MVD, MGC23284, SNAI3, RNF166, GALNS, TRAPPC2L, CBFA2T3, ACSF3, C16orf81, CDH15, ANKRD11, SPG7, RPL13, SNORD68, CDK10, SPATA2L, C16orf7, ZNF276, SYT16, GRIN2B, BCAT1, OVCH1, BEYLA, GPR125, and GBA3. If the number (a+b) is larger than a pre-set cutoff C (i.e. a+b>C), the corresponding sample is assigned the risk designation relapse or fast relapse, depending upon the list that is drawn from. In a particular non-limiting embodiment, in a+b>C, C=0 meaning that the threshold is 0 so that if a or b is a non-zero number, there is an increased risk of relapse.

In non-limiting embodiments, the invention provides for a method of determining that a prostate cancer patient is at increased risk for relapse comprising determining whether a gene is amplified or whether a gene is deleted in DNA from a sample of prostate cancer tissue from the patient, wherein (a) if one or more gene is amplified from the group consisting of HECTD1, MIR1827, UBXN8, SMAP1, C6orf147, DDX43, SLC17A5, LRRIQ4, LRRC31, SAMD7, LOC100128164, SEC62, GPR160, and PHC3 and/or (b) if one or more gene is deleted from the group consisting of SLC7A5, CASA, BANP, ZFPM1, ZC3H18, IL17C, CYBA, MVD, MGC23284, SNAI3, RNF166, GALNS, TRAPPC2L, CBFA2T3, ACSF3, C16orf81, CDH15, ANKRD11, SPG7, RPL13, SNORD68, CDK10, SPATA2L, C16orf7, ZNF276, SYT16, GRIN2B, BCAT1, OVCH1, BEYLA, GPR125, and GBA3, then the patient is deemed to be at increased risk for relapse.

In other non-limiting embodiments, genes in list "a" for rapid relapse include BRMS1L, KCNMB4, MIR548A1, ORC3L, SDAD1, CXCL9, ART3, CXCL10, CXCL11 Genes in list "b" for rapid relapse include GALNTL1, FLJ44817, KIAA0247, LOC100289511, SFRS5, SLC10A1, SLC8A3, SNORD56B, PABPC3, MTMR6, ATP8A2, NAV2, ZC3H12C, FDX1, ARHGAP20, C11orf88, LAYN, and CD28. In a particular non-limiting embodiment, in a+b>C, C=0, meaning that the threshold is 0 so that if a or b is a non-zero number, there is an increased risk of rapid relapse.

In non-limiting embodiments, the invention provides for a method of determining that a prostate cancer patient is at increased risk for relapse comprising determining whether a gene is amplified or whether a gene is deleted in DNA from a sample of prostate cancer tissue from the patient, wherein (a) if one or more gene is amplified from the group consisting of BRMS1L, KCNMB4, MIR548A1, ORC3L, SDAD1, CXCL9, ART3, CXCL10, and CXCL11 and/or (b)

if one or more gene is deleted from the group consisting of GALNTL1, FLJ44817, KIAA0247, LOC100289511, SFRS5, SLC10A1, SLC8A3, SNORD56B, PABPC3, MTMR6, ATP8A2, NAV2, ZC3H12C, FDX1, ARHGAP20, C11orf88, LAYN, CD28, then the patient is deemed to be at increased risk for rapid relapse.

In related embodiments applied to AT, two gene lists are utilized: one list for genes amplified (list "c") and one list for genes deleted (list "d"). Using Partek, the copy number change status of each gene for each sample could be determined; the status could be amplified, deleted or unchanged. For a given T sample, the number of genes in list "c" that are amplified and the number of genes in list "d" that are deleted are counted, and the number of amplified genes in list "c" may be designated "c" and the number of deleted genes in list "d" may be designated "d". Genes in list "c" for relapse include DZIP1, ZHX2, DERL1, WDR67, COL22A1, BHLHE40 and, in a non-limiting embodiment, there is no gene in list "d". In a particular non-limiting embodiment, in a+b>C, C=0 meaning that the threshold is 0 so that if c or d is a non-zero number, there is a likelihood of relapse. In other non-limiting embodiments applied to AT, genes in list "c" for rapid relapse include MAGEL2, NDN, RSU1, ADCY2, UBE2E1 and genes in list "d" for rapid relapse based on AT include RPL23AP82, RABL2B, CA10, C13orf36, SMAD9, ALG5, RETNLB, TRAT1, GUCA1C, MORC1. In a particular non-limiting embodiment, in a+b>C, C=1 meaning that the threshold is I so that if the sum of c and d is greater than one, there is a likelihood of rapid relapse.

In non-limiting embodiments, the invention provides for a method of determining that a prostate cancer patient is at increased risk for relapse comprising determining whether a gene is amplified in DNA from a sample of tissue adjacent to prostate cancer tissue from the patient, wherein if one or more genes is amplified from the group consisting of DZIP1, ZHX2, DERL1, WDR67, COL22A1, BHLHE40 then the patient is deemed to be at increased risk for relapse.

In non-limiting embodiments, the invention provides for a method of determining that a prostate cancer patient is at increased risk for rapid relapse comprising determining whether a gene is amplified or whether a gene is deleted in DNA from a sample of tissue adjacent to prostate cancer tissue from the patient, wherein (a) if one or more genes is amplified from the group consisting of MAGEL2, NDN, RSU1, ADCY2, UBE2E1 and/or (b) one or more genes is deleted from the group consisting of RPL23AP82, RABL2B, CA10, C13orf36, SMAD9, ALG5, RETNLB, TRAT1, GUCA1C, MORC1, wherein the total number of genes amplified from the group listed in (a) and/or deleted from the group listed in (b) is greater than or equal to 2, then the patient is deemed to be at increased risk for rapid relapse.

If is determined that the patient is at increased risk for relapse or rapid relapse, a healthcare provider may optionally take the further step of recommending and/or performing frequent monitoring of the patient for recurrence (e.g., a PSA test or imaging (e.g. ultrasound, CT scan, MRI or PET scan), digital rectal exam) and/or recommending and/or performing a therapeutic procedure, for example but not limited to surgical excision, radiotherapy, and/or chemotherapy.

If is determined that the patient is at decreased risk for relapse, a healthcare provider may optionally take the further step of recommending that the patient not seek imminent further treatment and/or performing frequent monitoring of the patient for recurrence (e.g., a PSA test or imaging (e.g. ultrasound, CT scan, MRI or PET scan), digital rectal exam) ("watchful waiting").

5.4 Kits

In non-limiting embodiments, the present invention provides for kits that may be used to practice the invention. Such kits may include an array comprising nucleic acid representing at least 3, at least 4, at least 5, at least 6, at least 7, at least 8, at least 9, at least 10, at least 11, at least 12, at least 15, at least 20, at least 30, at least 40, or at least 50 of the following genes, where the genes listed below constitute up to 50 percent or up to 60 percent or up to 70 percent or up to 80 percent or up to 90 percent or up to 95 percent or up to 100 percent of the total set of genes represented in the array:

genes listed in Table 2;
genes listed in Table 3;
genes listed in Table 4;
genes listed in Table 5;

HECTD1, MIR1827, UBXN8, SMAP1, C6orf147, DDX43, SLC17A5, LRRIQ4, LRRC31, SAMD7, LOC100128164, SEC62, GPR160, PHC3, SLC7A5, CASA, BANP, ZFPM1, ZC3H18, IL17C, CYBA, MVD, MGC23284, SNAI3, RNF166, GALNS, TRAPPC2L, CBFA2T3, ACSF3, C16orf81, CDH15, ANKRD11, SPG7, RPL13, SNORD68, CDK10, SPATA2L, C16orf7, ZNF276, SYT16, GRIN2B, BCAT1, OVCH1, BEYLA, GPR125, GBA3, BRMS1L, KCNMB4, MIR548A1, ORC3L, SDAD1, CXCL9, ART3, CXCL10, CXCL11, GALNTL1, FLJ44817, KIAA0247, LOC100289511, SFRS5, SLC10A1, SLC8A3, SNORD56B, PABPC3, MTMR6, ATP8A2, NAV2, ZC3H12C, FDX1, ARHGAP20, C11orf88, LAYN, CD28 DZIP1, ZHX2, DERL1, WDR67, COL22A1, BHLHE40, MAGEL2, NDN, RSU1, ADCY2, UBE2E1, RPL23AP82, RABL2B, CA10, C13orf36, SMAD9, ALG5, RETNLB, TRAT1, GUCA1C, and MORC1.

For example, but not by way of limitation, an array may comprise sets of genes as listed above for lists "a", "b", "c" and/or "d".

Such kits may optionally comprise software, or internet access to software, in electronically readable form, that determines the number and size of CNVs in the genes represented in the array, and optionally software, or internet access to software, in electronically readable form, that determines whether CNVs in a DNA sample exceed or fall below a threshold set forth herein that indicates an increased risk of relapse or an increased risk of rapid relapse of prostate cancer.

6. EXAMPLE: GENOME ABNORMALITIES PRECEDE PROSTATE CANCER AND PREDICT CLINICAL RELAPSE 6.1 Materials and Methods Tissue Processing, DNA Extraction, Amplicon Generation, Labeling, Hybridization, Washing and Scanning of SNP 6.0 Chips.

Prostate cancer samples were obtained from the University of Pittsburgh Medical Center Tissue Bank, Pittsburgh, Pa. These samples were collected from 1998 to 2009, To make the analysis balance, samples of short prostate specific antigen doubling time ("PSADT") (<4 months), long PSADT (>15 months), and no relapse (cancer free for >5 years after radical prostatectomy) each were made to constitute approximately one third of the total number. Whenever possible, nonrelapse samples were chosen to match pathological stages and Gleason grades of relapse samples.

A total of 214 samples were from whites, whereas 5 samples were from African Americans and 19 samples were from patients with an unknown race. The patients whom these samples were obtained from either experienced relapse or had no relapse for at least 5 years, based on chemical (serum PSA) and radiological evidence. Frozen tissues were used for blood, prostate cancer, and benign prostate tissue adjacent to cancer. Clinical follow-up was conducted by office examination record, blood PSA survey, and radiographical follow-up. These follow-up visits were performed for up to a 10-year period after the patient underwent a radical prostatectomy. The protocol was approved by the Institutional Review Board. For prostate cancer, microdissection was performed to achieve tumor purity >80%. For benign prostate tissues adjacent to cancer, benign tissues away from prostate cancer (at least 3 mm) were microdissected. Whenever available, whole blood or buffy coat from the same patients was used as a normal control. PC3, DU145, and LNCaP cells were obtained from American Type Culture Collection Inc, (Manassas, Va.) in 2000, 2001, and 2007, respectively. The genomes of these cell lines were tested for short tandem repeat DNA profiling on eight different loci (CSF1PO, D13S317, D16S539, D5S818, D7S820, THO1, TPDX, and vWA) of the genomes by PCR using the following sets of primers:

```
                                         (SEQ ID NO: 1)
CSF1PO, 5'-AACCTGAGTCTGCCAAGGACTAGC-3'
and
                                         (SEQ ID NO: 2)
5'-TTCCACACACCACTGGCCATCTTC-3';

(SEQ ID NO: 3)
D13S317, 5'-ACAGAAGTCTGGGATGTGGA-3'
and
                                         (SEQ ID NO: 4)
5'-GCCCAAAAAGACAGACAGAA-3';

(SEQ ID NO: 5)
D16S539, 5'-GATCCCAAGCTCTTCCTCTT-3'
and
                                         (SEQ ID NO: 6)
5-ACGTTTGTGTGTGCATCTGT-3';

(SEQ ID NO: 7)
D5S818, 5'-GGGTGATTTTCCTCTTTGGT-3'
and
                                         (SEQ ID NO: 8)
5'-TGATTCCAATCATAGCCACA-3';

(SEQ ID NO: 9)
D7S820, 5'-TGTCATAGTTTAGAACGAACTAACG-3'
and
                                         (SEQ ID NO: 10)
5'-CTGAGGTATCAAAAACTCAGAGG-3';

(SEQ ID NO: 11)
TH01, 5'-GTGGGCTGAAAAGCTCCCGATTAT-3'
and
                                         (SEQ ID NO: 12)
5'-ATTCAAAGGGTATCTGGGCTCTGG-3';

(SEQ ID NO: 13)
TPOX, 5'-CTGGCACAGAACAGGCACTTAGG-3'
and
                                         (SEQ ID NO: 14)
5'-GGAGGAACTGGGAACCACACAGGT-3';
and (SEQ ID NO: 15)
vWA, 5'-CCCTAGTGGATGATAAGAATAATCAGTATG-3'
and
                                         (SEQ ID N): 16)
5'-GGACAGATGATAAATACATAGGATGGATGG-3'.
```

These cell lines were authenticated because the short tandem repeat profiles of the cell lines have a perfect match with those published by American Type Culture Collection Inc. DNA was then extracted using a Qiagen tissue kit (Qiagen, Valencia, Calif.). Detailed case information is shown in Tables 1A-D. Genome DNA (500 ng), was digested with StyI and Nsp1 for 2 hours at 37° C. The digested DNA was purified and ligated with primer/adaptors at 16° C. for 12 to 16 hours. Amplicons were generated by performing PCR using primers provided by the manufacturer (Affymetrix, Santa Clara, Calif.) on the ligation products using the following program: 94° C. for 3 minutes and then 35 cycles of 94° C. for 30 seconds, 60° C. for 45 seconds, and 65° C. for 1 minute. This was followed by extension at 68° C. for 7 minutes. The PCR products were then purified and digested with DNaseI for 35 minutes at 37° C. to fragment the amplified DNA. The fragmented DNA was then labeled with biotinylated nucleotide through terminal deoxynucleotide transferase for 4 hours at 37° C. Fragmented DNA, 250 μg, was hybridized with a pre-equilibrated Affymetrix SNP 6.0 chip at 50° C. for 18 hours. Procedures of washing and scanning of SNP 6.0 chips followed the manuals provided by Affymetrix.

SYBR-Green Real Time Quantitation PCR:

LightCycler FastStart DNA Master SYBR-Green I kit was used for real time PCR amplification. The reaction was carried out in a MasterCycler Realplex™ (Eppendorf, Hauppauge, N.Y.). A quantitation standard curve of normal male DNA from 50,000 to 500,000 copies of genome was generated using known amounts of template copies. Twenty nanograms of genomic DNA were used for all of the experimental and control samples. Taq DNA polymerase was activated with a 2 min pre-incubation step at 94° C. Amplification of the following primers was performed:

```
ARL17B (ACTGTCATAGCAGTGCTGAGG(SEQ ID NO: 17)/
ACTTACCTACTGTAGGGACGG SEQ ID NO: 18),

SCAPER (AGGAAGGCCTATTCGTTCTCG SEQ ID NO: 19/
GAACAGTATGGGAGGAGTTCG(SEQ ID NO: 20),

WWOX (GCCAGTTGATGTGACAACTGC(SEQ ID NO: 21)/
CAGCTGAGAGTGGTTTCTTTGC(SEQ ID NO: 22)),

EPHA3 (ATCAGGACTTACCAGGTGTGC(SEQ ID NO: 23)/
ACCGTGTCTGGAAACATAGCC(SEQ ID NO: 24)),
and ERBB4 (AGTGGCCTGTCCTTGCTTATC(SEQ ID NO: 25)/
CAGAGCAACAATTCTGACCGG(SEQ ID NO: 26))
``` with 35 cycles of the following program: 94° C. for 30 s, 62° C. for 30 s, and 68° C. for 3 min. Realplex™ data software was used to quantify and to fit the data with a standard curve. A separate β-actin (TCTTTGCACTTTCTGCATGTCCCC (SEQ ID NO: 27) /GTCCATCACGATGCCAGTGGTAC (SEQ ID NO:28)) DNA quantification was also performed as an internal control for each analysis.

Statistical Analysis:

Two hundred forty-one cell files were analyzed with the Genotyping console 4.0 from Affymetrix, Inc. for quality control analysis. Samples with QC call above 80% and QC contrast ratio above 0.4 were admitted into the analysis. To analyze CNV, cell files were imported into Partek Genome-Suite 6.6 to generate copy number from raw intensity. To plot the histograms, GC adjust was performed. Deletion or amplification of genomes were analyzed by first limiting to the regions with p-value less than 0.05/total number of regions detected, i.e. family-wise error rate (FWER) is controlled using Bonferroni's correction (10). The selected regions were subsequently filtered by limiting to the regions with at least 100 markers and 10 kb. The regions were then mapped to known genes. For a subset of the sample (i.e. tumor or relapse with rapid progression), the frequencies of amplification/deletion are calculated on the gene level. The frequencies were plotted to the genome corresponding to the gene locations.

Prediction Analysis and ROC Curve:

The following prediction analysis for the comparison of (1) non-relapse versus fast-relapse+slow-relapse); (2) non-relapse+slow-relapse versus fast-relapse was performed. A test sample was first left out from prediction model construction. The remaining samples were used as the training set. Loci with more than r % amplification or r % deletion in the case group but none locus aberration in the control group were selected as predictive loci. To predict the left-out test sample, the percentage of locus aberration (amplification or deletion) among the identified predictive loci was calculated. The test sample was predicted as a case if the percent of aberration is greater than p % threshold, and control otherwise. The "leave-one-out" cross-validation was repeated until each sample was left out and predicted. In this prediction scheme, r is a parameter that determines the number of predictive loci used in the model. For a given r, the threshold p % was varied to locus rate an ROC curve with sensitivity/specificity trade-off. We selected r that produced the best "area under curve" (AUC)(11). To report the best sensitivity and specificity trade-off and overall accuracy rate, we chose the threshold p % such that the Youden index (sensitivity+specificity−1) is maximized. This criterion gave equal importance to sensitivity and specificity. To further evaluate whether the prediction result is better than obtained by random, AUC was used as a test statistics, and permutation analysis was performed to assess the statistical significance. Specifically, class labels (case and control) were randomly shuffled and AUC calculation was performed. Such permutations were repeated for 1000 times to generate the null distribution. The p-value was calculated as the percentage that the 1000 null AUCs from permutation are greater than the observed AUC. The genes that are overlapped with the loci used in the test and the frequency of utilization are listed in Tables 2-5. For Gleason score prediction, the ROC curve was generated by varying Gleason score threshold. AUC and its associated p-value were similarly calculated. For CNV size prediction, CNV was limited to >2 kb, p<0.001 and >10 markers. The ROC curve was generated by varying sizes of CNV threshold. AUC and its associated p-value were similarly calculated.

Prediction Analysis for Blood Versus Tumor:

To predict blood versus tumor, the total number of aberrations in each sample was counted instead of the predictive locus selection described above. The ROC curve, AUC and the associated p-value were similarly generated.

6.2 Results

Figure 1C:
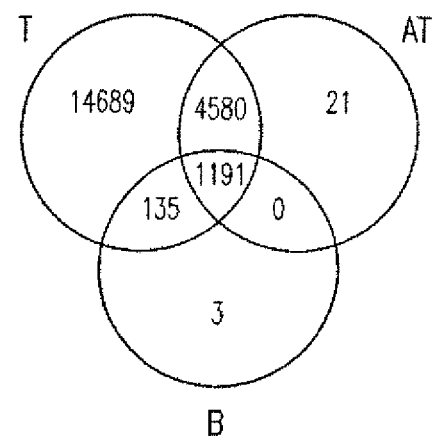
Figure 1D:
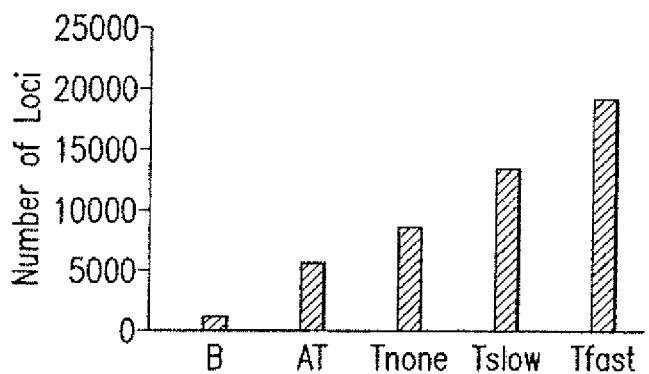

The SNP 6.0 chip hybridization results were analyzed through Partek Genome Suite 6.6™, using blood (B) samples as normal references. As shown in histograms of FIG. 1A, abnormalities of genome in copy number can be found in all chromosomes in prostate cancer. An average of 91.6 loci (minimum of 10 kb) per sample involving 1092 genes were identified either amplified or deleted in prostate cancer genomes as determined by more than 100 markers, p<5.5×10-9 (Bonferroni correction, FIG. 1B). Deletions of large segments of (>3 megabases) chromosome 8p, 13p, 16q and 17p occurred with high frequencies, while amplification of 8q and X chromosomes occurred in a subset of prostate cancer samples. Similar amplification and deletion of the same regions also occurred in benign prostate tissues adjacent to cancer, albeit with smaller sizes and lower frequency. Unexpectedly, the blood of prostate cancer patients contains significant abnormalities in genomes (1329 genes total, or 4.4 loci and 32.6 genes/sample). Most of these abnormalities are not unique and are overlapped with those of prostate cancer samples (FIG. 1C). Prostate cancers were then subdivided based on clinical behavior: those with no relapse after prostatectomy (Tnone); those with relapse and slow increase in serum prostate specific antigen (FSA, doubling in more than 15 months) (Tslow); those with relapse and rapid increase in serum PSA (doubling in less than 4 months) (Tfast). The kinetics of PSA increase after prostatectomy is predictive of prostate-cancer specific death, with rapid increases highly associated with lethal prostate cancer(12). The spectrum of locus abnormalities increases from blood to prostate cancer in an incremental fashion: the least in blood to the most in rapidly progressive prostate cancer (Tfast) (FIG. 1D).

Figure 5A:
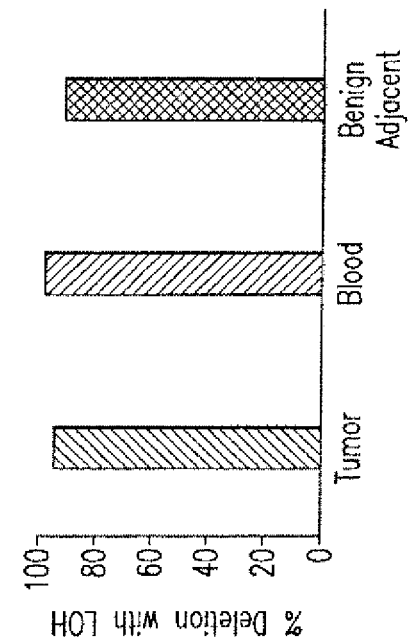
Figure 5B:
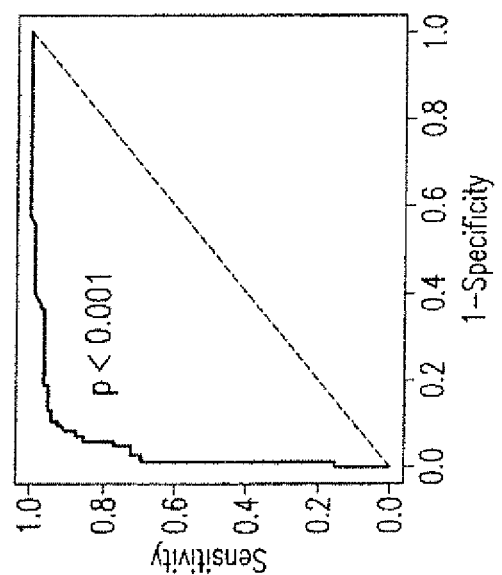

To assess the reproducibility of these analyses, a large set of reference normal samples (n=800) available to public through Partek, Inc. was used. This re-analysis showed genome segment abnormalities of B, AT and T overlapped at least 93 percent between these two analyses (FIG. 5A). In addition, a third analysis using a different set of normal samples (GeneSpring GX11, n=265) was performed, showing that 94% to 99% of the amplified or deleted genome segments from B, AT and T overlap with those obtained from Partek Genome Suite analyses using blood as baseline (FIG. 5A). Affymetrix SNP6.0 contains separate probe sets for SNP and CNV detection. The majority of large genome deletions are accompanied with loss of heterozygosity (LOH). Profiles of LOH for B, AT and T samples were generated to validate the deletions detected by CNV analysis. Genome deletion frequently accompanied LOH (91% to 98%), with average matches for B, AT and T ranging from 93% to 96% (FIG. 5B). This suggests that the analyses are reproducible and robust.

Figure 5C:
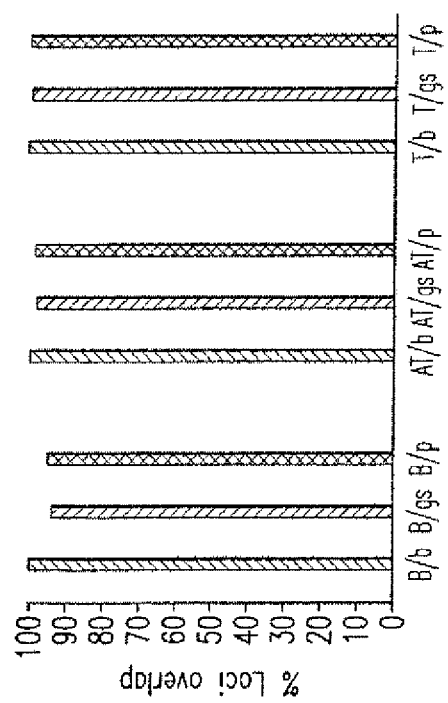
Figure 5D:
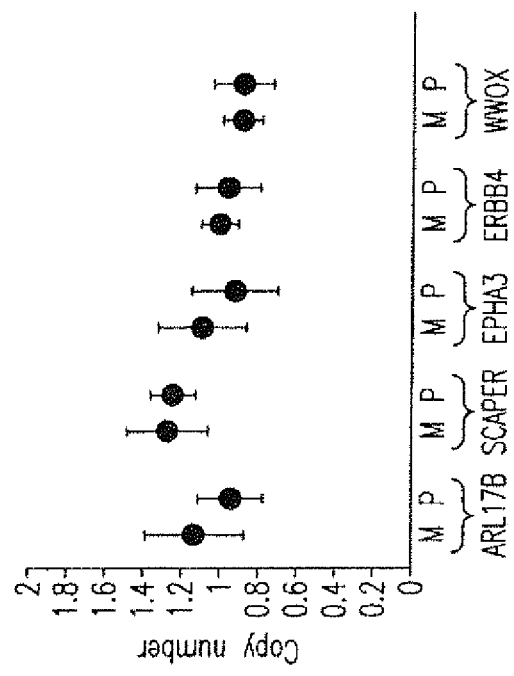
Figure 6A:
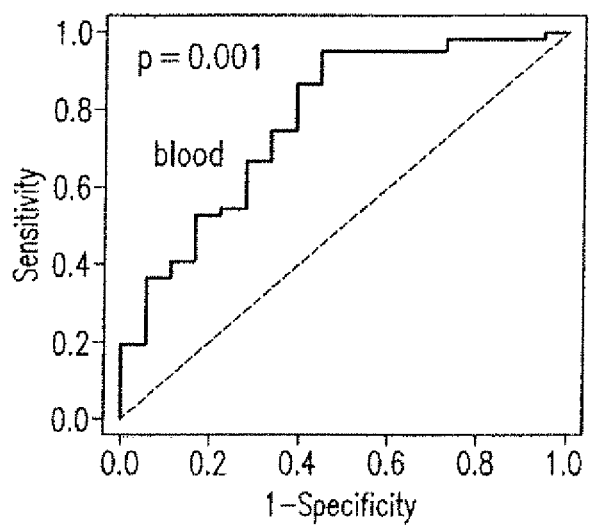
Figure 6B:
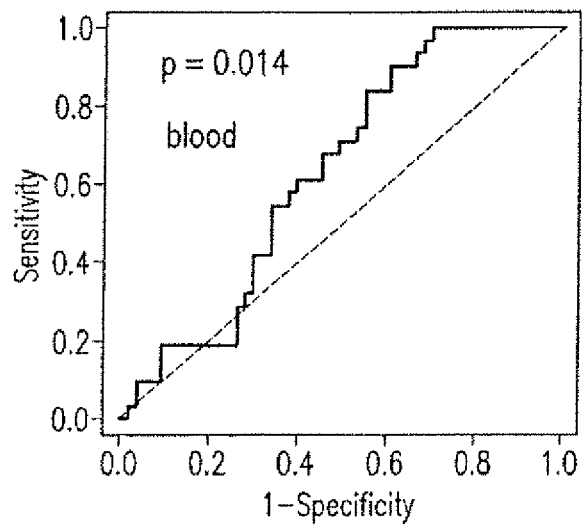
Figure 6C:
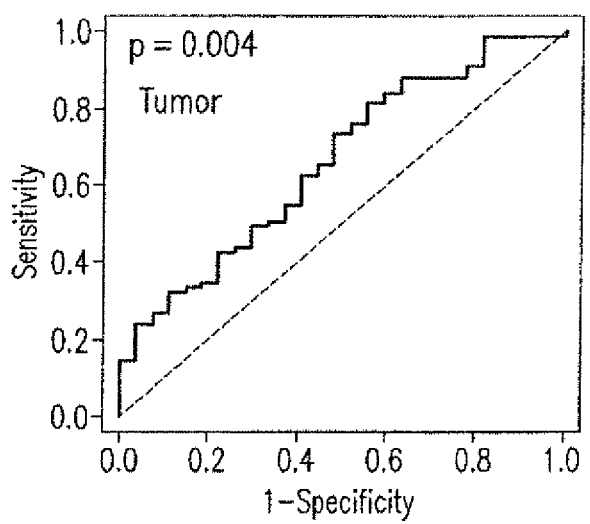
Figure 6D:
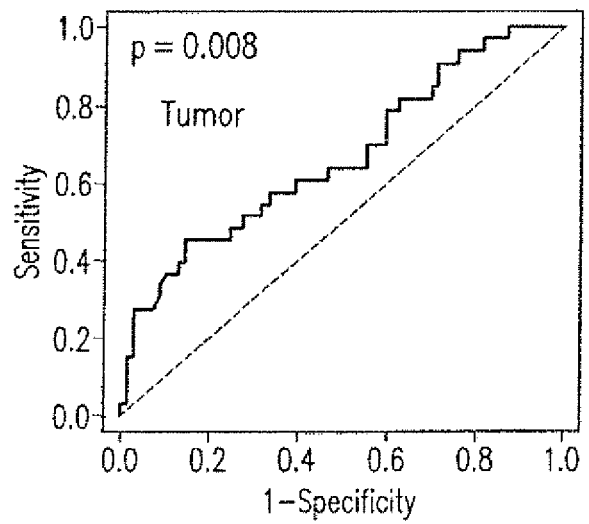

Five loci from chromosomes 16, 17, 3, 2 and 15 with deletions of at least 10 kb and overlapping with nearby genes were selected for quantitative-PCR analysis. As shown in FIG. 5C, a deletion by Q-PCR was found in 4 of 5 samples predicted to have a deletion in the region overlapping with ARL17B, a gene homologous to ADP-ribosylation factor located at 17q2113. Similar confirmation was found in Q-PCR of SCAPER, the S-phase cyclin A-associated protein in the ER located at 15q2414 (5 of 5 samples), of WWOX, WW domain containing oxidoreductase located at 16q2315-17 (5 of 5 samples), of EPHA3 or ephrin receptor 3, a protein tyrosine receptor frequently mutated in a variety of human cancers 18-20 (4 of 5 samples), and of ERBB4 or v-erb-a erythroblastic leukemia viral oncogene homolog 421,22 (5 of 5 samples) in blood samples from prostate cancer patients. The concordance rate of Q-PCR and copy number analysis was 92%. Our analysis indicates that copy number variation is not limited to prostate cancer or benign prostate tissue adjacent to cancer, but is also found in blood from prostate cancer patients.

To investigate whether the CNV profiles of B, AT and T are distinctive from each other, classification analysis was performed to predict genomes of blood versus those of prostate cancer, by aggregating genome loci that have differential amplification or deletion proportion between blood and prostate cancer (see methods for more detail). The prediction accuracy under unbiased "leave-one-out" cross-validation(23) was 89% for blood ($7\%_{85}$) and 94% for prostate cancer (98/104). The overall accuracy was 92% (174/189, FIG. 5D). To investigate whether AT is genetically more related to cancer or "normal" tissues, the CNV profiles of B and T samples were constructed into a logistic regression model as "normal" and "prostate cancer" training sets, respectively. This model was then utilized to classify each of the 49 AT samples as either "normal" or "prostate cancer". Such analysis predicts that 42 of 49 (86%) putatively benign prostate tissue is "cancer", while only 7 of the AT tissues were classified as "normal". All prostate cancer cell lines were classified as "cancer". These analyses clearly indicate that majority of AT samples have copy number profiles similar to prostate cancer's rather than to normal's, resembling a field effect similarly found for gene expression profiling(24).

The vast majority of prostate cancers are not lethal(25). Prediction analysis with "leave-one-out" cross-validation based on loci that have significant proportion of amplification or deletion in the group of relapse but none in the non-relapsed group was performed. The resulting Receiver Operating Characteristic curves (ROC) were generated by varying sensitivity-specificity trade-off (FIG. 2A,B). The cutoff that generates the best Youden index (i.e. sensitivity+ specificity-1) has an accuracy of 73% (74/102, ROC p=0.003, positive prediction=76% [57/75], negative prediction=63% [17/27]) for relapse prediction. Gleason's grading has been a strong predictor of recurrence but in this analysis it was statistically insignificant from baseline (ROC p=0.32) and much worse than CNV analysis.

Prostate cancers with rapid progression, as defined by rates of PSA rise, are lethal1(2,26). Those with PSA doubling time (PSADT)<4 months after relapse and those who died of prostate cancer were compared to those with PSADT >15 months or having no relapse. A similar prediction with "Leave-One-Out" cross-validation analysis was performed to examine the accuracy of CNV profiling (see the genes listed in TABLE 3) in predicting rapidly progressing prostate cancer. As shown in FIG. 2C, the accuracy of predicting rapid progression was 75% (p<0.001) with positive and negative predictive value of 58% and 83%, respectively. In contrast, the histology of the cancer, as defined by Gleason grading, failed to achieve >50% predictive values simultaneously on positive and negative predictions (ROC p=0.074).

Figure 3A:
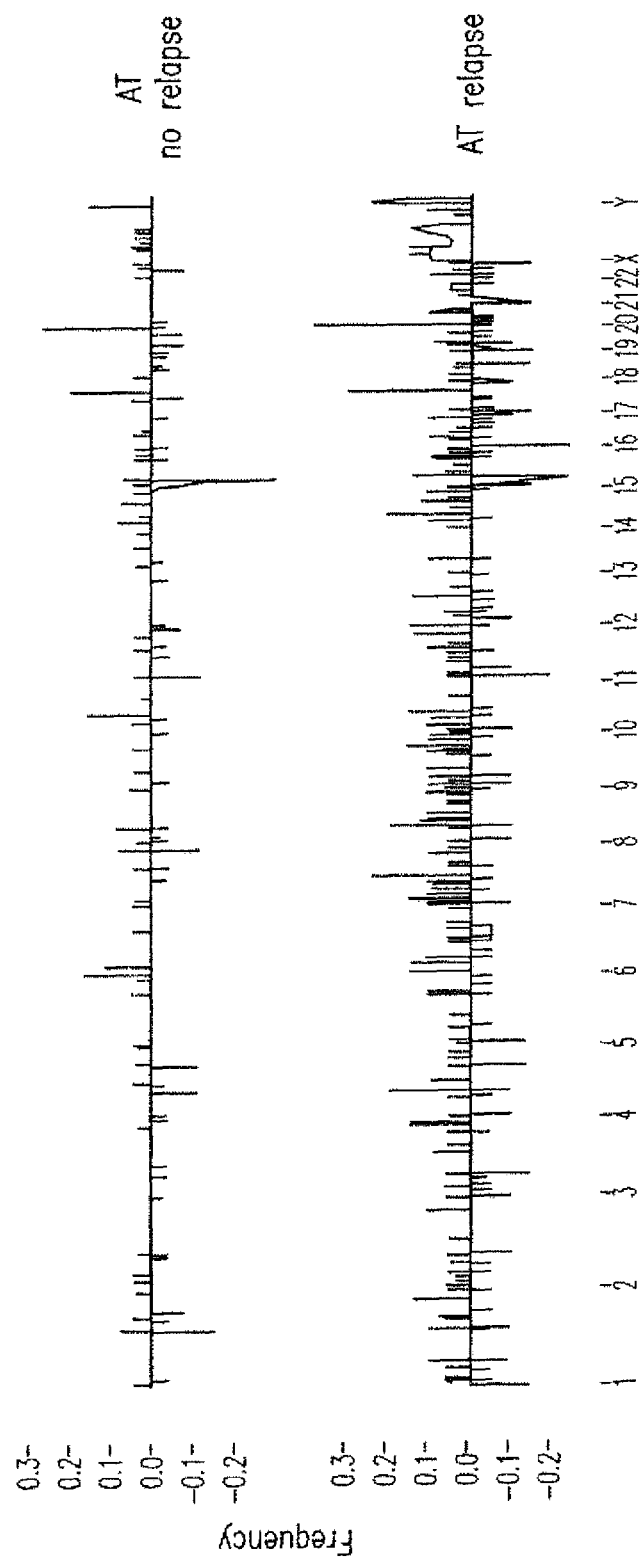
Figure 3B:
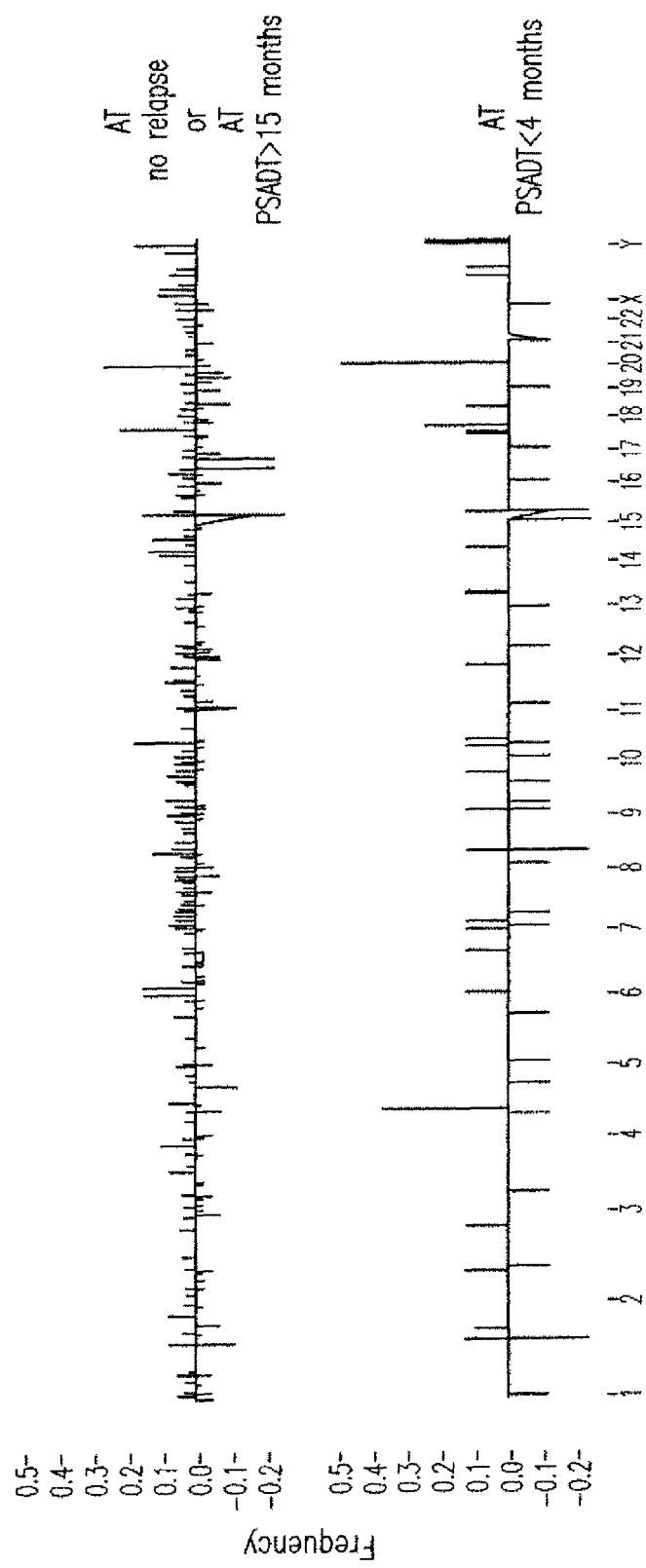
Figure 3C:
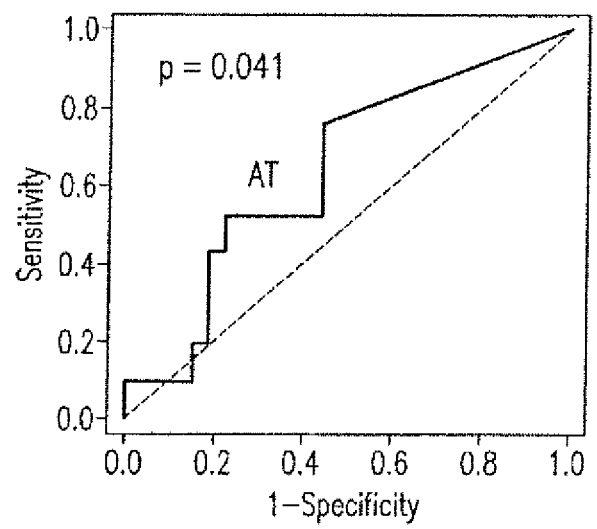
Figure 3D:
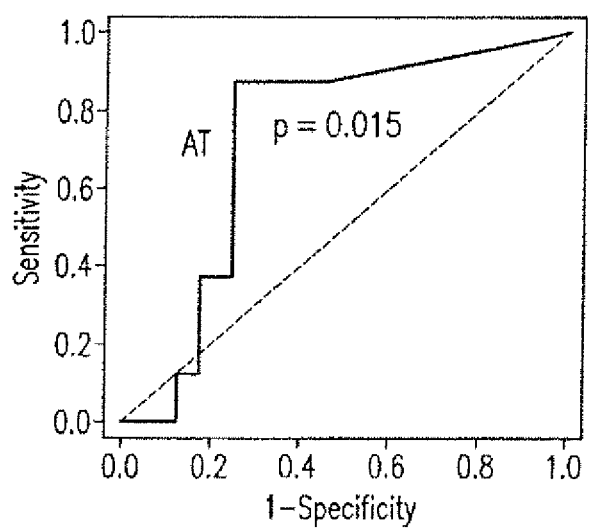
Figure 4A:
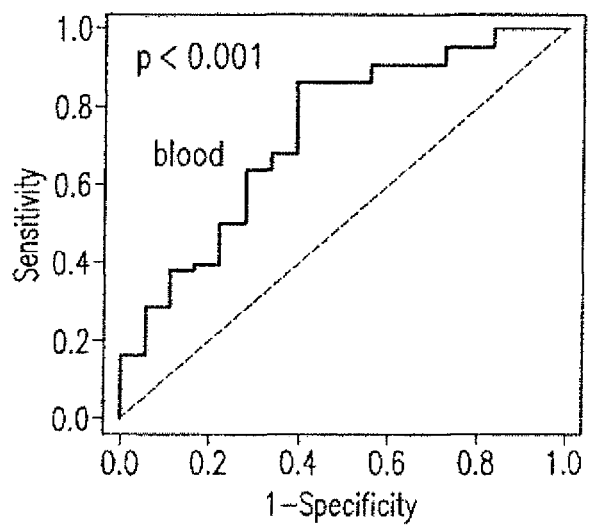
Figure 4B:
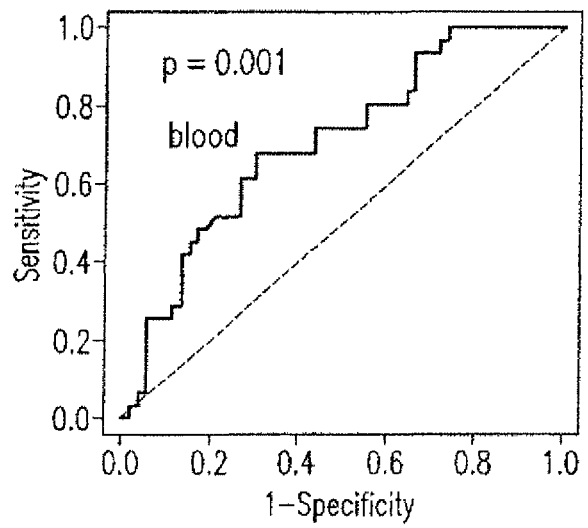
Figure 4C:
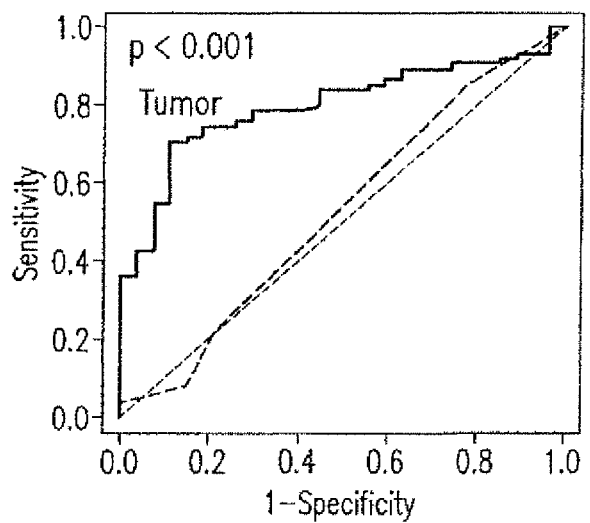
Figure 4D:
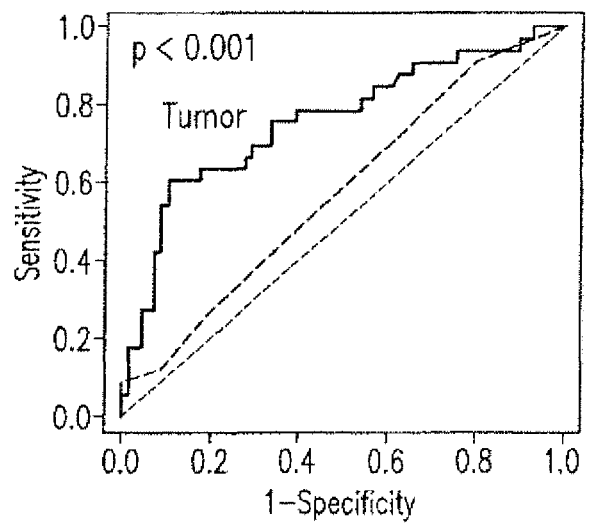

Since the genome alterations in AT are most similar to those of T, the CNV of AT to predict relapse was examined using cross-validation. As shown in FIGS. 3A and 3C, the CNV profile of AT is moderately predictive of prostate cancer relapse: a sensitivity of 76% and a specificity at 56% (ROC p=0.041) were observed. Surprisingly, the CNV profile of AT is more accurate in predicting fast relapse (88% sensitivity and 75% specificity, p=0.015, FIG. 3 B&D). Using the same approach, the CNV profiles from B failed to generate a ROC statistically different from baseline in predicting relapse or fast relapse. However, our analysis showed that the average and median sizes of CNV are significantly larger in blood samples (70 Kb and 23 kb, respectively) from patients with relapse than those without (40 kb and 17 kb). Based on the sizes of CNV, highly statistically significant ROCs were generated (FIG. 4A-B), predicting 81% (p<0.001) relapse and 69% (p=0.001) fast relapse correctly through median CNV sizes. The CNV size correlation with relapse was also found in T (817 kb mean and 647 kb median for relapse vs. 385 kb and 185 kb for non-relapse) and AT samples (246 kb mean and 18 kb median for relapse vs. 95 kb and 16 kb for non-relapse), suggesting a larger CNV size a common feature for prostate cancer relapse regardless tissues. Both median and mean sizes of CNV from T and B, and mean size of CNV from AT predict prostate cancer relapse, while mean and median sizes of CNV from T and B predict fast relapse (FIGS. 4A-D, 6A-D and 7A-B). Interestingly, similar relapse prediction results were also replicated using the sizes of either amplified or deleted loci of blood (FIGS. 8A-D and 9A-D).

To rule out aging being a factor in our analysis, correlation analyses between our gene-specific or size-based model and the patient age were performed, and revealed no significant correlation between age and our prediction methods. Age did not predict outcomes (FIG. 10A-F).

To investigate the reproducibility of our prediction models, we collected an additional 25 samples, including 10 tumors, 10 benign tissues adjacent to tumors, and 5 blood samples from patients with prostate cancer. These experiments and analyses were performed in a separate time period and by different personnel. By using a genespecific model, we correctly predicted 7 of 10 relapse and 8 of 10 short PSADT from tumor samples, whereas we correctly predicted 7 of 10 for both relapse and short PSADT from AT samples. By using mean size of CNV from tumor, we correctly predicted 7 of 10 cases of both relapse and short PSADT, 7 of 10 for relapse from AT, and 4 of 5 for relapse and 4 of 5 for short PSADT from blood. By using median size of CNV from tumors, we correctly predicted 6 of 10 for relapse and 7 of 10 for short PSADT, whereas from blood, we correctly predicted 5 of 5 for relapse and 4 of 5 for short PSADT. Taken together, the gene-specific CNV model has an overall prediction rate of 72.5% in the replication data set, similar to those found in the first set of data. The mean CNV sizes of blood, tumor, and benign prostate tissues have an overall prediction rate of 72% for relapse, and the mean CNV sizes of blood and tumor samples have an overall prediction rate of 73% for short PSADT, whereas the median CNV sizes of blood and tumor have overall prediction rates of 73% for relapse and 80% for short PSADT. These results are also similar to those found in the original study, reflecting good consistency and reproducibility of our prediction models.

6.3 Discussion

Genome-wide analyses of prostate cancer using other methodologies were performed previously(27-30). However, there was no attempt to construct a model to predict the prognosis of prostate cancer. The genome abnormality found in blood from prostate cancer patients in this study is novel. Even though a tiny amount (<0.1% of blood cell population) of circulating tumor cells may exist in the blood sample(31, 32), the stringency of CNV analysis (>30% contamination to be detected) ruled out contamination of tumor cells in the blood as a contending interpretation. Analysis of some of the previously published matched normal samples of other malignancies (33,34) also reveals significant CNV. This suggests that CNV is widely present in tissues of patients carrying malignancies. However, it is unclear whether healthy individuals carry these abnormalities. The CNV of blood may be somatic and acquired through aging; this alteration would tend to be random and spontaneous. Alternatively, genome copy number abnormalities may occur at germ line level. To distinguish these two possibilities, longitudinal blood samples of the same aging individual could identify if CNV is accumulated. Independent of the mechanism, however, genome CNV correlates with the eventual behavior of prostate cancer: This is observed in the primary prostate cancer, in the histologically normal tissue from a prostate gland containing cancer and in the blood of prostate cancer patient. The field effect of genome alterations appears to extend beyond the organ to the entire host.

Conceivably, CNV analysis offers a better option than Gleason's grading in predicting the behavior of prostate cancer not only because of a better prediction rate on the tumor samples, but also its applicability to non-tumor tissues. There are several salient potentials for clinical application using the CNV tests: For a patient being diagnosed of prostate cancer, CNV analysis done on the blood or perhaps other normal tissues from the patient would eliminate the need for additional invasive procedure to decide a treatment mode. For a patient already having a radical prostatectomy, the CNV analysis on tumor or blood sample may help to decide whether additional treatment is warranted to prevent relapse. When morphology becomes in-determinate in a biopsy sample, the gene specific CNV field effect in benign prostate tissues may help to obtain a firmer diagnosis. The main limitation of the genome CNV analysis for clinical test is its requirement of high quality genome DNA. Formalin-fixed paraffin-embedded tissues may not be suitable. When gene specific CNV prediction is performed, a training set containing samples with known outcome is required for the prediction (while there is no need of training set when size of CNV analysis is performed). Despite these limitations, CNV analysis on the genome of blood, normal prostate or tumor tissues of the prostate cancer patients holds promise to become a more efficient and accurate way to predict the behavior of prostate cancer.

7. REFERENCES

1. Jemal A, Bray F, Center M M, et al: Global cancer statistics. CA Cancer J Clin
2. Jemal A, Siegel R, Xu J, et al: Cancer statistics, 2010. CA Cancer J Clin 60:277-300
3. Jemal A, Siegel R, Ward E, et al: Cancer statistics, 2009. CA Cancer Clin 59:225-49, 2009
4. Pang S T, Weng W H, Flores-Morales A, et al: Cytogenetic and expression profiles associated with transformation to androgen-resistant prostate cancer. Prostate 66:157-72, 2006
5. Matsui S, LaDuca J, Rossi M R, et al: Molecular characterization of a consistent 4.5-megabase deletion at 4q28 in prostate cancer cells. Cancer Genet Cytogenet 159:18-26, 2005
6. Bettendorf O, Schmidt H, Eltze E, et al: Cytogenetic changes and loss of heterozygosity in atypical adenomatous hyperplasia, in carcinoma of the prostate and in non-neoplastic prostate tissue using comparative genomic hybridization and multiplex-PCR. Int J Oncol 26:267-74, 2005
7. Teixeira M R, Ribeiro F R, Eknaes M, et al: Genomic analysis of prostate carcinoma specimens obtained via ultrasound-guided needle biopsy may be of use in preoperative decision-making. Cancer 101:1786-93, 2004
8. Macoska J A, Paris P, Collins C, et al: Evolution of 8p loss in transformed human prostate epithelial cells. Cancer Genet Cytogenet 154:36-43, 2004
9. Kraus J, Pantel K, Pinkel D, et al: High-resolution genomic profiling of occult micrometastatic tumor cells. Genes Chromosomes Cancer 36:159-66, 2003
10. Strassburger K, Bretz F: Compatible simultaneous lower confidence bounds for the Holm procedure and other Bonferroni-based closed tests. Stat Med 27:4914-27, 2008
11. Hanczar B, Hua J, Sima C, et al: Small-sample precision of ROC-related estimates. Bioinformatics 26:822-30
12. Hanks G E, Hanlon A L, Lee W R, et al: Pretreatment prostate-specific antigen doubling times: clinical utility of this predictor of prostate cancer behavior. Tnt J Radiat Oncol Biol Phys 34:549-53, 1996
13. Strausberg R L, Feingold E A, Grouse L H, et al: Generation and initial analysis of more than 15,000 full-length human and mouse cDNA sequences. Proc Natl Acad Sci USA 99:16899-903, 2002
14. Tsang W Y, Wang L, Chen Z, et al: SCAPER, a novel cyclin A-interacting protein that regulates cell cycle progression. J Cell Biol 178:621-33, 2007
15. Yang J, Cogdell D, Yang D, et al: Deletion of the WWOX gene and frequent loss of its protein expression in human osteosarcoma. Cancer Lett 291:31-8
16. Nunez M I, Rosen D G, Ludes-Meyers J H, et al: WWOX protein expression varies among ovarian carcinoma histotypes and correlates with less favorable outcome. BMC Cancer 5:64, 2005
17. Yakicier M C, Legoix P, Vaury C, et al: Identification of homozygous deletions at chromosome 16q23 in aflatoxin B1 exposed hepatocellular carcinoma. Oncogene 20:5232-8, 2001
18. Blackford A, Parmigiani G, Kensler T W, et al: Genetic mutations associated with cigarette smoking in pancreatic cancer. Cancer Res 69:3681-8, 2009
19. Clifford N, Smith L M, Powell J, et al: The EphA3 receptor is expressed in a subset of rhabdomyosarcoma cell lines and suppresses cell adhesion and migration. J Cell Biochem 105:1250-9, 2008
20. Bae H J, Song J H, Noh J H, et al: Low frequency mutation of the Ephrin receptor A3 gene in hepatocellular carcinoma. Neoplasma 56:331-4, 2009
21. Koutras A K, Fountzilas G, Kalogeras K T, et al: The upgraded role of HER3 and HER4 receptors in breast cancer. Crit Rev Oncol Hematol 74:73-8
22. Lee S Y, Kim M J, Jin G, et al: Somatic mutations in epidermal growth factor receptor signaling pathway genes in non-small cell lung cancers. J Thorac Oncol 5:1734-40
23. Golub T R, Slonim D K, Tamayo P, et al: Molecular classification of cancer: class discovery and class prediction by gene expression monitoring. Science 286:531-7, 1999
24. Yu Y P, Landsittel D, Jing L, et al: Gene expression alterations in prostate cancer predicting tumor aggression and preceding development of malignancy. J Clin Oncol 22:2790-9, 2004
25. Isaacs J T: Molecular markers for prostate cancer metastasis. Developing diagnostic methods for predicting the aggressiveness of prostate cancer. Am J Pathol 150:1511-21, 1997
26. Stephenson A J, Shariat S F, Zelefsky M J, et al: Salvage radiotherapy for recurrent prostate cancer after radical prostatectomy. Jama 291:1325-32, 2004
27. Kim J H, Dhanasekaran S M, Mehra R, et al: Integrative analysis of genomic aberrations associated with prostate cancer progression. Cancer Res 67:8229-39, 2007
28. Zhao H, Kim Y, Wang P, et al: Genome-wide characterization of gene expression variations and DNA copy number changes in prostate cancer cell lines. Prostate 63:187-97, 2005
29. Ren B, Yu G, Tseng G C, et al: MCM7 amplification and overexpression are associated with prostate cancer progression. Oncogene 25:1090-8, 2006
30. Liu W, Laitinen S, Khan S, et al: Copy number analysis indicates monoclonal origin of lethal metastatic prostate cancer. Nat Med 15:559-65, 2009

31. Cristofanilli M, Budd G T, Ellis M J, et al: Circulating tumor cells, disease progression, and survival in metastatic breast cancer. N Engl J Med 351:781-91, 2004
32. Moreno J O, Croce C M, Fischer R, et al: Detection of hematogenous micrometastasis in patients with prostate cancer. Cancer Res 52:6110-2, 1992
33. Green M R, Monti S, Rodig S J, et al: Integrative analysis reveals selective 9p24.1 amplification, increased PD-I ligand expression, and further induction via JAK2 in nodular sclerosing Hodgkin lymphoma and primary mediastinal large B-cell lymphoma. Blood 116:3268-77, 2010
34. Parkin B, Erba H, Ouillette P, et al: Acquired genomic copy number aberrations and survival in adult acute myelogenous leukemia. Blood 116:4958-67, 2010

Various publications are cited herein, the contents of which are hereby incorporated by reference in their entireties.

TABLE 1A

Case pathology grading, Clinical outcome and Age

| Sample | Type | Relapse | Relapse Fast | Relapse Simple | Gleason's Grade | Age |
|---|---|---|---|---|---|---|
| LNCaP | C | | | | | |
| 5772T | T | none | nf | n | 7 | 60s |
| 3806T | T | | | | | |
| Du145 | C | | | | | |
| 20968T | T | slow | nf | y | 7 | 50s |
| 15463T | T | none | nf | n | 7 | 60s |
| 8629T | T | none | nf | n | 6 | 50s |
| PC3 | C | | | | | |
| 28685T | T | slow | nf | y | 7 | 50s |
| 11423T | T | slow | nf | y | 7 | 70s |
| 11462T | T | slow | nf | y | 7 | 50s |
| 25265T | T | none | nf | n | 7 | 60s |
| 25313T | T | none | nf | n | 8 | 50s |
| 2671T | T | slow | nf | y | 7 | 60s |
| 6647T | T | slow | nf | y | 7 | 40s |
| 9122T | T | none | nf | n | 7 | 50s |
| 678T | T | none | nf | n | 9 | 70s |
| 7270T | T | none | nf | n | 9 | 70s |
| 28925N | N | | | | | 50s |
| 1199T | T | slow | nf | y | 8 | 50s |
| 27086T | T | none | nf | n | 6 | 50s |
| 562T | T | none | nf | n | 6 | 60s |
| 34N | N | Nnone | Nnf | Nn | | 50s |
| 36N | N | Nnone | Nnf | Nn | | 50s |
| 9122N | N | Nnone | Nnf | Nn | | 50s |
| 28278T | T | none | nf | n | 7 | 50s |
| 2691T | T | none | nf | n | 7 | 50s |
| 8629N | N | Nnone | Nnf | Nn | | |
| 8378T | T | none | nf | n | 7 | 60s |
| 8432T | T | none | nf | n | 7 | 50s |
| 6837T | T | slow | nf | y | 6 | 70s |
| 7943N | N | Nnone | Nnf | Nn | | 60s |
| 8741T | T | none | nf | n | 6 | 60s |
| 34T | T | none | nf | n | 7 | 50s |
| 14878T | T | none | nf | n | 8 | 60s |
| 25313N | N | Nnone | Nnf | Nn | | 50s |
| 678N | N | Nnone | Nnf | Nn | | 70s |
| GB195T | T | slow | nf | y | 7 | 60s |
| HB591T | T | fast | f | y | 7 | 60s |
| IB071T | T | fast | f | y | 7 | 60s |
| JB426T | T | fast | f | y | 7 | 60s |
| PR079T | T | slow | nf | y | 7 | 60s |
| PR521T | T | slow | nf | y | 7 | 50s |
| TP08-S00530T | T | fast | f | y | 7 | 60s |
| TP09-S0006T | T | fast | f | y | 8 | 50s |
| 16464T | T | slow | nf | y | 7 | 60s |
| 16947T | T | slow | nf | y | 8 | 70s |
| DB237T | T | slow | nf | y | 6 | 70s |
| FB94T | T | slow | nf | y | 7 | 60s |
| JB378T | T | slow | nf | y | 6 | 60s |
| PR151T | T | slow | nf | y | 7 | 60s |
| PR304T | T | slow | nf | y | 8 | 60s |
| PR311T | T | slow | nf | y | 8 | 60s |
| 2644T | T | slow | nf | y | 9 | 50s |
| 19381T | T | none | nf | n | 6 | 60s |
| 7943T | T | none | nf | n | 7 | 60s |
| TP09-S0420T | T | fast | f | y | 7 | 50s |
| 18176N | N | Nslow | Nnf | Ny | | 50s |
| 19381N | N | Nnone | Nnf | Nn | | 50s |
| IB071N | N | Nfast | Nf | Ny | | 60s |
| JB426N | N | Nfast | Nf | Ny | | 60s |
| PR304N | N | Nslow | Nnf | Ny | | 60s |
| 2644N | N | Nslow | Nnf | Ny | | 50s |
| 15733N | N | Nnone | Nnf | Nn | | 50s |
| 15875N | N | Nnone | Nnf | Nn | | 40s |
| PR310T | T | fast | f | y | 7 | 60s |
| 29671T | T | slow | nf | y | 7 | 60s |
| 15733T | T | none | nf | n | 7 | 50s |
| 18176T | T | slow | nf | y | 6 | 50s |
| 5772N | N | Nnone | Nnf | Nn | | 60s |
| 7504T | T | none | nf | n | 9 | 70s |
| 28925T | T | | | | 7 | 50s |
| 15875T | T | none | nf | n | 7 | 40s |
| 15922T | T | none | nf | n | 7 | 60s |
| 28278N | N | Nnone | Nnf | Nn | | 50s |
| 4308T | T | none | nf | n | 6 | 60s |
| 7504N | N | Nnone | Nnf | Nn | | 70s |
| JB197T | T | fast | f | y | 7 | 50s |
| TP08-S00268N | N | Nfast | Nf | Ny | | 60s |
| TP08-S00268T | T | fast | f | y | 7 | 50s |
| TP09-S0420N | N | Nfast | Nf | Ny | | 50s |
| 1199B | B | Bslow | Bnf | By | | 50s |
| 9122B | B | Bnone | Bnf | Bn | | 50s |
| 18176B | B | Bslow | Bnf | By | | 50s |
| 25313B | B | Bnone | Bnf | Bn | | 50s |
| 6634B | B | Bnone | Bnf | Bn | | 50s |
| 678B | B | Bnone | Bnf | Bn | | 70s |
| 7504B | B | Bnone | Bnf | Bn | | 70s |
| 16464B | B | Bnone | Bnf | Bn | | 60s |
| 4336B | B | Bslow | Bnf | By | | 60s |
| 28685B | B | Bslow | Bnf | By | | 50s |
| 4851B | B | Bnone | Bnf | Bn | | 60s |
| 1942B | B | Bfast | Bf | By | | 60s |
| 13563B | B | Bnone | Bnf | Bn | | 70s |
| TP09-S0420B | B | Bfast | Bf | By | | 50s |
| TP08-S00268B | B | Bfast | Bf | By | | 60s |
| DB237B | B | Bslow | Bnf | By | | 70s |
| PR151B | B | Bslow | Bnf | By | | 60s |
| 13745B | B | | | | | 60s |
| TP09-S0006B | B | Bfast | Bf | By | | 50s |
| PR331B | B | Bslow | Bnf | By | | 60s |
| 28685B2 | B | Bslow | Bnf | By | | 50s |
| IB071B | B | Bfast | Bf | By | | 60s |
| PR304B | B | Bslow | Bnf | By | | 60s |
| JB426B | B | Bfast | Bf | By | | 60s |
| 7270B | B | Bnone | Bnf | Bn | | 70s |
| 27086B | B | Bnone | Bnf | Bn | | 50s |
| TP09-S0420B2 | B | Bfast | Bf | By | | 50s |
| DB237B2 | B | Bslow | Bnf | By | | 70s |
| PR151B2 | B | Bslow | Bnf | By | | 60s |
| PR310B | B | Bfast | Bf | By | | 60s |
| FB586B | B | Bslow | Bnf | By | | 50s |
| 6634B2 | B | Bnone | Bnf | Bn | | 50s |
| JB378B | B | Bslow | Bnf | By | | 60s |
| FB94B | B | Bslow | Bnf | By | | 60s |
| GB195B | B | Bslow | Bnf | By | | 60s |
| PR490B | B | Bslow | Bnf | By | | 60s |
| PR303B | B | Bslow | Bnf | By | | 70s |
| PR018B | B | Bslow | Bnf | By | | 60s |
| TP08-S00542B | B | Bfast | Bf | By | | 50s |
| GB400B | B | Bfast | Bf | By | | 60s |
| HB603B | B | Bfast | Bf | By | | 60s |
| DB237N | N | Nslow | Nnf | Ny | | 70s |
| 11423N | N | Nslow | Nnf | Ny | | 70s |
| 25265N | N | Nnone | Nnf | Nn | | 60s |
| 8378N | N | Nnone | Nnf | Nn | | 60s |

TABLE 1A-continued

Case pathology grading, Clinical outcome and Age

| Sample | Type | Relapse | Relapse Fast | Relapse Simple | Gleason's Grade | Age |
|---|---|---|---|---|---|---|
| 8432N | N | Nnone | Nnf | Nn | | 50s |
| 15463N | N | Nnone | Nnf | Nn | | 60s |
| 27086N | N | Nnone | Nnf | Nn | | 50s |
| 4308N | N | Nnone | Nnf | Nn | | 60s |
| 562N | N | Nnone | Nnf | Nn | | 60s |
| FB183T | T | slow | nf | y | 7 | 60s |
| GB400T | T | fast | f | y | 7 | 60s |
| HB021T | T | fast | f | y | 6 | 50s |
| HB261T | T | none | nf | n | 7 | 50s |
| HB312T | T | slow | nf | y | 8 | 70s |
| HB526T | T | fast | f | y | 6 | 60s |
| HB951T | T | fast | f | y | 7 | 60s |
| IB134T | T | none | nf | n | 9 | 70s |
| IB273T | T | fast | f | y | 7 | 50s |
| IB298T | T | slow | nf | y | 7 | 60s |
| 20968N | N | Nslow | Nnf | Ny | | 50s |
| 6647N | N | Nslow | Nnf | Ny | | 40s |
| 15922N | N | Nnone | Nnf | Nn | | 60s |
| 8741N | N | Nnone | Nnf | Nn | | 60s |
| FB183N | N | Nslow | Nnf | Ny | | 60s |
| HB526N | N | Nfast | Nf | Ny | | 60s |
| HB568T | T | fast | f | y | 7 | 60s |
| PR236T | T | fast | f | y | 10 | 60s |
| PR300T | T | fast | f | y | 7 | 50s |
| PR303N | N | Nslow | Nnf | Ny | | 70s |
| PR434T | T | slow | nf | y | 7 | 60s |
| TPG8-S00542N | N | Nfast | Nf | Ny | | 50s |
| FB120T | T | slow | nf | y | 7 | 60s |
| FB174T | T | fast | f | y | 7 | 60s |
| HB603T | T | slow | nf | y | 7 | 60s |
| IB113T | T | slow | nf | y | 7 | 70s |
| IB483T | T | fast | f | y | 7 | 50s |
| IB684T | T | slow | nf | y | 7 | 60s |
| KB170T | T | fast | f | y | 7 | 70s |
| PR018T | T | slow | nf | y | 7 | 60s |
| PR151N | N | Nslow | Nnf | Ny | | 60s |
| PR303T | T | slow | nf | y | 6 | 70s |
| PR311N | N | Nslow | Nnf | Ny | | 60s |
| 11462N | N | Nslow | Nnf | Ny | | 50s |
| 29671N | N | Nslow | Nnf | Ny | | 60s |
| 14878N | N | Nnone | Nnf | Nn | | 60s |
| 16464N | N | Nnone | Nnf | Nn | | 60s |
| PR521B | B | Bslow | Bnf | By | | 50s |
| PR363B | B | Bslow | Bnf | By | | 60s |
| FB174B | B | Bfast | Bf | By | | 60s |
| FB421B | B | Bfast | Bf | By | | 60s |
| FB421T | T | fast | f | y | 7 | 60s |
| HB033T | T | none | nf | n | 7 | 50s |
| HB526N2 | N | Nfast | Nf | Ny | | 60s |
| IB113B | B | Bslow | Bnf | By | | 70s |
| IB483T2 | T | fast | f | y | 7 | 50s |
| TP08-S00542T | T | fast | f | y | 7 | 50s |
| TP09-S0006N | N | Nfast | Nf | Ny | | 50s |
| PR079B | B | Bslow | Bnf | By | | 60s |
| FB183B | B | Bslow | Bnf | By | | 60s |
| FB120B | B | Bslow | Bnf | By | | 60s |
| HB305B | B | Bfast | Bf | By | | 60s |
| HB305T | T | fast | f | y | 6 | 60s |
| IB362T | T | slow | nf | y | 7 | 50s |
| IB684B | B | Bslow | Bnf | By | | 60s |
| JB770B | B | Bfast | Bf | By | | 60s |
| JB770T | T | fast | f | y | 8 | 60s |
| TP10-S093B | B | Bslow | Bnf | By | | 60s |
| TP10-S093T | T | slow | nf | y | 7 | 60s |
| TP09-S0408B | B | Bfast | Bf | By | | 70s |
| TP09-S0408T | T | fast | f | y | 8 | 70s |
| 2691N | N | Nnone | Nnf | Nn | | 50s |
| 28278N2 | N | Nnone | Nnf | Nn | | 50s |
| 4336T | T | slow | nf | y | 6 | 60s |
| 6634N | N | Nnone | Nnf | Nn | | 60s |
| 6837T2 | T | slow | nf | y | 6 | 70s |
| 7221T | T | fast | f | y | 7 | 50s |
| 4308B | B | Bnone | Bnf | Bn | | 60s |
| 5396B | B | Bnone | Bnf | Bn | | 60s |
| 9122B2 | B | Bnone | Bnf | Bn | | 50s |
| TP08-S00530B | B | Bfast | Bf | By | | 60s |
| 562B | B | Bnone | Bnf | Bn | | 60s |
| KB170B | B | Bfast | Bf | By | | 70s |
| IB298B | B | Bslow | Bnf | By | | 60s |
| HB591B | B | Bfast | Bf | By | | 60s |
| HB261B | B | Bnone | Bnf | Bn | | 50s |
| PR300B | B | Bfast | Bf | By | | 50s |
| PR236B | B | Bfast | Bf | By | | 60s |
| PR434B | B | Bslow | Bnf | By | | 60s |
| HB568B | B | Bfast | Bf | By | | 60s |
| IB134B | B | Bnone | Bnf | Bn | | 70s |
| IB483B | B | Bfast | Bf | By | | 50s |
| HB526B | B | Bfast | Bf | By | | 60s |
| HB021B | B | Bfast | Bf | By | | 50s |
| HB312B | B | Bslow | Bnf | By | | 70s |
| HB033B | B | Bnone | Bnf | Bn | | 50s |
| FB238T | T | slow | nf | y | 7 | 60s |
| FB493T | T | slow | nf | y | 6 | 50s |
| HB207T | T | fast | f | y | 9 | 60s |
| HB235T | T | slow | nf | y | 9 | 60s |
| HB504T | T | fast | f | y | 8 | 50s |
| IB112T | T | slow | nf | y | 7 | 60s |
| IB136T | T | fast | f | y | 8 | 50s |
| PR306T | T | slow | nf | y | 7 | 60s |
| TP10-S0638T | T | fast | f | y | 10 | 50s |
| HB235B | B | Bslow | Bnf | By | | 60s |
| PR375B | B | Bfast | Bf | By | | 50s |
| FB238B | B | Bslow | Bnf | By | | 60s |
| IB136B | B | Bfast | Bf | By | | 50s |
| TP09-S0721B | B | Bfast | Bf | By | | 50s |
| HB504B | B | Bfast | Bf | By | | 50s |
| IB112B | B | Bslow | Bnf | By | | 60s |
| HB207B | B | Bfast | Bf | By | | 60s |
| PR306B | B | Bslow | Bnf | By | | 60s |
| TP09-S0638B | B | Bfast | Bf | By | | 50s |
| HB46B | B | Bslow | Bnf | By | | 60s |
| FB493B | B | Bslow | Bnf | By | | 50s |
| HB46T | T | slow | nf | y | 8 | 60s |
| PR375T | T | fast | f | y | 7 | 50s |
| TP09-S0721T | T | fast | f | y | 10 | 50s |

TABLE 1B

Clinical and Pathological Characteristics of Prostate Cancer Samples

| | Relapse Status | | |
|---|---|---|---|
| | None (n = 28) | Long PSADT (n = 42) | Short PSADT (n = 33) |
| Mean Age (P = 0.0783) | 56.07 | 59.29 | 56.06 |
| Cancer Stage (P = 0.0224) | | | |
| pT1 | 3 (2.9) | 1 (1.0) | 0 (0) |
| pT2 | 10 (9.7) | 9 (8.7) | 7 (6.8) |
| pT3a | 7 (6.8) | 18 (17.5) | 6 (5.8) |
| pT3b | 8 (7.8) | 14 (13.6) | 20 (19.4) |
| Gleason grade (P = 0.6569) | | | |
| 6 | 6 (5.8) | 8 (7.8) | 3 (2.9) |
| 7 | 16 (15.5) | 26 (25.2) | 21 (20.4) |
| 8-10 | 6 (5.8) | 8 (7.8) | 9 (8.7) |
| Race (P = 0.2349) | | | |
| Black | 1 | 2 | 0 |
| Unknown | 4 | 1 | 2 |
| White | 23 | 39 | 31 |

TABLE 1B-continued

Clinical and Pathological Characteristics of Prostate Cancer Samples

| | Relapse Status | | |
|---|---|---|---|
| | None (n = 28) | Long PSADT (n = 42) | Short PSADT (n = 33) |
| Median follow-up (months) | 154 | 124.8 | 54.8 |
| Median time to progression (months) | NA | 47.355 | 1.87 |
| Median PSADT (months) | NA | 23.2 | 3.21 |
| Mean preoperative PSA (P = 0.42) | 8.61 | 12.31 | 10.79 |

Data are given as number (percentage) of the 103 samples unless otherwise indicated.
NA = not applicable

TABLE 1C

Clinical and Pathological Characteristics of Prostate Tissues Adjacent to Tumor

| | Relapse Status | | |
|---|---|---|---|
| | None (n = 28) | Long PSADT (n = 13) | Short PSADT (n = 8) |
| Mean Age (P = 0.554) | 55 | 57.69 | 56.06 |
| Cancer Stage (P = 0.541) | | | |
| pT1 | 3 (6.1) | 0 (0) | 0 (0) |
| pT2 | 11 (22.4) | 4 (8.2) | 3 (6.1) |
| pT3a | 7 (14.3) | 6 (12.2) | 1 (2.0) |
| pT3b | 7 (14.3) | 3 (6.1) | 4 (8.2) |
| Gleason grade (P = 0.9849) | | | |
| 5 | 1 (2.0) | 0 (0) | 0 (0) |
| 6 | 7 (14.3) | 3 (6.1) | 2 (4.1) |
| 7 | 16 (32.7) | 7 (14.3) | 5 (10.2) |
| 8-10 | 4 (8.2) | 3 (6.1) | 1 (2.0) |
| Race (P = 0.08387) | | | |
| Black | 0 | 1 | 0 |
| Unknown | 6 | 0 | 0 |
| White | 22 | 12 | 8 |
| Median follow up (months) | 155 | 149 | 29.205 |
| Median time to progression (months) | NA | 54.6 | 3.09 |

TABLE 1C-continued

Clinical and Pathological Characteristics of Prostate Tissues Adjacent to Tumor

| | Relapse Status | | |
|---|---|---|---|
| | None (n = 28) | Long PSADT (n = 13) | Short PSADT (n = 8) |
| Median (PSADT) months | NA | 26.9 | 2.46 |
| Mean preoperative PSA (P = 0.074) | 8.23 | 12.98 | 6.3 |

Data are given as number (percentage) of the 49 samples unless otherwise indicated.
NA = not applicable

TABLE 1D

Clinical and Pathological Characteristics of Blood Samples from Patients with Prostate Cancer

| | Relapse Status | | |
|---|---|---|---|
| | None (n = 18) | Long PSADT (n = 35) | Short PSADT (n = 31) |
| Mean age (P = 0.268) | 58.33 | 59.43 | 56.77 |
| Cancer Stage (P = 0.003893) | | | |
| pT1 | 5 (6.0) | 1 (1.2) | 0 (0) |
| pT2 | 6 (7.1) | 12 (14.3) | 6 (7.1) |
| pT3a | 1 (1.2) | 10 (11.9) | 5 (6.0) |
| pT3b | 6 (7.1) | 12 (14.3) | 20 (23.8) |
| Gleason grade (P = 0.2248) | | | |
| 6 | 5 (6.0) | 8 (9.5) | 3 (3.6) |
| 7 | 7 (8.3) | 21 (25.0) | 18 (21.4) |
| 8-10 | 6 (7.1) | 6 (7.1) | 10 (11.9) |
| Race (P = 0.08387) | | | |
| Black | 0 | 1 | 0 |
| Unknown | 3 | 1 | 2 |
| White | 15 | 33 | 29 |
| Median follow up (months) | 152 | 109.14 | 54.8 |
| Median time to progression (months) | NA | 47.27 | 3.23 |
| Median PSADT (months) | NA | 26 | 3.21 |
| Mean preoperative PSA (P = 0.868) | 10.48 | 12.17 | 10.87 |

Data are given as number (percentage) of the 84 samples unless otherwise indicated.
NA = not applicable

TABLE 2

Gene list for predicting prostate cancer relapse using prostate cancer tissue

| Symbol | freq. use | freq. amp. case | freq. del. case | freq. control | freq. control | Gene. Symbol | chromosome | cytoband | Transcript. start | Transcript. end |
|---|---|---|---|---|---|---|---|---|---|---|
| psiTPTE22 | 1 | 0.106667 | 0.133333 | 0.444444 | 0 | psiTPTE22 | 22 | 22q11.1 | 15462801 | 15509721 |
| XKR3 | 1 | 0.133333 | 0.133333 | 0.481481 | 0 | XKR3 | 22 | 22q11.1 | 15644306 | 15682585 |
| DNAL4 | 1 | 0.413333 | 0.133333 | 0.777778 | 0 | DNAL4 | 22 | 22q13.1 | 37504459 | 37520108 |
| BRD1 | 1 | 0.48 | 0.12 | 0.814815 | 0 | BRD1 | 22 | 22q13.33 | 48552941 | 48604457 |
| LOC90834 | 1 | 0.48 | 0.12 | 0.814815 | 0 | LOC90834 | 22 | 22q13.33 | 48557542 | 48559963 |
| ZBED4 | 1 | 0.48 | 0.12 | 0.814815 | 0 | ZBED4 | 22 | 22q13.33 | 48633501 | 48669731 |
| ALG12 | 1 | 0.48 | 0.12 | 0.814815 | 0 | ALG12 | 22 | 22q13.33 | 48682857 | 48698111 |
| CRELD2 | 1 | 0.48 | 0.12 | 0.814815 | 0 | CRELD2 | 22 | 22q13.33 | 48698287 | 48707191 |
| PIM3 | 1 | 0.48 | 0.12 | 0.814815 | 0 | PIM3 | 22 | 22q13.33 | 48740147 | 48743724 |
| IL17REL | 1 | 0.48 | 0.12 | 0.814815 | 0 | IL17REL | 22 | 22q13.33 | 48775069 | 48793183 |

TABLE 2-continued

Gene list for predicting prostate cancer relapse using prostate cancer tissue

| Symbol | freq. use | freq. amp. case | freq. del. case | freq. control | freq. control | Gene. Symbol | chromosome | cytoband | Transcript. start | Transcript. end |
|---|---|---|---|---|---|---|---|---|---|---|
| TTLL8 | 1 | 0.48 | 0.12 | 0.814815 | 0 | TTLL8 | 22 | 22q13.33 | 48795679 | 48835183 |
| PANX2 | 1 | 0.48 | 0.12 | 0.814815 | 0 | PANX2 | 22 | 22q13.33 | 48951287 | 48960851 |
| TRABD | 1 | 0.48 | 0.12 | 0.814815 | 0 | TRABD | 22 | 22q13.33 | 48966487 | 48980155 |
| SELO | 1 | 0.48 | 0.12 | 0.814815 | 0 | SELO | 22 | 22q13.33 | 48981535 | 48998173 |
| TUBGCP6 | 1 | 0.48 | 0.12 | 0.814815 | 0 | TUBGCP6 | 22 | 22q13.33 | 48998245 | 49025528 |
| KIF16B | 1 | 0.106667 | 0.12 | 0.074074 | 0 | KIF16B | 20 | 20p12.1 | 16200749 | 16502079 |
| PCSK2 | 1 | 0.146667 | 0.133333 | 0.222222 | 0 | PCSK2 | 20 | 20p12.1 | 17155631 | 17413223 |
| LGALS13 | 1 | 0.333333 | 0.145667 | 0.740741 | 0 | LGALS13 | 19 | 19q13.2 | 44785009 | 44789955 |
| LGALS14 | 1 | 0.346667 | 0.12 | 0.740741 | 0 | LGALS14 | 19 | 19q13.2 | 44886786 | 44891929 |
| CLC | 1 | 0.346667 | 0.12 | 0.740741 | 0 | CLC | 19 | 19q13.2 | 44913735 | 44920509 |
| RPH3AL | 1 | 0.48 | 0.12 | 0.814815 | 0 | RPH3AL | 17 | 17p13.3 | 62294 | 202577 |
| VPS53 | 1 | 0.48 | 0.12 | 0.777778 | 0 | VPS53 | 17 | 17p13.3 | 361480 | 564847 |
| GEMIN4 | 1 | 0.48 | 0.12 | 0.777778 | 0 | GEMIN4 | 17 | 17p13.3 | 594411 | 602252 |
| ELP2P | 1 | 0.48 | 0.12 | 0.777778 | 0 | ELP2P | 17 | 17p13.3 | 602650 | 605327 |
| NXN | 1 | 0.466667 | 0.133333 | 0.777778 | 0 | NXN | 17 | 17p13.3 | 649335 | 829761 |
| TIMM22 | 1 | 0.466667 | 0.133333 | 0.777778 | 0 | TIMM22 | 17 | 17p13.3 | 847107 | 852141 |
| ABR | 1 | 0.466667 | 0.133333 | 0.777778 | 0 | ABR | 17 | 17p13.3 | 853509 | 959075 |
| YWHAE | 1 | 0.453333 | 0.133333 | 0.777778 | 0 | YWHAE | 17 | 17p13.3 | 1194586 | 1250307 |
| CRK | 1 | 0.453333 | 0.133333 | 0.777778 | 0 | CRK | 17 | 17p13.3 | 1272208 | 1306295 |
| INPP5K | 1 | 0.466667 | 0.133333 | 0.777778 | 0 | INPP5K | 17 | 17p13.3 | 1344622 | 1366933 |
| LOC100306951 | 1 | 0.466667 | 0.133333 | 0.777778 | 0 | LOC1003066951 | 17 | 17p13.3 | 1366963 | 1368139 |
| PITPNA | 1 | 0.466667 | 0.133333 | 0.777778 | 0 | PITPNA | 17 | 17p13.3 | 1368033 | 1412861 |
| PRPF8 | 1 | 0.466667 | 0.133333 | 0.777778 | 0 | PRPF8 | 17 | 17p13.3 | 1500673 | 1534927 |
| WDR81 | 1 | 0.466667 | 0.133333 | 0.777778 | 0 | WDR81 | 17 | 17p13.3 | 1566567 | 1588644 |
| SERPINF2 | 1 | 0.466667 | 0.133333 | 0.777778 | 0 | SERPINF2 | 17 | 17p13.3 | 1592880 | 1605310 |
| SERPINF1 | 1 | 0.466667 | 0.133333 | 0.777778 | 0 | SERPINF1 | 17 | 17p13.3 | 1612009 | 1527619 |
| SMYD4 | 1 | 0.466667 | 0.133333 | 0.777778 | 0 | SMYD4 | 17 | 17p13.3 | 1629579 | 1679926 |
| RPA1 | 1 | 0.466667 | 0.133333 | 0.777778 | 0 | RPA1 | 17 | 17p13.3 | 1680023 | 1749599 |
| RTN4RL1 | 1 | 0.466667 | 0.133333 | 0.777778 | 0 | RTN4RL1 | 17 | 17p13.3 | 1784721 | 1874929 |
| SMG6 | 1 | 0.466667 | 0.133333 | 0.777778 | 0 | SMG6 | 17 | 17p13.3 | 1909883 | 2153564 |
| SRR | 1 | 0.453333 | 0.133333 | 0.777778 | 0 | SRR | 17 | 17p13.3 | 2153998 | 2175304 |
| METT10D | 1 | 0.413333 | 0.133333 | 0.740741 | 0 | METT10D | 17 | 17p13.3 | 2266098 | 2361951 |
| PAFAH1B1 | 1 | 0.413333 | 0.133333 | 0.740741 | 0 | PAFAH1B1 | 17 | 17p13.3 | 2443673 | 2535660 |
| KIAA0664 | 1 | 0.426667 | 0.133333 | 0.740741 | 0 | KIAA0664 | 17 | 17p13.3 | 2539430 | 2561678 |
| RAP1GAP2 | 1 | 0.426667 | 0.133333 | 0.740741 | 0 | RAP1GAP2 | 17 | 17p13.3 | 2646482 | 2887786 |
| OR3A2 | 1 | 0.28 | 0.146667 | 0.740741 | 0 | OR3A2 | 17 | 17p13.3 | 3127934 | 3129019 |
| TRPV3 | 1 | 0.413333 | 0.133333 | 0.740741 | 0 | TRPV3 | 17 | 17p13.3 | 3363236 | 3408040 |
| TRPV1 | 1 | 0.413333 | 0.133333 | 0.740741 | 0 | TRPV1 | 17 | 17p13.3 | 3415490 | 3447086 |
| SHPK | 1 | 0.413333 | 0.133333 | 0.740741 | 0 | SHPK | 17 | 17p13.3 | 3458305 | 3486366 |
| CTNS | 1 | 0.413333 | 0.133333 | 0.740741 | 0 | CTNS | 17 | 17p13.3 | 3486511 | 3513147 |
| TMEM93 | 1 | 0.413333 | 0.133333 | 0.740741 | 0 | TMEM93 | 17 | 17p13.3 | 3518839 | 3519712 |
| P2RX5 | 1 | 0.413333 | 0.133333 | 0.740741 | 0 | P2RX5 | 17 | 17p13.3 | 3523271 | 3546333 |
| ITGAE | 1 | 0.413333 | 0.133333 | 0.740741 | 0 | ITGAE | 17 | 17p13.3 | 3564568 | 3651287 |
| GSG2 | 1 | 0.413333 | 0.133333 | 0.740741 | 0 | GSG2 | 17 | 17p13.3 | 3573946 | 3576742 |
| C17orf85 | 1 | 0.4 | 0.133333 | 0.740741 | 0 | C17orf85 | 17 | 17p13.2 | 3661209 | 3696290 |
| CAMKK1 | 1 | 0.413333 | 0.146667 | 0.777778 | 0 | CAMKK1 | 17 | 17p13.2 | 3710366 | 3743087 |
| P2RX1 | 1 | 0.413333 | 0.133333 | 0.777778 | 0 | P2RX1 | 17 | 17p13.2 | 3746634 | 3766710 |
| CDRT15P | 1 | 0.106667 | 0.146667 | 0.296296 | 0 | CDRT15P | 17 | 17p12 | 13868540 | 13869641 |
| MIR1288 | 1 | 0.32 | 0.12 | 0.481481 | 0 | MIR1288 | 17 | 17p11.2 | 16126053 | 16126128 |
| TRPV2 | 1 | 0.346667 | 0.12 | 0.518519 | 0 | TRPV2 | 17 | 17p11.2 | 16259613 | 16281043 |
| NCRNA001 | 1 | 0.346667 | 0.12 | 0.518519 | 0 | NCRNA001 | 17 | 17p11.2 | 16283026 | 16286064 |
| SNORD49B | 1 | 0.346667 | 0.12 | 0.518519 | 0 | SNORD498 | 17 | 17p11.2 | 16283548 | 16283596 |
| SNORD49A | 1 | 0.346667 | 0.12 | 0.518519 | 0 | SNORD49A | 17 | 17p11.2 | 16284075 | 16284146 |
| SNORD65 | 1 | 0.346667 | 0.12 | 0.518519 | 0 | SNORD65 | 17 | 17p11.2 | 16285265 | 16285338 |
| C17orf76 | 1 | 0.346667 | 0.12 | 0.518519 | 0 | C17orf76 | 17 | 17p11.2 | 16286053 | 16336206 |
| ZNF287 | 1 | 0.346667 | 0.12 | 0.518519 | 0 | ZNF287 | 17 | 17p11.2 | 16394356 | 16413246 |
| MPP3 | 1 | 0.466667 | 0.12 | 0.777778 | 0 | MPP3 | 17 | 17q21.31 | 39233693 | 39266605 |
| CD300LG | 1 | 0.466667 | 0.12 | 0.777778 | 0 | CD300LG | 17 | 17q21.31 | 39280042 | 39291128 |
| MPP2 | 1 | 0.466667 | 0.12 | 0.777778 | 0 | MPP2 | 17 | 17q21.31 | 39308253 | 39340640 |
| PPY | 1 | 0.466667 | 0.133333 | 0.777778 | 0 | PPY | 17 | 17q21.31 | 39373698 | 39375360 |
| PYY | 1 | 0.466667 | 0.133333 | 0.777778 | 0 | PYY | 17 | 17q21.31 | 39385633 | 39437364 |
| NAGS | 1 | 0.466667 | 0.133333 | 0.777778 | 0 | NAGS | 17 | 17q21.31 | 39437558 | 39441963 |
| TMEM101 | 1 | 0.466667 | 0.133333 | 0.777778 | 0 | TMEM101 | 17 | 17q21.31 | 39444082 | 39447872 |
| LSM12 | 1 | 0.466667 | 0.133333 | 0.777778 | 0 | LSM12 | 17 | 17q21.31 | 39467530 | 39500514 |
| G6PC3 | 1 | 0.466667 | 0.133333 | 0.777778 | 0 | G6PC3 | 17 | 17q21.31 | 39503624 | 39509238 |
| HDAC5 | 1 | 0.466667 | 0.133333 | 0.777778 | 0 | HDAC5 | 17 | 17q21.31 | 39509647 | 39556541 |
| C17orf53 | 1 | 0.466667 | 0.133333 | 0.777778 | 0 | C17orf53 | 17 | 17q21.31 | 39574852 | 39595371 |
| ASB16 | 1 | 0.466667 | 0.133333 | 0.777778 | 0 | ASB16 | 17 | 17q21.31 | 39603600 | 39611978 |
| C17orf65 | 1 | 0.466667 | 0.133333 | 0.777778 | 0 | C17orf65 | 17 | 17q21.31 | 39608878 | 39619609 |
| TMUB2 | 1 | 0.466667 | 0.133333 | 0.777778 | 0 | TMUB2 | 17 | 17q21.31 | 39619880 | 39624626 |
| ATXN7L3 | 1 | 0.466667 | 0.133333 | 0.777778 | 0 | ATXN7L3 | 17 | 17q21.31 | 39624699 | 39631056 |
| UBTF | 1 | 0.466667 | 0.133333 | 0.777778 | 0 | UBTF | 17 | 17q21.31 | 39637927 | 39653777 |
| SLC4A1 | 1 | 0.466667 | 0.133333 | 0.777778 | 0 | SLC4A1 | 17 | 17q21.31 | 39681284 | 39701029 |
| SLC25A39 | 1 | 0.466667 | 0.12 | 0.777778 | 0 | SLC25A39 | 17 | 17q21.31 | 39752519 | 39757744 |

TABLE 2-continued

Gene list for predicting prostate cancer relapse using prostate cancer tissue

| Symbol | freq. use | freq. amp. case | freq. del. case | freq. control | freq. control | Gene. Symbol | chromo-some | cytoband | Transcript. start | Transcript. end |
|---|---|---|---|---|---|---|---|---|---|---|
| GRN | 1 | 0.466667 | 0.12 | 0.777778 | 0 | GRN | 17 | 17q21.31 | 39778017 | 39785997 |
| FAM171A2 | 1 | 0.466667 | 0.12 | 0.777778 | 0 | FAM171A2 | 17 | 17q21.31 | 39786627 | 39796762 |
| ITGA2B | 1 | 0.466667 | 0.12 | 0.777778 | 0 | ITGA2B | 17 | 17q21.31 | 39805076 | 39822400 |
| GPATCH8 | 1 | 0.466667 | 0.12 | 0.777778 | 0 | GPATCH8 | 17 | 17q21.31 | 39828176 | 39936329 |
| FZD2 | 1 | 0.426667 | 0.12 | 0.777778 | 0 | FZD2 | 17 | 17q21.31 | 39990451 | 39992434 |
| C17orf104 | 1 | 0.453333 | 0.12 | 0.777778 | 0 | C17orf104 | 17 | 17q21.31 | 40089288 | 40108690 |
| ADAM11 | 1 | 0.48 | 0.12 | 0.777778 | 0 | ADAM11 | 17 | 17q21.31 | 40192094 | 40214741 |
| HIGD1B | 1 | 0.466667 | 0.12 | 0.777778 | 0 | HIGD1B | 17 | 17q21.31 | 40280805 | 40283375 |
| EFTUD2 | 1 | 0.466667 | 0.12 | 0.777778 | 0 | EFTUD2 | 17 | 17q21.31 | 40283181 | 40332520 |
| KIF18B | 1 | 0.48 | 0.12 | 0.777778 | 0 | KIF18B | 17 | 17q21.31 | 40358974 | 40380609 |
| C1QL1 | 1 | 0.48 | 0.12 | 0.777778 | 0 | C1QL1 | 17 | 17q21.31 | 40392587 | 40401171 |
| DCAKD | 1 | 0.48 | 0.12 | 0.777778 | 0 | DCAKD | 17 | 17q21.31 | 40456232 | 40484505 |
| NMT1 | 1 | 0.48 | 0.12 | 0.777778 | 0 | NMT1 | 17 | 17q21.31 | 40494206 | 40541909 |
| PLCD3 | 1 | 0.48 | 0.12 | 0.777778 | 0 | PLCD3 | 17 | 17q21.31 | 40544534 | 40565418 |
| ACBD4 | 1 | 0.48 | 0.12 | 0.777778 | 0 | ACBD4 | 17 | 17q21.31 | 40565493 | 40577325 |
| HEXIM1 | 1 | 0.48 | 0.12 | 0.777778 | 0 | HEXIM1 | 17 | 17q21.31 | 40580467 | 40585252 |
| HEXIM2 | 1 | 0.48 | 0.12 | 0.777778 | 0 | HEXIM2 | 17 | 17q21.31 | 40594047 | 40603190 |
| FMNL1 | 1 | 0.48 | 0.12 | 0.777778 | 0 | FMNL1 | 17 | 17q21.31 | 40655075 | 40680467 |
| LOC100133991 | 1 | 0.48 | 0.12 | 0.777778 | 0 | LOC100133991 | 17 | 17q21.31 | 40681086 | 40701780 |
| C17orf46 | 1 | 0.48 | 0.12 | 0.777778 | 0 | C17orf46 | 17 | 17q21.31 | 40687543 | 40695263 |
| MAP3K14 | 1 | 0.48 | 0.12 | 0.777778 | 0 | MAP3K14 | 17 | 17q21.31 | 40696271 | 40750198 |
| ARHGAP27 | 1 | 0.48 | 0.12 | 0.777778 | 0 | ARHGAP27 | 17 | 17q21.31 | 40827051 | 40839233 |
| TNRC6A | 1 | 0.32 | 0.12 | 0.666667 | 0 | TNRC6A | 16 | 16p12.1 | 24648550 | 24745049 |
| FLJ30679 | 1 | 0.413333 | 0.133333 | 0.666667 | 0 | FLJ30679 | 16 | 16q24.1 | 85146427 | 85148407 |
| FOXC2 | 1 | 0.413333 | 0.133333 | 0.666667 | 0 | FOXC2 | 16 | 16q24.1 | 85158358 | 85160037 |
| FBXO31 | 1 | 0.426667 | 0.146667 | 0.665667 | 0 | FBXO31 | 16 | 16q24.2 | 85920445 | 85974896 |
| ZCCHC14 | 1 | 0.426667 | 0.146667 | 0.666667 | 0 | ZCCHC14 | 16 | 16q24.2 | 85997353 | 86082962 |
| JPH3 | 1 | 0.426667 | 0.173333 | 0.666667 | 0 | JPH3 | 16 | 16q24.2 | 86194000 | 86289263 |
| SLC7A5 | 1 | 0.426667 | 0.186667 | 0.666667 | 0 | SLC7A5 | 16 | 16q24.2 | 86421130 | 86460602 |
| CA5A | 1 | 0.426667 | 0.186667 | 0.666667 | 0 | CA5A | 16 | 16q24.2 | 86479126 | 86527614 |
| BANP | 1 | 0.426667 | 0.186667 | 0.666667 | 0 | BANP | 16 | 16q24.2 | 86542539 | 86668426 |
| ZFPM1 | 1 | 0.44 | 0.2 | 0.666667 | 0 | ZFPM1 | 16 | 16q24.2 | 87047515 | 87129076 |
| ZC3H18 | 1 | 0.44 | 0.2 | 0.666667 | 0 | ZC3H18 | 16 | 16q24.2 | 87164290 | 87225873 |
| IL17C | 1 | 0.44 | 0.2 | 0.703704 | 0 | IL17C | 16 | 16q24.3 | 87232502 | 87234384 |
| CYBA | 1 | 0.44 | 0.2 | 0.703704 | 0 | CYBA | 16 | 16q24.3 | 87237198 | 87244959 |
| MVD | 1 | 0.44 | 0.2 | 0.703704 | 0 | MVD | 16 | 16q24.3 | 87245849 | 87256997 |
| MGC23284 | 1 | 0.44 | 0.2 | 0.703704 | 0 | MGC23284 | 16 | 16q24.3 | 87257282 | 87281054 |
| SNAI3 | 1 | 0.44 | 0.2 | 0.703704 | 0 | SNAI3 | 16 | 16q24.3 | 87271591 | 87280384 |
| RNF166 | 1 | 0.44 | 0.2 | 0.703704 | 0 | RNF166 | 16 | 16q24.3 | 87290410 | 87300302 |
| GALNS | 1 | 0.466667 | 0.2 | 0.703704 | 0 | GALNS | 16 | 16q24.3 | 87407643 | 87450876 |
| TRAPPC2L | 1 | 0.466667 | 0.2 | 0.703704 | 0 | TRAPPC2L | 16 | 16q24.3 | 87451007 | 87455022 |
| CBFA2T3 | 1 | 0.466667 | 0.2 | 0.703704 | 0 | CBFA2T3 | 16 | 16q24.3 | 87468768 | 87570903 |
| ACSF3 | 1 | 0.466667 | 0.2 | 0.703704 | 0 | ACSF3 | 16 | 16q24.3 | 87687755 | 87748499 |
| C16orf81 | 1 | 0.466667 | 0.2 | 0.703704 | 0 | C16orf81 | 16 | 16q24.3 | 87753129 | 87757585 |
| CDH15 | 1 | 0.466667 | 0.2 | 0.703704 | 0 | CDH15 | 16 | 16q24.3 | 87765664 | 87789402 |
| ANKRD11 | 1 | 0.48 | 0.2 | 0.703704 | 0 | ANKRD11 | 16 | 16q24.3 | 87861536 | 88084471 |
| SPG7 | 1 | 0.48 | 0.186667 | 0.703704 | 0 | SPG7 | 16 | 16q24.3 | 88102306 | 88151676 |
| RPL13 | 1 | 0.48 | 0.186667 | 0.703704 | 0 | RPL13 | 16 | 16q24.3 | 88154591 | 88157570 |
| SNORD68 | 1 | 0.48 | 0.186667 | 0.703704 | 0 | SNORD68 | 16 | 16q24.3 | 88155339 | 88155411 |
| CDK10 | 1 | 0.48 | 0.186667 | 0.703704 | 0 | CDK10 | 16 | 16q24.3 | 88280577 | 88290273 |
| SPATA2L | 1 | 0.48 | 0.186667 | 0.703704 | 0 | SPATA2L | 16 | 16q24.3 | 88290266 | 88295601 |
| C16orf7 | 1 | 0.48 | 0.186667 | 0.703704 | 0 | C16orf7 | 16 | 16q24.3 | 88301042 | 88314896 |
| ZNF276 | 1 | 0.48 | 0.186667 | 0.703704 | 0 | ZNF276 | 16 | 16q24.3 | 88314894 | 88334834 |
| SPIRE2 | 1 | 0.48 | 0.173333 | 0.740741 | 0 | SPIRE2 | 16 | 16q24.3 | 88422403 | 88465229 |
| TUBB3 | 1 | 0.48 | 0.16 | 0.740741 | 0 | TUBB3 | 16 | 16q24.3 | 88517246 | 88530007 |
| DEF8 | 1 | 0.48 | 0.16 | 0.740741 | 0 | DEF8 | 16 | 16q24.3 | 88542652 | 88553276 |
| CENPBD1 | 1 | 0.48 | 0.16 | 0.740741 | 0 | CENPBD1 | 16 | 16q24.3 | 88563702 | 88566444 |
| OR11H4 | 1 | 0.08 | 0.12 | 0.111111 | 0 | OR11H4 | 14 | 14q11.2 | 19780791 | 19781766 |
| G2E3 | 1 | 0.026667 | 0.173333 | 0 | 0 | G2E3 | 14 | 14q12 | 30098080 | 30158798 |
| SCFD1 | 1 | 0.026667 | 0.133333 | 0 | 0 | SCFD1 | 14 | 14q12 | 30161272 | 30274770 |
| COCH | 1 | 0.053333 | 0.133333 | 0 | 0 | COCH | 14 | 14q12 | 30413492 | 30429574 |
| STRN3 | 1 | 0.16 | 0.053333 | 0 | 0 | STRN3 | 14 | 14q12 | 30432756 | 30565359 |
| AP4S1 | 1 | 0.173333 | 0.053333 | 0 | 0 | AP4S1 | 14 | 14q12 | 30564434 | 30632390 |
| HECTD1 | 1 | 0.186667 | 0.053333 | 0 | 0 | HECTD1 | 14 | 14q12 | 30639075 | 30746441 |
| AKAP6 | 1 | 0.04 | 0.146667 | 0 | 0 | AKAP6 | 14 | 14q13.1 | 31868230 | 32372020 |
| NPAS3 | 1 | 0.093333 | 0.133333 | 0 | 0 | NPAS3 | 14 | 14q13.1 | 32478210 | 33343133 |
| SAV1 | 1 | 0.12 | 0.013333 | 0 | 0.037037 | SAV1 | 14 | 14q22.1 | 50170110 | 50204774 |
| NIN | 1 | 0.12 | 0 | 0 | 0.037037 | NIN | 14 | 14q22.1 | 50256231 | 50367590 |
| BMP4 | 1 | 0.04 | 0.133333 | 0.037037 | 0 | BMP4 | 14 | 14q22.2 | 53486205 | 53493305 |
| SYT16 | 1 | 0.013333 | 0.2 | 0.037037 | 0 | SYT16 | 14 | 14q23.2 | 61532294 | 61638181 |
| GPHN | 1 | 0.08 | 0.173333 | 0.185185 | 0 | GPHN | 14 | 14q23.3 | 66043878 | 66718279 |
| ERH | 1 | 0.186667 | 0.133333 | 0.333333 | 0 | ERH | 14 | 14q24.1 | 68916593 | 68934775 |
| SMOC1 | 1 | 0.186667 | 0.12 | 0.333333 | 0 | SMOC1 | 14 | 14q24.2 | 69415896 | 69568837 |
| NRXN3 | 1 | 0.066667 | 0.173333 | 0.222222 | 0 | NRXN3 | 14 | 14q24.3 | 77939846 | 79400514 |

TABLE 2-continued

Gene list for predicting prostate cancer relapse using prostate cancer tissue

| Symbol | freq. use | freq. amp. case | freq. del. case | freq. control | freq. control | Gene. Symbol | chromo-some | cytoband | Tran-script. start | Tran-script. end |
|---|---|---|---|---|---|---|---|---|---|---|
| LOC100101 | 1 | 0.106667 | 0.16 | 0.259259 | 0 | LOC100101 | 13 | 13q12.11 | 18734941 | 18817114 |
| TSC22D1 | 1 | 0.12 | 0.226667 | 0 | 0.111111 | TSC22D1 | 13 | 13q14.11 | 43905655 | 44048702 |
| RCBTB1 | 1 | 0.12 | 0.253333 | 0 | 0.148148 | RCBTB1 | 13 | 13q14.3 | 49004083 | 49057721 |
| ARL11 | 1 | 0.12 | 0.253333 | 0 | 0.148148 | ARL11 | 13 | 13q14.3 | 49100625 | 49105733 |
| EBPL | 1 | 0.12 | 0.253333 | 0 | 0.148148 | EBPL | 13 | 13q14.3 | 49132811 | 49163625 |
| KPNA3 | 1 | 0.12 | 0.253333 | 0 | 0.148148 | KPNA3 | 13 | 13q14.3 | 49171445 | 49265057 |
| LOC220429 | 1 | 0.12 | 0.253333 | 0 | 0.148148 | LOC220429 | 13 | 13q14.3 | 49362546 | 49365518 |
| C13orf1 | 1 | 0.12 | 0.253333 | 0 | 0.148148 | C13orf1 | 13 | 13q14.3 | 49384843 | 49408627 |
| NDUFA9 | 1 | 0.213333 | 0.133333 | 0.592593 | 0 | NDUFA9 | 12 | 12p13.32 | 4628544 | 4666661 |
| VWF | 1 | 0.226667 | 0.133333 | 0.592593 | 0 | VWF | 12 | 12p13.31 | 5928301 | 6104098 |
| GABARAPL | 1 | 0.146667 | 0.133333 | 0.111111 | 0 | GABARAPL | 12 | 12p13.2 | 10256756 | 10266992 |
| ETV6 | 1 | 0.066667 | 0.16 | 0.111111 | 0 | ETV6 | 12 | 12p13.2 | 11694055 | 11939593 |
| BCL2L14 | 1 | 0.173333 | 0.146667 | 0.148148 | 0 | BCL2L14 | 12 | 12p13.2 | 12115145 | 12143895 |
| LRP6 | 1 | 0.16 | 0.146667 | 0.148148 | 0 | LRP6 | 12 | 12p13.2 | 12160228 | 12311079 |
| MANSC1 | 1 | 0.16 | 0.146667 | 0.148148 | 0 | MANSC1 | 12 | 12p13.2 | 12373485 | 12394437 |
| LOH12CR2 | 1 | 0.16 | 0.146667 | 0.148148 | 0 | LOH12CR2 | 12 | 12p13.2 | 12399611 | 12401269 |
| LOH12CR1 | 1 | 0.16 | 0.146667 | 0.148148 | 0 | LOH12CR1 | 12 | 12p13.2 | 12401287 | 12511106 |
| DUSP16 | 1 | 0.133333 | 0.146667 | 0.111111 | 0 | DUSP16 | 12 | 12p13.2 | 12520098 | 12606585 |
| CREBL2 | 1 | 0.106667 | 0.16 | 0.074074 | 0 | CREBL2 | 12 | 12p13.1 | 12656098 | 12689309 |
| GPR19 | 1 | 0.106667 | 0.16 | 0.074074 | 0 | GPR19 | 12 | 12p13.1 | 12705263 | 12740389 |
| CDKN1B | 1 | 0.106667 | 0.16 | 0.074074 | 0 | CDKN1B | 12 | 12p13.1 | 12761569 | 12766573 |
| APOLD1 | 1 | 0.106667 | 0.16 | 0.074074 | 0 | APOLD1 | 12 | 12p13.1 | 12770118 | 12835667 |
| MIR613 | 1 | 0.106667 | 0.16 | 0.074074 | 0 | MIR613 | 12 | 12p13.1 | 12808850 | 12808944 |
| DDX47 | 1 | 0.133333 | 0.146667 | 0.074074 | 0 | DDX47 | 12 | 12p13.1 | 12857547 | 12874183 |
| RPL13AP20 | 1 | 0.133333 | 0.146667 | 0.074074 | 0 | RPL13AP20 | 12 | 12p13.1 | 12919678 | 12920337 |
| GPRC5A | 1 | 0.133333 | 0.146667 | 0.074074 | 0 | GPRC5A | 12 | 12p13.1 | 12935223 | 12957868 |
| MIR614 | 1 | 0.133333 | 0.146667 | 0.074074 | 0 | MIR614 | 12 | 12p13.1 | 12960030 | 12960120 |
| GPRC5D | 1 | 0.133333 | 0.146667 | 0.074074 | 0 | GPRC5D | 12 | 12p13.1 | 12984976 | 12994586 |
| HEBP1 | 1 | 0.133333 | 0.146667 | 0.074074 | 0 | HEBP1 | 12 | 12p13.1 | 13019066 | 13044489 |
| KIAA1467 | 1 | 0.12 | 0.146667 | 0.074074 | 0 | KIAA1467 | 12 | 12p13.1 | 13088582 | 13127651 |
| GRIN2B | 1 | 0 | 0.186667 | 0.037037 | 0 | GRIN2B | 12 | 12p13.1 | 13605677 | 14024290 |
| ST8SIA1 | 1 | 0.013333 | 0.16 | 0 | 0 | ST8SIA1 | 12 | 12p12.1 | 22237592 | 22378916 |
| KIAA0528 | 1 | 0.066667 | 0.146667 | 0.037037 | 0 | KIAA0528 | 12 | 12p12.1 | 22492785 | 22588720 |
| ETNK1 | 1 | 0.066667 | 0.146667 | 0.037037 | 0 | ETNK1 | 12 | 12p12.1 | 22669343 | 22688617 |
| BCAT1 | 1 | 0.013333 | 0.213333 | 0.037037 | 0 | BCAT1 | 12 | 12p12.1 | 24855546 | 24993576 |
| CASC1 | 1 | 0.066667 | 0.16 | 0 | 0 | CASC1 | 12 | 12p12.1 | 25152490 | 25239362 |
| IFLTD1 | 1 | 0.013333 | 0.12 | 0.037037 | 0 | IFLTD1 | 12 | 12p12.1 | 25520283 | 25597446 |
| OVCH1 | 1 | 0 | 0.213333 | 0 | 0 | OVCH1 | 12 | 12p11.22 | 29471756 | 29541887 |
| TMTC1 | 1 | 0.013333 | 0.12 | 0 | 0 | TMTC1 | 12 | 12p11.22 | 29545024 | 29828960 |
| FAM60A | 1 | 0.186667 | 0.12 | 0.222222 | 0 | FAM60A | 12 | 12p11.21 | 31324794 | 31370389 |
| SRGAP1 | 1 | 0.146667 | 0.04 | 0 | 0 | SRGAP1 | 12 | 12q14.2 | 62524808 | 62827881 |
| RASSF3 | 1 | 0.16 | 0.013333 | 0 | 0.037037 | RASSF3 | 12 | 12q14.2 | 63290560 | 63375460 |
| UHRF1BP1L | 1 | 0.133333 | 0.093333 | 0 | 0 | UHRF1BP1L | 12 | 12q23.1 | 98954994 | 99060774 |
| MIR1827 | 1 | 0.213333 | 0.026667 | 0 | 0 | MIR1827 | 12 | 12q23.1 | 99107793 | 99107859 |
| SCYL2 | 1 | 0.145667 | 0.026667 | 0 | 0 | SCYL2 | 12 | 12q23.1 | 99185680 | 99258046 |
| SLC17A8 | 1 | 0.133333 | 0.026667 | 0 | 0 | SLC17A8 | 12 | 12q23.1 | 99274988 | 99339968 |
| NR1H4 | 1 | 0.146667 | 0.026667 | 0 | 0 | NR1H4 | 12 | 12q23.1 | 99391810 | 99481775 |
| GAS2L3 | 1 | 0.146667 | 0.026667 | 0 | 0 | GAS2L3 | 12 | 12q23.1 | 99491620 | 99542817 |
| SLC5A8 | 1 | 0.106667 | 0.133333 | 0.111111 | 0 | SLC5A8 | 12 | 12q23.2 | 1E+08 | 1E+08 |
| PAH | 1 | 0.093333 | 0.12 | 0.148148 | 0 | PAH | 12 | 12q23.2 | 1.02E+08 | 1.02E+08 |
| C12orf42 | 1 | 0.106667 | 0.12 | 0.148148 | 0 | C12orf42 | 12 | 12q23.2 | 1.02E+08 | 1.02E+08 |
| BTBD10 | 1 | 0.093333 | 0.12 | 0.148148 | 0 | BTBD10 | 11 | 11p15.2 | 13366132 | 13441415 |
| OR5B12 | 1 | 0.08 | 0.133333 | 0.148148 | 0 | OR5B12 | 11 | 11q12.1 | 57963256 | 57964201 |
| LPXN | 1 | 0.08 | 0.133333 | 0.148148 | 0 | LPXN | 11 | 11q12.1 | 58050922 | 58102216 |
| RAB30 | 1 | 0.12 | 0.04 | 0 | 0 | RAB30 | 11 | 11q14.1 | 82370126 | 82460533 |
| CCDC90B | 1 | 0.053333 | 0.12 | 0 | 0 | CCDC90B | 11 | 11q14.1 | 82650150 | 82675026 |
| FAT3 | 1 | 0.04 | 0.173333 | 0 | 0 | FAT3 | 11 | 11q14.3 | 91724910 | 92269284 |
| BIRC3 | 1 | 0.133333 | 0.066667 | 0 | 0.074074 | BIRC3 | 11 | 11q22.2 | 1.02E+08 | 1.02E+08 |
| MMP7 | 1 | 0.12 | 0.066667 | 0 | 0.074074 | MMP7 | 11 | 11q22.2 | 1.02E+08 | 1.02E+08 |
| DDX10 | 1 | 0.066667 | 0.16 | 0.111111 | 0 | DDX10 | 11 | 11q22.3 | 1.08E+08 | 1.08E+08 |
| FRMPD2 | 1 | 0.226667 | 0.16 | 0.37037 | 0 | FRMPD2 | 10 | 10q11.22 | 49034608 | 49152948 |
| ERCC6 | 1 | 0.226667 | 0.173333 | 0.333333 | 0 | ERCC6 | 10 | 10q11.23 | 50334497 | 50417154 |
| PGBD3 | 1 | 0.226667 | 0.173333 | 0.333333 | 0 | PGBD3 | 10 | 10q11.23 | 50393250 | 50402333 |
| SGMS1 | 1 | 0.133333 | 0.133333 | 0.222222 | 0 | SGMS1 | 10 | 10q11.23 | 51735351 | 52053744 |
| FAM13C | 1 | 0.12 | 0.133333 | 0 | 0.074074 | FAM13C | 10 | 10q21.1 | 60675896 | 60792359 |
| ARID5B | 1 | 0.146667 | 0.026667 | 0 | 0 | ARID5B | 10 | 10q21.2 | 63331449 | 63526710 |
| ADO | 1 | 0.146667 | 0.04 | 0 | 0 | ADO | 10 | 10q21.2 | 64234522 | 64238246 |
| EGR2 | 1 | 0.146667 | 0.04 | 0 | 0 | EGR2 | 10 | 10q21.2 | 64241766 | 64246133 |
| JMJD1C | 1 | 0.173333 | 0.026667 | 0 | 0 | JMJD1C | 10 | 10q21.2 | 64596994 | 64698093 |
| REEP3 | 1 | 0.173333 | 0.04 | 0 | 0 | REEP3 | 10 | 10q21.3 | 64951129 | 65051979 |
| SLC24A2 | 1 | 0.026667 | 0.173333 | 0.037037 | 0 | SLC24A2 | 9 | 9p22.1 | 19505978 | 19776927 |
| MLLT3 | 1 | 0.026667 | 0.133333 | 0 | 0 | MLLT3 | 9 | 9p21.3 | 20334968 | 20612515 |
| IFNA13 | 1 | 0.04 | 0.146667 | 0 | 0 | IFNA13 | 9 | 9p21.3 | 21357371 | 21358076 |
| IFNA1 | 1 | 0.026667 | 0.16 | 0 | 0 | IFNA1 | 9 | 9p21.3 | 21430440 | 21431316 |

TABLE 2-continued

Gene list for predicting prostate cancer relapse using prostate cancer tissue

| Symbol | freq. use | freq. amp. case | freq. del. case | freq. control | freq. control | Gene. Symbol | chromo- some | cytoband | Tran- script. start | Tran- script. end |
|---|---|---|---|---|---|---|---|---|---|---|
| LOC554202 | 1 | 0.026667 | 0.16 | 0 | 0 | LOC554202 | 9 | 9p21.3 | 21444267 | 21549698 |
| IFNE | 1 | 0.026667 | 0.16 | 0 | 0 | IFNE | 9 | 9p21.3 | 21470841 | 21472313 |
| 1-Dec | 1 | 0.12 | 0.133333 | 0.333333 | 0 | 1-Dec | 9 | 9q33.1 | 1.17E+08 | 1.17E+08 |
| PAPPA | 1 | 0.093333 | 0.12 | 0.259259 | 0 | PAPPA | 9 | 9q33.1 | 1.18E+08 | 1.18E+08 |
| TUBBP5 | 1 | 0.573333 | 0.12 | 0.851852 | 0 | TUBBP5 | 9 | 9q34.3 | 1.4E+08 | 1.4E+08 |
| TMEM66 | 1 | 0.12 | 0.36 | 0 | 0.185185 | TMEM66 | 8 | 8p12 | 30040173 | 30060192 |
| LEPROTL1 | 1 | 0.12 | 0.36 | 0 | 0.185185 | LEPROTL1 | 8 | 8p12 | 30072464 | 30114755 |
| MBOAT4 | 1 | 0.12 | 0.36 | 0 | 0.185185 | MBOAT4 | 8 | 8p12 | 30108729 | 30121743 |
| DCTN6 | 1 | 0.12 | 0.36 | 0 | 0.185185 | DCTN6 | 8 | 8p12 | 30133355 | 30160603 |
| RBPMS | 1 | 0.133333 | 0.36 | 0 | 0.185185 | RBPMS | 8 | 8p12 | 30361486 | 30549277 |
| UBXN8 | 1 | 0.186667 | 0.373333 | 0 | 0.185185 | UBXN8 | 8 | 8p12 | 30721232 | 30744063 |
| TEX15 | 1 | 0.133333 | 0.386667 | 0 | 0.222222 | TEX15 | 8 | 8p12 | 30808602 | 30826076 |
| BEYLA | 1 | 0.173333 | 0.186667 | 0.185185 | 0 | BEYLA | 8 | 8q11.1 | 47871673 | 47886573 |
| NKAIN3 | 1 | 0.106667 | 0.133333 | 0.111111 | 0 | NKAIN3 | 8 | 8q12.3 | 63324055 | 64066183 |
| STEAP1 | 1 | 0.146667 | 0.12 | 0 | 0.185185 | STEAP1 | 7 | 7q21.13 | 89621625 | 89632078 |
| GTPBP10 | 1 | 0.12 | 0.053333 | 0 | 0.074074 | GTPBP10 | 7 | 7q21.13 | 89813926 | 89854587 |
| CLDN12 | 1 | 0.12 | 0.053333 | 0 | 0.074074 | CLDN12 | 7 | 7q21.13 | 89870732 | 89883205 |
| ENPP5 | 1 | 0.04 | 0.133333 | 0.111111 | 0 | ENPP5 | 6 | 6p12.3 | 46235721 | 46246677 |
| CYP39A1 | 1 | 0.04 | 0.12 | 0.074074 | 0 | CYP39A1 | 6 | 6p12.3 | 46525404 | 46728483 |
| MEP1A | 1 | 0.04 | 0.12 | 0.074074 | 0 | MEP1A | 6 | 6p12.3 | 46869053 | 46915479 |
| SMAP1 | 1 | 0.186667 | 0.146667 | 0 | 0.185185 | SMAP1 | 6 | 6q13 | 71434200 | 71628438 |
| C6orf147 | 1 | 0.2 | 0.186667 | 0 | 0.111111 | C6orf147 | 6 | 6q13 | 74040583 | 74076810 |
| DDX43 | 1 | 0.186667 | 0.186667 | 0 | 0.111111 | DDX43 | 6 | 6q13 | 74161006 | 74184004 |
| MTO1 | 1 | 0.173333 | 0.2 | 0 | 0.111111 | MTO1 | 6 | 6q13 | 74228175 | 74267901 |
| SLC17A5 | 1 | 0.186667 | 0.186667 | 0 | 0.111111 | SLC17A5 | 6 | 6q13 | 74359823 | 74420459 |
| CD109 | 1 | 0.12 | 0.16 | 0 | 0.111111 | CD109 | 6 | 6q13 | 74462229 | 74594761 |
| MYO6 | 1 | 0.146667 | 0.173333 | 0 | 0.222222 | MYO6 | 6 | 6q14.1 | 76515629 | 76685975 |
| GABRR1 | 1 | 0.12 | 0.2 | 0 | 0.185185 | GABRR1 | 6 | 6q15 | 89943942 | 89984216 |
| GABRR2 | 1 | 0.133333 | 0.2 | 0 | 0.185185 | GABRR2 | 6 | 6q15 | 90023958 | 90081687 |
| RRAGD | 1 | 0.133333 | 0.2 | 0 | 0.185185 | RRAGD | 6 | 6q15 | 90131056 | 90178715 |
| ANKRD6 | 1 | 0.12 | 0.2 | 0 | 0.185185 | ANKRD6 | 6 | 6q15 | 90199616 | 90400125 |
| GJA1 | 1 | 0.133333 | 0.213333 | 0 | 0.296296 | GJA1 | 6 | 6q22.31 | 1.22E+08 | 1.22E+08 |
| ARHGAP18 | 1 | 0.013333 | 0.146667 | 0.037037 | 0 | ARHGAP18 | 6 | 6q22.33 | 1.3E+08 | 1.3E+08 |
| C6orf191 | 1 | 0.013333 | 0.133333 | 0 | 0 | C6orf191 | 6 | 6q22.33 | 1.3E+08 | 1.3E+08 |
| L3MBTL3 | 1 | 0.013333 | 0.133333 | 0 | 0 | L3MBTL3 | 6 | 6q23.1 | 1.3E+08 | 1.31E+08 |
| SAMD3 | 1 | 0.026667 | 0.12 | 0 | 0 | SAMD3 | 6 | 6q23.1 | 1.31E+08 | 1.31E+08 |
| RPS12 | 1 | 0.146667 | 0.026667 | 0 | 0 | RPS12 | 6 | 6q23.2 | 1.33E+08 | 1.33E+08 |
| SNORD101 | 1 | 0.146667 | 0.026667 | 0 | 0 | SNORD101 | 6 | 6q23.2 | 1.33E+08 | 1.33E+08 |
| SNORD100 | 1 | 0.133333 | 0.04 | 0 | 0 | SNORD100 | 6 | 6q23.2 | 1.33E+08 | 1.33E+08 |
| SNORA33 | 1 | 0.133333 | 0.04 | 0 | 0 | SNORA33 | 6 | 6q23.2 | 1.33E+08 | 1.33E+08 |
| EYA4 | 1 | 0 | 0.133333 | 0 | 0 | EYA4 | 6 | 6q23.2 | 1.34E+08 | 1.34E+08 |
| AHI1 | 1 | 0 | 0.146667 | 0 | 0 | AHI1 | 6 | 6q23.3 | 1.36E+08 | 1.36E+08 |
| ADAT2 | 1 | 0 | 0.133333 | 0 | 0 | ADAT2 | 6 | 6q24.2 | 1.44E+08 | 1.44E+08 |
| CKMT2 | 1 | 0.12 | 0.093333 | 0 | 0.037037 | CKMT2 | 5 | 5q14.1 | 80564895 | 80597974 |
| DMXL1 | 1 | 0.16 | 0.106667 | 0 | 0.111111 | DMXL1 | 5 | 5q23.1 | 1.18E+08 | 1.19E+08 |
| LARS | 1 | 0.16 | 0 | 0 | 0.037037 | LARS | 5 | 5q32 | 1.45E+08 | 1.46E+08 |
| RBM27 | 1 | 0.16 | 0 | 0 | 0.037037 | RBM27 | 5 | 5q32 | 1.46E+08 | 1.46E+08 |
| ZNF718 | 1 | 0.253333 | 0.133333 | 0.703704 | 0 | ZNF718 | 4 | 4p16.3 | 43277 | 146491 |
| MIR572 | 1 | 0.04 | 0.12 | 0.074074 | 0 | MIR572 | 4 | 4p15.33 | 10979549 | 10979643 |
| C1QTNF7 | 1 | 0.013333 | 0.133333 | 0 | 0 | C1QTNF7 | 4 | 4p15.33 | 14950658 | 15056889 |
| CD38 | 1 | 0.12 | 0.053333 | 0 | 0 | CD38 | 4 | 4p15.32 | 15389029 | 15459805 |
| FGFBP1 | 1 | 0.133333 | 0.053333 | 0 | 0 | FGFBP1 | 4 | 4p15.32 | 15546290 | 15549070 |
| PROM1 | 1 | 0.133333 | 0.053333 | 0 | 0 | PROM1 | 4 | 4p15.32 | 15578947 | 15694693 |
| TAPT1 | 1 | 0.026667 | 0.146667 | 0 | 0 | TAPT1 | 4 | 4p15.32 | 15771226 | 15837260 |
| FLJ39653 | 1 | 0.026667 | 0.146667 | 0 | 0 | FLJ39653 | 4 | 4p15.32 | 15837384 | 15868909 |
| LDB2 | 1 | 0.026667 | 0.133333 | 0 | 0 | LDB2 | 4 | 4p15.32 | 16112262 | 16509523 |
| QDPR | 1 | 0.146667 | 0.04 | 0 | 0 | QDPR | 4 | 4p15.32 | 17097118 | 17122956 |
| CLRN2 | 1 | 0.146667 | 0.04 | 0 | 0 | CLRN2 | 4 | 4p15.32 | 17125886 | 17137826 |
| LAP3 | 1 | 0.146667 | 0.04 | 0 | 0 | LAP3 | 4 | 4p15.32 | 17188025 | 17218689 |
| FAM184B | 1 | 0.146667 | 0.04 | 0 | 0 | FAM184B | 4 | 4p15.32 | 17242809 | 17392234 |
| DCAF16 | 1 | 0.146667 | 0.04 | 0 | 0 | DCAF16 | 4 | 4p15.32 | 17411376 | 17421486 |
| GPR125 | 1 | 0.026667 | 0.226667 | 0 | 0 | GPR125 | 4 | 4p15.31 | 21998097 | 22126771 |
| GBA3 | 1 | 0.026667 | 0.213333 | 0 | 0 | GBA3 | 4 | 4p15.31 | 22303646 | 22430291 |
| PARM1 | 1 | 0.04 | 0.146667 | 0 | 0 | PARM1 | 4 | 4q13.3 | 76077322 | 76194348 |
| FRAS1 | 1 | 0.026667 | 0.12 | 0 | 0 | FRAS1 | 4 | 4q21.21 | 79197748 | 79586810 |
| SLC10A6 | 1 | 0.12 | 0.026667 | 0 | 0 | SLC10A6 | 4 | 4q21.3 | 87963645 | 87989441 |
| AFF1 | 1 | 0.146667 | 0.013333 | 0 | 0 | AFF1 | 4 | 4q21.3 | 88075178 | 88281230 |
| KLHL8 | 1 | 0.12 | 0.013333 | 0 | 0 | KLHL8 | 4 | 4q22.1 | 88301238 | 88360699 |
| HSD17B13 | 1 | 0.12 | 0.013333 | 0 | 0 | HSD17B13 | 4 | 4q22.1 | 88443965 | 88463081 |
| HSD17B11 | 1 | 0.12 | 0.013333 | 0 | 0 | HSD17B11 | 4 | 4q22.1 | 88476715 | 88531480 |
| NUDT9 | 1 | 0.12 | 0.013333 | 0 | 0 | NUDT9 | 4 | 4q22.1 | 88562759 | 88598524 |
| SPARCL1 | 1 | 0.12 | 0.013333 | 0 | 0 | SPARCL1 | 4 | 4q22.1 | 88613512 | 88669680 |
| PHF17 | 1 | 0.133333 | 0.08 | 0 | 0.185185 | PHF17 | 4 | 4q28.2 | 1.3E+08 | 1.3E+08 |
| HHIP | 1 | 0.04 | 0.12 | 0 | 0 | HHIP | 4 | 4q31.22 | 1.46E+08 | 1.46E+08 |

TABLE 2-continued

Gene list for predicting prostate cancer relapse using prostate cancer tissue

| Symbol | freq. use | freq. amp. case | freq. del. case | freq. control | freq. control | Gene. Symbol | chromo-some | cytoband | Transcript. start | Transcript. end |
|---|---|---|---|---|---|---|---|---|---|---|
| TBC1D5 | 1 | 0.053333 | 0.16 | 0.148148 | 0 | TBC1D5 | 3 | 3p24.3 | 17173659 | 17759245 |
| LOC285401 | 1 | 0.013333 | 0.146667 | 0.037037 | 0 | LOC285401 | 3 | 3p14.2 | 63063404 | 63085776 |
| SYNPR | 1 | 0.026667 | 0.133333 | 0.037037 | 0 | SYNPR | 3 | 3p14.2 | 63238954 | 63577638 |
| SNTN | 1 | 0.013333 | 0.12 | 0.037037 | 0 | SNTN | 3 | 3p14.2 | 63613384 | 63625932 |
| SUCLG2 | 1 | 0.013333 | 0.146667 | 0.037037 | 0 | SUCLG2 | 3 | 3p14.1 | 67507833 | 67787729 |
| FAM19A4 | 1 | 0 | 0.133333 | 0.037037 | 0 | FAM19A4 | 3 | 3p14.1 | 68863607 | 69064402 |
| MINA | 1 | 0.173333 | 0.173333 | 0 | 0.259259 | MINA | 3 | 3q11.2 | 99143351 | 99173915 |
| TM4SF4 | 1 | 0.173333 | 0 | 0 | 0.037037 | TM4SF4 | 3 | 3q25.1 | 1.51E+08 | 1.51E+08 |
| WWTR1 | 1 | 0.133333 | 0 | 0 | 0.037037 | WWTR1 | 3 | 3q25.1 | 1.51E+08 | 1.51E+08 |
| SERP1 | 1 | 0.12 | 0 | 0 | 0 | SERP1 | 3 | 3q25.1 | 1.52E+08 | 1.52E+08 |
| EIF2A | 1 | 0.12 | 0 | 0 | 0 | EIF2A | 3 | 3q25.1 | 1.52E+08 | 1.52E+08 |
| SELT | 1 | 0.12 | 0 | 0 | 0 | SELT | 3 | 3q25.1 | 1.52E+08 | 1.52E+08 |
| FAM194A | 1 | 0.12 | 0 | 0 | 0 | FAM194A | 3 | 3q25.1 | 1.52E+08 | 1.52E+08 |
| SIAH2 | 1 | 0.12 | 0 | 0 | 0 | SIAH2 | 3 | 3q25.1 | 1.52E+08 | 1.52E+08 |
| KPNA4 | 1 | 0.053333 | 0.146667 | 0.037037 | 0 | KPNA4 | 3 | 3q26.1 | 1.62E+08 | 1.62E+08 |
| LRRIQ4 | 1 | 0.226667 | 0.013333 | 0 | 0.037037 | LRRIQ4 | 3 | 3q26.2 | 1.71E+08 | 1.71E+08 |
| LRRC31 | 1 | 0.226667 | 0.013333 | 0 | 0.037037 | LRRC31 | 3 | 3q26.2 | 1.71E+08 | 1.71E+08 |
| SAMD7 | 1 | 0.226667 | 0.013333 | 0 | 0.037037 | SAMD7 | 3 | 3q26.2 | 1.71E+08 | 1.71E+08 |
| LOC100128164 | 1 | 0.226667 | 0.013333 | 0 | 0.037037 | LOC100128164 | 3 | 3q26.2 | 1.71E+08 | 1.71E+08 |
| SEC62 | 1 | 0.226667 | 0.013333 | 0 | 0.037037 | SEC62 | 3 | 3q26.2 | 1.71E+08 | 1.71E+08 |
| GPR160 | 1 | 0.24 | 0.013333 | 0 | 0.037037 | GPR160 | 3 | 3q26.2 | 1.71E+08 | 1.71E+08 |
| PHC3 | 1 | 0.226667 | 0.013333 | 0 | 0.037037 | PHC3 | 3 | 3q26.2 | 1.71E+08 | 1.71E+08 |
| KCNMB2 | 1 | 0.053333 | 0.133333 | 0.037037 | 0 | KCNMB2 | 3 | 3q26.32 | 1.8E+08 | 1.8E+08 |
| CCDC50 | 1 | 0.133333 | 0.12 | 0 | 0.074074 | CCDC50 | 3 | 3q28 | 1.93E+08 | 1.93E+08 |
| MIR217 | 1 | 0 | 0.133333 | 0 | 0 | MIR217 | 2 | 2p16.1 | 56063606 | 56063716 |
| MIR216A | 1 | 0 | 0.133333 | 0 | 0 | MIR216A | 2 | 2p16.1 | 56069590 | 56069699 |
| MIR216B | 1 | 0 | 0.133333 | 0 | 0 | MIR216B | 2 | 2p16.1 | 56081354 | 56081435 |
| CCDC85A | 1 | 0 | 0.173333 | 0 | 0 | CCDC85A | 2 | 2p16.1 | 56264762 | 56466814 |
| NCRNA001 | 1 | 0.026667 | 0.12 | 0.074074 | 0 | NCRNA001 | 2 | 2q21.2 | 1.33E+08 | 1.33E+08 |
| B3GALT1 | 1 | 0.013333 | 0.133333 | 0.037037 | 0 | B3GALT1 | 2 | 2q24.3 | 1.68E+08 | 1.68E+08 |
| ABCB11 | 1 | 0 | 0.16 | 0.074074 | 0 | ABCB11 | 2 | 2q31.1 | 1.69E+08 | 1.7E+08 |
| MTX2 | 1 | 0.013333 | 0.133333 | 0.074074 | 0 | MTX2 | 2 | 2q31.1 | 1.77E+08 | 1.77E+08 |
| ELAVL4 | 1 | 0.08 | 0.16 | 0.333333 | 0 | ELAVL4 | 1 | 1p33 | 50286273 | 50440128 |
| LOC729467 | 1 | 0.04 | 0.133333 | 0.148148 | 0 | LOC729467 | 1 | 1p32.1 | 59370198 | 59385068 |
| FGGY | 1 | 0.053333 | 0.12 | 0.111111 | 0 | FGGY | 1 | 1p32.1 | 59535213 | 60000991 |
| HOOK1 | 1 | 0.04 | 0.146667 | 0.111111 | 0 | HOOK1 | 1 | 1p32.1 | 60053121 | 60114639 |
| C1orf87 | 1 | 0.053333 | 0.146667 | 0.111111 | 0 | C1orf87 | 1 | 1p32.1 | 60228654 | 60312015 |
| RPE65 | 1 | 0.026667 | 0.133333 | 0.074074 | 0 | RPE65 | 1 | 1p31.3 | 68667095 | 68688231 |
| ANKRD13C | 1 | 0.133333 | 0.08 | 0 | 0.074074 | ANKRD13C | 1 | 1p31.1 | 70497273 | 70593006 |
| HHLA3 | 1 | 0.133333 | 0.08 | 0 | 0.074074 | HHLA3 | 1 | 1p31.1 | 70593081 | 70606294 |
| CTH | 1 | 0.146667 | 0.066667 | 0 | 0.074074 | CTH | 1 | 1p31.1 | 70549543 | 70677842 |
| DDAH1 | 1 | 0.013333 | 0.16 | 0.037037 | 0 | DDAH1 | 1 | 1p22.3 | 85556757 | 85816635 |
| COL24A1 | 1 | 0.013333 | 0.146667 | 0.037037 | 0 | COL24A1 | 1 | 1p22.3 | 85967504 | 86394710 |
| CLCA2 | 1 | 0.026667 | 0.173333 | 0 | 0 | CLCA2 | 1 | 1p22.3 | 86662357 | 86694829 |
| CLCA1 | 1 | 0.026667 | 0.173333 | 0 | 0 | CLCA1 | 1 | 1p22.3 | 86707114 | 86738563 |
| CLCA3P | 1 | 0.013333 | 0.16 | 0 | 0 | CLCA3P | 1 | 1p22.3 | 86872547 | 86893647 |
| SH3GLB1 | 1 | 0.013333 | 0.146667 | 0 | 0 | SH3GLB1 | 1 | 1p22.3 | 86942845 | 86986456 |
| GBP7 | 1 | 0.04 | 0.12 | 0.037037 | 0 | GBP7 | 1 | 1p22.2 | 89370022 | 89414312 |
| GBP4 | 1 | 0.04 | 0.12 | 0.037037 | 0 | GBP4 | 1 | 1p22.2 | 89419419 | 89437222 |
| LOC400759 | 1 | 0.026667 | 0.133333 | 0.037037 | 0 | LOC400759 | 1 | 1p22.2 | 89645826 | 89663082 |
| LRRC8B | 1 | 0.013333 | 0.146667 | 0.037037 | 0 | LRRC8B | 1 | 1p22.2 | 89762985 | 89836007 |
| LRRC8C | 1 | 0.013333 | 0.12 | 0.111111 | 0 | LRRC8C | 1 | 1p22.2 | 89871232 | 89957682 |
| LRRC8D | 1 | 0.026667 | 0.12 | 0.074074 | 0 | LRRC8D | 1 | 1p22.2 | 90059161 | 90174576 |
| EVI5 | 1 | 0.066667 | 0.12 | 0.111111 | 0 | EVI5 | 1 | 1p22.1 | 92746841 | 93030550 |
| C1orf114 | 1 | 0.013333 | 0.146667 | 0.037037 | 0 | C1orf114 | 1 | 1q24.2 | 1.68E+08 | 1.68E+08 |
| F5 | 1 | 0 | 0.12 | 0.037037 | 0 | F5 | 1 | 1q24.2 | 1.68E+08 | 1.68E+08 |
| SELP | 1 | 0 | 0.133333 | 0.037037 | 0 | SELP | 1 | 1q24.2 | 1.68E+08 | 1.68E+08 |
| SELL | 1 | 0 | 0.133333 | 0.037037 | 0 | SELL | 1 | 1q24.2 | 1.68E+08 | 1.68E+08 |
| SELE | 1 | 0.026667 | 0.12 | 0.037037 | 0 | SELE | 1 | 1q24.2 | 1.68E+08 | 1.68E+08 |
| C4BPA | 1 | 0.146667 | 0.12 | 0.555556 | 0 | C4BPA | 1 | 1q32.2 | 2.05E+08 | 2.05E+08 |
| MIR548F3 | 1 | 0.04 | 0.146667 | 0.074074 | 0 | MIR548F3 | 1 | 1q41 | 2.13E+08 | 2.13E+08 |
| CHRM3 | 1 | 0.026667 | 0.146667 | 0.037037 | 0 | CHRM3 | 1 | 1q43 | 2.38E+08 | 2.38E+08 |
| FMN2 | 1 | 0.026667 | 0.133333 | 0.074074 | 0 | FMN2 | 1 | 1q43 | 2.38E+08 | 2.39E+08 |
| GAB4 | 0.921569 | 0.333333 | 0.106667 | 0.518519 | 0 | GAB4 | 22 | 22q11.1 | 15822827 | 15869113 |
| CECR6 | 0.921569 | 0.453333 | 0.106667 | 0.740741 | 0 | CECR6 | 22 | 22q11.1 | 15977189 | 15982258 |
| CECR5 | 0.921569 | 0.453333 | 0.106667 | 0.740741 | 0 | CECR5 | 22 | 22q11.1 | 15998410 | 16026178 |
| CECR4 | 0.921569 | 0.453333 | 0.106667 | 0.740741 | 0 | CECR4 | 22 | 22q11.1 | 16020279 | 16026335 |
| CECR1 | 0.921569 | 0.453333 | 0.106667 | 0.740741 | 0 | CECR1 | 22 | 22q11.1 | 16040192 | 16060546 |
| LOC646851 | 0.921569 | 0.426667 | 0.106667 | 0.740741 | 0 | LOC646851 | 22 | 22q13.1 | 37304071 | 37382581 |
| ATF4 | 0.921569 | 0.453333 | 0.106667 | 0.814815 | 0 | ATF4 | 22 | 22q13.1 | 38246515 | 38248638 |
| RPS19BP1 | 0.921569 | 0.453333 | 0.106667 | 0.814815 | 0 | RPS19BP1 | 22 | 22q13.1 | 38255044 | 38258807 |
| PPARA | 0.921569 | 0.48 | 0.106667 | 0.777778 | 0 | PPARA | 22 | 22q13.31 | 44925163 | 45018318 |
| TTC38 | 0.921569 | 0.48 | 0.106667 | 0.777778 | 0 | TTC38 | 22 | 22q13.31 | 45042525 | 45068570 |
| CELSR1 | 0.921569 | 0.48 | 0.106667 | 0.777778 | 0 | CELSR1 | 22 | 22q13.31 | 45135395 | 45311732 |

TABLE 2-continued

Gene list for predicting prostate cancer relapse using prostate cancer tissue

| Symbol | freq. use | freq. amp. case | freq. del. case | freq. control | freq. control | Gene. Symbol | chromo- some | cytoband | Tran- script. start | Tran- script. end |
|---|---|---|---|---|---|---|---|---|---|---|
| HDAC10 | 0.921569 | 0.48 | 0.106667 | 0.814815 | 0 | HDAC10 | 22 | 22q13.33 | 49025742 | 49031962 |
| SAPS2 | 0.921569 | 0.48 | 0.106667 | 0.814815 | 0 | SAPS2 | 22 | 22q13.33 | 49128626 | 49230381 |
| ADM2 | 0.921569 | 0.48 | 0.106667 | 0.814815 | 0 | ADM2 | 22 | 22q13.33 | 49266878 | 49271733 |
| MIOX | 0.921569 | 0.48 | 0.106667 | 0.814815 | 0 | MIOX | 22 | 22q13.33 | 49272079 | 49275617 |
| LMF2 | 0.921569 | 0.48 | 0.105667 | 0.814815 | 0 | LMF2 | 22 | 22q13.33 | 49288242 | 49293002 |
| NCAPH2 | 0.921569 | 0.48 | 0.106667 | 0.814815 | 0 | NCAPH2 | 22 | 22q13.33 | 49293511 | 49305058 |
| SCO2 | 0.921569 | 0.48 | 0.106667 | 0.814815 | 0 | SCO2 | 22 | 22q13.33 | 49308863 | 49310901 |
| DEFB115 | 0.921569 | 0.213333 | 0.106667 | 0.518519 | 0 | DEFB115 | 20 | 20q11.21 | 29309128 | 29311097 |
| UQCR | 0.921569 | 0.506667 | 0.106667 | 0.851852 | 0 | UQCR | 19 | 19p13.3 | 1548154 | 1556484 |
| TCF3 | 0.921569 | 0.506667 | 0.106667 | 0.851852 | 0 | TCF3 | 19 | 19p13.3 | 1560293 | 1601287 |
| COPE | 0.921569 | 0.48 | 0.106667 | 0.777778 | 0 | COPE | 19 | 19p13.1 | 18871323 | 18891200 |
| DDX49 | 0.921569 | 0.48 | 0.106667 | 0.777778 | 0 | DDX49 | 19 | 19p13.11 | 18891494 | 18900437 |
| HOMER3 | 0.921569 | 0.48 | 0.106667 | 0.777778 | 0 | HOMER3 | 19 | 19p13.11 | 18901010 | 18912162 |
| CEACAM7 | 0.921569 | 0.413333 | 0.106667 | 0.814815 | 0 | CEACAM7 | 19 | 19q13.2 | 46869075 | 46883937 |
| ANKRD30B | 0.921569 | 0.04 | 0.106667 | 0.074074 | 0 | ANKRD30B | 18 | 18p11.21 | 14738239 | 14842738 |
| CDRT4 | 0.921569 | 0.24 | 0.106667 | 0.407407 | 0 | CDRT4 | 17 | 17p12 | 15280063 | 15311651 |
| PIGL | 0.921569 | 0.32 | 0.106667 | 0.481481 | 0 | PIGL | 17 | 17p11.2 | 16051234 | 16170299 |
| TNFRSF13B | 0.921569 | 0.453333 | 0.106667 | 0.740741 | 0 | TNFRSF13B | 17 | 17p11.2 | 16783123 | 16816128 |
| MPRIP | 0.921569 | 0.466667 | 0.106667 | 0.740741 | 0 | MPRIP | 17 | 17p11.2 | 16886832 | 17029598 |
| PLD6 | 0.921569 | 0.466667 | 0.106667 | 0.740741 | 0 | PLD6 | 17 | 17p11.2 | 17045036 | 17050372 |
| FLCN | 0.921569 | 0.466667 | 0.106667 | 0.740741 | 0 | FLCN | 17 | 17p11.2 | 17056252 | 17081228 |
| COPS3 | 0.921569 | 0.466667 | 0.106667 | 0.740741 | 0 | COPS3 | 17 | 17p11.2 | 17090864 | 17125317 |
| NT5M | 0.921569 | 0.466667 | 0.106667 | 0.740741 | 0 | NT5M | 17 | 17p11.2 | 17147405 | 17191703 |
| MED9 | 0.921569 | 0.466667 | 0.106667 | 0.740741 | 0 | MED9 | 17 | 17p11.2 | 17321025 | 17337260 |
| RASD1 | 0.921569 | 0.466667 | 0.106667 | 0.740741 | 0 | RASD1 | 17 | 17p11.2 | 17338478 | 17340433 |
| PEMT | 0.921569 | 0.466667 | 0.106667 | 0.740741 | 0 | PEMT | 17 | 17p11.2 | 17349602 | 17426471 |
| RAI1 | 0.921569 | 0.48 | 0.106667 | 0.740741 | 0 | RAI1 | 17 | 17p11.2 | 17525512 | 17555491 |
| SREBF1 | 0.921569 | 0.466667 | 0.106667 | 0.740741 | 0 | SREBF1 | 17 | 17p11.2 | 17655393 | 17681051 |
| MIR33B | 0.921569 | 0.466667 | 0.106667 | 0.740741 | 0 | MIR33B | 17 | 17p11.2 | 17657875 | 17557971 |
| TOM1L2 | 0.921569 | 0.466667 | 0.106667 | 0.740741 | 0 | TOM1L2 | 17 | 17p11.2 | 17687547 | 17816510 |
| LRRC48 | 0.921569 | 0.466667 | 0.106667 | 0.740741 | 0 | LRRC48 | 17 | 17p11.2 | 17816852 | 17860915 |
| ATPAF2 | 0.921569 | 0.466667 | 0.106667 | 0.740741 | 0 | ATPAF2 | 17 | 17p11.2 | 17862059 | 17883206 |
| MYO15A | 0.921569 | 0.48 | 0.106667 | 0.740741 | 0 | MYO15A | 17 | 17p11.2 | 17952745 | 18023842 |
| ALKBH5 | 0.921569 | 0.466667 | 0.106667 | 0.740741 | 0 | ALKBH5 | 17 | 17p11.2 | 18027592 | 18053993 |
| SMCR8 | 0.921569 | 0.48 | 0.106667 | 0.740741 | 0 | SMCR8 | 17 | 17p11.2 | 18159319 | 18172096 |
| SHMT1 | 0.921569 | 0.48 | 0.106667 | 0.740741 | 0 | SHMT1 | 17 | 17p11.2 | 18171912 | 18207582 |
| EVPLL | 0.921569 | 0.48 | 0.106667 | 0.740741 | 0 | EVPLL | 17 | 17p11.2 | 18221804 | 18233684 |
| MEOX1 | 0.921569 | 0.466667 | 0.106667 | 0.777778 | 0 | MEOX1 | 17 | 17q21.31 | 39073284 | 39094789 |
| SOST | 0.921569 | 0.466667 | 0.106667 | 0.777778 | 0 | SOST | 17 | 17q21.31 | 39186625 | 39191683 |
| DUSP3 | 0.921569 | 0.466667 | 0.106667 | 0.777778 | 0 | DUSP3 | 17 | 17q21.31 | 39199015 | 39211895 |
| HS3ST2 | 0.921569 | 0.28 | 0.106667 | 0.666667 | 0 | HS3ST2 | 16 | 16p12.1 | 22733361 | 22835161 |
| PWRN1 | 0.921569 | 0.026667 | 0.106667 | 0.148148 | 0 | PWRN1 | 15 | 15q11.2 | 22354397 | 22384018 |
| AQP9 | 0.921569 | 0.04 | 0.106667 | 0.074074 | 0 | AQP9 | 15 | 15q22.1 | 56217700 | 56265403 |
| LOC91948 | 0.921569 | 0.04 | 0.106667 | 0.111111 | 0 | LOC91948 | 15 | 15q26.3 | 96086850 | 96218664 |
| ABHD12B | 0.921569 | 0.106667 | 0 | 0 | 0.037037 | ABHD12B | 14 | 14q22.1 | 50408628 | 50441439 |
| PYGL | 0.921569 | 0.106667 | 0 | 0 | 0.037037 | PYGL | 14 | 14q22.1 | 50441686 | 50480999 |
| PSPC1 | 0.921569 | 0.093333 | 0.106667 | 0.333333 | 0 | PSPC1 | 13 | 13q12.11 | 19146896 | 19255084 |
| DHRS12 | 0.921569 | 0.106667 | 0.226667 | 0 | 0.148148 | DHRS12 | 13 | 13q14.3 | 51240132 | 51276295 |
| FLJ37307 | 0.921569 | 0.106667 | 0.226667 | 0 | 0.148148 | FLJ37307 | 13 | 13q14.3 | 51285484 | 51317288 |
| ATP7B | 0.921569 | 0.106667 | 0.226657 | 0 | 0.148148 | ATP7B | 13 | 13q14.3 | 51404806 | 51483632 |
| ALG11 | 0.921569 | 0.106667 | 0.226667 | 0 | 0.148148 | ALG11 | 13 | 13q14.3 | 51484551 | 51501782 |
| UTP14C | 0.921569 | 0.106667 | 0.226667 | 0 | 0.148148 | UTP14C | 13 | 13q14.3 | 51496828 | 51505736 |
| NEK5 | 0.921569 | 0.106667 | 0.226667 | 0 | 0.148148 | NEK5 | 13 | 13q14.3 | 51536901 | 51601216 |
| NEK3 | 0.921569 | 0.106667 | 0.226667 | 0 | 0.148148 | NEK3 | 13 | 13q14.3 | 51604780 | 51631998 |
| THSD1 | 0.921569 | 0.106667 | 0.226667 | 0 | 0.148148 | THSD1 | 13 | 13q14.3 | 51849305 | 51878631 |
| HNRNPA1L2 | 0.921569 | 0.106667 | 0.226667 | 0 | 0.148148 | HNRNPA1L2 | 13 | 13q14.3 | 52089606 | 52115921 |
| LECT1 | 0.921569 | 0.106667 | 0.226667 | 0 | 0.148148 | LECT1 | 13 | 13q14.3 | 52175400 | 52211949 |
| ITPR2 | 0.921569 | 0.013333 | 0.106667 | 0.037037 | 0 | ITPR2 | 12 | 12p11.23 | 26379552 | 26877399 |
| CSRP2 | 0.921569 | 0.106667 | 0.106667 | 0 | 0.111111 | CSRP2 | 12 | 12q21.2 | 75776627 | 75796931 |
| PAWR | 0.921569 | 0.106667 | 0.12 | 0 | 0.296296 | PAWR | 12 | 12q21.2 | 78509876 | 78608922 |
| NEDD1 | 0.921569 | 0.066667 | 0.106667 | 0.074074 | 0 | NEDD1 | 12 | 12q23.1 | 95825132 | 95871593 |
| ANO4 | 0.921569 | 0.066667 | 0.106667 | 0 | 0 | ANO4 | 12 | 12q23.1 | 99712505 | 1E+08 |
| GVIN1 | 0.921569 | 0.053333 | 0.106667 | 0.037037 | 0 | GVIN1 | 11 | 11p15.4 | 6690954 | 6699687 |
| APIP | 0.921569 | 0.053333 | 0.106667 | 0.074074 | 0 | APIP | 11 | 11p13 | 34860419 | 34894516 |
| FAM181B | 0.921569 | 0.04 | 0.106667 | 0 | 0 | FAM181B | 11 | 11q14.1 | 82120694 | 82122555 |
| HEPHL1 | 0.921569 | 0.04 | 0.106667 | 0.074074 | 0 | HEPHL1 | 11 | 11q21 | 93394026 | 93487023 |
| HTR3B | 0.921569 | 0.213333 | 0.106657 | 0.37037 | 0 | HTR3B | 11 | 11q23.2 | 1.13E+08 | 1.13E+08 |
| FLJ35024 | 0.921569 | 0.013333 | 0.106667 | 0.037037 | 0 | FLJ35024 | 9 | 9p24.2 | 2525655 | 2612374 |
| RFX3 | 0.921569 | 0.026667 | 0.106667 | 0.037037 | 0 | RFX3 | 9 | 9p24.2 | 3214647 | 3515984 |
| FREM1 | 0.921569 | 0.026667 | 0.106667 | 0 | 0 | FREM1 | 9 | 9p22.3 | 14727151 | 14900235 |
| BNC2 | 0.921569 | 0.04 | 0.106667 | 0.074074 | 0 | BNC2 | 9 | 9p22.3 | 16399501 | 16860787 |
| TLE4 | 0.921569 | 0.053333 | 0.106667 | 0.111111 | 0 | TLE4 | 9 | 9q21.31 | 81376698 | 81531477 |
| RASEF | 0.921569 | 0.093333 | 0.106667 | 0.185185 | 0 | RASEF | 9 | 9q21.32 | 84787137 | 84867864 |
| CCDC129 | 0.921569 | 0.053333 | 0.106667 | 0.037037 | 0 | CCDC129 | 7 | 7p15.1 | 31523503 | 31659829 |

TABLE 2-continued

Gene list for predicting prostate cancer relapse using prostate cancer tissue

| Symbol | freq. use | freq. amp. case | freq. del. case | freq. control | freq. control | Gene. Symbol | chromo-some | cytoband | Tran-script. start | Tran-script. end |
|---|---|---|---|---|---|---|---|---|---|---|
| PDE1C | 0.921569 | 0.053333 | 0.106667 | 0.037037 | 0 | PDE1C | 7 | 7p14.3 | 31795772 | 32077517 |
| C7orf53 | 0.921569 | 0.106667 | 0.04 | 0 | 0.074074 | C7orf53 | 7 | 7q31.1 | 1.12E+08 | 1.12E+08 |
| CAV1 | 0.921569 | 0.106667 | 0.08 | 0 | 0.111111 | CAV1 | 7 | 7q31.2 | 1.16E+08 | 1.16E+08 |
| LOC100287718 | 0.921569 | 0.04 | 0.106667 | 0.074074 | 0 | LOC100287718 | 6 | 6p12.3 | 46822658 | 46834901 |
| IBTK | 0.921569 | 0.106667 | 0.226667 | 0 | 0.333333 | IBTK | 6 | 6q14.1 | 82936675 | 83014168 |
| PNRC1 | 0.921569 | 0.106667 | 0.2 | 0 | 0.185185 | PNRC1 | 6 | 6q15 | 89847148 | 89851599 |
| SFRS13B | 0.921569 | 0.106667 | 0.2 | 0 | 0.185185 | SFRS13B | 6 | 6q15 | 89862397 | 89884520 |
| CD180 | 0.921569 | 0.106667 | 0.146667 | 0 | 0.148148 | CD180 | 5 | 5q13.1 | 66513860 | 66528374 |
| ZCCHC9 | 0.921569 | 0.106667 | 0.106667 | 0 | 0.037037 | ZCCHC9 | 5 | 5q14.1 | 80633158 | 80644720 |
| ACOT12 | 0.921569 | 0.106667 | 0.106667 | 0 | 0.037037 | ACOT12 | 5 | 5q14.1 | 80661703 | 80725745 |
| PJA2 | 0.921569 | 0.106667 | 0.16 | 0 | 0.185185 | PJA2 | 5 | 5q21.3 | 1.09E+08 | 1.09E+08 |
| CDS1 | 0.921569 | 0.04 | 0.106667 | 0 | 0 | CDS1 | 4 | 4q21.23 | 85723081 | 85791518 |
| PTPN13 | 0.921569 | 0.106667 | 0.053333 | 0 | 0 | PTPN13 | 4 | 4q21.3 | 87734492 | 87955353 |
| OSTC | 0.921569 | 0.106667 | 0 | 0 | 0.037037 | OSTC | 4 | 4q25 | 1.1E+08 | 1.1E+08 |
| GAB1 | 0.921569 | 0.013333 | 0.106667 | 0 | 0 | GAB1 | 4 | 4q31.21 | 1.44E+08 | 1.45E+08 |
| SMARCA5 | 0.921569 | 0.013333 | 0.106667 | 0 | 0 | SMARCA5 | 4 | 4q31.21 | 1.45E+08 | 1.45E+08 |
| LOC441046 | 0.921569 | 0.013333 | 0.106667 | 0 | 0 | LOC441046 | 4 | 4q31.21 | 1.45E+08 | 1.45E+08 |
| FREM3 | 0.921569 | 0.013333 | 0.106667 | 0 | 0 | FREM3 | 4 | 4q31.21 | 1.45E+08 | 1.45E+08 |
| SCN10A | 0.921569 | 0.106667 | 0.106667 | 0.259259 | 0 | SCN10A | 3 | 3p22.2 | 38713841 | 38810506 |
| FHIT | 0.921569 | 0.066667 | 0.106667 | 0.148148 | 0 | FHIT | 3 | 3p14.2 | 59710076 | 61212174 |
| C3orf49 | 0.921569 | 0.026667 | 0.106667 | 0.037037 | 0 | C3orf49 | 3 | 3p14.1 | 63780081 | 63809351 |
| PROS1 | 0.921569 | 0.106667 | 0.173333 | 0 | 0.37037 | PROS1 | 3 | 3q11.2 | 95074572 | 95175625 |
| TMEM108 | 0.921569 | 0.066667 | 0.106667 | 0.074074 | 0 | TMEM108 | 3 | 3q22.1 | 1.34E+08 | 1.35E+08 |
| GYG1 | 0.921569 | 0.106667 | 0.026667 | 0 | 0.074074 | GYG1 | 3 | 3q24 | 1.5E+08 | 1.5E+08 |
| IQCJ | 0.921569 | 0.053333 | 0.106667 | 0.037037 | 0 | IQCJ | 3 | 3q25.33 | 1.6E+08 | 1.6E+08 |
| NMD3 | 0.921569 | 0.106667 | 0.04 | 0 | 0.074074 | NMD3 | 3 | 3q26.1 | 1.62E+08 | 1.62E+08 |
| TBL1XR1 | 0.921569 | 0.106667 | 0.013333 | 0 | 0 | TBL1XR1 | 3 | 3q26.32 | 1.78E+08 | 1.78E+08 |
| UTS2D | 0.921569 | 0.106667 | 0.12 | 0 | 0.074074 | UTS2D | 3 | 3q28 | 1.92E+08 | 1.93E+08 |
| LOC100271715 | 0.921569 | 0.013333 | 0.106667 | 0.074074 | 0 | LOC100271715 | 2 | 2p22.1 | 39000093 | 39056093 |
| SOS1 | 0.921569 | 0.013333 | 0.106667 | 0.074074 | 0 | SOS1 | 2 | 2p22.1 | 39062194 | 39201109 |
| GTF2A1L | 0.921569 | 0.04 | 0.106667 | 0.222222 | 0 | GTF2A1L | 2 | 2p16.3 | 48698452 | 48813791 |
| LHCGR | 0.921569 | 0.04 | 0.106667 | 0.222222 | 0 | LHCGR | 2 | 2p16.3 | 48767417 | 48836385 |
| ANTXR1 | 0.921569 | 0.093333 | 0.106667 | 0.222222 | 0 | ANTXR1 | 2 | 2p14 | 69093780 | 69226999 |
| LYPD1 | 0.921569 | 0.04 | 0.106667 | 0.074074 | 0 | LYPD1 | 2 | 2q21.2 | 1.33E+08 | 1.33E+08 |
| NCKAP5 | 0.921569 | 0.026667 | 0.106667 | 0.074074 | 0 | NCKAP5 | 2 | 2q21.2 | 1.33E+08 | 1.34E+08 |
| MGAT5 | 0.921569 | 0.093333 | 0.106667 | 0.148148 | 0 | MGAT5 | 2 | 2q21.3 | 1.35E+08 | 1.35E+08 |
| RAB3GAP1 | 0.921569 | 0.146667 | 0.106667 | 0.148148 | 0 | RAB3GAP1 | 2 | 2q21.3 | 1.36E+08 | 1.36E+08 |
| NEB | 0.921569 | 0.04 | 0.106667 | 0.037037 | 0 | NEB | 2 | 2q23.3 | 1.52E+08 | 1.52E+08 |
| BAZ2B | 0.921569 | 0.066667 | 0.106667 | 0.148148 | 0 | BAZ2B | 2 | 2q24.2 | 1.6E+08 | 1.6E+08 |
| LOC130691 | 0.921569 | 0.013333 | 0.106667 | 0.037037 | 0 | LOC130691 | 2 | 2q31.2 | 1.78E+08 | 1.78E+08 |
| SLC5A9 | 0.921569 | 0.146667 | 0.106667 | 0.518519 | 0 | SLC5A9 | 1 | 1p33 | 48460944 | 48486904 |
| BEND5 | 0.921569 | 0.146667 | 0.106667 | 0.37037 | 0 | BEND5 | 1 | 1p33 | 48966127 | 49015135 |
| ORC1L | 0.921569 | 0.28 | 0.106667 | 0.481481 | 0 | ORC1L | 1 | 1p32.3 | 52611089 | 52642720 |
| C8B | 0.921569 | 0.08 | 0.106667 | 0.111111 | 0 | C8B | 1 | 1p32.2 | 57167471 | 57204277 |
| DAB1 | 0.921569 | 0.08 | 0.106667 | 0.111111 | 0 | DAB1 | 1 | 1p32.2 | 57236167 | 58488800 |
| JUN | 0.921569 | 0.04 | 0.106667 | 0.074074 | 0 | JUN | 1 | 1p32.1 | 59019051 | 59022374 |
| EFCAB7 | 0.921569 | 0.093333 | 0.106667 | 0.074074 | 0 | EFCAB7 | 1 | 1p31.3 | 63761601 | 63810952 |
| CACHD1 | 0.921569 | 0.04 | 0.106667 | 0.074074 | 0 | CACHD1 | 1 | 1p31.3 | 64709064 | 64931330 |
| LEPR | 0.921569 | 0.12 | 0.106667 | 0.074074 | 0 | LEPR | 1 | 1p31.3 | 65658836 | 65873699 |
| LEPROT | 0.921569 | 0.12 | 0.106667 | 0.074074 | 0 | LEPROT | 1 | 1p31.3 | 65658836 | 65674277 |
| GNG5 | 0.921569 | 0.053333 | 0.106667 | 0.037037 | 0 | GNG5 | 1 | 1p22.3 | 84736594 | 84744851 |
| SPATA1 | 0.921569 | 0.053333 | 0.106667 | 0.037037 | 0 | SPATA1 | 1 | 1p22.3 | 84744562 | 84804464 |
| CTBS | 0.921569 | 0.04 | 0.106667 | 0.037037 | 0 | CTBS | 1 | 1p22.3 | 84791394 | 84812752 |
| C1orf180 | 0.921569 | 0.04 | 0.106667 | 0.037037 | 0 | C1orf180 | 1 | 1p22.3 | 84866501 | 84873292 |
| SSX2IP | 0.921569 | 0.04 | 0.106667 | 0.037037 | 0 | SSX2IP | 1 | 1p22.3 | 84881978 | 84928829 |
| LPAR3 | 0.921569 | 0.04 | 0.106667 | 0.037037 | 0 | LPAR3 | 1 | 1p22.3 | 85051674 | 95131485 |
| MCOLN2 | 0.921569 | 0.04 | 0.106667 | 0.037037 | 0 | MCOLN2 | 1 | 1p22.3 | 85163854 | 85235385 |
| MCOLN3 | 0.921569 | 0.026667 | 0.106667 | 0.037037 | 0 | MCOLN3 | 1 | 1p22.3 | 85256353 | 85286758 |
| WDR63 | 0.921569 | 0.026667 | 0.106667 | 0.037037 | 0 | WDR63 | 1 | 1p22.3 | 85300581 | 85371409 |
| HS2ST1 | 0.921569 | 0.04 | 0.106667 | 0 | 0 | HS2ST1 | 1 | 1p22.3 | 87152923 | 87336713 |
| RBMXL1 | 0.921569 | 0.066667 | 0.106667 | 0.037037 | 0 | RBMXL1 | 1 | 1p22.2 | 89217728 | 89231232 |
| TGFBR3 | 0.921569 | 0.04 | 0.106667 | 0.111111 | 0 | TGPBR3 | 1 | 1p22.2 | 91918490 | 92124375 |
| ARHGAP29 | 0.921569 | 0.066667 | 0.106667 | 0.148148 | 0 | ARHGAP29 | 1 | 1p22.1 | 94407051 | 94475896 |
| MGC4473 | 0.921569 | 0.013333 | 0.106667 | 0.037037 | 0 | MGC4473 | 1 | 1q24.2 | 1.67E+08 | 1.67E+08 |
| SLC19A2 | 0.921569 | 0.013333 | 0.106667 | 0.037037 | 0 | SLC19A2 | 1 | 1q24.2 | 1.68E+08 | 1.68E+08 |
| C1orf156 | 0.921569 | 0.04 | 0.106667 | 0.037037 | 0 | C1orf156 | 1 | 1q24.2 | 1.68E+08 | 1.68E+08 |
| C1orf112 | 0.921569 | 0.04 | 0.106667 | 0.037037 | 0 | C1orf112 | 1 | 1q24.2 | 1.68E+08 | 1.68E+08 |
| GORAB | 0.921569 | 0 | 0.106667 | 0.037037 | 0 | GORAB | 1 | 1q24.2 | 1.69E+08 | 1.69E+08 |
| RNF138P1 | 0.019608 | 0.12 | 0.146667 | 0.037037 | 0.037037 | RNF138P1 | 5 | 5q11.2 | 54860427 | 54866128 |
| MTX3 | 0.019608 | 0.12 | 0.133333 | 0.037037 | 0.037037 | MTX3 | 5 | 5q14.1 | 79308297 | 73322845 |
| USP33 | 0.019608 | 0.133333 | 0.106667 | 0.037037 | 0.037037 | USP33 | 1 | 1p31.1 | 77934262 | 77998126 |
| FAM73A | 0.019608 | 0.133333 | 0.106667 | 0.037037 | 0.037037 | FAM73A | 1 | 1p31.1 | 78017897 | 78116670 |
| TTTY12 | 0.009804 | 0.226667 | 0.12 | 0.259259 | 0.037037 | TTTY12 | Y | Yp11.2 | 7732965 | 7738724 |
| CECR7 | 0.009804 | 0.32 | 0.133333 | 0.481481 | 0.037037 | CECR7 | 22 | 22q11.1 | 15897460 | 15919683 |

TABLE 2-continued

Gene list for predicting prostate cancer relapse using prostate cancer tissue

| Symbol | freq. use | freq. amp. case | freq. del. case | freq. control | freq. control | Gene. Symbol | chromo-some | cytoband | Tran-script. start | Tran-script. end |
|---|---|---|---|---|---|---|---|---|---|---|
| EP300 | 0.009804 | 0.44 | 0.106667 | 0.740741 | 0.037037 | EP300 | 22 | 22q13.2 | 39818560 | 39906028 |
| MOV10L1 | 0.009804 | 0.48 | 0.12 | 0.777778 | 0.037037 | MOV10L1 | 22 | 22q13.33 | 48870562 | 48942243 |
| ABCC13 | 0.009804 | 0.04 | 0.146667 | 0.037037 | 0.037037 | ABCC13 | 21 | 21q11.2 | 14567991 | 14595564 |
| CYYR1 | 0.009804 | 0 | 0.146667 | 0 | 0.037037 | CYYR1 | 21 | 21q21.3 | 26760399 | 26867453 |
| HAO1 | 0.009804 | 0.053333 | 0.186667 | 0.143148 | 0.037037 | HAO1 | 20 | 20p12.3 | 7811631 | 7869094 |
| PLCB4 | 0.009804 | 0.066667 | 0.133333 | 0.074074 | 0.037037 | PLCB4 | 20 | 20p12.2 | 9024932 | 9409463 |
| PAK7 | 0.009804 | 0.106667 | 0.106667 | 0.074074 | 0.037037 | PAK7 | 20 | 20p12.2 | 9466037 | 9767688 |
| SNAP25 | 0.009804 | 0.08 | 0.12 | 0.074074 | 0.037037 | SNAP25 | 20 | 20p12.2 | 10147477 | 10236066 |
| BTBD3 | 0.009804 | 0.04 | 0.173333 | 0.074074 | 0.037037 | BTBD3 | 20 | 20p12.2 | 11819477 | 11855244 |
| ISM1 | 0.009804 | 0.066667 | 0.146667 | 0.111111 | 0.037037 | ISM1 | 20 | 20p12.1 | 13150418 | 13229298 |
| CRNKL1 | 0.009804 | 0.24 | 0.133333 | 0.481481 | 0.037037 | CRNKL1 | 20 | 20p11.23 | 19963012 | 19984691 |
| PSG1 | 0.009804 | 0.306667 | 0.133333 | 0.740741 | 0.037037 | PSG1 | 19 | 19q13.31 | 48063198 | 48075712 |
| ZNF180 | 0.009804 | 0.426667 | 0.106667 | 0.814815 | 0.037037 | ZNF180 | 19 | 19q13.31 | 49671699 | 49696415 |
| ZNF521 | 0.009804 | 0.026667 | 0.12 | 0.111111 | 0.037037 | ZNF521 | 18 | 18q11.2 | 20895886 | 21186213 |
| C18orf16 | 0.009804 | 0 | 0.133333 | 0 | 0.037037 | C18orf16 | 18 | 18q11.2 | 22699270 | 22769909 |
| CHST9 | 0.009804 | 0 | 0.133333 | 0 | 0.037037 | CHST9 | 18 | 18q11.2 | 22749595 | 23019288 |
| MOCOS | 0.009804 | 0.106667 | 0.093333 | 0.037037 | 0.074074 | MOCOS | 18 | 18q12.2 | 32021478 | 32102684 |
| FHOD3 | 0.009804 | 0.106667 | 0.093333 | 0.037037 | 0.037037 | FHOD3 | 18 | 18q12.2 | 32131700 | 32614017 |
| SLC14A2 | 0.009804 | 0.213333 | 0.106667 | 0.185185 | 0.037037 | SLC14A2 | 18 | 18q12.3 | 41448764 | 41517059 |
| SLC14A1 | 0.009804 | 0.226667 | 0.106667 | 0.185185 | 0.037037 | SLC14A1 | 18 | 18q12.3 | 41558090 | 41586483 |
| SIGLEC15 | 0.009804 | 0.226667 | 0.106667 | 0.185185 | 0.037037 | SIGLEC15 | 18 | 18q12.3 | 41659543 | 41676520 |
| KIAA1632 | 0.009804 | 0.226667 | 0.106667 | 0.185185 | 0.037037 | KIAA1632 | 18 | 18q12.3 | 41681572 | 41801304 |
| PSTPIP2 | 0.009804 | 0.226667 | 0.12 | 0.185185 | 0.037037 | PSTPIP2 | 18 | 18q21.1 | 41817500 | 41906249 |
| ATP5A1 | 0.009804 | 0.226667 | 0.12 | 0.185185 | 0.037037 | ATP5A1 | 18 | 18q21.1 | 41918108 | 41938198 |
| HAUS1 | 0.009804 | 0.226667 | 0.12 | 0.185185 | 0.037037 | HAUS1 | 18 | 18q21.1 | 41938296 | 41962297 |
| C18orf25 | 0.009804 | 0.226667 | 0.106667 | 0.222222 | 0.037037 | C18orf25 | 18 | 18q21.1 | 42007986 | 42100954 |
| RNF165 | 0.009804 | 0.253333 | 0.106667 | 0.222222 | 0.037037 | RNF165 | 18 | 18q21.1 | 42168185 | 42294782 |
| LOXHD1 | 0.009804 | 0.24 | 0.106667 | 0.222222 | 0.037037 | LOXHD1 | 18 | 18q21.1 | 42310935 | 42393251 |
| ST8SIA5 | 0.009804 | 0.24 | 0.106667 | 0.222222 | 0.037037 | ST8SIA5 | 18 | 18q21.1 | 42513079 | 42591038 |
| IER3IP1 | 0.009804 | 0.16 | 0.106667 | 0.222222 | 0.037037 | IER3IP1 | 18 | 18q21.1 | 42935411 | 42956744 |
| KIAA0427 | 0.009804 | 0.306667 | 0.106667 | 0.407407 | 0.037037 | KIAA0427 | 18 | 18q21.1 | 44319425 | 44643577 |
| SMAD7 | 0.009804 | 0.306667 | 0.106667 | 0.333333 | 0.037037 | SMAD7 | 18 | 18q21.1 | 44700221 | 44731080 |
| MYO5B | 0.009804 | 0.24 | 0.106667 | 0.259259 | 0.037037 | MYO5B | 18 | 18q21.1 | 45603154 | 45975450 |
| CCDC11 | 0.009804 | 0.213333 | 0.106667 | 0.259259 | 0.037037 | CCDC11 | 18 | 18q21.1 | 46007562 | 46046864 |
| SKA1 | 0.009804 | 0.2 | 0.12 | 0.259259 | 0.037037 | SKA1 | 18 | 18q21.1 | 46155390 | 46174537 |
| MAPK4 | 0.009804 | 0.16 | 0.16 | 0.259259 | 0.037037 | MAPK4 | 18 | 18q21.1 | 46340482 | 46512195 |
| MRO | 0.009804 | 0.24 | 0.106667 | 0.259259 | 0.037037 | MRO | 18 | 18q21.2 | 46575488 | 46605753 |
| ME2 | 0.009804 | 0.24 | 0.106667 | 0.259259 | 0.037037 | ME2 | 18 | 18q21.2 | 46659430 | 46730159 |
| ELAC1 | 0.009804 | 0.24 | 0.106667 | 0.259259 | 0.037037 | ELAC1 | 18 | 18q21.2 | 46748385 | 46768489 |
| ST8SIA3 | 0.009804 | 0.093333 | 0.133333 | 0.148148 | 0.037037 | ST8SIA3 | 18 | 18q21.31 | 53170719 | 53187160 |
| ONECUT2 | 0.009804 | 0.093333 | 0.133333 | 0.148148 | 0.037037 | ONECUT2 | 18 | 18q21.31 | 53253915 | 53309529 |
| ATP8B1 | 0.009804 | 0.186667 | 0.133333 | 0.185185 | 0.037037 | ATP8B1 | 18 | 18q21.31 | 53464657 | 53550038 |
| NEDD4L | 0.009804 | 0.186667 | 0.133333 | 0.148148 | 0.037037 | NEDD4L | 18 | 18q21.31 | 53862617 | 54219753 |
| ALPK2 | 0.009804 | 0.2 | 0.12 | 0.074074 | 0.037037 | ALPK2 | 18 | 18q21.31 | 54299462 | 54447170 |
| MALT1 | 0.009804 | 0.2 | 0.133333 | 0.074074 | 0.037037 | MALT1 | 18 | 18q21.32 | 54489598 | 54568351 |
| ZNF532 | 0.009804 | 0.213333 | 0.12 | 0.074074 | 0.037037 | ZNF532 | 18 | 18q21.32 | 54681041 | 54804690 |
| LOC390858 | 0.009804 | 0.186667 | 0.12 | 0.074074 | 0.037037 | LOC390858 | 18 | 18q21.32 | 54853951 | 54871427 |
| SEC11C | 0.009804 | 0.146667 | 0.12 | 0.074074 | 0.037037 | SEC11C | 18 | 18q21.32 | 54958105 | 54977044 |
| CPLX4 | 0.009804 | 0.146667 | 0.133333 | 0.074074 | 0.037037 | CPLX4 | 18 | 18q21.32 | 55113618 | 55136862 |
| LMAN1 | 0.009804 | 0.146667 | 0.133333 | 0.074074 | 0.037037 | LMAN1 | 18 | 18q21.32 | 55146037 | 55177489 |
| CCBE1 | 0.009804 | 0.146667 | 0.12 | 0.074074 | 0.037037 | CCBE1 | 18 | 18q21.32 | 55252129 | 55515625 |
| SOCS6 | 0.009804 | 0.106667 | 0.173333 | 0.037037 | 0.222222 | SOCS6 | 18 | 18q22.2 | 66107117 | 66148415 |
| ZNF516 | 0.009804 | 0.213333 | 0.106667 | 0.185185 | 0.037037 | ZNF516 | 18 | 18q23 | 72200607 | 72304044 |
| LOC284276 | 0.009804 | 0.24 | 0.106667 | 0.222222 | 0.037037 | LOC284276 | 18 | 18q23 | 72369600 | 72400772 |
| ZNF236 | 0.009804 | 0.253333 | 0.106667 | 0.222222 | 0.037037 | ZNF236 | 18 | 18q23 | 72665104 | 72811671 |
| C17orf97 | 0.009804 | 0.466667 | 0.12 | 0.740741 | 0.037037 | C17orf97 | 17 | 17p13.3 | 260434 | 264802 |
| OR1A2 | 0.009804 | 0.266667 | 0.16 | 0.703704 | 0.037037 | OR1A2 | 17 | 17p13.3 | 3047563 | 3048493 |
| ATP2A3 | 0.009804 | 0.413333 | 0.133333 | 0.740741 | 0.037037 | ATP2A3 | 17 | 17p13.2 | 3773918 | 3814486 |
| ZZEF1 | 0.009804 | 0.36 | 0.133333 | 0.740741 | 0.037037 | ZZEF1 | 17 | 17p13.2 | 3854488 | 3993003 |
| CYB5D2 | 0.009804 | 0.4 | 0.133333 | 0.740741 | 0.037037 | CYB5D2 | 17 | 17p13.2 | 3993211 | 4007741 |
| ANKFY1 | 0.009804 | 0.4 | 0.133333 | 0.740741 | 0.037037 | ANKFY1 | 17 | 17p13.2 | 4013414 | 4114024 |
| UBE2G1 | 0.009804 | 0.4 | 0.133333 | 0.740741 | 0.037037 | UBE2G1 | 17 | 17p13.2 | 4119251 | 4216719 |
| SPNS2 | 0.009804 | 0.413333 | 0.133333 | 0.740741 | 0.037037 | SPNS2 | 17 | 17p13.2 | 4348878 | 4389978 |
| SMTNL2 | 0.009804 | 0.413333 | 0.133333 | 0.740741 | 0.037037 | SMTNL2 | 17 | 17p13.2 | 4434025 | 4458364 |
| PELP1 | 0.009804 | 0.413333 | 0.133333 | 0.740741 | 0.037037 | PELP1 | 17 | 17p13.2 | 4521428 | 4554382 |
| ARRB2 | 0.009804 | 0.413333 | 0.133333 | 0.740741 | 0.037037 | ARRB2 | 17 | 17p13.2 | 4560538 | 4571545 |
| MED11 | 0.009804 | 0.413333 | 0.133333 | 0.740741 | 0.037037 | MED11 | 17 | 17p13.2 | 4581472 | 4583646 |
| CXCL16 | 0.009804 | 0.413333 | 0.133333 | 0.740741 | 0.037037 | CXCL16 | 17 | 17p13.2 | 4583577 | 4589973 |
| ZMYND15 | 0.009804 | 0.413333 | 0.133333 | 0.740741 | 0.037037 | ZMYND15 | 17 | 17p13.2 | 4590068 | 4596160 |
| TM4SF5 | 0.009804 | 0.413333 | 0.133333 | 0.740741 | 0.037037 | TM4SF5 | 17 | 17p13.2 | 4621936 | 4633254 |
| VMO1 | 0.009804 | 0.413333 | 0.133333 | 0.740741 | 0.037037 | VMO1 | 17 | 17p13.2 | 4635321 | 4636470 |
| GLTPD2 | 0.009804 | 0.413333 | 0.133333 | 0.740741 | 0.037037 | GLTPD2 | 17 | 17p13.2 | 4638994 | 4640426 |
| PSMB6 | 0.009804 | 0.413333 | 0.133333 | 0.740741 | 0.037037 | PSMB6 | 17 | 17p13.2 | 4646415 | 4648749 |
| PLD2 | 0.009804 | 0.413333 | 0.133333 | 0.740741 | 0.037037 | PLD2 | 17 | 17p13.2 | 4657378 | 4673695 |

TABLE 2-continued

Gene list for predicting prostate cancer relapse using prostate cancer tissue

| Symbol | freq. use | freq. amp. case | freq. del. case | freq. control | freq. control | Gene. Symbol | chromosome | cytoband | Transcript. start | Transcript. end |
|---|---|---|---|---|---|---|---|---|---|---|
| MINK1 | 0.009804 | 0.413333 | 0.133333 | 0.740741 | 0.037037 | MINK1 | 17 | 17p13.2 | 4683303 | 4742135 |
| RNF167 | 0.009804 | 0.413333 | 0.133333 | 0.740741 | 0.037037 | RNF167 | 17 | 17p13.2 | 4784375 | 4789263 |
| PFN1 | 0.009804 | 0.413333 | 0.133333 | 0.740741 | 0.037037 | PFN1 | 17 | 17p13.2 | 4789692 | 4792571 |
| ENO3 | 0.009804 | 0.413333 | 0.133333 | 0.740741 | 0.037037 | ENO3 | 17 | 17p13.2 | 4795131 | 4801149 |
| SPAG7 | 0.009804 | 0.413333 | 0.133333 | 0.740741 | 0.037037 | SPAG7 | 17 | 17p13.2 | 4803244 | 4811857 |
| CAMTA2 | 0.009804 | 0.413333 | 0.133333 | 0.740741 | 0.037037 | CAMTA2 | 17 | 17p13.2 | 4812017 | 4831656 |
| KIF1C | 0.009804 | 0.413333 | 0.133333 | 0.740741 | 0.037037 | KIF1C | 17 | 17p13.2 | 4842000 | 4868721 |
| GPR172B | 0.009804 | 0.413333 | 0.133333 | 0.740741 | 0.037037 | GPR172B | 17 | 17p13.2 | 4876621 | 4879452 |
| ZNF594 | 0.009804 | 0.373333 | 0.133333 | 0.740741 | 0.037037 | ZNF594 | 17 | 17p13.2 | 5023555 | 5035903 |
| C17orf87 | 0.009804 | 0.373333 | 0.133333 | 0.740741 | 0.037037 | C17orf87 | 17 | 17p13.2 | 5054625 | 5078808 |
| RABEP1 | 0.009804 | 0.373333 | 0.146667 | 0.740741 | 0.037037 | RABEP1 | 17 | 17p13.2 | 5126282 | 5229857 |
| C1Q8P | 0.009804 | 0.373333 | 0.133333 | 0.740741 | 0.037037 | C1QBP | 17 | 17p13.2 | 5276823 | 5283196 |
| DHX33 | 0.009804 | 0.373333 | 0.133333 | 0.740741 | 0.037037 | DHX33 | 17 | 17p13.2 | 5286315 | 5312906 |
| DERL2 | 0.009804 | 0.36 | 0.133333 | 0.740741 | 0.037037 | DERL2 | 17 | 17p13.2 | 5318337 | 5330219 |
| MIS12 | 0.009804 | 0.36 | 0.133333 | 0.740741 | 0.037037 | MIS12 | 17 | 17p13.2 | 5330971 | 5334855 |
| NLRP1 | 0.009804 | 0.36 | 0.133333 | 0.740741 | 0.037037 | NLRP1 | 17 | 17p13.2 | 5345443 | 5428557 |
| WSCD1 | 0.009804 | 0.386667 | 0.133333 | 0.740741 | 0.037037 | WSCD1 | 17 | 17p13.2 | 5914658 | 5968472 |
| PITPNM3 | 0.009804 | 0.4 | 0.133333 | 0.740741 | 0.037037 | PITPNM3 | 17 | 17p13.2 | 6295307 | 6400602 |
| KIAA0753 | 0.009804 | 0.36 | 0.186667 | 0.740741 | 0.037037 | KIAA0753 | 17 | 17p13.2 | 6422369 | 6484972 |
| SLC13A5 | 0.009804 | 0.4 | 0.146667 | 0.740741 | 0.037037 | SLC13A5 | 17 | 17p13.2 | 5528765 | 6557465 |
| XAF1 | 0.009804 | 0.386667 | 0.146667 | 0.740741 | 0.037037 | XAF1 | 17 | 17p13.2 | 6599880 | 6619689 |
| FBXO39 | 0.009804 | 0.386667 | 0.146667 | 0.740741 | 0.037037 | FBXO39 | 17 | 17p13.2 | 6620276 | 6631689 |
| TEKT1 | 0.009804 | 0.386667 | 0.146667 | 0.740741 | 0.037037 | TEKT1 | 17 | 17p13.2 | 6644024 | 6675785 |
| ALOX12P2 | 0.009804 | 0.386667 | 0.146667 | 0.740741 | 0.037037 | ALOX12P2 | 17 | 17p13.2 | 6697619 | 6744393 |
| ALOX12 | 0.009804 | 0.413333 | 0.146667 | 0.740741 | 0.037037 | ALOX12 | 17 | 17p13.1 | 6840108 | 6854780 |
| RNASEK | 0.009804 | 0.413333 | 0.146667 | 0.740741 | 0.037037 | RNASEK | 17 | 17p13.1 | 6856522 | 6858576 |
| C17orf49 | 0.009804 | 0.413333 | 0.146667 | 0.740741 | 0.037037 | C17orf49 | 17 | 17p13.1 | 6858797 | 6861563 |
| MIR195 | 0.009804 | 0.413333 | 0.146667 | 0.740741 | 0.037037 | MIR195 | 17 | 17p13.1 | 6861658 | 6861745 |
| MIR497 | 0.009804 | 0.413333 | 0.146667 | 0.740741 | 0.037037 | MIR497 | 17 | 17p13.1 | 6861954 | 6862066 |
| BCL6B | 0.009804 | 0.413333 | 0.146667 | 0.740741 | 0.037037 | BCL6B | 17 | 17p13.1 | 6867093 | 6873686 |
| SLC16A13 | 0.009804 | 0.413333 | 0.146667 | 0.740741 | 0.037037 | SLC16A13 | 17 | 17p13.1 | 6880118 | 6884164 |
| SLC16A11 | 0.009804 | 0.413333 | 0.146667 | 0.740741 | 0.037037 | SLC16A11 | 17 | 17p13.1 | 6885673 | 6887967 |
| ASGR2 | 0.009804 | 0.413333 | 0.146667 | 0.703704 | 0.037037 | ASGR2 | 17 | 17p13.1 | 6945365 | 6958853 |
| ASGR1 | 0.009804 | 0.413333 | 0.146667 | 0.703704 | 0.037037 | ASGR1 | 17 | 17p13.1 | 7017475 | 7023608 |
| DLG4 | 0.009804 | 0.413333 | 0.145667 | 0.703704 | 0.037037 | DLG4 | 17 | 17p13.1 | 7033934 | 7061653 |
| ACADVL | 0.009804 | 0.413333 | 0.146667 | 0.703704 | 0.037037 | ACADVL | 17 | 17p13.1 | 7063877 | 7069310 |
| MIR324 | 0.009804 | 0.413333 | 0.146667 | 0.703704 | 0.037037 | MIR324 | 17 | 17p13.1 | 7067340 | 7067423 |
| DVL2 | 0.009804 | 0.413333 | 0.146667 | 0.703704 | 0.037037 | DVL2 | 17 | 17p13.1 | 7069385 | 7078588 |
| PHF23 | 0.009804 | 0.413333 | 0.146667 | 0.703704 | 0.037037 | PHF23 | 17 | 17p13.1 | 7079071 | 7083550 |
| GABARAP | 0.009804 | 0.413333 | 0.146667 | 0.703704 | 0.037037 | GABARAP | 17 | 17p13.1 | 7084462 | 7086478 |
| DULLARD | 0.009804 | 0.413333 | 0.146667 | 0.703704 | 0.037037 | DULLARD | 17 | 17p13.1 | 7087630 | 7095720 |
| C17orf81 | 0.009804 | 0.413333 | 0.146667 | 0.703704 | 0.037037 | C17orf81 | 17 | 17p13.1 | 7096096 | 7103984 |
| CLDN7 | 0.009804 | 0.413333 | 0.146667 | 0.703704 | 0.037037 | CLDN7 | 17 | 17p13.1 | 7103946 | 7106520 |
| SLC2A4 | 0.009804 | 0.413333 | 0.146667 | 0.703704 | 0.037037 | SLC2A4 | 17 | 17p13.1 | 7125778 | 7132092 |
| YBX2 | 0.009804 | 0.413333 | 0.146667 | 0.703704 | 0.037037 | YBX2 | 17 | 17p13.1 | 7132295 | 7138601 |
| WRAP53 | 0.009804 | 0.4 | 0.16 | 0.703704 | 0.037037 | WRAP53 | 17 | 17p13.1 | 7530114 | 7547545 |
| EFNB3 | 0.009804 | 0.4 | 0.16 | 0.703704 | 0.037037 | EFNB3 | 17 | 17p13.1 | 7549245 | 7555419 |
| DNAH2 | 0.009804 | 0.4 | 0.16 | 0.703704 | 0.037037 | DNAH2 | 17 | 17p13.1 | 7563764 | 7677784 |
| KDM6B | 0.009804 | 0.4 | 0.16 | 0.703704 | 0.037037 | KDM6B | 17 | 17p13.1 | 7683960 | 7698844 |
| TMEM88 | 0.009804 | 0.4 | 0.16 | 0.703704 | 0.037037 | TMEM88 | 17 | 17p13.1 | 7699109 | 7700143 |
| LSMD1 | 0.009804 | 0.4 | 0.16 | 0.703704 | 0.037037 | LSMD1 | 17 | 17p13.1 | 7700728 | 7701898 |
| CYB5D1 | 0.009804 | 0.4 | 0.16 | 0.703704 | 0.037037 | CYB5D1 | 17 | 17p13.1 | 7701789 | 7706326 |
| CHD3 | 0.009804 | 0.4 | 0.16 | 0.703704 | 0.037037 | CHD3 | 17 | 17p13.1 | 7728848 | 7756801 |
| SCARNA21 | 0.009804 | 0.4 | 0.16 | 0.703704 | 0.037037 | SCARNA21 | 17 | 17p13.1 | 7750166 | 7750304 |
| LOC284023 | 0.009804 | 0.4 | 0.16 | 0.703704 | 0.037037 | LOC284023 | 17 | 17p13.1 | 7757366 | 7759991 |
| KCNAB3 | 0.009804 | 0.4 | 0.16 | 0.703704 | 0.037037 | KCNAB3 | 17 | 17p13.1 | 7766752 | 7773479 |
| TRAPPC1 | 0.009804 | 0.4 | 0.16 | 0.703704 | 0.037037 | TRAPPC1 | 17 | 17p13.1 | 7774388 | 7776043 |
| CNTROB | 0.009804 | 0.4 | 0.16 | 0.703704 | 0.037037 | CNTROB | 17 | 17p13.1 | 7776198 | 7793622 |
| GUCY2D | 0.009804 | 0.4 | 0.16 | 0.703704 | 0.037037 | GUCY2D | 17 | 17p13.1 | 7846713 | 7864384 |
| ALOX12B | 0.009804 | 0.4 | 0.146667 | 0.703704 | 0.037037 | ALOX12B | 17 | 17p13.1 | 7916679 | 7931747 |
| ALOXE3 | 0.009804 | 0.4 | 0.146667 | 0.703704 | 0.037037 | ALOXE3 | 17 | 17p13.1 | 7939943 | 7962586 |
| HES7 | 0.009804 | 0.4 | 0.146667 | 0.703704 | 0.037037 | HES7 | 17 | 17p13.1 | 7964633 | 7968136 |
| PER1 | 0.009804 | 0.4 | 0.146667 | 0.703704 | 0.037037 | PER1 | 17 | 17p13.1 | 7984513 | 7996479 |
| VAMP2 | 0.009804 | 0.4 | 0.146667 | 0.703704 | 0.037037 | VAMP2 | 17 | 17p13.1 | 8003190 | 8007019 |
| TMEM107 | 0.009804 | 0.4 | 0.146667 | 0.703704 | 0.037037 | TMEM107 | 17 | 17p13.1 | 8017021 | 8020440 |
| C17orf59 | 0.009804 | 0.4 | 0.146667 | 0.703704 | 0.037037 | C17orf59 | 17 | 17p13.1 | 8032376 | 8034290 |
| AURKB | 0.009804 | 0.4 | 0.146667 | 0.703704 | 0.037037 | AURKB | 17 | 17p13.1 | 8048774 | 8054609 |
| C17orf44 | 0.009804 | 0.4 | 0.146667 | 0.703704 | 0.037037 | C17orf44 | 17 | 17p13.1 | 8064673 | 8068087 |
| C17orf68 | 0.009804 | 0.4 | 0.146667 | 0.703704 | 0.037037 | C17orf68 | 17 | 17p13.1 | 8068864 | 8092139 |
| PFAS | 0.009804 | 0.4 | 0.146667 | 0.703704 | 0.037037 | PFAS | 17 | 17p13.1 | 8093321 | 8114534 |
| SLC25A35 | 0.009804 | 0.4 | 0.146667 | 0.703704 | 0.037037 | SLC25A35 | 17 | 17p13.1 | 8131807 | 8138896 |
| RANGRF | 0.009804 | 0.4 | 0.146667 | 0.703704 | 0.037037 | RANGRF | 17 | 17p13.1 | 8132714 | 8134131 |
| ARHGEF15 | 0.009804 | 0.4 | 0.146667 | 0.703704 | 0.037037 | ARHGEF15 | 17 | 17p13.1 | 8154315 | 8166555 |
| LOC100128288 | 0.009804 | 0.4 | 0.133333 | 0.703704 | 0.037037 | LOC100128288 | 17 | 17p13.1 | 8202456 | 8204585 |

TABLE 2-continued

Gene list for predicting prostate cancer relapse using prostate cancer tissue

| Symbol | freq. use | freq. amp. case | freq. del. case | freq. control | freq. control | Gene. Symbol | chromosome | cytoband | Transcript. start | Transcript. end |
|---|---|---|---|---|---|---|---|---|---|---|
| KRBA2 | 0.009804 | 0.4 | 0.133333 | 0.703704 | 0.037037 | KRBA2 | 17 | 17p13.1 | 8212698 | 8215584 |
| RPL26 | 0.009804 | 0.4 | 0.133333 | 0.703704 | 0.037037 | RPL26 | 17 | 17p13.1 | 8221559 | 8227291 |
| RNF222 | 0.009804 | 0.4 | 0.133333 | 0.703704 | 0.037037 | RNF222 | 17 | 17p13.1 | 8234750 | 8241870 |
| NDEL1 | 0.009804 | 0.4 | 0.133333 | 0.703704 | 0.037037 | NDEL1 | 17 | 17p13.1 | 8279904 | 8312207 |
| MYH10 | 0.009804 | 0.4 | 0.133333 | 0.703704 | 0.037037 | MYH10 | 17 | 17p13.1 | 8318255 | 8474762 |
| CCDC42 | 0.009804 | 0.4 | 0.12 | 0.703704 | 0.037037 | CCDC42 | 17 | 17p13.1 | 8573972 | 8588880 |
| SPDYE4 | 0.009804 | 0.4 | 0.12 | 0.703704 | 0.037037 | SPDYE4 | 17 | 17p13.1 | 8597149 | 8602603 |
| MFSD6L | 0.009804 | 0.373333 | 0.146667 | 0.703704 | 0.037037 | MFSD6L | 17 | 17p13.1 | 8641153 | 8643393 |
| PIK3R6 | 0.009804 | 0.373333 | 0.146667 | 0.703704 | 0.037037 | PIK3R6 | 17 | 17p13.1 | 8646780 | 8711720 |
| PIK3R5 | 0.009804 | 0.4 | 0.12 | 0.666667 | 0.037037 | PIK3R5 | 17 | 17p13.1 | 8722959 | 8809750 |
| NTN1 | 0.009804 | 0.386667 | 0.12 | 0.666667 | 0.037037 | NTN1 | 17 | 17p13.1 | 8865584 | 9088043 |
| STX8 | 0.009804 | 0.386667 | 0.12 | 0.666667 | 0.037037 | STX8 | 17 | 17p13.1 | 9094513 | 9420001 |
| WDR16 | 0.009804 | 0.386667 | 0.12 | 0.592593 | 0.037037 | WDR16 | 17 | 17p13.1 | 9420669 | 9487502 |
| USP43 | 0.009804 | 0.386667 | 0.12 | 0.592593 | 0.037037 | USP43 | 17 | 17p13.1 | 5489675 | 9573729 |
| GLP2R | 0.009804 | 0.373333 | 0.106667 | 0.555556 | 0.037037 | GLP2R | 17 | 17p13.1 | 9670106 | 9733748 |
| GAS7 | 0.009804 | 0.386667 | 0.106667 | 0.555556 | 0.037037 | GAS7 | 17 | 17p13.1 | 9754651 | 9870349 |
| MYH13 | 0.009804 | 0.36 | 0.106667 | 0.555556 | 0.037037 | MYH13 | 17 | 17p13.1 | 10144908 | 10217048 |
| C17orf39 | 0.009804 | 0.466667 | 0.106667 | 0.703704 | 0.037037 | C17orf39 | 17 | 17p11.2 | 17883336 | 17912444 |
| ACLY | 0.009804 | 0.466667 | 0.106667 | 0.703704 | 0.037037 | ACLY | 17 | 17q21.2 | 37276705 | 37328799 |
| KCNJ16 | 0.009804 | 0.106667 | 0.146667 | 0.296296 | 0.037037 | KCNJ16 | 17 | 17q24.3 | 65583021 | 65643342 |
| IRF8 | 0.009804 | 0.36 | 0.133333 | 0.62963 | 0.037037 | IRF8 | 16 | 16q24.1 | 84490275 | 84513713 |
| MAP1LC3B | 0.009804 | 0.426667 | 0.146667 | 0.62963 | 0.037037 | MAP1LC3B | 16 | 16q24.2 | 85983302 | 85995881 |
| KLHDC4 | 0.009804 | 0.426667 | 0.186667 | 0.62963 | 0.037037 | KLHDC4 | 16 | 16q24.2 | 86298919 | 86357044 |
| FANCA | 0.009804 | 0.48 | 0.186667 | 0.703704 | 0.037037 | FANCA | 16 | 16q24.3 | 88331460 | 88410567 |
| MEIS2 | 0.009804 | 0.013333 | 0.133333 | 0.037037 | 0.037037 | MEIS2 | 15 | 15q14 | 34970524 | 35180793 |
| SPRED1 | 0.009804 | 0.026667 | 0.146667 | 0.037037 | 0.037037 | SPRED1 | 15 | 15q14 | 36332344 | 36436743 |
| SHC4 | 0.009804 | 0.013333 | 0.106667 | 0.037037 | 0.037037 | SHC4 | 15 | 15q21.1 | 46903227 | 47042934 |
| ATP8B4 | 0.009804 | 0.013333 | 0.133333 | 0.074074 | 0.037037 | ATP8B4 | 15 | 15q21.2 | 47937727 | 48198712 |
| PIGB | 0.009804 | 0.12 | 0.026667 | 0.037037 | 0 | PIGB | 15 | 15q21.3 | 53398425 | 53435139 |
| CCPG1 | 0.009804 | 0.12 | 0.026667 | 0.037037 | 0 | CCPG1 | 15 | 15q21.3 | 53434730 | 53487835 |
| MIR628 | 0.009804 | 0.12 | 0.026667 | 0.037037 | 0 | MIR628 | 15 | 15q21.3 | 53452430 | 53452525 |
| DYX1C1 | 0.009804 | 0.12 | 0.026667 | 0.037037 | 0 | DYX1C1 | 15 | 15q21.3 | 53497246 | 53587725 |
| PYGO1 | 0.009804 | 0.12 | 0.026667 | 0.037037 | 0 | PYGO1 | 15 | 15q21.3 | 53625513 | 53668343 |
| PRTG | 0.009804 | 0.12 | 0.026667 | 0.037037 | 0 | PRTG | 15 | 15q21.3 | 53691042 | 53822470 |
| AGBL1 | 0.009804 | 0.106667 | 0.146667 | 0.296296 | 0.037037 | AGBL1 | 15 | 15q25.3 | 84486246 | 85373288 |
| MCTP2 | 0.009804 | 0.12 | 0 | 0.037037 | 0 | MCTP2 | 15 | 15q26.2 | 92642434 | 92828185 |
| STXBP6 | 0.009804 | 0.04 | 0.16 | 0.037037 | 0.037037 | STXBP6 | 14 | 14q12 | 24351144 | 24588936 |
| PRKD1 | 0.009804 | 0.04 | 0.2 | 0 | 0.037037 | PRKD1 | 14 | 14q12 | 29115438 | 29466651 |
| TRIM9 | 0.009804 | 0.106667 | 0 | 0.037037 | 0.037037 | TRIM9 | 14 | 14q22.1 | 50511731 | 50632173 |
| C14orf37 | 0.009804 | 0.013333 | 0.12 | 0 | 0.037037 | C14orf37 | 14 | 14q23.1 | 57540561 | 57688601 |
| ACTR10 | 0.009804 | 0.106667 | 0.013333 | 0.037037 | 0 | ACTR10 | 14 | 14q23.1 | 57736586 | 57772107 |
| PSMA3 | 0.009804 | 0.106667 | 0.04 | 0.037037 | 0 | PSMA3 | 14 | 14q23.1 | 57781346 | 57808480 |
| FLJ31306 | 0.009804 | 0.106667 | 0.04 | 0.037037 | 0 | FLJ31306 | 14 | 14q23.1 | 57801837 | 57834609 |
| FLJ43390 | 0.009804 | 0.013333 | 0.213333 | 0.037037 | 0.037037 | FLJ43390 | 14 | 14q23.2 | 61653828 | 61664886 |
| KCNH5 | 0.009804 | 0.013333 | 0.2 | 0.037037 | 0.037037 | KCNH5 | 14 | 14q23.2 | 62243698 | 62581709 |
| FUT8 | 0.009804 | 0.093333 | 0.106667 | 0.222222 | 0.037037 | FUT8 | 14 | 14q23.3 | 64947593 | 65279716 |
| DIO2 | 0.009804 | 0.013333 | 0.186667 | 0.037037 | 0.037037 | DIO2 | 14 | 14q31.1 | 79733622 | 79748279 |
| C14orf145 | 0.009804 | 0.013333 | 0.16 | 0.037037 | 0.037037 | C14orf145 | 14 | 14q31.1 | 80032574 | 80475638 |
| TSHR | 0.009804 | 0.026667 | 0.16 | 0 | 0.037037 | TSHR | 14 | 14q31.1 | 80491622 | 80682400 |
| POLR1D | 0.009804 | 0.16 | 0.12 | 0.333333 | 0.037037 | POLR1D | 13 | 13q12.2 | 27094003 | 27139549 |
| KL | 0.009804 | 0.106667 | 0.106667 | 0.037037 | 0.074074 | KL | 13 | 13q13.1 | 32488571 | 32538282 |
| STARD13 | 0.009804 | 0.106667 | 0.12 | 0.037037 | 0.074074 | STARD13 | 13 | 13q13.1 | 32575273 | 32678198 |
| MIR548F5 | 0.009804 | 0.12 | 0.186667 | 0.037037 | 0.111111 | MIR548F5 | 13 | 13q13.3 | 34946406 | 35413383 |
| SMAD9 | 0.009804 | 0.146667 | 0.186667 | 0.037037 | 0.111111 | SMAD9 | 13 | 13q13.3 | 36320207 | 36392410 |
| ALG5 | 0.009804 | 0.16 | 0.213333 | 0.037037 | 0.111111 | ALG5 | 13 | 13q13.3 | 36421310 | 36471505 |
| LOC646982 | 0.009804 | 0.066667 | 0.24 | 0.074074 | 0.037037 | LOC646982 | 13 | 13q14.11 | 39819273 | 39953144 |
| FOXO1 | 0.009804 | 0.12 | 0.226667 | 0.074074 | 0.037037 | FOXO1 | 13 | 13q14.11 | 40027801 | 40138735 |
| MIR320D1 | 0.009804 | 0.12 | 0.24 | 0.074074 | 0.037037 | MIR320D1 | 13 | 13q14.11 | 40199964 | 40200067 |
| MRPS31 | 0.009804 | 0.12 | 0.24 | 0.074074 | 0.037037 | MRPS31 | 13 | 13q14.11 | 40201432 | 40243348 |
| SLC25A15 | 0.009804 | 0.12 | 0.213333 | 0.074074 | 0.037037 | SLC25A15 | 13 | 13q14.11 | 40261547 | 40284596 |
| SUGT1L1 | 0.009804 | 0.106667 | 0.213333 | 0.074074 | 0.037037 | SUGT1L1 | 13 | 13q14.11 | 40269127 | 40393887 |
| MIR621 | 0.009804 | 0.106667 | 0.213333 | 0.074074 | 0.037037 | MIR621 | 13 | 13q14.11 | 40282902 | 40282998 |
| ELF1 | 0.009804 | 0.106667 | 0.213333 | 0.074074 | 0.037037 | ELF1 | 13 | 13q14.11 | 40404056 | 40454419 |
| WBP4 | 0.009804 | 0.12 | 0.213333 | 0.074074 | 0.037037 | WBP4 | 13 | 13q14.11 | 40533697 | 40556140 |
| KBTBD6 | 0.009804 | 0.106667 | 0.226667 | 0.074074 | 0.037037 | KBTBD6 | 13 | 13q14.11 | 40599709 | 40604937 |
| MTRF1 | 0.009804 | 0.08 | 0.226667 | 0.037037 | 0.037037 | MTRF1 | 13 | 13q14.11 | 40688516 | 40735714 |
| NARG1L | 0.009804 | 0.08 | 0.226667 | 0.037037 | 0.037037 | NARG1L | 13 | 13q14.11 | 40783341 | 40830855 |
| KIAA0564 | 0.009804 | 0.04 | 0.266667 | 0.037037 | 0.037037 | KIAA0564 | 13 | 13q14.11 | 41038961 | 41433222 |
| DGKH | 0.009804 | 0.013335 | 0.293333 | 0.037037 | 0.037037 | DGKH | 13 | 13q14.11 | 41520889 | 41701869 |
| NUFIP1 | 0.009804 | 0.12 | 0.24 | 0.037037 | 0.111111 | NUFIP1 | 13 | 13q14.12 | 44411384 | 44461614 |
| KIAA1704 | 0.009804 | 0.12 | 0.24 | 0.037037 | 0.111111 | KIAA1704 | 13 | 13q14.12 | 44461687 | 44500405 |
| GTF2F2 | 0.009804 | 0.12 | 0.24 | 0.037037 | 0.111111 | GTF2F2 | 13 | 13q14.12 | 44592631 | 44756240 |
| KCTD4 | 0.009804 | 0.12 | 0.24 | 0.037037 | 0.111111 | KCTD4 | 13 | 13q14.12 | 44664988 | 44673176 |
| TPT1 | 0.009804 | 0.12 | 0.253333 | 0.037037 | 0.111111 | TPT1 | 13 | 13q14.12 | 44809304 | 44813298 |

TABLE 2-continued

Gene list for predicting prostate cancer relapse using prostate cancer tissue

| Symbol | freq. use | freq. amp. case | freq. del. case | freq. control | freq. control | Gene. Symbol | chromo-some | cytoband | Tran-script. start | Tran-script. end |
|---|---|---|---|---|---|---|---|---|---|---|
| SNORA31 | 0.009804 | 0.12 | 0.253333 | 0.037037 | 0.111111 | SNORA31 | 13 | 13q14.12 | 44809615 | 44809745 |
| LOC100190939 | 0.009804 | 0.12 | 0.253333 | 0.037037 | 0.111111 | LOC100190939 | 13 | 13q14.12 | 44813480 | 44863617 |
| COG3 | 0.009804 | 0.12 | 0.253333 | 0.037037 | 0.111111 | COG3 | 13 | 13q14.12 | 44937072 | 45008762 |
| ABCC4 | 0.009804 | 0.133333 | 0.16 | 0.037037 | 0.222222 | ABCC4 | 13 | 13q32.1 | 94470084 | 94751689 |
| UBAC2 | 0.009804 | 0.2 | 0.12 | 0.037037 | 0.074074 | UBAC2 | 13 | 13q32.3 | 98650680 | 98836753 |
| MIR623 | 0.009804 | 0.226667 | 0.12 | 0.037037 | 0.074074 | MIR623 | 13 | 13q32.3 | 98806386 | 98806484 |
| TM9SF2 | 0.009804 | 0.146667 | 0.173333 | 0.037037 | 0.074074 | TM9SF2 | 13 | 13q32.3 | 98951729 | 99013278 |
| CLYBL | 0.009804 | 0.186667 | 0.12 | 0.037037 | 0.074074 | CLYBL | 13 | 13q32.3 | 99056920 | 99347389 |
| PCCA | 0.009804 | 0.16 | 0.12 | 0.037037 | 0.074074 | PCCA | 13 | 13q32.3 | 99539338 | 99980690 |
| TMTC4 | 0.009804 | 0.146667 | 0.12 | 0.037037 | 0.074074 | TMTC4 | 13 | 13q32.3 | 1E+08 | 1E+08 |
| ANKRD10 | 0.009804 | 0.293333 | 0.12 | 0.444444 | 0.037037 | ANKRD10 | 13 | 13q34 | 1.1E+08 | 1.1E+08 |
| C13orf28 | 0.009804 | 0.4 | 0.106667 | 0.62963 | 0.037037 | C13orf28 | 13 | 13q34 | 1.12E+08 | 1.12E+08 |
| TUBGCP3 | 0.009804 | 0.413333 | 0.12 | 0.592593 | 0.037037 | TUBGCP3 | 13 | 13q34 | 1.12E+08 | 1.12E+08 |
| C13orf35 | 0.009804 | 0.44 | 0.12 | 0.62963 | 0.037037 | C13orf35 | 13 | 13q34 | 1.12E+08 | 1.12E+08 |
| ATP11A | 0.009804 | 0.44 | 0.133333 | 0.666667 | 0.037037 | ATP11A | 13 | 13q34 | 1.12E+08 | 1.13E+08 |
| MCF2L | 0.009804 | 0.44 | 0.133333 | 0.666667 | 0.037037 | MCF2L | 13 | 13q34 | 1.13E+08 | 1.13E+08 |
| F7 | 0.009804 | 0.44 | 0.133333 | 0.666667 | 0.037037 | F7 | 13 | 13q34 | 1.13E+08 | 1.13E+08 |
| F10 | 0.009804 | 0.44 | 0.133333 | 0.666667 | 0.037037 | F10 | 13 | 13q34 | 1.13E+08 | 1.13E+08 |
| PROZ | 0.009804 | 0.44 | 0.133333 | 0.666667 | 0.037037 | PROZ | 13 | 13q34 | 1.13E+08 | 1.13E+08 |
| PCID2 | 0.009804 | 0.44 | 0.133333 | 0.666667 | 0.037037 | PCID2 | 13 | 13q34 | 1.13E+08 | 1.13E+08 |
| CUL4A | 0.009804 | 0.44 | 0.133333 | 0.666667 | 0.037037 | CUL4A | 13 | 13q34 | 1.13E+08 | 1.13E+08 |
| LAMP1 | 0.009804 | 0.44 | 0.133333 | 0.666667 | 0.037037 | LAMP1 | 13 | 13q34 | 1.13E+08 | 1.13E+08 |
| GRTP1 | 0.009804 | 0.44 | 0.133333 | 0.666667 | 0.037037 | GRTP1 | 13 | 13q34 | 1.13E+08 | 1.13E+08 |
| TMCO3 | 0.009804 | 0.466667 | 0.133333 | 0.62963 | 0.037037 | TMCO3 | 13 | 13q34 | 1.13E+08 | 1.13E+08 |
| TFDP1 | 0.009804 | 0.466667 | 0.12 | 0.666667 | 0.037037 | TFDP1 | 13 | 13q34 | 1.13E+08 | 1.13E+08 |
| GRK1 | 0.009804 | 0.466667 | 0.12 | 0.666667 | 0.037037 | GRK1 | 13 | 13q34 | 1.13E+08 | 1.13E+08 |
| FLJ44054 | 0.009804 | 0.466667 | 0.12 | 0.666667 | 0.037037 | FLJ44054 | 13 | 13q34 | 1.13E+08 | 1.14E+08 |
| GAS6 | 0.009804 | 0.466667 | 0.12 | 0.666667 | 0.037037 | GAS6 | 13 | 13q34 | 1.14E+08 | 1.14E+08 |
| FAM70B | 0.009804 | 0.466667 | 0.12 | 0.666667 | 0.037037 | FAM70B | 13 | 13q34 | 1.14E+08 | 1.14E+08 |
| RASA3 | 0.009804 | 0.466667 | 0.12 | 0.666667 | 0.037037 | RASA3 | 13 | 13q34 | 1.14E+08 | 1.14E+08 |
| CDC16 | 0.009804 | 0.466667 | 0.12 | 0.666667 | 0.037037 | CDC16 | 13 | 13q34 | 1.14E+08 | 1.14E+08 |
| ZNF828 | 0.009804 | 0.466667 | 0.12 | 0.666667 | 0.037037 | ZNF828 | 13 | 13q34 | 1.14E+08 | 1.14E+08 |
| ACSM4 | 0.009804 | 0.146667 | 0.146667 | 0.37037 | 0.037037 | ACSM4 | 12 | 12p13.31 | 7348195 | 7372237 |
| LOC374443 | 0.009804 | 0.013333 | 0.2 | 0.074074 | 0.037037 | LOC374443 | 12 | 12p13.31 | 9691910 | 9702276 |
| CLECL1 | 0.009804 | 0.013333 | 0.2 | 0.037037 | 0.037037 | CLECL1 | 12 | 12p13.31 | 9766358 | 9777128 |
| CD69 | 0.009804 | 0.013333 | 0.2 | 0.037037 | 0.037037 | CD69 | 12 | 12p13.31 | 9796351 | 9809189 |
| CLEC2A | 0.009804 | 0.026667 | 0.186667 | 0.037037 | 0.037037 | CLEC2A | 12 | 12p13.31 | 9957093 | 9976248 |
| CLEC12A | 0.009804 | 0.013333 | 0.213333 | 0.037037 | 0.037037 | CLEC12A | 12 | 12p13.2 | 10015275 | 10029462 |
| CLEC1B | 0.009804 | 0.04 | 0.186667 | 0.037037 | 0.037037 | CLEC1B | 12 | 12p13.2 | 10036929 | 10043167 |
| CLEC12B | 0.009804 | 0.026667 | 0.213333 | 0.037037 | 0.037037 | CLEC12B | 12 | 12p13.2 | 10054498 | 10062667 |
| CLEC9A | 0.009804 | 0.013333 | 0.213333 | 0.037037 | 0.037037 | CLEC9A | 12 | 12p13.2 | 10074543 | 10109833 |
| CLEC1A | 0.009804 | 0.013333 | 0.213333 | 0.037037 | 0.037037 | CLEC1A | 12 | 12p13.2 | 10114347 | 10142873 |
| KLRC1 | 0.009804 | 0.013333 | 0.2 | 0.037037 | 0.037037 | KLRC1 | 12 | 12p13.2 | 10489904 | 10497247 |
| STYK1 | 0.009804 | 0.013333 | 0.16 | 0.037037 | 0.037037 | STYK1 | 12 | 12p13.2 | 10662805 | 10718159 |
| CSDA | 0.009804 | 0.013333 | 0.16 | 0.037037 | 0.037037 | CSDA | 12 | 12p13.2 | 10742945 | 10767221 |
| PLBD1 | 0.009804 | 0.106667 | 0.146667 | 0.074074 | 0.037037 | PLBD1 | 12 | 12p13.1 | 14547864 | 14612059 |
| GUCY2C | 0.009804 | 0.08 | 0.146667 | 0.074074 | 0.037037 | GUCY2C | 12 | 12p13.1 | 14656836 | 14740787 |
| PLEKHA5 | 0.009804 | 0.053333 | 0.12 | 0.037037 | 0.037037 | PLEKHA5 | 12 | 12p12.3 | 19173915 | 19420599 |
| SOX5 | 0.009804 | 0 | 0.253333 | 0 | 0.037037 | SOX5 | 12 | 12p12.1 | 23576498 | 23993905 |
| C12orf67 | 0.009804 | 0 | 0.24 | 0 | 0.037037 | C12orf67 | 12 | 12p12.1 | 24611165 | 24628370 |
| CCDC91 | 0.009804 | 0.013333 | 0.253333 | 0 | 0.037037 | CCDC91 | 12 | 12p11.22 | 28301400 | 28594367 |
| YAF2 | 0.009804 | 0.12 | 0.04 | 0.037037 | 0 | YAF2 | 12 | 12q12 | 40837174 | 40918318 |
| ADAMTS20 | 0.009804 | 0.026667 | 0.16 | 0.074074 | 0.037037 | ADAMTS20 | 12 | 12q12 | 42034279 | 42231992 |
| TWF1 | 0.009804 | 0.053333 | 0.106667 | 0.074074 | 0.037037 | TWF1 | 12 | 12q12 | 42473793 | 42486446 |
| TMEM117 | 0.009804 | 0.053333 | 0.106667 | 0.074074 | 0.037037 | TMEM117 | 12 | 12q12 | 42516229 | 43069809 |
| DBX2 | 0.009804 | 0.026667 | 0.12 | 0.074074 | 0.037037 | DBX2 | 12 | 12q12 | 43694806 | 43731150 |
| MON2 | 0.009804 | 0.16 | 0.013333 | 0.037037 | 0.037037 | MON2 | 12 | 12q14.1 | 61146864 | 61277631 |
| PPM1H | 0.009804 | 0.173333 | 0.013333 | 0.037037 | 0.037037 | PPM1H | 12 | 12q14.1 | 61324031 | 61614933 |
| C12orf66 | 0.009804 | 0.12 | 0.026667 | 0.037037 | 0 | C12orf66 | 12 | 12q14.2 | 62872686 | 62902344 |
| C12orf56 | 0.009804 | 0.12 | 0.026667 | 0.037037 | 0 | C12orf56 | 12 | 12q14.2 | 62947032 | 63070613 |
| TBK1 | 0.009804 | 0.146667 | 0.026667 | 0.037037 | 0 | TBK1 | 12 | 12q14.2 | 63132204 | 63182159 |
| GNS | 0.009804 | 0.146667 | 0.026667 | 0.037037 | 0 | GNS | 12 | 12q14.2 -1 | 63393489 | 63439494 |
| CPM | 0.009804 | 0.106667 | 0.04 | 0.037037 | 0 | CPM | 12 | 12q15 | 67531225 | 67613247 |
| CPSF6 | 0.009804 | 0.16 | 0.013333 | 0.037037 | 0 | CPSF6 | 12 | 12q15 | 67919584 | 67954406 |
| MIR1279 | 0.009804 | 0.16 | 0.013333 | 0.037037 | 0 | MIR1279 | 12 | 12q15 | 67953204 | 67953265 |
| FRS2 | 0.009804 | 0.146667 | 0.013333 | 0.037037 | 0 | FRS2 | 12 | 12q15 | 68150396 | 68259830 |
| CCT2 | 0.009804 | 0.146667 | 0.013333 | 0.037037 | 0 | CCT2 | 12 | 12q15 | 68265475 | 68281625 |
| BEST3 | 0.009804 | 0.146667 | 0.013333 | 0.037037 | 0 | BEST3 | 12 | 12q15 | 68333656 | 68379464 |
| ZDHHC17 | 0.009804 | 0.106667 | 0.066667 | 0.037037 | 0.111111 | ZDHHC17 | 12 | 12q21.2 | 75681935 | 75771606 |
| WDR51B | 0.009804 | 0.106667 | 0.066667 | 0.037037 | 0.185185 | WDR51B | 12 | 12q21.33 | 88337634 | 88443909 |
| EEA1 | 0.009804 | 0.106667 | 0.013333 | 0.037037 | 0 | EEA1 | 12 | 12q22 | 91690416 | 91847239 |
| NUDT4 | 0.009804 | 0.186667 | 0.013333 | 0.037037 | 0 | NUDT4 | 12 | 12q22 | 92295832 | 92321156 |
| NUDT4P1 | 0.009804 | 0.186667 | 0.013333 | 0.037037 | 0 | NUDT4P1 | 12 | 12q22 | 92295877 | 92320183 |
| SOCS2 | 0.009804 | 0.133333 | 0.013333 | 0.037037 | 0 | SOCS2 | 12 | 12q22 | 92487729 | 92494110 |

TABLE 2-continued

Gene list for predicting prostate cancer relapse using prostate cancer tissue

| Symbol | freq. use | freq. amp. case | freq. del. case | freq. control | freq. control | Gene. Symbol | chromosome | cytoband | Transcript. start | Transcript. end |
|---|---|---|---|---|---|---|---|---|---|---|
| CRADD | 0.009804 | 0.133333 | 0.013333 | 0.037037 | 0 | CRADD | 12 | 12q22 | 92595282 | 92768663 |
| ANKS1B | 0.009804 | 0.12 | 0.066667 | 0.037037 | 0 | ANKS1B | 12 | 12q23.1 | 97653202 | 98072604 |
| OR51A7 | 0.009804 | 0.053333 | 0.12 | 0.037037 | 0.037037 | OR51A7 | 11 | 11p15.4 | 4885175 | 4886115 |
| OR52A1 | 0.009804 | 0.013333 | 0.133333 | 0 | 0.037037 | OR52A1 | 11 | 11p15.4 | 5129237 | 5130176 |
| OR51V1 | 0.009804 | 0.013333 | 0.146667 | 0 | 0.037037 | OR51V1 | 11 | 11p15.4 | 5177541 | 5178507 |
| OR51B4 | 0.009804 | 0.013333 | 0.12 | 0 | 0.037037 | OR51B4 | 11 | 11p15.4 | 5278820 | 5279753 |
| OR51B5 | 0.009804 | 0.013333 | 0.133333 | 0 | 0.037037 | OR51B5 | 11 | 11p15.4 | 5320392 | 5321331 |
| OR51B6 | 0.009804 | 0.013333 | 0.133333 | 0 | 0.037037 | OR51B6 | 11 | 11p15.4 | 5329314 | 5330253 |
| UBQLN3 | 0.009804 | 0.013333 | 0.133333 | 0 | 0.037037 | UBQLN3 | 11 | 11p15.4 | 5485106 | 5487730 |
| UBQLNL | 0.009804 | 0.013333 | 0.133333 | 0 | 0.037037 | UBQLNL | 11 | 11p15.4 | 5492199 | 5494533 |
| TRIM6 | 0.009804 | 0.173333 | 0.013333 | 0.037037 | 0.037037 | TRIM6 | 11 | 11p15.4 | 5573923 | 5590765 |
| TRIM6-TRIM34 | 0.009804 | 0.173333 | 0.013333 | 0.037037 | 0.037037 | TRIM6-TRIM34 | 11 | 11p15.4 | 5574460 | 5622200 |
| TRIM34 | 0.009804 | 0.173333 | 0.013333 | 0.037037 | 0.037037 | TRIM34 | 11 | 11p15.4 | 5597750 | 5622202 |
| FAM160A2 | 0.009804 | 0.12 | 0.013333 | 0.037037 | 0 | FAM160A2 | 11 | 11p15.4 | 6189140 | 6212518 |
| CNGA4 | 0.009804 | 0.12 | 0.013333 | 0.037037 | 0 | CNGA4 | 11 | 11p15.4 | 6216906 | 6222284 |
| CCKBR | 0.009804 | 0.12 | 0.013333 | 0.037037 | 0 | CCKBR | 11 | 11p15.4 | 6237542 | 6249933 |
| PRKCDBP | 0.009804 | 0.133333 | 0.013333 | 0.037037 | 0 | PRKCDBP | 11 | 11p15.4 | 6296752 | 6298317 |
| SMPD1 | 0.009804 | 0.133333 | 0.013333 | 0.037037 | 0 | SMPD1 | 11 | 11p15.4 | 6368231 | 6372803 |
| APBB1 | 0.009804 | 0.133333 | 0.013333 | 0.037037 | 0 | APBB1 | 11 | 11p15.4 | 6372931 | 6396877 |
| HPX | 0.009804 | 0.133333 | 0.013333 | 0.037037 | 0 | HPX | 11 | 11p15.4 | 6408844 | 6418831 |
| TRIM3 | 0.009804 | 0.133333 | 0.013333 | 0.037037 | 0 | TRIM3 | 11 | 11p15.4 | 6426419 | 6451782 |
| ARFIP2 | 0.009804 | 0.133333 | 0.013333 | 0.037037 | 0 | ARFIP2 | 11 | 11p15.4 | 6453502 | 6459172 |
| FXC1 | 0.009804 | 0.133333 | 0.013333 | 0.037037 | 0 | FXC1 | 11 | 11p15.4 | 6459253 | 6462488 |
| DNHD1 | 0.009804 | 0.133333 | 0.013333 | 0.037037 | 0 | DNHD1 | 11 | 11p15.4 | 6475102 | 6549829 |
| RRP8 | 0.009804 | 0.2 | 0.013333 | 0.037037 | 0.037037 | RRP8 | 11 | 11p15.4 | 6577728 | 6581388 |
| ILK | 0.009804 | 0.2 | 0.013333 | 0.037037 | 0.037037 | ILK | 11 | 11p15.4 | 6581540 | 6588676 |
| TAF10 | 0.009804 | 0.2 | 0.013333 | 0.037037 | 0 | TAF10 | 11 | 11p15.4 | 6588649 | 6590022 |
| TPP1 | 0.009804 | 0.2 | 0.013333 | 0.037037 | 0 | TPP1 | 11 | 11p15.4 | 6590573 | 6597269 |
| RBMXL2 | 0.009804 | 0.013333 | 0.146667 | 0.037037 | 0.037037 | RBMXL2 | 11 | 11p15.4 | 7066741 | 7068956 |
| SYT9 | 0.009804 | 0.013333 | 0.12 | 0.037037 | 0.037037 | SYT9 | 11 | 11p15.4 | 7229757 | 7446847 |
| PDE3B | 0.009804 | 0.04 | 0.106667 | 0.074074 | 0.037037 | PDE3B | 11 | 11p15.2 | 14621845 | 14850179 |
| FSHB | 0.009804 | 0.013333 | 0.186667 | 0.037037 | 0.037037 | FSHB | 11 | 11p14.1 | 30209139 | 30213401 |
| MPPED2 | 0.009804 | 0.026667 | 0.173333 | 0 | 0.037037 | MPPED2 | 11 | 11p14.1 | 30362616 | 30564507 |
| CSTF3 | 0.009804 | 0.16 | 0.12 | 0.185185 | 0.037037 | CSTF3 | 11 | 11p13 | 33062706 | 33139614 |
| OR4C16 | 0.009804 | 0.026667 | 0.2 | 0.037037 | 0.037037 | OR4C16 | 11 | 11q11 | 55096180 | 55097113 |
| SPRYD5 | 0.009804 | 0.053333 | 0.186667 | 0.074074 | 0.037037 | SPRYD5 | 11 | 11q11 | 55407349 | 55415859 |
| ZFP91 | 0.009804 | 0.08 | 0.133333 | 0.148148 | 0.037037 | ZFP91 | 11 | 11q12.1 | 58103163 | 58145092 |
| ZFP91-CNT | 0.009804 | 0.08 | 0.133333 | 0.148148 | 0.037037 | ZFP91-CNT | 11 | 11q12.1 | 58103163 | 58149780 |
| CNTF | 0.009804 | 0.08 | 0.133333 | 0.148148 | 0.037037 | CNTF | 11 | 11q12.1 | 58146722 | 58149780 |
| C11orf73 | 0.009804 | 0.106667 | 0.026667 | 0.037037 | 0 | C11orf73 | 11 | 11q14.2 | 85690901 | 85734633 |
| ME3 | 0.009804 | 0.12 | 0.026667 | 0.037037 | 0 | ME3 | 11 | 11q14.2 | 85829798 | 86060889 |
| GRM5 | 0.009804 | 0.04 | 0.173333 | 0 | 0.037037 | GRM5 | 11 | 11q14.2 | 87877393 | 88436465 |
| MTMR2 | 0.009804 | 0.026667 | 0.133333 | 0.037037 | 0.037037 | MTMR2 | 11 | 11q21 | 95205694 | 95297020 |
| MAML2 | 0.009804 | 0.04 | 0.12 | 0.037037 | 0.037037 | MAML2 | 11 | 11q21 | 95351088 | 95715993 |
| CWF19L2 | 0.009804 | 0.053333 | 0.146667 | 0.074074 | 0.037037 | CWF19L2 | 11 | 11q22.3 | 1.07E+08 | 1.07E+08 |
| NCAM1 | 0.009804 | 0.106667 | 0.146667 | 0.333333 | 0.037037 | NCAM1 | 11 | 11q23.1 | 1.12E+08 | 1.13E+08 |
| C11orf71 | 0.009804 | 0.106667 | 0.12 | 0.333333 | 0.037037 | C11orf71 | 11 | 11q23.2 | 1.14E+08 | 1.14E+08 |
| RBM7 | 0.009804 | 0.106667 | 0.12 | 0.333333 | 0.037037 | RBM7 | 11 | 11q23.2 | 1.14E+08 | 1.14E+08 |
| FAM55A | 0.009804 | 0.093333 | 0.146667 | 0.296296 | 0.037037 | FAM55A | 11 | 11q23.2 | 1.14E+08 | 1.14E+08 |
| FAM55B | 0.009804 | 0.093333 | 0.146667 | 0.333333 | 0.037037 | FAM55B | 11 | 11q23.2 | 1.14E+08 | 1.14E+08 |
| LOC399959 | 0.009804 | 0.093333 | 0.133333 | 0.37037 | 0.037037 | LOC399959 | 11 | 11q24.1 | 1.21E+08 | 1.22E+08 |
| TMEM225 | 0.009804 | 0.053333 | 0.16 | 0.148148 | 0.037037 | TMEM225 | 11 | 11q24.1 | 1.23E+08 | 1.23E+08 |
| OR8G2 | 0.009804 | 0.053333 | 0.12 | 0.074074 | 0.037037 | OR8G2 | 11 | 11q24.2 | 1.24E+08 | 1.24E+08 |
| OR8D1 | 0.009804 | 0.04 | 0.16 | 0.111111 | 0.037037 | OR8D1 | 11 | 11q24.2 | 1.24E+08 | 1.24E+08 |
| OR8D2 | 0.009804 | 0.04 | 0.16 | 0.111111 | 0.037037 | OR8D2 | 11 | 11q24.2 | 1.24E+08 | 1.24E+08 |
| OR8B4 | 0.009804 | 0.04 | 0.12 | 0.111111 | 0.037037 | OR8B4 | 11 | 11q24.2 | 1.24E+08 | 1.24E+08 |
| OR8A1 | 0.009804 | 0.04 | 0.106667 | 0.111111 | 0.037037 | OR8A1 | 11 | 11q24.2 | 1.24E+08 | 1.24E+08 |
| DNAJC1 | 0.009804 | 0.106667 | 0.026667 | 0.037037 | 0.074074 | DNAJC1 | 10 | 10p12.31 | 22085483 | 22332657 |
| RTKN2 | 0.009804 | 0.066667 | 0.12 | 0 | 0.037037 | RTKN2 | 10 | 10q21.2 | 63622959 | 63698473 |
| ZNF365 | 0.009804 | 0.066667 | 0.12 | 0 | 0.037037 | ZNF365 | 10 | 10q21.2 | 63803922 | 63832224 |
| NRG3 | 0.009804 | 0.106667 | 0.106667 | 0.037037 | 0.074074 | NRG3 | 10 | 10q23.1 | 83625050 | 84736916 |
| RBM20 | 0.009804 | 0.12 | 0.08 | 0.037037 | 0.111111 | RBM20 | 10 | 10q25.2 | 1.12E+08 | 1.13E+08 |
| GLIS3 | 0.009804 | 0.013333 | 0.173333 | 0.037037 | 0.037037 | GLIS3 | 9 | 9p24.2 | 3814128 | 4290036 |
| C9orf70 | 0.009804 | 0.013333 | 0.173333 | 0.037037 | 0.037037 | C9orf70 | 9 | 9p24.2 | 3888646 | 3891248 |
| NFIB | 0.009804 | 0.026667 | 0.106667 | 0 | 0.037037 | NFIB | 9 | 9p22.3 | 14071847 | 14303946 |
| ADAMTSL1 | 0.009804 | 0.026667 | 0.16 | 0.037037 | 0.037037 | ADAMTSL1 | 9 | 9p22.2 | 18464104 | 18900948 |
| KIAA1797 | 0.009804 | 0.026667 | 0.12 | 0 | 0.037037 | KIAA1797 | 9 | 9p21.3 | 20648309 | 20985955 |
| PTPLAD2 | 0.009804 | 0.026667 | 0.146667 | 0.037037 | 0.037037 | PTPLAD2 | 9 | 9p21.3 | 20996365 | 21021636 |
| IFNW1 | 0.009804 | 0.04 | 0.146667 | 0 | 0.037037 | IFNW1 | 9 | 9p21.3 | 21130631 | 21132145 |
| IFNA21 | 0.009804 | 0.04 | 0.146667 | 0 | 0.037037 | IFNA21 | 9 | 9p21.3 | 21155636 | 21156660 |
| MOBKL2B | 0.009804 | 0.133333 | 0.04 | 0.037037 | 0.037037 | MOBKL2B | 9 | 9p21.2 | 27315207 | 27519851 |
| KIF9 | 0.009804 | 0.106667 | 0 | 0.037037 | 0 | KIF9 | 9 | 9q21.11 | 72189333 | 72219394 |
| RORB | 0.009804 | 0.013333 | 0.146667 | 0.074074 | 0.037037 | RORB | 9 | 9q21.13 | 76302072 | 76491938 |
| LPPR1 | 0.009804 | 0.026667 | 0.133333 | 0.148148 | 0.037037 | LPPR1 | 9 | 9q31.1 | 1.03E+08 | 1.03E+08 |

TABLE 2-continued

Gene list for predicting prostate cancer relapse using prostate cancer tissue

| Symbol | freq. use | freq. amp. case | freq. del. case | freq. control | freq. control | Gene. Symbol | chromo-some | cytoband | Transcript. start | Transcript. end |
|---|---|---|---|---|---|---|---|---|---|---|
| MRPL50 | 0.009804 | 0.04 | 0.106667 | 0.111111 | 0.037037 | MRPL50 | 9 | 9q31.1 | 1.03E+08 | 1.03E+08 |
| ZNF189 | 0.009804 | 0.04 | 0.106667 | 0.111111 | 0.037037 | ZNF189 | 9 | 9q31.1 | 1.03E+08 | 1.03E+08 |
| ALDOB | 0.009804 | 0.04 | 0.12 | 0.111111 | 0.037037 | ALDOB | 9 | 9q31.1 | 1.03E+08 | 1.03E+08 |
| RNF20 | 0.009804 | 0.04 | 0.146667 | 0.111111 | 0.037037 | RNF20 | 9 | 9q31.1 | 1.03E+08 | 1.03E+08 |
| GRIN3A | 0.009804 | 0.026667 | 0.146667 | 0.111111 | 0.037037 | GRIN3A | 9 | 9q31.1 | 1.03E+08 | 1.04E+08 |
| ZNF462 | 0.009804 | 0.04 | 0.146667 | 0.074074 | 0.037037 | ZNF462 | 9 | 9q31.2 | 1.09E+08 | 1.09E+08 |
| DBC1 | 0.009804 | 0.12 | 0.106667 | 0.148148 | 0.037037 | DBC1 | 9 | 9q33.1 | 1.21E+08 | 1.21E+08 |
| ERICH1 | 0.009804 | 0.333333 | 0.186667 | 0.518519 | 0.037037 | ERICH1 | 8 | 8p23.3 | 604200 | 671227 |
| ASAH1 | 0.009804 | 0.106667 | 0.386667 | 0.037037 | 0.222222 | ASAH1 | 8 | 8p22 | 17958205 | 17986788 |
| DPYSL2 | 0.009804 | 0.106667 | 0.36 | 0.037037 | 0.185185 | DPYSL2 | 8 | 8p21.2 | 26491338 | 26571611 |
| STMN4 | 0.009804 | 0.133333 | 0.346667 | 0.037037 | 0.185185 | STMN4 | 8 | 8p21.2 | 27149731 | 27171821 |
| TRIM35 | 0.009804 | 0.133333 | 0.346667 | 0.037037 | 0.185185 | TRIM35 | 8 | 8p21.2 | 27198321 | 27224752 |
| PTK2B | 0.009804 | 0.146667 | 0.346667 | 0.037037 | 0.185185 | PTK2B | 8 | 8p21.2 | 27224916 | 27372821 |
| EPHX2 | 0.009804 | 0.146667 | 0.346667 | 0.037037 | 0.185185 | EPHX2 | 8 | 8p21.1 | 27404562 | 27458404 |
| CLU | 0.009804 | 0.146667 | 0.346667 | 0.037037 | 0.185135 | CLU | 8 | 8p21.1 | 27510368 | 27528245 |
| SCARA3 | 0.009804 | 0.12 | 0.373333 | 0.037037 | 0.185185 | SCARA3 | 8 | 8p21.1 | 27547496 | 27586457 |
| CCDC25 | 0.009804 | 0.106667 | 0.346667 | 0.037037 | 0.185185 | CCDC25 | 8 | 8p21.1 | 27646752 | 27686090 |
| ESCO2 | 0.009804 | 0.106667 | 0.346667 | 0.037037 | 0.185185 | ESCO2 | 8 | 8p21.1 | 27687977 | 27718344 |
| PBK | 0.009804 | 0.146667 | 0.346667 | 0.037037 | 0.185185 | PBK | 8 | 8p21.1 | 27723057 | 27751269 |
| SCARA5 | 0.009804 | 0.173333 | 0.346667 | 0.037037 | 0.185185 | SCARA5 | 8 | 8p21.1 | 27783669 | 27906118 |
| C8orf80 | 0.009804 | 0.16 | 0.346667 | 0.037037 | 0.185185 | C8orf80 | 8 | 8p21.1 | 27935400 | 27997308 |
| ELP3 | 0.009804 | 0.16 | 0.346667 | 0.037037 | 0.185185 | ELP3 | 8 | 8p21.1 | 28006503 | 28104589 |
| PNOC | 0.009804 | 0.16 | 0.346667 | 0.037037 | 0.185185 | PNOC | 8 | 8p21.1 | 28230568 | 28256788 |
| FBXO16 | 0.009804 | 0.106667 | 0.346667 | 0.037037 | 0.185185 | FBXO16 | 8 | 8p21.1 | 28341848 | 28403704 |
| EXTL3 | 0.009804 | 0.106667 | 0.346667 | 0.037037 | 0.185185 | EXTL3 | 8 | 8p21.1 | 28615072 | 28667122 |
| INTS9 | 0.009804 | 0.106667 | 0.346667 | 0.037037 | 0.185185 | INTS9 | 8 | 8p21.1 | 28681099 | 28803618 |
| KIF13B | 0.009804 | 0.12 | 0.36 | 0.037037 | 0.185185 | KIF13B | 8 | 8p21.1 | 28980714 | 29176530 |
| DUSP4 | 0.009804 | 0.106667 | 0.346667 | 0.037037 | 0.185185 | DUSP4 | 8 | 8p21.1 | 29249537 | 29262242 |
| FUT10 | 0.009804 | 0.16 | 0.36 | 0.037037 | 0.296296 | FUT10 | 8 | 8p12 | 33347886 | 33450207 |
| SNTG1 | 0.009804 | 0.12 | 0.16 | 0.111111 | 0.037037 | SNTG1 | 8 | 8q11.22 | 50987150 | 51867981 |
| ST18 | 0.009804 | 0.12 | 0.133333 | 0.111111 | 0.037037 | ST18 | 8 | 8q11.23 | 53185945 | 53484993 |
| MIR124-2 | 0.009804 | 0.106667 | 0.133333 | 0.111111 | 0.037037 | MIR124-2 | 8 | 8q12.3 | 65454260 | 65454367 |
| C8orf34 | 0.009804 | 0.133333 | 0.146667 | 0.111111 | 0.037037 | C8orf34 | 8 | 8q13.2 | 69512702 | 69893812 |
| KCNB2 | 0.009804 | 0.133333 | 0.106667 | 0.111111 | 0.037037 | KCNB2 | 8 | 8q13.3 | 73612180 | 74013139 |
| PGCP | 0.009804 | 0.16 | 0.106667 | 0.148148 | 0.037037 | PGCP | 8 | 8q22.1 | 97726675 | 98224899 |
| C1GALT1 | 0.009804 | 0.133333 | 0.106667 | 0.111111 | 0.037037 | C1GALT1 | 7 | 7p21.3 | 7188771 | 7250507 |
| EEPD1 | 0.009804 | 0.146667 | 0.013333 | 0.037037 | 0 | EEPD1 | 7 | 7p14.2 | 36159361 | 36307678 |
| ANLN | 0.009804 | 0.16 | 0 | 0.037037 | 0 | ANLN | 7 | 7p14.2 | 36395957 | 36459926 |
| AOAH | 0.009804 | 0.12 | 0 | 0.037037 | 0 | AOAH | 7 | 7p14.2 | 36519133 | 36730679 |
| RALA | 0.009804 | 0.133333 | 0 | 0.037037 | 0 | RALA | 7 | 7p14.1 | 39629687 | 39714243 |
| LOC349114 | 0.009804 | 0.146667 | 0 | 0.037037 | 0 | LOC349114 | 7 | 7p14.1 | 39739692 | 39800747 |
| CDK13 | 0.009804 | 0.186667 | 0 | 0.037037 | 0 | CDK13 | 7 | 7p14.1 | 39956484 | 40103257 |
| C7orf10 | 0.009804 | 0.2 | 0 | 0.037037 | 0 | C7orf10 | 7 | 7p14.1 | 40141100 | 40866883 |
| PION | 0.009804 | 0.133333 | 0 | 0.037037 | 0.074074 | PION | 7 | 7q11.23 | 76778004 | 76883654 |
| PTPN12 | 0.009804 | 0.146667 | 0.013333 | 0.037037 | 0.074074 | PTPN12 | 7 | 7q11.23 | 77004709 | 77107325 |
| TMEM60 | 0.009804 | 0.186667 | 0.013333 | 0.037037 | 0.074074 | TMEM60 | 7 | 7q11.23 | 77260982 | 77265684 |
| PHTF2 | 0.009804 | 0.186667 | 0.013333 | 0.037037 | 0.074074 | PHTF2 | 7 | 7q11.23 | 77266045 | 77424758 |
| MAGI2 | 0.009804 | 0.186667 | 0 | 0.037037 | 0 | MAGI2 | 7 | 7q21.11 | 77484310 | 78920827 |
| SEMA3C | 0.009804 | 0.146667 | 0.146667 | 0.037037 | 0.148148 | SEMA3C | 7 | 7q21.11 | 80209790 | 80386604 |
| CACNA2D1 | 0.009804 | 0.16 | 0.133333 | 0.037037 | 0.296296 | CACNA2D1 | 7 | 7q21.11 | 81417354 | 81910968 |
| SEMA3A | 0.009804 | 0.12 | 0.16 | 0.037037 | 0.333333 | SEMA3A | 7 | 7q21.11 | 83425595 | 83662154 |
| MTERF | 0.009804 | 0.186667 | 0.026667 | 0.037037 | 0 | MTERF | 7 | 7q21.2 | 91339957 | 91347953 |
| AKAP9 | 0.009804 | 0.213333 | 0 | 0.037037 | 0 | AKAP9 | 7 | 7q21.2 | 91408125 | 91577923 |
| CYP51A1 | 0.009804 | 0.173333 | 0 | 0.037037 | 0 | CYP51A1 | 7 | 7q21.2 | 91579399 | 91601777 |
| LOC401387 | 0.009804 | 0.173333 | 0 | 0.037037 | 0 | LOC401387 | 7 | 7q21.2 | 91612134 | 91632527 |
| KRIT1 | 0.009804 | 0.173333 | 0.013333 | 0.037037 | 0 | KRIT1 | 7 | 7q21.2 | 91666219 | 91713165 |
| CCDC132 | 0.009804 | 0.08 | 0.146667 | 0.037037 | 0.037037 | CCDC132 | 7 | 7q21.3 | 92699589 | 92826275 |
| GNGT1 | 0.009804 | 0.08 | 0.16 | 0.074074 | 0.037037 | GNGT1 | 7 | 7q21.3 | 93373756 | 93378422 |
| NRCAM | 0.009804 | 0.133333 | 0.08 | 0.037037 | 0.037037 | NRCAM | 7 | 7q31.1 | 1.08E+08 | 1.08E+08 |
| IFRD1 | 0.009804 | 0.12 | 0.04 | 0.037037 | 0.074074 | IFRD1 | 7 | 7q31.1 | 1.12E+08 | 1.12E+08 |
| MET | 0.009804 | 0.066667 | 0.106667 | 0.074074 | 0.037037 | MET | 7 | 7q31.2 | 1.16E+08 | 1.16E+08 |
| ST7 | 0.009804 | 0.106667 | 0.066667 | 0.037037 | 0.111111 | ST7 | 7 | 7q31.2 | 1.16E+08 | 1.17E+08 |
| ST7OT3 | 0.009804 | 0.106667 | 0.066667 | 0.037037 | 0.111111 | ST7OT3 | 7 | 7q31.2 | 1.17E+08 | 1.17E+08 |
| MBOAT1 | 0.009804 | 0.106667 | 0.013333 | 0.037037 | 0 | MBOAT1 | 6 | 6p22.3 | 20208914 | 20320650 |
| E2F3 | 0.009804 | 0.12 | 0.013333 | 0.037037 | 0 | E2F3 | 6 | 6p22.3 | 20510116 | 20601925 |
| CDKAL1 | 0.009804 | 0.146667 | 0.013333 | 0.037037 | 0 | CDKAL1 | 6 | 6p22.3 | 20642667 | 21339744 |
| SOX4 | 0.009804 | 0.173333 | 0.013333 | 0.037037 | 0 | SOX4 | 6 | 6p22.3 | 21701951 | 21706829 |
| FLJ22536 | 0.009804 | 0.16 | 0.013333 | 0.037037 | 0 | FLJ22536 | 6 | 6p22.3 | 21774654 | 22302594 |
| ZNRD1 | 0.009804 | 0.266667 | 0.106667 | 0.444444 | 0.037037 | ZNRD1 | 6 | 6p21.33 | 30137015 | 30140666 |
| DNAH8 | 0.009804 | 0.186667 | 0.133333 | 0.555556 | 0.037037 | DNAH8 | 6 | 6p21.2 | 38798530 | 39106546 |
| MIR206 | 0.009804 | 0.013333 | 0.106667 | 0.037037 | 0.037037 | MIR206 | 6 | 6p12.2 | 52117106 | 52117192 |
| MIR133B | 0.009804 | 0.013333 | 0.106667 | 0.037037 | 0.037037 | MIR133B | 6 | 6p12.2 | 52121680 | 52121798 |
| PAQR8 | 0.009804 | 0.12 | 0.013333 | 0.037037 | 0.037037 | PAQR8 | 6 | 6p12.2 | 52334885 | 52380535 |
| BACH2 | 0.009804 | 0.16 | 0.2 | 0.037037 | 0.185185 | BACH2 | 6 | 6q15 | 90692969 | 91063349 |

TABLE 2-continued

Gene list for predicting prostate cancer relapse using prostate cancer tissue

| Symbol | freq. use | freq. amp. case | freq. del. case | freq. control | freq. control | Gene. Symbol | chromo-some | cytoband | Transcript. start | Transcript. end |
|---|---|---|---|---|---|---|---|---|---|---|
| SOBP | 0.009804 | 0.12 | 0.16 | 0.037037 | 0.074074 | SOBP | 6 | 6q21 | 1.08E+08 | 1.08E+08 |
| SCML4 | 0.009804 | 0.146667 | 0.146667 | 0.037037 | 0.074074 | SCML4 | 6 | 6q21 | 1.08E+08 | 1.08E+08 |
| SEC63 | 0.009804 | 0.146667 | 0.146667 | 0.037037 | 0.074074 | SEC63 | 6 | 6q21 | 1.08E+08 | 1.08E+08 |
| OSTM1 | 0.009804 | 0.146667 | 0.146667 | 0.037037 | 0.074074 | OSTM1 | 6 | 6q21 | 1.08E+08 | 1.09E+08 |
| NR2E1 | 0.009804 | 0.146667 | 0.146667 | 0.037037 | 0.074074 | NR2E1 | 6 | 6q21 | 1.09E+08 | 1.09E+08 |
| SNX3 | 0.009804 | 0.146667 | 0.146667 | 0.037037 | 0.074074 | SNX3 | 6 | 6q21 | 1.09E+08 | 1.09E+08 |
| LACE1 | 0.009804 | 0.146667 | 0.146667 | 0.037037 | 0.074074 | LACE1 | 6 | 6q21 | 1.09E+08 | 1.09E+08 |
| FOXO3 | 0.009804 | 0.146667 | 0.146667 | 0.037037 | 0.074074 | FOXO3 | 6 | 6q21 | 1.09E+08 | 1.09E+08 |
| ARMC2 | 0.009804 | 0.146667 | 0.146667 | 0.037037 | 0.074074 | ARMC2 | 6 | 6q21 | 1.09E+08 | 1.09E+08 |
| SESN1 | 0.009804 | 0.133333 | 0.146667 | 0.037037 | 0.074074 | SESN1 | 6 | 6q21 | 1.09E+08 | 1.1E+08 |
| PPIL6 | 0.009804 | 0.146667 | 0.146667 | 0.037037 | 0.074074 | PPIL6 | 6 | 6q21 | 1.1E+08 | 1.1E+08 |
| SLC22A16 | 0.009804 | 0.133333 | 0.133333 | 0.037037 | 0.111111 | SLC22A16 | 6 | 6q21 | 1.11E+08 | 1.11E+08 |
| CDK19 | 0.009804 | 0.146667 | 0.133333 | 0.037037 | 0.111111 | CDK19 | 6 | 6q21 | 1.11E+08 | 1.11E+08 |
| SLC16A10 | 0.009804 | 0.133333 | 0.133333 | 0.037037 | 0.111111 | SLC16A10 | 6 | 6q21 | 1.12E+08 | 1.12E+08 |
| KIAA1919 | 0.009804 | 0.146667 | 0.133333 | 0.037037 | 0.111111 | KIAA1919 | 6 | 6q21 | 1.12E+08 | 1.12E+08 |
| REV3L | 0.009804 | 0.133333 | 0.146667 | 0.037037 | 0.111111 | REV3L | 6 | 6q21 | 1.12E+08 | 1.12E+08 |
| TRAF3IP2 | 0.009804 | 0.146667 | 0.145667 | 0.037037 | 0.111111 | TRAF3IP2 | 6 | 6q21 | 1.12E+08 | 1.12E+08 |
| FYN | 0.009804 | 0.133333 | 0.133333 | 0.037037 | 0.148148 | FYN | 6 | 6q21 | 1.12E+08 | 1.12E+08 |
| SGK1 | 0.009804 | 0.133333 | 0.026667 | 0.037037 | 0 | SGK1 | 6 | 6q23.2 | 1.35E+08 | 1.35E+08 |
| ALDH8A1 | 0.009804 | 0.12 | 0.026667 | 0.037037 | 0 | ALDH8A1 | 6 | 6q23.3 | 1.35E+08 | 1.35E+08 |
| C6orf217 | 0.009804 | 0 | 0.16 | 0 | 0.037037 | C6orf217 | 6 | 6q23.3 | 1.36E+08 | 1.36E+08 |
| PDE7B | 0.009804 | 0 | 0.173333 | 0 | 0.037037 | PDE7B | 6 | 6q23.3 | 1.36E+08 | 1.37E+08 |
| NHSL1 | 0.009804 | 0.146667 | 0.04 | 0.037037 | 0 | NHSL1 | 6 | 6q23.3 | 1.39E+08 | 1.39E+08 |
| CCDC28A | 0.009804 | 0.146667 | 0.04 | 0.037037 | 0 | CCDC28A | 6 | 6q24.1 | 1.39E+08 | 1.39E+08 |
| ECT2L | 0.009804 | 0.146667 | 0.04 | 0.037037 | 0 | ECT2L | 6 | 6q24.1 | 1.39E+08 | 1.39E+08 |
| C6orf115 | 0.009804 | 0.146667 | 0.04 | 0.037037 | 0 | C6orf115 | 6 | 6q24.1 | 1.39E+08 | 1.39E+08 |
| HECA | 0.009804 | 0.146667 | 0.04 | 0.037037 | 0 | HECA | 6 | 6q24.1 | 1.39E+08 | 1.4E+08 |
| TXLNB | 0.009804 | 0.146667 | 0.04 | 0.037037 | 0 | TXLNB | 6 | 6q24.1 | 1.4E+08 | 1.4E+08 |
| LOC153910 | 0.009804 | 0 | 0.146667 | 0.037037 | 0.037037 | LOC153910 | 6 | 6q24.1 - 6c24.2 | 1.43E+08 | 1.43E+08 |
| MLLT4 | 0.009804 | 0.186667 | 0.106667 | 0.37037 | 0.037037 | MLLT4 | 6 | 6q27 | 1.68E+08 | 1.68E+08 |
| BASP1 | 0.009804 | 0.146667 | 0.013333 | 0.037037 | 0.037037 | BASP1 | 5 | 5p15.1 | 17270750 | 17329944 |
| TTC33 | 0.009804 | 0.173333 | 0 | 0.037037 | 0 | TTC33 | 5 | 5p13.1 | 40747435 | 40791830 |
| PRKAA1 | 0.009804 | 0.173333 | 0 | 0.037037 | 0 | PRKAA1 | 5 | 5p13.1 | 40795238 | 40834055 |
| RPL37 | 0.009804 | 0.173333 | 0 | 0.037037 | 0 | RPL37 | 5 | 5p13.1 | 40867187 | 40871145 |
| SNORD72 | 0.009804 | 0.173333 | 0 | 0.037037 | 0 | SNORD72 | 5 | 5p13.1 | 40868515 | 40868595 |
| CARD6 | 0.009804 | 0.173333 | 0 | 0.037037 | 0 | CARD6 | 5 | 5p13.1 | 40877167 | 40891214 |
| C7 | 0.009804 | 0.04 | 0.12 | 0 | 0.037037 | C7 | 5 | 5p13.1 | 40945356 | 41018799 |
| HEATR7B2 | 0.009804 | 0.013333 | 0.12 | 0 | 0.037037 | HEATR7B2 | 5 | 5p13.1 | 41033879 | 41107202 |
| C6 | 0.009804 | 0.013333 | 0.133333 | 0 | 0.037037 | C6 | 5 | 5p13.1 | 41178093 | 41249425 |
| PLCXD3 | 0.009804 | 0.013333 | 0.133333 | 0 | 0.037037 | PLCXD3 | 5 | 5p13.1 | 41342805 | 41546498 |
| OXCT1 | 0.009804 | 0.013333 | 0.12 | 0 | 0.037037 | OXCT1 | 5 | 5p13.1 | 41765924 | 41906549 |
| C5orf51 | 0.009804 | 0.013333 | 0.12 | 0 | 0.037037 | C5orf51 | 5 | 5p13.1 | 41940227 | 41957496 |
| FBXO4 | 0.009804 | 0.013333 | 0.12 | 0 | 0.037037 | FBXO4 | 5 | 5p13.1 | 41961113 | 41977430 |
| GHR | 0.009804 | 0.013333 | 0.133333 | 0 | 0.037037 | GHR | 5 | 5p12 | 42459783 | 42757684 |
| SEPP1 | 0.009804 | 0.04 | 0.12 | 0 | 0.037037 | SEPP1 | 5 | 5p12 | 42835739 | 42847782 |
| MGC42105 | 0.009804 | 0.146667 | 0 | 0.037037 | 0 | MGC42105 | 5 | 5p12 | 43228084 | 43316710 |
| HMGCS1 | 0.009804 | 0.146667 | 0 | 0.037037 | 0 | HMGCS1 | 5 | 5p12 | 43325250 | 43349353 |
| C5orf28 | 0.009804 | 0.16 | 0.013333 | 0.037037 | 0 | C5orf28 | 5 | 5p12 | 43480111 | 43519750 |
| PAIP1 | 0.009804 | 0.133333 | 0.04 | 0.037037 | 0 | PAIP1 | 5 | 5p12 | 43562127 | 43592953 |
| ARL15 | 0.009804 | 0.04 | 0.16 | 0 | 0.037037 | ARL15 | 5 | 5q11.2 | 53216371 | 53642161 |
| HSPB3 | 0.009804 | 0.026667 | 0.146667 | 0 | 0.037037 | HSPB3 | 5 | 5q11.2 | 53787202 | 53787965 |
| GZMA | 0.009804 | 0.04 | 0.16 | 0.037037 | 0.057037 | GZMA | 5 | 5q11.2 | 54434231 | 54441838 |
| CDC20B | 0.009804 | 0.04 | 0.16 | 0.037037 | 0.037037 | CDC20B | 5 | 5q11.2 | 54444556 | 54504763 |
| CCNO | 0.009804 | 0.08 | 0.133333 | 0.037037 | 0.037037 | CCNO | 5 | 5q11.2 | 54562738 | 54565266 |
| DHX29 | 0.009804 | 0.08 | 0.133333 | 0.037037 | 0.037037 | DHX29 | 5 | 5q11.2 | 54587830 | 54639279 |
| SKIV2L2 | 0.009804 | 0.08 | 0.133333 | 0.037037 | 0.037037 | SKIV2L2 | 5 | 5q11.2 | 54639333 | 54757167 |
| PPAP2A | 0.009804 | 0.08 | 0.146667 | 0.037037 | 0.037037 | PPAP2A | 5 | 5q11.2 | 54756440 | 54866631 |
| SLC38A9 | 0.009804 | 0.093333 | 0.146667 | 0.037037 | 0.037037 | SLC38A9 | 5 | 5q11.2 | 54957433 | 55043921 |
| BDP1 | 0.009804 | 0.146667 | 0.12 | 0.037037 | 0.074074 | BDP1 | 5 | 5q13.2 | 70787198 | 70899406 |
| MCCC2 | 0.009804 | 0.133333 | 0.12 | 0.037037 | 0.074074 | MCCC2 | 5 | 5q13.2 | 70918871 | 70990287 |
| TMEM174 | 0.009804 | 0.08 | 0.12 | 0.037037 | 0.037037 | TMEM174 | 5 | 5q13.2 | 72504779 | 72506725 |
| FOXD1 | 0.009804 | 0.066667 | 0.106667 | 0.037037 | 0.037037 | FOXD1 | 5 | 5q13.2 | 72777841 | 72780109 |
| SV2C | 0.009804 | 0.013333 | 0.16 | 0.037037 | 0.037037 | SV2C | 5 | 5q13.3 | 75415061 | 75657173 |
| F2R | 0.009804 | 0.146667 | 0.08 | 0.037037 | 0.037037 | F2R | 5 | 5q13.3 | 76047624 | 76067352 |
| F2R11 | 0.009804 | 0.133333 | 0.08 | 0.037037 | 0.037037 | F2RL1 | 5 | 5q13.3 | 76150589 | 76166896 |
| S100Z | 0.009804 | 0.133333 | 0.08 | 0.037037 | 0.037037 | S100Z | 5 | 5q13.3 | 76181882 | 76252813 |
| LHFPL2 | 0.009804 | 0.106667 | 0.08 | 0.037037 | 0.037037 | LHFPL2 | 5 | 5q14.1 | 77816794 | 77980405 |
| DMGDH | 0.009804 | 0.08 | 0.133333 | 0.037037 | 0.037037 | DMGDH | 5 | 5q14.1 | 78329185 | 78401206 |
| BHMT2 | 0.009804 | 0.133333 | 0.08 | 0.037037 | 0.037037 | BHMT2 | 5 | 5q14.1 | 78401339 | 78421032 |
| BHMT | 0.009804 | 0.133333 | 0.08 | 0.037037 | 0.037037 | BHMT | 5 | 5q14.1 | 78443360 | 78463870 |
| JMY | 0.009804 | 0.133333 | 0.08 | 0.037037 | 0.037037 | JMY | 5 | 5q14.1 | 78567710 | 78658793 |
| HOMER1 | 0.009804 | 0.133333 | 0.08 | 0.037037 | 0.037037 | HOMER1 | 5 | 5q14.1 | 78705542 | 78845457 |
| CMYA5 | 0.009804 | 0.12 | 0.08 | 0.037037 | 0.037037 | CMYA5 | 5 | 5q14.1 | 79021415 | 79131806 |
| THBS4 | 0.009804 | 0.146667 | 0.08 | 0.037037 | 0.037037 | THBS4 | 5 | 5q14.1 | 79366747 | 79414864 |

TABLE 2-continued

Gene list for predicting prostate cancer relapse using prostate cancer tissue

| Symbol | freq. use | freq. amp. case | freq. del. case | freq. control | freq. control | Gene. Symbol | chromo-some | cytoband | Transcript. start | Transcript. end |
|---|---|---|---|---|---|---|---|---|---|---|
| SERINC5 | 0.009804 | 0.146667 | 0.08 | 0.037037 | 0.037037 | SERINC5 | 5 | 5q14.1 | 79443230 | 79587627 |
| FAM151B | 0.009804 | 0.146667 | 0.093333 | 0.037037 | 0.037037 | FAM151B | 5 | 5q14.1 | 79819556 | 79873963 |
| MSH3 | 0.009804 | 0.08 | 0.12 | 0.037037 | 0.037037 | MSH3 | 5 | 5q14.1 | 79986050 | 80208391 |
| 3-Mar | 0.009804 | 0.106667 | 0.08 | 0.037037 | 0.074074 | 3-Mar | 5 | 5q23.2 | 1.26E+08 | 1.26E+08 |
| STK32A | 0.009804 | 0.013333 | 0.133333 | 0 | 0.037037 | STK32A | 5 | 5q32 | 1.47E+08 | 1.47E+08 |
| TTC1 | 0.009804 | 0.133333 | 0.026667 | 0.037037 | 0.074074 | TTC1 | 5 | 5q33.3 | 1.59E+08 | 1.59E+08 |
| HSP90AB2P | 0.009804 | 0.013333 | 0.146667 | 0 | 0.037037 | HSP90AB2P | 4 | 4p15.33 | 12944135 | 12949029 |
| RAB28 | 0.009804 | 0.013333 | 0.16 | 0 | 0.037037 | RAB28 | 4 | 4p15.33 | 12978445 | 13095088 |
| KCNIP4 | 0.009804 | 0.026667 | 0.213333 | 0 | 0.037037 | KCNIP4 | 4 | 4p15.31 | 20339337 | 21308417 |
| PPARGC1A | 0.009804 | 0.026667 | 0.226667 | 0 | 0.037037 | PPARGC1A | 4 | 4p15.2 | 23402742 | 23500799 |
| LGI2 | 0.009804 | 0.106667 | 0.053333 | 0.037037 | 0 | LGI2 | 4 | 4p15.2 | 24609569 | 24641513 |
| SEPSECS | 0.009804 | 0.12 | 0.066667 | 0.037037 | 0 | SEPSECS | 4 | 4p15.2 | 24730726 | 24771303 |
| PI4K2B | 0.009804 | 0.12 | 0.053333 | 0.037037 | 0 | PI4K2B | 4 | 4p15.2 | 24844751 | 24889930 |
| ZCCHC4 | 0.009804 | 0.12 | 0.053333 | 0.037037 | 0 | ZCCHC4 | 4 | 4p15.2 | 24923494 | 24981104 |
| TLR10 | 0.009804 | 0.053333 | 0.186667 | 0.037037 | 0.037037 | TLR10 | 4 | 4p14 | 38450647 | 38460985 |
| UCHL1 | 0.009804 | 0.106667 | 0.053333 | 0.037037 | 0 | UCHL1 | 4 | 4p13 | 40953655 | 40965203 |
| LIMCH1 | 0.009804 | 0.106667 | 0.053333 | 0.037037 | 0 | LIMCH1 | 4 | 4p13 | 41057561 | 41396819 |
| PHOX2B | 0.009804 | 0.133333 | 0.066667 | 0.037037 | 0 | PHOX2B | 4 | 4p13 | 41440856 | 41445745 |
| TMEM33 | 0.009804 | 0.146667 | 0.053333 | 0.037037 | 0 | TMEM33 | 4 | 4p13 | 41631894 | 41657582 |
| SLC30A9 | 0.009804 | 0.16 | 0.053333 | 0.037037 | 0.037037 | SLC30A9 | 4 | 4p13 | 41687280 | 41784309 |
| BEND4 | 0.009804 | 0.16 | 0.053333 | 0.037037 | 0.037037 | BEND4 | 4 | 4p13 | 41807629 | 41849653 |
| RASL11B | 0.009804 | 0.12 | 0 | 0.037037 | 0 | RASL11B | 4 | 4q12 | 53423252 | 53427760 |
| SCFD2 | 0.009804 | 0.12 | 0 | 0.037037 | 0 | SCFD2 | 4 | 4q12 | 53433908 | 53927000 |
| PDGFRA | 0.009804 | 0.106667 | 0.013333 | 0.037037 | 0 | PDGFRA | 4 | 4q12 | 54790021 | 54859170 |
| AFP | 0.009804 | 0.04 | 0.133333 | 0 | 0.037037 | AFP | 4 | 4q13.3 | 74520797 | 74540357 |
| AFM | 0.009804 | 0.04 | 0.133333 | 0 | 0.037037 | AFM | 4 | 4q13.3 | 74566326 | 74588583 |
| RASSF6 | 0.009804 | 0.04 | 0.12 | 0 | 0.037037 | RASSF6 | 4 | 4q13.3 | 74657726 | 74704999 |
| CXCL6 | 0.009804 | 0.04 | 0.146667 | 0 | 0.037037 | CXCL6 | 4 | 4q13.3 | 74921137 | 74923342 |
| PPBPL1 | 0.009804 | 0.04 | 0.146667 | 0 | 0.037037 | PPBPL1 | 4 | 4q13.3 | 74932447 | 74933418 |
| PF4 | 0.009804 | 0.04 | 0.146667 | 0 | 0.037037 | PF4 | 4 | 4q13.3 | 75065660 | 75066580 |
| PPBP | 0.009804 | 0.04 | 0.146667 | 0 | 0.037037 | PPBP | 4 | 4q13.3 | 75071620 | 75072765 |
| CXCL3 | 0.009804 | 0.04 | 0.146667 | 0 | 0.037037 | CXCL3 | 4 | 4q13.3 | 75121176 | 75123355 |
| CXCL2 | 0.009804 | 0.04 | 0.146667 | 0 | 0.037037 | CXCL2 | 4 | 4q13.3 | 75181618 | 75183862 |
| MTHFD2L | 0.009804 | 0.04 | 0.16 | 0 | 0.037037 | MTHFD2L | 4 | 4q13.3 | 75242693 | 75387677 |
| AREG | 0.009804 | 0.04 | 0.146667 | 0 | 0.037037 | AREG | 4 | 4q13.3 | 75699653 | 75709510 |
| BTC | 0.009804 | 0.066667 | 0.133333 | 0 | 0.037037 | BTC | 4 | 4q13.3 | 75890472 | 75938907 |
| C4orf26 | 0.009804 | 0.133333 | 0.013333 | 0.037037 | 0 | C4orf26 | 4 | 4q21.1 | 76700232 | 76708952 |
| CDKL2 | 0.009804 | 0.106667 | 0.026667 | 0.037037 | 0 | CDKL2 | 4 | 4q21.1 | 76720728 | 76774746 |
| G3BP2 | 0.009804 | 0.12 | 0.013333 | 0.037037 | 0 | G3BP2 | 4 | 4q21.1 | 76786977 | 76817368 |
| ARD1B | 0.009804 | 0.026667 | 0.226667 | 0 | 0.037037 | ARD1B | 4 | 4q21.21 | 80457296 | 80466196 |
| GDEP | 0.009804 | 0.026667 | 0.213333 | 0 | 0.037037 | GDEP | 4 | 4q21.21 | 80967649 | 81003424 |
| PRDM8 | 0.009804 | 0.04 | 0.16 | 0 | 0.037037 | PRDM8 | 4 | 4q21.21 | 81325448 | 81344507 |
| C4orf22 | 0.009804 | 0.026667 | 0.16 | 0 | 0.037037 | C4orf22 | 4 | 4q21.21 | 81475898 | 82103927 |
| BMP3 | 0.009804 | 0.026667 | 0.186667 | 0 | 0.037037 | BMP3 | 4 | 4q21.21 | 82171143 | 82197710 |
| PRKG2 | 0.009804 | 0.026667 | 0.173333 | 0 | 0.037037 | PRKG2 | 4 | 4q21.21 | 82228861 | 82345240 |
| RASGEF1B | 0.009804 | 0.053333 | 0.12 | 0 | 0.037037 | RASGEF1B | 4 | 4q21.21 | 82567243 | 82612086 |
| TMEM150C | 0.009804 | 0.173333 | 0.04 | 0.037037 | 0 | TMEM150C | 4 | 4q21.22 | 83624628 | 83702151 |
| SCD5 | 0.009804 | 0.173333 | 0.04 | 0.037037 | 0 | SCD5 | 4 | 4q21.22 | 83769714 | 83939035 |
| SEC31A | 0.009804 | 0.173333 | 0.04 | 0.037037 | 0 | SEC31A | 4 | 4q21.22 | 83958838 | 84031425 |
| COPS4 | 0.009804 | 0.173333 | 0.04 | 0.037037 | 0 | COPS4 | 4 | 4q21.22 | 84175263 | 84215996 |
| PLAC8 | 0.009804 | 0.173333 | 0.04 | 0.037037 | 0 | PLAC8 | 4 | 4q21.22 | 84230235 | 84250037 |
| COQ2 | 0.009804 | 0.173333 | 0.04 | 0.037037 | 0 | COQ2 | 4 | 4q21.23 | 84404002 | 84425092 |
| HPSE | 0.009804 | 0.173333 | 0.04 | 0.037037 | 0 | HPSE | 4 | 4q21.23 | 84435492 | 84475059 |
| HELQ | 0.009804 | 0.173333 | 0.04 | 0.037037 | 0 | HELQ | 4 | 4q21.23 | 84547523 | 84596050 |
| MRPS18C | 0.009804 | 0.173333 | 0.04 | 0.037037 | 0 | MRPS18C | 4 | 4q21.23 | 84596142 | 84601954 |
| FAM175A | 0.009804 | 0.173333 | 0.04 | 0.037037 | 0 | FAM175A | 4 | 4q21.23 | 84601120 | 84625315 |
| AGPAT9 | 0.009804 | 0.173333 | 0.04 | 0.037037 | 0 | AGPAT9 | 4 | 4q21.23 | 84676677 | 84746051 |
| C4orf12 | 0.009804 | 0.026667 | 0.133333 | 0 | 0.037037 | C4orf12 | 4 | 4q21.23 | 86106995 | 86147193 |
| MAPK10 | 0.009804 | 0.026667 | 0.146667 | 0 | 0.037037 | MAPK10 | 4 | 4q21.3 | 87155300 | 87593308 |
| PKD2 | 0.009804 | 0.12 | 0.013333 | 0.037037 | 0 | PKD2 | 4 | 4q22.1 | 89147844 | 89217954 |
| ABCG2 | 0.009804 | 0.12 | 0.013333 | 0.037037 | 0 | ABCG2 | 4 | 4q22.1 | 89230440 | 89299036 |
| PPM1K | 0.009804 | 0.133333 | 0.013333 | 0.037037 | 0 | PPM1K | 4 | 4q22.1 | 89400556 | 89424913 |
| HERC6 | 0.009804 | 0.12 | 0.013333 | 0.037037 | 0 | HERC6 | 4 | 4q22.1 | 89518915 | 89583272 |
| HERC5 | 0.009804 | 0.12 | 0.013333 | 0.037037 | 0 | HERC5 | 4 | 4q22.1 | 89597291 | 89646338 |
| PIGY | 0.009804 | 0.12 | 0.013333 | 0.037037 | 0 | PIGY | 4 | 4q22.1 | 89661158 | 89663979 |
| ANK2 | 0.009804 | 0.16 | 0.053333 | 0.037037 | 0.074074 | ANK2 | 4 | 4q25 | 1.14E+08 | 1.15E+08 |
| CEP170L | 0.009804 | 0.12 | 0.16 | 0.037037 | 0.185185 | CEP170L | 4 | 4q26 | 1.2E+08 | 1.2E+08 |
| MFSD8 | 0.009804 | 0.146667 | 0.08 | 0.037037 | 0.111111 | MFSD8 | 4 | 4q28.1 - 4c | 1.29E+08 | 1.29E+08 |
| C4orf29 | 0.009804 | 0.146667 | 0.08 | 0.037037 | 0.111111 | C4orf29 | 4 | 4q28-2 | 1.29E+08 | 1.29E+08 |
| LARP1B | 0.009804 | 0.146667 | 0.066667 | 0.037037 | 0.111111 | LARP1B | 4 | 4q28.2 | 1.29E+08 | 1.29E+08 |
| USP38 | 0.009804 | 0.013333 | 0.186667 | 0 | 0.037037 | USP38 | 4 | 4q31.21 | 1.44E+08 | 1.44E+08 |
| GYPA | 0.009804 | 0.013333 | 0.16 | 0 | 0.037037 | GYPA | 4 | 4q31.22 | 1.45E+08 | 1.45E+08 |
| TMEM184C | 0.009804 | 0.12 | 0 | 0.037037 | 0 | TMEM184C | 4 | 4q31.23 | 1.49E+08 | 1.49E+08 |
| PRMT10 | 0.009804 | 0.12 | 0 | 0.037037 | 0 | PRMT10 | 4 | 4q31.23 | 1.49E+08 | 1.49E+08 |

TABLE 2-continued

Gene list for predicting prostate cancer relapse using prostate cancer tissue

| Symbol | freq. use | freq. amp. case | freq. del. case | freq. control | freq. control | Gene. Symbol | chromo- some | cytoband | Tran- script. start | Tran- script. end |
|---|---|---|---|---|---|---|---|---|---|---|
| ARHGAP10 | 0.009804 | 0.133333 | 0 | 0.037037 | 0 | ARHGAP10 | 4 | 4q31.23 | 1.49E+08 | 1.49E+08 |
| NR3C2 | 0.009804 | 0.106667 | 0 | 0.037037 | 0 | NR3C2 | 4 | 4q31.23 | 1.49E+08 | 1.5E+08 |
| DCLK2 | 0.009804 | 0.12 | 0.026667 | 0.037037 | 0.037037 | DCLK2 | 4 | 4q31.3 | 1.51E+08 | 1.51E+08 |
| LRBA | 0.009804 | 0.013333 | 0.133333 | 0.037037 | 0.037037 | LRBA | 4 | 4q31.3 | 1.51E+08 | 1.52E+08 |
| ANXA2P1 | 0.009804 | 0.186667 | 0.013333 | 0.037037 | 0.037037 | ANXA2P1 | 4 | 4q31.3 | 1.54E+08 | 1.54E+08 |
| MND1 | 0.009804 | 0.186667 | 0.013333 | 0.037037 | 0.037037 | MND1 | 4 | 4q31.3 | 1.54E+08 | 1.55E+08 |
| KIAA0922 | 0.009804 | 0.186667 | 0.013333 | 0.037037 | 0.037037 | KIAA0922 | 4 | 4q31.3 | 1.55E+08 | 1.55E+08 |
| DCHS2 | 0.009804 | 0.026667 | 0.12 | 0 | 0.037037 | DCHS2 | 4 | 4q32.1 | 1.55E+08 | 1.56E+08 |
| FGB | 0.009804 | 0.026667 | 0.12 | 0 | 0.037037 | FGB | 4 | 4q32.1 | 1.56E+08 | 1.56E+08 |
| FGA | 0.009804 | 0.026667 | 0.12 | 0 | 0.037037 | FGA | 4 | 4q32.1 | 1.56E+08 | 1.56E+08 |
| FGG | 0.009804 | 0.026667 | 0.12 | 0 | 0.037037 | FGG | 4 | 4q32.1 | 1.56E+08 | 1.56E+08 |
| RBM46 | 0.009804 | 0.026667 | 0.12 | 0 | 0.037037 | RBM46 | 4 | 4q32.1 | 1.56E+08 | 1.56E+08 |
| RXFP1 | 0.009804 | 0.08 | 0.106667 | 0 | 0.037037 | RXFP1 | 4 | 4q32.1 | 1.6E+08 | 1.6E+08 |
| SH3RF1 | 0.009804 | 0.12 | 0.026667 | 0.037037 | 0.037037 | SH3RF1 | 4 | 4q32.3 | 1.7E+08 | 1.7E+08 |
| NEK1 | 0.009804 | 0.12 | 0.026667 | 0.037037 | 0.037037 | NEK1 | 4 | 4q33 | 1.71E+08 | 1.71E+08 |
| CLCN3 | 0.009804 | 0.12 | 0.04 | 0.037037 | 0.037037 | CLCN3 | 4 | 4q33 | 1.71E+08 | 1.71E+08 |
| C4orf27 | 0.009804 | 0.12 | 0.04 | 0.037037 | 0.037037 | C4orf27 | 4 | 4q33 | 1.71E+08 | 1.71E+08 |
| MFAP3L | 0.009804 | 0.12 | 0.04 | 0.037037 | 0.037037 | MFAP3L | 4 | 4q33 | 1.71E+08 | 1.71E+08 |
| AADAT | 0.009804 | 0.106667 | 0.053333 | 0.037037 | 0.037037 | AADAT | 4 | 4q33 | 1.71E+08 | 1.71E+08 |
| IL5RA | 0.009804 | 0.106667 | 0.026667 | 0.037037 | 0.037037 | IL5RA | 3 | 3p26.3 | 3086401 | 3127059 |
| TRNT1 | 0.009804 | 0.106667 | 0.026667 | 0.037037 | 0.037037 | TRNT1 | 3 | 3p26.3 | 3143600 | 3155707 |
| GRM7 | 0.009804 | 0.013333 | 0.146667 | 0.037037 | 0.037037 | GRM7 | 3 | 3p26.1 | 6877802 | 7758219 |
| DVWA | 0.009804 | 0.093333 | 0.133333 | 0.296296 | 0.037037 | DVWA | 3 | 3p24.3 | 15181875 | 15222471 |
| RAB5A | 0.009804 | 0.186667 | 0.026667 | 0.037037 | 0.037037 | RAB5A | 3 | 3p24.3 | 19963576 | 20001663 |
| C3orf48 | 0.009804 | 0.186667 | 0.026667 | 0.037037 | 0.037037 | C3orf48 | 3 | 3p24.3 | 19996458 | 20028770 |
| KAT2B | 0.009804 | 0.173333 | 0.04 | 0.037037 | 0.037037 | KAT2B | 3 | 3p24.3 | 20056528 | 20170901 |
| THRB | 0.009804 | 0.026667 | 0.146667 | 0.037037 | 0.037037 | THRB | 3 | 3p24.2 | 24133649 | 24511318 |
| FAM19A1 | 0.009804 | 0.013333 | 0.133333 | 0 | 0.037037 | FAM19A1 | 3 | 3p14.1 | 68136144 | 68677462 |
| ARL13B | 0.009804 | 0.106667 | 0.173333 | 0.037037 | 0.333333 | ARL13B | 3 | 3q11.2 | 95181672 | 95256814 |
| STX19 | 0.009804 | 0.106667 | 0.173333 | 0.037037 | 0.333333 | STX19 | 3 | 3q11.2 | 95215905 | 95230145 |
| DHFRL1 | 0.009804 | 0.106667 | 0.173333 | 0.037037 | 0.333333 | DHFRL1 | 3 | 3q11.2 | 95259456 | 95264351 |
| RG9MTD1 | 0.009804 | 0.186667 | 0 | 0.037037 | 0.148148 | RG9MTD1 | 3 | 3q12.3 | 1.03E+08 | 1.03E+08 |
| PCNP | 0.009804 | 0.186667 | 0 | 0.037037 | 0.148148 | PCNP | 3 | 3q12.3 | 1.03E+08 | 1.03E+08 |
| ZBTB11 | 0.009804 | 0.186667 | 0 | 0.037037 | 0.148148 | ZBTB11 | 3 | 3q12.3 | 1.03E+08 | 1.03E+08 |
| LOC100009676 | 0.009804 | 0.186667 | 0 | 0.037037 | 0.148148 | LOC100009676 | 3 | 3q12.3 | 1.03E+08 | 1.03E+08 |
| RPL24 | 0.009804 | 0.186667 | 0 | 0.037037 | 0.148148 | RPL24 | 3 | 3q12.3 | 1.03E+08 | 1.03E+08 |
| CEP97 | 0.009804 | 0.173333 | 0 | 0.037037 | 0.148148 | CEP97 | 3 | 3q12.3 | 1.03E+08 | 1.03E+08 |
| FAM55C | 0.009804 | 0.173333 | 0 | 0.037037 | 0.148148 | FAM55C | 3 | 3q12.3 | 1.03E+08 | 1.03E+08 |
| NFKBIZ | 0.009804 | 0.16 | 0 | 0.037037 | 0.148148 | NFKBIZ | 3 | 3q12.3 | 1.03E+08 | 1.03E+08 |
| LOC152225 | 0.009804 | 0.16 | 0 | 0.037037 | 0.148148 | LOC152225 | 3 | 3q12.3 | 1.03E+08 | 1.03E+08 |
| BOC | 0.009804 | 0.146667 | 0 | 0.037037 | 0.074074 | BOC | 3 | 3q13.2 | 1.14E+08 | 1.14E+08 |
| NAT13 | 0.009804 | 0.173333 | 0 | 0.037037 | 0.074074 | NAT13 | 3 | 3q13.2 | 1.15E+08 | 1.15E+08 |
| GRAMD1C | 0.009804 | 0.186667 | 0 | 0.037037 | 0.074074 | GRAMD1C | 3 | 3q13.31 | 1.15E+08 | 1.15E+08 |
| KIAA1407 | 0.009804 | 0.106667 | 0.08 | 0.037037 | 0.074074 | KIAA1407 | 3 | 3q13.31 | 1.15E+08 | 1.15E+08 |
| QTRTD1 | 0.009804 | 0.106667 | 0.08 | 0.037037 | 0.074074 | QTRTD1 | 3 | 3q13.31 | 1.15E+08 | 1.15E+08 |
| DRD3 | 0.009804 | 0.133333 | 0.053333 | 0.037037 | 0.074074 | DRD3 | 3 | 3q13.31 | 1.15E+08 | 1.15E+08 |
| ZNF80 | 0.009804 | 0.12 | 0.053333 | 0.037037 | 0.074074 | ZNF80 | 3 | 3q13.31 | 1.15E+08 | 1.15E+08 |
| COL6A6 | 0.009804 | 0.093333 | 0.12 | 0.074074 | 0.037037 | COL6A6 | 3 | 3q22.1 | 1.32E+08 | 1.32E+08 |
| ATP2C1 | 0.009804 | 0.093333 | 0.12 | 0.074074 | 0.037037 | ATP2C1 | 3 | 3q22.1 | 1.32E+08 | 1.32E+08 |
| ASTE1 | 0.009804 | 0.106667 | 0.106667 | 0.074074 | 0.037037 | ASTE1 | 3 | 3q22.1 | 1.32E+08 | 1.32E+08 |
| NEK11 | 0.009804 | 0.106667 | 0.106667 | 0.074074 | 0.037037 | NEK11 | 3 | 3q22.1 | 1.32E+08 | 1.33E+08 |
| MRPL3 | 0.009804 | 0.093333 | 0.12 | 0.074074 | 0.037037 | MRPL3 | 3 | 3q22.1 | 1.33E+08 | 1.33E+08 |
| CPNE4 | 0.009804 | 0.093333 | 0.133333 | 0.074074 | 0.037037 | CPNE4 | 3 | 3q22.1 | 1.33E+08 | 1.33E+08 |
| AADACL2 | 0.009804 | 0.04 | 0.106667 | 0 | 0.037037 | AADACL2 | 3 | 3q25.1 | 1.53E+08 | 1.53E+08 |
| LOC401093 | 0.009804 | 0.04 | 0.106667 | 0 | 0.037037 | LOC401093 | 3 | 3q25.1 | 1.53E+08 | 1.53E+08 |
| MBNL1 | 0.009804 | 0.04 | 0.106667 | 0 | 0.037037 | MBNL1 | 3 | 3q25.1 | 1.53E+08 | 1.54E+08 |
| P2RY1 | 0.009804 | 0.04 | 0.12 | 0 | 0.037037 | P2RY1 | 3 | 3q25.2 | 1.54E+08 | 1.54E+08 |
| C3orf79 | 0.009804 | 0.04 | 0.106667 | 0.037037 | 0.037037 | C3orf79 | 3 | 3q25.2 | 1.55E+08 | 1.55E+08 |
| SGEF | 0.009804 | 0.04 | 0.12 | 0.037037 | 0.037037 | SGEF | 3 | 3q25.2 | 1.55E+08 | 1.55E+08 |
| DHX36 | 0.009804 | 0.04 | 0.106667 | 0.037037 | 0.037037 | DHX36 | 3 | 3q25.2 | 1.55E+08 | 1.56E+08 |
| MME | 0.009804 | 0.04 | 0.106667 | 0.037037 | 0.037037 | MME | 3 | 3q25.31 | 1.56E+08 | 1.56E+08 |
| SLC33A1 | 0.009804 | 0.186667 | 0 | 0.037037 | 0 | SLC33A1 | 3 | 3q25.31 | 1.57E+08 | 1.57E+08 |
| GMPS | 0.009804 | 0.186667 | 0 | 0.037037 | 0 | GMPS | 3 | 3q25.31 | 1.57E+08 | 1.57E+08 |
| CCNL1 | 0.009804 | 0.12 | 0.04 | 0.037037 | 0 | CCNL1 | 3 | 3q25.32 | 1.58E+08 | 1.58E+08 |
| GFM1 | 0.009804 | 0.106667 | 0.04 | 0.037037 | 0 | GFM1 | 3 | 3q25.32 | 1.6E+08 | 1.6E+08 |
| LXN | 0.009804 | 0.106667 | 0.04 | 0.037037 | 0 | LXN | 3 | 3q25.32 | 1.6E+08 | 1.6E+08 |
| SKIL | 0.009804 | 0.226667 | 0 | 0.037037 | 0.037037 | SKIL | 3 | 3q26.2 | 1.72E+08 | 1.72E+08 |
| CLDN11 | 0.009804 | 0.226667 | 0 | 0.037037 | 0.037037 | CLDN11 | 3 | 3q26.2 | 1.72E+08 | 1.72E+08 |
| SLC7A14 | 0.009804 | 0.2 | 0 | 0.037037 | 0.037037 | SLC7A14 | 3 | 3q26.2 | 1.72E+08 | 1.72E+08 |
| TMEM212 | 0.009804 | 0.146667 | 0 | 0.037037 | 0 | TMEM212 | 3 | 3q26.31 | 1.73E+08 | 1.73E+08 |
| FNDC3B | 0.009804 | 0.133333 | 0.013333 | 0.037037 | 0 | FNDC3B | 3 | 3q26.31 | 1.73E+08 | 1.74E+08 |
| GHSR | 0.009804 | 0.16 | 0.013333 | 0.037037 | 0 | GHSR | 3 | 3q26.31 | 1.74E+08 | 1.74E+08 |
| TNFSF10 | 0.009804 | 0.2 | 0 | 0.037037 | 0 | TNFSF10 | 3 | 3q26.31 | 1.74E+08 | 1.74E+08 |
| ECT2 | 0.009804 | 0.04 | 0.12 | 0.037037 | 0.037037 | ECT2 | 3 | 3q26.31 | 1.74E+08 | 1.74E+08 |

TABLE 2-continued

Gene list for predicting prostate cancer relapse using prostate cancer tissue

| Symbol | freq. use | freq. amp. case | freq. del. case | freq. control | freq. control | Gene. Symbol | chromo-some | cytoband | Transcript. start | Transcript. end |
|---|---|---|---|---|---|---|---|---|---|---|
| ZMAT3 | 0.009804 | 0.2 | 0.026667 | 0.037037 | 0.037037 | ZMAT3 | 3 | 3q26.32 | 1.8E+08 | 1.8E+08 |
| PEX5L | 0.009804 | 0.04 | 0.12 | 0.074074 | 0.037037 | PEX5L | 3 | 3q26.33 | 1.81E+08 | 1.81E+08 |
| CCDC39 | 0.009804 | 0.04 | 0.133333 | 0.074074 | 0.037037 | CCDC39 | 3 | 3q26.33 | 1.82E+08 | 1.82E+08 |
| TPRG1 | 0.009804 | 0.066667 | 0.12 | 0 | 0.037037 | TPRG1 | 3 | 3q28 | 1.9E+08 | 1.91E+08 |
| IL1RAP | 0.009804 | 0.053333 | 0.173333 | 0 | 0.037037 | IL1RAP | 3 | 3q28 | 1.92E+08 | 1.92E+08 |
| FAM157A | 0.009804 | 0.48 | 0.106667 | 0.62963 | 0.037037 | FAM157A | 3 | 3q29 | 1.99E+08 | 1.99E+08 |
| VSNL1 | 0.009804 | 0.026667 | 0.133333 | 0.111111 | 0.037037 | VSNL1 | 2 | 2p24.2 | 17585288 | 17701188 |
| LCLAT1 | 0.009804 | 0.093333 | 0.12 | 0.333333 | 0.037037 | LCLAT1 | 2 | 2p23.1 | 30523627 | 30720596 |
| HNRPLL | 0.009804 | 0.013333 | 0.146667 | 0.074074 | 0.037037 | HNRPLL | 2 | 2p22.1 | 38643832 | 38683683 |
| MTIF2 | 0.009804 | 0.12 | 0.013333 | 0.037037 | 0 | MTIF2 | 2 | 2p16.1 | 55317260 | 55349820 |
| CCDC88A | 0.009804 | 0.12 | 0.053333 | 0.037037 | 0 | CCDC88A | 2 | 2p16.1 | 55368484 | 55500562 |
| VRK2 | 0.009804 | 0.013333 | 0.213333 | 0 | 0.037037 | VRK2 | 2 | 2p16.1 | 58127233 | 58240560 |
| C2orf86 | 0.009804 | 0.106667 | 0.026667 | 0.037037 | 0 | C2orf86 | 2 | 2p15 | 63202039 | 63518591 |
| SLC5A7 | 0.009804 | 0.053333 | 0.173333 | 0.185185 | 0.037037 | SLC5A7 | 2 | 2q12.3 | 1.08E+08 | 1.08E+08 |
| EPB41L5 | 0.009804 | 0.16 | 0.106667 | 0.259259 | 0.037037 | EPB41L5 | 2 | 2q14.2 | 1.2E+08 | 1.21E+08 |
| NXPH2 | 0.009804 | 0.04 | 0.266667 | 0.037037 | 0.037037 | NXPH2 | 2 | 2q22.1 | 1.39E+08 | 1.39E+08 |
| LYPD6B | 0.009804 | 0.08 | 0.133333 | 0.111111 | 0.037037 | LYPD6B | 2 | 2q23.2 | 1.5E+08 | 1.5E+08 |
| LYPD6 | 0.009804 | 0.026667 | 0.186667 | 0.037037 | 0.037037 | LYPD6 | 2 | 2q23.2 | 1.5E+08 | 1.5E+08 |
| RND3 | 0.009804 | 0.025667 | 0.173333 | 0.037037 | 0.037037 | RND3 | 2 | 2q23.3 | 1.51E+08 | 1.51E+08 |
| FMNL2 | 0.009804 | 0.04 | 0.12 | 0.037037 | 0.037037 | FMNL2 | 2 | 2q23.3 | 1.53E+08 | 1.53E+08 |
| PRPF40A | 0.009804 | 0.026667 | 0.12 | 0.037037 | 0.037037 | PRPF40A | 2 | 2q23.3 | 1.53E+08 | 1.53E+08 |
| ACVR1 | 0.009804 | 0.066667 | 0.133333 | 0.074074 | 0.037037 | ACVR1 | 2 | 2q24.1 | 1.58E+08 | 1.58E+08 |
| UPP2 | 0.009804 | 0.053333 | 0.133333 | 0.074074 | 0.037037 | UPP2 | 2 | 2q24.1 | 1.59E+08 | 1.59E+08 |
| RBMS1 | 0.009804 | 0.013333 | 0.106667 | 0.074074 | 0.037037 | RBMS1 | 2 | 2q24.2 | 1.61E+08 | 1.61E+08 |
| SF3B1 | 0.009804 | 0.16 | 0.013333 | 0.037037 | 0.037037 | SF3B1 | 2 | 2q33.1 | 1.98E+08 | 1.98E+08 |
| COQ10B | 0.009804 | 0.16 | 0.013333 | 0.037037 | 0.037037 | COQ10B | 2 | 2q33.1 | 1.98E+08 | 1.98E+08 |
| HSPD1 | 0.009804 | 0.16 | 0.013333 | 0.037037 | 0.037037 | HSPD1 | 2 | 2q33.1 | 1.98E+08 | 1.98E+08 |
| PIKFYVE | 0.009804 | 0.173333 | 0.053333 | 0.037037 | 0.037037 | PIKFYVE | 2 | 2q33.3 | 2.09E+08 | 2.09E+08 |
| PTH2R | 0.009804 | 0.12 | 0.093333 | 0.037037 | 0 | PTH2R | 2 | 2q33.3 | 2.09E+08 | 2.09E+08 |
| KIAA1486 | 0.009804 | 0.013333 | 0.146567 | 0.074074 | 0.037037 | KIAA1486 | 2 | 2q36.3 | 2.26E+08 | 2.26E+08 |
| PRKAA2 | 0.009804 | 0.106667 | 0.106667 | 0.222222 | 0.037037 | PRKAA2 | 1 | 1p32.2 | 56883578 | 56953597 |
| PGM1 | 0.009804 | 0.106667 | 0.066667 | 0.037037 | 0 | PGM1 | 1 | 1p31.3 | 63831535 | 63898506 |
| PDE4B | 0.009804 | 0 | 0.186667 | 0 | 0.037037 | PDE4B | 1 | 1p31.3 | 66030781 | 66612851 |
| SGIP1 | 0.009804 | 0 | 0.2 | 0 | 0.037037 | SGIP1 | 1 | 1p31.3 | 66772413 | 66983357 |
| TCTEX1D1 | 0.009804 | 0 | 0.2 | 0 | 0.037037 | TCTEX1D1 | 1 | 1p31.3 | 66990728 | 67017318 |
| SLC35D1 | 0.009804 | 0 | 0.12 | 0 | 0.037037 | SLC35D1 | 1 | 1p31.3 | 67237604 | 67292669 |
| IL12RB2 | 0.009804 | 0.106667 | 0.053333 | 0.037037 | 0 | IL12RB2 | 1 | 1p31.3 | 67545635 | 67635172 |
| SERBP1 | 0.009804 | 0.12 | 0.053333 | 0.037037 | 0 | SERBP1 | 1 | 1p31.3 | 67646081 | 67668712 |
| DEPDC1 | 0.009804 | 0.013333 | 0.24 | 0 | 0.037037 | DEPDC1 | 1 | 1p31.2 | 68712423 | 68735388 |
| PTGER3 | 0.009804 | 0.013333 | 0.186667 | 0 | 0.037037 | PTGER3 | 1 | 1p31.1 | 71090624 | 71286080 |
| MSH4 | 0.009804 | 0.026667 | 0.146667 | 0 | 0.037037 | MSH4 | 1 | 1p31.1 | 76035218 | 76151512 |
| ASB17 | 0.009804 | 0.026667 | 0.146667 | 0 | 0.037037 | ASB17 | 1 | 1p31.1 | 76157148 | 76170705 |
| ST6GALNAC3 | 0.009804 | 0.013333 | 0.173333 | 0 | 0.037037 | ST6GALNAC3 | 1 | 1p31.1 | 76312977 | 75815479 |
| GIPC2 | 0.009804 | 0.013333 | 0.2 | 0 | 0.037037 | GIPC2 | 1 | 1p31.1 | 78284177 | 78375701 |
| MGC27382 | 0.009804 | 0.013333 | 0.24 | 0 | 0.037037 | MGC27382 | 1 | 1p31.1 | 78467871 | 78607734 |
| TTLL7 | 0.009804 | 0.013333 | 0.226667 | 0 | 0.037037 | TTLL7 | 1 | 1p31.1 | 84107645 | 84237422 |
| PRKACB | 0.009804 | 0.013333 | 0.2 | 0 | 0.037037 | PRKACB | 1 | 1p31.1 | 84316333 | 84476770 |
| SAMD13 | 0.009804 | 0.013333 | 0.186667 | 0.037037 | 0.037037 | SAMD13 | 1 | 1p31.1 | 84536637 | 84589069 |
| UOX | 0.009804 | 0.013333 | 0.186667 | 0.037037 | 0.037037 | UOX | 1 | 1p31.1 | 84603229 | 84636165 |
| DNASE2B | 0.009804 | 0.026667 | 0.173333 | 0.037037 | 0.037037 | DNASE2B | 1 | 1p31.1 | 84636803 | 84653280 |
| LOC339524 | 0.009804 | 0.16 | 0.08 | 0.037037 | 0 | LOC339524 | 1 | 1p22.3 | 87368036 | 87407473 |
| PKN2 | 0.009804 | 0.04 | 0.173333 | 0 | 0.037037 | PKN2 | 1 | 1p22.2 | 88922510 | 89074527 |
| GTF2B | 0.009804 | 0.16 | 0.093333 | 0.037037 | 0 | GTF2B | 1 | 1p22.2 | 89090909 | 89129890 |
| ABCD3 | 0.009804 | 0.04 | 0.146667 | 0.111111 | 0.037037 | ABCD3 | 1 | 1p21.3 | 94656521 | 94716849 |
| AGL | 0.009804 | 0.12 | 0.08 | 0.037037 | 0.074074 | AGL | 1 | 1p21.2 | 1E+08 | 1E+08 |
| SPRR2F | 0.009804 | 0.133333 | 0.146667 | 0.481481 | 0.037037 | SPRR2F | 1 | 1q21.3 | 1.51E+08 | 1.51E+08 |
| SPRR2C | 0.009804 | 0.16 | 0.106667 | 0.481481 | 0.037037 | SPRR2C | 1 | 1q21.3 | 1.51E+08 | 1.51E+08 |
| SPRR2G | 0.009804 | 0.16 | 0.106667 | 0.481481 | 0.037037 | SPRR2G | 1 | 1q21.3 | 1.51E+08 | 1.51E+08 |
| PYHIN1 | 0.009804 | 0.04 | 0.106667 | 0.037037 | 0.037037 | PYHIN1 | 1 | 1q23.1 | 1.57E+08 | 1.57E+08 |
| IFI16 | 0.009804 | 0.04 | 0.106667 | 0.074074 | 0.037037 | IFI16 | 1 | 1q23.1 | 1.57E+08 | 1.57E+08 |
| AIM2 | 0.009804 | 0.04 | 0.106667 | 0.074074 | 0.037037 | AIM2 | 1 | 1q23.1 - 1c | 1.57E+08 | 1.57E+08 |
| CD84 | 0.009804 | 0.093333 | 0.12 | 0.185185 | 0.037037 | CD84 | 1 | 1q23.2 - 1c | 1.59E+08 | 1.59E+08 |
| SLAMF1 | 0.009804 | 0.093333 | 0.12 | 0.185185 | 0.037037 | SLAMF1 | 1 | 1q23.3 | 1.59E+08 | 1.59E+08 |
| SLAMF7 | 0.009804 | 0.133333 | 0.106667 | 0.185185 | 0.037037 | SLAMF7 | 1 | 1q23.3 | 1.59E+08 | 1.59E+08 |
| C1orf111 | 0.009804 | 0.2 | 0.026667 | 0.037037 | 0 | C1orf111 | 1 | 1q23.3 | 1.61E+08 | 1.61E+08 |
| UHMK1 | 0.009804 | 0.146667 | 0.026667 | 0.037037 | 0 | UHMK1 | 1 | 1q23.3 | 1.61E+08 | 1.61E+08 |
| RGS5 | 0.009804 | 0.013333 | 0.133333 | 0 | 0.037037 | RGS5 | 1 | 1q23.3 | 1.61E+08 | 1.61E+08 |
| SFT2D2 | 0.009804 | 0.12 | 0.04 | 0.037037 | 0 | SFT2D2 | 1 | 1q24.2 | 1.66E+08 | 1.66E+08 |
| ANKRD36B | 0.009804 | 0.12 | 0.04 | 0.037037 | 0 | ANKRD36B | 1 | 1q24.2 | 1.66E+08 | 1.66E+08 |
| TBX19 | 0.009804 | 0.12 | 0.04 | 0.037037 | 0 | TBX19 | 1 | 1q24.2 | 1.67E+08 | 1.67E+08 |
| KIFAP3 | 0.009804 | 0 | 0.186667 | 0 | 0.037037 | KIFAP3 | 1 | 1q24.2 | 1.68E+08 | 1.68E+08 |
| METTL11B | 0.009804 | 0 | 0.16 | 0.037037 | 0.037037 | METTL11B | 1 | 1q24.2 | 1.68E+08 | 1.68E+08 |
| FMO3 | 0.009804 | 0 | 0.2 | 0.037037 | 0.037037 | FMO3 | 1 | 1q24.3 | 1.69E+08 | 1.69E+08 |
| MIR1295 | 0.009804 | 0 | 0.2 | 0.037037 | 0.037037 | MIR1295 | 1 | 1q24.3 | 1.69E+08 | 1.69E+08 |

TABLE 2-continued

Gene list for predicting prostate cancer relapse using prostate cancer tissue

| Symbol | freq. use | freq. amp. case | freq. del. case | freq. amp. control | freq. del. control | Gene. Symbol | chromo- some | cytoband | Transcript. start | Transcript. end |
|---|---|---|---|---|---|---|---|---|---|---|
| FMO2 | 0.009804 | 0 | 0.186667 | 0.037037 | 0.037037 | FMO2 | 1 | 1q24.3 | 1.69E+08 | 1.69E+08 |
| DNM3 | 0.009804 | 0.025667 | 0.106667 | 0.037037 | 0.037037 | DNM3 | 1 | 1q24.3 | 1.7E+08 | 1.71E+08 |
| C1orf105 | 0.009804 | 0 | 0.133333 | 0.037037 | 0.037037 | C1orf105 | 1 | 1q24.3 | 1.71E+08 | 1.71E+08 |
| RC3H1 | 0.009804 | 0.133333 | 0.013333 | 0.037037 | 0 | RC3H1 | 1 | 1q25.1 | 1.72E+08 | 1.72E+08 |
| RABGAP1L | 0.009804 | 0.12 | 0.013333 | 0.037037 | 0.037037 | RABGAP1L | 1 | 1q25.1 | 1.72E+08 | 1.73E+08 |
| NMNAT2 | 0.009804 | 0.146667 | 0 | 0.037037 | 0.074074 | NMNAT2 | 1 | 1q25.3 | 1.81E+08 | 1.82E+08 |
| NCF2 | 0.009804 | 0.106667 | 0.013333 | 0.037037 | 0.074074 | NCF2 | 1 | 1q25.3 | 1.82E+08 | 1.82E+08 |
| KCNK2 | 0.009804 | 0.066667 | 0.16 | 0.074074 | 0.037037 | KCNK2 | 1 | 1q41 | 2.13E+08 | 2.13E+08 |
| GPATCH2 | 0.009804 | 0.026667 | 0.12 | 0.037037 | 0.037037 | GPATCH2 | 1 | 1q41 | 2.16E+08 | 2.16E+08 |
| LOC400804 | 0.009804 | 0.053333 | 0.146667 | 0.074074 | 0.037037 | LOC400804 | 1 | 1q41 | 2.2E+08 | 2.2E+08 |
| RYR2 | 0.009804 | 0.146667 | 0.053333 | 0.037037 | 0 | RYR2 | 1 | 1q43 | 2.35E+08 | 2.36E+08 |
| AKT3 | 0.009804 | 0.026667 | 0.146667 | 0.074074 | 0.037037 | AKT3 | 1 | 1q44 | 2.42E+08 | 2.42E+08 |
| LOC148324 | 0.009804 | 0.106667 | 0.106667 | 0.222222 | 0.037037 | LOC148324 | 1 | 1q44 | 2.46E+08 | 2.46E+08 |
| OR2C3 | 0.009804 | 0.106667 | 0.106667 | 0.222222 | 0.037037 | OR2C3 | 1 | 1q44 | 2.46E+08 | 2.46E+08 |
| OR2L13 | 0.009804 | 0.066667 | 0.186667 | 0.185185 | 0.037037 | OR2L13 | 1 | 1q44 | 2.46E+08 | 2.46E+08 |
| OR2M5 | 0.009804 | 0.066667 | 0.2 | 0.185185 | 0.037037 | OR2M5 | 1 | 1q44 | 2.46E+08 | 2.46E+08 |

TABLE 3

| Symbol | freq. use | freq. amp. case | freq. del. case | freq. amp. control | freq. del. control | Gene. Symbol | chromo- some | cytoband | Transcript. start | Transcript. end |
|---|---|---|---|---|---|---|---|---|---|---|
| VAPA | 1 | 0.242424 | 0.121212 | 0.26087 | 0 | VAPA | 18 | 18p11.22 | 9903955 | 9950019 |
| C18orf19 | 1 | 0.181818 | 0.121212 | 0.217391 | 0 | C18orf19 | 18 | 18p11.21 | 13653346 | 13716592 |
| RNMT | 1 | 0.181818 | 0.121212 | 0.217391 | 0 | RNMT | 18 | 18p11.21 | 13716704 | 13754555 |
| ZNF267 | 1 | 0.181818 | 0.121212 | 0.434783 | 0 | ZNF267 | 16 | 16p11.2 | 31792580 | 31836129 |
| COCH | 1 | 0.121212 | 0.060606 | 0 | 0.115942 | COCH | 14 | 14q12 | 30413492 | 30429574 |
| BRMS1L | 1 | 0.151515 | 0.060606 | 0 | 0.057971 | BRMS1L | 14 | 14q13.2 | 35365348 | 35410921 |
| OTX2OS1 | 1 | 0.121212 | 0.060606 | 0 | 0.014493 | OTX2OS1 | 14 | 14q23.1 | 56349654 | 56467302 |
| TMEM30B | 1 | 0.090909 | 0.121212 | 0.086957 | 0 | TMEM30B | 14 | 14q23.1 | 60813842 | 60818284 |
| PRKCH | 1 | 0.090909 | 0.121212 | 0.086957 | 0 | PRKCH | 14 | 14q23.1 | 60858268 | 61087452 |
| HIF1A | 1 | 0.090909 | 0.121212 | 0.072464 | 0 | HIF1A | 14 | 14q23.2 | 61231872 | 61284731 |
| FAM71D | 1 | 0.181818 | 0.121212 | 0.188406 | 0 | FAM71D | 14 | 14q23.3 | 66725899 | 66765021 |
| MPP5 | 1 | 0.181818 | 0.121212 | 0.188406 | 0 | MPP5 | 14 | 14q23.3 | 66777774 | 66872290 |
| VTI1B | 1 | 0.212121 | 0.121212 | 0.217391 | 0 | VTI1B | 14 | 14q24.1 | 67187619 | 67211356 |
| RDH11 | 1 | 0.212121 | 0.121212 | 0.217391 | 0 | RDH11 | 14 | 14q24.1 | 67213271 | 67232264 |
| RDH12 | 1 | 0.212121 | 0.121212 | 0.217391 | 0 | RDH12 | 14 | 14q24.1 | 67238356 | 67270922 |
| ZFYVE26 | 1 | 0.212121 | 0.121212 | 0.217391 | 0 | ZFYVE26 | 14 | 14q24.1 | 67282990 | 67353060 |
| ACTN1 | 1 | 0.30303 | 0.121212 | 0.289855 | 0 | ACTN1 | 14 | 14q24.1 | 68410593 | 68515837 |
| GALNTL1 | 1 | 0.242424 | 0.151515 | 0.289855 | 0 | GALNTL1 | 14 | 14q24.1 | 68796434 | 68890944 |
| FLJ44817 | 1 | 0.242424 | 0.151515 | 0.289855 | 0 | FLJ44817 | 14 | 14q24.1 | 69021224 | 69064969 |
| KIAA0247 | 1 | 0.212121 | 0.151515 | 0.289855 | 0 | KIAA0247 | 14 | 14q24.1 | 69148063 | 69251613 |
| LOC100289511 | 1 | 0.212121 | 0.151515 | 0.289855 | 0 | LOC100289511 | 14 | 14q24.1- 14q24.2 | 69302753 | 69304184 |
| SFRS5 | 1 | 0.212121 | 0.151515 | 0.289855 | 0 | SFRS5 | 14 | 14q24.1- 14q24.2 | 69303582 | 69308476 |
| SLC10A1 | 1 | 0.212121 | 0.151515 | 0.289855 | 0 | SLC10A1 | 14 | 14q24.2 | 69312305 | 69333760 |
| SLC8A3 | 1 | 0.151515 | 0.151515 | 0.26087 | 0 | SLC8A3 | 14 | 14q24.2 | 69580687 | 69616677 |
| SYNJ2BP | 1 | 0.121212 | 0.121212 | 0.246377 | 0 | SYNJ2BP | 14 | 14q24.2 | 69902966 | 69953561 |
| MED6 | 1 | 0.151515 | 0.121212 | 0.275362 | 0 | MED6 | 14 | 14q24.2 | 70120710 | 70137138 |
| TTC9 | 1 | 0.151515 | 0.121212 | 0.289855 | 0 | TTC9 | 14 | 14q24.2 | 70178257 | 70211831 |
| MAP3K9 | 1 | 0.151515 | 0.121212 | 0.289855 | 0 | MAP3K9 | 14 | 14q24.2 | 70264607 | 70345642 |
| PCNX | 1 | 0.151515 | 0.121212 | 0.289855 | 0 | PCNX | 14 | 14q24.2 | 70443875 | 70651853 |
| SNORD56B | 1 | 0.212121 | 0.151515 | 0.289855 | 0 | SNORD56B | 14 | 14q24.2 | 70934807 | 70934878 |
| LOC145474 | 1 | 0.212121 | 0.121212 | 0.289855 | 0 | LOC145474 | 14 | 14q24.2 | 71024331 | 71026172 |
| SIPA1L1 | 1 | 0.212121 | 0.121212 | 0.289855 | 0 | SIPA1L1 | 14 | 14q24.2 | 71065795 | 71275874 |
| RGS6 | 1 | 0.181818 | 0.121212 | 0.289855 | 0 | RGS6 | 14 | 14q24.2 | 71469539 | 72102992 |
| DPF3 | 1 | 0.333333 | 0.121212 | 0.376812 | 0 | DPF3 | 14 | 14q24.2 | 72206413 | 72430563 |
| DCAF4 | 1 | 0.333333 | 0.121212 | 0.391304 | 0 | DCAF4 | 14 | 14q24.2 | 72462793 | 72496110 |
| ZFYVE1 | 1 | 0.333333 | 0.121212 | 0.391304 | 0 | ZFYVE1 | 14 | 14q24.2 | 72505912 | 72563593 |
| ENTPD5 | 1 | 0.333333 | 0.121212 | 0.449275 | 0 | ENTPD5 | 14 | 14q24.3 | 73502936 | 73555780 |
| C14orf45 | 1 | 0.333333 | 0.121212 | 0.449275 | 0 | C14orf45 | 14 | 14q24.3 | 73555812 | 73602549 |
| ALDH6A1 | 1 | 0.333333 | 0.121212 | 0.449275 | 0 | ALDH6A1 | 14 | 14q24.3 | 73596625 | 73620950 |
| ABCD4 | 1 | 0.363636 | 0.121212 | 0.376812 | 0 | ABCD4 | 14 | 14q24.3 | 73821733 | 73839521 |
| TMEM90A | 1 | 0.363636 | 0.121212 | 0.376812 | 0 | TMEM90A | 14 | 14q24.3 | 73942349 | 73962759 |
| BCYRN1 | 1 | 0.30303 | 0.121212 | 0.347826 | 0 | BCYRN1 | 14 | 14q24.3 | 75406358 | 75658554 |
| TGFB3 | 1 | 0.30303 | 0.121212 | 0.347826 | 0 | TGFB3 | 14 | 14q24.3 | 75494195 | 75517846 |
| C14orf179 | 1 | 0.30303 | 0.121212 | 0.347826 | 0 | C14orf179 | 14 | 14q24.3 | 75521849 | 75619846 |
| ESRRB | 1 | 0.363636 | 0.121212 | 0.376812 | 0 | ESRRB | 14 | 14q24.3 | 75907443 | 76037932 |
| VASH1 | 1 | 0.363636 | 0.121212 | 0.376812 | 0 | VASH1 | 14 | 14q24.3 | 76297988 | 76319117 |

TABLE 3-continued

| Symbol | freq. use | freq. amp. case | freq. del. case | freq. amp. control | freq. del. control | Gene. Symbol | chromo- some | cytoband | Transcript. start | Transcript. end |
|---|---|---|---|---|---|---|---|---|---|---|
| ANGEL1 | 1 | 0.363636 | 0.121212 | 0.376812 | 0 | ANGEL1 | 14 | 14q24.3 | 76323339 | 76349037 |
| C14orf166B | 1 | 0.363636 | 0.121212 | 0.376812 | 0 | C14orf166B | 14 | 14q24.3 | 76362478 | 76406399 |
| C14orf4 | 1 | 0.333333 | 0.121212 | 0.347826 | 0 | C14orf4 | 14 | 14q24.3 | 76560639 | 76564788 |
| KIAA1737 | 1 | 0.333333 | 0.121212 | 0.347826 | 0 | KIAA1737 | 14 | 14q24.3 | 76634331 | 76653384 |
| ZDHHC22 | 1 | 0.333333 | 0.121212 | 0.347826 | 0 | ZDHHC22 | 14 | 14q24.3 | 76667366 | 76677888 |
| TMEM63C | 1 | 0.333333 | 0.121212 | 0.347826 | 0 | TMEM63C | 14 | 14q24.3 | 76717855 | 76795592 |
| NGB | 1 | 0.333333 | 0.121212 | 0.347826 | 0 | NGB | 14 | 14q24.3 | 76801587 | 76807409 |
| MIR1260 | 1 | 0.333333 | 0.121212 | 0.347826 | 0 | MIR1260 | 14 | 14q24.3 | 76802314 | 76802385 |
| POMT2 | 1 | 0.333333 | 0.121212 | 0.347826 | 0 | POMT2 | 14 | 14q24.3 | 76811054 | 76856979 |
| GSTZ1 | 1 | 0.333333 | 0.121212 | 0.347826 | 0 | GSTZ1 | 14 | 14q24.3 | 76856983 | 76867694 |
| TMED8 | 1 | 0.333333 | 0.121212 | 0.347826 | 0 | TMED8 | 14 | 14q24.3 | 76877867 | 76913150 |
| C14orf174 | 1 | 0.333333 | 0.121212 | 0.347826 | 0 | C14orf174 | 14 | 14q24.3 | 76913515 | 76927341 |
| C14orf148 | 1 | 0.333333 | 0.121212 | 0.347826 | 0 | C14orf148 | 14 | 14q24.3 | 76930177 | 76959133 |
| C14orf133 | 1 | 0.30303 | 0.121212 | 0.347826 | 0 | C14orf133 | 14 | 14q24.3 | 76962771 | 76993658 |
| AHSA1 | 1 | 0.30303 | 0.121212 | 0.347826 | 0 | AHSA1 | 14 | 14q24.3 | 76994126 | 77005561 |
| ISM2 | 1 | 0.30303 | 0.121212 | 0.347826 | 0 | ISM2 | 14 | 14q24.3 | 77010493 | 77034964 |
| SPTLC2 | 1 | 0.272727 | 0.121212 | 0.333333 | 0 | SPTLC2 | 14 | 14q24.3 | 77043023 | 77152864 |
| C14orf156 | 1 | 0.272727 | 0.121212 | 0.318841 | 0 | C14orf156 | 14 | 14q24.3 | 77244178 | 77253697 |
| SNW1 | 1 | 0.272727 | 0.121212 | 0.318841 | 0 | SNW1 | 14 | 14q24.3 | 77253597 | 77297251 |
| C14orf178 | 1 | 0.272727 | 0.121212 | 0.318841 | 0 | C14orf178 | 14 | 14q24.3 | 77296646 | 77305839 |
| ADCK1 | 1 | 0.272727 | 0.121212 | 0.318841 | 0 | ADCK1 | 14 | 14q24.3 | 77336179 | 77470050 |
| KCNK10 | 1 | 0.090909 | 0.121212 | 0.318841 | 0 | KCNK10 | 14 | 14q31.3 | 87716207 | 87863010 |
| PTPN21 | 1 | 0.121212 | 0.121212 | 0.333333 | 0 | PTPN21 | 14 | 14q31.3 | 88001875 | 88090877 |
| ZC3H14 | 1 | 0.121212 | 0.121212 | 0.333333 | 0 | ZC3H14 | 14 | 14q31.3 | 88099006 | 88149606 |
| EML5 | 1 | 0.121212 | 0.121212 | 0.333333 | 0 | EML5 | 14 | 14q31.3 | 88150956 | 88328911 |
| TTC8 | 1 | 0.121212 | 0.121212 | 0.333333 | 0 | TTC8 | 14 | 14q31.3 | 88360731 | 88414089 |
| LOC284232 | 1 | 0.060606 | 0.121212 | 0.173913 | 0 | LOC284232 | 13 | 13q11 | 18306543 | 18344110 |
| EFHA1 | 1 | 0.181818 | 0.121212 | 0.173913 | 0 | EFHA1 | 13 | 13q12.11 | 20964839 | 21076308 |
| FGF9 | 1 | 0.181818 | 0.121212 | 0.15942 | 0 | FGF9 | 13 | 13q12.11 | 21143215 | 21176641 |
| SGCG | 1 | 0.181818 | 0.121212 | 0.173913 | 0 | SGCG | 13 | 13q12.12 | 22653060 | 22797305 |
| SACS | 1 | 0.181818 | 0.121212 | 0.188406 | 0 | SACS | 13 | 13q12.12 | 22800965 | 22905842 |
| TNFRSF19 | 1 | 0.212121 | 0.121212 | 0.173913 | 0 | TNFRSF19 | 13 | 13q12.12 | 23042723 | 23148233 |
| MIPEP | 1 | 0.121212 | 0.121212 | 0.173913 | 0 | MIPEP | 13 | 13q12.12 | 23202328 | 23361560 |
| SPATA13 | 1 | 0.181818 | 0.121212 | 0.202899 | 0 | SPATA13 | 13 | 13q12.12 | 23632861 | 23779213 |
| MIR2276 | 1 | 0.181818 | 0.121212 | 0.202899 | 0 | MIR2276 | 13 | 13q12.12 | 23634555 | 23634644 |
| C1QTNF9 | 1 | 0.212121 | 0.121212 | 0.202899 | 0 | C1QTNF9 | 13 | 13q12.12 | 23781716 | 23794670 |
| PARP4 | 1 | 0.181818 | 0.121212 | 0.217391 | 0 | PARP4 | 13 | 13q12.12 | 23893069 | 23984949 |
| RNF17 | 1 | 0.151515 | 0.121212 | 0.318841 | 0 | RNF17 | 13 | 13q12.12 | 24236301 | 24352059 |
| CENPJ | 1 | 0.151515 | 0.121212 | 0.318841 | 0 | CENPJ | 13 | 13q12.12 | 24354412 | 24395086 |
| PABPC3 | 1 | 0.151515 | 0.151515 | 0.318841 | 0 | PABPC3 | 13 | 13q12.13 | 24568276 | 24570705 |
| MTMR6 | 1 | 0.151515 | 0.151515 | 0.318841 | 0 | MTMR6 | 13 | 13q12.13 | 24718341 | 24759705 |
| ATP8A2 | 1 | 0.121212 | 0.151515 | 0.318841 | 0 | ATP8A2 | 13 | 13q12.13 | 24844209 | 25493421 |
| SHISA2 | 1 | 0.090909 | 0.121212 | 0.26087 | 0 | SHISA2 | 13 | 13q12.13 | 25516735 | 25523199 |
| RNF6 | 1 | 0.090909 | 0.121212 | 0.26087 | 0 | RNF6 | 13 | 13q12.13 | 25684905 | 25694509 |
| WASF3 | 1 | 0.121212 | 0.121212 | 0.333333 | 0 | WASF3 | 13 | 13q12.13 | 26029840 | 26161081 |
| USP12 | 1 | 0.151515 | 0.121212 | 0.333333 | 0 | USP12 | 13 | 13q12.13 | 26540438 | 26644039 |
| PAN3 | 1 | 0.060606 | 0.121212 | 0.231884 | 0 | PAN3 | 13 | 13q12.2 | 27610643 | 27767476 |
| MTUS2 | 1 | 0.090909 | 0.121212 | 0.246377 | 0 | MTUS2 | 13 | 13q12.3 | 28496748 | 28978085 |
| KCNMB4 | 1 | 0.151515 | 0.030303 | 0 | 0.028986 | KCNMB4 | 12 | 12q15 | 69046329 | 69111246 |
| PTPRR | 1 | 0.121212 | 0.060606 | 0 | 0.043478 | PTPRR | 12 | 12q15 | 69318129 | 69600852 |
| TPH2 | 1 | 0.121212 | 0.121212 | 0.181818 | 0.202899 | TPH2 | 12 | 12q21.1 | 70618893 | 70712489 |
| TRHDE | 1 | 0.121212 | 0.212121 | 0 | 0.231884 | TRHDE | 12 | 12q21.1 | 70952796 | 71345689 |
| C12orf12 | 1 | 0.121212 | 0.212121 | 0 | 0.217391 | C12orf12 | 12 | 12q21.33 | 89870123 | 89873085 |
| EPYC | 1 | 0.121212 | 0.212121 | 0 | 0.217391 | EPYC | 12 | 12q21.33 | 89881589 | 89922935 |
| NAV2 | 1 | 0.030303 | 0.151515 | 0.130435 | 0 | NAV2 | 11 | 11p15.1 | 19328847 | 20099724 |
| FLJ32810 | 1 | 0.121212 | 0.181818 | 0 | 0.101449 | FLJ32810 | 11 | 11q22.1 | 1E+08 | 1E+08 |
| MMP20 | 1 | 0.121212 | 0.181818 | 0 | 0.101449 | MMP20 | 11 | 11q22.2 | 1.02E+08 | 1.02E+08 |
| SLC35F2 | 1 | 0.242424 | 0.121212 | 0.246377 | 0 | SLC35F2 | 11 | 11q22.3 | 1.07E+08 | 1.07E+08 |
| RAB39 | 1 | 0.242424 | 0.121212 | 0.246377 | 0 | RAB39 | 11 | 11q22.3 | 1.07E+08 | 1.07E+08 |
| CUL5 | 1 | 0.212121 | 0.121212 | 0.246377 | 0 | CUL5 | 11 | 11q22.3 | 1.07E+08 | 1.07E+08 |
| C11orf65 | 1 | 0.181818 | 0.121212 | 0.188406 | 0 | C11orf65 | 11 | 11q22.3 | 1.08E+08 | 1.08E+08 |
| KDELC2 | 1 | 0.181818 | 0.121212 | 0.188406 | 0 | KDELC2 | 11 | 11q22.3 | 1.08E+08 | 1.08E+08 |
| EXPH5 | 1 | 0.181818 | 0.121212 | 0.188406 | 0 | EXPH5 | 11 | 11q22.3 | 1.08E+08 | 1.08E+08 |
| ZC3H12C | 1 | 0.151515 | 0.151515 | 0.144928 | 0 | ZC3H12C | 11 | 11q22.3 | 1.09E+08 | 1.1E+08 |
| FDX1 | 1 | 0.181818 | 0.151515 | 0.130435 | 0 | FDX1 | 11 | 11q22.3 | 1.1E+08 | 1.1E+08 |
| ARHGAP20 | 1 | 0.181818 | 0.151515 | 0.130435 | 0 | ARHGAP20 | 11 | 11q22.3 | 1.1E+08 | 1.1E+08 |
| POU2AF1 | 1 | 0.212121 | 0.121212 | 0.217391 | 0 | POU2AF1 | 11 | 11q23.1 | 1.11E+08 | 1.11E+08 |
| C11orf88 | 1 | 0.121212 | 0.151515 | 0.217391 | 0 | C11orf88 | 11 | 11q23.1 | 1.11E+08 | 1.11E+08 |
| LAYN | 1 | 0.121212 | 0.151515 | 0.217391 | 0 | LAYN | 11 | 11q23.1 | 1.11E+08 | 1.11E+08 |
| SIK2 | 1 | 0.212121 | 0.121212 | 0.217391 | 0 | SIK2 | 11 | 11q23.1 | 1.11E+08 | 1.11E+08 |
| PPP2R1B | 1 | 0.212121 | 0.121212 | 0.217391 | 0 | PPP2R1B | 11 | 11q23.1 | 1.11E+08 | 1.11E+08 |
| ALG9 | 1 | 0.181818 | 0.121212 | 0.217391 | 0 | ALG9 | 11 | 11q23.1 | 1.11E+08 | 1.11E+08 |
| IL18 | 1 | 0.181818 | 0.121212 | 0.217391 | 0 | IL18 | 11 | 11q23.1 | 1.12E+08 | 1.12E+08 |
| BCO2 | 1 | 0.151515 | 0.121212 | 0.217391 | 0 | BCO2 | 11 | 11q23.1 | 1.12E+08 | 1.12E+08 |
| PTS | 1 | 0.121212 | 0.121212 | 0.202899 | 0 | PTS | 11 | 11q23.1 | 1.12E+08 | 1.12E+08 |
| C11orf34 | 1 | 0.121212 | 0.121212 | 0.202899 | 0 | C11orf34 | 11 | 11q23.1 | 1.12E+08 | 1.12E+08 |

TABLE 3-continued

| Symbol | freq. use | freq. amp. case | freq. del. case | freq. amp. control | freq. del. control | Gene. Symbol | chromo-some | cytoband | Transcript. start | Transcript. end |
|---|---|---|---|---|---|---|---|---|---|---|
| TTC12 | 1 | 0.212121 | 0.121212 | 0.289855 | 0 | TTC12 | 11 | 11q23.1 | 1.13E+08 | 1.13E+08 |
| DRD2 | 1 | 0.212121 | 0.121212 | 0.304348 | 0 | DRD2 | 11 | 11q23.1 | 1.13E+08 | 1.13E+08 |
| TMPRSS5 | 1 | 0.212121 | 0.121212 | 0.304348 | 0 | TMPRSS5 | 11 | 11q23.2 | 1.13E+08 | 1.13E+08 |
| CLDN25 | 1 | 0.212121 | 0.121212 | 0.289855 | 0 | CLDN25 | 11 | 11q23.2 | 1.13E+08 | 1.13E+08 |
| USP28 | 1 | 0.212121 | 0.121212 | 0.289855 | 0 | USP28 | 11 | 11q23.2 | 1.13E+08 | 1.13E+08 |
| BUD13 | 1 | 0.242424 | 0.121212 | 0.449275 | 0 | BUD13 | 11 | 11q23.3 | 1.16E+08 | 1.16E+08 |
| ZNF259 | 1 | 0.242424 | 0.121212 | 0.449275 | 0 | ZNF259 | 11 | 11q23.3 | 1.16E+08 | 1.16E+08 |
| APOA5 | 1 | 0.242424 | 0.121212 | 0.449275 | 0 | APOA5 | 11 | 11q23.3 | 1.16E+08 | 1.16E+08 |
| SIK3 | 1 | 0.272727 | 0.121212 | 0.449275 | 0 | SIK3 | 11 | 11q23.3 | 1.16E+08 | 1.16E+08 |
| PAFAH1B2 | 1 | 0.242424 | 0.121212 | 0.449275 | 0 | PAFAH1B2 | 11 | 11q23.3 | 1.17E+08 | 1.17E+08 |
| TAGLN | 1 | 0.30303 | 0.121212 | 0.449275 | 0 | TAGLN | 11 | 11q23.3 | 1.17E+08 | 1.17E+08 |
| PCSK7 | 1 | 0.30303 | 0.121212 | 0.449275 | 0 | PCSK7 | 11 | 11q23.3 | 1.17E+08 | 1.17E+08 |
| RNF214 | 1 | 0.30303 | 0.121212 | 0.449275 | 0 | RNF214 | 11 | 11q23.3 | 1.17E+08 | 1.17E+08 |
| BACE1 | 1 | 0.30303 | 0.121212 | 0.449275 | 0 | BACE1 | 11 | 11q23.3 | 1.17E+08 | 1.17E+08 |
| HYOU1 | 1 | 0.393939 | 0.121212 | 0.507246 | 0 | HYOU1 | 11 | 11q23.3 | 1.18E+08 | 1.18E+08 |
| VPS11 | 1 | 0.393939 | 0.121212 | 0.507246 | 0 | VPS11 | 11 | 11q23.3 | 1.18E+08 | 1.18E+08 |
| HMBS | 1 | 0.393939 | 0.121212 | 0.507246 | 0 | HMBS | 11 | 11q23.3 | 1.18E+08 | 1.18E+08 |
| H2AFX | 1 | 0.393939 | 0.121212 | 0.507246 | 0 | H2AFX | 11 | 11q23.3 | 1.18E+08 | 1.18E+08 |
| DPAGT1 | 1 | 0.393939 | 0.121212 | 0.507246 | 0 | DPAGT1 | 11 | 11q23.3 | 1.18E+08 | 1.18E+08 |
| TRPM3 | 1 | 0.060606 | 0.121212 | 0.014493 | 0 | TRPM3 | 9 | 9q21.11 | 72339786 | 72926335 |
| MIR548A1 | 1 | 0.151515 | 0.090909 | 0 | 0.028986 | MIR548A1 | 6 | 6p22.3 | 18679994 | 18680091 |
| ORC3L | 1 | 0.151515 | 0.242424 | 0 | 0.202899 | ORC3L | 6 | 6q15 | 88356562 | 88433888 |
| C5orf33 | 1 | 0.121212 | 0.060606 | 0 | 0.028986 | C5orf33 | 5 | 5p13.2 | 36228451 | 36277658 |
| RANBP3L | 1 | 0.121212 | 0.060606 | 0 | 0.028986 | RANBP3L | 5 | 5p13.2 | 36284862 | 36337769 |
| EGFLAM | 1 | 0.121212 | 0 | 0 | 0 | EGFLAM | 5 | 5p13.2 | 38294290 | 38500408 |
| LIFR | 1 | 0.121212 | 0 | 0 | 0 | LIFR | 5 | 5p13.1 | 38510822 | 38592506 |
| OSMR | 1 | 0.121212 | 0 | 0 | 0 | OSMR | 5 | 5p13.1 | 38881717 | 38922516 |
| RICTOR | 1 | 0.121212 | 0 | 0 | 0 | RICTOR | 5 | 5p13.1 | 38973780 | 39110259 |
| DAB2 | 1 | 0.121212 | 0.030303 | 0 | 0.072464 | DAB2 | 5 | 5p13.1 | 39407537 | 39461093 |
| SDAD1 | 1 | 0.181818 | 0.030303 | 0 | 0.014493 | SDAD1 | 4 | 4q21.1 | 77090092 | 77131138 |
| CXCL9 | 1 | 0.181818 | 0.030303 | 0 | 0.014493 | CXCL9 | 4 | 4q21.1 | 77141647 | 77147666 |
| ART3 | 1 | 0.181818 | 0.030303 | 0 | 0.014493 | ART3 | 4 | 4q21.1 | 77151361 | 77252980 |
| CXCL10 | 1 | 0.181818 | 0.030303 | 0 | 0.014493 | CXCL10 | 4 | 4q21.1 | 77161295 | 77163675 |
| CXCL11 | 1 | 0.181818 | 0.030303 | 0 | 0.014493 | CXCL11 | 4 | 4q21.1 | 77173864 | 77176258 |
| CCNG2 | 1 | 0.121212 | 0.030303 | 0 | 0.043478 | CCNG2 | 4 | 4q21.1 | 78297381 | 78310238 |
| RASGEF1B | 1 | 0.121212 | 0.060606 | 0 | 0.115942 | RASGEF1B | 4 | 4q21.21 | 82567243 | 82612086 |
| SMAD1 | 1 | 0.121212 | 0.030303 | 0 | 0 | SMAD1 | 4 | 4q31.22 | 1.47E+08 | 1.47E+08 |
| MMAA | 1 | 0.121212 | 0 | 0 | 0 | MMAA | 4 | 4q31.22 | 1.47E+08 | 1.47E+08 |
| C4orf51 | 1 | 0.121212 | 0 | 0 | 0 | C4orf51 | 4 | 4q31.22 | 1.47E+08 | 1.47E+08 |
| ZNF827 | 1 | 0.121212 | 0 | 0 | 0 | ZNF827 | 4 | 4q31.22 | 1.47E+08 | 1.47E+08 |
| MPP4 | 1 | 0.060606 | 0.121212 | 0.15942 | 0 | MPP4 | 2 | 2q33.1 | 2.02E+08 | 2.02E+08 |
| ALS2 | 1 | 0.060606 | 0.121212 | 0.15942 | 0 | ALS2 | 2 | 2q33.1 | 2.02E+08 | 2.02E+08 |
| CD28 | 1 | 0.060606 | 0.151515 | 0.086957 | 0 | CD28 | 2 | 2q33.2 | 2.04E+08 | 2.04E+08 |
| ERO1LB | 1 | 0.181818 | 0.121212 | 0.202899 | 0 | ERO1LB | 1 | 1q42.3 | 2.34E+08 | 2.35E+08 |
| PLD5 | 1 | 0.090909 | 0.121212 | 0.086957 | 0 | PLD5 | 1 | 1q43 | 2.4E+08 | 2.41E+08 |
| LOC100101116 | 0.970588 | 0.212121 | 0.090909 | 0.231884 | 0 | LOC100101116 | Y | Yp11.2 | 6318442 | 6339606 |
| TTTY1 | 0.970588 | 0.212121 | 0.090909 | 0.231884 | 0 | TTTY1 | Y | Yp11.2 | 6318472 | 6339606 |
| LOC100101117 | 0.970588 | 0.212121 | 0.090909 | 0.231884 | 0 | LOC100101117 | Y | Yp11.2 | 6334285 | 6356486 |
| TTTY2 | 0.970588 | 0.212121 | 0.090909 | 0.231884 | 0 | TTTY2 | Y | Yp11.2 | 6334285 | 6356486 |
| LOC100192426 | 0.970588 | 0.090909 | 0.090909 | 0.217391 | 0 | LOC100192426 | 18 | 18p11.23 | 8350818 | 8357033 |
| RAB12 | 0.970588 | 0.242424 | 0.090909 | 0.246377 | 0 | RAB12 | 18 | 18p11.22 | 8599443 | 8629381 |
| KIAA0802 | 0.970588 | 0.242424 | 0.090909 | 0.246377 | 0 | KIAA0802 | 18 | 18p11.22 | 8707369 | 8822776 |
| RALBP1 | 0.970588 | 0.272727 | 0.090909 | 0.26087 | 0 | RALBP1 | 18 | 18p11.22 | 9465530 | 9528107 |
| APCDD1 | 0.970588 | 0.242424 | 0.090909 | 0.246377 | 0 | APCDD1 | 18 | 18p11.22 | 10444625 | 10478699 |
| NAPG | 0.970588 | 0.242424 | 0.090909 | 0.246377 | 0 | NAPG | 18 | 18p11.22 | 10515873 | 10542763 |
| FAM38B | 0.970588 | 0.272727 | 0.090909 | 0.231884 | 0 | FAM38B | 18 | 18p11.22 | 10660244 | 11138762 |
| GNAL | 0.970588 | 0.272727 | 0.090909 | 0.217391 | 0 | GNAL | 18 | 18p11.21 | 11679136 | 11873145 |
| CHMP1B | 0.970588 | 0.333333 | 0.090909 | 0.217391 | 0 | CHMP1B | 18 | 18p11.21 | 11841389 | 11844449 |
| IMPA2 | 0.970588 | 0.30303 | 0.090909 | 0.289855 | 0 | IMPA2 | 18 | 18p11.21 | 11971455 | 12020877 |
| CIDEA | 0.970588 | 0.272727 | 0.090909 | 0.231884 | 0 | CIDEA | 18 | 18p11.21 | 12244318 | 12267595 |
| AFG3L2 | 0.970588 | 0.272727 | 0.090909 | 0.231884 | 0 | AFG3L2 | 18 | 18p11.21 | 12319108 | 12367195 |
| SLMO1 | 0.970588 | 0.272727 | 0.090909 | 0.231884 | 0 | SLMO1 | 18 | 18p11.21 | 12397895 | 12422235 |
| SPIRE1 | 0.970588 | 0.212121 | 0.090909 | 0.202899 | 0 | SPIRE1 | 18 | 18p11.21 | 12436511 | 12647913 |
| PTPN2 | 0.970588 | 0.212121 | 0.090909 | 0.217391 | 0 | PTPN2 | 18 | 18p11.21 | 12775480 | 12874335 |
| SEH1L | 0.970588 | 0.181818 | 0.090909 | 0.217391 | 0 | SEH1L | 18 | 18p11.21 | 12937983 | 12977537 |
| CEP192 | 0.970588 | 0.181818 | 0.090909 | 0.217391 | 0 | CEP192 | 18 | 18p11.21 | 12981361 | 13115050 |
| C18orf1 | 0.970588 | 0.272727 | 0.090909 | 0.231884 | 0 | C18orf1 | 18 | 18p11.21 | 13208786 | 13642754 |
| MC2R | 0.970588 | 0.212121 | 0.090909 | 0.231884 | 0 | MC2R | 18 | 18p11.21 | 13872043 | 13905536 |
| ZNF519 | 0.970588 | 0.090909 | 0.090909 | 0.101449 | 0 | ZNF519 | 18 | 18p11.21 | 14094724 | 14122430 |
| GP2 | 0.970588 | 0.242424 | 0.090909 | 0.492754 | 0 | GP2 | 16 | 16p12.3 | 20229312 | 20246337 |
| GSG1L | 0.970588 | 0.424242 | 0.090909 | 0.565217 | 0 | GSG1L | 16 | 16p11.2 | 27706351 | 27982332 |
| NOVA1 | 0.970588 | 0.090909 | 0.181818 | 0 | 0.217391 | NOVA1 | 14 | 14q12 | 25984929 | 26136801 |
| PRKD1 | 0.970588 | 0.090909 | 0.121212 | 0 | 0.173913 | PRKD1 | 14 | 14q12 | 29115438 | 29466651 |
| ARHGAP5 | 0.970588 | 0.090909 | 0 | 0 | 0.043478 | ARHGAP5 | 14 | 14q12 | 31615246 | 31698686 |
| AKAP6 | 0.970588 | 0.090909 | 0.121212 | 0 | 0.101449 | AKAP6 | 14 | 14q13.1 | 31868230 | 32372020 |
| RALGAPA1 | 0.970588 | 0.090909 | 0.030303 | 0 | 0.115942 | RALGAPA1 | 14 | 14q13.2 | 35077309 | 35348184 |

TABLE 3-continued

| Symbol | freq. use | freq. amp. case | freq. del. case | freq. amp. control | freq. del. control | Gene. Symbol | chromo-some | cytoband | Transcript. start | Transcript. end |
|---|---|---|---|---|---|---|---|---|---|---|
| PTGDR | 0.970588 | 0.030303 | 0.090909 | 0.028986 | 0 | PTGDR | 14 | 14q22.1 | 51804181 | 51813193 |
| KIAA0586 | 0.970588 | 0.121212 | 0.090909 | 0.014493 | 0 | KIAA0586 | 14 | 14q23.1 | 57964463 | 58085303 |
| DACT1 | 0.970588 | 0.121212 | 0.090909 | 0.014493 | 0 | DACT1 | 14 | 14q23.1 | 58174510 | 58184792 |
| SGPP1 | 0.970588 | 0.242424 | 0.090909 | 0.217391 | 0 | SGPP1 | 14 | 14q23.2 | 63220688 | 63264510 |
| SYNE2 | 0.970588 | 0.242424 | 0.090909 | 0.217391 | 0 | SYNE2 | 14 | 14q23.2 | 63389436 | 63762923 |
| ATP6V1D | 0.970588 | 0.242424 | 0.090909 | 0.217391 | 0 | ATP6V1D | 14 | 14q23.3 | 66874342 | 66896345 |
| EIF2S1 | 0.970588 | 0.242424 | 0.090909 | 0.217391 | 0 | EIF2S1 | 14 | 14q23.3 | 66896787 | 66922987 |
| PLEK2 | 0.970588 | 0.242424 | 0.090909 | 0.217391 | 0 | PLEK2 | 14 | 14q23.3 | 66923453 | 66948582 |
| PLEKHH1 | 0.970588 | 0.242424 | 0.090909 | 0.217391 | 0 | PLEKHH1 | 14 | 14q24.1 | 67069761 | 67126009 |
| PIGH | 0.970588 | 0.212121 | 0.090909 | 0.217391 | 0 | PIGH | 14 | 14q24.1 | 67125776 | 67136771 |
| ARG2 | 0.970588 | 0.212121 | 0.090909 | 0.217391 | 0 | ARG2 | 14 | 14q24.1 | 67156332 | 67188190 |
| LTBP2 | 0.970588 | 0.333333 | 0.090909 | 0.376812 | 0 | LTBP2 | 14 | 14q24.3 | 74034639 | 74148788 |
| KIAA0317 | 0.970588 | 0.333333 | 0.090909 | 0.376812 | 0 | KIAA0317 | 14 | 14q24.3 | 74197708 | 74249561 |
| FCF1 | 0.970588 | 0.333333 | 0.090909 | 0.362319 | 0 | FCF1 | 14 | 14q24.3 | 74249603 | 74273144 |
| YLPM1 | 0.970588 | 0.333333 | 0.090909 | 0.362319 | 0 | YLPM1 | 14 | 14q24.3 | 74299822 | 74373767 |
| PROX2 | 0.970588 | 0.333333 | 0.090909 | 0.362319 | 0 | PROX2 | 14 | 14q24.3 | 74391588 | 74400291 |
| DLST | 0.970588 | 0.333333 | 0.090909 | 0.362319 | 0 | DLST | 14 | 14q24.3 | 74418347 | 74440204 |
| RPS6KL1 | 0.970588 | 0.363636 | 0.090909 | 0.362319 | 0 | RPS6KL1 | 14 | 14q24.3 | 74442099 | 74458899 |
| PGF | 0.970588 | 0.363636 | 0.090909 | 0.362319 | 0 | PGF | 14 | 14q24.3 | 74478291 | 74492045 |
| EIF2B2 | 0.970588 | 0.333333 | 0.090909 | 0.362319 | 0 | EIF2B2 | 14 | 14q24.3 | 74539365 | 74546047 |
| MLH3 | 0.970588 | 0.333333 | 0.090909 | 0.362319 | 0 | MLH3 | 14 | 14q24.3 | 74550220 | 74587989 |
| ACYP1 | 0.970588 | 0.333333 | 0.090909 | 0.362319 | 0 | ACYP1 | 14 | 14q24.3 | 74589681 | 74600490 |
| FAM164C | 0.970588 | 0.333333 | 0.090909 | 0.362319 | 0 | FAM164C | 14 | 14q24.3 | 74606052 | 74614553 |
| NEK9 | 0.970588 | 0.333333 | 0.090909 | 0.362319 | 0 | NEK9 | 14 | 14q24.3 | 74618572 | 74663532 |
| TMED10 | 0.970588 | 0.333333 | 0.090909 | 0.362319 | 0 | TMED10 | 14 | 14q24.3 | 74667924 | 74713103 |
| JDP2 | 0.970588 | 0.333333 | 0.090909 | 0.362319 | 0 | JDP2 | 14 | 14q24.3 | 74964262 | 75009156 |
| BATF | 0.970588 | 0.30303 | 0.090909 | 0.362319 | 0 | BATF | 14 | 14q24.3 | 75058537 | 75083081 |
| FLVCR2 | 0.970588 | 0.30303 | 0.090909 | 0.318841 | 0 | FLVCR2 | 14 | 14q24.3 | 75114693 | 75184266 |
| FOXN3 | 0.970588 | 0.151515 | 0.090909 | 0.333333 | 0 | FOXN3 | 14 | 14q31.3 | 88692269 | 89155248 |
| C14orf143 | 0.970588 | 0.212121 | 0.090909 | 0.376812 | 0 | C14orf143 | 14 | 14q32.11 | 89333222 | 89490843 |
| C14orf64 | 0.970588 | 0.060606 | 0.090909 | 0.26087 | 0 | C14orf64 | 14 | 14q32.2 | 97461700 | 97514215 |
| GPR12 | 0.970588 | 0.181818 | 0.090909 | 0.333333 | 0 | GPR12 | 13 | 13q12.13 | 26227341 | 26232923 |
| RPL21 | 0.970588 | 0.181818 | 0.090909 | 0.333333 | 0 | RPL21 | 13 | 13q12.2 | 26723692 | 26728703 |
| RPL21P28 | 0.970588 | 0.181818 | 0.090909 | 0.333333 | 0 | RPL21P28 | 13 | 13q12.2 | 26723693 | 26728699 |
| SNORD102 | 0.970588 | 0.181818 | 0.090909 | 0.333333 | 0 | SNORD102 | 13 | 13q12.2 | 26727201 | 26727273 |
| SNORA27 | 0.970588 | 0.181818 | 0.090909 | 0.333333 | 0 | SNORA27 | 13 | 13q12.2 | 26727538 | 26727664 |
| RASL11A | 0.970588 | 0.181818 | 0.090909 | 0.333333 | 0 | RASL11A | 13 | 13q12.2 | 26742464 | 26745828 |
| GTF3A | 0.970588 | 0.151515 | 0.090909 | 0.333333 | 0 | GTF3A | 13 | 13q12.2 | 26896681 | 26907847 |
| MTIF3 | 0.970588 | 0.151515 | 0.090909 | 0.333333 | 0 | MTIF3 | 13 | 13q12.2 | 26907776 | 26922335 |
| GSX1 | 0.970588 | 0.121212 | 0.090909 | 0.347826 | 0 | GSX1 | 13 | 13q12.2 | 27264780 | 27266090 |
| PDX1 | 0.970588 | 0.121212 | 0.090909 | 0.333333 | 0 | PDX1 | 13 | 13q12.2 | 27392168 | 27398452 |
| ATP5EP2 | 0.970588 | 0.121212 | 0.090909 | 0.333333 | 0 | ATP5EP2 | 13 | 13q12.2 | 27417343 | 27417771 |
| CDX2 | 0.970588 | 0.121212 | 0.090909 | 0.333333 | 0 | CDX2 | 13 | 13q12.2 | 27434278 | 27441318 |
| PRHOXNB | 0.970588 | 0.121212 | 0.090909 | 0.333333 | 0 | PRHOXNB | 13 | 13q12.2 | 27450243 | 27460775 |
| FLT3 | 0.970588 | 0.121212 | 0.090909 | 0.333333 | 0 | FLT3 | 13 | 13q12.2 | 27475411 | 27572730 |
| FLT1 | 0.970588 | 0.090909 | 0.090909 | 0.231884 | 0 | FLT1 | 13 | 13q12.2 | 27772483 | 27967266 |
| POMP | 0.970588 | 0.121212 | 0.090909 | 0.231884 | 0 | POMP | 13 | 13q12.3 | 28131241 | 28151092 |
| SLC46A3 | 0.970588 | 0.121212 | 0.090909 | 0.231884 | 0 | SLC46A3 | 13 | 13q12.3 | 28172220 | 28191151 |
| SLC7A1 | 0.970588 | 0.151515 | 0.090909 | 0.26087 | 0 | SLC7A1 | 13 | 13q12.3 | 28981552 | 29067826 |
| KATNAL1 | 0.970588 | 0.151515 | 0.090909 | 0.246377 | 0 | KATNAL1 | 13 | 13q12.3 | 29674767 | 29779164 |
| LOC10018949 | 0.970588 | 0.151515 | 0.090909 | 0.246377 | 0 | LOC10018949 | 13 | 13q12.3 | 29812409 | 29846037 |
| HMGB1 | 0.970588 | 0.181818 | 0.090909 | 0.246377 | 0 | HMGB1 | 13 | 13q12.3 | 29930879 | 29938082 |
| ALOX5AP | 0.970588 | 0.181818 | 0.090909 | 0.275362 | 0 | ALOX5AP | 13 | 13q12.3 | 30207669 | 30236557 |
| KRT3 | 0.970588 | 0.212121 | 0.090909 | 0.478261 | 0 | KRT3 | 12 | 12q13.13 | 51469736 | 51476516 |
| TSPAN8 | 0.970588 | 0.090909 | 0.090909 | 0 | 0.15942 | TSPAN8 | 12 | 12q21.1 | 69805144 | 69838047 |
| LGR5 | 0.970588 | 0.090909 | 0.121212 | 0 | 0.15942 | LGR5 | 12 | 12q21.1 | 70120080 | 70264889 |
| KITLG | 0.970588 | 0.090909 | 0.181818 | 0 | 0.246377 | KITLG | 12 | 12q21.32 | 87410698 | 87498370 |
| VEZT | 0.970588 | 0.181818 | 0.090909 | 0.188406 | 0 | VEZT | 12 | 12q22 | 94135653 | 94220698 |
| TMEM132C | 0.970588 | 0.060606 | 0.090909 | 0.275362 | 0 | TMEM132C | 12 | 12q24.32 | 1.27E+08 | 1.28E+08 |
| EIF3F | 0.970588 | 0.121212 | 0.090909 | 0.15942 | 0 | EIF3F | 11 | 11p15.4 | 7965443 | 7974295 |
| SBF2 | 0.970588 | 0.181818 | 0.090909 | 0.188406 | 0 | SBF2 | 11 | 11p15.4 | 9756790 | 10272331 |
| MICALCL | 0.970588 | 0.121212 | 0.090909 | 0.231884 | 0 | MICALCL | 11 | 11p15.3 | 12265023 | 12337268 |
| LDLRAD3 | 0.970588 | 0.121212 | 0.090909 | 0.130435 | 0 | LDLRAD3 | 11 | 11p13 | 35922188 | 35209418 |
| COMMD9 | 0.970588 | 0.151515 | 0.090909 | 0.130435 | 0 | COMMD9 | 11 | 11p13 | 36250418 | 36267576 |
| PRR5L | 0.970588 | 0.151515 | 0.090909 | 0.130435 | 0 | PRR5L | 11 | 11p13 | 36274301 | 36443330 |
| FAM181B | 0.970588 | 0.090909 | 0.121212 | 0 | 0.057971 | FAM181B | 11 | 11q14.1 | 82120694 | 82122555 |
| DLG2 | 0.970588 | 0.090909 | 0.181818 | 0 | 0.115942 | DLG2 | 11 | 11q14.1 | 82843706 | 85015963 |
| RAB38 | 0.970588 | 0.090909 | 0.181818 | 0 | 0.101449 | RAB38 | 11 | 11q14.2 | 87486079 | 87548248 |
| CTSC | 0.970588 | 0.090909 | 0.151515 | 0 | 0.130435 | CTSC | 11 | 11q14.2 | 87666408 | 87710590 |
| GRM5 | 0.970588 | 0.090909 | 0.181818 | 0 | 0.115942 | GRM5 | 11 | 11q14.2 | 87877393 | 88436465 |
| TRPC6 | 0.970588 | 0.090909 | 0.272727 | 0 | 0.188406 | TRPC6 | 11 | 11q22.1 | 1.01E+08 | 1.01E+08 |
| KIAA1377 | 0.970588 | 0.090909 | 0.212121 | 0 | 0.173913 | KIAA1377 | 11 | 11q22.1 | 1.01E+08 | 1.01E+08 |
| YAP1 | 0.970588 | 0.090909 | 0.181818 | 0 | 0.130435 | YAP1 | 11 | 11q22.1 | 1.01E+08 | 1.02E+08 |
| MMP27 | 0.970588 | 0.090909 | 0.151515 | 0 | 0.057971 | MMP27 | 11 | 11q22.2 | 1.02E+08 | 1.02E+08 |
| MMP8 | 0.970588 | 0.090909 | 0.151515 | 0 | 0.057971 | MMP8 | 11 | 11q22.2 | 1.02E+08 | 1.02E+08 |
| MMP10 | 0.970588 | 0.090909 | 0.151515 | 0 | 0.043478 | MMP10 | 11 | 11q22.2 | 1.02E+08 | 1.02E+08 |

TABLE 3-continued

| Symbol | freq. use | freq. amp. case | freq. del. case | freq. amp. control | freq. del. control | Gene. Symbol | chromo-some | cytoband | Transcript. start | Transcript. end |
|---|---|---|---|---|---|---|---|---|---|---|
| MMP1 | 0.970588 | 0.090909 | 0.151515 | 0 | 0.043478 | MMP1 | 11 | 11q22.2 | 1.02E+08 | 1.02E+08 |
| PDGFD | 0.970588 | 0.090909 | 0.212121 | 0 | 0.144928 | PDGFD | 11 | 11q22.3 | 1.03E+08 | 1.04E+08 |
| CASP4 | 0.970588 | 0.090909 | 0.272727 | 0 | 0.188406 | CASP4 | 11 | 11q22.3 | 1.04E+08 | 1.04E+08 |
| CASP5 | 0.970588 | 0.090909 | 0.272727 | 0 | 0.188406 | CASP5 | 11 | 11q22.3 | 1.04E+08 | 1.04E+08 |
| CARD16 | 0.970588 | 0.090909 | 0.272727 | 0 | 0.188406 | CARD16 | 11 | 11q22.3 | 1.04E+08 | 1.04E+08 |
| GRIA4 | 0.970588 | 0.090909 | 0.242424 | 0 | 0.15942 | GRIA4 | 11 | 11q22.3 | 1.05E+08 | 1.05E+08 |
| SLN | 0.970588 | 0.242424 | 0.090909 | 0.217391 | 0 | SLN | 11 | 11q22.3 | 1.07E+08 | 1.07E+08 |
| ACAT1 | 0.970588 | 0.212121 | 0.090909 | 0.246377 | 0 | ACAT1 | 11 | 11q22.3 | 1.07E+08 | 1.08E+08 |
| NPAT | 0.970588 | 0.212121 | 0.090909 | 0.246377 | 0 | NPAT | 11 | 11q22.3 | 1.08E+08 | 1.08E+08 |
| ATM | 0.970588 | 0.212121 | 0.090909 | 0.231884 | 0 | ATM | 11 | 11q22.3 | 1.08E+08 | 1.08E+08 |
| FDXACB1 | 0.970588 | 0.212121 | 0.090909 | 0.217391 | 0 | FDXACB1 | 11 | 11q23.1 | 1.11E+08 | 1.11E+08 |
| C11orf1 | 0.970588 | 0.212121 | 0.090909 | 0.217391 | 0 | C11orf1 | 11 | 11q23.1 | 1.11E+08 | 1.11E+08 |
| CRYAB | 0.970588 | 0.212121 | 0.090909 | 0.217391 | 0 | CRYAB | 11 | 11q23.1 | 1.11E+08 | 1.11E+08 |
| HSPB2 | 0.970588 | 0.212121 | 0.090909 | 0.217391 | 0 | HSPB2 | 11 | 11q23.1 | 1.11E+08 | 1.11E+08 |
| C11orf52 | 0.970588 | 0.212121 | 0.090909 | 0.217391 | 0 | C11orf52 | 11 | 11q23.1 | 1.11E+08 | 1.11E+08 |
| DIXDC1 | 0.970588 | 0.212121 | 0.090909 | 0.217391 | 0 | DIXDC1 | 11 | 11q23.1 | 1.11E+08 | 1.11E+08 |
| PIH1D2 | 0.970588 | 0.212121 | 0.090909 | 0.217391 | 0 | PIH1D2 | 11 | 11q23.1 | 1.11E+08 | 1.11E+08 |
| C11orf57 | 0.970588 | 0.212121 | 0.090909 | 0.217391 | 0 | C11orf57 | 11 | 11q23.1 | 1.11E+08 | 1.11E+08 |
| TIMM8B | 0.970588 | 0.212121 | 0.090909 | 0.217391 | 0 | TIMM8B | 11 | 11q23.1 | 1.11E+08 | 1.11E+08 |
| SDHD | 0.970588 | 0.212121 | 0.090909 | 0.217391 | 0 | SDHD | 11 | 11q23.1 | 1.11E+08 | 1.11E+08 |
| CEP164 | 0.970588 | 0.30303 | 0.090909 | 0.449275 | 0 | CEP164 | 11 | 11q23.3 | 1.17E+08 | 1.17E+08 |
| DSCAML1 | 0.970588 | 0.30303 | 0.090909 | 0.463768 | 0 | DSCAML1 | 11 | 11q23.3 | 1.17E+08 | 1.17E+08 |
| FXYD6 | 0.970588 | 0.30303 | 0.090909 | 0.478261 | 0 | FXYD6 | 11 | 11q23.3 | 1.17E+08 | 1.17E+08 |
| TMPRSS13 | 0.970588 | 0.30303 | 0.090909 | 0.478261 | 0 | TMPRSS13 | 11 | 11q23.3 | 1.17E+08 | 1.17E+08 |
| IL10RA | 0.970588 | 0.30303 | 0.090909 | 0.478261 | 0 | IL10RA | 11 | 11q23.3 | 1.17E+08 | 1.17E+08 |
| TMPRSS4 | 0.970588 | 0.30303 | 0.090909 | 0.478261 | 0 | TMPRSS4 | 11 | 11q23.3 | 1.17E+08 | 1.17E+08 |
| SCN4B | 0.970588 | 0.30303 | 0.090909 | 0.478261 | 0 | SCN4B | 11 | 11q23.3 | 1.18E+08 | 1.18E+08 |
| MPZL2 | 0.970588 | 0.30303 | 0.090909 | 0.478261 | 0 | MPZL2 | 11 | 11q23.3 | 1.18E+08 | 1.18E+08 |
| MLL | 0.970588 | 0.333333 | 0.090909 | 0.478261 | 0 | MLL | 11 | 11q23.3 | 1.18E+08 | 1.18E+08 |
| TMEM25 | 0.970588 | 0.393939 | 0.090909 | 0.507246 | 0 | TMEM25 | 11 | 11q23.3 | 1.18E+08 | 1.18E+08 |
| C11orf60 | 0.970588 | 0.393939 | 0.090909 | 0.507246 | 0 | C11orf60 | 11 | 11q23.3 | 1.18E+08 | 1.18E+08 |
| ARCN1 | 0.970588 | 0.393939 | 0.090909 | 0.507246 | 0 | ARCN1 | 11 | 11q23.3 | 1.18E+08 | 1.18E+08 |
| PHLDB1 | 0.970588 | 0.393939 | 0.090909 | 0.507246 | 0 | PHLDB1 | 11 | 11q23.3 | 1.18E+08 | 1.18E+08 |
| TREH | 0.970588 | 0.393939 | 0.090909 | 0.507246 | 0 | TREH | 11 | 11q23.3 | 1.18E+08 | 1.18E+08 |
| CXCR5 | 0.970588 | 0.393939 | 0.090909 | 0.507246 | 0 | CXCR5 | 11 | 11q23.3 | 1.18E+08 | 1.18E+08 |
| BCL9L | 0.970588 | 0.393939 | 0.090909 | 0.507246 | 0 | BCL9L | 11 | 11q23.3 | 1.18E+08 | 1.18E+08 |
| THY1 | 0.970588 | 0.393939 | 0.090909 | 0.507246 | 0 | THY1 | 11 | 11q23.3 | 1.19E+08 | 1.19E+08 |
| PVRL1 | 0.970588 | 0.363636 | 0.090909 | 0.507246 | 0 | PVRL1 | 11 | 11q23.3 | 1.19E+08 | 1.19E+08 |
| GRIK4 | 0.970588 | 0.30303 | 0.090909 | 0.463768 | 0 | GRIK4 | 11 | 11q23.3 | 1.2E+08 | 1.2E+08 |
| OPCML | 0.970588 | 0.090909 | 0.090909 | 0.173913 | 0 | OPCML | 11 | 11q25 | 1.32E+08 | 1.33E+08 |
| ZNF33A | 0.970588 | 0.090909 | 0.090909 | 0.15942 | 0 | ZNF33A | 10 | 10p11.21 | 38339584 | 38389002 |
| LOC728640 | 0.970588 | 0.090909 | 0.242424 | 0 | 0.202899 | LOC728640 | 10 | 10q21.1 | 60244781 | 60147298 |
| LOC389705 | 0.970588 | 0.090909 | 0.030303 | 0 | 0.014493 | LOC389705 | 9 | 9p22.3 | 14983325 | 15009723 |
| CNTLN | 0.970588 | 0.090909 | 0.121212 | 0 | 0.057971 | CNTLN | 9 | 9p22.2 | 17125038 | 17292050 |
| SH3GL2 | 0.970588 | 0.090909 | 0.090909 | 0 | 0.043478 | SH3GL2 | 9 | 9p22.2 | 17568953 | 17787121 |
| IFNW1 | 0.970588 | 0.090909 | 0.121212 | 0 | 0.115942 | IFNW1 | 9 | 9p21.3 | 21130631 | 21332145 |
| IFNA21 | 0.970588 | 0.090909 | 0.121212 | 0 | 0.115942 | IFNA21 | 9 | 9p21.3 | 21155636 | 21156660 |
| IFNA13 | 0.970588 | 0.090909 | 0.090909 | 0 | 0.115942 | IFNA13 | 9 | 9p21.3 | 21357371 | 21358076 |
| C9orf135 | 0.970588 | 0.060606 | 0.090909 | 0.014493 | 0 | C9orf135 | 9 | 9q21.11 | 71625551 | 71710969 |
| MAMDC2 | 0.970588 | 0.090909 | 0.090909 | 0.014493 | 0 | MAMDC2 | 9 | 9921.11 | 71848317 | 72031709 |
| RHEB | 0.970588 | 0.30303 | 0.090909 | 0.434783 | 0 | RHEB | 7 | 7q36.1 | 1.51E+08 | 1.51E+08 |
| RHACTR1 | 0.970588 | 0.060606 | 0.090909 | 0.072464 | 0 | PHACTR1 | 6 | 6p24.1 | 12825819 | 13395508 |
| SNHG5 | 0.970588 | 0.090909 | 0.30303 | 0 | 0.333333 | SNHG5 | 6 | 6q14.3 | 86443444 | 86445171 |
| SNORD50A | 0.970588 | 0.090909 | 0.30303 | 0 | 0.333333 | SNORD50A | 6 | 6q14.3 | 86443731 | 86443806 |
| SNORD50B | 0.970588 | 0.090909 | 0.30303 | 0 | 0.333333 | SNORD50B | 6 | 6q14.3 | 86444026 | 86444097 |
| GJB7 | 0.970588 | 0.090909 | 0.242424 | 0 | 0.202899 | GJB7 | 6 | 6q15 | 88049416 | 88095716 |
| C6orf162 | 0.970588 | 0.090909 | 0.242424 | 0 | 0.202899 | C6orf162 | 6 | 6q15 | 88089025 | 88108763 |
| C6orf163 | 0.970588 | 0.090909 | 0.242424 | 0 | 0.202899 | C6orf163 | 6 | 6q15 | 88111290 | 88131900 |
| C6orf164 | 0.970588 | 0.090909 | 0.242424 | 0 | 0.202899 | C6orf164 | 6 | 6q15 | 88163561 | 88166179 |
| C6orf165 | 0.970588 | 0.090909 | 0.242424 | 0 | 0.202899 | C6orf165 | 6 | 6q15 | 88174409 | 88230911 |
| SLC35A1 | 0.970588 | 0.090909 | 0.242424 | 0 | 0.202899 | SLC35A1 | 6 | 6q15 | 88239362 | 88278771 |
| RARS2 | 0.970588 | 0.090909 | 0.242424 | 0 | 0.202899 | RARS2 | 6 | 6q15 | 88280816 | 88356455 |
| TAAR8 | 0.970588 | 0.090909 | 0.060606 | 0 | 0.043478 | TAAR8 | 6 | 6q23.2 | 1.33E+08 | 1.33E+08 |
| FYB | 0.970588 | 0.090909 | 0 | 0 | 0.014493 | FYB | 5 | 5p13.1 | 39141114 | 39255425 |
| UGT2B10 | 0.970588 | 0.090909 | 0.272727 | 0 | 0.289855 | UGT2B10 | 4 | 4q13.2 | 69716302 | 69732329 |
| UGT2A3 | 0.970588 | 0.090909 | 0.272727 | 0 | 0.289855 | UGT2A3 | 4 | 4q13.2 | 69828766 | 69852099 |
| MUC7 | 0.970588 | 0.090909 | 0.181818 | 0 | 0.202899 | MUC7 | 4 | 4q13.3 | 71330798 | 71383303 |
| ADAMTS3 | 0.970588 | 0.090909 | 0.181818 | 0 | 0.289855 | ADAMTS3 | 4 | 4q13.3 | 73365551 | 73653381 |
| AFP | 0.970588 | 0.090909 | 0.121212 | 0 | 0.101449 | AFP | 4 | 4q13.3 | 74520797 | 74540357 |
| AFM | 0.970588 | 0.090909 | 0.121212 | 0 | 0.101449 | AFM | 4 | 4q13.3 | 74566326 | 74588583 |
| RASSF6 | 0.970588 | 0.090909 | 0.121212 | 0 | 0.086957 | RASSF6 | 4 | 4q13.3 | 74657726 | 74704999 |
| CXCL6 | 0.970588 | 0.090909 | 0.151515 | 0 | 0.101449 | CXCL6 | 4 | 4q13.3 | 74921137 | 74923342 |
| PPBPL1 | 0.970588 | 0.090909 | 0.151515 | 0 | 0.101449 | PPBPL1 | 4 | 4q13.3 | 74932447 | 74933418 |
| PF4 | 0.970588 | 0.090909 | 0.151515 | 0 | 0.101449 | PF4 | 4 | 4q13.3 | 75065660 | 75066580 |
| PPBP | 0.970588 | 0.090909 | 0.151515 | 0 | 0.101449 | PPBP | 4 | 4q13.3 | 75071620 | 75072765 |
| CXCL3 | 0.970588 | 0.090909 | 0.151515 | 0 | 0.101449 | CXCL3 | 4 | 4q13.3 | 75121176 | 75123355 |

TABLE 3-continued

| Symbol | freq. use | freq. amp. case | freq. del. case | freq. amp. control | freq. del. control | Gene. Symbol | chromo- some | cytoband | Transcript. start | Transcript. end |
|---|---|---|---|---|---|---|---|---|---|---|
| CXCL2 | 0.970588 | 0.090909 | 0.151515 | 0 | 0.101449 | CXCL2 | 4 | 4q13.3 | 75181618 | 75183862 |
| MTHFD2L | 0.970588 | 0.090909 | 0.151515 | 0 | 0.115942 | MTHFD2L | 4 | 4q13.3 | 75242693 | 75387677 |
| AREG | 0.970588 | 0.090909 | 0.121212 | 0 | 0.115942 | AREG | 4 | 4q13.3 | 75699653 | 75709510 |
| PARM1 | 0.970588 | 0.090909 | 0.151515 | 0 | 0.086957 | PARM1 | 4 | 4q13.3 | 76077322 | 76194348 |
| FAM47E | 0.970588 | 0.090909 | 0.030303 | 0 | 0.014493 | FAM47E | 4 | 4q21.1 | 77391877 | 77423948 |
| ANKRD56 | 0.970588 | 0.090909 | 0.060606 | 0 | 0.014493 | ANKRD56 | 4 | 4q21.1 | 78035106 | 78038027 |
| 11-Sep | 0.970588 | 0.090909 | 0.030303 | 0 | 0.014493 | 11-Sep | 4 | 4q21.1 | 78089919 | 78178793 |
| ANXA3 | 0.970588 | 0.090909 | 0.060606 | 0 | 0.028986 | ANXA3 | 4 | 4q21.21 | 79691766 | 79750630 |
| BMP2K | 0.970588 | 0.090909 | 0.090909 | 0 | 0.028986 | BMP2K | 4 | 4q21.21 | 79916556 | 80019619 |
| PRDM8 | 0.970588 | 0.090909 | 0.121212 | 0 | 0.130435 | PRDM8 | 4 | 4q21.21 | 81325448 | 81344507 |
| CDS1 | 0.970588 | 0.090909 | 0.151515 | 0 | 0.043478 | CDS1 | 4 | 4q21.23 | 85723081 | 85791518 |
| WDFY3 | 0.970588 | 0.090909 | 0.121212 | 0 | 0.043478 | WDFY3 | 4 | 4q21.23 | 85809723 | 86106569 |
| MANBA | 0.970588 | 0.090909 | 0.030303 | 0 | 0.101449 | MANBA | 4 | 4q24 | 1.04E+08 | 1.04E+08 |
| TET2 | 0.970588 | 0.090909 | 0.151515 | 0 | 0.231884 | TET2 | 4 | 4q24 | 1.06E+08 | 1.06E+08 |
| HHIP | 0.970588 | 0.090909 | 0.090909 | 0 | 0.086957 | HHIP | 4 | 4q31.22 | 1.46E+08 | 1.46E+08 |
| CLSTN2 | 0.970588 | 0.090909 | 0.090909 | 0.26087 | 0 | CLSTN2 | 3 | 3q23 | 1.41E+08 | 1.42E+08 |
| CDC42EP3 | 0.970588 | 0 | 0.090909 | 0.072464 | 0 | CDC42EP3 | 2 | 2p22.2 | 37724247 | 37752831 |
| C2orf89 | 0.970588 | 0.151515 | 0.090909 | 0.318841 | 0 | C2orf89 | 2 | 2p11.2 | 84902307 | 84961764 |
| IL1RL2 | 0.970588 | 0.151515 | 0.090909 | 0.202899 | 0 | IL1RL2 | 2 | 2q12.1 | 1.02E+08 | 1.02E+08 |
| PKN2 | 0.970588 | 0.090909 | 0.212121 | 0 | 0.101449 | PKN2 | 1 | 1p22.2 | 88922510 | 89074527 |
| PHGDH | 0.970588 | 0.060606 | 0.090909 | 0.086957 | 0 | PHGDH | 1 | 1p12 | 1.2E+08 | 1.2E+08 |
| REG4 | 0.970588 | 0.030303 | 0.090909 | 0.086957 | 0 | REG4 | 1 | 1p12 | 1.2E+08 | 1.2E+08 |
| NBPF7 | 0.970588 | 0.030303 | 0.090909 | 0.086957 | 0 | NBPF7 | 1 | 1p12 | 1.2E+08 | 1.2E+08 |
| ADAM30 | 0.970588 | 0.030303 | 0.090909 | 0.086957 | 0 | ADAM30 | 1 | 1p12 | 1.2E+08 | 1.2E+08 |
| NOTCH2 | 0.970588 | 0.030303 | 0.090909 | 0.086957 | 0 | NOTCH2 | 1 | 1p12 | 1.2E+08 | 1.2E+08 |
| NENF | 0.970588 | 0.121212 | 0.090909 | 0.246377 | 0 | NENF | 1 | 1q32.3 | 2.11E+08 | 2.11E+08 |
| CNIH4 | 0.970588 | 0.181818 | 0.090909 | 0.304348 | 0 | CNIH4 | 1 | 1q42.11 | 2.23E+08 | 2.23E+08 |
| SNAP47 | 0.970588 | 0.272727 | 0.090909 | 0.42029 | 0 | SNAP47 | 1 | 1q42.13 | 2.26E+08 | 2.26E+08 |
| SIPA1L2 | 0.970588 | 0.212121 | 0.090909 | 0.275362 | 0 | SIPA1L2 | 1 | 1q42.2 | 2.31E+08 | 2.31E+08 |
| KIAA1383 | 0.970588 | 0.151515 | 0.090909 | 0.246377 | 0 | KIAA1383 | 1 | 1q42.2 | 2.31E+08 | 2.31E+08 |
| C1orf57 | 0.970588 | 0.151515 | 0.090909 | 0.231884 | 0 | C1orf57 | 1 | 1q42.2 | 2.31E+08 | 2.31E+08 |
| PCNXL2 | 0.970588 | 0.151515 | 0.090909 | 0.231884 | 0 | PCNXL2 | 1 | 1q42.2 | 2.31E+08 | 2.31E+08 |
| KIAA1804 | 0.970588 | 0.151515 | 0.090909 | 0.231884 | 0 | KIAA1804 | 1 | 1q42.2 | 2.32E+08 | 2.32E+08 |
| KCNK1 | 0.970588 | 0.121212 | 0.090909 | 0.217391 | 0 | KCNK1 | 1 | 1q42.2 | 2.32E+08 | 2.32E+08 |
| SLC35F3 | 0.970588 | 0.121212 | 0.090909 | 0.217391 | 0 | SLC35F3 | 1 | 1q42.2 | 2.32E+08 | 2.33E+08 |
| TARBP1 | 0.970588 | 0.242424 | 0.090909 | 0.246377 | 0 | TARBP1 | 1 | 1q42.2 | 2.33E+08 | 2.33E+08 |
| B3GALNT2 | 0.970588 | 0.242424 | 0.090909 | 0.275362 | 0 | B3GALNT2 | 1 | 1q42.3 | 2.34E+08 | 2.34E+08 |
| GNG4 | 0.970588 | 0.242424 | 0.090909 | 0.275362 | 0 | GNG4 | 1 | 1q42.3 | 2.34E+08 | 2.34E+08 |
| LYST | 0.970588 | 0.212121 | 0.090909 | 0.275362 | 0 | LYST | 1 | 1q42.3 | 2.34E+08 | 2.34E+08 |
| NID1 | 0.970588 | 0.242424 | 0.090909 | 0.26087 | 0 | NID1 | 1 | 1q42.3 | 2.34E+08 | 2.34E+08 |
| GPR137B | 0.970588 | 0.272727 | 0.090909 | 0.26087 | 0 | GPR137B | 1 | 1q42.3 | 2.34E+08 | 2.34E+08 |
| EDARADD | 0.970588 | 0.272727 | 0.090909 | 0.246377 | 0 | EDARADD | 1 | 1q43 | 2.35E+08 | 2.35E+08 |
| HEATR1 | 0.970588 | 0.242424 | 0.090909 | 0.188406 | 0 | HEATR1 | 1 | 1q43 | 2.35E+08 | 2.35E+08 |
| SMC5 | 0.019608 | 0.090909 | 0.090909 | 0.014493 | 0.014493 | SMC5 | 9 | 9q21.11 | 72063698 | 72159610 |
| TTTY8 | 0.009804 | 0.212121 | 0.121212 | 0.202899 | 0.014493 | TTTY8 | Y | Yp11.2 | 10138709 | 10141309 |
| TTTY8B | 0.009804 | 0.212121 | 0.121212 | 0.202899 | 0.014493 | TTTY8B | Y | Yp11.2 | 10138709 | 10141309 |
| TTTY7 | 0.009804 | 0.212121 | 0.121212 | 0.202899 | 0.014493 | TTTY7 | Y | Yp11.2 | 10154433 | 10162872 |
| TTTY7B | 0.009804 | 0.212121 | 0.121212 | 0.202899 | 0.014493 | TTTY7B | Y | Yp11.2 | 10154433 | 10162872 |
| LOC100101115 | 0.009804 | 0.212121 | 0.121212 | 0.202899 | 0.014493 | LOC100101115 | Y | Yp11.2 | 10165262 | 10168906 |
| TTTY21 | 0.009804 | 0.212121 | 0.121212 | 0.202899 | 0.014493 | TTTY21 | Y | Yp11.2 | 10165262 | 10168906 |
| TTTY22 | 0.009804 | 0.212121 | 0.121212 | 0.202899 | 0.014493 | TTTY22 | Y | Yp11.2 | 10248762 | 10260855 |
| C22orf25 | 0.009804 | 0.424242 | 0.121212 | 0.681159 | 0.014493 | C22orf25 | 22 | 22q11.21 | 18388631 | 18433448 |
| MIR185 | 0.009804 | 0.424242 | 0.121212 | 0.681159 | 0.014493 | MIR185 | 22 | 22q11.21 | 18400662 | 18400743 |
| DGCR8 | 0.009804 | 0.424242 | 0.090909 | 0.681159 | 0.014493 | DGCR8 | 22 | 22q11.21 | 18447834 | 18479401 |
| ZNF74 | 0.009804 | 0.393939 | 0.090909 | 0.666667 | 0.014493 | ZNF74 | 22 | 22q11.21 | 19078480 | 19092753 |
| SCARF2 | 0.009804 | 0.393939 | 0.090909 | 0.666667 | 0.014493 | SCARF2 | 22 | 22q11.21 | 19108875 | 19122147 |
| KLHL22 | 0.009804 | 0.393939 | 0.090909 | 0.666667 | 0.014493 | KLHL22 | 22 | 22q11.21 | 19125806 | 19180123 |
| MED15 | 0.009804 | 0.393939 | 0.090909 | 0.666667 | 0.014493 | MED15 | 22 | 22q11.21 | 19191886 | 19271920 |
| POM121L4P | 0.009804 | 0.393939 | 0.090909 | 0.666667 | 0.014493 | POM121L4P | 22 | 22q11.21 | 19373843 | 19376010 |
| TMEM191A | 0.009804 | 0.393939 | 0.090909 | 0.666667 | 0.014493 | TMEM191A | 22 | 22q11.21 | 19385402 | 19388892 |
| PI4KA | 0.009804 | 0.393939 | 0.090909 | 0.666667 | 0.014493 | PI4KA | 22 | 22q11.21 | 19391979 | 19418956 |
| SERPIND1 | 0.009804 | 0.363636 | 0.090909 | 0.637681 | 0.014493 | SERPIND1 | 22 | 22q11.21 | 19458383 | 19472009 |
| SNAP29 | 0.009804 | 0.333333 | 0.090909 | 0.623188 | 0.014493 | SNAP29 | 22 | 22q11.21 | 19543292 | 19575500 |
| CRKL | 0.009804 | 0.333333 | 0.090909 | 0.623188 | 0.014493 | CRKL | 22 | 22q11.21 | 19601714 | 19638039 |
| FLI39582 | 0.009804 | 0.363636 | 0.090909 | 0.623188 | 0.014493 | FLI39582 | 22 | 22q11.21 | 19686211 | 19694663 |
| MGC16703 | 0.009804 | 0.363636 | 0.090909 | 0.623188 | 0.014493 | MGC16703 | 22 | 22q11.21 | 19692496 | 19698577 |
| P2RX6 | 0.009804 | 0.363636 | 0.090909 | 0.623188 | 0.014493 | P2RX6 | 22 | 22q11.21 | 19699442 | 19712303 |
| SLC7A4 | 0.009804 | 0.363636 | 0.090909 | 0.623188 | 0.014493 | SLC7A4 | 22 | 22q11.21 | 19713007 | 19716848 |
| PRAME | 0.009804 | 0.30303 | 0.090909 | 0.623188 | 0.014493 | PRAME | 22 | 22q11.22 | 21220123 | 21231697 |
| LOC648691 | 0.009804 | 0.30303 | 0.090909 | 0.623188 | 0.014493 | LOC648691 | 22 | 22q11.22 | 21231756 | 21239007 |
| RTDR1 | 0.009804 | 0.333333 | 0.090909 | 0.652174 | 0.014493 | RTDR1 | 22 | 22q11.22 | 21731593 | 21814242 |
| GNAZ | 0.009804 | 0.333333 | 0.090909 | 0.652174 | 0.014493 | GNAZ | 22 | 22q11.22 | 21742669 | 21797222 |
| RAB36 | 0.009804 | 0.333333 | 0.090909 | 0.652174 | 0.014493 | RAB36 | 22 | 22q11.23 | 21817513 | 21836532 |
| BCR | 0.009804 | 0.333333 | 0.090909 | 0.652174 | 0.014493 | BCR | 22 | 22q11.23 | 21852552 | 21990225 |
| ZDHHC8P | 0.009804 | 0.333333 | 0.090909 | 0.652174 | 0.014493 | ZDHHC8P | 22 | 22q11.23 | 22062792 | 22074800 |
| IGLL1 | 0.009804 | 0.363636 | 0.090909 | 0.637681 | 0.014493 | IGLL1 | 22 | 22q11.23 | 22245313 | 22252496 |

TABLE 3-continued

| Symbol | freq. use | freq. amp. case | freq. del. case | freq. amp. control | freq. del. control | Gene. Symbol | chromo-some | cytoband | Transcript. start | Transcript. end |
|---|---|---|---|---|---|---|---|---|---|---|
| LOC91316 | 0.009804 | 0.30303 | 0.121212 | 0.623188 | 0.014493 | LOC91316 | 22 | 22q11.23 | 22310676 | 22389611 |
| ZNF70 | 0.009804 | 0.363636 | 0.090909 | 0.637681 | 0.014493 | ZNF70 | 22 | 22q11.23 | 22413772 | 22423280 |
| MMP11 | 0.009804 | 0.363636 | 0.090909 | 0.637681 | 0.014493 | MMP11 | 22 | 22q11.23 | 22445036 | 22456504 |
| SMARCB1 | 0.009804 | 0.363636 | 0.090909 | 0.637681 | 0.014493 | SMARCB1 | 22 | 22q11.23 | 22459150 | 22506706 |
| CABIN1 | 0.009804 | 0.363636 | 0.121212 | 0.637681 | 0.014493 | CABIN1 | 22 | 22q11.23 | 22737765 | 22904597 |
| GGT5 | 0.009804 | 0.30303 | 0.121212 | 0.637681 | 0.014493 | GGT5 | 22 | 22q11.23 | 22945622 | 22971111 |
| UPB1 | 0.009804 | 0.272727 | 0.121212 | 0.623188 | 0.014493 | UPB1 | 22 | 22q11.23 | 23221251 | 23252554 |
| C22orf13 | 0.009804 | 0.272727 | 0.121212 | 0.623188 | 0.014493 | C22orf13 | 22 | 22q11.23 | 23266408 | 23281276 |
| SNRPD3 | 0.009804 | 0.272727 | 0.121212 | 0.623188 | 0.014493 | SNRPD3 | 22 | 22q11.23 | 23281618 | 23298510 |
| GGT1 | 0.009804 | 0.272727 | 0.121212 | 0.623188 | 0.014493 | GGT1 | 22 | 22q11.23 | 23309718 | 23354973 |
| C22orf36 | 0.009804 | 0.30303 | 0.121212 | 0.623188 | 0.014493 | C22orf36 | 22 | 22q11.23 | 23311591 | 23319036 |
| LOC644165 | 0.009804 | 0.30303 | 0.121212 | 0.623188 | 0.014493 | LOC644165 | 22 | 22q11.23 | 23358882 | 23379327 |
| SGSM1 | 0.009804 | 0.333333 | 0.121212 | 0.652174 | 0.014493 | SGSM1 | 22 | 22q11.23 | 23532136 | 23652814 |
| KIAA1671 | 0.009804 | 0.333333 | 0.121212 | 0.652174 | 0.014493 | KIAA1671 | 22 | 22q11.23 | 23753941 | 23923414 |
| CRYBB2 | 0.009804 | 0.333333 | 0.121212 | 0.652174 | 0.014493 | CRYBB2 | 22 | 22q11.23 | 23945612 | 23957837 |
| ADRBK2 | 0.009804 | 0.30303 | 0.090909 | 0.623188 | 0.014493 | ADRBK2 | 22 | 22q11.23 | 24290861 | 24455259 |
| MYO18B | 0.009804 | 0.30303 | 0.090909 | 0.623188 | 0.014493 | MYO18B | 22 | 22q12.1 | 24468120 | 24757008 |
| MIR1302-1 | 0.009804 | 0.212121 | 0.121212 | 0.57971 | 0.014493 | MIR1302-1 | 22 | 22q12.1 | 24513501 | 25125580 |
| HPS4 | 0.009804 | 0.30303 | 0.090909 | 0.608696 | 0.014493 | HPS4 | 22 | 22q12.1 | 25177446 | 25209821 |
| SRRD | 0.009804 | 0.30303 | 0.090909 | 0.608696 | 0.014493 | SRRD | 22 | 22q12.1 | 25209850 | 25217905 |
| TFIP11 | 0.009804 | 0.30303 | 0.090909 | 0.608696 | 0.014493 | TFIP11 | 22 | 22q12.1 | 25217895 | 25238438 |
| TPST2 | 0.009804 | 0.30303 | 0.090909 | 0.57971 | 0.014493 | TPST2 | 22 | 22q12.1 | 25251714 | 25291371 |
| MIR548J | 0.009804 | 0.30303 | 0.090909 | 0.57971 | 0.014493 | MIR548J | 22 | 22q12.1 | 25281178 | 25281290 |
| CRYBA4 | 0.009804 | 0.30303 | 0.090909 | 0.565217 | 0.014493 | CRYBA4 | 22 | 22q12.1 | 25347928 | 25356637 |
| MIAT | 0.009804 | 0.272727 | 0.090909 | 0.550725 | 0.014493 | MIAT | 22 | 22q12.1 | 25383484 | 25402439 |
| RFPL3 | 0.009804 | 0.242424 | 0.090909 | 0.608696 | 0.014493 | RFPL3 | 22 | 22q12.3 | 31080872 | 31087149 |
| RFP135 | 0.009804 | 0.242424 | 0.090909 | 0.608696 | 0.014493 | RFPL3S | 22 | 22q12.3 | 31085893 | 31097064 |
| C22orf28 | 0.009804 | 0.242424 | 0.090909 | 0.608696 | 0.014493 | C22orf28 | 22 | 22q12.3 | 31113562 | 31138275 |
| SYN3 | 0.009804 | 0.242424 | 0.090909 | 0.608696 | 0.014493 | SYN3 | 22 | 22q12.3 | 31238540 | 31784358 |
| TIMP3 | 0.009804 | 0.242424 | 0.090909 | 0.608696 | 0.014493 | TIMP3 | 22 | 22q12.3 | 31526802 | 31589029 |
| LARGE | 0.009804 | 0.242424 | 0.090909 | 0.594203 | 0.014493 | LARGE | 22 | 22q12.3 | 31999062 | 32646417 |
| ISX | 0.009804 | 0.151515 | 0.090909 | 0.57971 | 0.014493 | ISX | 22 | 22q12.3 | 33792130 | 33813381 |
| TOM1 | 0.009804 | 0.30303 | 0.090909 | 0.608696 | 0.014493 | TOM1 | 22 | 22q12.3 | 34025268 | 34073986 |
| HMOX1 | 0.009804 | 0.333333 | 0.090909 | 0.623188 | 0.014493 | HMOX1 | 22 | 22q12.3 | 34107087 | 34120195 |
| MCM5 | 0.009804 | 0.333333 | 0.090909 | 0.623188 | 0.014493 | MCM5 | 22 | 22q12.3 | 34126116 | 34150496 |
| RASD2 | 0.009804 | 0.333333 | 0.090909 | 0.623188 | 0.014493 | RASD2 | 22 | 22q12.3 | 34267298 | 34279992 |
| MB | 0.009804 | 0.30303 | 0.090909 | 0.637681 | 0.014493 | MB | 22 | 22q12.3 | 34332757 | 34343331 |
| ABCC13 | 0.009804 | 0.090909 | 0.121212 | 0.014493 | 0.115942 | ABCC13 | 21 | 21q11.2 | 14567991 | 14595564 |
| KRTAP11-1 | 0.009804 | 0.121212 | 0.090909 | 0.101449 | 0.014493 | KRTAP11-1 | 21 | 21q22.11 | 31174835 | 31175746 |
| KRTAP19-8 | 0.009804 | 0.151515 | 0.090909 | 0.144928 | 0.014493 | KRTAP19-8 | 21 | 21q22.11 | 31332349 | 31332667 |
| CLDN14 | 0.009804 | 0.30303 | 0.090909 | 0.463768 | 0.014493 | CLDN14 | 21 | 21q22.13 | 36754790 | 36760596 |
| SMCHD1 | 0.009804 | 0.090909 | 0.090909 | 0.173913 | 0.014493 | SMCHD1 | 18 | 18p11.32 | 2645886 | 2795916 |
| EMILIN2 | 0.009804 | 0.151515 | 0.090909 | 0.202899 | 0.014493 | EMILIN2 | 18 | 18p11.32 | 2837028 | 2904091 |
| LPIN2 | 0.009804 | 0.212121 | 0.090909 | 0.188406 | 0.014493 | LPIN2 | 18 | 18p11.32 | 2906992 | 3001946 |
| LOC727896 | 0.009804 | 0.060606 | 0.090909 | 0.15942 | 0.014493 | LOC727896 | 18 | 18p11.31 | 2933215 | 2936622 |
| TGIF1 | 0.009804 | 0.181818 | 0.090909 | 0.188406 | 0.014493 | TGIF1 | 18 | 18p11.31 | 3402072 | 3448407 |
| DLGAP1 | 0.009804 | 0.151515 | 0.090909 | 0.188406 | 0.014493 | DLGAP1 | 18 | 18p11.31 | 3488837 | 3835297 |
| FLJ35776 | 0.009804 | 0.151515 | 0.090909 | 0.188406 | 0.014493 | FLJ35776 | 18 | 18p11.31 | 3584112 | 3587377 |
| EPB41L3 | 0.009804 | 0.060606 | 0.121212 | 0.086957 | 0.014493 | EPB41L3 | 18 | 18p11.31 | 5382388 | 5533987 |
| L3MBTL4 | 0.009804 | 0.030303 | 0.121212 | 0.072464 | 0.014493 | L3MBTL4 | 18 | 18p11.31 | 5944705 | 6404911 |
| ARHGAP28 | 0.009804 | 0.090909 | 0.090909 | 0.144928 | 0.014493 | ARHGAP28 | 18 | 18p11.31 | 6824484 | 6905713 |
| LAMA1 | 0.009804 | 0.121212 | 0.090909 | 0.173913 | 0.014493 | LAMA1 | 18 | 18p11.31 | 6931886 | 7107814 |
| LRRC30 | 0.009804 | 0.121212 | 0.090909 | 0.173913 | 0.014493 | LRRC30 | 18 | 18p11.23 | 7221137 | 7222043 |
| ANKRD12 | 0.009804 | 0.242424 | 0.090909 | 0.246377 | 0.014493 | ANKRD12 | 18 | 18p11.22 | 9126758 | 9275207 |
| RAB31 | 0.009804 | 0.272727 | 0.090909 | 0.26087 | 0.014493 | RAB31 | 18 | 18p11.22 | 9698228 | 9852554 |
| ROCK1 | 0.009804 | 0.151515 | 0.121212 | 0.130435 | 0.014493 | ROCK1 | 18 | 18q11.1 | 16783701 | 16945811 |
| GREB1L | 0.009804 | 0.151515 | 0.121212 | 0.173913 | 0.014493 | GREB1L | 18 | 18q11.1 | 17076201 | 17356788 |
| ESCO1 | 0.009804 | 0.151515 | 0.121212 | 0.173913 | 0.014493 | ESCO1 | 18 | 18q11.2 | 17363260 | 17434692 |
| SNRPD1 | 0.009804 | 0.151515 | 0.121212 | 0.173913 | 0.014493 | SNRPD1 | 18 | 18q11.2 | 17446258 | 17464207 |
| ABHD3 | 0.009804 | 0.151515 | 0.121212 | 0.173913 | 0.014493 | ABHD3 | 18 | 18q11.2 | 17484856 | 17538765 |
| MIR320C1 | 0.009804 | 0.151515 | 0.121212 | 0.173913 | 0.014493 | MIR320C1 | 18 | 18q11.2 | 17517469 | 17517557 |
| MIB1 | 0.009804 | 0.151515 | 0.121212 | 0.173913 | 0.014493 | MIB1 | 18 | 18q11.2 | 17575543 | 17704911 |
| CTAGE1 | 0.009804 | 0.030303 | 0.121212 | 0.130435 | 0.014493 | CTAGE1 | 18 | 18q11.2 | 18247562 | 18251877 |
| EPN2 | 0.009804 | 0.393939 | 0.090909 | 0.594203 | 0.014493 | EPN2 | 17 | 17p11.2 | 19081283 | 19180622 |
| B9D1 | 0.009804 | 0.393939 | 0.090909 | 0.594203 | 0.014493 | B9D1 | 17 | 17p11.2 | 19187076 | 19206640 |
| MIR1180 | 0.009804 | 0.393939 | 0.090909 | 0.594203 | 0.014493 | MIR1180 | 17 | 17p11.2 | 19188412 | 19188481 |
| MAPK7 | 0.009804 | 0.393939 | 0.090909 | 0.594203 | 0.014493 | MAPK7 | 17 | 17p11.2 | 19221627 | 19227450 |
| MFAP4 | 0.009804 | 0.393939 | 0.090909 | 0.594203 | 0.014493 | MFAP4 | 17 | 17p11.2 | 19227348 | 19231087 |
| RNF112 | 0.009804 | 0.393939 | 0.090909 | 0.594203 | 0.014493 | RNF112 | 17 | 17p11.2 | 19255084 | 19261180 |
| PCTP | 0.009804 | 0.030303 | 0.090909 | 0.217391 | 0.014493 | PCTP | 17 | 17q22 | 51183355 | 51209748 |
| EIF3CL | 0.009804 | 0.424242 | 0.090909 | 0.565217 | 0.014493 | EIF3CL | 16 | 16p11.2 | 28298401 | 28322664 |
| EIF3C | 0.009804 | 0.424242 | 0.090909 | 0.565217 | 0.014493 | EIF3C | 16 | 16p11.2 | 28298404 | 28322667 |
| CLN3 | 0.009804 | 0.424242 | 0.090909 | 0.565217 | 0.014493 | CLN3 | 16 | 16p11.2 | 28396101 | 28410905 |
| APOB48R | 0.009804 | 0.424242 | 0.090909 | 0.565217 | 0.014493 | APOB48R | 16 | 16p11.2 | 28413494 | 28417784 |
| IL27 | 0.009804 | 0.424242 | 0.090909 | 0.565217 | 0.014493 | IL27 | 16 | 16p11.2 | 28418184 | 28425657 |
| NUPR1 | 0.009804 | 0.424242 | 0.090909 | 0.565217 | 0.014493 | NUPR1 | 16 | 16p11.2 | 28456163 | 28457997 |

TABLE 3-continued

| Symbol | freq. use | freq. amp. case | freq. del. case | freq. amp. control | freq. del. control | Gene. Symbol | chromo-some | cytoband | Transcript. start | Transcript. end |
|---|---|---|---|---|---|---|---|---|---|---|
| CCDC101 | 0.009804 | 0.424242 | 0.090909 | 0.565217 | 0.014493 | CCDC101 | 16 | 16q11.2 | 28472750 | 28510612 |
| ATXN2L | 0.009804 | 0.424242 | 0.090909 | 0.565217 | 0.014493 | ATXN2L | 16 | 16p11.2 | 28741915 | 28756060 |
| SH2B1 | 0.009804 | 0.424242 | 0.090909 | 0.565217 | 0.014493 | SH2B1 | 16 | 16p11.2 | 28782579 | 28793035 |
| ATP2A1 | 0.009804 | 0.424242 | 0.090909 | 0.565217 | 0.014493 | ATP2A1 | 16 | 16p11.2 | 28797310 | 28823332 |
| SPNS1 | 0.009804 | 0.424242 | 0.090909 | 0.565217 | 0.014493 | SPNS1 | 16 | 16p11.2 | 28893597 | 28903370 |
| LAT | 0.009804 | 0.424242 | 0.090909 | 0.565217 | 0.014493 | LAT | 16 | 16p11.2 | 28903648 | 28909606 |
| RUNDC2C | 0.009804 | 0.424242 | 0.090909 | 0.565217 | 0.014493 | RUNDC2C | 16 | 16p11.2 | 29210042 | 29293099 |
| SLC7A5P1 | 0.009804 | 0.424242 | 0.090909 | 0.565217 | 0.014493 | SLC7A5P1 | 16 | 16p11.2 | 29531925 | 29532540 |
| SPN | 0.009804 | 0.424242 | 0.090909 | 0.565217 | 0.014493 | SPN | 16 | 16p11.2 | 29581801 | 29589325 |
| QPRT | 0.009804 | 0.424242 | 0.090909 | 0.565217 | 0.014493 | QPRT | 16 | 16p11.2 | 29597942 | 29616816 |
| C16orf54 | 0.009804 | 0.424242 | 0.090909 | 0.565217 | 0.014493 | C16orf54 | 16 | 16p11.2 | 29661287 | 29664842 |
| MAZ | 0.009804 | 0.424242 | 0.090909 | 0.565217 | 0.014493 | MAZ | 16 | 16p11.2 | 29725356 | 29730006 |
| PRRT2 | 0.009804 | 0.424242 | 0.090909 | 0.565217 | 0.014493 | PRRT2 | 16 | 16p11.2 | 29730910 | 29734704 |
| C16orf53 | 0.009804 | 0.424242 | 0.090909 | 0.565217 | 0.014493 | C16orf53 | 16 | 16p11.2 | 29735029 | 29741318 |
| MVP | 0.009804 | 0.424242 | 0.090909 | 0.565217 | 0.014493 | MVP | 16 | 16p11.2 | 29739288 | 29766843 |
| CDIPT | 0.009804 | 0.424242 | 0.090909 | 0.565217 | 0.014493 | CDIPT | 16 | 16p11.2 | 29777179 | 29782080 |
| LOC440356 | 0.009804 | 0.424242 | 0.090909 | 0.565217 | 0.014493 | LOC440356 | 16 | 16p11.2 | 29782505 | 29786876 |
| SEZ6L2 | 0.009804 | 0.424242 | 0.090909 | 0.565217 | 0.014493 | SEZ6L2 | 16 | 16p11.2 | 29789981 | 29818082 |
| ASPHD1 | 0.009804 | 0.424242 | 0.090909 | 0.565217 | 0.014493 | ASPHD1 | 16 | 16p11.2 | 29819648 | 29824879 |
| KCTD13 | 0.009804 | 0.424242 | 0.090909 | 0.565217 | 0.014493 | KCTD13 | 16 | 16p11.2 | 29825162 | 29845047 |
| TMEM219 | 0.009804 | 0.424242 | 0.090909 | 0.565217 | 0.014493 | TMEM219 | 16 | 16p11.2 | 29880852 | 29891875 |
| TAOK2 | 0.009804 | 0.424242 | 0.090909 | 0.565217 | 0.014493 | TAOK2 | 16 | 16p11.2 | 29892723 | 29911083 |
| C16orf92 | 0.009804 | 0.424242 | 0.090909 | 0.565217 | 0.014493 | C16orf92 | 16 | 16p11.2 | 29942156 | 29943525 |
| FAM57B | 0.009804 | 0.424242 | 0.090909 | 0.565217 | 0.014493 | FAM57B | 16 | 16p11.2 | 29943249 | 29949688 |
| ALDOA | 0.009804 | 0.424242 | 0.090909 | 0.565217 | 0.014493 | ALDOA | 16 | 16p11.2 | 29971992 | 29989237 |
| ITGAM | 0.009804 | 0.393939 | 0.090909 | 0.565217 | 0.014493 | ITGAM | 16 | 16p11.2 | 31178789 | 31251715 |
| RASGRP1 | 0.009804 | 0 | 0.121212 | 0.057971 | 0.014493 | RASGRP1 | 15 | 15q14 | 36567594 | 36644300 |
| C15orf53 | 0.009804 | 0 | 0.121212 | 0.057971 | 0.014493 | C15orf53 | 15 | 15q14 | 36776091 | 36779532 |
| THBS1 | 0.009804 | 0.030303 | 0.121212 | 0.086957 | 0.014493 | THBS1 | 15 | 15q14 | 37660572 | 37676961 |
| SCG3 | 0.009804 | 0 | 0.090909 | 0.115942 | 0.014493 | SCG3 | 15 | 15q21.2 | 49760842 | 49800515 |
| TMOD3 | 0.009804 | 0.030303 | 0.090909 | 0.130435 | 0.014493 | TMOD3 | 15 | 15q21.2 | 49909181 | 49989139 |
| RAB27A | 0.009804 | 0.030303 | 0.121212 | 0.057971 | 0.014493 | RAB27A | 15 | 15q21.3 | 53283092 | 53349878 |
| STXBP6 | 0.009804 | 0.090909 | 0.121212 | 0.014493 | 0.130435 | STXBP6 | 14 | 14q12 | 24351144 | 24588936 |
| HEATR5A | 0.009804 | 0.121212 | 0 | 0.014493 | 0.043478 | HEATR5A | 14 | 14q12 | 30830745 | 30927933 |
| C14orf126 | 0.009804 | 0.121212 | 0 | 0.014493 | 0.043478 | C14orf126 | 14 | 14q12 | 30984994 | 30996432 |
| NUBPL | 0.009804 | 0.121212 | 0 | 0.014493 | 0.043478 | NUBPL | 14 | 14q12 | 31100342 | 31400181 |
| NPAS3 | 0.009804 | 0.181818 | 0.090909 | 0.014493 | 0.101449 | NPAS3 | 14 | 14q13.1 | 32478210 | 33343133 |
| SSTR1 | 0.009804 | 0.090909 | 0.151515 | 0.014493 | 0.130435 | SSTR1 | 14 | 14q21.1 | 37746955 | 37754704 |
| MAP4K5 | 0.009804 | 0.181818 | 0 | 0.014493 | 0.028986 | MAP4K5 | 14 | 14q22.1 | 49954993 | 50069127 |
| ATL1 | 0.009804 | 0.181818 | 0 | 0.014493 | 0.028986 | ATL1 | 14 | 14q22.1 | 50069550 | 50169535 |
| FRMD6 | 0.009804 | 0.030303 | 0.090909 | 0 | 0.014493 | FRMD6 | 14 | 14q22.1 | 51025605 | 51267195 |
| DDHD1 | 0.009804 | 0.090909 | 0.030303 | 0.014493 | 0 | DDHD1 | 14 | 14q22.2 | 52573210 | 52689797 |
| PELI2 | 0.009804 | 0.030303 | 0.090909 | 0 | 0.014493 | PELI2 | 14 | 14q22.3 | 55654846 | 55837785 |
| DAAM1 | 0.009804 | 0.060606 | 0.151515 | 0.014493 | 0.014493 | DAAM1 | 14 | 14q23.1 | 58725152 | 58906225 |
| JKAMP | 0.009804 | 0.060606 | 0.151515 | 0.028986 | 0.014493 | JKAMP | 14 | 14q23.1 | 59020914 | 59041835 |
| C14orf38 | 0.009804 | 0.060606 | 0.151515 | 0.028986 | 0.014493 | C14orf38 | 14 | 14q23.1 | 59041539 | 59113903 |
| RHOJ | 0.009804 | 0.121212 | 0.121212 | 0.101449 | 0.014493 | RHOJ | 14 | 14q23.2 | 62740898 | 62828313 |
| GPHB5 | 0.009804 | 0.121212 | 0.121212 | 0.101449 | 0.014493 | GPHB5 | 14 | 14q23.2 | 62849395 | 62854317 |
| PPP2R5E | 0.009804 | 0.151515 | 0.090909 | 0.101449 | 0.014493 | PPP2R5E | 14 | 14q23.2 | 62911108 | 63079833 |
| SMOC1 | 0.009804 | 0.121212 | 0.242424 | 0.275362 | 0.014493 | SMOC1 | 14 | 14q24.2 | 69415896 | 69568273 |
| COX16 | 0.009804 | 0.121212 | 0.151515 | 0.231884 | 0.014493 | COX16 | 14 | 14q24.2 | 69861552 | 69896198 |
| HEATR4 | 0.009804 | 0.363636 | 0.121212 | 0.42029 | 0.014493 | HEATR4 | 14 | 14q24.3 | 73014945 | 73095405 |
| DNAL1 | 0.009804 | 0.363636 | 0.121212 | 0.434783 | 0.014493 | DNAL1 | 14 | 14q24.3 | 73181331 | 73238403 |
| PNMA1 | 0.009804 | 0.363636 | 0.121212 | 0.434783 | 0.014493 | PNMA1 | 14 | 14q24.3 | 73248239 | 73250882 |
| C14orf43 | 0.009804 | 0.363636 | 0.121212 | 0.434783 | 0.014493 | C14orf43 | 14 | 14q24.3 | 73251578 | 73323650 |
| PTGR2 | 0.009804 | 0.333333 | 0.121212 | 0.434783 | 0.014493 | PTGR2 | 14 | 14q24.3 | 73388287 | 73421920 |
| ZNF410 | 0.009804 | 0.333333 | 0.121212 | 0.434783 | 0.014493 | ZNF410 | 14 | 14q24.3 | 73423339 | 73468557 |
| LIN52 | 0.009804 | 0.333333 | 0.121212 | 0.376812 | 0.014493 | LIN52 | 14 | 14q24.3 | 73621409 | 73736871 |
| TTLL5 | 0.009804 | 0.272727 | 0.121212 | 0.304348 | 0.014493 | TTLL5 | 14 | 14q24.3 | 75197374 | 75491076 |
| STON2 | 0.009804 | 0.121212 | 0.121212 | 0.043478 | 0.014493 | STON2 | 14 | 14q31.1 | 80806662 | 80934681 |
| GJA3 | 0.009804 | 0.272727 | 0.121212 | 0.304348 | 0.014493 | GJA3 | 13 | 13q12.11 | 19610395 | 19633184 |
| GJB2 | 0.009804 | 0.272727 | 0.121212 | 0.304348 | 0.014493 | GJB2 | 13 | 13q12.11 | 19659606 | 19665115 |
| GJB6 | 0.009804 | 0.272727 | 0.121212 | 0.304348 | 0.014493 | GJB6 | 13 | 13q12.11 | 19694101 | 19704535 |
| CRYL1 | 0.009804 | 0.272727 | 0.121212 | 0.304348 | 0.014493 | CRYL1 | 13 | 13q12.11 | 19875806 | 19998013 |
| IFT88 | 0.009804 | 0.242424 | 0.121212 | 0.289855 | 0.014493 | IFT88 | 13 | 13q12.11 | 20039208 | 20163577 |
| IL17D | 0.009804 | 0.272727 | 0.121212 | 0.289855 | 0.014493 | IL17D | 13 | 13q12.11 | 20175482 | 20195238 |
| N6AMT2 | 0.009804 | 0.272727 | 0.121212 | 0.289855 | 0.014493 | N6AMT2 | 13 | 13q12.11 | 20201073 | 20246058 |
| LATS2 | 0.009804 | 0.212121 | 0.121212 | 0.246377 | 0.014493 | LATS2 | 13 | 13q12.11 | 20445176 | 20533723 |
| SAP18 | 0.009804 | 0.212121 | 0.121212 | 0.217391 | 0.014493 | SAP18 | 13 | 13q12.11 | 20612653 | 20621224 |
| SKA3 | 0.009804 | 0.212121 | 0.121212 | 0.217391 | 0.014493 | SKA3 | 13 | 13q12.11 | 20625735 | 20648742 |
| ZDHHC20 | 0.009804 | 0.181818 | 0.121212 | 0.173913 | 0.014493 | ZDHHC20 | 13 | 13q12.11 | 20848508 | 20931644 |
| NUPL1 | 0.009804 | 0.121212 | 0.181818 | 0.304348 | 0.014493 | NUPL1 | 13 | 13q12.13 | 24773666 | 24814562 |
| B3GALTL | 0.009804 | 0.121212 | 0.090909 | 0.217391 | 0.014493 | B3GALTL | 13 | 13q12.3 | 30672112 | 30804412 |
| TPP2 | 0.009804 | 0.090909 | 0.333333 | 0.014493 | 0.086957 | TPP2 | 13 | 13q33.1 | 1.02E+08 | 1.02E+08 |
| COL4A1 | 0.009804 | 0.272727 | 0.181818 | 0.347826 | 0.014493 | COL4A1 | 13 | 13q34 | 1.1E+08 | 1.1E+08 |
| COL4A2 | 0.009804 | 0.272727 | 0.181818 | 0.347826 | 0.014493 | COL4A2 | 13 | 13q34 | 1.1E+08 | 1.1E+08 |

TABLE 3-continued

| Symbol | freq. use | freq. amp. case | freq. del. case | freq. amp. control | freq. del. control | Gene. Symbol | chromo-some | cytoband | Transcript. start | Transcript. end |
|---|---|---|---|---|---|---|---|---|---|---|
| RAB20 | 0.009804 | 0.333333 | 0.181818 | 0.376812 | 0.014493 | RAB20 | 13 | 13q34 | 1.1E+08 | 1.1E+08 |
| CARKD | 0.009804 | 0.333333 | 0.181818 | 0.405797 | 0.014493 | CARKD | 13 | 13q34 | 1.1E+08 | 1.1E+08 |
| CARS2 | 0.009804 | 0.333333 | 0.181818 | 0.405797 | 0.014493 | CARS2 | 13 | 13q34 | 1.1E+08 | 1.1E+08 |
| C13orf29 | 0.009804 | 0.30303 | 0.181818 | 0.391304 | 0.014493 | C13orf29 | 13 | 13q34 | 1.1E+08 | 1.1E+08 |
| ARHGEF7 | 0.009804 | 0.333333 | 0.181818 | 0.453768 | 0.014493 | ARHGEF7 | 13 | 13q34 | 1.11E+08 | 1.11E+08 |
| LEMD3 | 0.009804 | 0.030303 | 0.121212 | 0.014493 | 0.014493 | LEMD3 | 12 | 12q14.3 | 63849618 | 63928407 |
| PTPRB | 0.009804 | 0.090909 | 0.060606 | 0.014493 | 0.028986 | PTPRB | 12 | 12q15 | 69196899 | 69317487 |
| ZFC3H1 | 0.009804 | 0.090909 | 0.121212 | 0.014493 | 0.144928 | ZFC3H1 | 12 | 12q21.1 | 70289649 | 70344017 |
| KCNC2 | 0.009804 | 0.121212 | 0.242424 | 0.014493 | 0.289855 | KCNC2 | 12 | 12q21.1 | 73720163 | 73889779 |
| CAPS2 | 0.009804 | 0.121212 | 0.242424 | 0.014493 | 0.246377 | CAPS2 | 12 | 12q21.1 | 73956026 | 74010104 |
| GLIPR1L2 | 0.009804 | 0.121212 | 0.242424 | 0.014493 | 0.246377 | GLIPR1L2 | 12 | 12q21.1 | 74071156 | 74104088 |
| NAP1L1 | 0.009804 | 0.151515 | 0.060606 | 0.014493 | 0.101449 | NAP1L1 | 12 | 12q21.2 | 74724939 | 74765006 |
| NAV3 | 0.009804 | 0.090909 | 0.212121 | 0.014493 | 0.318841 | NAV3 | 12 | 12q21.2 | 76749200 | 77130922 |
| SYT1 | 0.009804 | 0.090909 | 0.212121 | 0.014493 | 0.304348 | SYT1 | 12 | 12q21.2 | 77781904 | 78369919 |
| LIN7A | 0.009804 | 0.090909 | 0.212121 | 0.014493 | 0.289855 | LIN7A | 12 | 12q21.31 | 79715302 | 79855826 |
| MIR618 | 0.009804 | 0.090909 | 0.181818 | 0.014493 | 0.289855 | MIR618 | 12 | 12q21.31 | 79853647 | 79853744 |
| PPFIA2 | 0.009804 | 0.090909 | 0.242424 | 0.014493 | 0.318841 | PPFIA2 | 12 | 12q21.31 | 80177487 | 80677241 |
| RASSF9 | 0.009804 | 0.090909 | 0.181818 | 0.014493 | 0.333333 | RASSF9 | 12 | 12q21.31 | 84722462 | 84754450 |
| LUM | 0.009804 | 0.121212 | 0.212121 | 0.014493 | 0.231884 | LUM | 12 | 12q21.33 | 90021363 | 90029674 |
| BTG1 | 0.009804 | 0.121212 | 0.090909 | 0.014493 | 0.028986 | BTG1 | 12 | 12q21.33 | 91058187 | 91063805 |
| PLEKHG7 | 0.009804 | 0.121212 | 0.090909 | 0.014493 | 0.028986 | PLEKHG7 | 12 | 12q22 | 91654396 | 91690000 |
| PLXNC1 | 0.009804 | 0.151515 | 0.090909 | 0.115942 | 0.014493 | PLXNC1 | 12 | 12q22 | 93066630 | 93223357 |
| SRRM4 | 0.009804 | 0.121212 | 0.090909 | 0.42029 | 0.014493 | SRRM4 | 12 | 12q24.23 | 1.18E+08 | 1.18E+08 |
| OR52B4 | 0.009804 | 0.030303 | 0.090909 | 0.144928 | 0.014493 | OR52B4 | 11 | 11p15.4 | 4345157 | 4346102 |
| OR52K2 | 0.009804 | 0 | 0.090909 | 0.130435 | 0.014493 | OR52K2 | 11 | 11p15.4 | 4427146 | 4428091 |
| OR52N2 | 0.009804 | 0.060606 | 0.090909 | 0.072464 | 0.014493 | OR52N2 | 11 | 11p15.4 | 5798142 | 5799108 |
| OR2AG2 | 0.009804 | 0.030303 | 0.121212 | 0.057971 | 0.014493 | OR2AG2 | 11 | 11p15.4 | 6745814 | 6746765 |
| PDHX | 0.009804 | 0.030303 | 0.151515 | 0.057971 | 0.014493 | PDHX | 11 | 11p13 | 34894253 | 34974251 |
| SLC1A2 | 0.009804 | 0.090909 | 0.090909 | 0.043478 | 0.014493 | SLC1A2 | 11 | 11p13 | 35229328 | 35397682 |
| PAMR1 | 0.009804 | 0.030303 | 0.151515 | 0.028986 | 0.014493 | PAMR1 | 11 | 11p13 | 35409952 | 35503753 |
| FJX1 | 0.009804 | 0.030303 | 0.181818 | 0.028986 | 0.014493 | FJX1 | 11 | 11p13 | 35596311 | 35598996 |
| TRIM44 | 0.009804 | 0.030303 | 0.181818 | 0.028986 | 0.014493 | TRIM44 | 11 | 11p13 | 35640929 | 35787507 |
| TRAF6 | 0.009804 | 0.121212 | 0.090909 | 0.101449 | 0.014493 | TRAF6 | 11 | 11p12 | 36467299 | 36488399 |
| PRCP | 0.009804 | 0.121212 | 0.090909 | 0.028986 | 0.014493 | PRCP | 11 | 11q14.1 | 82213057 | 82289206 |
| C11orf82 | 0.009804 | 0.121212 | 0.090909 | 0.028986 | 0.014493 | C11orf82 | 11 | 11q14.1 | 82290385 | 82323348 |
| CCDC90B | 0.009804 | 0.090909 | 0.151515 | 0.014493 | 0.057971 | CCDC90B | 11 | 11q14.1 | 82650150 | 82675026 |
| C11orf75 | 0.009804 | 0.090909 | 0.121212 | 0.130435 | 0.014493 | C11orf75 | 11 | 11q21 | 92851287 | 92916195 |
| PANX1 | 0.009804 | 0.090909 | 0.151515 | 0.043478 | 0.014493 | PANX1 | 11 | 11q21 | 93501742 | 93554746 |
| GPR83 | 0.009804 | 0.121212 | 0.090909 | 0.043478 | 0.014493 | GPR83 | 11 | 11q21 | 93750125 | 93774234 |
| MAML2 | 0.009804 | 0.090909 | 0.121212 | 0.014493 | 0.086957 | MAML2 | 11 | 11q21 | 95351088 | 95715993 |
| DYNC2H1 | 0.009804 | 0.090909 | 0.151515 | 0.014493 | 0.188406 | DYNC2H1 | 11 | 11q22.3 | 1.02E+08 | 1.03E+08 |
| DDI1 | 0.009804 | 0.151515 | 0.151515 | 0.014493 | 0.144928 | DDI1 | 11 | 11q22.3 | 1.03E+08 | 1.03E+08 |
| ZW10 | 0.009804 | 0.212121 | 0.121212 | 0.275362 | 0.014493 | ZW10 | 11 | 11q23.2 | 1.13E+08 | 1.13E+08 |
| AMICA1 | 0.009804 | 0.242424 | 0.151515 | 0.449275 | 0.014493 | AMICA1 | 11 | 11q23.3 | 1.18E+08 | 1.18E+08 |
| CD3G | 0.009804 | 0.333333 | 0.090909 | 0.478261 | 0.014493 | CD3G | 11 | 11q23.3 | 1.18E+08 | 1.18E+08 |
| UBE4A | 0.009804 | 0.333333 | 0.090909 | 0.478261 | 0.014493 | UBE4A | 11 | 11q23.3 | 1.18E+08 | 1.18E+08 |
| DDX6 | 0.009804 | 0.393939 | 0.090909 | 0.492754 | 0.014493 | DDX6 | 11 | 11q23.3 | 1.18E+08 | 1.18E+08 |
| LOC100216001 | 0.009804 | 0.030303 | 0.090909 | 0.15942 | 0.014493 | LOC100216001 | 10 | 10p15.1 | 4682378 | 4710263 |
| LOC338588 | 0.009804 | 0.030303 | 0.090909 | 0.15942 | 0.014493 | LOC338588 | 10 | 10p15.1 | 4688348 | 4694605 |
| tAKR | 0.009804 | 0 | 0.090909 | 0.188406 | 0.014493 | tAKR | 10 | 10p15.1 | 4903861 | 4948466 |
| C10orf18 | 0.009804 | 0.151515 | 0.090909 | 0.304348 | 0.014493 | C10orf18 | 10 | 10p15.1 | 5766807 | 5846950 |
| GDI2 | 0.009804 | 0.242424 | 0.090909 | 0.318841 | 0.014493 | GDI2 | 10 | 10p15.1 | 5847192 | 5895519 |
| ARHGAP12 | 0.009804 | 0.090909 | 0.090909 | 0.086957 | 0.014493 | ARHGAP12 | 10 | 10p11.22 | 32135231 | 32257777 |
| LOC100129055 | 0.009804 | 0 | 0.151515 | 0.115942 | 0.014493 | LOC100129055 | 10 | 10p11.21 | 38504605 | 38543279 |
| HSD17B7P2 | 0.009804 | 0 | 0.151515 | 0.115942 | 0.014493 | HSD17B7P2 | 10 | 10p11.21 | 38685314 | 38707440 |
| TFAM | 0.009804 | 0.090909 | 0.181818 | 0.014493 | 0.231884 | TFAM | 10 | 10q21.1 | 59815182 | 59825904 |
| BICC1 | 0.009804 | 0.090909 | 0.242424 | 0.014493 | 0.231884 | BICC1 | 10 | 10q21.1 | 59942910 | 60258852 |
| PGM5 | 0.009804 | 0.060606 | 0.121212 | 0.057971 | 0.014493 | PGM5 | 9 | 9q13 | 70161635 | 70335798 |
| LOC440173 | 0.009804 | 0.121212 | 0.090909 | 0.318841 | 0.014493 | LOC440173 | 9 | 9q21.33 | 88813187 | 88846862 |
| SLC7A2 | 0.009804 | 0.090909 | 0.393939 | 0.014493 | 0.333333 | SLC7A2 | 8 | 8p22 | 17398975 | 17472349 |
| MTUS1 | 0.009804 | 0.090909 | 0.393939 | 0.014493 | 0.318841 | MTUS1 | 8 | 8p22 | 17545584 | 17702707 |
| FGL1 | 0.009804 | 0.121212 | 0.393939 | 0.014493 | 0.333333 | FGL1 | 8 | 8p22 | 17766180 | 17797328 |
| TMEM106B | 0.009804 | 0.090909 | 0.151515 | 0.014493 | 0.173913 | TMEM106B | 7 | 7p21.3 | 12217373 | 12243415 |
| MEOX2 | 0.009804 | 0.121212 | 0.030303 | 0.014493 | 0.231884 | MEOX2 | 7 | 7p21.1 | 15617362 | 15692834 |
| AGR3 | 0.009804 | 0.121212 | 0.030303 | 0.014493 | 0.101449 | AGR3 | 7 | 7p21.1 | 16865555 | 16888139 |
| SNX13 | 0.009804 | 0.121212 | 0.030303 | 0.014493 | 0.15942 | SNX13 | 7 | 7p21.1 | 17796911 | 17946657 |
| PRPS1L1 | 0.009804 | 0.090909 | 0.060606 | 0.014493 | 0.15942 | PRPS1L1 | 7 | 7p21.1 | 18032925 | 18034012 |
| HDAC9 | 0.009804 | 0.090909 | 0.121212 | 0.014493 | 0.173913 | HDAC9 | 7 | 7p21.1 | 18501894 | 18674991 |
| CHN2 | 0.009804 | 0.030303 | 0.090909 | 0.072464 | 0.014493 | CHN2 | 7 | 7p15.1 | 29200646 | 29520470 |
| POU6F2 | 0.009804 | 0.030303 | 0.121212 | 0.057971 | 0.014493 | POU6F2 | 7 | 7p14.1 | 38984134 | 39470916 |
| GLI3 | 0.009804 | 0.090909 | 0.151515 | 0.043478 | 0.014493 | GLI3 | 7 | 7p14.1 | 41967075 | 42243144 |
| CDK6 | 0.009804 | 0.151515 | 0.121212 | 0.014493 | 0.130435 | CDK6 | 7 | 7q21.2 | 92072173 | 92303878 |
| CALD1 | 0.009804 | 0.121212 | 0.090909 | 0.115942 | 0.014493 | CALD1 | 7 | 7q33 | 1.34E+08 | 1.34E+08 |
| LY86 | 0.009804 | 0.181818 | 0.121212 | 0.289855 | 0.014493 | LY86 | 6 | 6p25.1 | 6533933 | 6600216 |
| BMP6 | 0.009804 | 0.181818 | 0.090909 | 0.304348 | 0.014493 | BMP6 | 6 | 6p24.3 | 7672010 | 7826961 |
| RNF144B | 0.009804 | 0.090909 | 0.151515 | 0.014493 | 0.043478 | RNF144B | 6 | 6p22.3 | 18495573 | 18576830 |

TABLE 3-continued

| Symbol | freq. use | freq. amp. case | freq. del. case | freq. amp. control | freq. del. control | Gene. Symbol | chromo- some | cytoband | Transcript. start | Transcript. end |
|---|---|---|---|---|---|---|---|---|---|---|
| GPR116 | 0.009804 | 0 | 0.090909 | 0.072464 | 0.014493 | GPR116 | 6 | 6p12.3 | 46928204 | 46997674 |
| GPR110 | 0.009804 | 0 | 0.090909 | 0.072464 | 0.014493 | GPR110 | 6 | 6p12.3 | 47075772 | 47118042 |
| COL9A1 | 0.009804 | 0.090909 | 0.212121 | 0.014493 | 0.26087 | COL9A1 | 6 | 6q13 | 70982464 | 71069508 |
| SNX14 | 0.009804 | 0.121212 | 0.272727 | 0.014493 | 0.289855 | SNX14 | 6 | 6q14.3 | 86271934 | 86360349 |
| SYNCRIP | 0.009804 | 0.121212 | 0.272727 | 0.014493 | 0.289855 | SYNCRIP | 6 | 6q14.3 | 86374222 | 86409360 |
| ZNF292 | 0.009804 | 0.090909 | 0.242424 | 0.014493 | 0.217391 | ZNF292 | 6 | 6q15 | 87921988 | 88030126 |
| RSPH4A | 0.009804 | 0.090909 | 0.333333 | 0.014493 | 0.26087 | RSPH4A | 6 | 6q22.1 | 1.17E+08 | 1.17E+08 |
| SLC22A3 | 0.009804 | 0.151515 | 0.030303 | 0.014493 | 0.014493 | SLC22A3 | 6 | 6q25.3 | 1.61E+08 | 1.61E+08 |
| LPA | 0.009804 | 0.030303 | 0.090909 | 0.014493 | 0.014493 | LPA | 6 | 6q25.3 | 1.61E+08 | 1.61E+08 |
| DNAH5 | 0.009804 | 0.151515 | 0.030303 | 0.014493 | 0.014493 | DNAH5 | 5 | 5p15.2 | 13743437 | 13997590 |
| PRLR | 0.009804 | 0.090909 | 0.060606 | 0.014493 | 0.072464 | PRLR | 5 | 5p13.2 | 35091559 | 35266552 |
| ERBB2IP | 0.009804 | 0.090909 | 0.151515 | 0.014493 | 0.130435 | ERBB2IP | 5 | 5q12.3 | 65258140 | 65412607 |
| LOC100303749 | 0.009804 | 0.090909 | 0.151515 | 0.014493 | 0.130435 | LOC100303749 | 5 | 5q12.3 | 65276391 | 65277158 |
| ENC1 | 0.009804 | 0.090909 | 0.121212 | 0.014493 | 0.057971 | ENC1 | 5 | 5q13.3 | 73958990 | 73973006 |
| HEXB | 0.009804 | 0.090909 | 0.121212 | 0.014493 | 0.057971 | HEXB | 5 | 5q13.3 | 74016725 | 74052870 |
| ZNF608 | 0.009804 | 0.090909 | 0.090909 | 0.014493 | 0.130435 | ZNF608 | 5 | 5q23.2 | 1.24E+08 | 1.24E+08 |
| YIPF7 | 0.009804 | 0.090909 | 0.212121 | 0.014493 | 0.289855 | YIPF7 | 4 | 4p13 | 44319111 | 44348416 |
| ATP10D | 0.009804 | 0.121212 | 0.121212 | 0.014493 | 0.188406 | ATP10D | 4 | 4p12 | 47182167 | 47290261 |
| LRRC66 | 0.009804 | 0.060506 | 0.121212 | 0.028986 | 0.014493 | LRRC66 | 4 | 4q12 | 52554623 | 52578544 |
| SPATA18 | 0.009804 | 0.060606 | 0.151515 | 0.028986 | 0.014493 | SPATA18 | 4 | 4q12 | 52612350 | 52658216 |
| USP46 | 0.009804 | 0.090909 | 0.090909 | 0.072464 | 0.014493 | USP46 | 4 | 4q12 | 53151886 | 53217517 |
| ANKRD17 | 0.009804 | 0.181818 | 0.060606 | 0.014493 | 0.072464 | ANKRD17 | 4 | 4q13.3 | 74159366 | 74343367 |
| BTC | 0.009804 | 0.121212 | 0.121212 | 0.014493 | 0.101449 | BTC | 4 | 4q13.3 | 75890472 | 75938907 |
| PPEF2 | 0.009804 | 0.181818 | 0.030303 | 0.014493 | 0 | PPEF2 | 4 | 4q21.1 | 77000050 | 77042706 |
| NAAA | 0.009804 | 0.181818 | 0.030303 | 0.014493 | 0 | NAAA | 4 | 4q21.1 | 77050832 | 77081191 |
| SCARB2 | 0.009804 | 0.090909 | 0.030303 | 0.014493 | 0.014493 | SCARB2 | 4 | 4q21.1 | 77298918 | 77354060 |
| CCNI | 0.009804 | 0.121212 | 0.030303 | 0.014493 | 0.014493 | CCNI | 4 | 4q21.1 | 78188199 | 78216150 |
| MRPL1 | 0.009804 | 0.121212 | 0.090909 | 0.014493 | 0.043478 | MRPL1 | 4 | 4q21.1 | 79002829 | 79092969 |
| PTPN13 | 0.009804 | 0.121212 | 0.090909 | 0.057971 | 0.014493 | PTPN13 | 4 | 4q21.3 | 87734492 | 87955353 |
| UBE2D3 | 0.009804 | 0.090909 | 0.030303 | 0.014493 | 0.086957 | UBE2D3 | 4 | 4q24 | 1.04E+08 | 1.04E+08 |
| CISD2 | 0.009804 | 0.090909 | 0.030303 | 0.014493 | 0.086957 | CISD2 | 4 | 4q24 | 1.04E+08 | 1.04E+08 |
| NHEDC1 | 0.009804 | 0.090909 | 0.030303 | 0.014493 | 0.086957 | NHEDC1 | 4 | 4q24 | 1.04E+08 | 1.04E+08 |
| HADH | 0.009804 | 0.090909 | 0.030303 | 0.014493 | 0.028986 | HADH | 4 | 4q25 | 1.09E+08 | 1.09E+08 |
| LEF1 | 0.009804 | 0.090909 | 0.030303 | 0.014493 | 0.028986 | LEF1 | 4 | 4q25 | 1.09E+08 | 1.09E+08 |
| CCDC109B | 0.009804 | 0.121212 | 0.030303 | 0.014493 | 0.014493 | CCDC109B | 4 | 4q25 | 1.11E+08 | 1.11E+08 |
| CFI | 0.009804 | 0.121212 | 0.030303 | 0.014493 | 0.014493 | CFI | 4 | 4q25 | 1.11E+08 | 1.11E+08 |
| LOC285501 | 0.009804 | 0.090909 | 0.030303 | 0.014493 | 0.202899 | LOC285501 | 4 | 4q34.3 | 1.79E+08 | 1.79E+08 |
| ADAMTS9 | 0.009804 | 0 | 0.090909 | 0.101449 | 0.014493 | ADAMTS9 | 3 | 3p14.1 | 64476371 | 64648406 |
| ROBO2 | 0.009804 | 0.090909 | 0.212121 | 0.014493 | 0.333333 | ROBO2 | 3 | 3p12.3 | 77171984 | 77779354 |
| GABRR3 | 0.009804 | 0.090909 | 0.272727 | 0.014493 | 0.26087 | GABRR3 | 3 | 3q11.2 | 99188217 | 99236522 |
| GUCA1C | 0.009804 | 0.090909 | 0.030303 | 0.014493 | 0.057971 | GUCA1C | 3 | 3q13.13 | 1.1E+08 | 1.1E+08 |
| MORC1 | 0.009804 | 0.090909 | 0.030303 | 0.014493 | 0.057971 | MORC1 | 3 | 3q13.13 | 1.1E+08 | 1.1E+08 |
| TNIK | 0.009804 | 0.060606 | 0.090909 | 0.072464 | 0.014493 | TNIK | 3 | 3q26.2 | 1.72E+08 | 1.73E+08 |
| ETV5 | 0.009804 | 0.151515 | 0.090909 | 0.333333 | 0.014493 | ETV5 | 3 | 3q27.2 | 1.87E+08 | 1.87E+08 |
| HRG | 0.009804 | 0.181818 | 0.090909 | 0.362319 | 0.014493 | HRG | 3 | 3q27.3 | 1.88E+08 | 1.88E+08 |
| MASP1 | 0.009804 | 0.121212 | 0.090909 | 0.246377 | 0.014493 | MASP1 | 3 | 3q27.3 | 1.88E+08 | 1.88E+08 |
| SST | 0.009804 | 0.090909 | 0.121212 | 0.246377 | 0.014493 | SST | 3 | 3q27.3 | 1.89E+08 | 1.89E+08 |
| CRIM1 | 0.009804 | 0.060606 | 0.090909 | 0.086957 | 0.014493 | CRIM1 | 2 | 2p22.2 | 36436901 | 36631783 |
| TACR1 | 0.009804 | 0.090909 | 0.090909 | 0.144928 | 0.014493 | TACR1 | 2 | 2p13.1 | 75127098 | 75280154 |
| UNC50 | 0.009804 | 0.121212 | 0.090909 | 0.246377 | 0.014493 | UNC50 | 2 | 2q11.2 | 98591474 | 98601410 |
| MGAT4A | 0.009804 | 0.121212 | 0.090909 | 0.246377 | 0.014493 | MGAT4A | 2 | 2q11.2 | 98602001 | 98714022 |
| PLA2R1 | 0.009804 | 0.030303 | 0.090909 | 0.043478 | 0.014493 | PLA2R1 | 2 | 2q24.2 | 1.61E+08 | 1.61E+08 |
| STK39 | 0.009804 | 0.090909 | 0.060606 | 0.014493 | 0.043478 | STK39 | 2 | 2q24.3 | 1.69E+08 | 1.69E+08 |
| C2orf77 | 0.009804 | 0.151515 | 0.121212 | 0.086957 | 0.014493 | C2orf77 | 2 | 2q31.1 | 1.7E+08 | 1.7E+08 |
| PHOSPHO2 | 0.009804 | 0.151515 | 0.090909 | 0.086957 | 0.014493 | PHOSPHO2 | 2 | 2q31.1 | 1.7E+08 | 1.7E+08 |
| KLHL23 | 0.009804 | 0.151515 | 0.090909 | 0.086957 | 0.014493 | KLHL23 | 2 | 2q31.1 | 1.7E+08 | 1.7E+08 |
| SSB | 0.009804 | 0.151515 | 0.090909 | 0.115942 | 0.014493 | SSB | 2 | 2q31.1 | 1.7E+08 | 1.7E+08 |
| METTL5 | 0.009804 | 0.151515 | 0.090909 | 0.115942 | 0.014493 | METTL5 | 2 | 2q31.1 | 1.7E+08 | 1.7E+08 |
| UBR3 | 0.009804 | 0.151515 | 0.090909 | 0.115942 | 0.014493 | UBR3 | 2 | 2q31.1 | 1.7E+08 | 1.71E+08 |
| ZAK | 0.009804 | 0.090909 | 0.090909 | 0.115942 | 0.014493 | ZAK | 2 | 2q31.1 | 1.74E+08 | 1.74E+08 |
| COL5A2 | 0.009804 | 0.090909 | 0.121212 | 0.014493 | 0.130435 | COL5A2 | 2 | 2q32.2 | 1.9E+08 | 1.9E+08 |
| SLC40A1 | 0.009804 | 0.090909 | 0.090909 | 0.014493 | 0.130435 | SLC40A1 | 2 | 2q32.2 | 1.9E+08 | 1.9E+08 |
| ASNSD1 | 0.009804 | 0.121212 | 0.090909 | 0.014493 | 0.130435 | ASNSD1 | 2 | 2q32.2 | 1.9E+08 | 1.9E+08 |
| ANKAR | 0.009804 | 0.090909 | 0.090909 | 0.014493 | 0.101449 | ANKAR | 2 | 2q32.2 | 1.9E+08 | 1.9E+08 |
| OSGEPL1 | 0.009804 | 0.090909 | 0.090909 | 0.0144193 | 0.101449 | OSGEPL1 | 2 | 2q32.2 | 1.9E+08 | 1.9E+08 |
| ORMDL1 | 0.009804 | 0.090909 | 0.090909 | 0.014493 | 0.101449 | ORMDL1 | 2 | 2q32.2 | 1.9E+08 | 1.9E+08 |
| PMS1 | 0.009804 | 0.090909 | 0.090909 | 0.014493 | 0.101449 | PMS1 | 2 | 2q32.2 | 1.9E+08 | 1.9E+08 |
| STAT1 | 0.009804 | 0.090909 | 0.030303 | 0.014493 | 0.043478 | STAT1 | 2 | 2q32.2 | 1.92E+08 | 1.92E+08 |
| MYO1B | 0.009804 | 0.090909 | 0.090909 | 0.014493 | 0.043478 | MYO1B | 2 | 2q32.3 | 1.92E+08 | 1.92E+08 |
| TMEFF2 | 0.009804 | 0.090909 | 0.151515 | 0.014493 | 0.144928 | TMEFF2 | 2 | 2q32.3 | 1.93E+08 | 1.93E+08 |
| ANKRD44 | 0.009804 | 0.090909 | 0.060606 | 0.014493 | 0.028986 | ANKRD44 | 2 | 2q33.1 | 1.98E+08 | 1.98E+08 |
| MAP2 | 0.009804 | 0.090909 | 0.212121 | 0.014493 | 0.144928 | MAP2 | 2 | 2q34 | 2.1E+08 | 2.1E+08 |
| UNC80 | 0.009804 | 0.090909 | 0.181818 | 0.014493 | 0.15942 | UNC80 | 2 | 2q34 | 2.1E+08 | 2.11E+08 |
| ACADL | 0.009804 | 0.090909 | 0.090909 | 0.014493 | 0.130435 | ACADL | 2 | 2q34 | 2.11E+08 | 2.11E+08 |
| MYL1 | 0.009804 | 0.151515 | 0.090909 | 0.014493 | 0.130435 | MYL1 | 2 | 2q34 | 2.11E+08 | 2.11E+08 |
| LANCL1 | 0.009804 | 0.090909 | 0.181818 | 0.014493 | 0.130435 | LANCL1 | 2 | 2q34 | 2.11E+08 | 2.11E+08 |

TABLE 3-continued

| Symbol | freq. use | freq. amp. case | freq. del. case | freq. amp. control | freq. del. control | Gene. Symbol | chromo-some | cytoband | Transcript. start | Transcript. end |
|---|---|---|---|---|---|---|---|---|---|---|
| CPS1 | 0.009804 | 0.090909 | 0.212121 | 0.014493 | 0.217391 | CPS1 | 2 | 2q34 | 2.11E+08 | 2.11E+08 |
| ERBB4 | 0.009804 | 0.090909 | 0.212121 | 0.014493 | 0.246377 | ERBB4 | 2 | 2q34 | 2.12E+08 | 2.13E+08 |
| LOC728323 | 0.009804 | 0.363636 | 0.121212 | 0.608696 | 0.014493 | LOC728323 | 2 | 2q37.3 | 2.43E+08 | 2.43E+08 |
| PPAP2B | 0.009804 | 0.090909 | 0.121212 | 0.217391 | 0.014493 | PPAP2B | 1 | 1p32.2 | 56733021 | 56817846 |
| TACSTD2 | 0.009804 | 0.060606 | 0.181818 | 0.188406 | 0.014493 | TACSTD2 | 1 | 1p32.1 | 58813683 | 58815755 |
| NFIA | 0.009804 | 0.060606 | 0.121212 | 0.115942 | 0.014493 | NFIA | 1 | 1p31.3 | 61315534 | 61701048 |
| TM2D1 | 0.009804 | 0.121212 | 0.121212 | 0.173913 | 0.014493 | TM2D1 | 1 | 1p31.3 | 61919307 | 61963684 |
| INADL | 0.009804 | 0.090909 | 0.121212 | 0.173913 | 0.014493 | INADL | 1 | 1p31.3 | 61980737 | 62402180 |
| KANK4 | 0.009804 | 0.121212 | 0.121212 | 0.15942 | 0.014493 | KANK4 | 1 | 1p31.3 | 62474425 | 62557672 |
| USP1 | 0.009804 | 0.121212 | 0.121212 | 0.115942 | 0.014493 | USP1 | 1 | 1p31.3 | 62674563 | 62690064 |
| DOCK7 | 0.009804 | 0.121212 | 0.121212 | 0.115942 | 0.014493 | DOCK7 | 1 | 1p31.3 | 62692985 | 62926558 |
| ALG6 | 0.009804 | 0.060606 | 0.151515 | 0.115942 | 0.014493 | ALG6 | 1 | 1p31.3 | 63605849 | 63676821 |
| PGM1 | 0.009804 | 0.090909 | 0.121212 | 0.086957 | 0.014493 | PGM1 | 1 | 1p31.3 | 63831535 | 63898506 |
| ROR1 | 0.009804 | 0.090909 | 0.181818 | 0.086957 | 0.014493 | ROR1 | 1 | 1p31.3 | 64012278 | 64381641 |
| JAK1 | 0.009804 | 0.151515 | 0.090909 | 0.173913 | 0.014493 | JAK1 | 1 | 1p31.3 | 65071494 | 65204776 |
| MIR101-1 | 0.009804 | 0.121212 | 0.090909 | 0.130435 | 0.014493 | MIR101-1 | 1 | 1p31.3 | 65296705 | 65296780 |
| AK3L1 | 0.009804 | 0.121212 | 0.090909 | 0.130435 | 0.014493 | AK3L1 | 1 | 1p31.3 | 65385820 | 65465764 |
| LOC339524 | 0.009804 | 0.151515 | 0.151515 | 0.115942 | 0.014493 | LOC339524 | 1 | 1p22.3 | 87368036 | 87407473 |
| GTF2B | 0.009804 | 0.151515 | 0.181818 | 0.115942 | 0.014493 | GTF2B | 1 | 1p22.2 | 89090909 | 89129890 |
| CCBL2 | 0.009804 | 0.121212 | 0.181818 | 0.043478 | 0.014493 | CCBL2 | 1 | 1p22.2 | 89174044 | 89231232 |
| GBP7 | 0.009804 | 0.090909 | 0.151515 | 0.014493 | 0.057971 | GBP7 | 1 | 1p22.2 | 89370022 | 89414312 |
| GBP4 | 0.009804 | 0.090909 | 0.151515 | 0.014493 | 0.057971 | GBP4 | 1 | 1p22.2 | 89419419 | 89437222 |
| ZNF644 | 0.009804 | 0.090909 | 0.121212 | 0.072464 | 0.014493 | ZNF644 | 1 | 1p22.2 | 91153445 | 91259619 |
| HFM1 | 0.009804 | 0.030303 | 0.151515 | 0.057971 | 0.014493 | HFM1 | 1 | 1p22.2 | 91498911 | 91643015 |
| HSP90B3P | 0.009804 | 0.121212 | 0.151515 | 0.072464 | 0.014493 | HSP90B3P | 1 | 1p22.2 | 91873156 | 91881923 |
| TGFBR3 | 0.009804 | 0.060606 | 0.212121 | 0.057971 | 0.014493 | TGFBR3 | 1 | 1p22.2 | 91918490 | 92124376 |
| BRDT | 0.009804 | 0.181818 | 0.121212 | 0.115942 | 0.014493 | BRDT | 1 | 1p22.1 | 92187516 | 92252574 |
| EPHX4 | 0.009804 | 0.181818 | 0.121212 | 0.115942 | 0.014493 | EPHX4 | 1 | 1p22.1 | 92268121 | 92301682 |
| BTBD8 | 0.009804 | 0.181818 | 0.121212 | 0.115942 | 0.014493 | BTBD8 | 1 | 1p22.1 | 92318450 | 92385994 |
| KIAA1107 | 0.009804 | 0.181818 | 0.121212 | 0.115942 | 0.014493 | KIAA1107 | 1 | 1p22.1 | 92405197 | 92422868 |
| GFI1 | 0.009804 | 0.181818 | 0.121212 | 0.130435 | 0.014493 | GFI1 | 1 | 1p22.1 | 92712906 | 92721945 |
| RPL5 | 0.009804 | 0.121212 | 0.151515 | 0.101449 | 0.014493 | RPL5 | 1 | 1p22.1 | 93070182 | 93080070 |
| SNORD21 | 0.009804 | 0.121212 | 0.151515 | 0.101449 | 0.014493 | SNORD21 | 1 | 1p22.1 | 93075434 | 93075529 |
| FAM69A | 0.009804 | 0.121212 | 0.121212 | 0.101449 | 0.014493 | FAM69A | 1 | 1p22.1 | 93080309 | 93199668 |
| MTF2 | 0.009804 | 0.121212 | 0.121212 | 0.101449 | 0.014493 | MTF2 | 1 | 1p22.1 | 93317380 | 93377225 |
| DR1 | 0.009804 | 0.151515 | 0.181818 | 0.101449 | 0.014493 | DR1 | 1 | 1p22.1 | 93584066 | 93600737 |
| FNBP1L | 0.009804 | 0.151515 | 0.151515 | 0.101449 | 0.014493 | FNBP1L | 1 | 1p22.1 | 93686427 | 93792807 |
| BCAR3 | 0.009804 | 0.181818 | 0.151515 | 0.144928 | 0.014493 | BCAR3 | 1 | 1p22.1 | 93799937 | 93919974 |
| DNTTIP2 | 0.009804 | 0.181818 | 0.121212 | 0.15942 | 0.014493 | DNTTIP2 | 1 | 1p22.1 | 94107924 | 94117331 |
| GCLM | 0.009804 | 0.181818 | 0.121212 | 0.15942 | 0.014493 | GCLM | 1 | 1p22.1 | 94125178 | 94147601 |
| ABCA4 | 0.009804 | 0.181818 | 0.121212 | 0.173913 | 0.014493 | ABCA4 | 1 | 1p22.1 | 94230982 | 94359294 |
| TMEM56 | 0.009804 | 0.090909 | 0.151515 | 0.115942 | 0.014493 | TMEM56 | 1 | 1p21.3 | 95355482 | 95435748 |
| FAM102B | 0.009804 | 0.030303 | 0.121212 | 0.086957 | 0.014493 | FAM102B | 1 | 1p13.3 | 1.09E+08 | 1.09E+08 |
| C1orf59 | 0.009804 | 0.090909 | 0.090909 | 0.115942 | 0.014493 | C1orf59 | 1 | 1p13.3 | 1.09E+08 | 1.09E+08 |
| PRPF38B | 0.009804 | 0.090909 | 0.090909 | 0.115942 | 0.014493 | PRPF38B | 1 | 1p13.3 | 1.09E+08 | 1.09E+08 |
| FNDC7 | 0.009804 | 0.060606 | 0.090909 | 0.115942 | 0.014493 | FNDC7 | 1 | 1p13.3 | 1.09E+08 | 1.09E+08 |
| STXBP3 | 0.009804 | 0.060606 | 0.090909 | 0.115942 | 0.014493 | STXBP3 | 1 | 1p13.3 | 1.09E+08 | 1.09E+08 |
| AKNAD1 | 0.009804 | 0.060606 | 0.090909 | 0.130435 | 0.014493 | AKNAD1 | 1 | 1p13.3 | 1.09E+08 | 1.09E+08 |
| GPSM2 | 0.009804 | 0.090909 | 0.090909 | 0.173913 | 0.014493 | GPSM2 | 1 | 1p13.3 | 1.09E+08 | 1.09E+08 |
| CLCC1 | 0.009804 | 0.090909 | 0.090909 | 0.173913 | 0.014493 | CLCC1 | 1 | 1p13.3 | 1.09E+08 | 1.09E+08 |
| WDR47 | 0.009804 | 0.090909 | 0.090909 | 0.188406 | 0.014493 | WDR47 | 1 | 1p13.3 | 1.09E+08 | 1.09E+08 |
| MYBPHL | 0.009804 | 0.151515 | 0.090909 | 0.202899 | 0.014493 | MYBPHL | 1 | 1p13.3 | 1.1E+08 | 1.1E+08 |
| SORT1 | 0.009804 | 0.121212 | 0.090909 | 0.202899 | 0.014493 | SORT1 | 1 | 1p13.3 | 1.1E+08 | 1.1E+08 |
| ATXN7L2 | 0.009804 | 0.121212 | 0.090909 | 0.231884 | 0.014493 | ATXN7L2 | 1 | 1p13.3 | 1.1E+08 | 1.1E+08 |
| CYB561D1 | 0.009804 | 0.121212 | 0.090909 | 0.231884 | 0.014493 | CYB561D1 | 1 | 1p13.3 | 1.1E+08 | 1.1E+08 |
| AMIGO1 | 0.009804 | 0.121212 | 0.090909 | 0.231884 | 0.014493 | AMIGO1 | 1 | 1p13.3 | 1.1E+08 | 1.1E+08 |
| CD53 | 0.009804 | 0 | 0.090909 | 0.144928 | 0.014493 | CD53 | 1 | 1p13.3 | 1.11E+08 | 1.11E+08 |
| C1orf103 | 0.009804 | 0 | 0.121212 | 0.15942 | 0.014493 | C1orf103 | 1 | 1p13.3 | 1.11E+08 | 1.11E+08 |
| FAM46C | 0.009804 | 0.121212 | 0.090909 | 0.173913 | 0.014493 | FAM46C | 1 | 1p12 | 1.18E+08 | 1.18E+08 |
| WARS2 | 0.009804 | 0.090909 | 0.090909 | 0.072464 | 0.014493 | WARS2 | 1 | 1p12 | 1.19E+08 | 1.19E+08 |
| HAO2 | 0.009804 | 0 | 0.121212 | 0.057971 | 0.014493 | HAO2 | 1 | 1p12 | 1.2E+08 | 1.2E+08 |
| HSD3B2 | 0.009804 | 0 | 0.121212 | 0.057971 | 0.014493 | HSD3B2 | 1 | 1p12 | 1.2E+08 | 1.2E+08 |
| HSD3B1 | 0.009804 | 0.060606 | 0.121212 | 0.072464 | 0.014493 | HSD3B1 | 1 | 1p12 | 1.2E+08 | 1.2E+08 |
| ZNF697 | 0.009804 | 0.030303 | 0.121212 | 0.057971 | 0.014493 | ZNF697 | 1 | 1p12 | 1.2E+08 | 1.2E+08 |
| CHD1L | 0.009804 | 0.060606 | 0.121212 | 0.188406 | 0.014493 | CHD1L | 1 | 1q21.1 | 1.45E+08 | 1.45E+08 |
| NOS1AP | 0.009804 | 0.030303 | 0.121212 | 0.086957 | 0.014493 | NOS1AP | 1 | 1q23.3 | 1.6E+08 | 1.61E+08 |
| C1orf156 | 0.009804 | 0.090909 | 0.060606 | 0.014493 | 0.086957 | C1orf156 | 1 | 1q24.2 | 1.68E+08 | 1.68E+08 |
| C1orf112 | 0.009804 | 0.090909 | 0.060606 | 0.014493 | 0.086957 | C1orf112 | 1 | 1q24.2 | 1.68E+08 | 1.68E+08 |
| RGL1 | 0.009804 | 0.090909 | 0.030303 | 0.014493 | 0.043478 | RGL1 | 1 | 1q25.3 | 1.82E+08 | 1.82E+08 |
| APOBEC4 | 0.009804 | 0.090909 | 0.030303 | 0.014493 | 0.043478 | APOBEC4 | 1 | 1q25.3 | 1.82E+08 | 1.82E+08 |
| C1orf21 | 0.009804 | 0.121212 | 0.030303 | 0.014493 | 0.057971 | C1orf21 | 1 | 1q25.3 | 1.83E+08 | 1.83E+08 |
| TPR | 0.009804 | 0.090909 | 0.060606 | 0.014493 | 0.115942 | TPR | 1 | 1q31.1 | 1.85E+08 | 1.85E+08 |
| C1orf27 | 0.009804 | 0.090909 | 0.060606 | 0.014493 | 0.115942 | C1orf27 | 1 | 1q31.1 | 1.85E+08 | 1.85E+08 |
| PDC | 0.009804 | 0.090909 | 0.060606 | 0.014493 | 0.115942 | PDC | 1 | 1q31.1 | 1.85E+08 | 1.85E+08 |
| CRB1 | 0.009804 | 0.121212 | 0.151515 | 0.014493 | 0.275362 | CRB1 | 1 | 1q31.3 | 1.96E+08 | 1.96E+08 |
| C4BPB | 0.009804 | 0.181818 | 0.090909 | 0.362319 | 0.014493 | C4BPB | 1 | 1q32.2 | 2.05E+08 | 2.05E+08 |

TABLE 3-continued

| Symbol | freq. use | freq. amp. case | freq. del. case | freq. amp. control | freq. del. control | Gene. Symbol | chromo-some | cytoband | Transcript. start | Transcript. end |
|---|---|---|---|---|---|---|---|---|---|---|
| DUSP10 | 0.009804 | 0.060606 | 0.181818 | 0.057971 | 0.014493 | DUSP10 | 1 | 1q41 | 2.2E+08 | 2.2E+08 |
| NVL | 0.009804 | 0.181818 | 0.090909 | 0.304348 | 0.014493 | NVL | 1 | 1q42.11 | 2.22E+08 | 2.23E+08 |
| H3F3A | 0.009804 | 0.30303 | 0.090909 | 0.405797 | 0.014493 | H3F3A | 1 | 1q42.12 | 2.24E+08 | 2.24E+08 |
| LOC440926 | 0.009804 | 0.30303 | 0.090909 | 0.405797 | 0.014493 | LOC440926 | 1 | 1q42.12 | 2.24E+08 | 2.24E+08 |
| GGPS1 | 0.009804 | 0.242424 | 0.090909 | 0.289855 | 0.014493 | GGPS1 | 1 | 1q42.3 | 2.34E+08 | 2.34E+08 |
| TBCE | 0.009804 | 0.242424 | 0.090909 | 0.289855 | 0.014493 | TBCE | 1 | 1q42.3 | 2.34E+08 | 2.34E+08 |
| ACTN2 | 0.009804 | 0.242424 | 0.090909 | 0.130435 | 0.014493 | ACTN2 | 1 | 1q43 | 2.35E+08 | 2.35E+08 |
| MTR | 0.009804 | 0.242424 | 0.090909 | 0.15942 | 0.014493 | MTR | 1 | 1q43 | 2.35E+08 | 2.35E+08 |
| RYR2 | 0.009804 | 0.121212 | 0.090909 | 0.115942 | 0.014493 | RYR2 | 1 | 1q43 | 2.35E+08 | 2.36E+08 |
| LOC100130331 | 0.009804 | 0.060606 | 0.090909 | 0.014493 | 0.014493 | LOC100130331 | 1 | 1q43 | 2.36E+08 | 2.36E+08 |
| ZP4 | 0.009804 | 0.060606 | 0.090909 | 0.014493 | 0.014493 | ZP4 | 1 | 1q43 | 2.36E+08 | 2.36E+08 |

TABLE 4

Gene list for predicting prostate cancer relapse using AT

| Symbol | freq. use | freq. amp. case | freq. del. case | freq. amp. control | freq. del. control | Gene. Symbol | chromo-some | cytoband | Transcript. start | Transcript. end |
|---|---|---|---|---|---|---|---|---|---|---|
| RNF160 | 1 | 0.142857 | 0.047619 | 0 | 0.037037 | RNF160 | 21 | 21q21.3 | 29222337 | 29287149 |
| BTBD3 | 1 | 0 | 0.142857 | 0 | 0 | BTBD3 | 20 | 20p12.2 | 11819477 | 11855244 |
| SPTLC3 | 1 | 0 | 0.142857 | 0 | 0 | SPTLC3 | 20 | 20p12.1 | 12937627 | 13095412 |
| ISM1 | 1 | 0 | 0.142857 | 0 | 0 | ISM1 | 20 | 20p12.1 | 13150418 | 13229298 |
| TASP1 | 1 | 0 | 0.142857 | 0 | 0 | TASP1 | 20 | 20p12.1 | 13318036 | 13567584 |
| MACROD2 | 1 | 0 | 0.142857 | 0 | 0 | MACROD2 | 20 | 20p12.1 | 13924146 | 15981842 |
| PSG1 | 1 | 0.333333 | 0.142857 | 0.481481 | 0 | PSG1 | 19 | 19q13.31 | 48063198 | 48075712 |
| ST8SIA3 | 1 | 0.238095 | 0 | 0 | 0 | ST8SIA3 | 18 | 18q21.31 | 53170719 | 53187160 |
| ONECUT2 | 1 | 0.238095 | 0 | 0 | 0 | ONECUT2 | 18 | 18q21.31 | 53253915 | 53309529 |
| TNFRSF11A | 1 | 0.190476 | 0 | 0 | 0 | TNFRSF11A | 18 | 18q21.33 | 58143528 | 58204485 |
| ZCCHC2 | 1 | 0.238095 | 0 | 0 | 0 | ZCCHC2 | 18 | 18q21.33 | 58341638 | 58396799 |
| ZNF407 | 1 | 0.190476 | 0 | 0 | 0 | ZNF407 | 18 | 18q22.3 | 70471907 | 70762000 |
| TSHZ1 | 1 | 0.190476 | 0 | 0 | 0 | TSHZ1 | 18 | 18q22.3 | 71051719 | 71130890 |
| RBL2 | 1 | 0.190476 | 0 | 0 | 0.037037 | R8L2 | 16 | 16q12.2 | 52025852 | 52083062 |
| CDH11 | 1 | 0.142857 | 0.095238 | 0 | 0.037037 | CDH11 | 16 | 16q21 | 63538184 | 63713421 |
| LOC283867 | 1 | 0.142857 | 0.047619 | 0 | 0 | LOC283867 | 16 | 16q21 | 63875903 | 64167705 |
| MAGEL2 | 1 | 0.142857 | 0 | 0 | 0 | MAGEL2 | 15 | 15q11.2 | 21439791 | 21444087 |
| NDN | 1 | 0.142857 | 0 | 0 | 0 | NDN | 15 | 15q11.2 | 21481647 | 21483544 |
| MIR548A3 | 1 | 0.047619 | 0.190476 | 0 | 0 | MIR548A3 | 15 | 15q21.1 | 44584617 | 45037888 |
| NEDD4 | 1 | 0.142857 | 0 | 0 | 0 | NEDD4 | 15 | 15q21.3 | 53906414 | 54073128 |
| CGNL1 | 1 | 0.190476 | 0 | 0 | 0 | CGNL1 | 15 | 15q21.3 | 55455997 | 55630214 |
| OR11G2 | 1 | 0.238095 | 0 | 0 | 0.074074 | OR11G2 | 14 | 14q11.2 | 19735335 | 19736373 |
| OR11H4 | 1 | 0.238095 | 0 | 0 | 0.074074 | OR11H4 | 14 | 14q11.2 | 19780791 | 19781766 |
| AP4S1 | 1 | 0.238095 | 0 | 0 | 0 | AP4S1 | 14 | 14q12 | 30564434 | 30632390 |
| HECTD1 | 1 | 0.238095 | 0 | 0 | 0 | HECTD1 | 14 | 14q12 | 30639075 | 30746441 |
| SSTR1 | 1 | 0 | 0.142857 | 0 | 0 | SSTR1 | 14 | 14q21.1 | 37746955 | 37752020 |
| PPIL5 | 1 | 0.142857 | 0 | 0 | 0 | PPIL5 | 14 | 14q22.1 | 49135165 | 49151141 |
| RPL36AL | 1 | 0.142857 | 0 | 0 | 0 | RPL36AL | 14 | 14q22.1 | 49155157 | 49157100 |
| MGAT2 | 1 | 0.142857 | 0 | 0 | 0 | MGAT2 | 14 | 14q22.1 | 49157239 | 49159950 |
| C14orf104 | 1 | 0.142857 | 0 | 0 | 0 | C14orf104 | 14 | 14q22.1 | 49161642 | 49171699 |
| POLE2 | 1 | 0.142857 | 0 | 0 | 0 | POLE2 | 14 | 14q22.1 | 49180029 | 49224686 |
| KLHDC1 | 1 | 0.142857 | 0 | 0 | 0 | KLHDC1 | 14 | 14q22.1 | 49229635 | 49289615 |
| ARF6 | 1 | 0.142857 | 0 | 0 | 0 | ARF6 | 14 | 14q22.1 | 49429486 | 49433523 |
| C14orf182 | 1 | 0.142857 | 0 | 0 | 0 | C14orf182 | 14 | 14q22.1 | 49518180 | 49543989 |
| CGRRF1 | 1 | 0.142857 | 0 | 0 | 0 | CGRRF1 | 14 | 14q22.2 | 54046337 | 54075085 |
| SAMD4A | 1 | 0.142857 | 0 | 0 | 0 | SAMD4A | 14 | 14q22.2 | 54104387 | 54329784 |
| TMEM30B | 1 | 0.142857 | 0 | 0 | 0 | TMEM30B | 14 | 14q23.1 | 60813842 | 60818284 |
| PRKCH | 1 | 0.142857 | 0 | 0 | 0 | PRKCH | 14 | 14q23.1 | 60858268 | 61087452 |
| ZDHHC20 | 1 | 0.142857 | 0 | 0 | 0 | ZDHHC20 | 13 | 13q12.11 | 20848508 | 20931424 |
| EFHA1 | 1 | 0.142857 | 0 | 0 | 0 | EFHA1 | 13 | 13q12.11 | 20964839 | 21076308 |
| FGF9 | 1 | 0.142857 | 0 | 0 | 0 | FGF9 | 13 | 13q12.11 | 21143215 | 21176641 |
| FAM48A | 1 | 0 | 0.190476 | 0 | 0 | FAM48A | 13 | 13q13.3 | 36481451 | 36531851 |
| FREM2 | 1 | 0 | 0.142857 | 0 | 0 | FREM2 | 13 | 13q13.3 | 38159173 | 38359268 |
| C13orf23 | 1 | 0 | 0.142857 | 0 | 0 | C13orf23 | 13 | 13q13.3 | 38482002 | 38510253 |
| DHRS12 | 1 | 0.142857 | 0 | 0 | 0 | DHRS12 | 13 | 13q14.3 | 51240132 | 51276295 |
| FLJ37307 | 1 | 0.142857 | 0 | 0 | 0 | FLJ37307 | 13 | 13q14.3 | 51285484 | 51317288 |
| ATP7B | 1 | 0.142857 | 0 | 0 | 0 | ATP7B | 13 | 13q14.3 | 51404806 | 51483632 |
| ALG11 | 1 | 0.142857 | 0 | 0 | 0 | ALG11 | 13 | 13q14.3 | 51484551 | 51501782 |
| UTP14C | 1 | 0.142857 | 0 | 0 | 0 | UTP14C | 13 | 13q14.3 | 51496828 | 51505736 |
| NEK5 | 1 | 0.142857 | 0 | 0 | 0 | NEK5 | 13 | 13q14.3 | 51536901 | 51601216 |
| NEK3 | 1 | 0.142857 | 0 | 0 | 0 | NEK3 | 13 | 13q14.3 | 51604780 | 51631998 |
| THSD1 | 1 | 0.142857 | 0 | 0 | 0 | THSD1 | 13 | 13q14.3 | 51849305 | 51878631 |
| LOC647288 | 1 | 0 | 0.142857 | 0 | 0 | LOC647288 | 13 | 13q22.2 | 74709890 | 74712519 |

TABLE 4-continued

Gene list for predicting prostate cancer relapse using AT

| Symbol | freq. use | freq. amp. case | freq. del. case | freq. amp. control | freq. del. control | Gene. Symbol | chromo-some | cytoband | Transcript. start | Transcript. end |
|---|---|---|---|---|---|---|---|---|---|---|
| ABCC4 | 1 | 0.190476 | 0 | 0 | 0 | ABCC4 | 13 | 13q32.1 | 94470084 | 94751689 |
| DZIP1 | 1 | 0.380952 | 0 | 0 | 0 | DZIP1 | 13 | 13q32.1 | 95028457 | 95094959 |
| DNAJC3 | 1 | 0.190476 | 0 | 0 | 0 | DNAJC3 | 13 | 13q32.1 | 95127403 | 95245243 |
| TM9SF2 | 1 | 0.190476 | 0 | 0 | 0 | TM9SF2 | 13 | 13q32.3 | 98951729 | 99013278 |
| PCCA | 1 | 0.190476 | 0 | 0 | 0 | PCCA | 13 | 13q32.3 | 99539338 | 99980690 |
| ITGBL1 | 1 | 0 | 0.142857 | 0 | 0 | ITGBL1 | 13 | 13q33.1 | 1.01E+08 | 1.01E+08 |
| FGF14 | 1 | 0 | 0.142857 | 0 | 0 | FGF14 | 13 | 13q33.1 | 1.01E+08 | 1.01E+08 |
| IRS2 | 1 | 0.190476 | 0 | 0 | 0 | IRS2 | 13 | 13q34 | 1.09E+08 | 1.09E+08 |
| KLRC1 | 1 | 0 | 0.142857 | 0.037037 | 0 | KLRC1 | 12 | 12p13.2 | 10489904 | 10497247 |
| PRR4 | 1 | 0 | 0.142857 | 0.037037 | 0 | PRR4 | 12 | 12p13.2 | 10889715 | 11215481 |
| PRH1 | 1 | 0 | 0.142857 | 0.037037 | 0 | PRH1 | 12 | 12p13.2 | 10924827 | 11215478 |
| TAS2R30 | 1 | 0 | 0.142857 | 0.037037 | 0 | TAS2R30 | 12 | 12p13.2 | 11177151 | 11178111 |
| PRB3 | 1 | 0 | 0.142857 | 0.037037 | 0 | PRB3 | 12 | 12p13.2 | 11310124 | 11313909 |
| FAR2 | 1 | 0 | 0.142857 | 0 | 0 | FAR2 | 12 | 12p11.22 | 29267865 | 29378274 |
| OVCH1 | 1 | 0 | 0.142857 | 0 | 0 | OVCH1 | 12 | 12p11.22 | 29471756 | 29541887 |
| PRICKLE1 | 1 | 0.142857 | 0 | 0 | 0 | PRICKLE1 | 12 | 12q12 | 41138408 | 41269840 |
| NEUROD4 | 1 | 0.047619 | 0.190476 | 0.259259 | 0 | NEUROD4 | 12 | 12q13.2 | 53699996 | 53710069 |
| CDK17 | 1 | 0.142857 | 0 | 0 | 0 | CDK17 | 12 | 12q23.1 | 95196173 | 95318437 |
| ANKS1B | 1 | 0.190476 | 0 | 0 | 0 | ANKS1B | 12 | 12q23.1 | 97653202 | 98072604 |
| UBQLN3 | 1 | 0 | 0.142857 | 0 | 0 | UBQLN3 | 11 | 11P15.4 | 5485106 | 5487730 |
| UBQLNL | 1 | 0 | 0.142857 | 0 | 0 | UBQLNL | 11 | 11p15.4 | 5492199 | 5494533 |
| TRIM6 | 1 | 0.142857 | 0 | 0 | 0 | TRIM6 | 11 | 11p15.4 | 5573923 | 5590765 |
| TRIM6-T1m34 | 1 | 0.142857 | 0 | 0 | 0 | TRIM6-T1M34 | 11 | 11p15.4 | 5574460 | 5622200 |
| TRIM34 | 1 | 0.142857 | 0 | 0 | 0 | TRIM34 | 11 | 11p15.4 | 5597750 | 5622202 |
| SERGEF | 1 | 0.142857 | 0 | 0 | 0 | SERGEF | 11 | 11p15.1 | 17766172 | 17991214 |
| TPH1 | 1 | 0.142857 | 0 | 0 | 0 | TPH1 | 11 | 11p15.1 | 17998660 | 18018912 |
| MRGPRX3 | 1 | 0.142857 | 0 | 0 | 0 | MRGPRX3 | 11 | 11p15.1 | 18099078 | 18116602 |
| MRGPRX4 | 1 | 0.142857 | 0 | 0 | 0 | MRGPRX4 | 11 | 11p15.1 | 18150960 | 18152404 |
| ELP4 | 1 | 0.190476 | 0.047619 | 0 | 0.037037 | ELP4 | 11 | 11p13 | 31487873 | 31761906 |
| PAX6 | 1 | 0.190476 | 0.047619 | 0 | 0.037037 | PAX6 | 11 | 11p13 | 31762916 | 31789456 |
| LOC441601 | 1 | 0 | 0.238095 | 0.037037 | 0 | LOC441601 | 11 | 11p11.12 | 50195575 | 50214200 |
| PRCP | 1 | 0.142857 | 0 | 0 | 0.074074 | PRCP | 11 | 11q14.1 | 82213057 | 82289206 |
| C11orf82 | 1 | 0.142857 | 0 | 0 | 0.074074 | C11orf82 | 11 | 11q14.1 | 82290385 | 82323348 |
| RAB30 | 1 | 0.142857 | 0 | 0 | 0.037037 | RAB30 | 11 | 11q14.1 | 82370126 | 82460533 |
| CCDC82 | 1 | 0 | 0.142857 | 0 | 0 | CCDC82 | 11 | 11q21 | 95725577 | 95762732 |
| JRKL | 1 | 0 | 0.142857 | 0 | 0 | JRKL | 11 | 11q21 | 95762806 | 95766376 |
| LOC254312 | 1 | 0.190476 | 0 | 0 | 0 | LOC254312 | 10 | 10p14 | 11016910 | 11034133 |
| CUGBP2 | 1 | 0.190476 | 0 | 0 | 0 | CUGBP2 | 10 | 10p14 | 11087265 | 11418679 |
| PTER | 1 | 0.142857 | 0 | 0 | 0 | PTER | 10 | 10p13 | 16518973 | 16595743 |
| MLLT10 | 1 | 0.142857 | 0 | 0 | 0 | MLLT10 | 10 | 10p12.31 | 21863108 | 22072561 |
| DNAJC1 | 1 | 0.142857 | 0 | 0 | 0 | DNAJC1 | 10 | 10p12.31 | 22085483 | 22332657 |
| PRINS | 1 | 0.142857 | 0 | 0 | 0 | PRINS | 10 | 10p12.1 | 24576060 | 24584982 |
| MIR603 | 1 | 0.142857 | 0 | 0 | 0 | MIR603 | 10 | 10p12.1 | 24604620 | 24604717 |
| ARHGAP21 | 1 | 0.142857 | 0 | 0 | 0 | ARHGAP21 | 10 | 10p12.1 | 24912544 | 25052604 |
| PRTFDC1 | 1 | 0.142857 | 0 | 0 | 0 | PRTFDC1 | 10 | 10p12.1 | 25177560 | 25281540 |
| GPR158 | 1 | 0 | 0.190476 | 0 | 0 | GPR158 | 10 | 10p12.1 | 25504296 | 25931164 |
| ZEB1 | 1 | 0 | 0.142857 | 0.037037 | 0 | ZEB1 | 10 | 10p11.22 | 31647430 | 31858134 |
| FAM13C | 1 | 0 | 0.142857 | 0 | 0 | FAM13C | 10 | 10q21.1 | 60675896 | 60792359 |
| RNLS | 1 | 0 | 0.142857 | 0 | 0 | RNLS | 10 | 10q23.31 | 90023601 | 90333063 |
| UPN | 1 | 0 | 0.142857 | 0 | 0 | UPN | 10 | 10q23.31 | 90511143 | 90527980 |
| KDM4C | 1 | 0.238095 | 0 | 0 | 0 | KDM4C | 9 | 9p24.1 | 6710863 | 7067265 |
| PGM5 | 1 | 0.142857 | 0.047619 | 0 | 0 | PGM5 | 9 | 9q13 | 70161635 | 70335798 |
| C9orf71 | 1 | 0.142857 | 0 | 0 | 0 | C9orf71 | 9 | 9q13 | 70341318 | 70345604 |
| PIP5K1B | 1 | 0.142857 | 0 | 0 | 0 | P5P5K1B | 9 | 9q21.11 | 70510436 | 70813912 |
| FAM108B1 | 1 | 0.142857 | 0 | 0 | 0 | FAM108B1 | 9 | 9q21.13 | 73667188 | 73715969 |
| PAPPA | 1 | 0.047619 | 0.142857 | 0 | 0 | PAPPA | 9 | 9q33.1 | 1.18E+08 | 1.18E+08 |
| ZDHHC2 | 1 | 0.142857 | 0 | 0 | 0 | ZDHHC2 | 8 | 8p22 | 17058207 | 17124612 |
| CSGALNAC | 1 | 0.142857 | 0 | 0 | 0 | CSGALNAC | 8 | 8p21.3 | 19305952 | 19504337 |
| INTS10 | 1 | 0.142857 | 0 | 0 | 0 | INTS10 | 8 | 8p21.3 | 19719198 | 19753867 |
| LPL | 1 | 0.142857 | 0 | 0 | 0 | LPL | 8 | 8p21.3 | 19840862 | 19869051 |
| FUT10 | 1 | 0.190476 | 0.047619 | 0 | 0.037037 | FUT10 | 8 | 8p12 | 33347886 | 33450207 |
| FAM150A | 1 | 0.142857 | 0 | 0 | 0 | FAM150A | 8 | 8q11.23 | 53609151 | 53640575 |
| OPRK1 | 1 | 0.142857 | 0 | 0 | 0 | OPRK1 | 8 | 8q11.23 | 54300829 | 54326748 |
| ATP6V1H | 1 | 0.142857 | 0 | 0 | 0 | ATP6V1H | 8 | 8q11.23 | 54790668 | 54918404 |
| RGS20 | 1 | 0.142857 | 0 | 0 | 0 | RGS20 | 8 | 8q11.23 | 54926921 | 55034415 |
| TGS1 | 1 | 0.142857 | 0 | 0 | 0 | TGS1 | 8 | 8q12.1 | 56848345 | 56900560 |
| LYN | 1 | 0.142857 | 0 | 0 | 0 | LYN | 8 | 8q12.1 | 56954940 | 57086495 |
| RPS20 | 1 | 0.142857 | 0 | 0 | 0 | RPS20 | 8 | 8q12.1 | 57143293 | 57149695 |
| SNORD54 | 1 | 0.142857 | 0 | 0 | 0 | SNORD54 | 8 | 8q12.1 | 57148952 | 57149016 |
| MOS | 1 | 0.142857 | 0 | 0 | 0 | MOS | 8 | 8q12.1 | 57188055 | 57189096 |
| PLAG1 | 1 | 0.142857 | 0 | 0 | 0 | PLAG1 | 8 | 8q12.1 | 57236022 | 57286414 |
| CHCHD7 | 1 | 0.142857 | 0 | 0 | 0 | CHCHD7 | 8 | 8q12.1 | 57286869 | 57293731 |
| CSPP1 | 1 | 0.190476 | 0 | 0 | 0 | CSPP1 | 8 | 8q13.2 | 68139157 | 68271051 |
| ARFGEF1 | 1 | 0.142857 | 0 | 0 | 0 | ARFGEF1 | 8 | 8q13.2 | 68272451 | 68418467 |

TABLE 4-continued

Gene list for predicting prostate cancer relapse using AT

| Symbol | freq. use | freq. amp. case | freq. del. case | freq. amp. control | freq. del. control | Gene. Symbol | chromo-some | cytoband | Transcript. start | Transcript. end |
|---|---|---|---|---|---|---|---|---|---|---|
| CPA6 | 1 | 0.142857 | 0 | 0 | 0 | CPA6 | 8 | 8q13.2 | 68496959 | 68821175 |
| TERF1 | 1 | 0.142857 | 0.047619 | 0 | 0 | TERF1 | 8 | 8q21.11 | 74083651 | 74122542 |
| MRPS28 | 1 | 0.142857 | 0.047619 | 0 | 0.111111 | MRPS28 | 8 | 8q21.13 | 80993650 | 81105062 |
| TPD52 | 1 | 0.142857 | 0.047619 | 0 | 0.111111 | TPD52 | 8 | 8q21.13 | 81109660 | 81155566 |
| ZNF704 | 1 | 0.190476 | 0 | 0 | 0.111111 | ZNF704 | 8 | 8q21.13 | 81713324 | 81949572 |
| PAG1 | 1 | 0.142857 | 0 | 0 | 0.111111 | PAG1 | 8 | 8q21.13 | 82042601 | 82186859 |
| PDP1 | 1 | 0.190476 | 0 | 0 | 0 | PDP1 | 8 | 8q22.1 | 94998259 | 95007471 |
| PTDSS1 | 1 | 0.190476 | 0 | 0 | 0 | PTDSS1 | 8 | 8q22.1 | 97343343 | 97415951 |
| SDC2 | 1 | 0.190476 | 0 | 0 | 0 | SDC2 | 8 | 8q22.1 | 97575058 | 97693214 |
| PGCP | 1 | 0.142857 | 0.047619 | 0 | 0 | PGCP | 8 | 8q22.1 | 97726675 | 98224899 |
| LAPTM4B | 1 | 0.190476 | 0 | 0 | 0 | LAPTM4B | 8 | 8q22.1 | 98856985 | 98934007 |
| MATN2 | 1 | 0.190476 | 0 | 0 | 0 | MATN2 | 8 | 8q22.1 | 98950487 | 99118123 |
| C8orf47 | 1 | 0.190476 | 0 | 0 | 0 | C8orf47 | 8 | 8q22.2 | 99145926 | 99175015 |
| NIPAL2 | 1 | 0.142857 | 0.047619 | 0 | 0 | NIPAL2 | 8 | 8q22.2 | 99273563 | 99375798 |
| STK3 | 1 | 0.142857 | 0.047619 | 0 | 0 | STK3 | 8 | 8q22.2 | 99536037 | 99907086 |
| VPS13B | 1 | 0.142857 | 0.047619 | 0 | 0 | VPS13B | 8 | 8q22.2 | 1E+08 | 1E+08 |
| HAS2 | 1 | 0.142857 | 0 | 0 | 0 | HAS2 | 8 | 3q24.13 | 1.23E+08 | 1.23E+08 |
| ZHX2 | 1 | 0.285714 | 0 | 0 | 0 | ZHX2 | 8 | 8q24.13 | 1.24E+08 | 1.24E+08 |
| DERL1 | 1 | 0.285714 | 0 | 0 | 0 | DERL1 | 8 | 8q24.13 | 1.24E+08 | 1.24E+08 |
| WDR67 | 1 | 0.285714 | 0 | 0 | 0 | WDR67 | 8 | 8q24.13 | 1.24E+08 | 1.24E+08 |
| ASAP1 | 1 | 0.142857 | 0 | 0 | 0 | ASAP1 | 8 | 8q24.21 | 1.31E+08 | 1.31E+08 |
| ADCY8 | 1 | 0.142857 | 0 | 0 | 0 | ADCY8 | 8 | 8q24.22 | 1.32E+08 | 1.32E+08 |
| ZFAT | 1 | 0.190476 | 0 | 0 | 0 | ZFAT | 8 | 8q24.22 | 1.36E+08 | 1.36E+08 |
| ZFATAS | 1 | 0.190476 | 0 | 0 | 0 | ZFATAS | 8 | 8q24.22 | 1.36E+08 | 1.36E+08 |
| KHDRBS3 | 1 | 0.142857 | 0 | 0 | 0 | KHDRBS3 | 8 | 8q24.23 | 1.37E+08 | 1.37E+08 |
| FAM135B | 1 | 0.142857 | 0.047619 | 0 | 0 | FAM135B | 8 | 8q24.23 | 1.39E+08 | 1.4E+08 |
| COL22A1 | 1 | 0.333333 | 0 | 0 | 0 | COL22A1 | 8 | 8q24.23 | 1.4E+08 | 1.4E+08 |
| GPNMB | 1 | 0.142857 | 0 | 0 | 0 | GPNMB | 7 | 7p15.3 | 23252841 | 23281255 |
| RPS2P32 | 1 | 0.190476 | 0 | 0 | 0 | RPS2P32 | 7 | 7p153 | 23496532 | 23497555 |
| C7orf46 | 1 | 0.190476 | 0 | 0 | 0 | C7orf46 | 7 | 7p15.3 | 23686274 | 23708795 |
| HOXA3 | 1 | 0.190476 | 0 | 0 | 0 | HOXA3 | 7 | 7p15.2 | 27112334 | 27125740 |
| HOXA4 | 1 | 0.190476 | 0 | 0 | 0 | HOXA4 | 7 | 7p15.2 | 27134651 | 27136925 |
| EVX1 | 1 | 0.190476 | 0 | 0 | 0 | EVX1 | 7 | 7p15.2 | 27248689 | 27252718 |
| HIBADH | 1 | 0.190476 | 0 | 0 | 0 | HIBADH | 7 | 7p15.2 | 27531586 | 27669128 |
| C7orf25 | 1 | 0.190476 | 0 | 0 | 0 | C7orf25 | 7 | 7p14.1 | 42915397 | 42918215 |
| PSMA2 | 1 | 0.190476 | 0 | 0 | 0 | PSMA2 | 7 | 7p14.1 | 42922987 | 42938331 |
| HECW1 | 1 | 0.190476 | 0 | 0 | 0 | HECW1 | 7 | 7p14.1 | 43118723 | 43569464 |
| C7orf44 | 1 | 0.190476 | 0 | 0 | 0 | C7orf44 | 7 | 7p13 | 43645384 | 43735609 |
| BLVRA | 1 | 0.190476 | 0 | 0 | 0 | BLVRA | 7 | 7p13 | 43754797 | 43813467 |
| PEX1 | 1 | 0.190476 | 0 | 0 | 0 | PEX1 | 7 | 7q21.2 | 91954273 | 91995782 |
| C7orf64 | 1 | 0.190476 | 0 | 0 | 0 | C7orf64 | 7 | 7q21.2 | 91996023 | 92004760 |
| MGC16142 | 1 | 0.190476 | 0 | 0 | 0 | MGC16142 | 7 | 7q21.2 | 92005725 | 92007014 |
| FAM133B | 1 | 0.190476 | 0 | 0 | 0 | FAM133B | 7 | 7q21.2 | 92028008 | 92057643 |
| SLC26A5 | 1 | 0.142857 | 0 | 0 | 0 | SLC26A5 | 7 | 7q22.1 | 1.03E+08 | 1.03E+08 |
| RELN | 1 | 0.142857 | 0 | 0 | 0 | RELN | 7 | 7q22.1 | 1.03E+08 | 1.03E+08 |
| ORC5L | 1 | 0.142857 | 0 | 0 | 0 | ORC5L | 7 | 7q22.1 | 1.04E+08 | 1.046E+08 |
| LHFPL3 | 1 | 0.142857 | 0 | 0 | 0 | LHFPL3 | 7 | 7q22.1 | 1.04E+08 | 1.04E+08 |
| STRA8 | 1 | 0.142857 | 0 | 0 | 0 | STRA8 | 7 | 7q33 | 1.35E+08 | 1.35E+08 |
| CNOT4 | 1 | 0.142857 | 0 | 0 | 0 | CNOT4 | 7 | 7q33 | 1.35E+08 | 1.35E+08 |
| MRPS33 | 1 | 0.142857 | 0 | 0 | 0 | MRPS33 | 7 | 7q34 | 1.4E+08 | 1.4E+08 |
| HIVEP1 | 1 | 0.142857 | 0 | 0 | 0 | HIVEP1 | 6 | 6p24.1 | 12120710 | 12273219 |
| MRS2 | 1 | 0.142857 | 0 | 0 | 0 | MRS2 | 6 | 6p22.2 | 24511132 | 24533796 |
| GPLD1 | 1 | 0.142857 | 0 | 0 | 0 | GPLD1 | 6 | 6p22.2 | 24536384 | 24597830 |
| ALDH5A1 | 1 | 0.142857 | 0 | 0 | 0 | ALDH5A1 | 6 | 6p22.2 | 24603176 | 24645415 |
| SUPT3H | 1 | 0 | 0.190476 | 0.074074 | 0 | SUPT3H | 6 | 6p21.1 | 44904448 | 45453649 |
| AHI1 | 1 | 0 | 0.142857 | 0 | 0 | AHI1 | 6 | 6q23.3 | 1.36E+08 | 1.36E+08 |
| C6orf217 | 1 | 0 | 0.142857 | 0 | 0 | C6orf217 | 6 | 6q23.3 | 1.36E+08 | 1.36E+08 |
| PDE7B | 1 | 0 | 0.142857 | 0 | 0 | PDE7B | 6 | 6q23.3 | 1.36E+08 | 1.37E+08 |
| UTRN | 1 | 0.142857 | 0 | 0 | 0 | UTRN | 6 | 6q24.2 | 1.45E+08 | 1.45E+08 |
| GRM1 | 1 | 0 | 0.142857 | 0 | 0 | GRM1 | 6 | 6q24.3 | 1.46E+08 | 1.47E+08 |
| OPRM1 | 1 | 0 | 0.190476 | 0 | 0 | OPRM1 | 6 | 6q25.2 | 1.54E+08 | 1.54E+08 |
| CNKSR3 | 1 | 0.190476 | 0 | 0 | 0 | CNKSR3 | 6 | 6q25.2 | 1.55E+08 | 1.55E+08 |
| RBM16 | 1 | 0.190476 | 0 | 0 | 0 | RBM16 | 6 | 6q25.2 | 1.55E+08 | 1.55E+08 |
| TIAM2 | 1 | 0.190476 | 0 | 0 | 0 | TIAM2 | 6 | 6q25.2 | 1.55E+08 | 1.56E+08 |
| TFB1M | 1 | 0.190476 | 0 | 0 | 0 | TFB1M | 6 | 6q25.3 | 1.56E+08 | 1.56E+08 |
| CLDN20 | 1 | 0.190476 | 0 | 0 | 0 | CLDN20 | 6 | 6q25.3 | 1.56E+08 | 1.56E+08 |
| ARID1B | 1 | 0.190476 | 0 | 0 | 0 | ARID1B | 6 | 6q25.3 | 1.57E+08 | 1.58E+08 |
| ZDHHC14 | 1 | 0.190476 | 0 | 0 | 0 | ZDHHC14 | 6 | 6q25.3 | 1.58E+08 | 1.58E+08 |
| SLC22A2 | 1 | 0.142857 | 0 | 0 | 0 | SLC22A2 | 6 | 6q25.3 | 1.61E+08 | 1.61E+08 |
| PLG | 1 | 0.142857 | 0 | 0 | 0 | PLG | 6 | 6q26 | 1.61E+08 | 1.61E+08 |
| BASP1 | 1 | 0.142857 | 0 | 0 | 0.037037 | BASP1 | 5 | 5p15.1 | 17270750 | 17329944 |
| C5orf22 | 1 | 0.190476 | 0 | 0 | 0 | C5orf22 | 5 | 5p13.3 | 31568130 | 31590923 |
| ZFR | 1 | 0.190476 | 0 | 0 | 0 | ZFR | 5 | 5p13.3 | 32390213 | 32480602 |
| C5orf42 | 1 | 0.142857 | 0 | 0 | 0 | C5orf42 | 5 | 5p13.2 | 37142087 | 37285288 |

TABLE 4-continued

Gene list for predicting prostate cancer relapse using AT

| Symbol | freq. use | freq. amp. case | freq. del. case | freq. amp. control | freq. del. control | Gene. Symbol | chromo- some | cytoband | Transcript. start | Transcript. end |
|---|---|---|---|---|---|---|---|---|---|---|
| WDR70 | 1 | 0.190476 | 0 | 0 | 0 | WDR70 | 5 | 5p13.2 | 37415169 | 37788532 |
| F2RL2 | 1 | 0 | 0.142857 | 0.037037 | 0 | F2RL2 | 5 | 5q13.3 | 75947063 | 75954997 |
| TRIM36 | 1 | 0.047619 | 0.142857 | 0 | 0 | TRIM36 | 5 | 5q22.3 | 1.14E+08 | 1.15E+08 |
| DMXL1 | 1 | 0.190476 | 0.047619 | 0 | 0 | DMXL1 | 5 | 5q23.1 | 1.18E+08 | 1.19E+08 |
| SGCD | 1 | 0 | 0.190476 | 0 | 0 | SGCD | 5 | 5q33.3 | 1.56E+08 | 1.56E+08 |
| HTRA3 | 1 | 0.47619 | 0.142857 | 0.703704 | 0 | HTRA3 | 4 | 4p16.1 | 8322392 | 8359735 |
| NCAPG | 1 | 0 | 0.238095 | 0 | 0 | NCAPG | 4 | 4p15.32 | 17421623 | 17455586 |
| LCORL | 1 | 0 | 0.238095 | 0 | 0 | LCORL | 4 | 4p15.32 | 17453938 | 17532582 |
| TLR1 | 1 | 0.190476 | 0 | 0 | 0 | TLR1 | 4 | 4p14 | 38474271 | 38482808 |
| TLR6 | 1 | 0.190476 | 0 | 0 | 0 | TLR6 | 4 | 4p14 | 38501728 | 38534833 |
| FAM114A1 | 1 | 0.190476 | 0 | 0 | 0 | FAM114A1 | 4 | 4p14 | 38545832 | 38621822 |
| MIR574 | 1 | 0.190476 | 0 | 0 | 0 | MIR574 | 4 | 4p14 | 38546048 | 38546144 |
| TMEM156 | 1 | 0.190476 | 0 | 0 | 0 | TMEM156 | 4 | 4p14 | 38644836 | 38710437 |
| KLHL5 | 1 | 0.190476 | 0 | 0 | 0 | KLHL5 | 4 | 4p14 | 38723054 | 38800225 |
| WDR19 | 1 | 0.190476 | 0 | 0 | 0 | WDR19 | 4 | 4p14 | 38860419 | 38963826 |
| RFC1 | 1 | 0.190476 | 0 | 0 | 0 | RFC1 | 4 | 4p14 | 38965471 | 39044391 |
| KLB | 1 | 0.238095 | 0 | 0 | 0 | KLB | 4 | 4p14 | 39084868 | 39129547 |
| RPL9 | 1 | 0.238095 | 0 | 0 | 0 | RPL9 | 4 | 4p14 | 39132140 | 39136964 |
| LIAS | 1 | 0.238095 | 0 | 0 | 0 | LIAS | 4 | 4p14 | 39137060 | 39155667 |
| LOC401127 | 1 | 0.238095 | 0 | 0 | 0 | LOC401127 | 4 | 4p14 | 39158270 | 39159917 |
| UGDH | 1 | 0.238095 | 0 | 0 | 0 | UGDH | 4 | 4p14 | 39176770 | 39205607 |
| C4orf34 | 1 | 0.238095 | 0 | 0 | 0 | C4orf34 | 4 | 4p14 | 39228941 | 39316877 |
| EPGN | 1 | 0 | 0.142857 | 0 | 0 | EPGN | 4 | 4q13.3 | 75393068 | 75398172 |
| AREG | 1 | 0 | 0.142857 | 0 | 0 | AREG | 4 | 4q13.3 | 75699653 | 75709510 |
| BTC | 1 | 0 | 0.142857 | 0 | 0 | BTC | 4 | 4q13.3 | 75890472 | 75938907 |
| BMP3 | 1 | 0 | 0.142857 | 0 | 0 | BMP3 | 4 | 4q21.21 | 82171143 | 82197710 |
| PRKG2 | 1 | 0 | 0.142857 | 0 | 0 | PRKG2 | 4 | 4q21.21 | 82228861 | 82345240 |
| RASGEF1B | 1 | 0 | 0.142857 | 0 | 0 | RASGEF1B | 4 | 4q21.21 | 82567243 | 82612086 |
| TBC1D9 | 1 | 0 | 0.142857 | 0 | 0 | TBC1D9 | 4 | 4q31.21 | 1.42E+08 | 1.42E+08 |
| RNF150 | 1 | 0 | 0.142857 | 0 | 0 | RNF150 | 4 | 4q31.21 | 1.42E+08 | 1.42E+08 |
| IL15 | 1 | 0 | 0.142857 | 0 | 0 | IL15 | 4 | 4q31.21 | 1.43E+08 | 1.43E+08 |
| INPP4B | 1 | 0 | 0.142857 | 0 | 0 | INPP4B | 4 | 4q31.21 | 1.43E+08 | 1.44E+08 |
| RPS3A | 1 | 0.142857 | 0 | 0 | 0 | RPS3A | 4 | 4q31.3 | 1.52E+08 | 1.52E+08 |
| SNORD73A | 1 | 0.142857 | 0 | 0 | 0 | SNORD73A | 4 | 4q31.3 | 1.52E+08 | 1.52E+08 |
| SH3D19 | 1 | 0.142857 | 0 | 0 | 0 | SH3D19 | 4 | 4q31.3 | 1.52E+08 | 1.52E+08 |
| SUMF1 | 1 | 0 | 0.142857 | 0 | 0 | SUMF1 | 3 | 3p25.2 | 4377829 | 4483967 |
| EGOT | 1 | 0.190476 | 0 | 0 | 0 | EGOT | 3 | 3p26.2 | 4765878 | 4768275 |
| BHLHE40 | 1 | 0.333333 | 0 | 0 | 0 | BHLHE40 | 3 | 3p26.2 | 4996097 | 5001864 |
| TPRXL | 1 | 0.190476 | 0.142857 | 0.259259 | 0 | TPRXL | 3 | 3p25.1 | 13953808 | 14082481 |
| TBC1D5 | 1 | 0 | 0.142857 | 0 | 0 | TBC1D5 | 3 | 3p24.3 | 17173659 | 17759245 |
| RAB5A | 1 | 0.142857 | 0.095238 | 0 | 0.037037 | RAB5A | 3 | 3p24.3 | 19963576 | 20001663 |
| C3orf48 | 1 | 0.142857 | 0.095238 | 0 | 0.037037 | C3orf48 | 3 | 3p24.3 | 19996458 | 20028770 |
| KAT2B | 1 | 0.142857 | 0.095238 | 0 | 0.037037 | KAT2B | 3 | 3p24.3 | 20056528 | 20170901 |
| NGLY1 | 1 | 0.047619 | 0.142857 | 0 | 0 | NGLY1 | 3 | 3p24.2 | 25735440 | 25799994 |
| OSBPL10 | 1 | 0.190476 | 0.095238 | 0 | 0.037037 | OSBPL10 | 3 | 3p23 | 31677321 | 31998243 |
| MITF | 1 | 0 | 0.142857 | 0 | 0 | MITF | 3 | 3p14.1 | 69871323 | 70100178 |
| MIR1284 | 1 | 0.142857 | 0.047619 | 0 | 0 | MIR1284 | 3 | 3p14.1 | 71673811 | 71673931 |
| CEP97 | 1 | 0.142857 | 0.047619 | 0 | 0.074074 | CEP97 | 3 | 3q12.3 | 1.03E+08 | 1.03E+08 |
| FAM55C | 1 | 0.142857 | 0.047619 | 0 | 0.074074 | FAM55C | 3 | 3q12.3 | 1.03E+08 | 1.03E+08 |
| LOC151658 | 1 | 0 | 0.142857 | 0 | 0 | LOC151658 | 3 | 3q13.12 | 1.09E+08 | 1.09E+08 |
| LOC285205 | 1 | 0 | 0.142857 | 0 | 0 | LOC285205 | 3 | 3q13.12 | 1.09E+08 | 1.09E+08 |
| HHLA2 | 1 | 0 | 0.142857 | 0 | 0 | HHLA2 | 3 | 3q13.13 | 1.1E+08 | 1.1E+08 |
| MYH15 | 1 | 0 | 0.142857 | 0 | 0 | MYH15 | 3 | 3q13.13 | 1.1E+08 | 1.1E+08 |
| KIAA1524 | 1 | 0 | 0.142857 | 0 | 0 | KIAA1524 | 3 | 3q13.13 | 1.1E+08 | 1.1E+08 |
| DZIP3 | 1 | 0 | 0.142857 | 0 | 0 | DZIP3 | 3 | 3q13.13 | 1.1E+08 | 1.1E+08 |
| STXBP5L | 1 | 0 | 0.142857 | 0 | 0 | STXBP5L | 3 | 3q13.33 | 1.22E+08 | 1.23E+08 |
| SPSB4 | 1 | 0.142857 | 0 | 0 | 0 | SPSB4 | 3 | 3q23 | 1.42E+08 | 1.42E+08 |
| ACPL2 | 1 | 0.142857 | 0 | 0 | 0 | ACPL2 | 3 | 3q23 | 1.42E+08 | 1.42E+08 |
| ZBTB38 | 1 | 0.142857 | 0 | 0 | 0 | ZBTB38 | 3 | 3q23 | 1.43E+08 | 1.43E+08 |
| RNF7 | 1 | 0.238095 | 0 | 0 | 0 | RNF7 | 3 | 3q23 | 1.43E+08 | 1.43E+08 |
| GRK7 | 1 | 0.238095 | 0 | 0 | 0 | GRK7 | 3 | 3q23 | 1.43E+08 | 1.43E+08 |
| ATP1B3 | 1 | 0.238095 | 0 | 0 | 0 | ATP1B3 | 3 | 3q23 | 1.43E+08 | 1.43E+08 |
| TFDP2 | 1 | 0.238095 | 0 | 0 | 0 | TFDP2 | 3 | 3q23 | 1.43E+08 | 1.43E+08 |
| GK5 | 1 | 0.238095 | 0 | 0 | 0 | GK5 | 3 | 3q23 | 1.43E+08 | 1.43E+08 |
| XRN1 | 1 | 0.238095 | 0 | 0 | 0 | XRN1 | 3 | 3q23 | 1.44E+08 | 1.44E+08 |
| ATR | 1 | 0.238095 | 0 | 0 | 0 | ATR | 3 | 3q23 | 1.44E+08 | 1.44E+08 |
| PLS1 | 1 | 0.190476 | 0 | 0 | 0 | PLS1 | 3 | 3q23 | 1.44E+08 | 1.44E+08 |
| PCOLCE2 | 1 | 0.190476 | 0 | 0 | 0 | PCOLCE2 | 3 | 3q23 | 1.44E+08 | 1.44E+08 |
| LOC201651 | 1 | 0 | 0.142857 | 0 | 0 | LOC201651 | 3 | 3q25.1 | 1.53E+08 | 1.53E+08 |
| AADAC | 1 | 0 | 0.142857 | 0 | 0 | AADAC | 3 | 3q25.1 | 1.53E+08 | 1.53E+08 |
| LOC401093 | 1 | 0 | 0.142857 | 0 | 0 | LOC401093 | 3 | 3q25.1 | 1.53E+08 | 1.53E+08 |
| MBNL1 | 1 | 0 | 0.142857 | 0 | 0 | MBNL1 | 3 | 3q25.1 | 1.53E+08 | 1.54E+08 |
| P2RY1 | 1 | 0 | 0.142857 | 0 | 0 | P2RY1 | 3 | 3q25.2 | 1.54E+08 | 1.54E+08 |
| LEKR1 | 1 | 0 | 0.142857 | 0 | 0 | LEKR1 | 3 | 3q25.31 | 1.58E+08 | 1.58E+08 |

TABLE 4-continued

Gene list for predicting prostate cancer relapse using AT

| Symbol | freq. use | freq. amp. case | freq. del. case | freq. amp. control | freq. del. control | Gene. Symbol | chromosome | cytoband | Transcript. start | Transcript. end |
|---|---|---|---|---|---|---|---|---|---|---|
| GFM1 | 1 | 0 | 0.142857 | 0 | 0 | GFM1 | 3 | 3q25.32 | 1.6E+08 | 1.6E+08 |
| LXN | 1 | 0 | 0.142857 | 0 | 0 | LXN | 3 | 3q25.32 | 1.6E+08 | 1.6E+08 |
| KPNA4 | 1 | 0 | 0.190476 | 0 | 0 | KPNA4 | 3 | 3q26.1 | 1.62E+08 | 1.62E+08 |
| PPM1L | 1 | 0 | 0.142857 | 0 | 0 | PPM1L | 3 | 3q26.1 | 1.62E+08 | 1.62E+08 |
| KCNMB2 | 1 | 0 | 0.190476 | 0 | 0 | KCNMB2 | 3 | 3q26.32 | 1.8E+08 | 1.8E+08 |
| ZMAT3 | 1 | 0 | 0.190476 | 0 | 0 | ZMAT3 | 3 | 3q26.32 | 1.8E+08 | 1.8E+08 |
| PIK3CA | 1 | 0 | 0.190476 | 0 | 0 | PIK3CA | 3 | 3q26.32 | 1.8E+08 | 1.8E+08 |
| PEX5L | 1 | 0 | 0.142857 | 0 | 0 | PEX5L | 3 | 3q26.33 | 1.81E+08 | 1.81E+08 |
| CCDC39 | 1 | 0.047619 | 0.142857 | 0 | 0 | CCDC39 | 3 | 3q26.33 | 1.82E+08 | 1.82E+08 |
| FXR1 | 1 | 0.142857 | 0.047619 | 0 | 0 | FXR1 | 3 | 3q26.33 | 1.82E+08 | 1.82E+08 |
| ATP11B | 1 | 0.142857 | 0 | 0 | 0 | ATP11B | 3 | 3q26.33 | 1.84E+08 | 1.84E+08 |
| UTS2D | 1 | 0 | 0.142857 | 0 | 0 | UTS2D | 3 | 3q28 | 1.92E+08 | 1.93E+08 |
| PYDC2 | 1 | 0 | 0.142857 | 0 | 0 | PYDC2 | 3 | 3q28 | 1.93E+08 | 1.93E+08 |
| VSNL1 | 1 | 0.047619 | 0.142857 | 0 | 0 | VSNL1 | 2 | 2p24.2 | 17585288 | 17701188 |
| KLHL29 | 1 | 0.190476 | 0 | 0 | 0 | KLHL29 | 2 | 2p24.1 | 23461803 | 23784986 |
| MTIF2 | 1 | 0.190476 | 0 | 0 | 0 | MTIF2 | 2 | 2p16.1 | 55317260 | 55349820 |
| CCDC88A | 1 | 0.190476 | 0 | 0 | 0 | CCDC88A | 2 | 2p16.1 | 55368484 | 55500562 |
| MIR217 | 1 | 0 | 0.142857 | 0 | 0 | MIR217 | 2 | 2p16.1 | 56063606 | 56063716 |
| MIR216A | 1 | 0 | 0.142857 | 0 | 0 | MIR216A | 2 | 2p16.1 | 56069590 | 56069699 |
| MIR216B | 1 | 0 | 0.142857 | 0 | 0 | MIR216B | 2 | 2p16.1 | 56081354 | 56081435 |
| CCDC85A | 1 | 0 | 0.142857 | 0 | 0 | CCDC85A | 2 | 2p16.1 | 56264762 | 56466814 |
| BCL11A | 1 | 0.238095 | 0 | 0 | 0 | BCL11A | 2 | 2p16.1 | 60531806 | 60634138 |
| FAM161A | 1 | 0.142857 | 0 | 0 | 0 | FAM161A | 2 | 2p15 | 61905487 | 61934783 |
| CCT4 | 1 | 0.142857 | 0 | 0 | 0 | CCT4 | 2 | 2p15 | 61948766 | 61969296 |
| COMMD1 | 1 | 0.142857 | 0 | 0 | 0 | COMMD1 | 2 | 2p15 | 61986307 | 62216710 |
| B3GNT2 | 1 | 0.142857 | 0 | 0 | 0 | B3GNT2 | 2 | 2p15 | 62276766 | 62305371 |
| IL18RAP | 1 | 0.142857 | 0 | 0 | 0 | IL18RAP | 2 | 2q12.1 | 1.02E+08 | 1.02E+08 |
| SLC9A4 | 1 | 0.142857 | 0 | 0 | 0 | SLC9A4 | 2 | 2q12.1 | 1.02E+08 | 1.03E+08 |
| TNFA1P6 | 1 | 0.190475 | 0 | 0 | 0 | TNFA1P6 | 2 | 2q23.3 | 1.52E+08 | 1.52E+08 |
| STAM2 | 1 | 0 | 0.142857 | 0 | 0 | STAM2 | 2 | 2q23.3 | 1.53E+08 | 1.53E+08 |
| EVX2 | 1 | 0.142857 | 0 | 0 | 0 | EVX2 | 2 | 2q31.1 | 1.77E+08 | 1.77E+08 |
| HOXD13 | 1 | 0.142857 | 0 | 0 | 0 | HOXD13 | 2 | 2q31.1 | 1.77E+08 | 1.77E+08 |
| HOXD12 | 1 | 0.142857 | 0 | 0 | 0 | HOXD12 | 2 | 2q31.1 | 1.77E+08 | 1.77E+08 |
| HOXD11 | 1 | 0.142857 | 0 | 0 | 0 | HOXD11 | 2 | 2q31.1 | 1.77E+08 | 1.77E+08 |
| HOXD10 | 1 | 0.142857 | 0 | 0 | 0 | HOXD10 | 2 | 2q31.1 | 1.77E+08 | 1.77E+08 |
| HOXD9 | 1 | 0.142857 | 0 | 0 | 0 | HOXD9 | 2 | 2q31.1 | 1.77E+08 | 1.77E+08 |
| HOXD8 | 1 | 0.142857 | 0 | 0 | 0 | HOXD8 | 2 | 2q31.1 | 1.77E+08 | 1.77E+08 |
| CD28 | 1 | 0.142857 | 0 | 0 | 0 | CD28 | 2 | 2q33.2 | 2.04E+08 | 2.04E+08 |
| CTLA4 | 1 | 0.142857 | 0 | 0 | 0 | CTLA4 | 2 | 2q33.2 | 2.04E+08 | 2.04E+08 |
| ICOS | 1 | 0.142857 | 0 | 0 | 0 | ICOS | 2 | 2q33.2 | 2.05E+08 | 2.05E+08 |
| PLEKHM3 | 1 | 0.142857 | 0 | 0 | 0.037037 | PLEKHM3 | 2 | 2q33.3 | 2.08E+08 | 2.09E+08 |
| CRYGD | 1 | 0.142857 | 0 | 0 | 0 | CRYGD | 2 | 2q33.3 | 2.09E+08 | 2.09E+08 |
| CRYGC | 1 | 0.142857 | 0 | 0 | 0 | CRYGC | 2 | 2q33.3 | 2.09E+08 | 2.09E+08 |
| PIKFYVE | 1 | 0.142857 | 0 | 0 | 0 | PIKFYVE | 2 | 2q33.3 | 2.09E+08 | 2.09E+08 |
| KIAA1486 | 1 | 0 | 0.142857 | 0 | 0 | KIAA1486 | 2 | 2q36.3 | 2.26E+08 | 2.26E+08 |
| PDE48 | 1 | 0 | 0.142857 | 0 | 0 | PDE48 | 1 | 1p31.3 | 66030781 | 66612851 |
| IL23R | 1 | 0.142857 | 0 | 0 | 0 | IL23R | 1 | 1p31.3 | 67404757 | 67498239 |
| IL12RB2 | 1 | 0.142857 | 0 | 0 | 0 | IL12RB2 | 1 | 1p31.3 | 67545635 | 67635172 |
| CCBL2 | 1 | 0.142857 | 0 | 0 | 0 | CCBL2 | 1 | 1p22.2 | 89174044 | 89231232 |
| RPL5 | 1 | 0.142857 | 0 | 0 | 0 | RPL5 | 1 | 1p22.1 | 93070182 | 93080070 |
| SNORD21 | 1 | 0.142857 | 0 | 0 | 0 | SNORD21 | 1 | 1p22.1 | 93075434 | 93075529 |
| FAM69A | 1 | 0.142857 | 0 | 0 | 0 | FAM69A | 1 | 1p22.1 | 93080309 | 93199668 |
| MTF2 | 1 | 0.142857 | 0 | 0 | 0 | MTF2 | 1 | 1p22.1 | 93317380 | 93377225 |
| DR1 | 1 | 0.142857 | 0 | 0 | 0 | DR1 | 1 | 1p22.1 | 93584066 | 93600737 |
| FNBP1L | 1 | 0.142857 | 0 | 0 | 0 | FNBP1L | 1 | 1p22.1 | 93686427 | 93792807 |
| RC3H1 | 1 | 0.142857 | 0 | 0 | 0 | RC3H1 | 1 | 1q25.1 | 1.72E+08 | 1.72E+08 |
| GPR52 | 1 | 0 | 0.142857 | 0 | 0 | GPR52 | 1 | 1q25.1 | 1.73E+08 | 1.73E+08 |
| C1orf49 | 1 | 0.142857 | 0 | 0 | 0 | C1orf49 | 1 | 1q25.2 | 1.77E+08 | 1.77E+08 |
| C1orf220 | 1 | 0.142857 | 0 | 0 | 0 | C1orf220 | 1 | 1q25.2 | 1.77E+08 | 1.77E+08 |
| FAM20B | 1 | 0.238095 | 0 | 0 | 0 | FAM20B | 1 | 1q25.2 | 1.77E+08 | 1.77E+08 |
| ABL2 | 1 | 0.238095 | 0 | 0 | 0 | ABL2 | 1 | 1q25.2 | 1.77E+08 | 1.77E+08 |
| SOAT1 | 1 | 0.190476 | 0 | 0 | 0 | SOAT1 | 1 | 1q25.2 | 1.78E+08 | 1.78E+08 |
| C1orf125 | 1 | 0.190476 | 0 | 0 | 0 | C1orf125 | 1 | 1425.2 | 1.78E+08 | 1.78E+08 |
| NPHS2 | 1 | 0.190476 | 0 | 0 | 0 | NPHS2 | 1 | 1q25.2 | 1.78E+08 | 1.78E+08 |
| TDRD5 | 1 | 0.142857 | 0.047619 | 0 | 0 | TDRD5 | 1 | 1q25.2 | 1.78E+08 | 1.78E+08 |
| FAM163A | 1 | 0.190476 | 0 | 0 | 0 | FAM163A | 1 | 1q25.2 | 1.78E+08 | 1.78E+08 |
| TOR1AIP2 | 1 | 0.190476 | 0 | 0 | 0 | TOR1AIP2 | 1 | 1q25.2 | 1.78E+08 | 1.78E+08 |
| CEP350 | 1 | 0.142857 | 0.047619 | 0 | 0 | CEP350 | 1 | 1q25.2 | 1.78E+08 | 1.78E+08 |
| STX6 | 1 | 0.142857 | 0 | 0 | 0 | STX6 | 1 | 1q25.3 | 1.79E+08 | 1.79E+08 |
| MR1 | 1 | 0.142857 | 0 | 0 | 0 | MR1 | 1 | 1q25.3 | 1.79E+08 | 1.79E+08 |
| OR2M5 | 1 | 0.095238 | 0.190476 | 0.111111 | 0 | OR2M5 | 1 | 1q44 | 2.46E+08 | 2.46E+08 |
| OR2M2 | 1 | 0.095238 | 0.190476 | 0.111111 | 0 | OR2M2 | 1 | 1q44 | 2.46E+08 | 2.46E+08 |
| OR2T6 | 1 | 0.095238 | 0.190476 | 0.111111 | 0 | OR2T6 | 1 | 1q44 | 2.47E+08 | 2.47E+08 |
| RFX7 | 0.4375 | 0.095238 | 0.095238 | 0 | 0 | RFX7 | 15 | 15q21.3 | 54170023 | 54322776 |

TABLE 4-continued

Gene list for predicting prostate cancer relapse using AT

| Symbol | freq. use | freq. amp. case | freq. del. case | freq. amp. control | freq. del. control | Gene. Symbol | chromo- some | cytoband | Transcript. start | Transcript. end |
|---|---|---|---|---|---|---|---|---|---|---|
| ZNF462 | 0.4375 | 0.095238 | 0.095238 | 0 | 0 | ZNF462 | 9 | 9q31.2 | 1.09E+08 | 1.09E+08 |
| IPCEF1 | 0.4375 | 0.095238 | 0.095238 | 0 | 0 | IPCEF1 | 6 | 6q25.2 | 1.55E+08 | 1.55E+08 |
| TLR10 | 0.4375 | 0.095238 | 0.095238 | 0 | 0 | TLR10 | 4 | 4p14 | 38450647 | 38460985 |
| PDZRN3 | 0.4375 | 0.095238 | 0.095238 | 0 | 0 | PDZRN3 | 3 | 3p13 | 73514342 | 73756763 |
| SR140 | 0.4375 | 0.095238 | 0.095238 | 0 | 0 | SR140 | 3 | 3q23 | 1.44E+08 | 1.44E+08 |
| CCDC50 | 0.4375 | 0.095238 | 0.095238 | 0 | 0 | CCDC50 | 3 | 3q28 | 1.93E+08 | 1.93E+08 |
| FCRLB | 0.4375 | 0.095238 | 0.095238 | 0 | 0 | FCRLB | 1 | 1q23.3 | 1.6E+08 | 1.6E+08 |
| ALG5 | 0.416667 | 0.142857 | 0.095238 | 0.037037 | 0 | ALG5 | 13 | 13q13.3 | 36421910 | 36471505 |
| NEDD9 | 0.416667 | 0.190476 | 0.095233 | 0.037037 | 0 | NEDD9 | 6 | 6p24.1 | 11291518 | 11490568 |
| SGOL1 | 0.416667 | 0.095238 | 0.142857 | 0 | 0.037037 | SGOL1 | 3 | 3p24.3 | 20177089 | 20202688 |
| RASA2 | 0.416667 | 0.095238 | 0.142857 | 0 | 0.037037 | RASA2 | 3 | 3q23 | 1.43E+08 | 1.43E+08 |
| VAMP7 | 0.395833 | 0.285714 | 0.095238 | 0.333333 | 0 | VAMP7 | X | Xq28 | 1.55E+08 | 1.55E+08 |
| IL9R | 0.395833 | 0.285714 | 0.095238 | 0.333333 | 0 | IL9R | X | Xq28 | 1.55E+08 | 1.55E+08 |
| RPL23AP82 | 0.395833 | 0.809524 | 0.095238 | 0.777778 | 0 | RPL23AP82 | 22 | 22q13.33 | 49542380 | 49584931 |
| RABL2B | 0.395833 | 0.809524 | 0.095238 | 0.777778 | 0 | RABL2B | 22 | 22q13.33 | 49552786 | 49568954 |
| C21orf7 | 0.395833 | 0.095238 | 0.047619 | 0 | 0 | C21orf7 | 21 | 21q21.3 | 29374744 | 29470074 |
| CLDN17 | 0.395833 | 0.047619 | 0.095238 | 0 | 0 | CLDN17 | 21 | 21q21.3 | 30460132 | 30460807 |
| KRTAP19-3 | 0.395833 | 0.047619 | 0.095238 | 0 | 0 | KRTAP19-3 | 21 | 21q22.11 | 30785653 | 30786147 |
| KRTAP19-4 | 0.395833 | 0.047619 | 0.095238 | 0 | 0 | KRTAP19-4 | 21 | 21q22.11 | 30791045 | 30791300 |
| KRTAP19-5 | 0.395833 | 0.047619 | 0.095238 | 0 | 0 | KRTAP19-5 | 21 | 21q22.11 | 30796061 | 30796280 |
| KRTAP19-7 | 0.395833 | 0.047619 | 0.095238 | 0 | 0 | KRTAP19-7 | 21 | 21q22.11 | 30855288 | 30855480 |
| KRTAP20-2 | 0.395833 | 0.047619 | 0.095238 | 0.037037 | 0 | KRTAP20-2 | 21 | 21q22.11 | 30929454 | 30929652 |
| KRTAP20-3 | 0.395833 | 0.047619 | 0.095238 | 0.037037 | 0 | KRTAP20-3 | 21 | 21q22.11 | 30937054 | 30937327 |
| HAO1 | 0.395833 | 0 | 0.095238 | 0 | 0 | HAO1 | 20 | 20p12.3 | 7811631 | 7869094 |
| TMX4 | 0.395833 | 0 | 0.095238 | 0 | 0 | TMX4 | 20 | 20p12.3 | 7909716 | 7948394 |
| PLCB1 | 0.395833 | 0 | 0.095238 | 0 | 0 | PLCB1 | 20 | 20p12.3 | 8061296 | 8813548 |
| PLCB4 | 0.395833 | 0 | 0.095238 | 0 | 0 | PLCB4 | 20 | 20p12.2 | 9024932 | 9409463 |
| PAK7 | 0.395833 | 0 | 0.095238 | 0 | 0 | PAK7 | 20 | 20p12.2 | 9466037 | 9767688 |
| SNAP25 | 0.395833 | 0 | 0.095238 | 0 | 0 | SNAP25 | 20 | 20p12.2 | 10147477 | 10236066 |
| C20orf94 | 0.395833 | 0 | 0.095238 | 0 | 0 | C20orf94 | 20 | 20p12.2 | 10363951 | 10552028 |
| JAG1 | 0.395833 | 0 | 0.095238 | 0 | 0 | JAG1 | 20 | 20p12.2 | 10566332 | 10602695 |
| ESF1 | 0.395833 | 0.095238 | 0.047619 | 0 | 0 | ESF1 | 20 | 20p12.1 | 13642969 | 13713533 |
| C20orf7 | 0.395833 | 0.095238 | 0.047619 | 0 | 0 | C20orf7 | 20 | 20p12.1 | 13713672 | 13747066 |
| KIF16B | 0.395833 | 0 | 0.095238 | 0 | 0 | KIF16B | 20 | 20p12.1 | 16200749 | 16502079 |
| DOK5 | 0.395833 | 0.095238 | 0.095238 | 0.148148 | 0 | DOK5 | 20 | 20q13.2 | 52525673 | 52701118 |
| CETN1 | 0.395833 | 0.095238 | 0 | 0 | 0 | CETN1 | 18 | 18p11.32 | 570369 | 571525 |
| CLUL1 | 0.395833 | 0.095238 | 0 | 0 | 0 | CLUL1 | 18 | 18p11.32 | 586998 | 640294 |
| TYMS | 0.395333 | 0.095238 | 0 | 0 | 0 | TYMS | 18 | 18p11.32 | 647604 | 663500 |
| ENOSF1 | 0.395833 | 0.095233 | 0 | 0 | 0 | ENOSF1 | 18 | 18p11.32 | 662544 | 702663 |
| YES1 | 0.395833 | 0.095238 | 0 | 0 | 0 | YES1 | 18 | 18p11.32 | 711592 | 802328 |
| LOC642597 | 0.395833 | 0 | 0.095238 | 0 | 0 | LOC642597 | 18 | 18p11.31 | 5133672 | 5187256 |
| ZNF519 | 0.395833 | 0.095238 | 0.095238 | 0.074074 | 0 | ZNF519 | 18 | 18p11.21 | 14094724 | 14122430 |
| ANKRD30B | 0.395833 | 0.095238 | 0.095238 | 0.074074 | 0 | ANKRD30B | 18 | 13p11.21 | 14738239 | 14842738 |
| SERPINB13 | 0.395833 | 0.095238 | 0 | 0 | 0.037037 | SERPINB13 | 18 | 18q21.33 | 59405514 | 59417413 |
| SERPINB8 | 0.395833 | 0.095238 | 0 | 0 | 0.037037 | SERPINB8 | 18 | 18q21.33 | 59788243 | 59804868 |
| SOCS6 | 0.395833 | 0.095238 | 0 | 0 | 0.037037 | SOCS6 | 18 | 18q22.2 | 66107117 | 66148415 |
| KRT25 | 0.395833 | 0.190476 | 0.095238 | 0.259259 | 0 | KRT25 | 17 | 17q21.2 | 36157800 | 36165111 |
| KRT26 | 0.395833 | 0.190476 | 0.095238 | 0.259259 | 0 | KRT26 | 17 | 17q21.2 | 36176018 | 36181938 |
| CA10 | 0.395833 | 0.142857 | 0.095238 | 0.185185 | 0 | CA10 | 17 | 17q21.33 | 47062673 | 47592161 |
| TANC2 | 0.395833 | 0.238095 | 0.095238 | 0.333333 | 0 | TANC2 | 17 | 17q23.3 | 58440630 | 58558800 |
| KCNJ16 | 0.395833 | 0.047613 | 0.095238 | 0.222222 | 0 | KCNJ16 | 17 | 17q24.3 | 65583021 | 65643342 |
| TOX3 | 0.395833 | 0.047619 | 0.095238 | 0 | 0 | TOX3 | 16 | 16q12.1 | 51029419 | 51138308 |
| CNTNAP4 | 0.395833 | 0.095238 | 0.047619 | 0 | 0 | CNTNAP4 | 16 | 16q23.1 | 74868677 | 75150637 |
| SCG5 | 0.395833 | 0.095238 | 0 | 0 | 0 | SCG5 | 15 | 15q13.3 | 30721162 | 30776591 |
| AVEN | 0.395833 | 0.095238 | 0 | 0 | 0 | AVEN | 15 | 15q14 | 31945720 | 32118596 |
| CHRM5 | 0.395833 | 0.095238 | 0 | 0 | 0 | CHRM5 | 15 | 15q14 | 32048381 | 32144580 |
| PGBD4 | 0.395833 | 0.095238 | 0 | 0 | 0 | PGBD4 | 15 | 15q14 | 32181566 | 32183884 |
| C15orf29 | 0.395833 | 0.095238 | 0 | 0 | 0 | C15orf29 | 15 | 15q14 | 32220167 | 32289590 |
| TMEM85 | 0.395833 | 0.095238 | 0 | 0 | 0 | TMEM85 | 15 | 15q14 | 32304537 | 32309645 |
| SLC12A6 | 0.395833 | 0.095238 | 0 | 0 | 0 | SLC12A6 | 15 | 15q14 | 32309489 | 32417254 |
| NOP10 | 0.395833 | 0.095238 | 0 | 0 | 0 | NOP10 | 15 | 15q14 | 32421209 | 32422655 |
| C15orf55 | 0.395833 | 0.095238 | 0 | 0 | 0 | C15orf55 | 15 | 15q14 | 32425358 | 32437224 |
| MEIS2 | 0.395833 | 0.047619 | 0.095238 | 0 | 0 | MEIS2 | 15 | 15q14 | 34970524 | 35180793 |
| SPRED1 | 0.395833 | 0.047619 | 0.095238 | 0.037037 | 0 | SPRED1 | 15 | 15q14 | 36332344 | 36436743 |
| DMXL2 | 0.395833 | 0.095238 | 0.095238 | 0.037037 | 0 | DMXL2 | 15 | 15q21.2 | 49527231 | 49702260 |
| ONECUT1 | 0.395833 | 0.095238 | 0 | 0 | 0.037037 | ONECUT1 | 15 | 15q21.2 | 50836645 | 50869502 |
| RAB27A | 0.395833 | 0.095238 | 0 | 0 | 0 | RAB27A | 15 | 15q21.3 | 53283092 | 53349878 |
| PIGB | 0.395833 | 0.095238 | 0 | 0 | 0 | PIGB | 15 | 15q21.3 | 53398425 | 53435139 |
| CCPG1 | 0.395833 | 0.095238 | 0 | 0 | 0 | CCPG1 | 15 | 15q21.3 | 53434730 | 53487835 |
| MIR628 | 0.395833 | 0.095238 | 0 | 0 | 0 | MIR628 | 15 | 15q21.3 | 53452430 | 53452525 |
| DYX1C1 | 0.395833 | 0.095238 | 0 | 0 | 0 | DYX1C1 | 15 | 15q21.3 | 53497246 | 53587725 |
| PYGO1 | 0.395833 | 0.095238 | 0 | 0 | 0 | PYGO1 | 15 | 15q21.3 | 53625513 | 53668343 |
| PRTG | 0.395833 | 0.095238 | 0 | 0 | 0 | PRTG | 15 | 15q21.3 | 53691042 | 53822470 |
| TEX9 | 0.395833 | 0.095238 | 0.095238 | 0 | 0.037037 | TEX9 | 15 | 15q21.3 | 54444935 | 54525365 |

TABLE 4-continued

Gene list for predicting prostate cancer relapse using AT

| Symbol | freq. use | freq. amp. case | freq. del. case | freq. amp. control | freq. del. control | Gene. Symbol | chromo-some | cytoband | Transcript. start | Transcript. end |
|---|---|---|---|---|---|---|---|---|---|---|
| ZNF280D | 0.395833 | 0.095238 | 0 | 0 | 0 | ZNF280D | 15 | 15q21.3 | 54709666 | 54813080 |
| TCF12 | 0.395833 | 0.095238 | 0.047619 | 0 | 0 | TCF12 | 15 | 15q21.3 | 54998125 | 55368007 |
| NEO1 | 0.395833 | 0.190476 | 0.095238 | 0.333333 | 0 | NEO1 | 15 | 15q24.1 | 71131928 | 71384599 |
| LOC91948 | 0.395833 | 0.047619 | 0.095238 | 0.074074 | 0 | LOC91948 | 15 | 15q26.2 | 96086850 | 96218664 |
| C15orf51 | 0.395833 | 0.190476 | 0.095238 | 0.185185 | 0 | C15orf51 | 15 | 15q26.3 | 98147884 | 98164656 |
| COCH | 0.395833 | 0.095238 | 0 | 0 | 0.037037 | COCH | 14 | 14q12 | 30413492 | 30429574 |
| EGLN3 | 0.395833 | 0.095238 | 0 | 0 | 0 | EGLN3 | 14 | 14q13.1 | 33463172 | 33490036 |
| MIPOL1 | 0.395833 | 0 | 0.095238 | 0 | 0 | MIPOL1 | 14 | 14q21.1 | 36736869 | 37086619 |
| RPS29 | 0.395833 | 0.095238 | 0 | 0 | 0 | RPS29 | 14 | 14q22.1 | 49113792 | 49122845 |
| C14orf183 | 0.395833 | 0.095238 | 0 | 0 | 0 | C14orf183 | 14 | 14q22.1 | 49620119 | 49629112 |
| SOS2 | 0.395833 | 0.095238 | 0 | 0 | 0 | SOS2 | 14 | 14q22.1 | 49653596 | 49767850 |
| L2HGDH | 0.395833 | 0.095238 | 0 | 0 | 0 | L2HGDH | 14 | 14q22.1 | 49778902 | 49848698 |
| ATP5S | 0.395833 | 0.095238 | 0 | 0 | 0 | ATP5S | 14 | 14q22.1 | 49848797 | 49862419 |
| CDKL1 | 0.395833 | 0.095238 | 0 | 0 | 0 | CDKL1 | 14 | 14q22.1 | 49866470 | 49932368 |
| MAP4K5 | 0.395833 | 0.095238 | 0 | 0 | 0 | MAP4K5 | 14 | 14q22.1 | 49954993 | 50069127 |
| ATL1 | 0.395833 | 0.095238 | 0 | 0 | 0 | ATL1 | 14 | 14q22.1 | 50069550 | 50169535 |
| SAV1 | 0.395833 | 0.095238 | 0 | 0 | 0 | SAV1 | 14 | 14q22.1 | 50170110 | 50204774 |
| NIN | 0.395833 | 0.095238 | 0 | 0 | 0 | NIN | 14 | 14q22.1 | 50256231 | 50367590 |
| ABHD12B | 0.395833 | 0.095238 | 0 | 0 | 0 | ABHD12B | 14 | 14q22.1 | 50408628 | 50441439 |
| PYGL | 0.395833 | 0.095238 | 0 | 0 | 0 | PYGL | 14 | 14q22.1 | 50441686 | 50480999 |
| TRIM9 | 0.395833 | 0.095238 | 0 | 0 | 0 | TRIM9 | 14 | 14q22.1 | 50511731 | 50632173 |
| FRMD6 | 0.395833 | 0.095238 | 0 | 0 | 0 | FRMD6 | 14 | 14q22.1 | 51025605 | 51267195 |
| CDKN3 | 0.395833 | 0.095238 | 0 | 0 | 0 | CDKN3 | 14 | 14q22.2 | 53933423 | 53956683 |
| ACTR10 | 0.395833 | 0.095238 | 0 | 0 | 0 | ACTR10 | 14 | 14q23.1 | 57736586 | 57772107 |
| PSMA3 | 0.395833 | 0.095238 | 0 | 0 | 0.037037 | PSMA3 | 14 | 14q23.1 | 57781346 | 57808480 |
| FL131306 | 0.395833 | 0.095238 | 0 | 0 | 0.037037 | FL131306 | 14 | 14q23.1 | 57801837 | 57834609 |
| ARID4A | 0.395833 | 0.095238 | 0 | 0 | 0 | ARID4A | 14 | 14q23.1 | 57834975 | 57910205 |
| NRXN3 | 0.395833 | 0.047619 | 0.095238 | 0.074074 | 0 | NRXN3 | 14 | 14q24.3 | 77939846 | 79400514 |
| ZMYM2 | 0.395833 | 0.190476 | 0.095238 | 0.111111 | 0 | ZMYM2 | 13 | 13q12.11 | 19430810 | 19558940 |
| KL | 0.395833 | 0.095238 | 0 | 0 | 0 | KL | 13 | 13q13.1 | 32488571 | 32538282 |
| STARD13 | 0.395833 | 0.095238 | 0 | 0 | 0 | STARD13 | 13 | 13q13.1 | 32575273 | 32678188 |
| NBEA | 0.395833 | 0 | 0.095238 | 0 | 0 | NBEA | 13 | 13q13.2 | 34414456 | 35144874 |
| C13orf36 | 0.395833 | 0.047619 | 0.095238 | 0 | 0 | C13orf36 | 13 | 13q13.3 | 36146049 | 36169976 |
| SMAD9 | 0.395833 | 0.095238 | 0.095238 | 0.037037 | 0 | SMAD9 | 13 | 13q13.3 | 36320207 | 36392410 |
| TSC22D1 | 0.395833 | 0.095238 | 0 | 0 | 0 | TSC22D1 | 13 | 13q14.11 | 43905655 | 44048702 |
| NUFIP1 | 0.395833 | 0.095238 | 0 | 0 | 0 | NUFIP1 | 13 | 13q14.12 | 44411384 | 44461614 |
| KIAA1704 | 0.395833 | 0.095238 | 0 | 0 | 0 | KIAA1704 | 13 | 13q14.12 | 44461687 | 44500405 |
| GTF2F2 | 0.395833 | 0.095238 | 0 | 0 | 0 | GTF2F2 | 13 | 13q14.12 | 44592631 | 44756240 |
| KCTD4 | 0.395833 | 0.095238 | 0 | 0 | 0 | KCTD4 | 13 | 13q14.12 | 44664988 | 44673176 |
| TPT1 | 0.395833 | 0.095238 | 0 | 0 | 0 | TPT1 | 13 | 13q14.12 | 44809304 | 44813298 |
| SNORA31 | 0.395833 | 0.095238 | 0 | 0 | 0 | SNORA31 | 13 | 13q14.12 | 44809615 | 44809745 |
| LOC1001939 | 0.395833 | 0.095238 | 0 | 0 | 0 | LOC1001939 | 13 | 13q14.12 | 44813480 | 44853617 |
| COG3 | 0.395833 | 0.095238 | 0 | 0 | 0 | COG3 | 13 | 13q14.12 | 44937072 | 45008762 |
| FAM194B | 0.395833 | 0.095238 | 0 | 0 | 0 | FAM194B | 13 | 13q14.12 | 45013433 | 45087876 |
| esd | 0.395833 | 0 | 0.095238 | 0 | 0 | esd | 13 | 13q14.2 | 46243392 | 46269369 |
| HTR2A | 0.395833 | 0 | 0.095238 | 0 | 0 | HTR2A | 13 | 13q14.2 | 46305514 | 46369171 |
| SUCLA2 | 0.395833 | 0.095238 | 0 | 0 | 0 | SUCLA2 | 13 | 13q14.2 | 47414792 | 47473464 |
| NUDT15 | 0.395833 | 0.095238 | 0 | 0 | 0 | NUDT15 | 13 | 13q14.2 | 47509704 | 47519284 |
| MED4 | 0.395833 | 0.095238 | 0 | 0 | 0 | MED4 | 13 | 13q14.2 | 47548093 | 47567242 |
| ITM2B | 0.395833 | 0.095238 | 0 | 0 | 0 | ITM2B | 13 | 13q14.2 | 47705275 | 47734234 |
| RNASEH2B | 0.395833 | 0.095238 | 0 | 0 | 0 | RNASEH2B | 13 | 13q14.3 | 50381893 | 50442596 |
| GUCY1B2 | 0.395833 | 0.095238 | 0 | 0 | 0 | GUCY1B2 | 13 | 13q14.3 | 50466649 | 50538295 |
| FAM124A | 0.395833 | 0.095238 | 0 | 0 | 0 | FAM124A | 13 | 13q14.3 | 50694508 | 50753618 |
| SERPINE3 | 0.395833 | 0.095238 | 0 | 0 | 0 | SERPINE3 | 13 | 13q14.3 | 50813169 | 50834241 |
| INTS6 | 0.395833 | 0.095238 | 0 | 0 | 0 | INTS6 | 13 | 13q14.3 | 50833702 | 50925277 |
| WDFY2 | 0.395833 | 0.095238 | 0 | 0 | 0 | WDFY2 | 13 | 13q14.3 | 51056485 | 51234173 |
| HNRNPA1L | 0.395833 | 0.095238 | 0 | 0 | 0 | HNRNPA1L | 13 | 13q14.3 | 52089606 | 52115921 |
| KLF12 | 0.395833 | 0 | 0.095238 | 0 | 0 | KLF12 | 13 | 13q22.1 | 73158150 | 73606068 |
| TBC1D4 | 0.395833 | 0 | 0.095238 | 0 | 0 | TBC1D4 | 13 | 13q22.2 | 74756810 | 74954252 |
| COMMD6 | 0.395833 | 0 | 0.095238 | 0 | 0 | COMMD6 | 13 | 13q22.2 | 74997351 | 75009993 |
| LM07 | 0.395833 | 0 | 0.095238 | 0 | 0 | LM07 | 13 | 13q22.2 | 75092571 | 75332006 |
| DCT | 0.395833 | 0.095238 | 0.095238 | 0 | 0.111111 | DCT | 13 | 13q32.1 | 93889842 | 93929938 |
| TMTC4 | 0.395833 | 0.095238 | 0 | 0 | 0 | TMTC4 | 13 | 13q32.3 | 1E+08 | 1E+08 |
| LOC374443 | 0.395833 | 0 | 0.095238 | 0.037037 | 0 | LOC374443 | 12 | 12p13.31 | 9691910 | 9702276 |
| CLECL1 | 0.395833 | 0 | 0.095238 | 0.037037 | 0 | CLECL1 | 12 | 12p13.31 | 9766358 | 9777128 |
| CD69 | 0.395833 | 0 | 0.095238 | 0.037037 | 0 | CD69 | 12 | 12p13.31 | 9796351 | 9804765 |
| CLEC2A | 0.395833 | 0 | 0.095238 | 0.037037 | 0 | CLEC2A | 12 | 12p13.31 | 9957093 | 9976248 |
| CLEC12A | 0.395833 | 0 | 0.095238 | 0.037037 | 0 | CLEC12A | 12 | 12p13.2 | 10015275 | 10029462 |
| CLEC1B | 0.395833 | 0 | 0.095238 | 0.037037 | 0 | CLEC1B | 12 | 12p13.2 | 10036929 | 10043167 |
| CLEC12B | 0.395833 | 0 | 0.095238 | 0.037037 | 0 | CLEC12B | 12 | 12p13.2 | 10054498 | 10062667 |
| CLEC9A | 0.395833 | 0 | 0.095238 | 0.037037 | 0 | CLEC9A | 12 | 12p13.2 | 10074543 | 10109833 |
| CLEC1A | 0.395833 | 0 | 0.095238 | 0.037037 | 0 | CLEC1A | 12 | 12p13.2 | 10114347 | 10142873 |
| STYK1 | 0.395833 | 0 | 0.095238 | 0.037037 | 0 | STYK1 | 12 | 12p13.2 | 10662805 | 10718159 |
| CSDA | 0.395833 | 0 | 0.095238 | 0.037037 | 0 | CSDA | 12 | 12p13.2 | 10742945 | 10767221 |

TABLE 4-continued

Gene list for predicting prostate cancer relapse using AT

| Symbol | freq. use | freq. amp. case | freq. del. case | freq. amp. control | freq. del. control | Gene. Symbol | chromo-some | cytoband | Transcript. start | Transcript. end |
|---|---|---|---|---|---|---|---|---|---|---|
| KIAAD528 | 0.395833 | 0 | 0.095238 | 0 | 0 | KIAAD528 | 12 | 12P12.1 | 22492785 | 22588720 |
| ETNK1 | 0.395833 | 0 | 0.095238 | 0 | 0 | ETNK1 | 12 | 12p12.1 | 22669343 | 22688617 |
| TMTC1 | 0.395833 | 0 | 0.095238 | 0 | 0 | TMTC1 | 12 | 12p11.22 | 29545024 | 29828960 |
| GXYLT1 | 0.395833 | 0 | 0.095238 | 0 | 0 | GXYLT1 | 12 | 12q12 | 40761915 | 40824941 |
| ZCRB1 | 0.395833 | 0.095238 | 0 | 0 | 0 | ZCRB1 | 12 | 12q12 | 40992155 | 41006200 |
| PPHLN1 | 0.395833 | 0.095238 | 0 | 0 | 0 | PPHLN1 | 12 | 12q12 | 41006214 | 41128690 |
| ADAMTS20 | 0.395833 | 0 | 0.095238 | 0 | 0 | ADAMTS20 | 12 | 12q12 | 42034279 | 42231992 |
| NELL2 | 0.395833 | 0.047619 | 0.095238 | 0 | 0 | NELL2 | 12 | 12q12 | 43188325 | 43556901 |
| DBX2 | 0.395833 | 0.047619 | 0.095238 | 0 | 0 | DBX2 | 12 | 12q12 | 43694806 | 43731150 |
| KIAA0748 | 0.395833 | 0.095238 | 0.095238 | 0.259259 | 0 | KIAA0748 | 12 | 12q13.2 | 53630132 | 53664724 |
| MON2 | 0.395833 | 0.095238 | 0 | 0 | 0.037037 | MON2 | 12 | 12q14.1 | 61146864 | 61277631 |
| SRGAP1 | 0.395833 | 0.095238 | 0 | 0 | 0 | SRGAP1 | 12 | 12q14.2 | 62524808 | 62827881 |
| C12orf66 | 0.395833 | 0.095238 | 0 | 0 | 0 | C12orf66 | 12 | 12q14.2 | 62872686 | 62902344 |
| C12orf56 | 0.395833 | 0.095238 | 0 | 0 | 0 | C12orf56 | 12 | 12q14.2 | 62947032 | 63070613 |
| TBK1 | 0.395833 | 0.095238 | 0 | 0 | 0 | TBK1 | 12 | 12q14.2 | 63132204 | 63182159 |
| GNS | 0.395833 | 0.095238 | 0 | 0 | 0 | GNS | 12 | 12q14.2-12q14.3 | 63393489 | 63439494 |
| TBC1D15 | 0.395833 | 0.095238 | 0.095238 | 0 | 0.037037 | TBC1D15 | 12 | 12q21.1 | 70519754 | 70606895 |
| MRS2P2 | 0.395833 | 0.095238 | 0.095238 | 0 | 0.037037 | MRS2P2 | 12 | 12q21.1 | 70528343 | 70531031 |
| METAP2 | 0.395833 | 0.095238 | 0 | 0 | 0 | METAP2 | 12 | 12q22 | 94391953 | 94433745 |
| USP44 | 0.395833 | 0.095238 | 0 | 0 | 0 | USP44 | 12 | 12q22 | 94435018 | 94466752 |
| NTN4 | 0.395833 | 0.095238 | 0 | 0 | 0 | NTN4 | 12 | 12q22 | 94575714 | 94708668 |
| CCDC38 | 0.395833 | 0.095238 | 0 | 0 | 0 | CCDC38 | 12 | 12q23.1 | 94784958 | 94860560 |
| AMDHD1 | 0.395833 | 0.095238 | 0 | 0 | 0 | AMDHD1 | 12 | 12q23.1 | 94861202 | 94886501 |
| HAL | 0.395833 | 0.095238 | 0 | 0 | 0 | HAL | 12 | 12q23.1 | 94891273 | 94914203 |
| C12orf42 | 0.395833 | 0 | 0.095238 | 0.111111 | 0 | C12orf42 | 12 | 12q23.2 | 1.02E+08 | 1.02 E+08 |
| OR51F1 | 0.395833 | 0 | 0.095238 | 0 | 0 | OR51F1 | 11 | 11p15.4 | 4746785 | 4747724 |
| OR51S1 | 0.395833 | 0 | 0.095238 | 0 | 0 | OR51S1 | 11 | 11p15.4 | 4826043 | 4827015 |
| OR51A7 | 0.395833 | 0 | 0.095238 | 0 | 0 | OR51A7 | 11 | 11p15.4 | 4885176 | 4886115 |
| OR51G2 | 0.395833 | 0 | 0.095238 | 0 | 0 | OR51G2 | 11 | 11p15.4 | 4892525 | 4893470 |
| OR51L1 | 0.395833 | 0 | 0.095238 | 0 | 0 | OR51L1 | 11 | 11p15.4 | 4976789 | 4977737 |
| OR52J3 | 0.395833 | 0 | 0.095238 | 0 | 0 | OR52J3 | 11 | 11p15.4 | 5024332 | 5025268 |
| OR52E2 | 0.395833 | 0 | 0.095238 | 0 | 0 | OR52E2 | 11 | 11p15.4 | 5036456 | 5037434 |
| OR52A1 | 0.395833 | 0 | 0.095238 | 0 | 0 | OR52A1 | 11 | 11p15.4 | 5129237 | 5130176 |
| OR51V1 | 0.395833 | 0 | 0.095238 | 0 | 0 | OR51V1 | 11 | 11p15.4 | 5177541 | 5178507 |
| OR51B4 | 0.395833 | 0 | 0.095238 | 0 | 0 | OR51B4 | 11 | 11p15.4 | 5278820 | 5279753 |
| OR51B5 | 0.395833 | 0 | 0.095238 | 0 | 0 | OR51B5 | 11 | 11p15.4 | 5320392 | 5321331 |
| OR51B6 | 0.395833 | 0 | 0.095238 | 0 | 0 | OR51B6 | 11 | 11P15.4 | 5329314 | 5330253 |
| OR5P3 | 0.395833 | 0 | 0.095238 | 0.074074 | 0 | OR5P3 | 11 | 11p15.4 | 7803160 | 7804096 |
| PSMA1 | 0.395833 | 0 | 0.095238 | 0 | 0 | PSMA1 | 11 | 11p15.2 | 14482999 | 14621757 |
| PDE3B | 0.395833 | 0 | 0.095238 | 0 | 0 | PDE3B | 11 | 11p15.2 | 14621845 | 14850179 |
| INSC | 0.395833 | 0.095238 | 0 | 0 | 0 | INSC | 11 | 11p15.2 | 15090546 | 15225331 |
| LDLRAD3 | 0.395833 | 0.095238 | 0 | 0 | 0 | LDLRAD3 | 11 | 11p13 | 35922188 | 36209418 |
| COMMDS | 0.395833 | 0.095238 | 0 | 0 | 0 | COMMDS | 11 | 11p13 | 36250418 | 36267576 |
| PRR5L | 0.395833 | 0.095238 | 0 | 0 | 0 | PRR5L | 11 | 11p13 | 36274301 | 36443330 |
| PCF11 | 0.395833 | 0.095238 | 0.047619 | 0 | 0.074074 | PCF11 | 11 | 11q14.1 | 82545785 | 82574484 |
| ANKRD42 | 0.395833 | 0.095238 | 0.047619 | 0 | 0.074074 | ANKRD42 | 11 | 11q14.1 | 82582939 | 82637662 |
| MMP7 | 0.395833 | 0.095238 | 0 | 0 | 0.037037 | MMP7 | 11 | 11q22.2 | 1.02E+08 | 1.02E+08 |
| FAM55A | 0.395833 | 0.190476 | 0.095238 | 0.148148 | 0 | FAM55A | 11 | 11q23.2 | 1.14E+08 | 1.14E+08 |
| FAM55B | 0.395833 | 0.190476 | 0.095238 | 0.148148 | 0 | FAM55B | 11 | 11q23.2 | 1.14E+08 | 1.14E+08 |
| RSU1 | 0.395833 | 0.095238 | 0 | 0 | 0 | RSU1 | 10 | 10p13 | 16672623 | 16899460 |
| ST8SIA6 | 0.395833 | 0.095238 | 0 | 0 | 0 | ST8SIA6 | 10 | 10p12.33 | 17402682 | 17536261 |
| PTPLA | 0.395833 | 0.095238 | 0 | 0 | 0 | PTPLA | 10 | 10p12.33 | 17671964 | 17699380 |
| STAM | 0.395833 | 0.095238 | 0 | 0 | 0 | STAM | 10 | 10p12.33 | 17726130 | 17797914 |
| SLC39A12 | 0.395833 | 0.095238 | 0 | 0 | 0 | SLC39A12 | 10 | 10p12.33 | 18280774 | 18372228 |
| CACNB2 | 0.395833 | 0.095238 | 0 | 0 | 0 | CACNB2 | 10 | 10p12.33 | 18469612 | 18870695 |
| NSUN6 | 0.395833 | 0.095238 | 0 | 0 | 0 | NSUN6 | 10 | 10p12.33 | 18874270 | 18980557 |
| ARL5B | 0.395833 | 0.095238 | 0 | 0 | 0 | ARL5B | 10 | 10p12.33 | 18988319 | 19006947 |
| GAD2 | 0.395833 | 0.095238 | 0 | 0 | 0 | GAD2 | 10 | 10p12.1 | 26545242 | 26633498 |
| APB1IP | 0.395833 | 0.095238 | 0 | 0 | 0 | APB1IP | 10 | 10p12.1 | 26767272 | 26896739 |
| C10orf50 | 0.395833 | 0.095238 | 0 | 0 | 0 | C10orf50 | 10 | 10p12.1 | 26918800 | 26923256 |
| LOC731789 | 0.395833 | 0.095238 | 0 | 0 | 0 | LOC731789 | 10 | 10p12.1 | 26972043 | 26982389 |
| PDSS1 | 0.395833 | 0.095238 | 0 | 0 | 0 | PDSS1 | 10 | 10p12.1 | 27026601 | 27075733 |
| ABI1 | 0.395833 | 0.095238 | 0 | 0 | 0 | ABI1 | 10 | 10p12.1 | 27075531 | 27189966 |
| KIF5B | 0.395833 | 0.095238 | 0 | 0 | 0 | KIF5B | 10 | 10p11.22 | 32337944 | 32385378 |
| EPC1 | 0.395833 | 0.095238 | 0 | 0 | 0 | EPC1 | 10 | 10p11.22 | 32597865 | 32676120 |
| CCDC7 | 0.395833 | 0.047619 | 0.095238 | 0 | 0 | CCDC7 | 10 | 10p11.22 | 32775047 | 32903499 |
| LOC100129055 | 0.395833 | 0 | 0.095238 | 0 | 0 | LOC100129055 | 10 | 10p11.21 | 38504605 | 38543279 |
| HSD17B7P2 | 0.395833 | 0 | 0.095238 | 0 | 0 | HSD17B7P2 | 10 | 10p11.21 | 38685314 | 38707440 |
| LRIT2 | 0.395833 | 0.095238 | 0 | 0 | 0 | LRIT2 | 10 | 10q23.1 | 85970229 | 85975265 |
| LRIT1 | 0.395833 | 0.095238 | 0 | 0 | 0 | LRIT1 | 10 | 10q23.1 | 85981256 | 85991198 |
| RGR | 0.395833 | 0.095238 | 0 | 0 | 0 | RGR | 10 | 10q23.1 | 85994789 | 86008925 |
| PTEN | 0.395833 | 0 | 0.095238 | 0 | 0 | PTEN | 10 | 10q23.31 | 89613175 | 89718513 |
| LIPK | 0.395833 | 0.047619 | 0.095238 | 0.037037 | 0 | LIPK | 10 | 10q23.31 | 90474281 | 90502494 |

TABLE 4-continued

Gene list for predicting prostate cancer relapse using AT

| Symbol | freq. use | freq. amp. case | freq. del. case | freq. amp. control | freq. del. control | Gene. Symbol | chromo-some | cytoband | Transcript. start | Transcript. end |
|---|---|---|---|---|---|---|---|---|---|---|
| STAMBPL1 | 0.395833 | 0 | 0.095238 | 0 | 0 | STAMBPL1 | 10 | 10q23.31 | 90630006 | 90673225 |
| ACTA2 | 0.395833 | 0 | 0.095238 | 0 | 0 | ACTA2 | 10 | 10q23.31 | 90684813 | 90741128 |
| LIPA | 0.395833 | 0 | 0.095238 | 0 | 0 | LIPA | 10 | 10q23.31 | 90963306 | 91001641 |
| IFIT3 | 0.395833 | 0 | 0.095238 | 0 | 0 | IFIT3 | 10 | 10q23.31 | 91077582 | 91090705 |
| IFIT5 | 0.395333 | 0 | 0.095238 | 0 | 0 | IFIT5 | 10 | 10q23.31 | 91164305 | 91170739 |
| SLC16A12 | 0.395833 | 0 | 0.095238 | 0 | 0 | SLC16A12 | 10 | 10q23.31 | 91180036 | 91285294 |
| PANK1 | 0.395833 | 0 | 0.095238 | 0 | 0 | PANK1 | 10 | 10q23.31 | 91332729 | 91393628 |
| MIR107 | 0.395833 | 0 | 0.095238 | 0 | 0 | MIR107 | 10 | 10q23.31 | 91342485 | 91342565 |
| TM9SF3 | 0.395833 | 0.285714 | 0.095238 | 0.259259 | 0 | TM9SF3 | 10 | 10q24.1 | 98267857 | 98336800 |
| PIK3AP1 | 0.395833 | 0.285714 | 0.095238 | 0.259259 | 0 | PIK3AP1 | 10 | 10q24.1 | 98343059 | 98470270 |
| CCDC147 | 0.395833 | 0.095238 | 0.095238 | 0.037037 | 0 | CCDC147 | 10 | 10q25.1 | 1.06E+08 | 1.06E+08 |
| SLC1A1 | 0.395833 | 0.095238 | 0 | 0 | 0 | SLC1A1 | 9 | 9p24.2 | 4480444 | 4577470 |
| UHRF2 | 0.395833 | 0.095238 | 0 | 0 | 0 | UHRF2 | 9 | 9p24.1 | 6403151 | 6497052 |
| PTPLAD2 | 0.395833 | 0 | 0.095238 | 0 | 0 | PTPLAD2 | 9 | 9p21.3 | 20996365 | 21021636 |
| IFNW1 | 0.395833 | 0 | 0.095238 | 0 | 0 | IFNW1 | 9 | 9p21.3 | 21130631 | 21132145 |
| IFNA21 | 0.395833 | 0 | 0.095238 | 0 | 0 | IFNA21 | 9 | 9p21.3 | 21155636 | 21156660 |
| MOBKL2B | 0.395833 | 0.095238 | 0.047619 | 0 | 0.111111 | MOBKL2B | 9 | 9p21.2 | 27315207 | 27519851 |
| KLF9 | 0.395833 | 0.095238 | 0 | 0 | 0 | KLF9 | 9 | 9q21.11 | 72189333 | 72219394 |
| TRPM3 | 0.395833 | 0.095238 | 0 | 0 | 0 | TRPM3 | 9 | 9q21.11 | 72339786 | 72926335 |
| TMEM2 | 0.395833 | 0.095238 | 0 | 0 | 0 | TMEM2 | 9 | 9q21.13 | 73488102 | 73573621 |
| GDA | 0.395833 | 0.095238 | 0 | 0 | 0 | GDA | 9 | 9q21.13 | 73954113 | 74056961 |
| ZFAND5 | 0.395833 | 0.095238 | 0 | 0 | 0 | ZFAND5 | 9 | 9q21.13 | 74156161 | 74169984 |
| TMC1 | 0.395833 | 0.095238 | 0 | 0 | 0 | TMC1 | 9 | 9q21.13 | 74326537 | 74641088 |
| ALDH1A1 | 0.395833 | 0 | 0.095238 | 0 | 0 | ALDH1A1 | 9 | 9q21.13 | 74705407 | 74757790 |
| PRUNE2 | 0.395833 | 0.095238 | 0 | 0 | 0 | PRUNE2 | 9 | 9q21.13 | 78416112 | 78710824 |
| GAS1 | 0.395833 | 0.142857 | 0.095238 | 0.222222 | 0 | GAS1 | 9 | 9q21.33 | 88749097 | 88751925 |
| CKS2 | 0.395833 | 0.333333 | 0.095238 | 0.296296 | 0 | CKS2 | 9 | 9q22.2 | 91115933 | 91121439 |
| 5ECISBP2 | 0.395833 | 0.333333 | 0.095238 | 0.296296 | 0 | 5ECISBP2 | 9 | 9q22.2 | 91123232 | 91164382 |
| LPPR1 | 0.395833 | 0 | 0.095238 | 0.037037 | 0 | LPPR1 | 9 | 9q31.1 | 1.03E+08 | 1.03E+08 |
| MRPL50 | 0.395833 | 0.047619 | 0.095238 | 0.037037 | 0 | MRPL50 | 9 | 9q31.1 | 1.03E+08 | 1.03E+08 |
| ZNF189 | 0.395833 | 0.047619 | 0.095238 | 0.037037 | 0 | ZNF189 | 9 | 9q31.1 | 1.03E+08 | 1.03E+08 |
| ALDOB | 0.395833 | 0.047619 | 0.095238 | 0.037037 | 0 | ALDOB | 9 | 9q31.1 | 1.03E+08 | 1.03E+08 |
| RNF20 | 0.395833 | 0.047619 | 0.095238 | 0.037037 | 0 | RNF20 | 9 | 9q31.1 | 1.03E+08 | 1.03E+08 |
| GRIN3A | 0.395833 | 0.047619 | 0.095238 | 0.037037 | 0 | GRIN3A | 9 | 9q31.1 | 1.03E+08 | 1.04E+08 |
| NIPSNAP3A | 0.395833 | 0.095238 | 0.047619 | 0 | 0.037037 | NIPSNAP3A | 9 | 9q31.1 | 1.07E+08 | 1.07E+08 |
| FSD1L | 0.395833 | 0.047619 | 0.095238 | 0 | 0 | FSD1L | 9 | 9q31.2 | 1.07E+08 | 1.07E+08 |
| FKTN | 0.395833 | 0.047619 | 0.095238 | 0 | 0 | FKTN | 9 | 9q31.2 | 1.07E+08 | 1.07E+08 |
| TAL2 | 0.395833 | 0.095238 | 0.047619 | 0 | 0 | TAL2 | 9 | 9q31.2 | 1.07E+08 | 1.07E+08 |
| IKBKAP | 0.395833 | 0.095238 | 0 | 0 | 0 | IKBKAP | 9 | 9q31.3 | 1.11E+08 | 1.11E+08 |
| CTNNAL1 | 0.395833 | 0.095238 | 0 | 0 | 0 | CTNNAL1 | 9 | 9q31.3 | 1.11E+08 | 1.11E+08 |
| C9orf5 | 0.395833 | 0.095238 | 0 | 0 | 0 | C9orf5 | 9 | 9q31.3 | 1.11E+08 | 1.11E+08 |
| TNFSF15 | 0.395833 | 0.095238 | 0.095238 | 0.037037 | 0 | TNFSF15 | 9 | 9q32 | 1.17E+08 | 1.17E+08 |
| TNFSF8 | 0.395833 | 0.095238 | 0.095238 | 0.037037 | 0 | TNFSF8 | 9 | 9q33.1 | 1.17E+08 | 1.17E+08 |
| TNC | 0.395833 | 0.095238 | 0.095238 | 0.037037 | 0 | TNC | 9 | 9q33.1 | 1.17E+08 | 1.17E+08 |
| ASTN2 | 0.395833 | 0.095238 | 0.047619 | 0 | 0 | ASTN2 | 9 | 9q33.1 | 1.18E+08 | 1.19E+08 |
| DBC1 | 0.395833 | 0.047619 | 0.095238 | 0 | 0 | DBC1 | 9 | 9q33.1 | 1.21E+08 | 1.21E+08 |
| SH2D4A | 0.395833 | 0.095238 | 0 | 0 | 0 | SH2D4A | 8 | 8p21.3 | 19215487 | 19297597 |
| ADAM7 | 0.395833 | 0 | 0.095238 | 0.037037 | 0 | ADAM7 | 8 | 8p21.2 | 24354454 | 24422166 |
| ADAM9 | 0.395833 | 0 | 0.095238 | 0.037037 | 0 | ADAM9 | 8 | 8p11.23 | 38973662 | 39081937 |
| ADAM32 | 0.395833 | 0 | 0.095238 | 0.037037 | 0 | ADAM32 | 8 | 8p11.23 | 39084207 | 39261594 |
| POTEA | 0.395833 | 0.047619 | 0.095238 | 0.148148 | 0 | POTEA | 8 | 8p11.1 | 43266742 | 43337486 |
| SNTG1 | 0.395833 | 0.095238 | 0.047619 | 0 | 0.037037 | SNTG1 | 8 | 8q11.22 | 50987150 | 51867981 |
| PXDNL | 0.395833 | 0.095238 | 0 | 0 | 0 | PXDNL | 8 | 8q11.22 | 52394690 | 52884559 |
| ST18 | 0.395833 | 0.047619 | 0.095238 | 0 | 0 | ST18 | 8 | 8q11.23 | 53185945 | 53484993 |
| RB1CC1 | 0.395833 | 0.095238 | 0 | 0 | 0 | RB1CC1 | 8 | 8q11.23 | 53697571 | 53789580 |
| XKR4 | 0.395833 | 0.095238 | 0 | 0 | 0 | XKR4 | 8 | 8q12.1 | 56177571 | 56601265 |
| SDR16C6 | 0.395833 | 0.095238 | 0 | 0 | 0 | SDR16C6 | 8 | 8q12.1 | 57448181 | 57470479 |
| FAM110B | 0.395833 | 0.095238 | 0 | 0 | 0 | FAM110B | 8 | 8q12.1 | 59069667 | 59224832 |
| UBXN2B | 0.395833 | 0.095238 | 0.047619 | 0 | 0 | UBXN2B | 8 | 8q12.1 | 59486377 | 59526615 |
| NSMAF | 0.395833 | 0.095238 | 0.047619 | 0 | 0 | NSMAF | 8 | 8q12.1 | 59658620 | 59734521 |
| TOX | 0.395833 | 0.095238 | 0.047619 | 0 | 0 | TOX | 8 | 8q12.1 | 59880531 | 60194322 |
| CA8 | 0.395833 | 0.095238 | 0 | 0 | 0 | CA8 | 8 | 8q12.1 | 61263977 | 61356509 |
| RAB2A | 0.395833 | 0.095238 | 0 | 0 | 0 | RAB2A | 8 | 8q12.1 | 61592113 | 61696184 |
| CHD7 | 0.395833 | 0.095238 | 0 | 0 | 0 | CHD7 | 8 | 8q12.2 | 61753893 | 61942022 |
| CLVS1 | 0.395833 | 0.095238 | 0 | 0 | 0 | CLVS1 | 8 | 8q12.2 | 62363079 | 62576757 |
| ASPH | 0.395833 | 0.095238 | 0 | 0 | 0 | ASPH | 8 | 8q12.3 | 62575670 | 62764963 |
| NKAIN3 | 0.395833 | 0.095238 | 0.047619 | 0 | 0.037037 | NKAIN3 | 8 | 8q12.3 | 63324055 | 64066183 |
| ARMC1 | 0.395833 | 0.095238 | 0 | 0 | 0 | ARMC1 | 8 | 8q13.1 | 66677628 | 66708987 |
| MTFR1 | 0.395833 | 0.095238 | 0 | 0 | 0 | MTFR1 | 8 | 8q13.1 | 66719442 | 66783127 |
| PDE7A | 0.395833 | 0.095238 | 0 | 0 | 0 | PDE7A | 8 | 8q13.1 | 66792460 | 66863876 |
| DNAJC5B | 0.395833 | 0.095238 | 0 | 0 | 0 | DNAJC5B | 8 | 8q13.1 | 67096345 | 67175310 |
| TRIM55 | 0.395833 | 0.095238 | 0 | 0 | 0 | TRIM55 | 8 | 8q13.1 | 67201832 | 67250273 |
| STAU2 | 0.395833 | 0.095238 | 0.095238 | 0 | 0.037037 | STAU2 | 8 | 8q21.11 | 74495160 | 74821717 |
| TMEM70 | 0.395833 | 0.095238 | 0.095238 | 0 | 0.037037 | TMEM70 | 8 | 8q21.11 | 75050984 | 75057568 |

TABLE 4-continued

Gene list for predicting prostate cancer relapse using AT

| Symbol | freq. use | freq. amp. case | freq. del. case | freq. amp. control | freq. del. control | Gene. Symbol | chromo-some | cytoband | Transcript. start | Transcript. end |
|---|---|---|---|---|---|---|---|---|---|---|
| FABP5 | 0.395833 | 0.095238 | 0.095238 | 0 | 0.148148 | FABP5 | 8 | 8q21.13 | 82355340 | 82359564 |
| RGS22 | 0.395833 | 0.095238 | 0 | 0 | 0 | RGS22 | 8 | 8q22.2 | 1.01E+08 | 1.01E+08 |
| FBXO43 | 0.395833 | 0.095238 | 0 | 0 | 0 | FBXO43 | 8 | 8q22.2 | 1.01E+08 | 1.01E+08 |
| POLR2K | 0.395833 | 0.095238 | 0 | 0 | 0 | POLR2K | 8 | 8q22.2 | 1.01E+08 | 1.01E+08 |
| SPAG1 | 0.395833 | 0.095238 | 0 | 0 | 0 | SPAG1 | 8 | 8q22.2 | 1.01E+08 | 1.01E+08 |
| DPYS | 0.395833 | 0.095238 | 0 | 0 | 0.148148 | DPYS | 8 | 8q22.3 | 1.05E+08 | 1.06E+08 |
| COL14A1 | 0.395833 | 0.095238 | 0.047619 | 0 | 0 | COL14A1 | 8 | 8q24.12 | 1.21E+08 | 1.21E+08 |
| MRPL13 | 0.395833 | 0 | 0.095238 | 0 | 0 | MRPL13 | 8 | 8q24.12 | 1.21E+08 | 1.22E+08 |
| MTBP | 0.395833 | 0 | 0.095238 | 0 | 0 | MTBP | 8 | 8q24.12 | 1.22E+08 | 1.22E+08 |
| LOC727677 | 0.395833 | 0.095238 | 0.047619 | 0 | 0 | LOC727677 | 8 | 8q24.21 | 1.29E+08 | 1.29E+08 |
| GSDMC | 0.395833 | 0.095238 | 0 | 0 | 0.037037 | GSDMC | 8 | 8q24.21 | 1.31E+08 | 1.31E+08 |
| FAM49B | 0.395833 | 0.095238 | 0 | 0 | 0.037037 | FAM49B | 8 | 8q24.21 | 1.31E+08 | 1.31E+08 |
| OC90 | 0.395333 | 0.095238 | 0 | 0 | 0 | OC90 | 8 | 8q24.22 | 1.33E+08 | 1.33E+08 |
| HHLA1 | 0.395833 | 0.095238 | 0 | 0 | 0 | HHLA1 | 8 | 8q24.22 | 1.33E+08 | 1.33E+08 |
| KCNQ3 | 0.395833 | 0.095238 | 0 | 0 | 0 | KCNQ3 | 8 | 8q24.22 | 1.33E+08 | 1.34E+08 |
| HPYR1 | 0.395833 | 0.095238 | 0 | 0 | 0 | HPYR1 | 8 | 8q24.22 | 1.34E+08 | 1.34E+08 |
| TMEM71 | 0.395833 | 0.095238 | 0 | 0 | 0 | TMEM71 | 8 | 8q24.22 | 1.34E+08 | 1.34E+08 |
| COL28A1 | 0.395833 | 0.095238 | 0.047619 | 0 | 0.111111 | COL28A1 | 7 | 7p21.3 | 7364769 | 7541986 |
| RPA3 | 0.395833 | 0.095238 | 0.047619 | 0 | 0.074074 | RPA3 | 7 | 7p21.3 | 7643100 | 7724764 |
| GLCCI1 | 0.395833 | 0.095238 | 0.047619 | 0 | 0.074074 | GLCCI1 | 7 | 7p21.3 | 7974948 | 8095235 |
| TOMM7 | 0.395833 | 0.095238 | 0 | 0 | 0 | TOMM7 | 7 | 7p15.3 | 22818777 | 22828947 |
| KLHL7 | 0.395833 | 0.095238 | 0 | 0 | 0 | KLHL7 | 7 | 7p15.3 | 23111878 | 23181564 |
| NUPL2 | 0.395833 | 0.095238 | 0 | 0 | 0 | NUPL2 | 7 | 7p15.3 | 23187971 | 23207155 |
| C7orf30 | 0.395833 | 0.095238 | 0.047619 | 0 | 0 | C7orf30 | 7 | 7p15.3 | 23305465 | 23315706 |
| IGF2BP3 | 0.395833 | 0.095238 | 0.047619 | 0 | 0 | IGF2BP3 | 7 | 7p15.3 | 23316353 | 23476521 |
| STK31 | 0.395833 | 0.095238 | 0 | 0 | 0 | STK31 | 7 | 7p15.3 | 23716363 | 23838653 |
| CPVL | 0.395833 | 0.095238 | 0 | 0 | 0 | CPVL | 7 | 7p15.1 | 29001772 | 29152679 |
| CHN2 | 0.395833 | 0.095238 | 0 | 0 | 0 | CHN2 | 7 | 7p15.1 | 29200646 | 29520470 |
| NEUROD6 | 0.395833 | 0.095238 | 0 | 0 | 0 | NEUROD6 | 7 | 7p15.1 | 31343605 | 31347064 |
| AVL9 | 0.395833 | 0.095238 | 0 | 0 | 0 | AVL9 | 7 | 7p14.3 | 32501701 | 32590305 |
| KBTBD2 | 0.395833 | 0.095238 | 0 | 0 | 0 | KBTBD2 | 7 | 7p14.3 | 32874303 | 32897994 |
| NT5C3 | 0.395833 | 0.095238 | 0 | 0 | 0 | NT5C3 | 7 | 7p14.3 | 33020267 | 33068935 |
| RP9 | 0.395833 | 0.095238 | 0 | 0 | 0 | RP9 | 7 | 7p14.3 | 33100935 | 33115528 |
| BMPER | 0.395833 | 0.095238 | 0 | 0 | 0 | BMPER | 7 | 7p14.3 | 33911637 | 34160637 |
| EEPD1 | 0.395833 | 0.095238 | 0 | 0 | 0 | EEPD1 | 7 | 7p14.2 | 36159361 | 36307678 |
| ANLN | 0.395833 | 0.095238 | 0 | 0 | 0 | ANLN | 7 | 7p14.2 | 36395957 | 36459926 |
| AOAH | 0.395833 | 0.095238 | 0 | 0 | 0 | AOAH | 7 | 7p14.2 | 36519133 | 36730679 |
| ABCA13 | 0.395833 | 0.095238 | 0.047619 | 0 | 0.037037 | ABCA13 | 7 | 7p12.3 | 48208389 | 48657638 |
| MTERF | 0.395833 | 0.095238 | 0 | 0 | 0 | MTERF | 7 | 7q21.2 | 91339957 | 91347953 |
| AKAP9 | 0.395833 | 0.095238 | 0 | 0 | 0 | AKAP9 | 7 | 7q21.2 | 91408125 | 91577923 |
| CYP51A1 | 0.395833 | 0.095238 | 0 | 0 | 0 | CYP51A1 | 7 | 7q21.2 | 91579399 | 91601777 |
| LOC401387 | 0.395833 | 0.095238 | 0 | 0 | 0 | LOC401387 | 7 | 7q21.2 | 91612134 | 91632527 |
| KRIT1 | 0.395833 | 0.095238 | 0 | 0 | 0 | KRIT1 | 7 | 7q21.2 | 91566219 | 91713165 |
| LMTK2 | 0.395833 | 0.333333 | 0.095238 | 0.296296 | 0 | LMTK2 | 7 | 7q21.3 | 97574133 | 97676879 |
| LAMB1 | 0.395833 | 0.095238 | 0 | 0 | 0 | LAMB1 | 7 | 7q31.1 | 1.07E+08 | 1.07E+08 |
| AKR1B1 | 0.395833 | 0.095238 | 0 | 0 | 0 | AKR1B1 | 7 | 7q33 | 1.34E+08 | 1.34E+08 |
| AKR1B10 | 0.395833 | 0.095238 | 0 | 0 | 0 | AKR1B10 | 7 | 7q33 | 1.34E+08 | 1.34E+08 |
| C6orf105 | 0.395833 | 0.095238 | 0 | 0 | 0 | C6orf105 | 6 | 6p24.1 | 11821876 | 11887267 |
| RNF144B | 0.395833 | 0.095238 | 0 | 0 | 0.037037 | RNF144B | 6 | 6p22.3 | 18495573 | 18576830 |
| SOX4 | 0.395833 | 0.095238 | 0 | 0 | 0 | SOX4 | 6 | 6p22.3 | 21701951 | 21706829 |
| FLJ22536 | 0.395833 | 0.095238 | 0 | 0 | 0 | FLJ22536 | 6 | 6p22.3 | 21774654 | 22302594 |
| DCDC2 | 0.395833 | 0.095238 | 0.047619 | 0 | 0 | DCDC2 | 6 | 6p22.2 | 24279962 | 24466260 |
| KIAA0319 | 0.395833 | 0.095238 | 0 | 0 | 0 | KIAA0319 | 6 | 6p22.2 | 24652311 | 24754363 |
| ACOT13 | 0.395833 | 0.095238 | 0 | 0 | 0 | ACOT13 | 6 | 6p22.2 | 24775242 | 24813273 |
| C6orf62 | 0.395833 | 0.095238 | 0 | 0 | 0 | C6orf62 | 6 | 6p22.2 | 24813070 | 24827383 |
| FAM65B | 0.395833 | 0.095238 | 0 | 0 | 0 | FAM65B | 6 | 6p22.2 | 24912492 | 25019175 |
| SCGN | 0.395833 | 0.047619 | 0.095238 | 0.037037 | 0 | SCGN | 6 | 6p22.2 | 25760408 | 25809988 |
| SLC17A1 | 0.395833 | 0.047619 | 0.095238 | 0.037037 | 0 | SLC17A1 | 6 | 6p22.2 | 25891105 | 25940267 |
| NCRNA00171 | 0.395833 | 0.285714 | 0.095238 | 0.259259 | 0 | NCRNA00171 | 6 | 6p21.33 | 30076768 | 30135941 |
| ZNRD1 | 0.395833 | 0.285714 | 0.095238 | 0.259259 | 0 | ZNRD1 | 6 | 6p21.33 | 30137015 | 30140666 |
| C6orf141 | 0.395833 | 0.095238 | 0.190476 | 0 | 0.074074 | C6orf141 | 6 | 6p12.3 | 49626072 | 49627766 |
| GCM1 | 0.395833 | 0.095238 | 0 | 0 | 0 | GCM1 | 6 | 6p12.1 | 53099721 | 53121584 |
| SMAP1 | 0.395833 | 0.095238 | 0.095238 | 0 | 0.148148 | SMAP1 | 6 | 6q13 | 71434200 | 71628438 |
| MYO6 | 0.395833 | 0.095238 | 0.095238 | 0 | 0.111111 | MYO6 | 6 | 6q14.1 | 76515629 | 76685975 |
| HTR1E | 0.395833 | 0 | 0.095238 | 0 | 0 | HTR1E | 6 | 6q15 | 87703743 | 87783110 |
| GJA1 | 0.395833 | 0.095238 | 0.095238 | 0 | 0.111111 | GJA1 | 6 | 6q22.31 | 1.22E+08 | 1.22E+08 |
| EPM2A | 0.395833 | 0 | 0.095238 | 0 | 0 | EPM2A | 6 | 6q24.3 | 1.46E+08 | 1.46E+08 |
| NOX3 | 0.395833 | 0.095238 | 0 | 0 | 0 | NOX3 | 6 | 6q25.3 | 1.56E+08 | 1.56E+08 |
| SLC22A3 | 0.395833 | 0.095238 | 0 | 0 | 0 | SLC22A3 | 6 | 6q25.3 | 1.61E+08 | 1.61E+08 |
| LPA | 0.395833 | 0.095238 | 0 | 0 | 0 | LPA | 6 | 6q25.3 | 1.61E+08 | 1.61E+08 |
| ADCY2 | 0.395833 | 0.095238 | 0 | 0 | 0 | ADCY2 | 5 | 5p15.31 | 7449343 | 7883195 |
| NPR3 | 0.395833 | 0.095238 | 0 | 0 | 0 | NPR3 | 5 | 5p13.3 | 32747422 | 32823012 |
| DAB2 | 0.395833 | 0 | 0.095238 | 0 | 0 | DAB2 | 5 | 5p13.1 | 39407537 | 39461093 |
| TTC33 | 0.395833 | 0.095238 | 0 | 0 | 0 | TTC33 | 5 | 5p13.1 | 40747435 | 40791830 |

TABLE 4-continued

Gene list for predicting prostate cancer relapse using AT

| Symbol | freq. use | freq. amp. case | freq. del. case | freq. amp. control | freq. del. control | Gene. Symbol | chromo- some | cytoband | Tran- script. start | Tran- script. end |
|---|---|---|---|---|---|---|---|---|---|---|
| PRKAA1 | 0.395833 | 0.095238 | 0 | 0 | 0 | PRKAA1 | 5 | 5p13.1 | 40795238 | 40834055 |
| RPL37 | 0.395833 | 0.095238 | 0 | 0 | 0 | RPL37 | 5 | 5p13.1 | 40867187 | 40871145 |
| SNORD72 | 0.395833 | 0.095238 | 0 | 0 | 0 | SNORD72 | 5 | 5p13.1 | 40868515 | 40868595 |
| CARD6 | 0.395833 | 0.095238 | 0 | 0 | 0 | CARD6 | 5 | 5p13.1 | 40877167 | 40891214 |
| C7 | 0.395833 | 0 | 0.095238 | 0.037037 | 0 | C7 | 5 | 5p13.1 | 40945356 | 41018799 |
| ACTBL2 | 0.395833 | 0.095238 | 0.047619 | 0 | 0 | ACTBL2 | 5 | 5q11.2 | 56811600 | 56814394 |
| IPO11 | 0.395833 | 0.095238 | 0 | 0 | 0.037037 | IPO11 | 5 | 5q12.1 | 61744330 | 61960172 |
| LHFPL2 | 0.395833 | 0.095238 | 0 | 0 | 0 | LHFPL2 | 5 | 5q14.1 | 77816794 | 77980405 |
| ARSB | 0.395833 | 0.095238 | 0 | 0 | 0 | ARSB | 5 | 5q14.1 | 78108793 | 78318114 |
| RASGRF2 | 0.395833 | 0.095238 | 0 | 0 | 0.037037 | RASGRF2 | 5 | 5q14.1 | 80292314 | 80557710 |
| CKMT2 | 0.395833 | 0.095238 | 0 | 0 | 0.037037 | CKMT2 | 5 | 5q14.1 | 80564895 | 80597974 |
| ZCCHC9 | 0.395833 | 0.095238 | 0 | 0 | 0.037037 | ZCCHC9 | 5 | 5q14.1 | 80633158 | 80644720 |
| ACOT12 | 0.395833 | 0.095238 | 0 | 0 | 0.037037 | ACOT12 | 5 | 5q14.1 | 80661703 | 80725745 |
| MEF2C | 0.395833 | 0.095238 | 0.238095 | 0 | 0.185185 | MEF2C | 5 | 5q14.3 | 88049815 | 88235626 |
| RHOBTB3 | 0.395833 | 0.095238 | 0.047619 | 0 | 0.148148 | RHOBTB3 | 5 | 5q15 | 95092606 | 95157828 |
| GLRX | 0.395833 | 0.095238 | 0.047619 | 0 | 0.148148 | GLRX | 5 | 5q15 | 95175309 | 95184334 |
| C5orf27 | 0.395833 | 0.095238 | 0.047619 | 0 | 0.148148 | C5orf27 | 5 | 5q15 | 95213592 | 95221591 |
| TSSK1B | 0.395833 | 0 | 0.095238 | 0 | 0 | TSSK1B | 5 | 5q22.2 | 1.13E+08 | 1.13E+08 |
| 3-Mar | 0.395833 | 0.095238 | 0.047619 | 0 | 0.037037 | 3-Mar | 5 | 5q23.2 | 1.26E+08 | 1.26E+08 |
| CDC42SE2 | 0.395833 | 0.095238 | 0 | 0 | 0 | CDC42SE2 | 5 | 5q31.1 | 1.31E+08 | 1.31E+08 |
| RAPGEF6 | 0.395833 | 0.095238 | 0 | 0 | 0 | RAPGEF6 | 5 | 5q31.1 | 1.31E+08 | 1.31E+08 |
| FNIP1 | 0.395833 | 0.095238 | 0 | 0 | 0 | FNIP1 | 5 | 5q31.1 | 1.31E+08 | 1.31E+08 |
| GRIA1 | 0.395833 | 0 | 0.095238 | 0 | 0 | GRIA1 | 5 | 5q33.2 | 1.53E+08 | 1.53E+08 |
| GEMIN5 | 0.395833 | 0.047619 | 0.095238 | 0.148148 | 0 | GEMIN5 | 5 | 5q33.2 | 1.54E+08 | 1.54E+08 |
| KIF4B | 0.395833 | 0 | 0.095238 | 0.111111 | 0 | KIF4B | 5 | 5q33.2 | 1.54E+08 | 1.54E+08 |
| EBF1 | 0.395833 | 0 | 0.095238 | 0 | 0 | EBF1 | 5 | 5q33.3 | 1.58E+08 | 1.58E+08 |
| TTC1 | 0.395833 | 0.095238 | 0 | 0 | 0 | TTC1 | 5 | 5q33.3 | 1.59E+08 | 1.59E+08 |
| C5orf54 | 0.395833 | 0.095238 | 0.095238 | 0.037037 | 0 | C5orf54 | 5 | 5q33.3 | 1.6E+08 | 1.6E+08 |
| QDPR | 0.395833 | 0.095238 | 0 | 0 | 0 | QDPR | 4 | 4p15.32 | 17097118 | 17122956 |
| CLRN2 | 0.395833 | 0.095238 | 0 | 0 | 0 | CLRN2 | 4 | 4p15.32 | 17125886 | 17137826 |
| LAP3 | 0.395833 | 0.095238 | 0 | 0 | 0 | LAP3 | 4 | 4p15.32 | 17188025 | 17218689 |
| FAM184B | 0.395833 | 0.095238 | 0 | 0 | 0 | FAM184B | 4 | 4p15.32 | 17242809 | 17392234 |
| DCAF16 | 0.395833 | 0.095238 | 0 | 0 | 0 | DCAF16 | 4 | 4p15.32 | 17411376 | 17421480 |
| C4orf19 | 0.395833 | 0.095238 | 0 | 0 | 0.037037 | C4orf19 | 4 | 4p14 | 37131947 | 37271528 |
| RELL1 | 0.395833 | 0.095238 | 0 | 0 | 0 | RELL1 | 4 | 4p14 | 37268817 | 37364395 |
| PGM2 | 0.395833 | 0.095238 | 0 | 0 | 0 | PGM2 | 4 | 4p14 | 37504677 | 37540955 |
| T8C1D1 | 0.395833 | 0.095238 | 0 | 0 | 0 | T8C1D1 | 4 | 4p14 | 37569115 | 37817190 |
| FLI13197 | 0.395833 | 0.095238 | 0 | 0 | 0 | FLI13197 | 4 | 4p14 | 38290717 | 38342645 |
| ANKRD17 | 0.395833 | 0 | 0.095238 | 0 | 0 | ANKRD17 | 4 | 4q13.3 | 74159366 | 74343367 |
| AFP | 0.395833 | 0 | 0.095238 | 0 | 0 | AFP | 4 | 4q13.3 | 74520797 | 74540357 |
| AFM | 0.395833 | 0 | 0.095238 | 0 | 0 | AFM | 4 | 4q13.3 | 74566326 | 74588583 |
| RA5SF6 | 0.395833 | 0 | 0.095238 | 0 | 0 | RA5SF6 | 4 | 4q13.3 | 74657726 | 74704999 |
| DCLK2 | 0.395833 | 0.047619 | 0.095238 | 0 | 0 | DCLK2 | 4 | 4q31.3 | 1.51E+08 | 1.51E+08 |
| FAM160A1 | 0.395833 | 0.095238 | 0 | 0 | 0 | FAM160A1 | 4 | 4q31.3 | 1.53E+08 | 1.53E+08 |
| ITPR1 | 0.395833 | 0.095238 | 0.047819 | 0 | 0 | ITPR1 | 3 | 3p26.2 | 4510032 | 4864523 |
| DVWA | 0.395833 | 0.238095 | 0.095238 | 0.185185 | 0 | DVWA | 3 | 3p24.3 | 15181875 | 15222471 |
| PLCL2 | 0.395833 | 0 | 0.095238 | 0 | 0 | PLCL2 | 3 | 3p24.3 | 16901456 | 17107102 |
| UBE2E2 | 0.395833 | 0 | 0.095238 | 0 | 0 | UBE2E2 | 3 | 3p24.3 | 23219788 | 23607301 |
| UBE2E1 | 0.395833 | 0.095238 | 0.047619 | 0 | 0 | UBE2E1 | 3 | 3p24.2 | 23822443 | 23907812 |
| PDCD6IP | 0.395833 | 0.095238 | 0.047619 | 0 | 0.037037 | PDCD6IP | 3 | 3p22.3 | 33815070 | 33886199 |
| FOXPI | 0.395833 | 0.095238 | 0.047619 | 0 | 0 | FOXPI | 3 | 3p14.1 | 71087426 | 71715831 |
| GXYLT2 | 0.395833 | 0.095238 | 0.047619 | 0 | 0 | GXYLT2 | 3 | 3p13 | 73020075 | 73107213 |
| PPP4R2 | 0.395833 | 0.095238 | 0.047619 | 0 | 0 | PPP4R2 | 3 | 3p13 | 73128809 | 73197702 |
| RETNLB | 0.395833 | 0 | 0.095238 | 0 | 0 | RETNLB | 3 | 3q13.13 | 1.1E+08 | 1.1E+08 |
| TRAT1 | 0.395833 | 0 | 0.095238 | 0 | 0 | TRAT1 | 3 | 3q13.13 | 1.1E+08 | 1.1E+08 |
| GUCA1C | 0.395833 | 0 | 0.095238 | 0 | 0 | GUCA1C | 3 | 3q13.13 | 1.1E+08 | 1.1E+08 |
| MORC1 | 0.395833 | 0 | 0.095238 | 0 | 0 | MORC1 | 3 | 3q13.13 | 1.1E+08 | 1.1E+08 |
| BOC | 0.395833 | 0.095238 | 0.047619 | 0 | 0.037037 | BOC | 3 | 3q13.2 | 1.14E+08 | 1.14E+08 |
| NAT13 | 0.395833 | 0.095238 | 0.047619 | 0 | 0 | NAT13 | 3 | 3q13.2 | 1.15E+08 | 1.15E+08 |
| POLQ | 0.395833 | 0.095238 | 0.047619 | 0 | 0 | POLQ | 3 | 3q13.33 | 1.23E+08 | 1.23E+08 |
| ARGFX | 0.395833 | 0.095238 | 0.047619 | 0 | 0 | ARGFX | 3 | 3q13.33 | 1.23E+08 | 1.23E+08 |
| FBXO40 | 0.395833 | 0.095238 | 0.047619 | 0 | 0 | FBXO40 | 3 | 3q13.33 | 1.23E+08 | 1.23E+08 |
| GOLGB1 | 0.395833 | 0.047619 | 0.095238 | 0 | 0 | GOLGB1 | 3 | 3q13.33 | 1.23E+08 | 1.23E+08 |
| ACAD11 | 0.395833 | 0 | 0.095238 | 0 | 0 | ACAD11 | 3 | 3q22.1 | 1.34E+08 | 1.34E+08 |
| CCRL1 | 0.395833 | 0 | 0.095238 | 0 | 0 | CCRL1 | 3 | 3q22.1 | 1.34E+08 | 1.34E+08 |
| UBA5 | 0.395833 | 0 | 0.095238 | 0 | 0 | UBA5 | 3 | 3q22.1 | 1.34E+08 | 1.34E+08 |
| NCRNA001 | 0.395833 | 0 | 0.095238 | 0 | 0 | NCRNA001 | 3 | 3q22.1 | 1.34E+08 | 1.34E+08 |
| TMEM108 | 0.395833 | 0 | 0.095238 | 0 | 0 | TMEM108 | 3 | 3q22.1 | 1.34E+08 | 1.35E+08 |
| C3orf79 | 0.395833 | 0 | 0.095238 | 0 | 0 | C3orf79 | 3 | 3q25.2 | 1.55E+08 | 1.55E+08 |
| PLCH1 | 0.395833 | 0 | 0.095238 | 0 | 0 | PLCH1 | 3 | 3q25.31 | 1.57E+08 | 1.57E+08 |
| SHOX2 | 0.395833 | 0 | 0.095238 | 0 | 0 | SHOX2 | 3 | 3q25.32 | 1.59E+08 | 1.59E+08 |
| RSRC1 | 0.395833 | 0 | 0.095238 | 0 | 0 | RSRC1 | 3 | 3q25.32 | 1.59E+08 | 1.6E+08 |
| MFSD1 | 0.395833 | 0 | 0.095238 | 0 | 0 | MFSD1 | 3 | 3q25.33 | 1.6E+08 | 1.6E+08 |
| IQCI | 0.395833 | 0 | 0.095238 | 0 | 0 | IQCI | 3 | 3q25.33 | 1.6E+08 | 1.6E+08 |

TABLE 4-continued

Gene list for predicting prostate cancer relapse using AT

| Symbol | freq. use | freq. amp. case | freq. del. case | freq. amp. control | freq. del. control | Gene. Symbol | chromo- some | cytoband | Tran- script. start | Tran- script. end |
|---|---|---|---|---|---|---|---|---|---|---|
| SCHIP1 | 0.395833 | 0 | 0.095238 | 0 | 0 | SCHIP1 | 3 | 3q25.33 | 1.6E+08 | 1.61E+08 |
| C3orf57 | 0.395833 | 0 | 0.095238 | 0 | 0 | C3orf57 | 3 | 3q26.1 | 1.63E+08 | 1.63E+08 |
| TBL1XR1 | 0.395833 | 0.095238 | 0 | 0 | 0 | TBL1XR1 | 3 | 3q26.32 | 1.78E+08 | 1.78E+08 |
| ZNF639 | 0.395833 | 0.095238 | 0 | 0 | 0 | ZNF639 | 3 | 3q26.32 | 1.81E+08 | 1.81E+08 |
| GN84 | 0.395833 | 0.095238 | 0 | 0 | 0 | GN84 | 3 | 3q26.33 | 1.81E+08 | 1.81E+08 |
| ACTL6A | 0.395833 | 0.095238 | 0 | 0 | 0 | ACTL6A | 3 | 3q26.33 | 1.81E+08 | 1.81E+08 |
| MRPL47 | 0.395833 | 0.095238 | 0.047619 | 0 | 0 | MRPL47 | 3 | 3q26.33 | 1.81E+08 | 1.81E+08 |
| USP13 | 0.395833 | 0.095238 | 0 | 0 | 0 | USP13 | 3 | 3q26.33 | 1.81E+08 | 1.81E+08 |
| SOX2OT | 0.395833 | 0.095238 | 0.095238 | 0 | 0.037037 | SOX2OT | 3 | 3q26.33 | 1.83E+08 | 1.83E+08 |
| TPRG1 | 0.395833 | 0 | 0.095238 | 0.037037 | 0 | TPRG1 | 3 | 3q28 | 1.9E+08 | 1.91E+08 |
| TP63 | 0.395833 | 0 | 0.095238 | 0.037037 | 0 | TP63 | 3 | 3q28 | 1.91E+08 | 1.91E+08 |
| LEPREL1 | 0.395833 | 0 | 0.095233 | 0 | 0 | LEPREL1 | 3 | 3q28 | 1.91E+08 | 1.91E+08 |
| CLDN1 | 0.395833 | 0 | 0.095238 | 0 | 0 | CLDN1 | 3 | 3q28 | 1.92E+08 | 1.92E+08 |
| IL1RAP | 0.395833 | 0 | 0.095238 | 0 | 0 | IL1RAP | 3 | 3q28 | 1.92E+08 | 1.92E+08 |
| LOC647309 | 0.395833 | 0 | 0.095238 | 0 | 0 | LOC647309 | 3 | 3q28 | 1.92E+08 | 1.92E+08 |
| SNAR-I | 0.395833 | 0 | 0.095238 | 0 | 0 | SNAR-I | 3 | 3q28 | 1.92E+08 | 1.92E+08 |
| HRASLS | 0.395833 | 0.047619 | 0.095238 | 0 | 0 | HRASLS | 3 | 3q29 | 1.94E+08 | 1.94E+08 |
| ATP13A5 | 0.395833 | 0.047619 | 0.095238 | 0 | 0 | ATP13A5 | 3 | 3q29 | 1.94E+08 | 1.95E+08 |
| ROCK2 | 0.395833 | 0.333333 | 0.095238 | 0.259259 | 0 | ROCK2 | 2 | 2p25.1 | 11239229 | 11402163 |
| C2orf43 | 0.395833 | 0.047619 | 0.095238 | 0 | 0 | C2orf43 | 2 | 2p24.1 | 20748299 | 20886309 |
| CRIM1 | 0.395833 | 0.095238 | 0 | 0 | 0 | CRIM1 | 2 | 2p22.2 | 36436901 | 36631783 |
| CDKL4 | 0.395833 | 0.095238 | 0 | 0 | 0 | CDKL4 | 2 | 2p22.1 | 39259192 | 39310178 |
| MAP4K3 | 0.395833 | 0.095238 | 0 | 0 | 0 | MAP4K3 | 2 | 2p22.1 | 39329926 | 39517724 |
| SLC9A2 | 0.395833 | 0.095238 | 0.047619 | 0 | 0 | SLC9A2 | 2 | 2q12.1 | 1.03E+08 | 1.03E+08 |
| SLC5A7 | 0.395833 | 0.047619 | 0.095238 | 0.074074 | 0 | SLC5A7 | 2 | 2q12.3 | 1.08E+08 | 1.08E+08 |
| DDX18 | 0.395833 | 0.095238 | 0 | 0 | 0.037037 | DDX18 | 2 | 2q14.1 | 1.18E+08 | 1.18E+08 |
| CCDC93 | 0.395833 | 0.095238 | 0 | 0 | 0.037037 | CCDC93 | 2 | 2q14.1 | 1.18E+08 | 1.18E+08 |
| MGAT5 | 0.395833 | 0.095238 | 0 | 0 | 0 | MGAT5 | 2 | 2q21.3 | 1.35E+08 | 1.35E+08 |
| KIFSC | 0.395833 | 0.095238 | 0.047619 | 0 | 0.037037 | KIFSC | 2 | 2q23.1 | 1.49E+08 | 1.5E+08 |
| MIR1978 | 0.395833 | 0.095238 | 0.047619 | 0 | 0.037037 | MIR1978 | 2 | 2q23.1 | 1.49E+08 | 1.49E+08 |
| RND3 | 0.395833 | 0 | 0.095238 | 0 | 0 | RND3 | 2 | 2q23.3 | 1.51E+08 | 1.51E+08 |
| DPP4 | 0.395833 | 0.095238 | 0 | 0 | 0.111111 | DPP4 | 2 | 2q24.2 | 1.63E+08 | 1.63E+08 |
| DYNC1I2 | 0.395833 | 0.047619 | 0.095238 | 0.074074 | 0 | DYNC1I2 | 2 | 2q31.1 | 1.72E+08 | 1.72E+08 |
| OLA1 | 0.395833 | 0.095238 | 0.047619 | 0 | 0 | OLA1 | 2 | 2q31.1 | 1.75E+08 | 1.75E+08 |
| GPR155 | 0.395833 | 0.095238 | 0 | 0 | 0 | GPR155 | 2 | 2q31.1 | 1.75E+08 | 1.75E+08 |
| WIPF1 | 0.395833 | 0.095238 | 0 | 0 | 0 | WIPF1 | 2 | 2q31.1 | 1.75E+08 | 1.75E+08 |
| CHRNA1 | 0.395833 | 0.095238 | 0 | 0 | 0 | CHRNA1 | 2 | 2q31.1 | 1.75E+08 | 1.75E+08 |
| KCTD18 | 0.395833 | 0.095238 | 0 | 0 | 0 | KCTD18 | 2 | 2q33.1 | 2.01E+08 | 2.01E+08 |
| SGOL2 | 0.395833 | 0.095238 | 0 | 0 | 0 | SGOL2 | 2 | 2q33.1 | 2.01E+08 | 2.01E+08 |
| AOX1 | 0.395833 | 0.095238 | 0 | 0 | 0 | AOX1 | 2 | 2q33.1 | 2.01E+08 | 2.01E+08 |
| PARD3B | 0.395833 | 0 | 0.095238 | 0 | 0 | PARD3B | 2 | 2q33.2 | 2.05E+08 | 2.06E+08 |
| TMEM57 | 0.395833 | 0.47619 | 0.095238 | 0.592593 | 0 | TMEM57 | 1 | 1p36.11 | 25629975 | 25699284 |
| LDLRAP1 | 0.395833 | 0.47619 | 0.095238 | 0.592593 | 0 | LDLRAP1 | 1 | 1p36.11 | 25742663 | 25767965 |
| SKINTL | 0.395833 | 0.047619 | 0.095238 | 0.222222 | 0 | SKINTL | 1 | 1p33 | 48349974 | 48420688 |
| DNAJC6 | 0.395833 | 0.095238 | 0 | 0 | 0 | DNAJC6 | 1 | 1p31.3 | 65503018 | 65654141 |
| LEPR | 0.395833 | 0.095238 | 0 | 0 | 0 | LEPR | 1 | 1p31.3 | 65558836 | 65873699 |
| LEPROT | 0.395833 | 0.095238 | 0 | 0 | 0 | LEPROT | 1 | 1p31.3 | 65658836 | 65674277 |
| TCTEX1D1 | 0.395833 | 0 | 0.095238 | 0 | 0 | TCTEX1D1 | 1 | 1p31.3 | 66990728 | 67017318 |
| WDR78 | 0.395833 | 0 | 0.095238 | 0 | 0 | WDR78 | 1 | 1p31.3 | 67051161 | 67163159 |
| SLC35D1 | 0.395833 | 0 | 0.095238 | 0 | 0 | SLC35D1 | 1 | 1p31.3 | 67237604 | 67292669 |
| SERBP1 | 0.395833 | 0.095238 | 0 | 0 | 0 | SERBP1 | 1 | 1p31.3 | 67646081 | 67668712 |
| HFM1 | 0.395833 | 0.095238 | 0 | 0 | 0 | HFM1 | 1 | 1p22.2 | 91498911 | 91643015 |
| CDC7 | 0.395833 | 0.095238 | 0 | 0 | 0 | CDC7 | 1 | 1p22.2 | 91738992 | 91763909 |
| HSP90B3P | 0.395833 | 0.095238 | 0 | 0 | 0 | HSP90B3P | 1 | 1p22.2 | 91873156 | 91881923 |
| TGFBR3 | 0.395833 | 0.095238 | 0 | 0 | 0 | TGFBR3 | 1 | 1p22.2 | 91918490 | 92124376 |
| BRDT | 0.395833 | 0.095238 | 0 | 0 | 0 | BRDT | 1 | 1p22.1 | 92187516 | 92252574 |
| EPHX4 | 0.395833 | 0.095238 | 0 | 0 | 0 | EPHX4 | 1 | 1p22.1 | 92268121 | 92301682 |
| BTBD8 | 0.395833 | 0.095238 | 0 | 0 | 0 | BTBD8 | 1 | 1p22.1 | 92318450 | 92385984 |
| KIAA1107 | 0.395833 | 0.095238 | 0 | 0 | 0 | KIAA1107 | 1 | 1p22.1 | 92405197 | 92422868 |
| GFI1 | 0.395833 | 0.095238 | 0 | 0 | 0 | GFI1 | 1 | 1p22.1 | 92712906 | 92721945 |
| EV15 | 0.395833 | 0.095238 | 0 | 0 | 0 | EV15 | 1 | 1p22.1 | 92746841 | 93030550 |
| ABCD3 | 0.395833 | 0.095238 | 0.047619 | 0 | 0 | ABCD3 | 1 | 1p21.3 | 94656521 | 94716849 |
| SLC44A3 | 0.395833 | 0.095238 | 0 | 0 | 0 | SLC44A3 | 1 | 1p21.3 | 95058489 | 35133391 |
| CNN3 | 0.395833 | 0.095238 | 0 | 0 | 0 | CNN3 | 1 | 1p21.3 | 95135095 | 95165324 |
| ALG14 | 0.395833 | 0.095238 | 0 | 0 | 0 | ALG14 | 1 | 1p21.3 | 95220867 | 95311096 |
| TMEM56 | 0.395833 | 0.095238 | 0.047619 | 0 | 0.037037 | TMEM56 | 1 | 1p21.3 | 95355482 | 95435748 |
| GDAP2 | 0.395833 | 0 | 0.095238 | 0.037037 | 0 | GDAP2 | 1 | 1p12 | 1.18E+08 | 1.18E+08 |
| SPAG17 | 0.395833 | 0 | 0.095238 | 0.037037 | 0 | SPAG17 | 1 | 1p12 | 1.18E+08 | 1.19E+08 |
| TBX15 | 0.395833 | 0 | 0.095238 | 0 | 0 | TBX15 | 1 | 1p12 | 1.19E+08 | 1.19E+08 |
| SPRR2F | 0.395833 | 0.095238 | 0.095238 | 0.185185 | 0 | SPRR2F | 1 | 1q21.3 | 1.51E+08 | 1.51E+08 |
| SPRR2C | 0.395833 | 0.095238 | 0.095238 | 0.185185 | 0 | SPRR2C | 1 | 1q21.3 | 1.51E+08 | 1.51E+08 |
| SPRR2G | 0.395833 | 0.095238 | 0.095238 | 0.185185 | 0 | SPRR2G | 1 | 1q21.3 | 1.51E+08 | 1.51E+08 |
| CD1D | 0.395833 | 0.047619 | 0.095238 | 0.074074 | 0 | CD1D | 1 | 1q23.1 | 1.56E+08 | 1.56E+08 |
| CD1A | 0.395833 | 0.047619 | 0.095238 | 0.074074 | 0 | CD1A | 1 | 1q23.1 | 1.56E+08 | 1.56E+08 |

TABLE 4-continued

Gene list for predicting prostate cancer relapse using AT

| Symbol | freq. use | freq. amp. case | freq. del. case | freq. amp. control | freq. del. control | Gene. Symbol | chromo- some | cytoband | Tran- script. start | Tran- script. end |
|---|---|---|---|---|---|---|---|---|---|---|
| SPTA1 | 0.395833 | 0.047619 | 0.095238 | 0.074074 | 0 | SPTA1 | 1 | 1q23.1 | 1.57E+08 | 1.57E+08 |
| OR6K6 | 0.395833 | 0.047619 | 0.095238 | 0.074074 | 0 | OR6K6 | 1 | 1q23.1 | 1.57E+08 | 1.57E+08 |
| PYHIN1 | 0.395833 | 0.047619 | 0.095238 | 0.074074 | 0 | PYHIN1 | 1 | 1q23.1 | 1.57E+08 | 1.57E+08 |
| IFI16 | 0.395833 | 0.047519 | 0.095238 | 0.074074 | 0 | IFI16 | 1 | 1q23.1 | 1.57E+08 | 1.57E+08 |
| AIM2 | 0.395833 | 0.047619 | 0.095238 | 0.074074 | 0 | AIM2 | 1 | 1q23.1-1q23.2 | 1.57E+08 | 1.57E+08 |
| DUSP12 | 0.395833 | 0.047619 | 0.095238 | 0 | 0 | DUSP12 | 1 | 1q23.3 | 1.6E+08 | 1.6E+08 |
| ATF6 | 0.395833 | 0.047619 | 0.095238 | 0 | 0 | ATF6 | 1 | 1q23.3 | 1.6E+08 | 1.6E+08 |
| M1R556 | 0.395833 | 0.095233 | 0 | 0 | 0 | M1R556 | 1 | 1q23.3 | 1.61E+08 | 1.61E+08 |
| UHMK1 | 0.395833 | 0.095238 | 0 | 0 | 0 | UHMK1 | 1 | 1q23.3 | 1.61E+08 | 1.61E+08 |
| FAM78B | 0.395833 | 0.095238 | 0 | 0 | 0 | FAM78B | 1 | 1q24.1 | 1.64E+08 | 1.64E+08 |
| GPA33 | 0.395833 | 0.095238 | 0 | 0 | 0 | GPA33 | 1 | 1q24.1 | 1.65E+08 | 1.65E+08 |
| DUSP27 | 0.395833 | 0.095238 | 0 | 0 | 0 | DUSP27 | 1 | 1q24.1 | 1.65E+08 | 1.65E+08 |
| POU2F1 | 0.395833 | 0.095238 | 0 | 0 | 0 | POU2F1 | 1 | 1q24.2 | 1.65E+08 | 1.66E+08 |
| CD247 | 0.395833 | 0.095238 | 0 | 0 | 0 | CD247 | 1 | 1q24.2 | 1.66E+08 | 1.66E+08 |
| CREG1 | 0.395833 | 0.095238 | 0 | 0 | 0 | CREG1 | 1 | 1q24.2 | 1.66E+08 | 1.06E+08 |
| RCSD1 | 0.395833 | 0.095238 | 0 | 0 | 0 | RCSD1 | 1 | 1q24.2 | 1.66E+08 | 1.66E+08 |
| MPZL1 | 0.395833 | 0.095238 | 0 | 0 | 0 | MPZL1 | 1 | 1q24.2 | 1.66E+08 | 1.66E+08 |
| ADCY10 | 0.395833 | 0.095238 | 0 | 0 | 0 | ADCY10 | 1 | 1q24.2 | 1.66E+08 | 1.66E+08 |
| BRP44 | 0.395833 | 0.095238 | 0 | 0 | 0 | BRP44 | 1 | 1q24.2 | 1.66E+08 | 1.66E+08 |
| DCAF6 | 0.395833 | 0.095238 | 0 | 0 | 0 | DCAF6 | 1 | 1q24.2 | 1.66E+08 | 1.66E+08 |
| GPR161 | 0.395833 | 0.095238 | 0 | 0 | 0 | GPR161 | 1 | 1q24.2 | 1.66E+08 | 1.66E+08 |
| ANKRD36B | 0.395833 | 0.095238 | 0 | 0 | 0 | ANKRD36B | 1 | 1q24.2 | 1.66E+08 | 1.66E+08 |
| MIR557 | 0.395833 | 0.095238 | 0 | 0 | 0 | MIR557 | 1 | 1q24.2 | 1.67E+08 | 1.67E+08 |
| KIFAP3 | 0.395833 | 0 | 0.095238 | 0 | 0 | KIFAP3 | 1 | 1q24.2 | 1.68E+08 | 1.68E+08 |
| METTL11B | 0.395833 | 0 | 0.095238 | 0 | 0 | METTL11B | 1 | 1q24.2 | 1.68E+08 | 1.68E+08 |
| FMO3 | 0.395833 | 0 | 0.095238 | 0 | 0 | FMO3 | 1 | 1q24.3 | 1.69E+08 | 1.69E+08 |
| MIR1295 | 0.395833 | 0 | 0.095238 | 0 | 0 | MIR1295 | 1 | 1q24.3 | 1.69E+08 | 1.69E+08 |
| FMO2 | 0.395833 | 0 | 0.095238 | 0 | 0 | FMO2 | 1 | 1q24.3 | 1.69E+08 | 1.69E+08 |
| FMO1 | 0.395833 | 0 | 0.095238 | 0 | 0 | FMO1 | 1 | 1q24.3 | 1.69E+08 | 1.7E+08 |
| FMO4 | 0.395833 | 0.095238 | 0 | 0 | 0 | FMO4 | 1 | 1q24.3 | 1.7E+08 | 1.7E+08 |
| TOP1P1 | 0.395833 | 0.095238 | 0 | 0 | 0 | TOP1P1 | 1 | 1q24.3 | 1.7E+08 | 1.7E+08 |
| BAT2L2 | 0.395833 | 0.095238 | 0 | 0 | 0 | BAT2L2 | 1 | 1q24.3 | 1.7E+08 | 1.7E+08 |
| MYOC | 0.395833 | 0.095238 | 0 | 0 | 0 | MYOC | 1 | 1q24.3 | 1.7E+08 | 1.7E+08 |
| C1orf105 | 0.395833 | 0 | 0.095238 | 0 | 0 | C1orf105 | 1 | 1q24.3 | 1.71E+08 | 1.71E+08 |
| C1orf9 | 0.395833 | 0 | 0.095238 | 0 | 0 | C1orf9 | 1 | 1q24.3 | 1.71E+08 | 1.71E+08 |
| RABGAP1L | 0.395833 | 0.095238 | 0.047619 | 0 | 0 | RABGAP1L | 1 | 1q25.1 | 1.72E+08 | 1.73E+08 |
| XPR1 | 0.395833 | 0.095238 | 0 | 0 | 0 | XPR1 | 1 | 1q25.3 | 1.79E+08 | 1.79E+08 |
| CACNA1E | 0.395833 | 0.095238 | 0 | 0 | 0 | CACNA1E | 1 | 1q25.3 | 1.8E+08 | 1.8E+08 |
| LAMC1 | 0.395833 | 0.095238 | 0 | 0 | 0 | LAMC1 | 1 | 1q25.3 | 1.81E+08 | 1.81E+08 |
| LAMC2 | 0.395833 | 0.095238 | 0 | 0 | 0 | LAMC2 | 1 | 1q25.3 | 1.81E+08 | 1.81E+08 |
| C4BPA | 0.395833 | 0.095238 | 0.095238 | 0.259259 | 0 | C4BPA | 1 | 1q32.2 | 2.05E+08 | 2.05E+08 |
| SYT14 | 0.395833 | 0.095238 | 0.095238 | 0.111111 | 0 | SYT14 | 1 | 1q32.2 | 2.08E+08 | 2.08E+08 |
| LOC400804 | 0.395833 | 0 | 0.095238 | 0 | 0 | LOC400804 | 1 | 1q41 | 2.2E+08 | 2.2E+08 |
| AKT3 | 0.395833 | 0 | 0.095238 | 0 | 0 | AKT3 | 1 | 1q44 | 2.42E+08 | 2.42E+08 |
| OR2L13 | 0.395833 | 0.095238 | 0.095238 | 0.111111 | 0 | OR2L13 | 1 | 1q44 | 2.46E+08 | 2.46E+08 |
| C21orf34 | 0.020833 | 0 | 0.142857 | 0 | 0.037037 | C21orf34 | 21 | 21q21.1 | 16364713 | 16903966 |
| SMCHD1 | 0.020833 | 0.190476 | 0 | 0.037037 | 0 | SMCHD1 | 18 | 18p11.3 | 2645886 | 2795016 |
| LOC727896 | 0.020833 | 0.238095 | 0 | 0.037037 | 0 | LOC727896 | 18 | 18p11.3 | 2933215 | 2936622 |
| ARHGAP28 | 0.020833 | 0.190475 | 0 | 0.037037 | 0 | ARHGAP28 | 18 | 18p11.31 | 6824484 | 6905713 |
| PTPRM | 0.020833 | 0.190476 | 0 | 0.037037 | 0 | PTPRM | 18 | 18p11.23 | 7557314 | 8396860 |
| CTAGE1 | 0.020833 | 0.190476 | 0 | 0.037037 | 0 | CTAGE1 | 18 | 18q11.2 | 18247562 | 18251877 |
| RBBP8 | 0.020833 | 0.285714 | 0 | 0.037037 | 0.111111 | RBBP8 | 18 | 18q11.2 | 18767293 | 18860448 |
| MAPRE2 | 0.020833 | 0 | 0.142857 | 0 | 0.037037 | MAPRE2 | 18 | 18q12.1 | 30810890 | 30976376 |
| FHOD3 | 0.020833 | 0.142857 | 0 | 0.037037 | 0 | FHOD3 | 18 | 18q12.2 | 32131700 | 32614017 |
| KIAA1328 | 0.020833 | 0 | 0.142857 | 0.037037 | 0.037037 | KIAA1328 | 18 | 18q12.2 | 32663078 | 33059287 |
| DYM | 0.020833 | 0.047619 | 0.142857 | 0.148148 | 0.037037 | DYM | 18 | 18q21.1 | 44824170 | 45241078 |
| ALPK2 | 0.020833 | 0.238095 | 0 | 0.037037 | 0 | ALPK2 | 18 | 18q21.31 | 54299462 | 54447170 |
| MALT1 | 0.020833 | 0.238095 | 0 | 0.037037 | 0 | MALT1 | 18 | 18q21.32 | 54489598 | 54568351 |
| ZNF532 | 0.020833 | 0.238095 | 0 | 0.037037 | 0 | ZNF532 | 18 | 18q21.32 | 54681041 | 54804690 |
| LOC390858 | 0.020833 | 0.238095 | 0 | 0.037037 | 0 | LOC390858 | 18 | 18q21.32 | 54853951 | 54871427 |
| SEC11C | 0.020833 | 0.238095 | 0 | 0.037037 | 0 | SEC11C | 18 | 18q21.32 | 54958105 | 54977044 |
| CPLX4 | 0.020833 | 0.238095 | 0 | 0.037037 | 0 | CPLX4 | 18 | 18q21.32 | 55113618 | 55136862 |
| LMAN1 | 0.020833 | 0.238095 | 0 | 0.037037 | 0 | LMAN1 | 18 | 18q21.32 | 55146037 | 55177489 |
| CCBE1 | 0.020833 | 0.238095 | 0 | 0.037037 | 0 | CCBE1 | 18 | 18q21.32 | 55252129 | 55515625 |
| PHLPP1 | 0.020833 | 0.190476 | 0 | 0.037037 | 0 | PHLPP1 | 18 | 18q21.33 | 58533714 | 58798647 |
| SERPINB3 | 0.020833 | 0 | 0.190476 | 0 | 0.037037 | SERPINB3 | 18 | 18q21.33 | 59473411 | 59480178 |
| CYB5A | 0.020833 | 0.238095 | 0 | 0.037037 | 0 | CYB5A | 18 | 18q22.3 | 70071507 | 70110202 |
| FAM69C | 0.020833 | 0.238095 | 0 | 0.037037 | 0 | FAM69C | 18 | 18q22.3 | 70253943 | 70275484 |
| CNDP2 | 0.020833 | 0.238095 | 0 | 0.037037 | 0 | CNDP2 | 18 | 18q22.3 | 70314480 | 70341668 |
| CHD9 | 0.020833 | 0.190476 | 0 | 0.037037 | 0 | CHD9 | 16 | 16q12.2 | 51646446 | 51918916 |
| AKTIP | 0.020833 | 0.142857 | 0 | 0.037037 | 0 | AKTIP | 16 | 16q12.2 | 52082693 | 52094672 |
| IRX3 | 0.020833 | 0.142857 | 0 | 0.037037 | 0 | IRX3 | 16 | 16q12.2 | 52574713 | 52877880 |
| WWOX | 0.020833 | 0.142857 | 0.047619 | 0.037037 | 0 | WWOX | 16 | 16q23.1 | 76691052 | 77804066 |

TABLE 4-continued

Gene list for predicting prostate cancer relapse using AT

| Symbol | freq. use | freq. amp. case | freq. del. case | freq. amp. control | freq. del. control | Gene. Symbol | chromo-some | cytoband | Transcript. start | Transcript. end |
|---|---|---|---|---|---|---|---|---|---|---|
| SNRPN | 0.020833 | 0.190476 | 0 | 0.037037 | 0 | SNRPN | 15 | 15q11.2 | 22619887 | 22774823 |
| ATPBD4 | 0.020833 | 0.047619 | 0.142857 | 0 | 0.037037 | ATPBD4 | 15 | 15q14 | 33450462 | 33625697 |
| C15orf41 | 0.020833 | 0.047619 | 0.142857 | 0 | 0.037037 | C15orf41 | 15 | 15q14 | 34659104 | 34889742 |
| CSNK1A1P | 0.020833 | 0.047619 | 0.142857 | 0 | 0.037037 | CSNK1A1P | 15 | 15q14 | 34878594 | 34898000 |
| LOC145845 | 0.020833 | 0.047619 | 0.142857 | 0 | 0.037037 | LOC145845 | 15 | 15q14 | 34943936 | 34966027 |
| GLDN | 0.020833 | 0.190476 | 0 | 0.037037 | 0 | GLDN | 15 | 15q21.2 | 49421005 | 49487502 |
| GCOM1 | 0.020833 | 0.190476 | 0 | 0.037037 | 0 | GCOM1 | 15 | 15q21.3 | 55671406 | 55797046 |
| GRINL1A | 0.020833 | 0.190476 | 0 | 0.037037 | 0 | GRINL1A | 15 | 15q21.3 | 55786193 | 55797046 |
| AQP9 | 0.020833 | 0.142857 | 0.047619 | 0.037037 | 0 | AQP9 | 15 | 15q22.1 | 56217700 | 56265403 |
| SCAPER | 0.020833 | 0.238095 | 0.142857 | 0.481481 | 0.037037 | SCAPER | 15 | 15q24.3 | 74427584 | 74941341 |
| TTC5 | 0.020833 | 0.238095 | 0 | 0.037037 | 0.037037 | TTC5 | 14 | 14q11.2 | 19827141 | 19843994 |
| CCNB1IP1 | 0.020833 | 0.238095 | 0 | 0.037037 | 0.037037 | CCNB1IP1 | 14 | 14q11.2 | 19849369 | 19871298 |
| SNORD126 | 0.020833 | 0.238095 | 0 | 0.037037 | 0.037037 | SNORD126 | 14 | 14q11.2 | 19864440 | 19864539 |
| MIR1201 | 0.020833 | 0.238095 | 0 | 0.037037 | 0.037037 | MIR1201 | 14 | 14q11.2 | 19864449 | 19864531 |
| RPPH1 | 0.020833 | 0.238095 | 0 | 0.037037 | 0.037037 | RPPH1 | 14 | 14q11.2 | 19881070 | 19881411 |
| PARP2 | 0.020833 | 0.238095 | 0 | 0.037037 | 0.037037 | PARP2 | 14 | 14q11.2 | 19881613 | 19895904 |
| METT11D1 | 0.020833 | 0.285724 | 0 | 0.037037 | 0 | METT11D1 | 14 | 14q11.2 | 20527805 | 20535035 |
| S1C39A2 | 0.020833 | 0.285714 | 0 | 0.037037 | 0 | S1C39A2 | 14 | 14q11.2 | 20537259 | 20539871 |
| NDRG2 | 0.020833 | 0.285714 | 0 | 0.037037 | 0 | NDRG2 | 14 | 14q11.2 | 20554762 | 20563776 |
| TPPP2 | 0.020833 | 0.285714 | 0 | 0.037037 | 0 | TPPP2 | 14 | 14q11.2 | 20568185 | 20570171 |
| RNASE13 | 0.020833 | 0.285714 | 0 | 0.037037 | 0 | RNASE13 | 14 | 14q11.2 | 20570819 | 20572785 |
| RNASE7 | 0.020833 | 0.285714 | 0 | 0.037037 | 0 | RNASE7 | 14 | 14q11.2 | 20580225 | 20582233 |
| RNASE8 | 0.020833 | 0.285714 | 0 | 0.037037 | 0 | RNASE8 | 14 | 14q11.2 | 20595892 | 20596357 |
| FLI10357 | 0.020833 | 0.285714 | 0 | 0.037037 | 0 | FLI10357 | 14 | 14q11.2 | 20608367 | 20627877 |
| ZNF219 | 0.020833 | 0.285714 | 0 | 0.037037 | 0 | ZNF219 | 14 | 14q11.2 | 20628045 | 20637014 |
| C14orf176 | 0.020833 | 0.285714 | 0 | 0.037037 | 0 | C14orf176 | 14 | 14q11.2 | 20636936 | 20641723 |
| OR5AU1 | 0.020833 | 0.285714 | 0 | 0.037037 | 0 | OR5AU1 | 14 | 14q11.2 | 20692936 | 20694025 |
| HNRNPC | 0.020833 | 0.285714 | 0 | 0.037037 | 0 | HNRNPC | 14 | 14q11.2 | 20747136 | 20807473 |
| RPGRIP1 | 0.020833 | 0.285714 | 0 | 0.037037 | 0 | RPGRIP1 | 14 | 14q11.2 | 20825976 | 20889301 |
| SUPT16H | 0.020833 | 0.285714 | 0 | 0.037037 | 0 | SUPT16H | 14 | 14q11.2 | 20889472 | 20922266 |
| RAB2B | 0.020833 | 0.285714 | 0 | 0.037037 | 0 | RAB2B | 14 | 14q11.2 | 20997020 | 21014673 |
| TOX4 | 0.020833 | 0.285714 | 0 | 0.037037 | 0 | TOX4 | 14 | 14q11.2 | 21015175 | 21037160 |
| METTL3 | 0.020833 | 0.285714 | 0 | 0.037037 | 0 | METTL3 | 14 | 14q11.2 | 21036122 | 21049298 |
| SALL2 | 0.020833 | 0.285714 | 0 | 0.037037 | 0 | SALL2 | 14 | 14q11.2 | 21059072 | 21075178 |
| OR10G3 | 0.020833 | 0.285714 | 0 | 0.037037 | 0 | OR10G3 | 14 | 14q11.2 | 21107774 | 21108716 |
| STRN3 | 0.020833 | 0.285714 | 0 | 0.037037 | 0 | STRN3 | 14 | 14q12 | 30432756 | 30565359 |
| MIA2 | 0.020833 | 0.142857 | 0.047619 | 0.037037 | 0.074074 | MIA2 | 14 | 14q21.1 | 38772876 | 38792327 |
| CTAGE5 | 0.020833 | 0.142857 | 0.047619 | 0.037037 | 0.074074 | CTAGE5 | 14 | 14q21.1 | 38804227 | 38890149 |
| GCH1 | 0.020833 | 0.190476 | 0 | 0.037037 | 0 | GCH1 | 14 | 14q22.2 | 54378474 | 54439293 |
| WDHD1 | 0.020833 | 0.190476 | 0 | 0.037037 | 0 | WDHD1 | 14 | 14q22.3 | 54476692 | 54563558 |
| MAPK1IP1L | 0.020833 | 0.190476 | 0 | 0.037037 | 0 | MAPK1IP1L | 14 | 14q22.3 | 54588115 | 54606666 |
| DLGAP5 | 0.020833 | 0.190476 | 0 | 0.037037 | 0 | DLGAP5 | 14 | 14q22.3 | 54684589 | 54728150 |
| FBXO34 | 0.020833 | 0.190476 | 0 | 0.037037 | 0 | FBXO34 | 14 | 14q22.3 | 54807774 | 54890081 |
| KIAA0831 | 0.020833 | 0.190476 | 0 | 0.037037 | 0 | KIAA0831 | 14 | 14q22.3 | 54902863 | 54948330 |
| TBPL2 | 0.020833 | 0.190476 | 0 | 0.037037 | 0 | TBPL2 | 14 | 14q22.3 | 54950683 | 54977017 |
| HIF1A | 0.020833 | 0.142857 | 0 | 0.037037 | 0 | HIF1A | 14 | 14q23.2 | 61231872 | 61284731 |
| DIO2 | 0.020833 | 0 | 0.142857 | 0 | 0.037037 | DIO2 | 14 | 14q31.1 | 79733622 | 79748279 |
| LOC284232 | 0.020833 | 0.142857 | 0 | 0.037037 | 0.074074 | LOC284232 | 13 | 13q11 | 18306543 | 18344110 |
| SGCG | 0.020833 | 0.238095 | 0 | 0.037037 | 0 | SGCG | 13 | 13q12.12 | 22653060 | 22797305 |
| MIPEP | 0.020833 | 0.238095 | 0 | 0.037037 | 0 | MIPEP | 13 | 13q12.12 | 23202328 | 23361560 |
| TRPC4 | 0.020833 | 0 | 0.190476 | 0 | 0.037037 | TRPC4 | 13 | 13q13.3 | 37108775 | 37341940 |
| CLDN10 | 0.020833 | 0.380952 | 0 | 0.037037 | 0 | CLDN10 | 13 | 13q32.1 | 94883854 | 95030012 |
| UBAC2 | 0.020833 | 0.238095 | 0 | 0.037037 | 0 | UBAC2 | 13 | 13q32.3 | 98650680 | 98836753 |
| MIR623 | 0.020833 | 0.190476 | 0 | 0.037037 | 0 | MIR623 | 13 | 13q32.3 | 98806386 | 98806484 |
| CLYBL | 0.020833 | 0.190476 | 0 | 0.037037 | 0 | CLYBL | 13 | 13q32.3 | 99056920 | 99347389 |
| A2LD1 | 0.020833 | 0.142857 | 0 | 0.037037 | 0 | A2LD1 | 13 | 13q32.3 | 99981811 | 99983999 |
| CCDC91 | 0.020833 | 0 | 0.190476 | 0 | 0.037037 | CCDC91 | 12 | 12p11.22 | 28301400 | 28594367 |
| LRIG3 | 0.020833 | 0 | 0.190476 | 0 | 0.037037 | LRIG3 | 12 | 12q14.1 | 57552204 | 57600530 |
| TPH2 | 0.020833 | 0 | 0.190476 | 0 | 0.037037 | TPH2 | 12 | 12q21.1 | 70618893 | 70712489 |
| LOC100128191 | 0.020833 | 0.333333 | 0 | 0.037037 | 0 | LOC100128191 | 12 | 12q23.1 | 97430884 | 97434136 |
| TMPO | 0.020833 | 0.333333 | 0 | 0.037037 | 0 | TMPO | 12 | 12q23.1 | 97433540 | 97466867 |
| SLC25A3 | 0.020833 | 0.333333 | 0 | 0.037037 | 0 | SLC25A3 | 12 | 12q23.1 | 97511534 | 97519909 |
| APAF1 | 0.020833 | 0.285714 | 0 | 0.037037 | 0 | APAF1 | 12 | 12q23.1 | 97563209 | 97653343 |
| SOX6 | 0.020833 | 0.047619 | 0.190476 | 0 | 0.037037 | SOX6 | 11 | 11p15.2-11p15.1 | 15944572 | 16387007 |
| ABCC8 | 0.020833 | 0.285714 | 0 | 0.037037 | 0 | ABCC8 | 11 | 11p15.1 | 17371008 | 17455026 |
| USH1C | 0.020833 | 0.285714 | 0 | 0.037037 | 0 | USH1C | 11 | 11p15.1 | 17472019 | 17522540 |
| LOC494141 | 0.020833 | 0.142857 | 0 | 0.037037 | 0 | LOC494141 | 11 | 11p15.1 | 18187261 | 18189631 |
| SAA4 | 0.020833 | 0.142857 | 0 | 0.037037 | 0 | SAA4 | 11 | 11p15.1 | 18209480 | 18214932 |
| SAA2 | 0.020833 | 0.142857 | 0 | 0.037037 | 0 | SAA2 | 11 | 11p15.1 | 18217164 | 18226759 |
| SAA1 | 0.020833 | 0.142857 | 0 | 0.037037 | 0 | SAA1 | 11 | 11p15.1 | 18244348 | 18248103 |
| HPS5 | 0.020833 | 0.142857 | 0 | 0.037037 | 0 | HPS5 | 11 | 11p15.1 | 18256793 | 18300298 |
| GTF2H1 | 0.020833 | 0.142857 | 0 | 0.037037 | 0 | GTF2H1 | 11 | 11p15.1 | 18300392 | 18345167 |
| CCDC73 | 0.020833 | 0.285714 | 0 | 0.037037 | 0 | CCDC73 | 11 | 11p13 | 32580202 | 32772764 |

TABLE 4-continued

Gene list for predicting prostate cancer relapse using AT

| Symbol | freq. use | freq. amp. case | freq. del. case | freq. amp. control | freq. del. control | Gene. Symbol | chromo-some | cytoband | Transcript. start | Transcript. end |
|---|---|---|---|---|---|---|---|---|---|---|
| QSER1 | 0.020833 | 0.285714 | 0 | 0.037037 | 0 | QSER1 | 11 | 11p13 | 32871368 | 32958391 |
| DEPDC7 | 0.020833 | 0.285714 | 0 | 0.037037 | 0.037037 | DEPDC7 | 11 | 11p13 | 32993986 | 33011705 |
| TCP11L1 | 0.020833 | 0.285714 | 0 | 0.037037 | 0.037037 | TCP11L1 | 11 | 11p13 | 33017539 | 33051685 |
| LOC283267 | 0.020833 | 0.285714 | 0 | 0.037037 | 0 | LOC283267 | 11 | 11p13 | 33054272 | 33057576 |
| CSTF3 | 0.020833 | 0.238095 | 0.047619 | 0.037037 | 0 | CSTF3 | 11 | 11p13 | 33062706 | 33139614 |
| ABTB2 | 0.020833 | 0.238095 | 0 | 0.037037 | 0 | ABTB2 | 11 | 11p13 | 34129111 | 34335379 |
| CAT | 0.020833 | 0.238095 | 0 | 0.037037 | 0 | CAT | 11 | 11p13 | 34417048 | 34450183 |
| ZDHHC5 | 0.020833 | 0.285714 | 0 | 0.037037 | 0 | ZDHHC5 | 11 | 11q12.1 | 57192050 | 57225236 |
| MED19 | 0.020833 | 0.285714 | 0 | 0.037037 | 0 | MED19 | 11 | 11q12.1 | 57227763 | 57236250 |
| TMX2 | 0.020833 | 0.285714 | 0 | 0.037037 | 0 | TMX2 | 11 | 11q12.1 | 57236618 | 57265021 |
| C11orf31 | 0.020833 | 0.285714 | 0 | 0.037037 | 0 | C11orf31 | 11 | 11q12.1 | 57265298 | 57267460 |
| BTBD18 | 0.020833 | 0.285714 | 0 | 0.037037 | 0 | BTBD18 | 11 | 11q12.1 | 57267563 | 57275830 |
| CTNND1 | 0.020833 | 0.285714 | 0 | 0.037037 | 0 | CTNND1 | 11 | 11q12.1 | 57285810 | 57343229 |
| OR9Q1 | 0.020833 | 0.190476 | 0 | 0.037037 | 0 | OR9Q1 | 11 | 11q12.1 | 57547929 | 57705615 |
| OR6Q1 | 0.020833 | 0.190476 | 0 | 0.037037 | 0 | OR6Q1 | 11 | 11q12.1 | 57555001 | 57555955 |
| KIAA1377 | 0.020833 | 0 | 0.190476 | 0 | 0.037037 | KIAA1377 | 11 | 11q22.1 | 1.01E+08 | 1.01E+08 |
| CADM1 | 0.020833 | 0.142857 | 0.190476 | 0.185185 | 0.037037 | CADM1 | 11 | 11q23.2 | 1.15E+08 | 1.15E+08 |
| LOC399959 | 0.020833 | 0.047619 | 0.142857 | 0.111111 | 0.037037 | LOC399959 | 11 | 11q24.1 | 1.21E+08 | 1.22E+08 |
| MKX | 0.020833 | 0.190476 | 0 | 0.037037 | 0 | MKX | 10 | 10p12.1 | 28001809 | 28074785 |
| ARMC4 | 0.020833 | 0.190476 | 0 | 0.037037 | 0 | ARMC4 | 10 | 10p12.1 | 28141103 | 28327984 |
| MPP7 | 0.020833 | 0.190476 | 0 | 0.037037 | 0 | MPP7 | 10 | 10p11.23 | 28379929 | 28611074 |
| CREM | 0.020833 | 0.238095 | 0 | 0.037037 | 0 | CREM | 10 | 10p11.21 | 35455507 | 35508782 |
| CCNY | 0.020833 | 0.238095 | 0 | 0.037037 | 0 | CCNY | 10 | 10p11.21 | 35575959 | 35900854 |
| LOC728640 | 0.020833 | 0 | 0.238095 | 0 | 0.037037 | LOC728640 | 10 | 10q21.1 | 60144781 | 60147298 |
| C10orf107 | 0.020333 | 0 | 0.142857 | 0 | 0.037037 | C10orf107 | 10 | 10q21.2 | 63092725 | 63196096 |
| ANXA2P3 | 0.020833 | 0 | 0.190476 | 0 | 0.037037 | ANXA2P3 | 10 | 10q21.3 | 66255291 | 66256641 |
| LIPF | 0.020833 | 0 | 0.142857 | 0 | 0.037037 | LIPF | 10 | 10q23.31 | 90414074 | 90428553 |
| TCF7L2 | 0.020833 | 0.190476 | 0 | 0.037037 | 0 | TCF7L2 | 10 | 10q25.2 | 1.15E+08 | 1.15E+08 |
| HABP2 | 0.020833 | 0.142857 | 0.047619 | 0.037037 | 0 | HABP2 | 10 | 10q25.3 | 1.15E+08 | 1.15E+08 |
| NRAP | 0.020833 | 0.190476 | 0.047619 | 0.037037 | 0 | NRAP | 10 | 10q25.3 | 1.15E+08 | 1.15E+08 |
| CASP7 | 0.020833 | 0.190476 | 0 | 0.037037 | 0 | CASP7 | 10 | 10q25.3 | 1.15E+08 | 1.15E+08 |
| C10orf81 | 0.020833 | 0.190476 | 0 | 0.037037 | 0 | C10orf81 | 10 | 10q25.3 | 1.16E+08 | 1.16E+08 |
| NHLRC2 | 0.020833 | 0.190476 | 0 | 0.037037 | 0 | NHLRC2 | 10 | 10q25.3 | 1.16E+08 | 1.16E+08 |
| ADRB1 | 0.020833 | 0.190476 | 0 | 0.037037 | 0 | ADRB1 | 10 | 10q25.3 | 1.16E+08 | 1.16E+08 |
| C10orf118 | 0.020833 | 0.238095 | 0 | 0.037037 | 0 | C10orf118 | 10 | 10q25.3 | 1.16E+08 | 1.16E+08 |
| MIR2110 | 0.020833 | 0.238095 | 0 | 0.037037 | 0 | MIR2110 | 10 | 10q25.3 | 1.16E+08 | 1.16E+08 |
| TDRD1 | 0.020833 | 0.238095 | 0 | 0.037037 | 0 | TDRD1 | 10 | 10q25.3 | 1.16E+08 | 1.16E+08 |
| ATRNL1 | 0.020833 | 0.047619 | 0.238095 | 0.074074 | 0.037037 | ATRNL1 | 10 | 10q25.3 | 1.17E+08 | 1.18E+08 |
| DOCK8 | 0.020833 | 0.285714 | 0 | 0.037037 | 0 | DOCK8 | 9 | 9p24.3 | 204865 | 455250 |
| KANK1 | 0.020833 | 0.333333 | 0 | 0.037037 | 0 | KANK1 | 9 | 9p24.3 | 494703 | 736104 |
| SNAPC3 | 0.020833 | 0.142857 | 0 | 0.037037 | 0 | SNAPC3 | 9 | 9p22.3 | 15412782 | 15451628 |
| C9orf93 | 0.020833 | 0.142857 | 0 | 0.037037 | 0 | C9orf93 | 9 | 9p22.3 | 15543097 | 15961898 |
| IFNA14 | 0.020833 | 0 | 0.142857 | 0 | 0.037037 | IFNA14 | 9 | 9p21.3 | 21229201 | 21229979 |
| C9orf82 | 0.020833 | 0.142857 | 0.047619 | 0.037037 | 0.074074 | C9orf82 | 9 | 9p21.2 | 26830684 | 26882827 |
| IFT74 | 0.020833 | 0.142857 | 0.047619 | 0.037037 | 0.037037 | IFT74 | 9 | 9p21.2 | 26937037 | 27052932 |
| FXN | 0.020833 | 0.238095 | 0 | 0.037037 | 0 | FXN | 9 | 9q21.11 | 70840299 | 70883814 |
| TJP2 | 0.020833 | 0.238095 | 0 | 0.037037 | 0 | TJP2 | 9 | 9q21.11 | 70926044 | 71059945 |
| FAM189A2 | 0.020833 | 0.142857 | 0 | 0.037037 | 0 | FAM189A2 | 9 | 9q21.11 | 71129308 | 71197191 |
| APBA1 | 0.020833 | 0.238095 | 0 | 0.037037 | 0 | APBA1 | 9 | 9q21.11 | 71232269 | 71477096 |
| RASEF | 0.020833 | 0 | 0.142857 | 0.037037 | 0.037037 | RASEF | 9 | 9q21.32 | 84787137 | 84867864 |
| SLC44A1 | 0.020833 | 0.238095 | 0 | 0.037037 | 0 | SLC44A1 | 9 | 9q31.1 | 1.07E+08 | 1.07E+08 |
| KLF4 | 0.020833 | 0.190476 | 0 | 0.037037 | 0 | KLF4 | 9 | 9q31.2 | 1.09E+08 | 1.09E+08 |
| EPB4114B | 0.020833 | 0.190476 | 0 | 0.037037 | 0 | EPB4114B | 9 | 9q31.3 | 1.11E+08 | 1.11E+08 |
| PALM2 | 0.020833 | 0.142857 | 0 | 0.037037 | 0 | PALM2 | 9 | 9q31.3 | 1.11E+08 | 1.12E+08 |
| PALM2-AKAP2 | 0.020833 | 0.142857 | 0 | 0.037037 | 0 | PALM2-AKAP2 | 9 | 9q31.3 | 1.12E+08 | 1.12E+08 |
| AKAP2 | 0.020833 | 0.142857 | 0 | 0.037037 | 0 | AKAP2 | 9 | 9q31.3 | 1.12E+08 | 1.12E+08 |
| C9orf152 | 0.020833 | 0.142857 | 0 | 0.037037 | 0 | C9orf152 | 9 | 9q31.3 | 1.12E+08 | 1.12E+08 |
| FGF20 | 0.020833 | 0 | 0.142857 | 0 | 0.037037 | FGF20 | 8 | 8p22 | 16894705 | 16904046 |
| MAK16 | 0.020833 | 0.238035 | 0 | 0.037037 | 0.037037 | MAK16 | 8 | 8p12 | 33462227 | 33478320 |
| TCEA1 | 0.020833 | 0.142857 | 0 | 0.037037 | 0 | TCEA1 | 8 | 8q11.23 | 55041669 | 55097562 |
| RRS1 | 0.020833 | 0.190476 | 0 | 0.037037 | 0 | RRS1 | 8 | 8q13.1 | 67503817 | 67505523 |
| ADHFE1 | 0.020833 | 0.190476 | 0 | 0.037037 | 0 | ADHFE1 | 8 | 8q13.1 | 67507272 | 67543599 |
| C8orf46 | 0.020833 | 0.190476 | 0 | 0.037037 | 0 | C8orf46 | 8 | 8q13.1 | 67568045 | 67593312 |
| VCPIP1 | 0.020833 | 0.238095 | 0 | 0.037037 | 0 | VCPIP1 | 8 | 8q13.1 | 67705042 | 67742007 |
| C8orf44 | 0.020833 | 0.238095 | 0 | 0.037037 | 0 | C8orf44 | 8 | 8q13.1 | 67751008 | 67755790 |
| SGK3 | 0.020833 | 0.190476 | 0 | 0.037037 | 0 | SGK3 | 8 | 8q13.1 | 67787445 | 67936812 |
| NCOA2 | 0.020833 | 0.190476 | 0 | 0.037037 | 0 | NCOA2 | 8 | 8q13.3 | 71186821 | 71478575 |
| KCNB2 | 0.020833 | 0.047619 | 0.142857 | 0 | 0.037037 | KCNB2 | 8 | 8q13.3 | 73612180 | 74013139 |
| C8orf84 | 0.020833 | 0.142857 | 0.047619 | 0.037037 | 0 | C8orf84 | 8 | 8q21.11 | 74139334 | 74168062 |
| RDH10 | 0.020833 | 0.142857 | 0.047619 | 0.037037 | 0 | RDH10 | 8 | 8q21.11 | 74369819 | 74400069 |
| UBE2W | 0.020833 | 0.190476 | 0.047619 | 0.037037 | 0 | UBE2W | 8 | 8q21.11 | 74865394 | 74953665 |
| TCEB1 | 0.020833 | 0.190476 | 0.047619 | 0.037037 | 0 | TCEB1 | 8 | 8q21.11 | 75021188 | 75046901 |
| HEY1 | 0.020833 | 0.142857 | 0.047619 | 0.037037 | 0.111111 | HEY1 | 8 | 8q21.13 | 80838800 | 80842654 |

TABLE 4-continued

Gene list for predicting prostate cancer relapse using AT

| Symbol | freq. use | freq. amp. case | freq. del. case | freq. amp. control | freq. del. control | Gene. Symbol | chromo- some | cytoband | Tran- script. start | Tran- script. end |
|---|---|---|---|---|---|---|---|---|---|---|
| RUNX1T1 | 0.020833 | 0.047619 | 0.142857 | 0 | 0.037037 | RUNX1T1 | 8 | 8q21.3 | 93040328 | 93144368 |
| C8orf83 | 0.020833 | 0 | 0.333333 | 0 | 0.037037 | C8orf83 | 8 | 8q22.1 | 93965039 | 94047516 |
| CDH17 | 0.020833 | 0.238095 | 0 | 0.037037 | 0 | CDH17 | 8 | 8q22.1 | 95208570 | 95298708 |
| GEM | 0.020833 | 0.238095 | 0 | 0.037037 | 0 | GEM | 8 | 8q22.1 | 95330663 | 95343724 |
| TSPYL5 | 0.020833 | 0.190476 | 0 | 0.037037 | 0 | TSPYL5 | 8 | 8q22.1 | 98354890 | 98359353 |
| MTDH | 0.020833 | 0.190476 | 0 | 0.037037 | 0 | MTDH | 8 | 8q22.1 | 98725583 | 98811664 |
| ANKRD46 | 0.020833 | 0.238095 | 0 | 0.037037 | 0 | ANKRD46 | 8 | 8q22.2-8q22.3 | 1.02E+08 | 1.02E+08 |
| SNX31 | 0.020833 | 0.238095 | 0 | 0.037037 | 0 | SNX31 | 8 | 8q22.3 | 1.02E+08 | 1.02E+08 |
| NACAP1 | 0.020833 | 0.190476 | 0 | 0.037037 | 0 | NACAP1 | 8 | 8q22.3 | 1.02E+08 | 1.02E+08 |
| GRHL2 | 0.020833 | 0.190476 | 0 | 0.037037 | 0 | GRHL2 | 8 | 8q22.3 | 1.03E+08 | 1.03E+08 |
| ATAD2 | 0.020833 | 0.285714 | 0 | 0.037037 | 0 | ATAD2 | 8 | 8q24.13 | 1.24E+08 | 1.24E+08 |
| WDYHV1 | 0.020833 | 0.285714 | 0 | 0.037037 | 0 | WDYHV1 | 8 | 8q24.13 | 1.24E+08 | 1.25E+08 |
| FBXO32 | 0.020833 | 0.285714 | 0 | 0.037037 | 0 | FBXO32 | 8 | 8q24.13 | 1.25E+08 | 1.25E+08 |
| ANXA13 | 0.020833 | 0.285714 | 0 | 0.037037 | 0 | ANXA13 | 8 | 8q24.13 | 1.25E+08 | 1.25E+08 |
| FAM91A1 | 0.020833 | 0.285714 | 0 | 0.037037 | 0 | FAM91A1 | 8 | 8q24.13 | 1.25E+08 | 1.25E+08 |
| FER1L6 | 0.020833 | 0.238095 | 0 | 0.037037 | 0 | FER1L6 | 8 | 8q24.13 | 1.25E+08 | 1.25E+08 |
| TRMT12 | 0.020833 | 0.285714 | 0 | 0.037037 | 0 | TRMT12 | 8 | 8q24.13 | 1.26E+08 | 1.26E+08 |
| RNF139 | 0.020833 | 0.285714 | 0 | 0.037037 | 0 | RNF139 | 8 | 8q24.13 | 1.26E+08 | 1.26E+08 |
| TATDN1 | 0.020833 | 0.285714 | 0 | 0.037037 | 0 | TATDN1 | 8 | 8q24.13 | 1.26E+08 | 1.26E+08 |
| NDUFB9 | 0.020833 | 0.285714 | 0 | 0.037037 | 0 | NDUFB9 | 8 | 8q24.13 | 1.26E+08 | 1.26E+08 |
| MTSS1 | 0.020833 | 0.285714 | 0 | 0.037037 | 0 | MTSS1 | 8 | 8q24.13 | 1.26E+08 | 1.26E+08 |
| LOC157381 | 0.020833 | 0.285714 | 0 | 0.037037 | 0 | LOC157381 | 8 | 8q24.13 | 1.26E+08 | 1.26E+08 |
| ZNF572 | 0.020833 | 0.285714 | 0 | 0.037037 | 0 | ZNF572 | 8 | 8q24.13 | 1.26E+08 | 1.26E+08 |
| SQLE | 0.020833 | 0.285714 | 0 | 0.037037 | 0 | SQLE | 8 | 8q24.13 | 1.26E+08 | 1.26E+08 |
| KIAA0196 | 0.020833 | 0.285714 | 0 | 0.037037 | 0 | KIAA0196 | 8 | 8q24.13 | 1.26E+08 | 1.26E+08 |
| NSMCE2 | 0.020833 | 0.285714 | 0 | 0.037037 | 0 | NSMCE2 | 8 | 8q24.13 | 1.26E+08 | 1.25E+08 |
| ASAP1IT1 | 0.020833 | 0.142857 | 0 | 0.037037 | 0 | ASAP1IT1 | 8 | 8q24.21 | 1.31E+08 | 1.31E+08 |
| TG | 0.020833 | 0.238095 | 0 | 0.037037 | 0 | TG | 8 | 8q24.22 | 1.34E+08 | 1.34E+08 |
| SLA | 0.020833 | 0.285714 | 0 | 0.037037 | 0 | SLA | 8 | 8q24.22 | 1.34E+08 | 1.34E+08 |
| CLK2P | 0.020833 | 0.190476 | 0 | 0.037037 | 0 | CLK2P | 7 | 7p15.3 | 23590860 | 23592672 |
| CCDC126 | 0.020833 | 0.190476 | 0 | 0.037037 | 0 | CCDC126 | 7 | 7p15.3 | 23603523 | 23650853 |
| WIPF3 | 0.020833 | 0.142857 | 0 | 0.037037 | 0 | WIPF3 | 7 | 7p15.1 | 29840866 | 29912317 |
| SCRN1 | 0.020833 | 0.142857 | 0 | 0.037037 | 0 | SCRN1 | 7 | 7p15.1 | 29326245 | 29996260 |
| C7orf41 | 0.020833 | 0.342857 | 0 | 0.037037 | 0 | C7orf41 | 7 | 7p15.1 | 30141077 | 30168907 |
| NOD1 | 0.020833 | 0.142857 | 0 | 0.037037 | 0 | NOD1 | 7 | 7p15.1 | 30430668 | 30484919 |
| CRHR2 | 0.020833 | 0.190476 | 0 | 0.037037 | 0 | CRHR2 | 7 | 7p15.1 | 30659388 | 30588666 |
| INMT | 0.020833 | 0.190476 | 0 | 0.037037 | 0 | INMT | 7 | 7p15.1 | 30758276 | 30763744 |
| FAM188B | 0.020833 | 0.190476 | 0 | 0.037037 | 0 | FAM188B | 7 | 7p15.1 | 30777558 | 30898528 |
| AQP1 | 0.020833 | 0.190476 | 0 | 0.037037 | 0 | AQP1 | 7 | 7p15.1 | 30917993 | 30931657 |
| GHRHR | 0.020833 | 0.190476 | 0 | 0.037037 | 0 | GHRHR | 7 | 7p15.1 | 30970161 | 30985669 |
| ADCYAP1R | 0.020833 | 0.190476 | 0 | 0.037037 | 0 | ADCYAP1R | 7 | 7p15.1 | 31058667 | 31112837 |
| CDK13 | 0.020833 | 0.142857 | 0 | 0.037037 | 0 | CDK13 | 7 | 7p14.1 | 39956484 | 40103257 |
| C7orf10 | 0.020833 | 0.238095 | 0 | 0.037037 | 0 | C7orf10 | 7 | 7p14.1 | 40141100 | 40866883 |
| HUS1 | 0.020833 | 0.285714 | 0 | 0.037037 | 0 | HUS1 | 7 | 7p12.3 | 47970308 | 47985772 |
| UPP1 | 0.020833 | 0.238095 | 0 | 0.037037 | 0 | UPP1 | 7 | 7p12.3 | 48094880 | 48114856 |
| RSBN1L | 0.020833 | 0.190476 | 0 | 0.037037 | 0.074074 | RSBN1L | 7 | 7q11.23 | 77163679 | 77247057 |
| CCDC132 | 0.020833 | 0 | 0.190476 | 0 | 0.037037 | CCDC132 | 7 | 7q21.3 | 92699589 | 92826275 |
| GNGT1 | 0.020833 | 0 | 0.190476 | 0 | 0.037037 | GNGT1 | 7 | 7q21.3 | 93373756 | 93378422 |
| COL1A2 | 0.020833 | 0 | 0.190476 | 0 | 0.037037 | COL1A2 | 7 | 7q21.3 | 93861809 | 93898481 |
| CASD1 | 0.020833 | 0 | 0.142857 | 0 | 0.037037 | CASD1 | 7 | 7q21.3 | 93977106 | 94024265 |
| SGCE | 0.020833 | 0 | 0.142857 | 0 | 0.037037 | SGCE | 7 | 7q21.3 | 94052472 | 94123458 |
| FAM185A | 0.020833 | 0.142857 | 0 | 0.037037 | 0 | FAM185A | 7 | 7q22.1 | 1.02E+08 | 1.02E+08 |
| FBXL13 | 0.020833 | 0.142857 | 0 | 0.037037 | 0 | FBXL13 | 7 | 7q22.1 | 1.02E+08 | 1.03E+08 |
| WDR91 | 0.020833 | 0.142857 | 0 | 0.037037 | 0 | WDR91 | 7 | 7q33 | 1.35E+08 | 1.35E+08 |
| NUP205 | 0.020833 | 0.190476 | 0 | 0.037037 | 0 | NUP205 | 7 | 7q33 | 1.35E+08 | 1.35E+08 |
| PL-5283 | 0.020833 | 0.190476 | 0 | 0.037037 | 0 | PL-5283 | 7 | 7q33 | 1.35E+08 | 1.35E+08 |
| SLC13A4 | 0.020833 | 0.190476 | 0 | 0.037037 | 0 | SLC13A4 | 7 | 7q33 | 1.35E+08 | 1.35E+08 |
| TRPV5 | 0.020833 | 0.142857 | 0 | 0.037037 | 0 | TRPV5 | 7 | 7q34 | 1.42E+08 | 1.42E+08 |
| C7orf34 | 0.020833 | 0.142857 | 0 | 0.037037 | 0 | C7orf34 | 7 | 7q34 | 1.42E+08 | 1.42E+08 |
| KEL | 0.020833 | 0.142857 | 0 | 0.037037 | 0 | KEL | 7 | 7q34 | 1.42E+08 | 1.42E+08 |
| TAS2R39 | 0.020833 | 0.142857 | 0 | 0.037037 | 0.037037 | TAS2R39 | 7 | 7q34 | 1.43E+08 | 1.43E+08 |
| TAS2R40 | 0.020833 | 0.142857 | 0 | 0.037037 | 0 | TAS2R40 | 7 | 7q34 | 1.43E+08 | 1.43E+08 |
| TMEM139 | 0.020833 | 0.142857 | 0 | 0.037037 | 0 | TMEM139 | 7 | 7q34 | 1.43E+08 | 1.43E+08 |
| CASP2 | 0.020833 | 0.142857 | 0 | 0.037037 | 0 | CASP2 | 7 | 7q34 | 1.43E+08 | 1.43E+08 |
| CLCN1 | 0.020833 | 0.142857 | 0 | 0.037037 | 0 | CLCN1 | 7 | 7q34 | 1.43E+08 | 1.43E+08 |
| FAM131B | 0.020833 | 0.142857 | 0 | 0.037037 | 0 | FAM131B | 7 | 7q34 | 1.43E+08 | 1.43E+08 |
| TFAP2A | 0.020833 | 0.238095 | 0 | 0.037037 | 0 | TFAP2A | 6 | 6p24.3 | 10504902 | 10520594 |
| C6orf218 | 0.020833 | 0.238095 | 0 | 0.037037 | 0 | C6orf218 | 6 | 6p24.3 | 10536004 | 10543042 |
| SLC17A2 | 0.020833 | 0.190476 | 0 | 0.037037 | 0 | SLC17A2 | 6 | 6p22.2 | 26020963 | 26038819 |
| TRIM38 | 0.020833 | 0.190476 | 0 | 0.037037 | 0 | TRIM38 | 6 | 6p22.2 | 26071050 | 26093332 |
| HIST1H4C | 0.020833 | 0.190476 | 0 | 0.037037 | 0 | HIST1H4C | 6 | 6p22.1 | 26212155 | 26212545 |
| HIST1H1T | 0.020833 | 0.190476 | 0 | 0.037037 | 0 | HIST1H1T | 6 | 6p22.1 | 26215619 | 26216344 |
| HIST1H2BC | 0.020833 | 0.238095 | 0 | 0.037037 | 0 | HIST1H2BC | 6 | 6p22.1 | 26231674 | 26232112 |

TABLE 4-continued

Gene list for predicting prostate cancer relapse using AT

| Symbol | freq. use | freq. amp. case | freq. del. case | freq. amp. control | freq. del. control | Gene. Symbol | chromo-some | cytoband | Tran-script. start | Tran-script. end |
|---|---|---|---|---|---|---|---|---|---|---|
| HIST1H2AC | 0.020833 | 0.238095 | 0 | 0.037037 | 0 | HIST1H2AC | 6 | 6p22.1 | 26232352 | 26232898 |
| HIST1H1E | 0.020833 | 0.238095 | 0 | 0.037037 | 0.037037 | HIST1H1E | 6 | 6p22.1 | 26264538 | 26265323 |
| HIST1H2BD | 0.020833 | 0.238095 | 0 | 0.037037 | 0.037037 | HIST1H2BD | 6 | 6p22.1 | 26266328 | 26266851 |
| HIST1H1D | 0.020833 | 0.190476 | 0 | 0.037037 | 0.037037 | HIST1H1D | 6 | 6p22.1 | 26342419 | 26343196 |
| HIST1H4F | 0.020833 | 0.190476 | 0 | 0.037037 | 0.037037 | HIST1H4F | 6 | 6p22.1 | 26348633 | 26349001 |
| BTN3A2 | 0.020833 | 0.190476 | 0 | 0.037037 | 0 | BTN3A2 | 6 | 6p22.1 | 26473377 | 26486528 |
| BTN3A1 | 0.020833 | 0.190476 | 0 | 0.037037 | 0 | BTN3A1 | 6 | 6p22.1 | 26510444 | 26523422 |
| BTN2A3 | 0.020833 | 0.190476 | 0 | 0.037037 | 0 | BTN2A3 | 6 | 6p22.1 | 26529598 | 26538796 |
| BTN3A3 | 0.020833 | 0.190476 | 0 | 0.037037 | 0 | BTN3A3 | 6 | 6p22.1 | 26548679 | 26561622 |
| BTN2A1 | 0.020833 | 0.190476 | 0 | 0.037037 | 0 | BTN2A1 | 6 | 6p22.1 | 26566168 | 26577845 |
| BTN1A1 | 0.020833 | 0.190476 | 0 | 0.037037 | 0 | BTN1A1 | 6 | 6p22.1 | 26509474 | 26618632 |
| HCG11 | 0.020833 | 0.190476 | 0 | 0.037037 | 0 | HCG11 | 6 | 6p22.1 | 26629913 | 26635590 |
| HMGN4 | 0.020833 | 0.190476 | 0 | 0.037037 | 0 | HMGN4 | 6 | 6p22.1 | 26646551 | 26655144 |
| ABT1 | 0.020833 | 0.190476 | 0 | 0.037037 | 0 | ABT1 | 6 | 6p22.1 | 26705159 | 26708257 |
| ZNF322A | 0.020833 | 0.190476 | 0 | 0.037037 | 0 | ZNF322A | 6 | 6p22.1 | 26742590 | 26767943 |
| PRSS16 | 0.020833 | 0.238035 | 0 | 0.037037 | 0 | PRSS16 | 6 | 6p22.1 | 27323481 | 27332378 |
| POM121L2 | 0.020833 | 0.238095 | 0 | 0.037037 | 0 | POM121L2 | 6 | 6p22.1 | 27384821 | 27387991 |
| FKSG83 | 0.020833 | 0.238095 | 0 | 0.037037 | 0 | FKSG83 | 6 | 6p22.1 | 27400557 | 27401721 |
| ZNF204P | 0.020833 | 0.238035 | 0 | 0.037037 | 0 | ZNF204P | 6 | 6p22.1 | 27433582 | 27447284 |
| ZNF391 | 0.020833 | 0.285714 | 0 | 0.037037 | 0 | ZNF391 | 6 | 6p22.1 | 27464503 | 27477207 |
| GPR111 | 0.020833 | 0 | 0.190476 | 0 | 0.037037 | GPR111 | 6 | 6p12.3 | 47732285 | 47773491 |
| GPR115 | 0.020833 | 0 | 0.190476 | 0 | 0.037037 | GPR115 | 6 | 6p12.3 | 47774248 | 47797717 |
| OPN5 | 0.020833 | 0 | 0.190476 | 0 | 0.037037 | OPN5 | 6 | 6p12.3 | 47857757 | 47902076 |
| C6orf138 | 0.020833 | 0 | 0.190476 | 0 | 0.037037 | C6orf138 | 6 | 6p12.3 | 47953723 | 48144385 |
| PKHD1 | 0.020833 | 0 | 0.190476 | 0 | 0.037037 | PKHD1 | 6 | 6p12.2 | 51588104 | 52050383 |
| C6orf142 | 0.020833 | 0 | 0.190476 | 0 | 0.037037 | C6orf142 | 6 | 6p12.1 | 53991673 | 54239038 |
| GTF3C6 | 0.020833 | 0.190476 | 0 | 0.037037 | 0 | GTF3C6 | 6 | 6q21 | 1.11E+08 | 1.11E+08 |
| RPF2 | 0.020833 | 0.190476 | 0 | 0.037037 | 0 | RPF2 | 6 | 6q21 | 1.11E+08 | 1.11E+08 |
| RFX6 | 0.020833 | 0 | 0.238095 | 0 | 0.037037 | RFX6 | 6 | 6q22.2 | 1.17E+08 | 1.17E+08 |
| ROS1 | 0.020833 | 0 | 0.238095 | 0 | 0.037037 | ROS1 | 6 | 6q22.2 | 1.18E+08 | 1.18E+08 |
| DCBLD1 | 0.020833 | 0 | 0.238095 | 0 | 0.037037 | DCBLD1 | 6 | 6q22.2 | 1.18E+08 | 1.18E+08 |
| NUS1 | 0.020833 | 0 | 0.142857 | 0 | 0.037037 | NUS1 | 6 | 6q22.2 | 1.18E+08 | 1.18E+08 |
| LAMA2 | 0.020833 | 0 | 0.142857 | 0 | 0.037037 | LAMA2 | 6 | 6q22.33 | 1.29E+08 | 1.3E+08 |
| GPR126 | 0.020833 | 0 | 0.142857 | 0 | 0.037037 | GPR126 | 6 | 6q24.1 | 1.43E+08 | 1.43E+08 |
| UST | 0.020833 | 0.142857 | 0 | 0.037037 | 0 | UST | 6 | 6q25.1 | 1.49E+08 | 1.49E+08 |
| MAP3K7IP2 | 0.020833 | 0.142857 | 0 | 0.037037 | 0 | MAP3K7IP2 | 6 | 6q25.1 | 1.5E+08 | 1.5E+08 |
| SUMO4 | 0.020833 | 0.142857 | 0 | 0.037037 | 0 | SUMO4 | 6 | 6q25.1 | 1.5E+08 | 1.5E+08 |
| SNX9 | 0.020833 | 0.238095 | 0 | 0.037037 | 0 | SNX9 | 6 | 6q25.3 | 1.58E+08 | 1.58E+08 |
| GTF2H5 | 0.020833 | 0.238095 | 0 | 0.037037 | 0 | GTF2H5 | 6 | 6q25.3 | 1.59E+08 | 1.59E+08 |
| TAGAP | 0.020833 | 0.238095 | 0 | 0.037037 | 0 | TAGAP | 6 | 6q25.3 | 1.59E+08 | 1.59E+08 |
| FNDC1 | 0.020833 | 0.238095 | 0 | 0.037037 | 0 | FNDC1 | 6 | 6q25.3 | 1.6E+08 | 1.6E+08 |
| WTAP | 0.020833 | 0.238095 | 0 | 0.037037 | 0 | WTAP | 6 | 6q25.3 | 1.6E+08 | 1.6E+08 |
| ACAT2 | 0.020833 | 0.238095 | 0 | 0.037037 | 0 | ACAT2 | 6 | 6q25.3 | 1.6E+08 | 1.6E+08 |
| IGF2R | 0.020833 | 0.238095 | 0 | 0.037037 | 0 | IGF2R | 6 | 6q25.3 | 1.6E+08 | 1.6E+08 |
| LOC729603 | 0.020833 | 0.238095 | 0 | 0.037037 | 0 | LOC729603 | 6 | 6q25.3 | 1.6E+08 | 1.6E+08 |
| SLC22A1 | 0.020833 | 0.238095 | 0 | 0.037037 | 0 | SLC22A1 | 6 | 6q25.3 | 1.6E+08 | 1.6E+08 |
| MAP3K4 | 0.020833 | 0.190476 | 0 | 0.037037 | 0 | MAP3K4 | 6 | 6q26 | 1.61E+08 | 1.61E+08 |
| PARK2 | 0.020833 | 0.190476 | 0 | 0.037037 | 0 | PARK2 | 6 | 6q26 | 1.62E+08 | 1.63E+08 |
| LOC285796 | 0.020833 | 0.190476 | 0 | 0.037037 | 0 | LOC285796 | 6 | 6q26 | 1.64E+08 | 1.64E+08 |
| ADAMTS16 | 0.020833 | 0.142857 | 0 | 0.037037 | 0 | ADAMTS16 | 5 | 5p15.32 | 5193443 | 5373413 |
| FU33360 | 0.020833 | 0.285714 | 0 | 0.037037 | 0 | FU33360 | 5 | 5p15.31 | 6363554 | 6390406 |
| MED10 | 0.020833 | 0.285714 | 0 | 0.037037 | 0 | MED10 | 5 | 5p15.31 | 6425039 | 6431640 |
| UBE2QL1 | 0.020833 | 0.285714 | 0 | 0.037037 | 0 | UBE2QL1 | 5 | 5p15.31 | 6501736 | 6545706 |
| LOC255167 | 0.020833 | 0.285714 | 0 | 0.037037 | 0 | LOC255167 | 5 | 5p15.31 | 6635287 | 6641613 |
| NSUN2 | 0.020833 | 0.285714 | 0 | 0.037037 | 0 | NSUN2 | 5 | 5p15.31 | 6652352 | 6686158 |
| SRD5A1 | 0.020833 | 0.285714 | 0 | 0.037037 | 0 | SRD5A1 | 5 | 5p15.31 | 6686500 | 6722676 |
| POLS | 0.020833 | 0.285714 | 0 | 0.037037 | 0 | POLS | 5 | 5p15.31 | 6767718 | 6810162 |
| FBXL7 | 0.020833 | 0 | 0.190475 | 0 | 0.037037 | FBXL7 | 5 | 5p15.1 | 15553305 | 15992901 |
| 11-Mar | 0.020833 | 0 | 0.142857 | 0 | 0.037037 | 11-Mar | 5 | 5p15.1 | 16120474 | 16232898 |
| LOC285696 | 0.020833 | 0.238095 | 0 | 0.037037 | 0.037037 | LOC285696 | 5 | 5p15.1 | 17183137 | 17270532 |
| PDZD2 | 0.020833 | 0.238095 | 0 | 0.037037 | 0 | PDZD2 | 5 | 5p13.3 | 31834788 | 32146796 |
| MTMR12 | 0.020833 | 0.238095 | 0 | 0.037037 | 0 | MTMR12 | 5 | 5p13.3 | 32262868 | 32348872 |
| PLCXD3 | 0.020833 | 0 | 0.142857 | 0 | 0.037037 | PLCXD3 | 5 | 5p13.1 | 41342805 | 41546488 |
| OXCT1 | 0.020833 | 0 | 0.142857 | 0 | 0.037037 | OXCT1 | 5 | 5p13.1 | 41765924 | 41906549 |
| C5orf51 | 0.020833 | 0 | 0.142857 | 0 | 0.037037 | C5orf51 | 5 | 5p13.1 | 41940227 | 41957496 |
| FBXO4 | 0.020833 | 0 | 0.142857 | 0 | 0.037037 | FBXO4 | 5 | 5p13.1 | 41961113 | 41977430 |
| GHR | 0.020833 | 0 | 0.142857 | 0 | 0.037037 | GHR | 5 | 5p12 | 42459783 | 42757684 |
| SEPP1 | 0.020833 | 0 | 0.142857 | 0 | 0.037037 | SEPP1 | 5 | 5p12 | 42835739 | 42847782 |
| GAPT | 0.020833 | 0 | 0.190476 | 0 | 0.037037 | GAPT | 5 | 5q11.2 | 57823087 | 57827943 |
| RAB3C | 0.020833 | 0 | 0.190476 | 0 | 0.037037 | RAB3C | 5 | 5q11.2 | 57914696 | 58183164 |
| PDE4D | 0.020833 | 0 | 0.142857 | 0 | 0.037037 | PDE4D | 5 | 5q11.2 | 58300623 | 59225379 |
| S1C30A5 | 0.020833 | 0.190476 | 0 | 0.037037 | 0 | S1C30A5 | 5 | 5q13.2 | 68425574 | 68436324 |
| CCNB1 | 0.020833 | 0.190476 | 0 | 0.037037 | 0 | CCNB1 | 5 | 5q13.2 | 58498669 | 68509827 |
| CENPH | 0.020833 | 0.190476 | 0 | 0.037037 | 0 | CENPH | 5 | 5q13.2 | 68521131 | 68541941 |

TABLE 4-continued

Gene list for predicting prostate cancer relapse using AT

| Symbol | freq. use | freq. amp. case | freq. del. case | freq. amp. control | freq. del. control | Gene. Symbol | chromo- some | cytoband | Tran- script. start | Tran- script. end |
|---|---|---|---|---|---|---|---|---|---|---|
| MRPS36 | 0.020833 | 0.190476 | 0 | 0.037037 | 0 | MRPS36 | 5 | 5q13.2 | 68549329 | 68561742 |
| CDK7 | 0.020833 | 0.190476 | 0 | 0.037037 | 0 | CDK7 | 5 | 5q13.2 | 68566378 | 68609014 |
| CCDC125 | 0.020833 | 0.190476 | 0 | 0.037037 | 0 | CCDC125 | 5 | 5q13.2 | 68612275 | 68652167 |
| TAF9 | 0.020833 | 0.190476 | 0 | 0.037037 | 0 | TAF9 | 5 | 5q13.2 | 68683309 | 68701597 |
| RAD17 | 0.020833 | 0.190476 | 0 | 0.037037 | 0 | RAD17 | 5 | 5q13.2 | 68700880 | 68746388 |
| LOC653391 | 0.020833 | 0.190476 | 0 | 0.037037 | 0 | LOC653391 | 5 | 5q13.2 | 68713443 | 69917304 |
| MARVELD2 | 0.020833 | 0.190476 | 0 | 0.037037 | 0 | MARVELD2 | 5 | 5q13.2 | 68746699 | 68775593 |
| OCLN | 0.020833 | 0.190476 | 0 | 0.037037 | 0 | OCLN | 5 | 5q13.2 | 68823875 | 68885890 |
| BDP1 | 0.020833 | 0.142857 | 0 | 0.037037 | 0 | BDP1 | 5 | 5q13.2 | 70787198 | 70899406 |
| MCCC2 | 0.020833 | 0.142857 | 0 | 0.037037 | 0 | MCCC2 | 5 | 5q13.2 | 70918871 | 70990287 |
| FBXL17 | 0.020833 | 0 | 0.142857 | 0 | 0.037037 | FBXL17 | 5 | 5q21.3 | 1.07E+08 | 1.08E+08 |
| C5orf13 | 0.020833 | 0 | 0.190476 | 0 | 0.037037 | C5orf13 | 5 | 5q22.1 | 1.11E+08 | 1.11E+08 |
| EPB41L4A | 0.020833 | 0 | 0.142857 | 0 | 0.037037 | EPB41L4A | 5 | 5q22.2 | 1.12E+08 | 1.12E+08 |
| KCNN2 | 0.020833 | 0 | 0.238095 | 0 | 0.037037 | KCNN2 | 5 | 5q22.3 | 1.14E+08 | 1.14E+08 |
| DTWD2 | 0.020833 | 0 | 0.285714 | 0 | 0.037037 | DTWD2 | 5 | 5q23.1 | 1.18E+08 | 1.18E+08 |
| SNCAIP | 0.020833 | 0 | 0.142857 | 0 | 0.037037 | SNCAIP | 5 | 5q23.2 | 1.22E+08 | 1.22E+08 |
| PRDM6 | 0.020833 | 0 | 0.142857 | 0 | 0.037037 | PRDM6 | 5 | 5q23.2 | 1.22E+08 | 1.23E+08 |
| CEP120 | 0.020833 | 0 | 0.285714 | 0 | 0.037037 | CEP120 | 5 | 5q23.2 | 1.23E+08 | 1.23E+08 |
| CSNK1G3 | 0.020833 | 0 | 0.285714 | 0 | 0.037037 | CSNK1G3 | 5 | 5q23.2 | 1.23E+08 | 1.23E+08 |
| ZNF608 | 0.020833 | 0 | 0.190476 | 0 | 0.037037 | ZNF608 | 5 | 5q23.2 | 1.24E+08 | 1.24E+08 |
| SLC27A6 | 0.020833 | 0 | 0.142857 | 0 | 0.037037 | SLC27A6 | 5 | 5q23.3 | 1.28E+08 | 1.28E+08 |
| ISOC1 | 0.020833 | 0 | 0.142857 | 0 | 0.037037 | ISOC1 | 5 | 5q23.3 | 1.28E+08 | 1.28E+08 |
| ADAMTS19 | 0.020833 | 0 | 0.190476 | 0 | 0.037037 | ADAMTS19 | 5 | 5q23.3 | 1.29E+08 | 1.29E+08 |
| CHSY3 | 0.020833 | 0 | 0.190476 | 0 | 0.037037 | CHSY3 | 5 | 5q23.3 | 1.29E+08 | 1.3E+08 |
| KCTD16 | 0.020833 | 0 | 0.142857 | 0 | 0.037037 | KCTD16 | 5 | 5q32 | 1.44E+08 | 1.44E+08 |
| TIMD4 | 0.020833 | 0.190476 | 0 | 0.037037 | 0 | TIMD4 | 5 | 5q33.3 | 1.56E+08 | 1.56E+08 |
| MIR146A | 0.020833 | 0.047619 | 0.142857 | 0 | 0.037037 | MIR146A | 5 | 5q33.3 | 1.6E+08 | 1.6E+08 |
| ATP10B | 0.020833 | 0 | 0.190476 | 0 | 0.037037 | ATP10B | 5 | 5q34 | 2.6E+08 | 1.6E+08 |
| HSP90AB2P | 0.020833 | 0 | 0.142857 | 0 | 0.037037 | HSP90AB2P | 4 | 4p15.33 | 12944135 | 12949024 |
| RAB28 | 0.020833 | 0 | 0.190476 | 0 | 0.037037 | RAB28 | 4 | 4p15.33 | 12978445 | 13095088 |
| ARAP2 | 0.020833 | 0.190476 | 0.190476 | 0.037037 | 0.111111 | ARAP2 | 4 | 4p14 | 35744017 | 35922375 |
| SPINK2 | 0.020833 | 0.142857 | 0 | 0.037037 | 0 | SPINK2 | 4 | 4q12 | 57370791 | 57382651 |
| REST | 0.020833 | 0.142857 | 0 | 0.037037 | 0 | REST | 4 | 4q12 | 57468799 | 57493098 |
| CSN1S2A | 0.020833 | 0 | 0.285714 | 0 | 0.037037 | CSN1S2A | 4 | 4q13.3 | 70967692 | 70985578 |
| CSN1S2B | 0.020833 | 0 | 0.285714 | 0 | 0.037037 | CSN1S2B | 4 | 4q13.3 | 71033910 | 71047011 |
| C4orf40 | 0.020833 | 0 | 0.285714 | 0 | 0.037037 | C4orf40 | 4 | 4q13.3 | 71054493 | 71066916 |
| ODAM | 0.020833 | 0 | 0.285714 | 0 | 0.037037 | ODAM | 4 | 4q13.3 | 71096833 | 71104883 |
| SMR3A | 0.020833 | 0 | 0.285714 | 0 | 0.037037 | SMR3A | 4 | 4q13.3 | 71261082 | 71267413 |
| MUC7 | 0.020833 | 0 | 0.238095 | 0 | 0.037037 | MUC7 | 4 | 4q13.3 | 71330798 | 71383303 |
| RUFY3 | 0.020833 | 0.190476 | 0.095238 | 0.037037 | 0.037037 | RUFY3 | 4 | 4q13.3 | 71783518 | 71874478 |
| MOBKL1A | 0.020833 | 0.190476 | 0.095238 | 0.037037 | 0.037037 | MOBKL1A | 4 | 4q13.3 | 71986928 | 72072756 |
| DCK | 0.020833 | 0.190476 | 0.095238 | 0.037037 | 0.037037 | DCK | 4 | 4q13.3 | 72078129 | 72115494 |
| CXCL6 | 0.020833 | 0 | 0.142857 | 0 | 0.037037 | CXCL6 | 4 | 4q13.3 | 74921137 | 74923342 |
| PPBPL1 | 0.020833 | 0 | 0.142857 | 0 | 0.037037 | PPBPL1 | 4 | 4q13.3 | 74932447 | 74933418 |
| PF4 | 0.020833 | 0 | 0.142857 | 0 | 0.037037 | PF4 | 4 | 4q13.3 | 75065660 | 75066580 |
| PPBP | 0.020833 | 0 | 0.142857 | 0 | 0.037037 | PPBP | 4 | 4q13.3 | 75071620 | 75072765 |
| CXCL3 | 0.020833 | 0 | 0.142857 | 0 | 0.037037 | CXCL3 | 4 | 4q13.3 | 75121176 | 75123355 |
| CXCL2 | 0.020833 | 0 | 0.142857 | 0 | 0.037037 | CXCL2 | 4 | 4q13.3 | 75181618 | 75183862 |
| MTHFD2L | 0.020833 | 0 | 0.142857 | 0 | 0.037037 | MTHFD2L | 4 | 4q13.3 | 75242693 | 75387677 |
| ARD1B | 0.020833 | 0 | 0.142857 | 0 | 0.037037 | ARD1B | 4 | 4q21.21 | 80457296 | 80466196 |
| GDEP | 0.020833 | 0 | 0.190476 | 0 | 0.037037 | GDEP | 4 | 4q21.21 | 80967649 | 81003424 |
| PRDM8 | 0.020833 | 0 | 0.190476 | 0 | 0.037037 | PRDM8 | 4 | 4q21.21 | 81325448 | 81344507 |
| C4orf22 | 0.020833 | 0 | 0.190476 | 0 | 0.037037 | C4orf22 | 4 | 4q21.21 | 81475898 | 82103927 |
| MANBA | 0.020833 | 0.095238 | 0.142857 | 0.037037 | 0.037037 | MANBA | 4 | 4q24 | 1.04E+08 | 1.04E+08 |
| SCOC | 0.020833 | 0.142857 | 0 | 0.037037 | 0 | SCOC | 4 | 4q31.1 | 1.41E+08 | 1.42E+08 |
| USP38 | 0.020833 | 0 | 0.142857 | 0 | 0.037037 | USP38 | 4 | 4q31.21 | 1.44E+08 | 1.44E+08 |
| TMEM154 | 0.020833 | 0.142857 | 0 | 0.037037 | 0 | TMEM154 | 4 | 4q31.3 | 1.54E+08 | 1.54E+08 |
| FHDC1 | 0.020833 | 0.142857 | 0 | 0.037037 | 0 | FHDC1 | 4 | 4q31.3 | 1.54E+08 | 1.54E+08 |
| TRIM2 | 0.020833 | 0.142857 | 0 | 0.037037 | 0 | TRIM2 | 4 | 4q31.3 | 1.54E+08 | 1.54E+08 |
| ANXA2P1 | 0.020833 | 0.142857 | 0 | 0.037037 | 0 | ANXA2P1 | 4 | 4q31.3 | 1.54E+08 | 1.54E+08 |
| MND1 | 0.020833 | 0.142857 | 0 | 0.037037 | 0 | MND1 | 4 | 4q31.3 | 1.54E+08 | 1.55E+08 |
| KIAA0922 | 0.020833 | 0.142857 | 0 | 0.037037 | 0 | KIAA0922 | 4 | 4q31.3 | 1.55E+08 | 1.55E+08 |
| RBM46 | 0.020333 | 0 | 0.142857 | 0 | 0.037037 | RBM46 | 4 | 4q32.1 | 1.56E+08 | 1.56E+08 |
| NPY2R | 0.020833 | 0 | 0.190476 | 0 | 0.037037 | NPY2R | 4 | 4q32.1 | 1.56E+08 | 1.56E+08 |
| MAP9 | 0.020833 | 0 | 0.190476 | 0 | 0.037037 | MAP9 | 4 | 4q32.1 | 1.56E+08 | 1.57E+08 |
| GUCY1A3 | 0.020833 | 0 | 0.190476 | 0 | 0.037037 | GUCY1A3 | 4 | 4q32.1 | 1.57E+08 | 1.57E+08 |
| GUCY1B3 | 0.020833 | 0 | 0.190476 | 0 | 0.037037 | GUCY1B3 | 4 | 4q32.1 | 1.57E+08 | 1.57E+08 |
| TD02 | 0.020833 | 0 | 0.190476 | 0 | 0.037037 | TD02 | 4 | 4q32.1 | 1.57E+08 | 1.57E+08 |
| CTSO | 0.020833 | 0 | 0.190475 | 0 | 0.037037 | CTSO | 4 | 4q32.1 | 1.57E+08 | 1.57E+08 |
| ZFP42 | 0.020833 | 0.238095 | 0 | 0.037037 | 0 | ZFP42 | 4 | 4q35.2 | 1.89E+08 | 1.89E+08 |
| TRIML2 | 0.020833 | 0.238095 | 0 | 0.037037 | 0 | TRIML2 | 4 | 4q35.2 | 1.89E+08 | 1.89E+08 |
| TRIML1 | 0.020833 | 0.285714 | 0 | 0.037037 | 0 | TRIML1 | 4 | 4q35.2 | 1.89E+08 | 1.89E+08 |
| CNTN4 | 0.020833 | 0 | 0.142857 | 0 | 0.037037 | CNTN4 | 3 | 3p26.3 | 2117247 | 3074646 |
| SATB1 | 0.020833 | 0 | 0.238095 | 0 | 0.037037 | SATB1 | 3 | 3p24.3 | 18364270 | 18455257 |

TABLE 4-continued

Gene list for predicting prostate cancer relapse using AT

| Symbol | freq. use | freq. amp. case | freq. del. case | freq. amp. control | freq. del. control | Gene. Symbol | chromo- some | cytoband | Tran- script. start | Tran- script. end |
|---|---|---|---|---|---|---|---|---|---|---|
| KCNH8 | 0.020833 | 0 | 0.238095 | 0 | 0.037037 | KCNH8 | 3 | 3p24.3 | 19165021 | 19552140 |
| CMC1 | 0.020833 | 0.047619 | 0.190476 | 0 | 0.037037 | CMC1 | 3 | 3p24.1 | 28258128 | 28336268 |
| TGFBR2 | 0.020833 | 0.047619 | 0.238095 | 0 | 0.037037 | TGFBR2 | 3 | 3p24.1 | 30622998 | 30710638 |
| GADL1 | 0.020833 | 0.047619 | 0.238095 | 0 | 0.037037 | GADL1 | 3 | 3p24.1-3p | 30742696 | 30911158 |
| CLASP2 | 0.020833 | 0.238095 | 0 | 0.037037 | 0 | CLASP2 | 3 | 3p22.3 | 33512742 | 33734853 |
| CCDC66 | 0.020833 | 0.333333 | 0 | 0.037037 | 0 | CCDC66 | 3 | 3p14.3 | 56566224 | 56630887 |
| C3orf63 | 0.020833 | 0.333333 | 0 | 0.037037 | 0 | C3orf63 | 3 | 3p14.3 | 56629200 | 56692176 |
| ARHGEF3 | 0.020833 | 0.333333 | 0 | 0.037037 | 0 | ARHGEF3 | 3 | 3p14.3 | 56736486 | 57088377 |
| SPATA12 | 0.020833 | 0.380952 | 0 | 0.037037 | 0 | SPATA12 | 3 | 3p14.3 | 57069509 | 57084501 |
| IL17RD | 0.020833 | 0.380952 | 0 | 0.037037 | 0 | IL17RD | 3 | 3p14.3 | 57099050 | 57174444 |
| DNAH12 | 0.020833 | 0.333333 | 0 | 0.037037 | 0.037037 | DNAH12 | 3 | 3p14.3 | 57302767 | 57505112 |
| EIF4E3 | 0.020833 | 0.142857 | 0.047619 | 0.037037 | 0 | EIF4E3 | 3 | 3p13 | 71811132 | 71886223 |
| GPR27 | 0.020833 | 0.142857 | 0.047619 | 0.037037 | 0 | GPR27 | 3 | 3p13 | 71885891 | 71887019 |
| PROK2 | 0.020833 | 0.142857 | 0.047619 | 0.037037 | 0 | PROK2 | 3 | 3p13 | 71903496 | 71917048 |
| RG9MTD1 | 0.020833 | 0.238095 | 0 | 0.037037 | 0.037037 | RG9MTD1 | 3 | 3q12.3 | 1.03E+08 | 1.03E+08 |
| PCNP | 0.020833 | 0.238095 | 0 | 0.037037 | 0.037037 | PCNP | 3 | 3q12.3 | 1.03E+08 | 1.03E+08 |
| ZBTB11 | 0.020833 | 0.285714 | 0 | 0.037037 | 0.037037 | ZBTB11 | 3 | 3q12.3 | 1.03E+08 | 1.03E+08 |
| LOC100009676 | 0.020833 | 0.285714 | 0 | 0.037037 | 0.037037 | LOC100009676 | 3 | 3q12.3 | 1.03E+08 | 1.03E+08 |
| RPL24 | 0.020833 | 0.285714 | 0 | 0.037037 | 0.037037 | RPL24 | 3 | 3q12.3 | 1.03E+08 | 1.03E+08 |
| LOC100302640 | 0.020833 | 0 | 0.190476 | 0 | 0.037037 | LOC100302640 | 3 | 3q13.12 | 1.08E+08 | 1.08E+08 |
| LOC344595 | 0.020833 | 0 | 0.190476 | 0 | 0.037037 | LOC344595 | 3 | 3q13.12 | 1.08E+08 | 1.08E+08 |
| CCDC54 | 0.020833 | 0 | 0.142857 | 0 | 0.037037 | CCDC54 | 3 | 3q13.12 | 1.09E+08 | 1.09E+08 |
| BBX | 0.020833 | 0 | 0.142857 | 0 | 0.037037 | BBX | 3 | 3q13.12 | 1.09E+08 | 1.09E+08 |
| FLJ25363 | 0.020833 | 0.238095 | 0 | 0.037037 | 0 | FLJ25363 | 3 | 3q13.13 | 1.11E+08 | 1.11E+08 |
| TMPRSS7 | 0.020833 | 0 | 0.142857 | 0 | 0.037037 | TMPRSS7 | 3 | 3q13.2 | 1.13E+08 | 1.13E+08 |
| SLC9A10 | 0.020833 | 0 | 0.142857 | 0 | 0.037037 | SLC9A10 | 3 | 3q13.2 | 1.13E+08 | 1.13E+08 |
| CD200 | 0.020833 | 0 | 0.142857 | 0 | 0.037037 | CD200 | 3 | 3q13.2 | 1.14E+08 | 1.14E+08 |
| BTLA | 0.020833 | 0 | 0.142857 | 0 | 0.037037 | BTLA | 3 | 3q13.2 | 1.14E+08 | 1.14E+08 |
| SLC35A5 | 0.020833 | 0 | 0.142857 | 0 | 0.037037 | SLC35A5 | 3 | 3q13.2 | 1.14E+08 | 1.14E+08 |
| CCDC80 | 0.020833 | 0 | 0.142857 | 0 | 0.037037 | CCDC80 | 3 | 3q13.2 | 1.14E+08 | 1.14E+08 |
| CD200R1L | 0.020833 | 0 | 0.142857 | 0 | 0.037037 | CD200R1L | 3 | 3q13.2 | 1.14E+08 | 1.14E+08 |
| ZBTB20 | 0.020833 | 0 | 0.142857 | 0 | 0.037037 | ZBTB20 | 3 | 3q13.31 | 1.16E+08 | 1.16E+08 |
| COL29A1 | 0.020833 | 0 | 0.142857 | 0.074074 | 0.037037 | COL29A1 | 3 | 3q22.1 | 1.32E+08 | 1.32E+08 |
| COL6A6 | 0.020833 | 0 | 0.142857 | 0 | 0.037037 | COL6A6 | 3 | 3q22.1 | 1.32E+08 | 1.32E+08 |
| PIK3R4 | 0.020833 | 0 | 0.190476 | 0 | 0.037037 | PIK3R4 | 3 | 3q22.1 | 1.32E+08 | 1.32E+08 |
| ATP2C1 | 0.020833 | 0 | 0.190476 | 0 | 0.037037 | ATP2C1 | 3 | 3q22.1 | 1.32E+08 | 1.32E+08 |
| ASTE1 | 0.020833 | 0 | 0.190476 | 0 | 0.037037 | ASTE1 | 3 | 3q22.1 | 1.32E+08 | 1.32E+08 |
| NEK11 | 0.020833 | 0 | 0.190476 | 0 | 0.037037 | NEK11 | 3 | 3q22.1 | 1.32E+08 | 1.33E+08 |
| NUDT16 | 0.020833 | 0 | 0.142857 | 0 | 0.037037 | NUDT16 | 3 | 3q22.1 | 1.33E+08 | 1.33E+08 |
| MRPL3 | 0.020833 | 0 | 0.142857 | 0 | 0.037037 | MRPL3 | 3 | 3q22.1 | 1.33E+08 | 1.33E+08 |
| CPNE4 | 0.020833 | 0 | 0.142857 | 0 | 0.037037 | CPNE4 | 3 | 3q22.1 | 1.33E+08 | 1.33E+08 |
| BFSP2 | 0.020833 | 0.142857 | 0 | 0.037037 | 0 | BFSP2 | 3 | 3q22.1 | 1.35E+08 | 1.35E+08 |
| CDV3 | 0.020833 | 0.190476 | 0 | 0.037037 | 0 | CDV3 | 3 | 3q22.1 | 1.35E+08 | 1.35E+08 |
| TOPBP1 | 0.020833 | 0.190476 | 0 | 0.037037 | 0 | TOPBP1 | 3 | 3q22.1 | 1.35E+08 | 1.35E+08 |
| TF | 0.020833 | 0.190476 | 0 | 0.037037 | 0 | TF | 3 | 3q22.1 | 1.35E+08 | 1.35E+08 |
| DZIP1L | 0.020833 | 0.190476 | 0 | 0.037037 | 0 | DZIP1L | 3 | 3q22.3 | 1.39E+08 | 1.39E+08 |
| DBR1 | 0.020833 | 0.190476 | 0 | 0.037037 | 0 | DBR1 | 3 | 3q22.3 | 1.39E+08 | 1.39E+08 |
| ARMC8 | 0.020833 | 0.190476 | 0 | 0.037037 | 0 | ARMC8 | 3 | 3q22.3 | 1.39E+08 | 1.39E+08 |
| TXNDC6 | 0.020833 | 0.238095 | 0 | 0.037037 | 0 | TXNDC6 | 3 | 3q22.3 | 1.39E+08 | 1.4E+08 |
| MRAS | 0.020833 | 0.238095 | 0 | 0.037037 | 0 | MRAS | 3 | 3q22.3 | 1.4E+08 | 1.4E+08 |
| ESYT3 | 0.020833 | 0.238095 | 0 | 0.037037 | 0 | ESYT3 | 3 | 3q22.3 | 1.4E+08 | 1.4E+08 |
| CEP70 | 0.020833 | 0.190475 | 0 | 0.037037 | 0 | CEP70 | 3 | 3q22.3 | 1.4E+08 | 1.4E+08 |
| FAIM | 0.020833 | 0.190476 | 0 | 0.037037 | 0 | FAIM | 3 | 3q22.3 | 1.4E+08 | 1.4E+08 |
| PIK3CB | 0.020833 | 0.190476 | 0 | 0.037037 | 0 | PIK3CB | 3 | 3q22.3 | 1.4E+08 | 1.4E+08 |
| FOXL2 | 0.020833 | 0.190476 | 0 | 0.037037 | 0 | FOXL2 | 3 | 3q22.3 | 1.4E+08 | 1.4E+08 |
| C3orf72 | 0.020833 | 0.190476 | 0 | 0.037037 | 0 | C3orf72 | 3 | 3q22.3 | 1.4E+08 | 1.4E+08 |
| BPESC1 | 0.020833 | 0.190476 | 0 | 0.037037 | 0 | BPESC1 | 3 | 3q22.3 | 1.4E+08 | 1.4E+08 |
| AADACL2 | 0.020833 | 0 | 0.142857 | 0 | 0.037037 | AADACL2 | 3 | 3q25.1 | 1.53E+08 | 1.53E+08 |
| SLC33A1 | 0.020833 | 0.285714 | 0 | 0.037037 | 0 | SLC33A1 | 3 | 3q25.31 | 1.57E+08 | 1.57E+08 |
| GMPS | 0.020833 | 0.285714 | 0 | 0.037037 | 0 | GMPS | 3 | 3q25.31 | 1.57E+08 | 1.57E+08 |
| LRRIQ4 | 0.020833 | 0.238095 | 0 | 0.037037 | 0 | LRRIQ4 | 3 | 3q26.2 | 1.71E+08 | 1.71E+08 |
| LRRC31 | 0.020833 | 0.238095 | 0 | 0.037037 | 0 | LRRC31 | 3 | 3q26.2 | 1.71E+08 | 1.71E+08 |
| SAMD7 | 0.020833 | 0.238095 | 0 | 0.037037 | 0 | SAMD7 | 3 | 3q26.2 | 1.71E+08 | 1.71E+08 |
| LOC100128164 | 0.020833 | 0.238095 | 0 | 0.037037 | 0 | LOC100128164 | 3 | 3q26.2 | 1.71E+08 | 1.71E+08 |
| SEC62 | 0.020833 | 0.238095 | 0 | 0.037037 | 0 | SEC62 | 3 | 3q26.2 | 1.71E+08 | 1.71E+08 |
| MCCC1 | 0.020833 | 0.333333 | 0 | 0.037037 | 0 | MCCC1 | 3 | 3q27.1 | 1.84E+08 | 1.84E+08 |
| FGF12 | 0.020833 | 0 | 0.142857 | 0 | 0.037037 | FGF12 | 3 | 3q28 | 1.93E+08 | 1.94E+08 |
| DLG1 | 0.020833 | 0.238095 | 0.142857 | 0.407407 | 0.037037 | DLG1 | 3 | 3q29 | 1.98E+08 | 1.99E+08 |
| KIDINS220 | 0.020833 | 0.190476 | 0.142857 | 0.185185 | 0.037037 | KIDINS220 | 2 | 2p25.1 | 8786438 | 8895207 |
| KCNS3 | 0.020833 | 0.142857 | 0 | 0.037037 | 0 | KCNS3 | 2 | 2p24.2 | 17923426 | 17977707 |
| GALM | 0.020833 | 0.142857 | 0 | 0.037037 | 0 | GALM | 2 | 2p22.1 | 38746556 | 38815413 |
| GEMIN6 | 0.020833 | 0.142857 | 0 | 0.037037 | 0 | GEMIN6 | 2 | 2p22.1 | 38858831 | 38862611 |
| DHX57 | 0.020833 | 0.142857 | 0 | 0.037037 | 0 | DHX57 | 2 | 2p22.1 | 38878379 | 38956525 |
| MORN2 | 0.020833 | 0.142857 | 0 | 0.037037 | 0 | MORN2 | 2 | 2p22.1 | 38956607 | 38963353 |

TABLE 4-continued

Gene list for predicting prostate cancer relapse using AT

| Symbol | freq. use | freq. amp. case | freq. del. case | freq. amp. control | freq. del. control | Gene. Symbol | chromo- some | cytoband | Tran- script. start | Tran- script. end |
|---|---|---|---|---|---|---|---|---|---|---|
| SLC8A1 | 0.020833 | 0 | 0.142857 | 0 | 0.037037 | SLC8A1 | 2 | 2p22.1 | 40192790 | 40510949 |
| MSH6 | 0.020833 | 0.142857 | 0 | 0.037037 | 0.074074 | MSH6 | 2 | 2p16.3 | 47863725 | 47887597 |
| FBXO11 | 0.020833 | 0.142857 | 0 | 0.037037 | 0.074074 | FBXO11 | 2 | 2p16.3 | 47887563 | 47986319 |
| VRK2 | 0.020833 | 0 | 0.142857 | 0 | 0.037037 | VRK2 | 2 | 2p16.1 | 58127233 | 58240560 |
| FANCL | 0.020833 | 0 | 0.142857 | 0 | 0.037037 | FANCL | 2 | 2p16.1 | 58239882 | 58322020 |
| PAPOLG | 0.020833 | 0.238095 | 0 | 0.037037 | 0 | PAPOLG | 2 | 2p16.1 | 60836887 | 60879603 |
| REL | 0.020833 | 0.238095 | 0 | 0.037037 | 0 | REL | 2 | 2p16.1 | 60962256 | 61003683 |
| PUS10 | 0.020833 | 0.238095 | 0 | 0.037037 | 0 | PUS10 | 2 | 2p16.1 | 61021054 | 61098870 |
| KIAA1841 | 0.020833 | 0.238095 | 0 | 0.037037 | 0 | KIAA1841 | 2 | 2p15 | 61146510 | 61204918 |
| C2orf74 | 0.020833 | 0.238095 | 0 | 0.037037 | 0 | C2orf74 | 2 | 2p15 | 61225747 | 61245469 |
| USP34 | 0.020833 | 0.238095 | 0 | 0.037037 | 0 | USP34 | 2 | 2p15 | 61268094 | 61551354 |
| XPO1 | 0.020833 | 0.285714 | 0 | 0.037037 | 0 | XPO1 | 2 | 2p15 | 61558573 | 61618923 |
| RAB1A | 0.020833 | 0.142857 | 0 | 0.037037 | 0 | RAB1A | 2 | 2p14 | 65167493 | 65210940 |
| MAP4K4 | 0.020833 | 0.190476 | 0 | 0.037037 | 0 | MAP4K4 | 2 | 2q11.2 | 1.02E+08 | 1.02E+08 |
| IL1R2 | 0.020833 | 0.190476 | 0 | 0.037037 | 0 | IL1R2 | 2 | 2q11.2 | 1.02E+08 | 1.02E+08 |
| IL1R1 | 0.020833 | 0.142857 | 0 | 0.037037 | 0 | IL1R1 | 2 | 2q12.1 | 1.02E+08 | 1.02E+08 |
| IL1RL2 | 0.020833 | 0.142857 | 0 | 0.037037 | 0 | IL1RL2 | 2 | 2q12.1 | 1.02E+08 | 1.02E+08 |
| IL1RL1 | 0.020833 | 0.142857 | 0 | 0.037037 | 0 | IL1RL1 | 2 | 2q12.1 | 1.02E+08 | 1.02E+08 |
| IL18R1 | 0.020833 | 0.142857 | 0 | 0.037037 | 0 | IL18R1 | 2 | 2q12.1 | 1.02E+08 | 1.02E+08 |
| MFSD9 | 0.020833 | 0 | 0.142857 | 0 | 0.037037 | MFSD9 | 2 | 2q12.1 | 1.03E+08 | 1.03E+08 |
| TMEM182 | 0.020833 | 0 | 0.142857 | 0 | 0.037037 | TMEM182 | 2 | 2q12.1 | 1.03E+08 | 1.03E+08 |
| MRPS9 | 0.020833 | 0.142857 | 0 | 0.037037 | 0 | MRPS9 | 2 | 2q12.1 | 1.05E+08 | 1.05E+08 |
| PLGLA | 0.020833 | 0.190476 | 0 | 0.037037 | 0 | PLGLA | 2 | 2q12.2 | 1.06E+08 | 1.06E+08 |
| RGPD3 | 0.020833 | 0.190476 | 0 | 0.037037 | 0 | RGPD3 | 2 | 2q12.2 | 1.06E+08 | 1.06E+08 |
| ACVR2A | 0.020833 | 0 | 0.190476 | 0 | 0.037037 | ACVR2A | 2 | 2q22.3 | 1.48E+08 | 1.48E+08 |
| MBD5 | 0.020833 | 0 | 0.142857 | 0 | 0.037037 | MBD5 | 2 | 2q23.1 | 1.49E+08 | 1.49E+08 |
| EPC2 | 0.020833 | 0 | 0.238095 | 0 | 0.037037 | EPC2 | 2 | 2q23.1 | 1.49E+08 | 1.49E+08 |
| DAPL1 | 0.020833 | 0.142857 | 0 | 0.037037 | 0 | DAPL1 | 2 | 2q24.1 | 1.59E+08 | 1.59E+08 |
| TANC1 | 0.020833 | 0.142857 | 0 | 0.037037 | 0 | TANC1 | 2 | 2q24.1 | 1.6E+08 | 1.6E+08 |
| TTN | 0.020833 | 0 | 0.142857 | 0 | 0.037037 | TTN | 2 | 2q31.2 | 1.79E+08 | 1.79E+08 |
| CCDC141 | 0.020833 | 0 | 0.142857 | 0 | 0.037037 | CCDC141 | 2 | 2q31.2 | 1.79E+08 | 1.79E+08 |
| SESTD1 | 0.020833 | 0 | 0.142857 | 0 | 0.037037 | SESTD1 | 2 | 2q31.2 | 1.8E+08 | 1.8E+08 |
| ZNF385B | 0.020833 | 0 | 0.190475 | 0 | 0.037037 | ZNF385B | 2 | 2q31.2 | 1.8E+08 | 1.8E+08 |
| MIR1258 | 0.020833 | 0 | 0.190476 | 0 | 0.037037 | MIR1258 | 2 | 2q31.3 | 1.8E+08 | 1.8E+08 |
| SF3B1 | 0.020833 | 0.238095 | 0 | 0.037037 | 0 | SF3B1 | 2 | 2q33.1 | 1.98E+08 | 1.98E+08 |
| COQ10B | 0.020833 | 0.238095 | 0 | 0.037037 | 0 | COQ10B | 2 | 2q33.1 | 1.98E+08 | 1.98E+08 |
| HSPD1 | 0.020833 | 0.238095 | 0 | 0.037037 | 0 | HSPD1 | 2 | 2q33.1 | 1.98E+08 | 1.98E+08 |
| RFTN2 | 0.020833 | 0 | 0.142857 | 0 | 0.037037 | RFTN2 | 2 | 2q33.1 | 1.98E+08 | 1.98E+08 |
| PLCL1 | 0.020833 | 0 | 0.142857 | 0 | 0.037037 | PLCL1 | 2 | 2q33.1 | 1.98E+08 | 1.99E+08 |
| BZW1 | 0.020833 | 0.142857 | 0 | 0.037037 | 0 | BZW1 | 2 | 2q33.1 | 2.01E+08 | 2.01E+08 |
| BZW1L1 | 0.020833 | 0.142857 | 0 | 0.037037 | 0 | BZW1L1 | 2 | 2q33.1 | 2.01E+08 | 2.01E+08 |
| PPIL3 | 0.020833 | 0.142857 | 0 | 0.037037 | 0 | PPIL3 | 2 | 2q33.1 | 2.01E+08 | 2.01E+08 |
| NIF3L1 | 0.020833 | 0.142857 | 0 | 0.037037 | 0 | NIF3L1 | 2 | 2q33.1 | 2.01E+08 | 2.01E+08 |
| ORC2L | 0.020833 | 0.142857 | 0 | 0.037037 | 0 | ORC2L | 2 | 2q33.1 | 2.01E+08 | 2.02E+08 |
| FAM126B | 0.020833 | 0.190476 | 0 | 0.037037 | 0 | FAM126B | 2 | 2q33.1 | 2.02E+08 | 2.02E+08 |
| NDUFB3 | 0.020833 | 0.190476 | 0 | 0.037037 | 0 | NDUFB3 | 2 | 2q33.1 | 2.02E+08 | 2.02E+08 |
| CFLAR | 0.020833 | 0.190476 | 0 | 0.037037 | 0 | CFLAR | 2 | 2q33.1 | 2.02E+08 | 2.02E+08 |
| CASP10 | 0.020833 | 0.142857 | 0 | 0.037037 | 0 | CASP10 | 2 | 2q33.1 | 2.02E+08 | 2.02E+08 |
| CASP8 | 0.020833 | 0.142857 | 0 | 0.037037 | 0 | CASP8 | 2 | 2q33.1 | 2.02E+08 | 2.02E+08 |
| ALS2CR12 | 0.020833 | 0.142857 | 0 | 0.037037 | 0 | ALS2CR12 | 2 | 2q33.1 | 2.02E+08 | 2.02E+08 |
| TRAK2 | 0.020833 | 0.142857 | 0.047619 | 0.037037 | 0 | TRAK2 | 2 | 2q33.1 | 2.02E+08 | 2.02E+08 |
| STRAD8 | 0.020833 | 0.142857 | 0.047619 | 0.037037 | 0 | STRAD8 | 2 | 2q33.1 | 2.02E+08 | 2.02E+08 |
| MPP4 | 0.020833 | 0.190476 | 0 | 0.037037 | 0 | MPP4 | 2 | 2q33.1 | 2.02E+08 | 2.02E+08 |
| ALS2 | 0.020833 | 0.190476 | 0 | 0.037037 | 0 | ALS2 | 2 | 2q33.1 | 2.02E+08 | 2.02E+08 |
| CDK15 | 0.020833 | 0.190476 | 0 | 0.037037 | 0 | CDK15 | 2 | 2q33.1 | 2.02E+08 | 2.02E+08 |
| FAM117B | 0.020833 | 0.238095 | 0 | 0.037037 | 0 | FAM117B | 2 | 2q33.1 | 2.03E+08 | 2.03E+08 |
| ALS2CR8 | 0.020833 | 0.190476 | 0 | 0.037037 | 0 | ALS2CR8 | 2 | 2q33.2 | 2.03E+08 | 2.04E+08 |
| NBEAL1 | 0.020833 | 0.190476 | 0 | 0.037037 | 0 | NBEAL1 | 2 | 2q33.2 | 2.04E+08 | 2.04E+08 |
| CYP20A1 | 0.020833 | 0.190476 | 0 | 0.037037 | 0 | CYP20A1 | 2 | 2q33.2 | 2.04E+08 | 2.04E+08 |
| ABI2 | 0.020833 | 0.190476 | 0 | 0.037037 | 0 | ABI2 | 2 | 2q33.2 | 2.04E+08 | 2.04E+08 |
| RAPH1 | 0.020833 | 0.190476 | 0 | 0.037037 | 0 | RAPH1 | 2 | 2q33.2 | 2.04E+08 | 2.04E+08 |
| INO80D | 0.020833 | 0.142857 | 0 | 0.037037 | 0 | INO80D | 2 | 2q33.3 | 2.07E+08 | 2.07E+08 |
| NDUFS1 | 0.020833 | 0.142857 | 0 | 0.037037 | 0 | NDUFS1 | 2 | 2q33.3 | 2.07E+08 | 2.07E+08 |
| EEF1B2 | 0.020833 | 0.142857 | 0 | 0.037037 | 0 | EEF1B2 | 2 | 2q33.3 | 2.07E+08 | 2.07E+08 |
| SNORD51 | 0.020833 | 0.142857 | 0 | 0.037037 | 0 | SNORD51 | 2 | 2q33.3 | 2.07E+08 | 2.07E+08 |
| SNORA41 | 0.020833 | 0.142857 | 0 | 0.037037 | 0 | SNORA41 | 2 | 2q33.3 | 2.07E+08 | 2.07E+08 |
| GPR1 | 0.020833 | 0.142857 | 0 | 0.037037 | 0 | GPR1 | 2 | 2q33.3 | 2.07E+08 | 2.07E+08 |
| CCNYL1 | 0.020833 | 0.142857 | 0 | 0.037037 | 0 | CCNYL1 | 2 | 2q33.3 | 2.08E+08 | 2.08E+08 |
| PECR | 0.020833 | 0.142857 | 0 | 0.037037 | 0 | PECR | 2 | 2q35 | 2.17E+08 | 2.17E+08 |
| 4-Mar | 0.020833 | 0.142857 | 0 | 0.037037 | 0 | 4-Mar | 2 | 2q35 | 2.17E+08 | 2.17E+08 |
| DEPDC1 | 0.020833 | 0 | 0.190476 | 0 | 0.037037 | DEPDC1 | 1 | 1p31.2 | 68712423 | 68735388 |
| LRRC7 | 0.020833 | 0 | 0.190476 | 0 | 0.037037 | LRRC7 | 1 | 1p31.1 | 69998446 | 70361760 |
| PIN1L | 0.020833 | 0 | 0.190476 | 0 | 0.037037 | PIN1L | 1 | 1p31.1 | 70157593 | 70158589 |
| ANKRD13C | 0.020833 | 0 | 0.142857 | 0 | 0.037037 | ANKRD13C | 1 | 1p31.1 | 70497273 | 70593006 |

TABLE 4-continued

Gene list for predicting prostate cancer relapse using AT

| Symbol | freq. use | freq. amp. case | freq. del. case | freq. amp. control | freq. del. control | Gene. Symbol | chromo- some | cytoband | Tran- script. start | Tran- script. end |
|---|---|---|---|---|---|---|---|---|---|---|
| HHLA3 | 0.020833 | 0 | 0.142857 | 0 | 0.037037 | HHLA3 | 1 | 1p31.1 | 70593081 | 70606294 |
| CTH | 0.020833 | 0 | 0.142857 | 0 | 0.037037 | CTH | 1 | 1p31.1 | 70649543 | 70677842 |
| USP33 | 0.020833 | 0.142857 | 0 | 0.037037 | 0.074074 | USP33 | 1 | 1p31.1 | 77934262 | 77998126 |
| FAM73A | 0.020833 | 0.190476 | 0 | 0.037037 | 0.074074 | FAM73A | 1 | 1p31.1 | 78017897 | 78116670 |
| TTLL7 | 0.020833 | 0 | 0.142857 | 0 | 0.037037 | TTLL7 | 1 | 1p31.1 | 84107645 | 84237422 |
| PRKACB | 0.020833 | 0 | 0.142857 | 0 | 0.037037 | PRKACB | 1 | 1p31.1 | 84316333 | 84476770 |
| SAMD13 | 0.020833 | 0 | 0.142857 | 0 | 0.037037 | SAMD13 | 1 | 1p31.1 | 84536637 | 84589069 |
| UOX | 0.020833 | 0 | 0.142857 | 0 | 0.037037 | UOX | 1 | 1p31.1 | 84603229 | 84636165 |
| PKN2 | 0.020833 | 0 | 0.142857 | 0 | 0.037037 | PKN2 | 1 | 1p22.2 | 88922510 | 89074527 |
| GTF2B | 0.020833 | 0.142857 | 0 | 0.037037 | 0 | GTF2B | 1 | 1p22.2 | 89090909 | 89129890 |
| BCAR3 | 0.020833 | 0.142857 | 0 | 0.037037 | 0 | BCAR3 | 1 | 1p22.1 | 93799937 | 93919974 |
| TRIM33 | 0.020833 | 0.142857 | 0 | 0.037037 | 0 | TRIM33 | 1 | 1p13.1 | 1.15E+08 | 1.15E+08 |
| DENND2C | 0.020833 | 0.142857 | 0 | 0.037037 | 0 | DENND2C | 1 | 1p13.2 | 1.15E+08 | 1.15E+08 |
| AMPD1 | 0.020833 | 0.142857 | 0 | 0.037037 | 0 | AMPD1 | 1 | 1p13.2 | 1.15E+08 | 1.15E+08 |
| NRAS | 0.020833 | 0.142857 | 0 | 0.037037 | 0 | NRAS | 1 | 1p13.2 | 1.15E+08 | 1.15E+08 |
| CSDE1 | 0.020833 | 0.142857 | 0 | 0.037037 | 0 | CSDE1 | 1 | 1p13.2 | 1.15E+08 | 1.15E+08 |
| SIKE1 | 0.020833 | 0.142857 | 0 | 0.037037 | 0 | SIKE1 | 1 | 1p13.2 | 1.15E+08 | 1.15E+08 |
| FAM46C | 0.020833 | 0.190476 | 0 | 0.037037 | 0 | FAM46C | 1 | 1p12 | 1.18E+08 | 1.18E+08 |
| HFE2 | 0.020833 | 0.285714 | 0 | 0.037037 | 0 | HFE2 | 1 | 1q11.1 | 1.44E+08 | 1.44E+08 |
| PQLR3GL | 0.020833 | 0.238095 | 0 | 0.037037 | 0 | PQLR3GL | 1 | 1q21.1 | 1.44E+08 | 1.44E+08 |
| LIX1L | 0.020833 | 0.238095 | 0 | 0.037037 | 0 | LIX1L | 1 | 1q21.1 | 1.44E+08 | 1.44E+08 |
| RBM8A | 0.020833 | 0.238095 | 0 | 0.037037 | 0 | RBM8A | 1 | 1q21.1 | 1.44E+08 | 1.44E+08 |
| GNRHR2 | 0.020833 | 0.238095 | 0 | 0.037037 | 0 | GNRHR2 | 1 | 1q21.1 | 1.44E+08 | 1.44E+08 |
| PEX11B | 0.020833 | 0.238095 | 0 | 0.037037 | 0 | PEX11B | 1 | 1q21.1 | 1.44E+08 | 1.44E+08 |
| ITGA10 | 0.020833 | 0.238095 | 0 | 0.037037 | 0 | ITGA10 | 1 | 1q21.1 | 1.44E+08 | 1.44E+08 |
| ANKRD35 | 0.020833 | 0.238095 | 0 | 0.037037 | 0 | ANKRD35 | 1 | 1q21.1 | 1.44E+08 | 1.44E+08 |
| RNF115 | 0.020833 | 0.238095 | 0 | 0.037037 | 0 | RNF115 | 1 | 1q21.1 | 1.44E+08 | 1.44E+08 |
| SLAMF6 | 0.020833 | 0.190476 | 0 | 0.037037 | 0 | SLAMF6 | 1 | 1q23.2 | 1.59E+08 | 1.59E+08 |
| CD84 | 0.020833 | 0.190476 | 0 | 0.037037 | 0 | CD84 | 1 | 1q23.2-1c | 1.59E+08 | 1.59E+08 |
| SLAMF7 | 0.020833 | 0.142857 | 0 | 0.037037 | 0 | SLAMF7 | 1 | 1q23.3 | 1.59E+08 | 1.59E+08 |
| CD244 | 0.020833 | 0.190476 | 0 | 0.037037 | 0 | CD244 | 1 | 1q23.3 | 1.59E+08 | 1.59E+08 |
| UFC1 | 0.020833 | 0.238095 | 0 | 0.037037 | 0.037037 | UFC1 | 1 | 1q23.3 | 1.59E+08 | 1.59E+08 |
| USP21 | 0.020833 | 0.238095 | 0 | 0.037037 | 0.037037 | USP21 | 1 | 1q23.3 | 1.59E+08 | 1.59E+08 |
| PPOX | 0.020833 | 0.238095 | 0 | 0.037037 | 0.037037 | PPOX | 1 | 1q23.3 | 1.59E+08 | 1.59E+08 |
| B4GALT3 | 0.020833 | 0.238095 | 0 | 0.037037 | 0.037037 | B4GALT3 | 1 | 1q23.3 | 1.59E+08 | 1.59E+08 |
| NR1I3 | 0.020833 | 0.238095 | 0 | 0.037037 | 0 | NR1I3 | 1 | 1q23.3 | 1.59E+08 | 1.59E+08 |
| PCP4L1 | 0.020833 | 0.238095 | 0 | 0.037037 | 0 | PCP4L1 | 1 | 1q23.3 | 1.59E+08 | 1.6E+08 |
| MPZ | 0.020833 | 0.238095 | 0 | 0.037037 | 0 | MPZ | 1 | 1q23.3 | 1.6E+08 | 1.6E+08 |
| SDHC | 0.020833 | 0.238095 | 0 | 0.037037 | 0 | SDHC | 1 | 1q23.3 | 1.6E+08 | 1.6E+08 |
| LOC642502 | 0.020833 | 0.238095 | 0 | 0.037037 | 0 | LOC64250 | 1 | 1q23.3 | 1.6E+08 | 1.6E+08 |
| C1orf192 | 0.020833 | 0.238095 | 0 | 0.037037 | 0 | C1orf192 | 1 | 1q23.3 | 1.6E+08 | 1.6E+08 |
| OLFML2B | 0.020833 | 0.190476 | 0 | 0.037037 | 0 | OLFML2B | 1 | 1q23.3 | 1.6E+08 | 1.6E+08 |
| NOS1AP | 0.020833 | 0.142857 | 0 | 0.037037 | 0 | NOS1AP | 1 | 1q23.3 | 1.6E+08 | 1.61E+08 |
| C1orf11 | 0.020833 | 0.190476 | 0 | 0.037037 | 0 | C1orf11 | 1 | 1q23.3 | 1.61E+08 | 1.61E+08 |
| RGS5 | 0.020833 | 0 | 0.142857 | 0 | 0.037037 | RGS5 | 1 | 1q23.3 | 1.61E+08 | 1.61E+08 |
| KIAA1614 | 0.020833 | 0.238095 | 0 | 0.037037 | 0 | KIAA1614 | 1 | 1q25.3 | 1.79E+08 | 1.79E+08 |
| HEATR1 | 0.020833 | 0.190476 | 0 | 0.037037 | 0 | HEATR1 | 1 | 1q43 | 2.35E+08 | 2.35E+08 |
| ACTN2 | 0.020833 | 0.190476 | 0 | 0.037037 | 0 | ACTN2 | 1 | 1q43 | 2.35E+08 | 2.35E+08 |
| RYR2 | 0.020833 | 0.142857 | 0 | 0.037037 | 0 | RYR2 | 1 | 1q43 | 2.35E+08 | 2.36E+08 |
| ZNF238 | 0.020833 | 0.238095 | 0 | 0.037037 | 0 | ZNF238 | 1 | 1q44 | 2.42E+08 | 2.42E+08 |
| C1orf100 | 0.020833 | 0.238095 | 0 | 0.037037 | 0 | C1orf100 | 1 | 1q44 | 2.43E+08 | 2.43E+08 |
| ADSS | 0.020833 | 0.238095 | 0 | 0.037037 | 0 | ADSS | 1 | 1q44 | 2.43E+08 | 2.43E+08 |
| C1orf101 | 0.020833 | 0.238095 | 0 | 0.037037 | 0 | C1orf101 | 1 | 1q44 | 2.43E+08 | 2.43E+08 |
| PPPDE1 | 0.020833 | 0.190476 | 0.047619 | 0.037037 | 0 | PPPDE1 | 1 | 1q44 | 2.43E+08 | 2.43E+08 |
| FAM36A | 0.020833 | 0.238095 | 0 | 0.037037 | 0 | FAM36A | 1 | 1q44 | 2.43E+08 | 2.43E+08 |
| EFCAB2 | 0.020833 | 0.238095 | 0 | 0.037037 | 0 | EFCAB2 | 1 | 1q44 | 2.43E+08 | 2.43E+08 |
| KIF26B | 0.020833 | 0.238095 | 0 | 0.037037 | 0 | KIF26B | 1 | 1q44 | 2.43E+08 | 2.44E+08 |

TABLE 5

Gene list for predicting prostate cancer fast relapse using AT

| Symbol | freq.use | freq.amp. case | freq.del. case | freq.amp. control | freq.del. control | Gene.Symbol | chromosome | cytoband | Transcript. start | Transcript. end |
|---|---|---|---|---|---|---|---|---|---|---|
| RPL23AP82 | 1 | 0.75 | 0.25 | 0.8 | 0 | RPL23AP82 | 22 | 22q13.33 | 49542380 | 49584931 |
| RABL2B | 1 | 0.75 | 0.25 | 0.8 | 0 | RABL2B | 22 | 22q13.33 | 49552786 | 49568954 |
| CA10 | 1 | 0.25 | 0.25 | 0.15 | 0 | CA10 | 17 | 17q21.33 | 47062673 | 47592161 |
| MAGEL2 | 1 | 0.375 | 0 | 0 | 0 | MAGEL2 | 15 | 15q11.2 | 21439791 | 21444087 |
| NDN | 1 | 0.375 | 0 | 0 | 0 | NDN | 15 | 15q11.2 | 21481647 | 21483544 |
| C13orf36 | 1 | 0 | 0.25 | 0.025 | 0 | C13orf36 | 13 | 13q13.3 | 36146049 | 36169976 |

TABLE 5-continued

Gene list for predicting prostate cancer fast relapse using AT

| Symbol | freq.use | freq.amp. case | freq.del. case | freq.amp. control | freq.del. control | Gene.Symbol | chromosome | cytoband | Transcript. start | Transcript. end |
|---|---|---|---|---|---|---|---|---|---|---|
| SMAD9 | 1 | 0 | 0.25 | 0.075 | 0 | SMAD9 | 13 | 13q13.3 | 36320207 | 36392410 |
| ALG5 | 1 | 0.125 | 0.25 | 0.075 | 0 | ALG5 | 13 | 13q13.3 | 36421910 | 36471505 |
| RSU1 | 1 | 0.25 | 0 | 0 | 0 | RSU1 | 10 | 10p13 | 16672623 | 16899460 |
| ADCY2 | 1 | 0.25 | 0 | 0 | 0 | ADCY2 | 5 | 5p15.31 | 7449343 | 7883195 |
| UBE2E1 | 1 | 0.25 | 0 | 0 | 0.025 | UBE2E1 | 3 | 3p24.2 | 23822443 | 23907812 |
| RETNLB | 1 | 0 | 0.25 | 0 | 0 | RETNLB | 3 | 3q13.13 | 1.1E+08 | 1.1E+08 |
| TRAT1 | 1 | 0 | 0.25 | 0 | 0 | TRAT1 | 3 | 3q13.13 | 1.1E+08 | 1.1E+08 |
| GUCA1C | 1 | 0 | 0.25 | 0 | 0 | GUCA1C | 3 | 3q13.13 | 1.1E+08 | 1.1E+08 |
| MORC1 | 1 | 0 | 0.25 | 0 | 0 | MORC1 | 3 | 3q13.13 | 1.1E+08 | 1.1E+08 |
| TTTY8 | 0.979167 | 0.125 | 0.125 | 0.275 | 0 | TTTY8 | Y | Yp11.2 | 10138709 | 10141309 |
| TTTY8B | 0.979167 | 0.125 | 0.125 | 0.275 | 0 | TTTY8B | Y | Yp11.2 | 10138709 | 10141309 |
| TTTY7 | 0.979167 | 0.125 | 0.125 | 0.275 | 0 | TTTY7 | Y | Yp11.2 | 10154433 | 10162872 |
| TTTY7B | 0.979167 | 0.125 | 0.125 | 0.275 | 0 | TTTY7B | Y | Yp11.2 | 10154433 | 10162872 |
| LOC100101115 | 0.979167 | 0.125 | 0.125 | 0.275 | 0 | LOC100101115 | Y | Yp11.2 | 10165262 | 10168906 |
| TTTY21 | 0.979167 | 0.125 | 0.125 | 0.275 | 0 | TTTY21 | Y | Yp11.2 | 10165262 | 10168906 |
| YIPF6 | 0.979167 | 0.125 | 0.125 | 0.275 | 0 | YIPF6 | X | Xq12 | 67635611 | 67669027 |
| LOC96610 | 0.979167 | 0.625 | 0.125 | 0.575 | 0 | LOC96610 | 22 | 22q11.22 | 20982463 | 21007325 |
| STX16 | 0.979167 | 0.5 | 0.125 | 0.45 | 0 | STX16 | 20 | 20q13.32 | 56659734 | 56687989 |
| ZNF440 | 0.979167 | 0.875 | 0.125 | 0.625 | 0 | ZNF440 | 19 | 19p13.2 | 11786107 | 11807017 |
| FKBP8 | 0.979167 | 0.75 | 0.125 | 0.575 | 0 | FKBP8 | 19 | 19p13.11 | 18503568 | 18515384 |
| ZNF30 | 0.979167 | 0.875 | 0.125 | 0.5 | 0 | ZNF30 | 19 | 19q13.11 | 40109647 | 40127917 |
| PSMC4 | 0.979167 | 0.875 | 0.125 | 0.55 | 0 | PSMC4 | 19 | 19q13.2 | 45168913 | 45179194 |
| MAMSTR | 0.979167 | 0.75 | 0.125 | 0.575 | 0 | MAMSTR | 19 | 19q13.33 | 53908067 | 53914789 |
| RASIP1 | 0.979167 | 0.75 | 0.125 | 0.575 | 0 | RASIP1 | 19 | 19q13.33 | 53915654 | 53935783 |
| IZUMO1 | 0.979167 | 0.75 | 0.125 | 0.575 | 0 | IZUMO1 | 19 | 19q13.33 | 53935957 | 53941979 |
| DSG2 | 0.979167 | 0.125 | 0 | 0 | 0.05 | DSG2 | 18 | 18q12.1 | 27332025 | 27382813 |
| ZNF287 | 0.979167 | 0.375 | 0.125 | 0.325 | 0 | ZNF287 | 17 | 17p11.2 | 16394356 | 16413246 |
| SLC4A1 | 0.979167 | 0.5 | 0.125 | 0.5 | 0 | SLC4A1 | 17 | 17q21.31 | 39681284 | 39701029 |
| SPAG9 | 0.979167 | 0.5 | 0.125 | 0.225 | 0 | SPAG9 | 17 | 17q21.33 | 46394535 | 46553226 |
| NME1 | 0.979167 | 0.5 | 0.125 | 0.275 | 0 | NME1 | 17 | 17q21.33 | 46585919 | 46594450 |
| NME1-NME2 | 0.979167 | 0.5 | 0.125 | 0.275 | 0 | NME1-NME2 | 17 | 17q21.33 | 46585919 | 46604105 |
| NME2 | 0.979167 | 0.5 | 0.125 | 0.275 | 0 | NME2 | 17 | 17q21.33 | 46597890 | 46604105 |
| MBTD1 | 0.979167 | 0.375 | 0.125 | 0.2 | 0 | MBTD1 | 17 | 17q21.33 | 46609785 | 46692427 |
| UTP18 | 0.979167 | 0.375 | 0.125 | 0.2 | 0 | UTP18 | 17 | 17q21.33 | 46692896 | 46730292 |
| TOM1L1 | 0.979167 | 0 | 0.125 | 0.1 | 0 | TOM1L1 | 17 | 17q22 | 50333051 | 50394328 |
| COX11 | 0.979167 | 0 | 0.125 | 0.1 | 0 | COX11 | 17 | 17q22 | 50384258 | 50401064 |
| STXBP4 | 0.979167 | 0 | 0.125 | 0.1 | 0 | STXBP4 | 17 | 17q22 | 50401125 | 50596449 |
| RSL1D1 | 0.979167 | 0.5 | 0.125 | 0.425 | 0 | RSL1D1 | 16 | 16q13.13 | 11835556 | 11852944 |
| VPS4A | 0.979167 | 0.625 | 0.125 | 0.375 | 0 | VPS4A | 16 | 16q22.1 | 67902788 | 67916448 |
| COG8 | 0.979167 | 0.625 | 0.125 | 0.375 | 0 | COG8 | 16 | 16q22.1 | 67920025 | 67931028 |
| PDF | 0.979167 | 0.625 | 0.125 | 0.375 | 0 | PDF | 16 | 16q22.1 | 67920025 | 67922000 |
| NIP7 | 0.979167 | 0.625 | 0.125 | 0.375 | 0 | NIP7 | 16 | 16q22.1 | 67931047 | 67934511 |
| TMED6 | 0.979167 | 0.625 | 0.125 | 0.375 | 0 | TMED6 | 16 | 16q22.1 | 67934650 | 67943214 |
| PAR1 | 0.979167 | 0.125 | 0 | 0 | 0.075 | PAR1 | 15 | 15q11.2 | 22931882 | 22934294 |
| FSIP1 | 0.979167 | 0 | 0.125 | 0.125 | 0 | FSIP1 | 15 | 15q14 | 37679524 | 37862332 |
| NRG4 | 0.979167 | 0.5 | 0.125 | 0.45 | 0 | NRG4 | 15 | 15q24.2 | 74022899 | 74091841 |
| NTRK3 | 0.979167 | 0.375 | 0.125 | 0.25 | 0 | NTRK3 | 15 | 15q25.3 | 86220992 | 86600666 |
| FBXO33 | 0.979167 | 0.125 | 0.125 | 0 | 0.1 | FBXO33 | 14 | 14q21.1 | 38936628 | 38971456 |
| DDHD1 | 0.979167 | 0.125 | 0 | 0 | 0 | DDHD1 | 14 | 14q22.2 | 52573210 | 52689797 |
| FUT8 | 0.979167 | 0 | 0.125 | 0.175 | 0 | FUT8 | 14 | 14q23.3 | 64947593 | 65279716 |
| CYP46A1 | 0.979167 | 0.5 | 0.125 | 0.475 | 0 | CYP46A1 | 14 | 14q32.2 | 99220508 | 99263392 |
| RFC3 | 0.979167 | 0 | 0.125 | 0 | 0 | RFC3 | 13 | 13q13.2 | 33290206 | 33438696 |
| MIR548F5 | 0.979167 | 0 | 0.125 | 0.05 | 0 | MIR548F5 | 13 | 13q13.3 | 34946406 | 35413383 |
| DCLK1 | 0.979167 | 0 | 0.125 | 0 | 0 | DCLK1 | 13 | 13q13.3 | 35241123 | 35603465 |
| SOHLH2 | 0.979167 | 0 | 0.125 | 0 | 0 | SOHLH2 | 13 | 13q13.3 | 35640347 | 35686753 |
| CCNA1 | 0.979167 | 0 | 0.125 | 0 | 0 | CCNA1 | 13 | 13q13.3 | 35903967 | 35915020 |
| MYO16 | 0.979167 | 0.125 | 0 | 0 | 0.025 | MYO16 | 13 | 13q33.3 | 1.08E+08 | 1.09E+08 |
| YAF2 | 0.979167 | 0 | 0.125 | 0.025 | 0 | YAF2 | 12 | 12q12 | 40837174 | 40918318 |
| WDR51B | 0.979167 | 0 | 0.25 | 0 | 0.05 | WDR51B | 12 | 12q21.33 | 88337634 | 88443909 |
| OR51E1 | 0.979167 | 0.125 | 0 | 0 | 0 | OR51E1 | 11 | 11p15.4 | 4621732 | 4633291 |
| OR51E2 | 0.979167 | 0.125 | 0 | 0 | 0 | OR51E2 | 11 | 11p15.4 | 4657977 | 4675653 |
| FLJ46111 | 0.979167 | 0.125 | 0.125 | 0.25 | 0 | FLJ46111 | 11 | 11p15.4 | 9072486 | 9074314 |
| DNAJC24 | 0.979167 | 0.125 | 0 | 0 | 0.075 | DNAJC24 | 11 | 11p13 | 31347953 | 31410959 |
| ASRGL1 | 0.979167 | 0.5 | 0.125 | 0.45 | 0 | ASRGL1 | 11 | 11q12.3 | 61861350 | 61917464 |
| SCGB1A1 | 0.979167 | 0.5 | 0.125 | 0.45 | 0 | SCGB1A1 | 11 | 11q12.3 | 61943099 | 61947244 |
| PAK1 | 0.979167 | 0.125 | 0.125 | 0.2 | 0 | PAK1 | 11 | 11q14.1 | 76710708 | 76862757 |
| AKR1C1 | 0.979167 | 0 | 0.125 | 0.1 | 0 | AKR1C1 | 10 | 10p15.1 | 4995454 | 5010159 |
| AKR1C2 | 0.979167 | 0 | 0.125 | 0.1 | 0 | AKR1C2 | 10 | 10p15.1 | 5021965 | 5050208 |
| CUBN | 0.979167 | 0.125 | 0 | 0 | 0 | CUBN | 10 | 10p13 | 16905971 | 17211823 |
| MYO3A | 0.979167 | 0.125 | 0 | 0 | 0 | MYO3A | 10 | 10p12.2 | 26263008 | 26541472 |
| CCDC6 | 0.979167 | 0.125 | 0 | 0 | 0 | CCDC6 | 10 | 10q21.2 | 61218527 | 61336825 |
| KCNMA1 | 0.979167 | 0.25 | 0.125 | 0.175 | 0 | KCNMA1 | 10 | 10q22.3 | 78299365 | 79067584 |
| PDCD4 | 0.979167 | 0 | 0.125 | 0.05 | 0 | PDCD4 | 10 | 10q25.2 | 1.13E+08 | 1.13E+08 |
| RLN1 | 0.979167 | 0 | 0.125 | 0 | 0 | RLN1 | 9 | 9p24.1 | 5324969 | 5329874 |
| SLC24A2 | 0.979167 | 0.125 | 0 | 0 | 0.025 | SLC24A2 | 9 | 9p22.1 | 19505978 | 19776927 |

TABLE 5-continued

Gene list for predicting prostate cancer fast relapse using AT

| Symbol | freq.use | freq.amp. case | freq.del. case | freq.amp. control | freq.del. control | Gene.Symbol | chromosome | cytoband | Transcript. start | Transcript. end |
|---|---|---|---|---|---|---|---|---|---|---|
| LOC440173 | 0.979167 | 0.25 | 0.125 | 0.175 | 0 | LOC440173 | 9 | 9q21.33 | 88813187 | 88846862 |
| ASTN2 | 0.979167 | 0 | 0.125 | 0.05 | 0 | ASTN2 | 9 | 9q33.1 | 1.18E+08 | 1.19E+08 |
| LHX3 | 0.979167 | 0.875 | 0.125 | 0.725 | 0 | LHX3 | 9 | 9q34.3 | 1.38E+08 | 1.38E+08 |
| QSOX2 | 0.979167 | 0.875 | 0.125 | 0.725 | 0 | QSOX2 | 9 | 9q34.3 | 1.38E+08 | 1.38E+08 |
| TNFRSF10C | 0.979167 | 0.25 | 0.125 | 0.175 | 0 | TNFRSF10C | 8 | 8p21.3 | 23016379 | 23030896 |
| TERF1 | 0.979167 | 0 | 0.125 | 0.075 | 0 | TERF1 | 8 | 8q21.11 | 74083651 | 74122542 |
| C8orf84 | 0.979167 | 0 | 0.125 | 0.1 | 0 | C8orf84 | 8 | 8q21.11 | 74139334 | 74168062 |
| RDH10 | 0.979167 | 0 | 0.125 | 0.1 | 0 | RDH10 | 8 | 8q21.11 | 74369819 | 74400069 |
| UBE2W | 0.979167 | 0.125 | 0.125 | 0.1 | 0 | UBE2W | 8 | 8q21.11 | 74865394 | 74953665 |
| TCEB1 | 0.979167 | 0.125 | 0.125 | 0.1 | 0 | TCEB1 | 8 | 8q21.11 | 75021188 | 75046901 |
| C7orf30 | 0.979167 | 0 | 0.125 | 0.05 | 0 | C7orf30 | 7 | 7p15.3 | 23305465 | 23315706 |
| IGF2BP3 | 0.979167 | 0 | 0.125 | 0.05 | 0 | IGF2BP3 | 7 | 7p15.3 | 23316353 | 23476521 |
| CALU | 0.979167 | 0.25 | 0.125 | 0.3 | 0 | CALU | 7 | 7q32.1 | 1.28E+08 | 1.28E+08 |
| MIR548A1 | 0.979167 | 0.125 | 0 | 0 | 0.025 | MIR548A1 | 6 | 6p22.3 | 18679994 | 18680091 |
| HMGA1 | 0.979167 | 0.625 | 0.125 | 0.425 | 0 | HMGA1 | 6 | 6p21.31 | 34312555 | 34321986 |
| TCP11 | 0.979167 | 0.5 | 0.125 | 0.325 | 0 | TCP11 | 6 | 6p21.31 | 35193827 | 35217166 |
| KLEHL31 | 0.979167 | 0 | 0.125 | 0 | 0 | KLHL31 | 6 | 6p12.1 | 53620658 | 53638466 |
| LRRC1 | 0.979167 | 0 | 0.125 | 0 | 0 | LRRC1 | 6 | 6p12.1 | 53767737 | 53896879 |
| SLC22A16 | 0.979167 | 0.125 | 0 | 0 | 0 | SLC22A16 | 6 | 6q21 | 1.11E+08 | 1.11E+08 |
| RICTOR | 0.979167 | 0 | 0.125 | 0 | 0 | RICTOR | 5 | 5p13.1 | 38973780 | 39110259 |
| FYB | 0.979167 | 0 | 0.125 | 0 | 0 | FYB | 5 | 5p13.1 | 39141114 | 39255425 |
| FAM169A | 0.979167 | 0 | 0.125 | 0 | 0 | FAM169A | 5 | 5q13.3 | 74109155 | 74198372 |
| SEMA6A | 0.979167 | 0 | 0.125 | 0 | 0 | SEMA6A | 5 | 5q23.1 | 1.16E+08 | 1.16E+08 |
| DMXL1 | 0.979167 | 0.125 | 0.125 | 0.075 | 0 | DMXL1 | 5 | 5q23.1 | 1.18E+08 | 1.19E+08 |
| TNFAIP8 | 0.979167 | 0 | 0.125 | 0.025 | 0 | TNFAIP8 | 5 | 5q23.1 | 1.19E+08 | 1.19E+08 |
| SAR1B | 0.979167 | 0.375 | 0.125 | 0.35 | 0 | SAR1B | 5 | 5q31.1 | 1.34E+08 | 1.34E+08 |
| RNF130 | 0.979167 | 0.5 | 0.125 | 0.525 | 0 | RNF130 | 5 | 5q35.3 | 1.79E+08 | 1.79E+08 |
| MIR340 | 0.979167 | 0.5 | 0.125 | 0.525 | 0 | MIR340 | 5 | 5q35.3 | 1.79E+08 | 1.79E+08 |
| SLC30A9 | 0.979167 | 0.125 | 0.125 | 0 | 0.05 | SLC30A9 | 4 | 4p13 | 41687280 | 41784309 |
| BEND4 | 0.979167 | 0.125 | 0.125 | 0 | 0.05 | BEND4 | 4 | 4p13 | 41807629 | 41849653 |
| POLR2B | 0.979167 | 0 | 0.125 | 0 | 0 | POLR2B | 4 | 4q12 | 57539866 | 57592092 |
| IGFBP7 | 0.979167 | 0 | 0.125 | 0 | 0 | IGFBP7 | 4 | 4q12 | 57592001 | 57671297 |
| HELQ | 0.979167 | 0.125 | 0.125 | 0.125 | 0 | HELQ | 4 | 4q21.23 | 84547523 | 84596050 |
| MRPS18C | 0.979167 | 0.125 | 0.125 | 0.125 | 0 | MRPS18C | 4 | 4q21.23 | 84596142 | 84601954 |
| FAM175A | 0.979167 | 0.125 | 0.125 | 0.125 | 0 | FAM175A | 4 | 4q21.23 | 84601120 | 84625315 |
| DCLK2 | 0.979167 | 0.125 | 0.125 | 0 | 0.025 | DCLK2 | 4 | 4q31.3 | 1.51E+08 | 1.51E+08 |
| TRIM61 | 0.979167 | 0.125 | 0.125 | 0 | 0.05 | TRIM61 | 4 | 4q32.3 | 1.66E+08 | 1.66E+08 |
| C4orf39 | 0.979167 | 0.125 | 0.125 | 0 | 0.05 | C4orf39 | 4 | 4q32.3 | 1.66E+08 | 1.66E+08 |
| NKTR | 0.979167 | 0.25 | 0.125 | 0.275 | 0 | NKTR | 3 | 3p22.1 | 42617151 | 42665238 |
| DOCK3 | 0.979167 | 0.375 | 0.125 | 0.275 | 0 | DOCK3 | 3 | 3p21.31 | 50687676 | 51396670 |
| LRIG1 | 0.979167 | 0.125 | 0 | 0 | 0 | LRIG1 | 3 | 3p14.1 | 66511911 | 66633536 |
| GXYLT2 | 0.979167 | 0 | 0.125 | 0.05 | 0 | GXYLT2 | 3 | 3p13 | 73020075 | 73107213 |
| PPP4R2 | 0.979167 | 0 | 0.125 | 0.05 | 0 | PPP4R2 | 3 | 3p13 | 73128809 | 73197702 |
| WDR52 | 0.979167 | 0 | 0.125 | 0.025 | 0 | WDR52 | 3 | 3q13.2 | 1.14E+08 | 1.15E+08 |
| SIDT1 | 0.979167 | 0 | 0.125 | 0.025 | 0 | SIDT1 | 3 | 3q13.2 | 1.15E+08 | 1.15E+08 |
| NAT13 | 0.979167 | 0 | 0.125 | 0.05 | 0 | NAT13 | 3 | 3q13.2 | 1.15E+08 | 1.15E+08 |
| POLQ | 0.979167 | 0 | 0.125 | 0.05 | 0 | POLQ | 3 | 3q13.33 | 1.23E+08 | 1.23E+08 |
| ARGFX | 0.979167 | 0 | 0.125 | 0.05 | 0 | ARGFX | 3 | 3q13.33 | 1.23E+08 | 1.23E+08 |
| FBXO40 | 0.979167 | 0 | 0.125 | 0.05 | 0 | FBXO40 | 3 | 3q13.33 | 1.23E+08 | 1.23E+08 |
| PLSCR1 | 0.979167 | 0.125 | 0.375 | 0 | 0.175 | PLSCR1 | 3 | 3q24 | 1.48E+08 | 1.48E+08 |
| TM4SF4 | 0.979167 | 0.125 | 0 | 0 | 0.025 | TM4SF4 | 3 | 3q25.1 | 1.51E+08 | 1.51E+08 |
| WWTR1 | 0.979167 | 0.125 | 0 | 0 | 0.025 | WWTR1 | 3 | 3q25.1 | 1.51E+08 | 1.51E+08 |
| NMD3 | 0.979167 | 0 | 0.125 | 0.025 | 0 | NMD3 | 3 | 3q26.1 | 1.62E+08 | 1.62E+08 |
| MRPL47 | 0.979167 | 0.125 | 0.125 | 0.025 | 0 | MRPL47 | 3 | 3q26.33 | 1.81E+08 | 1.81E+08 |
| TMEM17 | 0.979167 | 0.125 | 0 | 0 | 0 | TMEM17 | 2 | 2p15 | 62580860 | 62587109 |
| EHBP1 | 0.979167 | 0 | 0.125 | 0 | 0 | EHBP1 | 2 | 2p15 | 62754517 | 63127124 |
| C2orf86 | 0.979167 | 0 | 0.125 | 0.025 | 0 | C2orf86 | 2 | 2p15 | 63202039 | 63518591 |
| MDH1 | 0.979167 | 0 | 0.125 | 0.025 | 0 | MDH1 | 2 | 2p15 | 63669626 | 63687833 |
| RPL31 | 0.979167 | 0.25 | 0.125 | 0.175 | 0 | RPL31 | 2 | 2q11.2 | 1.01E+08 | 1.01E+08 |
| SLC9A2 | 0.979167 | 0 | 0.125 | 0.05 | 0 | SLC9A2 | 2 | 2q12.1 | 1.03E+08 | 1.03E+08 |
| GCG | 0.979167 | 0.125 | 0 | 0 | 0.125 | GCG | 2 | 2q24.2 | 1.63E+08 | 1.63E+08 |
| FAP | 0.979167 | 0.125 | 0 | 0 | 0.125 | FAP | 2 | 2q24.2 | 1.63E+08 | 1.63E+08 |
| C2orf77 | 0.979167 | 0.125 | 0 | 0 | 0 | C2orf77 | 2 | 2q311 | 1.7E+08 | 1.7E+08 |
| PHOSPHO2 | 0.979167 | 0.125 | 0 | 0 | 0 | PHOSPHO2 | 2 | 2q31.1 | 1.7E+08 | 1.7E+08 |
| KLHL23 | 0.979167 | 0.125 | 0 | 0 | 0 | KLHL23 | 2 | 2q31.1 | 1.7E+08 | 1.7E+08 |
| SSB | 0.979167 | 0.125 | 0 | 0 | 0 | SSB | 2 | 2q31.1 | 1.7E+08 | 1.7E+08 |
| METTL5 | 0.979167 | 0.125 | 0 | 0 | 0 | METTL5 | 2 | 2q31.1 | 1.7E+08 | 1.7E+08 |
| UBR3 | 0.979167 | 0.125 | 0 | 0 | 0 | UBR3 | 2 | 2q31.1 | 1.7E+08 | 1.71E+08 |
| C1orf64 | 0.979167 | 0.625 | 0.125 | 0.575 | 0 | C1orf64 | 1 | 1p36.13 | 16203318 | 16205772 |
| CYP4A22 | 0.979167 | 0.375 | 0.125 | 0.325 | 0 | CYP4A22 | 1 | 1p33 | 47375694 | 47387114 |
| C1orf141 | 0.979167 | 0 | 0.125 | 0.025 | 0 | C1orf141 | 1 | 1p31.3 | 67330447 | 67366809 |
| ABCD3 | 0.979167 | 0.125 | 0.125 | 0.025 | 0 | ABCD3 | 1 | 1p21.3 | 94656521 | 94716849 |
| RABGAP1L | 0.979167 | 0 | 0.125 | 0.05 | 0 | RABGAP1L | 1 | 1q25.1 | 1.72E+08 | 1.73E+08 |
| RBBP5 | 0.979167 | 0.375 | 0.125 | 0.35 | 0 | RBBP5 | 1 | 1q32.1 | 2.03E+08 | 2.03E+08 |
| RFX7 | 0.041667 | 0.125 | 0.125 | 0.025 | 0.025 | RFX7 | 15 | 15q21.3 | 54170023 | 54322776 |

TABLE 5-continued

Gene list for predicting prostate cancer fast relapse using AT

| Symbol | freq.use | freq.amp. case | freq.del. case | freq.amp. control | freq.del. control | Gene.Symbol | chromosome | cytoband | Transcript. start | Transcript. end |
|---|---|---|---|---|---|---|---|---|---|---|
| IPCEF1 | 0.041667 | 0.125 | 0.125 | 0.025 | 0.025 | IPCEF1 | 6 | 6q25.2 | 1.55E+08 | 1.55E+08 |
| TLR10 | 0.041667 | 0.125 | 0.125 | 0.025 | 0.025 | TLR10 | 4 | 4p14 | 38450647 | 38460985 |
| PHOX2B | 0.041667 | 0.125 | 0.125 | 0.025 | 0.025 | PHOX2B | 4 | 4p13 | 41440856 | 41445745 |
| PDCD6IP | 0.041667 | 0.125 | 0.125 | 0.025 | 0.025 | PDCD6IP | 3 | 3p22.3 | 33815070 | 33886199 |
| SR140 | 0.041667 | 0.125 | 0.125 | 0.025 | 0.025 | SR140 | 3 | 3q23 | 1.44E+08 | 1.44E+08 |
| KIF5C | 0.041667 | 0.125 | 0.125 | 0.025 | 0.025 | KIF5C | 2 | 2q23.1 | 1.49E+08 | 1.5E+08 |
| MIR1978 | 0.041667 | 0.125 | 0.125 | 0.025 | 0.025 | MIR1978 | 2 | 2q23.1 | 1.49E+08 | 1.49E+08 |
| VAMP7 | 0.020833 | 0.375 | 0.125 | 0.3 | 0.025 | VAMP7 | X | Xq28 | 1.55E+08 | 1.55E+08 |
| IL9R | 0.020833 | 0.375 | 0.125 | 0.3 | 0.025 | IL9R | X | Xq28 | 1.55E+08 | 1.55E+08 |
| ATXN10 | 0.020833 | 0.625 | 0.125 | 0.575 | 0.025 | ATXN10 | 22 | 22q13.31 | 44446342 | 44619851 |
| RNF160 | 0.020833 | 0.125 | 0.125 | 0.05 | 0.025 | RNF160 | 21 | 21q21.3 | 29222337 | 29287149 |
| C21orf7 | 0.020833 | 0.125 | 0 | 0.025 | 0.025 | C21orf7 | 21 | 21q21.3 | 29374744 | 29470074 |
| CLDN17 | 0.020833 | 0 | 0.125 | 0.025 | 0.025 | CLDN17 | 21 | 21q21.3 | 30460132 | 30460807 |
| KRTAP19-3 | 0.020833 | 0 | 0.125 | 0.025 | 0.025 | KRTAP19-3 | 21 | 21q22.11 | 30785653 | 30786147 |
| KRTAPI9-4 | 0.020833 | 0 | 0.125 | 0.025 | 0.025 | KRTAP19-4 | 21 | 21q22.11 | 30791045 | 30791300 |
| KRTAP19-5 | 0.020833 | 0 | 0.125 | 0.025 | 0.025 | KRTAP19-5 | 21 | 21q22.11 | 30796061 | 30796289 |
| KRTAP19-7 | 0.020833 | 0 | 0.125 | 0.025 | 0.025 | KRTAP19-7 | 21 | 21q22.11 | 30855288 | 30855480 |
| KRTAP20-2 | 0.020833 | 0 | 0.125 | 0.05 | 0.025 | KRTAP20-2 | 21 | 21q22.11 | 30929454 | 30929652 |
| KRTAP20-3 | 0.020833 | 0 | 0.125 | 0.05 | 0.025 | KRTAP20-3 | 21 | 21q22.11 | 30937054 | 30937327 |
| PSG1 | 0.020833 | 0.5 | 0.25 | 0.4 | 0.025 | PSG1 | 19 | 19q13.31 | 48063198 | 48075712 |
| ZNF519 | 0.020833 | 0.125 | 0.125 | 0.075 | 0.025 | ZNF519 | 18 | 18p11.21 | 14094724 | 14122430 |
| ANKRD30B | 0.020833 | 0.125 | 0.125 | 0.075 | 0.025 | ANKRD30B | 18 | 18p11.21 | 14738239 | 14842738 |
| TTR | 0.020833 | 0.125 | 0 | 0.025 | 0.025 | TTR | 18 | 18q12.1 | 27425728 | 27432983 |
| B4GALT6 | 0.020833 | 0.125 | 0 | 0.025 | 0.025 | B4GALT6 | 18 | 18q12.1 | 27456207 | 27518685 |
| MCART2 | 0.020833 | 0.125 | 0 | 0.025 | 0.025 | MCART2 | 18 | 18q12.1 | 27593657 | 27594842 |
| KIAA1012 | 0.020833 | 0.125 | 0 | 0.025 | 0.025 | KIAA1012 | 18 | 18q12.1 | 27663134 | 27777090 |
| SERPINB13 | 0.020833 | 0.125 | 0 | 0.025 | 0.025 | SERPINB13 | 18 | 18q21.33 | 59405514 | 59417413 |
| TANC2 | 0.020833 | 0.375 | 0.125 | 0.275 | 0.025 | TANC2 | 17 | 17q23.3 | 58440630 | 58858800 |
| CDH11 | 0.020833 | 0.25 | 0 | 0.025 | 0.075 | CDH11 | 16 | 16q21 | 63538184 | 63713421 |
| LOC283867 | 0.020833 | 0.25 | 0 | 0.025 | 0.025 | LOC283867 | 16 | 16q21 | 63875903 | 64167705 |
| CNTNAP4 | 0.020833 | 0.125 | 0 | 0.025 | 0.025 | CNTNAP4 | 16 | 16q23.1 | 74868677 | 75150637 |
| SCG5 | 0.020833 | 0.125 | 0 | 0.025 | 0 | SCG5 | 15 | 15q13.3 | 30721162 | 30776591 |
| MEIS2 | 0.020833 | 0 | 0.125 | 0.025 | 0.025 | MEIS2 | 15 | 15q14 | 34970524 | 35180793 |
| DMXL2 | 0.020833 | 0.125 | 0.125 | 0.05 | 0.025 | DMXL2 | 15 | 15q21.2 | 49527231 | 49702260 |
| RAB27A | 0.020833 | 0.125 | 0 | 0.025 | 0 | RAB27A | 15 | 15q21.3 | 53283092 | 53349878 |
| PIGB | 0.020833 | 0.125 | 0 | 0.025 | 0 | PIGB | 15 | 15q21.3 | 53398425 | 53435139 |
| CCPG1 | 0.020833 | 0.125 | 0 | 0.025 | 0 | CCPG1 | 15 | 15q21.3 | 53434730 | 53487835 |
| MIR628 | 0.020833 | 0.125 | 0 | 0.025 | 0 | MIR628 | 15 | 15q21.3 | 53452430 | 53452525 |
| DYX1C1 | 0.020833 | 0.125 | 0 | 0.025 | 0 | DYX1C1 | 15 | 15q21.3 | 53497246 | 53587725 |
| PYGO1 | 0.020833 | 0.125 | 0 | 0.025 | 0 | PYGO1 | 15 | 15q21.3 | 53625513 | 53668343 |
| PRTG | 0.020833 | 0.125 | 0 | 0.025 | 0 | PRTG | 15 | 15q21.3 | 53691042 | 53822470 |
| NEDD4 | 0.020833 | 0.25 | 0 | 0.025 | 0 | NEDD4 | 15 | 15q21.3 | 53906414 | 54073128 |
| TEX9 | 0.020833 | 0.125 | 0.125 | 0.025 | 0.05 | TEX9 | 15 | 15q21.3 | 54444936 | 54525365 |
| ZNF280D | 0.020833 | 0.125 | 0 | 0.025 | 0 | ZNF280D | 15 | 15q21.3 | 54709666 | 54813080 |
| TCF12 | 0.020833 | 0.125 | 0 | 0.025 | 0.025 | TCF12 | 15 | 15q21.3 | 54998125 | 55368007 |
| NEO1 | 0.020833 | 0.25 | 0.125 | 0.275 | 0.025 | NEO1 | 15 | 15q24.1 | 71131928 | 71384599 |
| MIPOL1 | 0.020833 | 0 | 0.125 | 0 | 0.025 | MIPOL1 | 14 | 14q21.1 | 36736869 | 37086619 |
| CDKN3 | 0.020833 | 0.125 | 0 | 0.025 | 0 | CDKN3 | 14 | 14q22.2 | 53933423 | 53956683 |
| C14orf145 | 0.020833 | 0 | 0.25 | 0 | 0.025 | C14orf145 | 14 | 14q31.1 | 80032574 | 80475638 |
| TSHR | 0.020833 | 0 | 0.25 | 0 | 0.025 | TSHR | 14 | 14q31.1 | 80491622 | 80682400 |
| STON2 | 0.020833 | 0 | 0.25 | 0.025 | 0.025 | STON2 | 14 | 14q31.1 | 80806662 | 80934681 |
| SEL1L | 0.020833 | 0 | 0.25 | 0.025 | 0.025 | SEL1L | 14 | 14q31.1 | 81008994 | 81069959 |
| ZMYM2 | 0.020833 | 0.125 | 0.125 | 0.15 | 0.025 | ZMYM2 | 13 | 13q12.11 | 19430810 | 19558940 |
| NBEA | 0.020833 | 0 | 0.125 | 0 | 0.025 | NBEA | 13 | 13q13.2 | 34414456 | 35144874 |
| SPG20 | 0.020833 | 0 | 0.125 | 0 | 0.025 | SPG20 | 13 | 13q13.3 | 35773777 | 35842318 |
| COG6 | 0.020833 | 0 | 0.125 | 0 | 0.025 | COG6 | 13 | 13q13.3 | 39127764 | 39263803 |
| RNASEH2B | 0.020833 | 0.125 | 0 | 0.025 | 0 | RNASEH2B | 13 | 13q14.3 | 50381893 | 50442596 |
| GUCY1B2 | 0.020833 | 0.125 | 0 | 0.025 | 0 | GUCY1B2 | 13 | 13q14.3 | 50466649 | 50538295 |
| FAM124A | 0.020833 | 0.125 | 0 | 0.025 | 0 | FAM124A | 13 | 13q14.3 | 50694508 | 50753618 |
| SERPINE3 | 0.020833 | 0.125 | 0 | 0.025 | 0 | SERPINE3 | 13 | 13q14.3 | 50813169 | 50834241 |
| INTS6 | 0.020833 | 0.125 | 0 | 0.025 | 0 | INTS6 | 13 | 13q14.3 | 50833702 | 50925277 |
| DCT | 0.020833 | 0.125 | 0.125 | 0.025 | 0.1 | DCT | 13 | 13q32.1 | 93889842 | 93929938 |
| DNAJC3 | 0.020833 | 0.375 | 0 | 0.025 | 0 | DNAJC3 | 13 | 13q32.1 | 95127403 | 95245243 |
| TMTC4 | 0.020833 | 0.125 | 0 | 0.025 | 0 | TMTC4 | 13 | 13q32.3 | 1E+08 | 1E+08 |
| AEBP2 | 0.020833 | 0.125 | 0 | 0.025 | 0.075 | AEBP2 | 12 | 12p12.3 | 19483875 | 19566441 |
| GXYLT1 | 0.020833 | 0 | 0.125 | 0 | 0.025 | GXYLT1 | 12 | 12q12 | 40761915 | 40824941 |
| SRGAP1 | 0.020833 | 0.125 | 0 | 0.025 | 0 | SRGAP1 | 12 | 12q14.2 | 62524808 | 62827881 |
| C12orf66 | 0.020833 | 0.125 | 0 | 0.025 | 0 | C12orf66 | 12 | 12q14.2 | 62872686 | 62902344 |
| C12orf56 | 0.020833 | 0.125 | 0 | 0.025 | 0 | C12orf56 | 12 | 12q14.2 | 62947032 | 63070613 |
| TBK1 | 0.020833 | 0.125 | 0 | 0.025 | 0 | TBK1 | 12 | 12q14.2 | 63132204 | 63182159 |
| GNS | 0.020833 | 0.125 | 0 | 0.025 | 0 | GNS | 12 | 12q14.2-12q14.3 | 63393489 | 63439494 |
| ZFC3H1 | 0.020833 | 0 | 0.25 | 0 | 0.025 | ZFC3H1 | 12 | 12q21.1 | 70289649 | 70344017 |
| TBC1D15 | 0.020833 | 0 | 0.25 | 0.05 | 0.025 | TBC1D15 | 12 | 12q21.1 | 70519754 | 70606895 |
| MRS2P2 | 0.020833 | 0 | 0.25 | 0.05 | 0.025 | MRS2P2 | 12 | 12q21.1 | 70528343 | 70531031 |

TABLE 5-continued

Gene list for predicting prostate cancer fast relapse using AT

| Symbol | freq.use | freq.amp. case | freq.del. case | freq.amp. control | freq.del. control | Gene.Symbol | chromosome | cytoband | Transcript. start | Transcript. end |
|---|---|---|---|---|---|---|---|---|---|---|
| METAP2 | 0.020833 | 0.125 | 0 | 0.025 | 0 | METAP2 | 12 | 12q22 | 94391953 | 94433745 |
| USP44 | 0.020833 | 0.125 | 0 | 0.025 | 0 | USP44 | 12 | 12q22 | 94435018 | 94466752 |
| NTN4 | 0.020833 | 0.125 | 0 | 0.025 | 0 | NTN4 | 12 | 12q22 | 94575714 | 94708668 |
| CCDC38 | 0.020833 | 0.125 | 0 | 0.025 | 0 | CCDC38 | 12 | 12q23.1 | 94784958 | 94860560 |
| AMDHD1 | 0.020833 | 0.125 | 0 | 0.025 | 0 | AMDHD1 | 12 | 12q23.1 | 94861202 | 94886501 |
| HAL | 0.020833 | 0.125 | 0 | 0.025 | 0 | HAL | 12 | 12q23.1 | 94891273 | 94914203 |
| OR52K2 | 0.020833 | 0.125 | 0 | 0.025 | 0.025 | OR52K2 | 11 | 11p15.4 | 4427146 | 4428091 |
| C11orf40 | 0.020833 | 0.125 | 0 | 0.025 | 0.025 | C11orf40 | 11 | 11p15.4 | 4549229 | 4555627 |
| API5 | 0.020833 | 0.25 | 0 | 0.025 | 0 | API5 | 11 | 11p12 | 43290081 | 43322659 |
| TTC17 | 0.020833 | 0.25 | 0 | 0.025 | 0 | TTC17 | 11 | 11p12 | 43337067 | 43472072 |
| MIR670 | 0.020833 | 0.25 | 0 | 0.025 | 0 | MIR670 | 11 | 11p11.2 | 43537782 | 43537880 |
| CCDC82 | 0.020833 | 0 | 0.25 | 0 | 0.025 | CCDC82 | 11 | 11q21 | 95725577 | 95762732 |
| JRKL | 0.020833 | 0 | 0.25 | 0 | 0.025 | JRKL | 11 | 11q21 | 95762806 | 95766376 |
| OR8D1 | 0.020833 | 0.125 | 0 | 0.025 | 0.025 | OR8D1 | 11 | 11q24.2 | 1.24E+08 | 1.24E+08 |
| OR8D2 | 0.020833 | 0.125 | 0 | 0.025 | 0.025 | OR8D2 | 11 | 11q24.2 | 1.24E+08 | 1.24E+08 |
| C10orf18 | 0.020833 | 0.375 | 0.125 | 0.225 | 0.025 | C10orf18 | 10 | 10p15.1 | 5766807 | 5846950 |
| LOC254312 | 0.020833 | 0.375 | 0 | 0.025 | 0 | LOC254312 | 10 | 10p14 | 11016910 | 11034133 |
| CUGBP2 | 0.020833 | 0.375 | 0 | 0.025 | 0 | CUGBP2 | 10 | 10p14 | 11087265 | 11418679 |
| PTER | 0.020833 | 0.25 | 0 | 0.025 | 0 | PTER | 10 | 10p13 | 16518973 | 16595743 |
| GAD2 | 0.020833 | 0.125 | 0 | 0.025 | 0 | GAD2 | 10 | 10p12.1 | 26545242 | 26633498 |
| APBB1IP | 0.020833 | 0.125 | 0 | 0.025 | 0 | APBB1IP | 10 | 10p12.1 | 26767272 | 26896739 |
| C10orf50 | 0.020833 | 0.125 | 0 | 0.025 | 0 | C10orf50 | 10 | 10p12.1 | 26918800 | 26923256 |
| LOC731789 | 0.020833 | 0.125 | 0 | 0.025 | 0 | LOC731789 | 10 | 10p12.1 | 26972043 | 26982389 |
| PDSS1 | 0.020833 | 0.125 | 0 | 0.025 | 0 | PDSS1 | 10 | 10p12.1 | 27026601 | 27075733 |
| ABI1 | 0.020833 | 0.125 | 0 | 0.025 | 0 | ABI1 | 10 | 10p12.1 | 27075531 | 27189966 |
| CCDC7 | 0.020833 | 0 | 0.125 | 0.025 | 0.025 | CCDC7 | 10 | 10p11.22 | 32775047 | 32903499 |
| FAM13C | 0.020833 | 0 | 0.25 | 0 | 0.025 | FAM13C | 10 | 10q21.1 | 60675896 | 60792359 |
| TM9SF3 | 0.020833 | 0.25 | 0.125 | 0.275 | 0.025 | TM9SF3 | 10 | 10q24.1 | 98267857 | 98336800 |
| PIK3AP1 | 0.020833 | 0.25 | 0.125 | 0.275 | 0.025 | PIK3AP1 | 10 | 10q24.1 | 98343059 | 98470270 |
| PLAA | 0.020833 | 0.125 | 0.125 | 0.1 | 0.025 | PLAA | 9 | 9p21.2 | 26893369 | 26937469 |
| IFT74 | 0.020833 | 0.125 | 0.125 | 0.075 | 0.025 | IFT74 | 9 | 9p21.2 | 26937037 | 27052932 |
| ALDH1A1 | 0.020833 | 0 | 0.125 | 0 | 0.025 | ALDH1A1 | 9 | 9q21.13 | 74705407 | 74757790 |
| GAS1 | 0.020833 | 0.25 | 0.125 | 0.175 | 0.025 | GAS1 | 9 | 9q21.33 | 88749097 | 88751925 |
| LPPR1 | 0.020833 | 0 | 0.125 | 0.025 | 0.025 | LPPR1 | 9 | 9q31.1 | 1.03E+08 | 1.03E+08 |
| MRPL50 | 0.020833 | 0 | 0.125 | 0.05 | 0.025 | MRPL50 | 9 | 9q31.1 | 1.03E+08 | 1.03E+08 |
| ZNF189 | 0.020833 | 0 | 0.125 | 0.05 | 0.025 | ZNF189 | 9 | 9q31.1 | 1.03E+08 | 1.03E+08 |
| ALDOB | 0.020833 | 0 | 0.125 | 0.05 | 0.025 | ALDOB | 9 | 9q31.1 | 1.03E+08 | 1.03E+08 |
| RNF20 | 0.020833 | 0 | 0.125 | 0.05 | 0.025 | RNF20 | 9 | 9q31.1 | 1.03E+08 | 1.03E+08 |
| GRIN3A | 0.020833 | 0 | 0.125 | 0.05 | 0.025 | GRIN3A | 9 | 9q31.1 | 1.03E+08 | 1.04E+08 |
| TNFSF15 | 0.020833 | 0 | 0.125 | 0.075 | 0.025 | TNFSF15 | 9 | 9q32 | 1.17E+08 | 1.17E+08 |
| TNFSF8 | 0.020833 | 0 | 0.125 | 0.075 | 0.025 | TNFSF8 | 9 | 9q33.1 | 1.17E+08 | 1.17E+08 |
| TNC | 0.020833 | 0 | 0.125 | 0.075 | 0.025 | TNC | 9 | 9q33.1 | 1.17E+08 | 1.17E+08 |
| PAPPA | 0.020833 | 0 | 0.25 | 0.025 | 0.025 | PAPPA | 9 | 9q33.1 | 1.18E+08 | 1.18E+08 |
| DBC1 | 0.020833 | 0 | 0.125 | 0.025 | 0.025 | DBC1 | 9 | 9q33.1 | 1.21E+08 | 1.21E+08 |
| ADAM9 | 0.020833 | 0 | 0.125 | 0.025 | 0.025 | ADAM9 | 8 | 8p11.23 | 38973662 | 39081794 |
| ADAM32 | 0.020833 | 0 | 0.125 | 0.025 | 0.025 | ADAM32 | 8 | 8p11.23 | 39084207 | 39261594 |
| ADAM18 | 0.020833 | 0 | 0.125 | 0.025 | 0.025 | ADAM18 | 8 | 8p11.22 | 39561299 | 39706645 |
| ADAM2 | 0.020833 | 0 | 0.125 | 0.025 | 0.025 | ADAM2 | 8 | 8p11.22 | 39720412 | 39814937 |
| POTEA | 0.020833 | 0 | 0.125 | 0.125 | 0.025 | POTEA | 8 | 8p11.1 | 43266742 | 43337486 |
| ST18 | 0.020833 | 0 | 0.125 | 0.025 | 0.025 | ST18 | 8 | 8q11.23 | 53185945 | 53484993 |
| ARMC1 | 0.020833 | 0.125 | 0 | 0.025 | 0 | ARMC1 | 8 | 8q13.1 | 66677628 | 66708987 |
| MTFR1 | 0.020833 | 0.125 | 0 | 0.025 | 0 | MTFR1 | 8 | 8q13.1 | 66719442 | 66783127 |
| PDE7A | 0.020833 | 0.125 | 0 | 0.025 | 0 | PDE7A | 8 | 8q13.1 | 66792460 | 66863876 |
| DNAJC5B | 0.020833 | 0.125 | 0 | 0.025 | 0 | DNAJC5B | 8 | 8q13.1 | 67096345 | 67175310 |
| TRIM55 | 0.020833 | 0.125 | 0 | 0.025 | 0 | TRIM55 | 8 | 8q13.1 | 67201832 | 67250273 |
| TMEM70 | 0.020833 | 0 | 0.25 | 0.05 | 0.025 | TMEM70 | 8 | 8q21.11 | 75050984 | 75057568 |
| JPH1 | 0.020833 | 0 | 0.25 | 0.025 | 0.025 | JPH1 | 8 | 8q21.11 | 75309493 | 75396118 |
| COL14A1 | 0.020833 | 0.125 | 0 | 0.025 | 0 | COL14A1 | 8 | 8q24.12 | 1.21E+08 | 1.21E+08 |
| MRPL13 | 0.020833 | 0 | 0.125 | 0 | 0.025 | MRPL13 | 8 | 8q24.12 | 1.21E+08 | 1.22E+08 |
| MTBP | 0.020833 | 0 | 0.125 | 0 | 0.025 | MTBP | 8 | 8q24.12 | 1.22E+08 | 1.22E+08 |
| C1GALT1 | 0.020833 | 0.125 | 0.125 | 0.075 | 0.025 | C1GALT1 | 7 | 7p21.3 | 7188771 | 7250507 |
| COL28A1 | 0.020833 | 0.125 | 0.125 | 0.075 | 0.025 | COL28A1 | 7 | 7p21.3 | 7364769 | 7541986 |
| RPA3 | 0.020833 | 0.125 | 0.125 | 0.025 | 0.05 | RPA3 | 7 | 7p21.3 | 7643100 | 7724764 |
| GLCCI1 | 0.020833 | 0.125 | 0.125 | 0.025 | 0.05 | GLCCI1 | 7 | 7p21.3 | 7974948 | 8095235 |
| ABCA13 | 0.020833 | 0.125 | 0 | 0.025 | 0.05 | ABCA13 | 7 | 7p12.3 | 48208389 | 48657638 |
| PION | 0.020833 | 0.125 | 0 | 0.025 | 0.075 | PION | 7 | 7q11.23 | 76778004 | 76883654 |
| CDK6 | 0.020833 | 0 | 0.125 | 0.075 | 0.025 | CDK6 | 7 | 7q21.2 | 92072173 | 92303878 |
| LAMB1 | 0.020833 | 0.125 | 0 | 0.025 | 0 | LAMB1 | 7 | 7q31.1 | 1.07E+08 | 1.07E+08 |
| AKR1B1 | 0.020833 | 0.125 | 0 | 0.025 | 0 | AKR1B1 | 7 | 7q33 | 1.34E+08 | 1.34E+08 |
| AKR1B10 | 0.020833 | 0.125 | 0 | 0.025 | 0 | AKR1B10 | 7 | 7q33 | 1.34E+08 | 1.34E+08 |
| RNF144B | 0.020833 | 0.125 | 0 | 0.025 | 0.025 | RNF144B | 6 | 6p22.3 | 18495573 | 18576830 |
| SOX4 | 0.020833 | 0.125 | 0 | 0.025 | 0 | SOX4 | 6 | 6p22.3 | 21701951 | 21706829 |
| FLJ22536 | 0.020833 | 0.125 | 0 | 0.025 | 0 | FLJ22536 | 6 | 6p22.3 | 21774654 | 22302594 |
| LOC100287718 | 0.020833 | 0 | 0.125 | 0 | 0.025 | LOC100287718 | 6 | 6p12.3 | 46822658 | 46834901 |
| MEP1A | 0.020833 | 0 | 0.125 | 0 | 0.025 | MEP1A | 6 | 6p12.3 | 46869053 | 46915479 |

TABLE 5-continued

Gene list for predicting prostate cancer fast relapse using AT

| Symbol | freq.use | freq.amp. case | freq.del. case | freq.amp. control | freq.del. control | Gene.Symbol | chromosome | cytoband | Transcript. start | Transcript. end |
|---|---|---|---|---|---|---|---|---|---|---|
| GPR116 | 0.020833 | 0 | 0.125 | 0 | 0.025 | GPR116 | 6 | 6p12.3 | 46928204 | 46997674 |
| GPR110 | 0.020833 | 0 | 0.125 | 0 | 0.025 | GPR110 | 6 | 6p12.3 | 47075772 | 47118042 |
| TNFRSF21 | 0.020833 | 0 | 0.125 | 0 | 0.025 | TNFRSF21 | 6 | 6p12.3 | 47307227 | 47385640 |
| CD2AP | 0.020833 | 0 | 0.25 | 0 | 0.025 | CD2AP | 6 | 6p12.3 | 47553484 | 47702956 |
| SMAP1 | 0.020833 | 0.125 | 0.125 | 0.025 | 0.125 | SMAP1 | 6 | 6q13 | 71434200 | 71628438 |
| CDK19 | 0.020833 | 0.125 | 0 | 0.025 | 0 | CDK19 | 6 | 6q21 | 1.11E+08 | 1.11E+08 |
| SLC22A3 | 0.020833 | 0.125 | 0 | 0.025 | 0 | SLC22A3 | 6 | 6q25.3 | 1.61E+08 | 1.61E+08 |
| LPA | 0.020833 | 0.125 | 0 | 0.025 | 0 | LPA | 6 | 6q25.3 | 1.61E+08 | 1.61E+08 |
| DAB2 | 0.020833 | 0 | 0.125 | 0 | 0.025 | DAB2 | 5 | 5p13.1 | 39407537 | 39461093 |
| TTC33 | 0.020833 | 0.125 | 0 | 0.025 | 0 | TTC33 | 5 | 5p13.1 | 40747435 | 40791830 |
| PRKAA1 | 0.020833 | 0.125 | 0 | 0.025 | 0 | PRKAA1 | 5 | 5p13.1 | 40795238 | 40834055 |
| RPL37 | 0.020833 | 0.125 | 0 | 0.025 | 0 | RPL37 | 5 | 5p13.1 | 40867187 | 40871145 |
| SNORD72 | 0.020833 | 0.125 | 0 | 0.025 | 0 | SNORD72 | 5 | 5p13.1 | 40868515 | 40868595 |
| CARD6 | 0.020833 | 0.125 | 0 | 0.025 | 0 | CARD6 | 5 | 5p13.1 | 40877167 | 40891214 |
| C7 | 0.020833 | 0 | 0.125 | 0.025 | 0.025 | C7 | 5 | 5p13.1 | 40945356 | 41018799 |
| IPO11 | 0.020833 | 0.125 | 0 | 0.025 | 0.025 | IPO11 | 5 | 5q12.1 | 61744330 | 61960172 |
| RHOBTB3 | 0.020833 | 0.125 | 0.125 | 0.025 | 0.1 | RHOBTB3 | 5 | 5q15 | 95092606 | 95157828 |
| GLRX | 0.020833 | 0.125 | 0.125 | 0.025 | 0.1 | GLRX | 5 | 5q15 | 95175309 | 95184334 |
| C5orf27 | 0.020833 | 0.125 | 0.125 | 0.025 | 0.1 | C5orf27 | 5 | 5q15 | 95213692 | 95221591 |
| TSSK1B | 0.020833 | 0 | 0.125 | 0 | 0.025 | TSSK1B | 5 | 5q22.2 | 1.13E+08 | 1.13E+08 |
| SNX2 | 0.020833 | 0 | 0.25 | 0 | 0.025 | SNX2 | 5 | 5q23.2 | 1.22E+08 | 1.22E+08 |
| SNX24 | 0.020833 | 0 | 0.25 | 0 | 0.025 | SNX24 | 5 | 5q23.2 | 1.22E+08 | 1.22E+08 |
| PPIC | 0.020833 | 0 | 0.25 | 0 | 0.025 | PPIC | 5 | 5q23.2 | 1.22E+08 | 1.22E+08 |
| 3-Mar | 0.020833 | 0 | 0.125 | 0.05 | 0.025 | 3-Mar | 5 | 5q23.2 | 1.26E+08 | 1.26E+08 |
| CDC42SE2 | 0.020833 | 0.125 | 0 | 0.025 | 0 | CDC42SE2 | 5 | 5q31.1 | 1.31E+08 | 1.31E+08 |
| RAPGEF6 | 0.020833 | 0.125 | 0 | 0.025 | 0 | RAPGEF6 | 5 | 5q31.1 | 1.31E+08 | 1.31E+08 |
| FNIP1 | 0.020833 | 0.125 | 0 | 0.025 | 0 | FNIP1 | 5 | 5q31.1 | 1.31E+08 | 1.31E+08 |
| GEMIN5 | 0.020833 | 0 | 0.125 | 0.125 | 0.025 | GEMIN5 | 5 | 5q33.2 | 1.54E+08 | 1.54E+08 |
| KIF4B | 0.020833 | 0 | 0.125 | 0.075 | 0.025 | KIF4B | 5 | 5q33.2 | 1.54E+08 | 1.54E+08 |
| EBF1 | 0.020833 | 0 | 0.125 | 0 | 0.025 | EBF1 | 5 | 5q33.3 | 1.58E+08 | 1.58E+08 |
| C5orf54 | 0.020833 | 0 | 0.125 | 0.075 | 0.025 | C5orf54 | 5 | 5q33.3 | 1.6E+08 | 1.6E+08 |
| ZNF718 | 0.020833 | 0.375 | 0.125 | 0.5 | 0.025 | ZNF718 | 4 | 4p16.3 | 43277 | 146491 |
| ZNF876P | 0.020833 | 0.375 | 0.125 | 0.5 | 0.025 | ZNF876P | 4 | 4p16.3 | 196389 | 239772 |
| HTRA3 | 0.020833 | 0.5 | 0.25 | 0.625 | 0.025 | HTRA3 | 4 | 4p16.1 | 8322392 | 8359735 |
| QDPR | 0.020833 | 0.125 | 0 | 0.025 | 0 | QDPR | 4 | 4p15.32 | 17097118 | 17122956 |
| CLRN2 | 0.020833 | 0.125 | 0 | 0.025 | 0 | CLRN2 | 4 | 4p15.32 | 17125886 | 17137826 |
| LAP3 | 0.020833 | 0.125 | 0 | 0.025 | 0 | LAP3 | 4 | 4p15.32 | 17188025 | 17218689 |
| FAM184B | 0.020833 | 0.125 | 0 | 0.025 | 0 | FAM184B | 4 | 4p15.32 | 17242809 | 17392234 |
| DCAF16 | 0.020833 | 0.125 | 0 | 0.025 | 0 | DCAF16 | 4 | 4p15.32 | 17411376 | 17421480 |
| TMEM33 | 0.020833 | 0.25 | 0 | 0.025 | 0.025 | TMEM33 | 4 | 4p13 | 41631894 | 41657582 |
| CNGA1 | 0.020833 | 0 | 0.25 | 0.025 | 0.025 | CNGA1 | 4 | 4p12 | 47632751 | 47709719 |
| NIPAL1 | 0.020833 | 0 | 0.25 | 0 | 0.025 | NIPAL1 | 4 | 4p12 | 47713548 | 47733838 |
| TXK | 0.020833 | 0 | 0.25 | 0 | 0.025 | TXK | 4 | 4p12 | 47763167 | 47831031 |
| TEC | 0.020833 | 0 | 0.25 | 0 | 0.025 | TEC | 4 | 4p12 | 47832557 | 47966572 |
| RUFY3 | 0.020833 | 0.375 | 0.25 | 0.05 | 0.025 | RUFY3 | 4 | 4q13.3 | 71789518 | 71874478 |
| MOBKL1A | 0.020833 | 0.375 | 0.25 | 0.05 | 0.025 | MOBKL1A | 4 | 4q13.3 | 71986928 | 72072756 |
| DCK | 0.020833 | 0.375 | 0.25 | 0.05 | 0.025 | DCK | 4 | 4q13.3 | 72078129 | 72115494 |
| EIF4E | 0.020833 | 0.125 | 0 | 0.025 | 0.05 | EIF4E | 4 | 4q23 | 1E+08 | 1E+08 |
| SGMS2 | 0.020833 | 0 | 0.125 | 0.025 | 0.025 | SGMS2 | 4 | 4q25 | 1.09E+08 | 1.09E+08 |
| CYP2U1 | 0.020833 | 0 | 0.125 | 0 | 0.025 | CYP2U1 | 4 | 4q25 | 1.09E+08 | 1.09E+08 |
| GAB1 | 0.020833 | 0 | 0.125 | 0 | 0.025 | GAB1 | 4 | 4q31.21 | 1.44E+08 | 1.45E+08 |
| SMARCA5 | 0.020833 | 0 | 0.125 | 0 | 0.025 | SMARCA5 | 4 | 4q31.21 | 1.45E+08 | 1.45E+08 |
| LOC441046 | 0.020833 | 0 | 0.125 | 0 | 0.025 | LOC441046 | 4 | 4q31.21 | 1.45E+08 | 1.45E+08 |
| FREM3 | 0.020833 | 0 | 0.125 | 0 | 0.025 | FREM3 | 4 | 4q31.21 | 1.45E+08 | 1.45E+08 |
| GYPA | 0.020833 | 0 | 0.125 | 0 | 0.025 | GYPA | 4 | 4q31.22 | 1.45E+08 | 1.45E+08 |
| FAM160A1 | 0.020833 | 0.125 | 0 | 0.025 | 0 | FAM160A1 | 4 | 4q31.3 | 1.53E+08 | 1.53E+08 |
| PLCL2 | 0.020833 | 0 | 0.125 | 0 | 0.025 | PLCL2 | 3 | 3p24.3 | 16901456 | 17107102 |
| RAB5A | 0.020833 | 0.125 | 0.25 | 0.05 | 0.025 | RAB5A | 3 | 3p24.3 | 19963576 | 20001663 |
| C3orf48 | 0.020833 | 0.125 | 0.25 | 0.05 | 0.025 | C3orf48 | 3 | 3p24.3 | 19996458 | 20028770 |
| KAT2B | 0.020833 | 0.125 | 0.25 | 0.05 | 0.025 | KAT2B | 3 | 3p24.3 | 20056528 | 20170901 |
| SGOL1 | 0.020833 | 0.125 | 0.25 | 0.025 | 0.05 | SGOL1 | 3 | 3p24.3 | 20177089 | 20202688 |
| UBE2E2 | 0.020833 | 0 | 0.125 | 0 | 0.025 | UBE2E2 | 3 | 3p24.3 | 23219788 | 23607301 |
| C3orf67 | 0.020833 | 0.25 | 0 | 0.025 | 0.025 | C3orf67 | 3 | 3p14.2 | 58702777 | 59010756 |
| PDZRN3 | 0.020833 | 0 | 0.125 | 0.05 | 0.025 | PDZRN3 | 3 | 3p13 | 73514342 | 73756763 |
| LOC151658 | 0.020833 | 0 | 0.25 | 0 | 0.025 | LOC151658 | 3 | 3q13.12 | 1.09E+08 | 1.09E+08 |
| LOC285205 | 0.020833 | 0 | 0.25 | 0 | 0.025 | LOC285205 | 3 | 3q13.12 | 1.09E+08 | 1.09E+08 |
| HHLA2 | 0.020833 | 0 | 0.25 | 0 | 0.025 | HHLA2 | 3 | 3q13.13 | 1.1E+08 | 1.1E+08 |
| MYH15 | 0.020833 | 0 | 0.25 | 0 | 0.025 | MYH15 | 3 | 3q13.13 | 1.1E+08 | 1.1E+08 |
| KIAA1524 | 0.020833 | 0 | 0.25 | 0 | 0.025 | KIAA1524 | 3 | 3q13.13 | 1.1E+08 | 1.1E+08 |
| DZIP3 | 0.020833 | 0 | 0.125 | 0 | 0.025 | DZIP3 | 3 | 3q13.13 | 1.1E+08 | 1.1E+08 |
| C3orf66 | 0.020833 | 0 | 0.125 | 0 | 0.025 | C3orf66 | 3 | 3q13.13 | 1.1E+08 | 1.1E+08 |
| BOC | 0.020833 | 0 | 0.125 | 0.05 | 0.025 | BOC | 3 | 3q13.2 | 1.14E+08 | 1.14E+08 |
| GOLGB1 | 0.020833 | 0 | 0.125 | 0.025 | 0.025 | GOLGB1 | 3 | 3q13.33 | 1.23E+08 | 1.23E+08 |
| ACAD11 | 0.020833 | 0 | 0.125 | 0 | 0.025 | ACAD11 | 3 | 3q22.1 | 1.34E+08 | 1.34E+08 |
| CCRL1 | 0.020833 | 0 | 0.125 | 0 | 0.025 | CCRL1 | 3 | 3q22.1 | 1.34E+08 | 1.34E+08 |

TABLE 5-continued

Gene list for predicting prostate cancer fast relapse using AT

| Symbol | freq.use | freq.amp. case | freq.del. case | freq.amp. control | freq.del. control | Gene.Symbol | chromosome | cytoband | Transcript. start | Transcript. end |
|---|---|---|---|---|---|---|---|---|---|---|
| UBA5 | 0.020833 | 0 | 0.125 | 0 | 0.025 | UBA5 | 3 | 3q22.1 | 1.34E+08 | 1.34E+08 |
| NCRNA00119 | 0.020833 | 0 | 0.125 | 0 | 0.025 | NCRNA00119 | 3 | 3q22.1 | 1.34E+08 | 1.34E+08 |
| TMEM108 | 0.020833 | 0 | 0.125 | 0 | 0.025 | TMEM108 | 3 | 3q22.1 | 1.34E+08 | 1.35E+08 |
| RNF13 | 0.020833 | 0 | 0.125 | 0 | 0.025 | RNF13 | 3 | 3q25.1 | 1.51E+08 | 1.51E+08 |
| C3orf57 | 0.020833 | 0 | 0.125 | 0 | 0.025 | C3orf57 | 3 | 3q26.1 | 1.63E+08 | 1.63E+08 |
| ZNF639 | 0.020833 | o | 0.125 | 0.025 | 0 | ZNF639 | 3 | 3q26.32 | 1.81E+08 | 1.81E+08 |
| GNB4 | 0.020833 | 0.125 | 0 | 0.025 | 0 | GNB4 | 3 | 3q26.33 | 1.81E+08 | 1.81E+08 |
| ACTL6A | 0.020833 | 0.125 | 0 | 0.025 | 0 | ACTL6A | 3 | 3q26.33 | 1.81E+08 | 1.81E+08 |
| USP13 | 0.020833 | 0.125 | 0 | 0.025 | 0 | USP13 | 3 | 3q26.33 | 1.81E+08 | 1.81E+08 |
| CCDC50 | 0.020833 | 0 | 0.125 | 0.05 | 0.025 | CCDC50 | 3 | 3q28 | 1.93E+08 | 1.93E+08 |
| ROCK2 | 0.020833 | 0.375 | 0.125 | 0.275 | 0.025 | ROCK2 | 2 | 2p25.1 | 11239229 | 11402163 |
| GTF2A1L | 0.020833 | 0.125 | 0 | 0.025 | 0.1 | GTF2A1L | 2 | 2p16.3 | 48698452 | 48813791 |
| LHCGR | 0.020833 | 0.125 | 0 | 0.025 | 0.1 | LHCGR | 2 | 2p16.3 | 48767417 | 48836385 |
| DDX18 | 0.020833 | 0.125 | 0 | 0.025 | 0.025 | DDX18 | 2 | 2q14.1 | 1.18E+08 | 1.18E+08 |
| CCDC93 | 0.020833 | 0.125 | 0 | 0.025 | 0.025 | CCDC93 | 2 | 2q14.1 | 1.18E+08 | 1.18E+08 |
| LYPD6B | 0.020833 | 0 | 0.125 | 0 | 0.025 | LYPD6B | 2 | 2q23.2 | 1.5E+08 | 1.5E+08 |
| LYPD6 | 0.020833 | 0 | 0.125 | 0 | 0.025 | LYPD6 | 2 | 2q23.2 | 1.5E+08 | 1.5E+08 |
| DPP4 | 0.020833 | 0.125 | 0 | 0.025 | 0.075 | DPP4 | 2 | 2q24.2 | 1.63E+08 | 1.63E+08 |
| OLA1 | 0.020833 | 0.125 | 0 | 0.025 | 0.025 | OLA1 | 2 | 2q31.1 | 1.75E+08 | 1.75E+08 |
| KCTD18 | 0.020833 | 0.125 | 0 | 0.025 | 0 | KCTD18 | 2 | 2q33.1 | 2.01E+08 | 2.01E+08 |
| SGOL2 | 0.020833 | 0.125 | 0 | 0.025 | 0 | SGOL2 | 2 | 2q33.1 | 2.01E+08 | 2.01E+08 |
| AOX1 | 0.020833 | 0.125 | 0 | 0.025 | 0 | AOX1 | 2 | 2q33.1 | 2.01E+08 | 2.01E+08 |
| ZCCHC17 | 0.020833 | 0.625 | 0.125 | 0.475 | 0.025 | ZCCHC17 | 1 | 1p35.2 | 31542429 | 31610368 |
| TCTEX1D1 | 0.020833 | 0 | 0.125 | 0 | 0.025 | TCTEX1D1 | 1 | 1p31.3 | 66990728 | 67017318 |
| WDR78 | 0.020833 | 0 | 0.125 | 0 | 0.025 | WDR78 | 1 | 1p31.3 | 67051161 | 67163159 |
| SLC35D1 | 0.020833 | 0 | 0.125 | 0 | 0.025 | SLC35D1 | 1 | 1p31.3 | 67237604 | 67292669 |
| HFM1 | 0.020833 | 0.125 | 0 | 0.025 | 0 | HFM1 | 1 | 1p22.2 | 91498911 | 91643015 |
| CDC7 | 0.020833 | 0.125 | 0 | 0.025 | 0 | CDC7 | 1 | 1p22.2 | 91738992 | 91763909 |
| HSP90B3P | 0.020833 | 0.125 | 0 | 0.025 | 0 | HSP90B3P | 1 | 1p22.2 | 91873156 | 91881923 |
| TGFBR3 | 0.020833 | 0.125 | 0 | 0.025 | 0 | TGFBR3 | 1 | 1p22.2 | 91918490 | 92124376 |
| BRDT | 0.020833 | 0.125 | 0 | 0.025 | 0 | BRDT | 1 | 1p22.1 | 92187516 | 92252574 |
| EPHX4 | 0.020833 | 0.125 | 0 | 0.025 | 0 | EPHX4 | 1 | 1p22.1 | 92268121 | 92301682 |
| BTBD8 | 0.020833 | 0.125 | 0 | 0.025 | 0 | BTBD8 | 1 | 1p22.1 | 92318450 | 92385984 |
| KIAA1107 | 0.020833 | 0.125 | 0 | 0.025 | 0 | KIAA1107 | 1 | 1p22.1 | 92405197 | 92422868 |
| GFI1 | 0.020833 | 0.125 | 0 | 0.025 | 0 | GFI1 | 1 | 1p22.1 | 92712906 | 92721945 |
| EVI5 | 0.020833 | 0.125 | 0 | 0.025 | 0 | EVI5 | 1 | 1p22.1 | 92746841 | 93030550 |
| RPL5 | 0.020833 | 0.25 | 0 | 0.025 | 0 | RPL5 | 1 | 1p22.1 | 93070182 | 93080070 |
| SNORD21 | 0.020833 | 0.25 | 0 | 0.025 | 0 | SNORD21 | 1 | 1p22.1 | 93075434 | 93075529 |
| FAM69A | 0.020833 | 0.25 | 0 | 0.025 | 0 | FAM69A | 1 | 1p22.1 | 93080309 | 93199668 |
| MTF2 | 0.020833 | 0.25 | 0 | 0.025 | 0 | MTF2 | 1 | 1p22.1 | 93317380 | 93377225 |
| ARHGAP29 | 0.020833 | 0.125 | 0 | 0.025 | 0.025 | ARHGAP29 | 1 | 1p22.1 | 94407051 | 94475896 |
| FCRLB | 0.020833 | 0.125 | 0 | 0.025 | 0.05 | FCRLB | 1 | 1q23.3 | 1.6E+08 | 1.6E+08 |
| FAM78B | 0.020833 | 0.125 | 0 | 0.025 | 0 | FAM78B | 1 | 1q24.1 | 1.64E+08 | 1.64E+08 |
| XPR1 | 0.020833 | 0.125 | 0 | 0.025 | 0 | XPR1 | 1 | 1q25.3 | 1.79E+08 | 1.79E+08 |
| CACNA1E | 0.020833 | 0.125 | 0 | 0.025 | 0 | CACNA1E | 1 | 1q25.3 | 1.8E+08 | 1.8E+08 |
| AKT3 | 0.020833 | 0 | 0.125 | 0 | 0.025 | AKT3 | 1 | 1q44 | 2.42E+08 | 2.42E+08 |

What is claimed is:

1. A method of treating prostate cancer in a human patient in need thereof comprising:
   a) obtaining a sample from a patient;
   b) determining whether gene the SDA1 Domain Containing 1 (SDAD1) gene is amplified in DNA obtained from the sample;
   c) determining that the patient is at increased risk of rapid relapse of prostate cancer when the SDAD1 gene is amplified; and
   d) upon determination that the patient is at increased risk of rapid relapse of prostate cancer then treating the patient that is at increased risk of rapid relapse of prostate cancer by performing frequent monitoring for recurrence by prostate specific antigen test, ultrasound imaging, CT imaging, MRI imaging, PET scan or digital rectal exam or performing a surgical excision, a radiotherapy and/or a chemotherapy.

2. The method of claim 1, wherein the sample is selected from the group consisting of a prostate tissue sample and a blood sample.

* * * * *